United States Patent
Lowinger et al.

(10) Patent No.: US 11,964,024 B2
(45) Date of Patent: Apr. 23, 2024

(54) B7H4-TARGETED ANTIBODY-DRUG CONJUGATES AND METHODS OF USE THEREOF

(71) Applicant: Mersana Therapeutics, Inc., Cambridge, MA (US)

(72) Inventors: Timothy B. Lowinger, Carlisle, MA (US); Chen-Ni Chin, Somerville, MA (US); Marc I. Damelin, Needham, MA (US); Dorin Toader, Cambridge, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/568,376

(22) Filed: Jan. 4, 2022

(65) Prior Publication Data

US 2022/0233707 A1    Jul. 28, 2022

Related U.S. Application Data

(60) Provisional application No. 63/172,968, filed on Apr. 9, 2021, provisional application No. 63/133,707, filed on Jan. 4, 2021.

(51) Int. Cl.
| | |
|---|---|
| *A61K 47/68* | (2017.01) |
| *A61K 39/395* | (2006.01) |
| *A61P 35/00* | (2006.01) |
| *C07K 16/28* | (2006.01) |
| *C07K 16/30* | (2006.01) |
| *C07K 16/32* | (2006.01) |

(52) U.S. Cl.
CPC ...... *A61K 47/6803* (2017.08); *A61K 47/6857* (2017.08); *A61K 47/6869* (2017.08); *A61K 47/6883* (2017.08); *A61P 35/00* (2018.01); *C07K 16/3023* (2013.01); *C07K 16/3069* (2013.01); *C07K 16/32* (2013.01); *C07K 2317/21* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 6,602,677 B1 | 8/2003 | Wood et al. |
| 7,931,896 B2 | 4/2011 | Chen |
| 8,323,645 B2 | 12/2012 | Veiby et al. |
| 8,609,816 B2 | 12/2013 | Korman et al. |
| 8,759,490 B2 | 6/2014 | Veiby et al. |
| 8,852,599 B2 | 10/2014 | Zhang et al. |
| 9,121,853 B2 | 9/2015 | Kwon et al. |
| 9,186,416 B2 | 11/2015 | Zhang et al. |
| 9,296,822 B2 | 3/2016 | Korman et al. |
| 9,421,277 B2 | 8/2016 | Veiby et al. |
| 9,562,099 B2 | 2/2017 | Leong et al. |
| 9,574,000 B2 | 2/2017 | Langermann et al. |
| 9,676,854 B2 | 6/2017 | Liu et al. |
| 9,926,378 B2 | 3/2018 | Veiby et al. |
| 9,988,453 B2 | 6/2018 | Korman et al. |
| 10,059,768 B2 | 8/2018 | Leong et al. |
| 10,150,813 B2 | 12/2018 | Leong et al. |
| 10,626,176 B2 | 4/2020 | Sathyanarayanan et al. |
| 10,814,011 B1 | 10/2020 | Schilling et al. |
| 2007/0218032 A1 | 9/2007 | Kwon et al. |
| 2011/0085970 A1 | 4/2011 | Terrett et al. |
| 2015/0315275 A1 | 11/2015 | Langermann et al. |
| 2016/0159910 A1 | 6/2016 | Leong et al. |
| 2016/0222119 A1 | 8/2016 | Scholler et al. |
| 2016/0319030 A1 | 11/2016 | Veiby et al. |
| 2017/0239366 A1 | 8/2017 | Leong et al. |
| 2019/0062432 A1 | 2/2019 | Leong et al. |
| 2019/0085080 A1 | 3/2019 | Kaplan et al. |
| 2019/0241663 A1 | 8/2019 | Leong et al. |
| 2019/0343964 A1 | 11/2019 | Akiyama et al. |
| 2021/0032346 A1 | 2/2021 | Langermann et al. |
| 2021/0032347 A1 | 2/2021 | Bao et al. |
| 2021/0070861 A1 | 3/2021 | Quan et al. |
| 2021/0070862 A1 | 3/2021 | Inamdar et al. |
| 2021/0292418 A1 | 9/2021 | Koopman et al. |
| 2021/0332137 A1 | 10/2021 | Inamdar et al. |

FOREIGN PATENT DOCUMENTS

| | | | |
|---|---|---|---|
| WO | WO-2004063344 A2 | 7/2004 | |
| WO | WO-2007005874 A2 | 1/2007 | |
| WO | WO-2007067991 A2 * | 6/2007 | ......... A61K 47/6849 |
| WO | WO-2009073533 A2 | 6/2009 | |
| WO | WO-2009102820 A2 | 8/2009 | |

(Continued)

OTHER PUBLICATIONS

Altan, et al., "B7-H3 expression in NSCLC and its association with B7-H4, PD-L1 and tumor-infiltrating lymphocytes". Clinical Cancer Research. Sep. 1, 2017; 23(17): 5202-9.
Clardy et al. "Unique pharmacologic properties of Dolaflexin-based ADCs—a controlled bystander effect". Cancer Research. Jul. 1, 2018; 78(13_Supplement): 2 pages.
Collin et al. "EndoS, a novel secreted protein from *Streptococcus pyogenes* with endoglycosidase activity on human IgG", The EMBO Journal, 2001, vol. 20, No. 12, p. 3046-3055.
Cree et al., "Methotrexate chemosensitivity by ATP luminescence in human leukemia cell lines and in breast cancer primary cultures: comparison of the TCA-100 assay with a clonogenic assay. Anti-Cancer Drugs". Jun. 1, 1995; 6(3): 398-404.
Crouch et al., The use of ATP bioluminescence as a measure of cell proliferation and cytotoxicity. Journal of immunological methods. Jan. 1, 1993;160(1): 81-8.

(Continued)

*Primary Examiner* — Laura B Goddard
(74) *Attorney, Agent, or Firm* — COOLEY LLP; Cynthia A. Kozakiewicz; Ivor Elrifi

(57) ABSTRACT

The present disclosure relates generally to antibody-drug conjugates comprising monoclonal antibodies that specifically bind the human B7-H4 in soluble form, or membrane bound (i.e., when expressed on a cell surface) and to methods of using these conjugates as therapeutics and/or diagnostics.

30 Claims, 14 Drawing Sheets

Specification includes a Sequence Listing.

(56) References Cited

FOREIGN PATENT DOCUMENTS

| WO | WO-2012171020 A1 | 12/2012 |
|----|------------------|---------|
| WO | WO-2013037824 A1 | 3/2013 |
| WO | WO-2015054659 A1 | 4/2015 |
| WO | WO-2016170186 A1 | 10/2016 |
| WO | WO-2017137459 A1 | 8/2017 |
| WO | WO-2018098269 A2 | 5/2018 |
| WO | WO-2018195302 A1 | 10/2018 |
| WO | WO-2019154315 A1 | 8/2019 |
| WO | WO-2019237442 A1 | 12/2019 |
| WO | WO-2020081497 A1 | 4/2020 |
| WO | WO-2020092385 A1 | 5/2020 |
| WO | WO-2020244657 A1 | 12/2020 |
| WO | WO-2021142199 A1 | 7/2021 |
| WO | WO-2021155307 A1 | 8/2021 |
| WO | WO-2021202984 A1 | 10/2021 |
| WO | WO-2022002012 A1 | 1/2022 |
| WO | WO-2022147532 A1 | 7/2022 |

OTHER PUBLICATIONS

Francisco et al., "cAC10-vcMMAE, an anti-CD30-monomethyl auristatin E conjugate with potent and selective antitumor activity". Blood. Aug. 15, 2003; 102(4): 1458-65.

Gray et al., "854 SGN-B7H4V, a novel, investigational vedotin antibody-drug conjugate directed to the T cell checkpoint ligand B7-H4, shows promising activity in preclinical models.", Poster No. 854, Society for Immunotherapy of Cancer Virtual, Nov. 10-14, 2021, 1 page.

Hoskins et al. "Sequence Finishing and Mapping of *Drosophila melanogaster* Heterochromatin", Science, 2007, vol. 316, No. 5831, p. 1625-1628.

International Search Report and Written Opinion for International Application No. PCT/US2022/011119, dated Jun. 13, 2022, 20 pages.

Kaplan et al., "FPA150, a novel B7-H4 therapeutic antibody with checkpoint blockade and ADCC activities". Annals of Oncology. Sep. 1, 2017; 28: 1 page.

Kawar et al. "Molecular Cloning and Enzymatic Characterization of a UDP-GalNAc:GlcNAcβ-R β1,4-N-Acetylgalactosaminyltransferase from Caenorhabditis elegans", Journal of Biological Chemistry, 2002, vol. 277, Issue 368, p. 34924-34932.

Khidekel et al. "A Chemoenzymatic Approach toward the Rapid and Sensitive Detection of O-GlcNAc Posttranslational Modifications", Journal of American Chemical Society, 2003, vol. 125, p. 16162-16163.

Leong et al., "An anti-B7-H4 antibody-drug conjugate for the treatment of breast cancer". Molecular Pharmaceutics, (2015) 12(6), pp. 1717-1729.

Leong, et al.,. "Supporting Information: An anti-B7-H4 antibody-drug conjugate for the treatment of breast cancer. Molecular pharmaceutics". Jun. 1, 2015; 12(6): 1717-29.

Li et al., "Tumor-Associated Macrophages Can Contribute to Antitumor Activity through FcγR-Mediated Processing of Antibody-Drug ConjugatesRole of TAMs in ADC Antitumor Activity". Molecular cancer therapeutics. Jul. 1, 2017; 16(7): 1347-54.

MacGregor et al., "Molecular Pathways: Evaluating the Potential for B7-H4 as an Immunoregulatory Target Evaluating B7-H4 as a Potential Immunoregulatory Target". Clinical Cancer Research. Jun. 15, 2017; 23(12): 2934-41.

Poldojil et al., "B7-H4 modulates regulatory CD4+ T cell induction and function via ligation of a Semaphorin 3a/Plexin A4/Neuropilin-1 complex". The Journal of Immunology. Aug. 1, 2018;201(3):897-907.

Pouilly et al. "Evaluation of Analogues of GalNAc as Substrates for Enzymes of the Mammalian GalNAc Salvage Pathway", ACS Chemical Biology, 2012, vol. 7, p. 753-760.

Qasba et al. "A chemoenzymatic approach toward the rapid and sensitive detection of O-GlcNAc posttranslational modifications". Journal of the American Chemical Society. Dec. 31, 2003; 125(52): 16162-3.

Qasba et al., "The N-terminal stem region of bovine and human β1,4-galactosyltransferase I increases the in vitro folding efficiency of their catalytic domain from inclusion bodies". Protein Expression and Purification. Aug. 1, 2003; 30(2): 219-29.

Qasba et al., "Structure-based design of β1, 4-galactosyltransferase I (β4Gal-T1) with equally efficient N-acetylgalactosaminyltransferase activity: point mutation broadens β4Gal-T1 donor specificity". Journal of Biological Chemistry. Jun. 7, 2002; 277(23): 20833-9.

Ramakrishnan et al. "Structure-based Design of β1,4-Galactosyltransferase I (β4Gal-T1) with Equally Efficient N-Acetylgalactosaminyltransferase Activity: Point Mutation Broadens β4Gal-T1 Donor Specificity", Journal of Biological Chemistry, 2002, vol. 277, Issue 23, p. 20833-20839.

Ramanjulu et al., "Design of amidobenzimidazole STING receptor agonists with systemic activity", Nature. Dec. 20, 2018; 564(7736): 439-43.

Sachdev, et al. (2019). "Phase 1a/1b Study of First-in-Class B7-H4 Antibody, FPA150 as Monotherapy in Patients with Advanced Solid Tumors". Poster presented at the Annual ASCO Meeting, (2019), 1 page.

Schmaltz et al. "Enzymes in the Synthesis of Glycoconjugates", Chemical Reviews, 2011, vol. 111, p. 4259-4307.

Smith et al., "Tumor regression and delayed onset toxicity following B7-H4 CAR T cell therapy". Molecular Therapy. Nov. 1, 2016; 24(11): 1987-99.

Strohl et al, "Development issues: antibody stability, developability, immunogenicity, and comparability" In: "Therapeutic Antibody Engineering", Oct. 16, 2012 (Oct. 16, 2012), Woodhead Publishing Limited, GB, XP055688183, pp. 377-403.

Traore, et al., "Synergy of an anti-HER2 ADC TAK-522 (XMT-1522) in combination with anti-PD1 monoclonal antibody (mAb) in a syngeneic breast cancer model expressing human HER2". The Journal of Immunology. May 1, 2018; 200 (1_Supplement): 122-29.

Vadaie et al. "Molecular Cloning and Functional Characterization of a Lepidopteran Insect β4-N-Acetylgalactosaminyltransferase with Broad Substrate Specificity, a Functional Role in Glycoprotein Biosynthesis, and a Potential Functional Role in Glycolipid Biosynthesis", Journal of Biological Chemistry, 2004, vol. 279, Issue 32, p. 33501-33518.

Wainberg et al., "FPA150 (B7-H4 antibody) phase I update in advanced solid tumours: Monotherapy and in combination with pembrolizumab". Annals of Oncology. Oct. 1, 2019;30: 1 page.

Wang et al., "B7-H4, a promising target for immunotherapy". Cellular Immunology. Jan. 1, 2020; 347: pp. 1-13.

\* cited by examiner

→ Vehicle
⋅△⋅ Conjugate 1-2, 1.79/0.059 mg/kg
⊸△⊸ Conjugate 1-2, 5.37/0.177 mg/kg
⋅✕⋅ Conjugate 9-2, 4.56/0.150 mg/kg
⋅▫⋅ Conjugate 2-1, 4.60/0.050 mg/kg
⊸▫⊸ Conjugate 2-1, 13.45/0.150 mg/kg
⋅★⋅ Conjugate 10, 14.37/0.150 mg/kg

SEQUENCE LISTING

```
<160> NUMBER OF SEQ ID NOS: 61

<210> SEQ ID NO 1
<211> LENGTH: 116
<212> TYPE: PRT
<213> ORGANISM: Homo Sapiens

<400> SEQUENCE: 1

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Cys Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Gly Asp Tyr Gly Met Asp Val Trp Gly Gln Gly Thr Thr Val
            100                 105                 110

Thr Val Ser Ser
        115

<210> SEQ ID NO 2
<211> LENGTH: 8
<212> TYPE: PRT
<213> ORGANISM: Homo Sapiens

<400> SEQUENCE: 2

Gly Phe Ile Val Ser Arg Asn Tyr
1               5

<210> SEQ ID NO 3
<211> LENGTH: 7
<212> TYPE: PRT
<213> ORGANISM: Homo Sapiens
```

```
<400> SEQUENCE: 3

Ile Tyr Gly Ser Gly Arg Thr
1               5

<210> SEQ ID NO 4
<211> LENGTH: 10
<212> TYPE: PRT
<213> ORGANISM: Homo Sapiens

<400> SEQUENCE: 4

Ala Arg Asp Gly Asp Tyr Gly Met Asp Val
1               5                   10

<210> SEQ ID NO 5
<211> LENGTH: 116
<212> TYPE: PRT
<213> ORGANISM: Homo Sapiens

<400> SEQUENCE: 5

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Asp Tyr Gly Met Asp Val Trp Gly Gln Gly Thr Thr Val
            100                 105                 110

Thr Val Ser Ser
        115

<210> SEQ ID NO 6
<211> LENGTH: 329
<212> TYPE: PRT
<213> ORGANISM: Homo Sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
                115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 7
<211> LENGTH: 446
<212> TYPE: PRT
<213> ORGANISM: Homo Sapiens

<400> SEQUENCE: 7

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Asp Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 8
<211> LENGTH: 116
<212> TYPE: PRT
<213> ORGANISM: Homo Sapiens

<400> SEQUENCE: 8

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Asp Ala Asp Tyr Gly Met Asp Val Trp Gly Gln Gly Thr Thr Val
                100                 105                 110

Thr Val Ser Ser
        115

<210> SEQ ID NO 9
<211> LENGTH: 446
<212> TYPE: PRT
<213> ORGANISM: Homo Sapiens

<400> SEQUENCE: 9

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Met Asp Val Trp Gly Gln Gly Thr Thr Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
```

```
                340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 10
<211> LENGTH: 10
<212> TYPE: PRT
<213> ORGANISM: Homo Sapiens

<400> SEQUENCE: 10

Ala Arg Asp Ala Asp Tyr Gly Met Asp Val
1               5                   10

<210> SEQ ID NO 11
<211> LENGTH: 115
<212> TYPE: PRT
<213> ORGANISM: Homo Sapiens

<400> SEQUENCE: 11

Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Ile Val Ser Arg Asn
            20                  25                  30
Tyr Met Asn Trp Val Arg Gln Ala Pro Gly Lys Gly Leu Glu Trp Val
        35                  40                  45
Ser Val Ile Tyr Gly Ser Gly Arg Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Thr Tyr Ala Met Asp Val Trp Gly Gln Gly Thr Thr Val Thr
            100                 105                 110
Val Ser Ser
        115

<210> SEQ ID NO 12
<211> LENGTH: 445
<212> TYPE: PRT
<213> ORGANISM: Homo Sapiens

<400> SEQUENCE: 12

Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Ile Val Ser Arg Asn
            20                  25                  30
Tyr Met Asn Trp Val Arg Gln Ala Pro Gly Lys Gly Leu Glu Trp Val
        35                  40                  45
```

-continued

```
Ser Val Ile Tyr Gly Ser Gly Arg Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Ala Met Asp Val Trp Gly Gln Gly Thr Thr Val Thr
            100                 105                 110

Val Ser Ser Ala Ser Thr Lys Gly Pro Ser Val Phe Pro Leu Ala Pro
       115                 120                 125

Ser Ser Lys Ser Thr Ser Gly Gly Thr Ala Ala Leu Gly Cys Leu Val
   130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
       195                 200                 205

Val Asp Lys Lys Val Glu Pro Lys Ser Cys Asp Lys Thr His Thr Cys
   210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
       275                 280                 285

Pro Arg Glu Glu Gln Tyr Asn Ser Thr Tyr Arg Val Val Ser Val Leu
   290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
       355                 360                 365

Gly Phe Tyr Pro Ser Asp Ile Ala Val Glu Trp Glu Ser Asn Gly Gln
   370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
       435                 440                 445

<210> SEQ ID NO 13
<211> LENGTH: 9
```

```
<212> TYPE: PRT
<213> ORGANISM: Homo Sapiens

<400> SEQUENCE: 13

Ala Arg Asp Thr Tyr Ala Met Asp Val
1               5

<210> SEQ ID NO 14
<211> LENGTH: 116
<212> TYPE: PRT
<213> ORGANISM: Homo Sapiens

<400> SEQUENCE: 14

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
            100                 105                 110

Thr Val Ser Ser
        115

<210> SEQ ID NO 15
<211> LENGTH: 446
<212> TYPE: PRT
<213> ORGANISM: Homo Sapiens

<400> SEQUENCE: 15

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
        260                 265                 270
Lys Phe Asn Trp Tyr Val Asp Gly Val Glu Val His Asn Ala Lys Thr
    275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
        340                 345                 350
Ser Arg Asp Glu Leu Thr Lys Asn Gln Val Ser Leu Thr Cys Leu Val
    355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
        420                 425                 430
Asn His Tyr Thr Gln Lys Ser Leu Ser Leu Ser Pro Gly Lys
    435                 440                 445

<210> SEQ ID NO 16
<211> LENGTH: 10
<212> TYPE: PRT
<213> ORGANISM: Homo Sapiens

<400> SEQUENCE: 16

Ala Arg Asp Ala Asp Tyr Gly Leu Asp Val
1               5                   10

<210> SEQ ID NO 17
<211> LENGTH: 115
<212> TYPE: PRT
<213> ORGANISM: Homo Sapiens

<400> SEQUENCE: 17

Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Ile Val Ser Arg Asn
            20                  25                  30
Tyr Met Asn Trp Val Arg Gln Ala Pro Gly Lys Gly Leu Glu Trp Val
```

```
                35                  40                  45
Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Asp Thr Tyr Ala Leu Asp Val Trp Gly Gln Gly Thr Thr Val Thr
            100                 105                 110

Val Ser Ser
        115

<210> SEQ ID NO 18
<211> LENGTH: 445
<212> TYPE: PRT
<213> ORGANISM: Homo Sapiens

<400> SEQUENCE: 18

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Asp Thr Tyr Ala Leu Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 19
<211> LENGTH: 9
<212> TYPE: PRT
<213> ORGANISM: Homo Sapiens

<400> SEQUENCE: 19

Ala Arg Asp Thr Tyr Ala Leu Asp Val
1               5

<210> SEQ ID NO 20
<211> LENGTH: 116
<212> TYPE: PRT
<213> ORGANISM: Homo Sapiens

<400> SEQUENCE: 20

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Asp Tyr Gly Met Asp Val Trp Gly Gln Gly Thr Thr Val
                100                 105                 110

Thr Val Ser Ser
        115

<210> SEQ ID NO 21
<211> LENGTH: 446
<212> TYPE: PRT
<213> ORGANISM: Homo Sapiens
```

```
<400> SEQUENCE: 21

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Gly Asp Tyr Gly Met Asp Val Trp Gly Gln Gly Thr Thr Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415
```

```
Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 22
<211> LENGTH: 116
<212> TYPE: PRT
<213> ORGANISM: Homo Sapiens

<400> SEQUENCE: 22

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Met Asp Val Trp Gly Gln Gly Thr Thr Val
                100                 105                 110

Thr Val Ser Ser
        115

<210> SEQ ID NO 23
<211> LENGTH: 446
<212> TYPE: PRT
<213> ORGANISM: Homo Sapiens

<400> SEQUENCE: 23

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Met Asp Val Trp Gly Gln Gly Thr Thr Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 24
<211> LENGTH: 116
<212> TYPE: PRT
<213> ORGANISM: Homo Sapiens

<400> SEQUENCE: 24

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
```

```
                    100                 105                 110

Thr Val Ser Ser
        115

<210> SEQ ID NO 25
<211> LENGTH: 446
<212> TYPE: PRT
<213> ORGANISM: Homo Sapiens

<400> SEQUENCE: 25

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 26
<211> LENGTH: 115
<212> TYPE: PRT
<213> ORGANISM: Homo Sapiens

<400> SEQUENCE: 26

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser
        115

<210> SEQ ID NO 27
<211> LENGTH: 445
<212> TYPE: PRT
<213> ORGANISM: Homo Sapiens

<400> SEQUENCE: 27

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110
```

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 28
<211> LENGTH: 115
<212> TYPE: PRT
<213> ORGANISM: Homo Sapiens

<400> SEQUENCE: 28

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45
```

```
Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Ala Leu Asp Val Trp Gly Gln Gly Thr Thr Val Thr
                100                 105                 110

Val Ser Ser
        115

<210> SEQ ID NO 29
<211> LENGTH: 445
<212> TYPE: PRT
<213> ORGANISM: Homo Sapiens

<400> SEQUENCE: 29

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Ile Val Ser Arg Asn
                 20                  25                  30

Tyr Met Asn Trp Val Arg Gln Ala Pro Gly Lys Gly Leu Glu Trp Val
             35                  40                  45

Ser Val Ile Tyr Gly Ser Gly Arg Thr Asp Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Ala Leu Asp Val Trp Gly Gln Gly Thr Thr Val Thr
                100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
                290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 30
<211> LENGTH: 116
<212> TYPE: PRT
<213> ORGANISM: Homo Sapiens

<400> SEQUENCE: 30

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
                35                  40                  45

Ser Val Ile Tyr Gly Ser Gly Arg Thr Asp Ala Ala Asp Ser Val Lys
            50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Asp Tyr Gly Met Asp Val Trp Gly Gln Gly Thr Thr Val
                100                 105                 110

Thr Val Ser Ser
            115

<210> SEQ ID NO 31
<211> LENGTH: 446
<212> TYPE: PRT
<213> ORGANISM: Homo Sapiens

<400> SEQUENCE: 31

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
                20                  25                  30

Tyr Met Asn Trp Val Arg Gln Ala Pro Gly Lys Gly Leu Glu Trp Val
                35                  40                  45

Ser Val Ile Tyr Gly Ser Gly Arg Thr Asp Ala Ala Asp Ser Val Lys
```

```
            50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Gly Asp Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 32
<211> LENGTH: 116
<212> TYPE: PRT
<213> ORGANISM: Homo Sapiens
```

<400> SEQUENCE: 32

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Ala Asp Tyr Gly Met Asp Val Trp Gly Gln Gly Thr Thr Val
        100                 105                 110

Thr Val Ser Ser
        115

<210> SEQ ID NO 33
<211> LENGTH: 446
<212> TYPE: PRT
<213> ORGANISM: Homo Sapiens

<400> SEQUENCE: 33

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Ala Asp Tyr Gly Met Asp Val Trp Gly Gln Gly Thr Thr Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

```
Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 34
<211> LENGTH: 116
<212> TYPE: PRT
<213> ORGANISM: Homo Sapiens

<400> SEQUENCE: 34

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
            100                 105                 110

Thr Val Ser Ser
        115

<210> SEQ ID NO 35
<211> LENGTH: 446
<212> TYPE: PRT
<213> ORGANISM: Homo Sapiens

<400> SEQUENCE: 35
```

-continued

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Ala Asp Tyr Gly Leu Asp Val Trp Gly Gln Gly Thr Thr Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415
```

```
Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 36
<211> LENGTH: 115
<212> TYPE: PRT
<213> ORGANISM: Homo Sapiens

<400> SEQUENCE: 36

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser
        115
```

<210> SEQ ID NO 37
<211> LENGTH: 445
<212> TYPE: PRT
<213> ORGANISM: Homo Sapiens

<400> SEQUENCE: 37

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 38
<211> LENGTH: 115
<212> TYPE: PRT
<213> ORGANISM: Homo Sapiens

<400> SEQUENCE: 38

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
            35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Leu Asp Val Trp Gly Gln Gly Thr Thr Val Thr
            100                 105                 110
```

Val Ser Ser
    115

<210> SEQ ID NO 39
<211> LENGTH: 445
<212> TYPE: PRT
<213> ORGANISM: Homo Sapiens

<400> SEQUENCE: 39

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ala Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Leu Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys

```
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 40
<211> LENGTH: 116
<212> TYPE: PRT
<213> ORGANISM: Homo Sapiens

<400> SEQUENCE: 40

Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Ile Val Ser Arg Asn
            20                  25                  30
Tyr Met Asn Trp Val Arg Gln Ala Pro Gly Lys Gly Leu Glu Trp Val
        35                  40                  45
Ser Val Ile Tyr Gly Ser Gly Arg Thr Asp Ser Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Gly Asp Tyr Gly Met Asp Val Trp Gly Gln Gly Thr Thr Val
            100                 105                 110
Thr Val Ser Ser
            115

<210> SEQ ID NO 41
<211> LENGTH: 446
<212> TYPE: PRT
<213> ORGANISM: Homo Sapiens

<400> SEQUENCE: 41

Glu Val Gln Leu Val Glu Ser Gly Gly Gly Leu Ile Gln Pro Gly Gly
1               5                   10                  15
Ser Leu Arg Leu Ser Cys Ala Ala Ser Gly Phe Ile Val Ser Arg Asn
            20                  25                  30
Tyr Met Asn Trp Val Arg Gln Ala Pro Gly Lys Gly Leu Glu Trp Val
        35                  40                  45
Ser Val Ile Tyr Gly Ser Gly Arg Thr Asp Ser Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Gly Asp Tyr Gly Met Asp Val Trp Gly Gln Gly Thr Thr Val
            100                 105                 110
Thr Val Ser Ser Ala Ser Thr Lys Gly Pro Ser Val Phe Pro Leu Ala
```

```
                115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 42
<211> LENGTH: 116
<212> TYPE: PRT
<213> ORGANISM: Homo Sapiens

<400> SEQUENCE: 42

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45
```

```
Ser Val Ile Tyr Gly Ser Gly Arg Thr Asp Ser Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Ala Asp Tyr Gly Met Asp Val Trp Gly Gln Gly Thr Thr Val
                100                 105                 110

Thr Val Ser Ser
            115

<210> SEQ ID NO 43
<211> LENGTH: 446
<212> TYPE: PRT
<213> ORGANISM: Homo Sapiens

<400> SEQUENCE: 43

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ile Val Ser Arg Asn
                 20                  25                  30

Tyr Met Asn Trp Val Arg Gln Ala Pro Gly Lys Gly Leu Glu Trp Val
             35                  40                  45

Ser Val Ile Tyr Gly Ser Gly Arg Thr Asp Ser Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Ala Asp Tyr Gly Met Asp Val Trp Gly Gln Gly Thr Thr Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 44
<211> LENGTH: 116
<212> TYPE: PRT
<213> ORGANISM: Homo Sapiens

<400> SEQUENCE: 44

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Asp Tyr Gly Leu Asp Val Trp Gly Gln Gly Thr Thr Val
            100                 105                 110

Thr Val Ser Ser
        115

<210> SEQ ID NO 45
<211> LENGTH: 446
<212> TYPE: PRT
<213> ORGANISM: Homo Sapiens

<400> SEQUENCE: 45

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Ala Asp Tyr Gly Leu Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 46
<211> LENGTH: 115
<212> TYPE: PRT
<213> ORGANISM: Homo Sapiens
```

<400> SEQUENCE: 46

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser
        115

<210> SEQ ID NO 47
<211> LENGTH: 445
<212> TYPE: PRT
<213> ORGANISM: Homo Sapiens

<400> SEQUENCE: 47

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

```
Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 48
<211> LENGTH: 115
<212> TYPE: PRT
<213> ORGANISM: Homo Sapiens

<400> SEQUENCE: 48

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Leu Asp Val Trp Gly Gln Gly Thr Thr Val Thr
            100                 105                 110

Val Ser Ser
        115

<210> SEQ ID NO 49
<211> LENGTH: 445
<212> TYPE: PRT
<213> ORGANISM: Homo Sapiens

<400> SEQUENCE: 49
```

-continued

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Asp Ser Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Thr Tyr Ala Leu Asp Val Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
```

-continued

```
                   420                 425                 430
His Tyr Thr Gln Lys Ser Leu Ser Leu Ser Pro Gly Lys
        435                 440                 445

<210> SEQ ID NO 50
<211> LENGTH: 109
<212> TYPE: PRT
<213> ORGANISM: Homo Sapiens

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Tyr Thr Phe Gly Gln Gly Thr Lys Leu Glu Ile Lys
            100                 105

<210> SEQ ID NO 51
<211> LENGTH: 107
<212> TYPE: PRT
<213> ORGANISM: Homo Sapiens

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 216
<212> TYPE: PRT
<213> ORGANISM: Homo Sapiens

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
             85                  90                  95

Leu Tyr Thr Phe Gly Gln Gly Thr Lys Leu Glu Ile Lys Arg Thr Val
        100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 53
<211> LENGTH: 7
<212> TYPE: PRT
<213> ORGANISM: Homo Sapiens

<400> SEQUENCE: 53

Gln Ser Val Ser Ser Ser Tyr
1               5

<210> SEQ ID NO 54
<211> LENGTH: 3
<212> TYPE: PRT
<213> ORGANISM: Homo Sapiens

<400> SEQUENCE: 54

Gly Ala Ser
1

<210> SEQ ID NO 55
<211> LENGTH: 10
<212> TYPE: PRT
<213> ORGANISM: Homo Sapiens

<400> SEQUENCE: 55

Gln Gln Tyr Gly Ser Ser Pro Leu Tyr Thr
1               5                   10

<210> SEQ ID NO 56
<211> LENGTH: 446
<212> TYPE: PRT
<213> ORGANISM: Homo Sapiens

<400> SEQUENCE: 56

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn

```
                    20                  25                  30
        Tyr Met Asn Trp Val Arg Gln Ala Pro Gly Lys Gly Leu Glu Trp Val
                         35                  40                  45
        Ser Val Ile Tyr Gly Ser Gly Arg Thr Asp Cys Ala Asp Ser Val Lys
         50                  55                  60
        Gly Arg Phe Thr Ile Ser Arg Asp Asn Ser Lys Asn Thr Leu Tyr Leu
         65                  70                  75                  80
        Gln Met Asn Ser Leu Arg Ala Glu Asp Thr Ala Val Tyr Tyr Cys Ala
                         85                  90                  95
        Arg Asp Gly Asp Tyr Gly Met Asp Val Trp Gly Gln Gly Thr Thr Val
                        100                 105                 110
        Thr Val Ser Ser Ala Ser Thr Lys Gly Pro Ser Val Phe Pro Leu Ala
                        115                 120                 125
        Pro Ser Ser Lys Ser Thr Ser Gly Gly Thr Ala Ala Leu Gly Cys Leu
                        130                 135                 140
        Val Lys Asp Tyr Phe Pro Glu Pro Val Thr Val Ser Trp Asn Ser Gly
        145                 150                 155                 160
        Ala Leu Thr Ser Gly Val His Thr Phe Pro Ala Val Leu Gln Ser Ser
                        165                 170                 175
        Gly Leu Tyr Ser Leu Ser Ser Val Val Thr Val Pro Ser Ser Ser Leu
                        180                 185                 190
        Gly Thr Gln Thr Tyr Ile Cys Asn Val Asn His Lys Pro Ser Asn Thr
                        195                 200                 205
        Lys Val Asp Lys Lys Val Glu Pro Lys Ser Cys Asp Lys Thr His Thr
                        210                 215                 220
        Cys Pro Pro Cys Pro Ala Pro Glu Leu Leu Gly Gly Pro Ser Val Phe
        225                 230                 235                 240
        Leu Phe Pro Pro Lys Pro Lys Asp Thr Leu Met Ile Ser Arg Thr Pro
                        245                 250                 255
        Glu Val Thr Cys Val Val Val Asp Val Ser His Glu Asp Pro Glu Val
                        260                 265                 270
        Lys Phe Asn Trp Tyr Val Asp Gly Val Glu Val His Asn Ala Lys Thr
                        275                 280                 285
        Lys Pro Arg Glu Glu Gln Tyr Asn Ser Thr Tyr Arg Val Val Ser Val
                        290                 295                 300
        Leu Thr Val Leu His Gln Asp Trp Leu Asn Gly Lys Glu Tyr Lys Cys
        305                 310                 315                 320
        Lys Val Ser Asn Lys Ala Leu Pro Ala Pro Ile Glu Lys Thr Ile Ser
                        325                 330                 335
        Lys Ala Lys Gly Gln Pro Arg Glu Pro Gln Val Tyr Thr Leu Pro Pro
                        340                 345                 350
        Ser Arg Asp Glu Leu Thr Lys Asn Gln Val Ser Leu Thr Cys Leu Val
                        355                 360                 365
        Lys Gly Phe Tyr Pro Ser Asp Ile Ala Val Glu Trp Glu Ser Asn Gly
                        370                 375                 380
        Gln Pro Glu Asn Asn Tyr Lys Thr Thr Pro Pro Val Leu Asp Ser Asp
        385                 390                 395                 400
        Gly Ser Phe Phe Leu Tyr Ser Lys Leu Thr Val Asp Lys Ser Arg Trp
                        405                 410                 415
        Gln Gln Gly Asn Val Phe Ser Cys Ser Val Met His Glu Ala Leu His
                        420                 425                 430
        Asn His Tyr Thr Gln Lys Ser Leu Ser Leu Ser Pro Gly Lys
                        435                 440                 445
```

<210> SEQ ID NO 57
<211> LENGTH: 326
<212> TYPE: PRT
<213> ORGANISM: Homo Sapiens

<400> SEQUENCE: 57

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 58
<211> LENGTH: 327
<212> TYPE: PRT
<213> ORGANISM: Homo Sapiens

<400> SEQUENCE: 58

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 59
<211> LENGTH: 282
<212> TYPE: PRT
<213> ORGANISM: Homo sapiens

<400> SEQUENCE: 59

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
```

-continued

```
                35                  40                  45
Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 60
<211> LENGTH: 115
<212> TYPE: PRT
<213> ORGANISM: Homo sapiens

<400> SEQUENCE: 60

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Asn Trp Val Arg Gln Ala Pro Gly Lys Gly Leu Glu Trp Val
         35                  40                  45

Ser Val Ile Tyr Gly Ser Gly Arg Thr Tyr Tyr Ala Asp Ser Val Lys
     50                  55                  60

Gly Arg Val Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Ala Met Asp Val Trp Gly Gln Gly Thr Thr Val Thr
            100                 105                 110

Val Ser Ser
        115
```

```
<210> SEQ ID NO 61
<211> LENGTH: 330
<212> TYPE: PRT
<213> ORGANISM: Homo sapiens

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

B7H4-TARGETED ANTIBODY-DRUG CONJUGATES AND METHODS OF USE THEREOF

RELATED APPLICATIONS

This application claims priority to, and the benefit of, U.S. Provisional Application No. 63/133,707 filed Jan. 4, 2021 and U.S. Provisional Application No. 63/172,968 filed Apr. 9, 2021. The contents of each of these applications are hereby incorporated by reference in their entireties.

INCORPORATION BY REFERENCE OF SEQUENCE LISTING

The contents of the text file named "MRSN-034_001US_SeqList.txt", which was created on Dec. 14, 2023 and is 123,978 bytes in size, are hereby incorporated by reference in their entirety.

BACKGROUND

B7-H4, also known as B7-H4, B7x, B7S1, B7-S1, and VTCN1, is a Type I transmembrane protein and is a member of the B7 superfamily of proteins that provides co-signal in conjunction with a T-cell receptor antigenic signal. B7-H4 is a negative regulator of T-cell function and ligation of T-cells inhibits their growth, cytokine secretion and cytotoxicity. Elimination of B7-H4 in mice does not affect immune cell homeostasis and no signs of autoimmunity. The receptor for B7-H4 is unknown and unidentified.

Human B7-H4 has been mapped on chromosome 1 and is comprised of six exons and five introns spanning 66 kb, of which exon 6 is used for alternative splicing to generate two different transcripts. It is a 282 amino acid protein (including the amino-terminal signal sequence), of which –227 amino acids are predicted to be in the extracellular space following cleavage of the amino-terminal signal sequence. B7-H4 comprises an Ig-like V-domain, an Ig-like C domain, a transmembrane domain and a short cytoplasmic tail.

While B7-H4 expression in healthy tissues is relatively limited at the protein level, B7-H4 is consistently overexpressed in several solid tumors such as gynecological carcinomas of the breast, ovary, and endometrium. Expression of B7-H4 in tumors tends to correlate with poor prognosis. The receptor for B7-H4 is unknown, but it is believed to be expressed on T cells. B7-H4 is believed to directly inhibit T cell activity.

A wide variety of therapeutic modalities are available for the treatment of advanced cancers including radiotherapy, conventional chemotherapy with cytotoxic antitumor agents, hormone therapy (aromatase inhibitors, luteinizing-hormone releasing-hormone analogues), bisphosphonates and signal-transduction inhibitors. Unfortunately, however, many patients either respond poorly or not at all to any of these therapeutic modalities. Thus, there is a need to identify new therapeutic agents that target the biological activities of B7-H4.

Accordingly, there exists a need for therapies that target the biological activities of B7-H4.

SUMMARY OF THE INVENTION

In some aspects, the disclosure provides an isolated antibody that specifically binds B7-H4 comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55).

In some aspects, the isolated antibody comprises a heavy chain variable sequence comprising the amino acid sequence of SEQ ID NO: 44 and a light chain variable sequence comprising the amino acid sequence of SEQ ID NO: 50. In some aspects, the isolated antibody comprises a heavy chain comprising the amino acid sequence of SEQ ID NO: 45 and a light chain comprising the amino acid sequence of SEQ ID NO: 52. In some aspects, the isolated antibody comprises a heavy chain variable sequence comprising the amino acid sequence of SEQ ID NO: 22 and a light chain variable sequence comprising the amino acid sequence of SEQ ID NO: 50. In some aspects, the isolated antibody comprises a heavy chain comprising the amino acid sequence of SEQ ID NO: 23 and a light chain comprising the amino acid sequence of SEQ ID NO: 52.

In some aspects, the isolated antibody is a monoclonal antibody. In some aspects, the isolated antibody is a rabbit, mouse, chimeric, humanized or fully human monoclonal antibody. In some aspects, the isolated antibody is an IgG isotype. In some aspects, the isolated antibody is an IgG1 isotype.

In some aspects, the isolated antibody competes for specific binding to human B7-H4 with an isolated antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55). In some aspects, the isolated antibody competes for specific binding to human B7-H4 with an isolated antibody comprising a heavy chain variable sequence comprising the amino acid sequence of SEQ ID NO: 44 and a light chain variable sequence comprising the amino acid sequence of SEQ ID NO: 50 or with an isolated antibody comprising a heavy chain comprising the amino acid sequence of SEQ ID NO: 45 and a light chain comprising the amino acid sequence of SEQ ID NO: 52.

In some aspects, the disclosure provides a B7-H4 antibody-drug conjugate comprising an isolated antibody of the disclosure.

In some aspects, one or more Linker-Drug moieties covalently linked to the targeting moiety, wherein: each Linker-Drug moiety comprises a Multifunctional Linker that connects the targeting moiety to one or more Drug Units (e.g., one or more therapeutic agents (D)) through intermediacy of a Releasable Assembly Unit for each Drug Unit, and connects a hydrophilic group to the Drug Units of each Linker-Drug moiety; the Releasable Assembly unit is capable of releasing free drug in proximity to a target site targeted by the targeting moiety; and the Multifunctional Linker comprises a peptide moiety between the targeting moiety and the hydrophilic group, wherein the peptide moiety comprises at least two amino acids.

In some aspects, the disclosure provides a conjugate selected from any one of the conjugates of Table A1 and Table A2.

In some aspects, the disclosure provides a conjugate selected from any one of the conjugates of Table B1 and Table B2.

In some aspects, the disclosure provides a method of treating or preventing a disease or disorder in a subject in need thereof, comprising administering to the subject a therapeutically effective amount of a conjugate of the disclosure.

In some aspects, the disclosure provides a conjugate, for use in treating or preventing a disease or disorder in a subject in need thereof.

In some aspects, the disclosure provides a use of a conjugate of the disclosure in the manufacture of a medicament for treating a disease or disorder in a subject in need thereof. In some aspects, the disclosure provides a use of a conjugate of the disclosure for the treatment or prevention of a disease or disorder in a subject in need thereof.

In some aspects, the method, conjugate, or use of any one the embodiments of the disclosure, said conjugate releases one or more therapeutic agents upon biodegradation.

In some aspects, the method, conjugate, or use of any one the embodiments of the disclosure, the disease or disorder is cancer. In some aspects, the method, conjugate, or use of any one the embodiments of the disclosure, the cancer is a B7-H4 positive cancer.

In some aspects, the method, conjugate, or use of any one the embodiments of the disclosure, the B7-H4 positive cancer is selected from the group consisting of bile duct carcinoma, breast cancer, endometrial cancer, ovarian cancer, non-small cell lung cancer, small cell lung cancer, uterine cancer, thyroid cancer, kidney cancer, head and neck cancer, gastric cancer, melanoma, bile duct carcinoma, cholangial carcinoma, pancreatic cancer, colon cancer and bladder cancer.

In some aspects, the subject is human.

In some aspects, the disclosure further comprises administration of a therapeutic agent to the subject.

DETAILED DESCRIPTION

Figure 1:
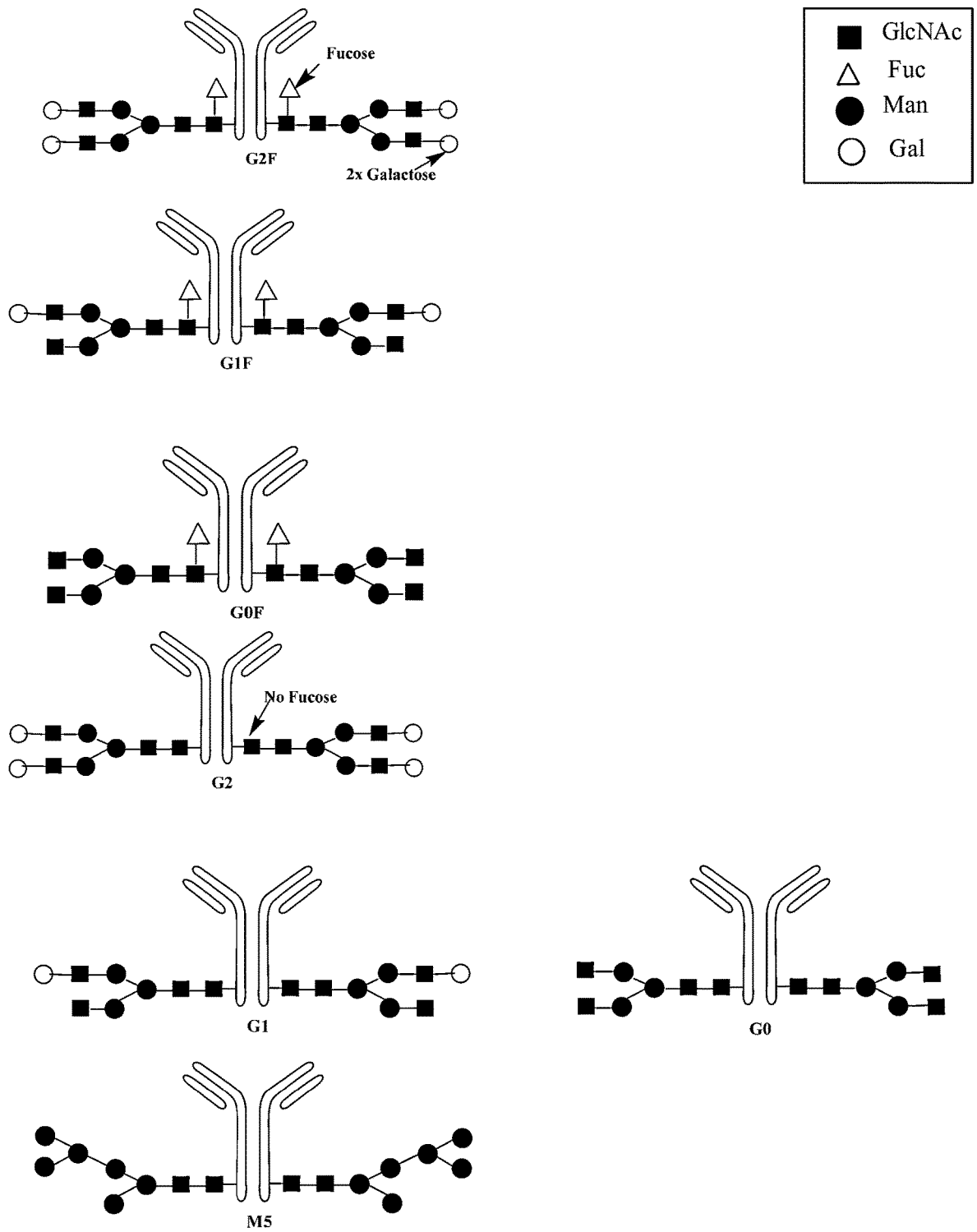
FIG. 1 is a graph showing different glycoforms of antibody glycan (G0, G1, G2, G0F, G1F, G2F, and M5).

The present invention provides monoclonal antibodies that specifically bind the human B7-H4 in soluble form, or membrane bound (i.e., when expressed on a cell surface).

The invention further provides monoclonal antibodies that specifically bind B7-H4. These antibodies are collectively referred to herein as "B7-H4" antibodies.

Definitions

The chemical names provided for the intermediate compounds and/or the compounds of this disclosure described herein may refer to any one of the tautomeric representations of such compounds (in some instances, such alternate names are provided with the experimental). It is to be understood that any reference to a named compound (an intermediate compound or a compound of the disclosure) or a structurally depicted compound (an intermediate compound or a compound of the disclosure) is intended to encompass all tautomeric forms including zwitterionic forms of such compounds and any mixture thereof.

It is to be understood that the terms "In some embodiments", "In some embodiments of the present disclosure", and "In some embodiments of a compound of the present disclosure" may be used interchangeably where appropriate.

The term "about", "approximately", or "approximate", when used in connection with a numerical value, means that a collection or range of values is included. In some embodiments, "about X" includes a range of values that are ±25%, ±20%, ±15%, ±10%, ±5%, ±2%, %, ±0.5%, ±0.2%, or ±0.1% of X, where X is a numerical value. In some embodiments, the term "about" refers to a range of values which are 5% more or less than the specified value. In some embodiments, the term "about" refers to a range of values which are 2% more or less than the specified value. In some embodiments, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. In some embodiments, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

As utilized in accordance with the present disclosure, the following terms, unless otherwise indicated, shall be understood to have the following meanings:

As used herein, the terms "anti-B7-H4 antibody", "B7-H4 antibody" and "an antibody that binds to B7-H4" refer to an antibody that is capable of binding B7-H4 with sufficient affinity such that the antibody is useful as a diagnostic and/or therapeutic agent in targeting B7-H4.

The term "B7-H4," as used herein, refers to any native, mature B7-H4 which results from processing of a B7-H4 precursor protein in a cell. The term includes B7-H4 from any vertebrate source, including mammals such as primates (e.g. humans and cynomolgus monkeys) and rodents (e.g., mice and rats), unless otherwise indicated. The term also includes naturally occurring variants of B7-H4, e.g., splice variants or allelic variants.

The term "B7-H4-positive cancer" refers to a cancer comprising cells that express B7-H4 on their surface. In some embodiments, expression of B7-H4 on the cell surface is determined, for example, using antibodies to B7-H4 in a method such as immunohistochemistry, FACS, etc.

Alternatively, B7-H4 mRNA expression is considered to correlate to B7-H4 expression on the cell surface and can be determined by a method selected from in situ hybridization and RT-PCR (including quantitative RT-PCR).

The term "B7-H4-positive cell" refers to a cell that expresses B7-H4 on its surface.

The term "antibody" as used herein, is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Various methods are known in the art for numbering the amino acids sequences of antibodies and identification of the complementary determining regions. For example, the Kabat numbering system (See Kabat, E. A., et al., Sequences of Protein of immunological interest, Fifth Edition, US Department of Health and Human Services, US Government Printing Office (1991)) or the IMGT numbering system (See IMGT®, the international ImMunoGeneTics information System®. Available online. http://www.imgt.org/). The IMGT numbering system is routinely used and accepted as a reliable and accurate system in the art to determine amino acid positions in coding sequences, alignment of alleles, and to easily compare sequences in immunoglobulin (IG) and T-cell receptor (TR) from all vertebrate species. The accuracy and the consistency of the IMGT data are based on IMGT-ONTOLOGY, the first, and so far unique, ontology for immunogenetics and immunoinformatics (See Lefranc. M. P. et al., Biomolecules, 2014 December; 4(4), 1102-1139). IMGT tools and databases run against IMGT reference directories built from a large repository of sequences. In the IMGT system the IG V-DOMAIN and IG C-DOMAIN are delimited taking into account the exon delimitation, whenever appropriate. Therefore, the availability of more sequences to the IMGT database, the IMGT exon numbering system can be and "is used" by those skilled in the art reliably to determine amino acid positions in coding sequences and for alignment of alleles. Additionally, correspondences between the IMGT unique numbering with other numberings (i.e., Kabat) are available in the IMGT Scientific chart (See Lefranc. M. P. et al., Biomolecules, 2014 December; 4(4), 1102-1139).

The term "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "antibody that binds to the same epitope" as a reference antibody as used herein, refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgGi, IgG2, IgG3, IgG4, IgAi, and IgA2. The heavy chain constant domains that correspond to the different classes of immunoglobulins are called α, δ, ε, γ, and μ, respectively.

The term "monoclonal antibody" as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term a "naked antibody" refers to an antibody that is not conjugated to a heterologous moiety (e.g., a cytotoxic moiety or STING agonist drug moiety). The naked antibody may be present in a pharmaceutical formulation.

The term "native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3). Similarly, from— to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

The term "epitope" refers to the particular site on an antigen molecule to which an antibody binds.

The term "humanized antibody" of an antibody refers to an antibody that is derived from a non-human antibody (e.g., murine) that retains or substantially retains the antigen-binding properties of the parent antibody but is less immunogenic in humans. Humanized as used herein is intended to include deimmunized antibodies.

The term "humanized form" of an antibody, e.g., a non-human antibody, refers to an antibody that has undergone humanization.

The term "competes with" or "cross-competes with" when used herein in the context of two or more antibodies, indicates that the two or more antibodies compete for binding to B7-H4, e.g., compete for B7-H4 binding. An antibody "blocks" or "cross-blocks" one or more other antibodies from binding to B7-H4 if the antibody competes with the one or more other antibodies 25% or more, with 25%-74% representing "partial block" and 75%-400% representing "full block". Unless otherwise defined or negated by context, the terms "competes with", "cross-competes with", "blocks" or "cross-blocks" when used herein is also intended to cover such pairs of antibodies.

As used herein, an antibody that "specifically binds to human B7-H4" is intended to refer to an antibody that binds to human B7-H4 with a $K_D$ of $1 \times 10^{-7}$ or less, more typically $5 \times 10^{-8}$ M or less, more typically $3 \times 10^{-8}$ M or less, more typically $1 \times 10^{-9}$ M or less, even more typically $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-8}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "cytotoxic agents" or "cytotoxic drug moiety" refer to compounds which cause cell death primarily by interfering directly with the cell's functioning or inhibit or interfere with cell myosis, including, but not limited to, alkylating agents, tumor necrosis factors, intercalators, microtubulin inhibitors, and topoisomerase inhibitors.

The term "STING agonist", as used herein, refers to a compound or moiety which is capable of interacting with STING, e.g., by binding to STING and/or inducing downstream signal transduction (e.g., characterized by activation of the molecules associated with STING function).

This includes direct phosphorylation of STING, IRF3 and/or NF-kB and could also include STAT6. In some embodiments, STING pathway activation results in increased production of type 1 interferons (mainly IFN-α and IFN-b) and/or expression of interferon-stimulated genes.

The term "STING agonist drug moiety", as used herein, refers to a moiety derived from a STING agonist and capable of interacting with STING. In some embodiments, the STING agonist drug moiety is a STING agonist that is modified to allow for the moiety to be linked to the rest of a conjugate of the present disclosure.

The term "sugar" refers to a monosaccharide, for example glucose (Glc), galactose (Gal), mannose (Man) and fucose (Fuc). The term "sugar derivative" refers to a derivative of a monosaccharide sugar, i.e. a monosaccharide sugar comprising substituents and/or functional groups. Examples of a sugar derivative include, but are not limited to, amino sugars and sugar acids. Examples of a sugar derivative also include compounds denoted as $S'(F')_{x1}$, wherein S' is a sugar or a sugar derivative, F' is a functional group and xi indicates the number of functional groups.

The term "core-GlcNAc moiety", as used herein, refers to a monosaccharide, polysaccharide, or oligosaccharide moiety comprising a GlcNAc (e.g., a core-GlcNAc) which is attached to an antibody (e.g., via the C1 position of the GlcNAc). In some embodiments, the GlcNAc is attached to the antibody via an N-glycosidic bond to the amide nitrogen atom in the side chain of an asparagine amino acid of the antibody. In some embodiments, the core-GlcNAc moiety is present at a native glycosylation site of an antibody or is introduced on a different site on the antibody. In some embodiments, the core-GlcNAc moiety is a monosaccharide (e.g., the core-GlcNAc moiety is also a terminal-GlcNAc moiety). In some embodiments, the core-GlcNAc moiety further comprises a fucose, e.g., the core-GlcNAc moiety is a disaccharide core-GlcNAc-(α1-6-Fuc) moiety (which may be referred to as GlcNAc(Fuc)). Thus, when antibody comprises a core-GlcNAc moiety, the antibody may comprise a monosaccharide or a disaccharide core-GlcNAc moiety, and the core-GlcNAc moiety may further comprise a fucose (e.g., a disaccharide core-GlcNAc(Fuc) moiety). If the core-GlcNAc moiety further comprises a fucose, the fucose may be linked α-1,6 to O-6 of the core-GlcNAc moiety. A core-GlcNAc moiety further comprising a fucose may be referred to as core-GlcNAc(Fuc).

The term "core-GlcNAc" refers to the inner GlcNAc that is a portion of a polysaccharide or oligosaccharide, wherein the polysaccharide or oligosaccharide is attached to an antibody via the inner GlcNAc.

The term "terminal-GlcNAc moiety", as used herein, refers to a moiety comprising a GlcNAc which is attached to an antibody and has a terminal functional group being available for further modification (e.g., with a compound of P"-S"-A"). In some embodiments, the terminal-GlcNAc moiety further comprises a fucose. In some embodiments, the terminal-GlcNAc moiety is formed by reacting the core-GlcNAc moiety of a glycoprotein (e.g., an antibody glycan) with an endoglycosidase.

The term "nucleotide" is used in its normal scientific meaning and refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be referred to as a nucleoside monophosphate, a nucleoside diphosphate or a nucleoside triphosphate. The nucleobase may be adenine, guanine, cytosine, uracil or thymine.

The term "protein" is used in its normal scientific meaning and includes polypeptides comprising about 10 or more amino acids. A protein may comprise natural or unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), to an amide function on the protein (N-glycoprotein), or to a carbon on the protein (C-glycoprotein). A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein.

The term "glycan" is herein used in its normal scientific meaning and refers to a monosaccharide or oligosaccharide chain that is linked to a protein. Glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is also considered a glycan. A glycan of a glycoprotein may be a monosaccharide. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan, or a C-linked glycan. In a delinked glycan, a monosaccharide or oligosaccharide glycan is bonded to a C-atom in an amino acid of the protein.

The term "glycosyltransferase" refers to a superfamily of enzymes that are involved in the synthesis of complex carbohydrates present on glycoproteins and glycolipids.

The term "N-acetylgalactosaminyl transferase" (GalNAc-T) is a N-acetyl-D-galactosamine transferase enzyme that catalyzes the addition of N-acetyl-D-galactosamine to proteins.

The term "PEG unit" is used herein refers to a polyethylene glycol subunit having the formula

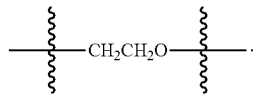

In some embodiments, the PEG unit comprises multiple PEG subunits.

The term "alkyl", as used herein, represents a saturated, straight or branched hydrocarbon group having the specified number of carbon atoms. The term "$C_1$-$C_6$ alkyl" or "$C_{1-6}$ alkyl" refers to a methyl moiety or a straight or branched alkyl moiety comprising from 2 to 6 carbon atoms.

Exemplary alkyls include, but are not limited to methyl, ethyl, n-propyl, isopropyl, n-butyl, isobutyl, s-butyl, t-butyl, pentyl and hexyl.

The term "halo(alkyl)", as used herein, represents a saturated, straight or branched hydrocarbon group having the specified number (n) of carbon atoms and one or more (up to 2n+1) halogen atoms. Examples of "halo($C_{1-4}$ alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

The term "alkenyl", as used herein, refers to straight or branched hydrocarbon group having the specified number of carbon atoms and at least 1 and up to 3 carbon-carbon double bonds. Examples include ethenyl and propenyl.

The term "alkynyl", as used herein, refers to straight or branched hydrocarbon group having the specified number of carbon atoms and at least 1 and up to 3 carbon-carbon triple bonds. Examples include ethynyl and propynyl.

The term "alkoxy-" or "(alkyl)oxy-", as used herein, refers to an "alkyl-oxy-" group, comprising an alkyl moiety, having the specified number of carbon atoms, attached through an oxygen linking atom. Exemplary "$C_{1-4}$ alkoxy-" or "($C_{1-4}$ alkyl)oxy-" groups include, but are not limited to, methoxy, ethoxy, n-propoxy, isopropoxy, n-butoxy, s-butoxy, and t-butoxy.

The term "halo(alkoxy)-", as used herein, represents a saturated, straight or branched hydrocarbon group having the specified number (n) of carbon atoms and one or more (up to 2n+1) halogen atoms, attached through an oxygen linking atom. Exemplary "halo($C_{1-4}$ alkoxy)-" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

The term "amino" as used herein refers to a substituent comprising at least one nitrogen atom. Specifically, —$NH_2$, —$NH(C_{1-4}$ alkyl), alkylamino, or ($C_{1-4}$ alkyl)amino- or ($C_{1-4}$ alkyl)($C_{1-4}$ alkyl)amino- or dialkylamino, amide-, carbamide-, urea, and sulfamide substituents are included in the term "amino".

The term "carbocyclic group or moiety" as used herein, refers to a cyclic group or moiety in which the ring members are carbon atoms, which may be saturated, partially unsaturated (non-aromatic) or fully unsaturated (aromatic).

The term "cycloalkyl", as used herein, refers to a non-aromatic, saturated, hydrocarbon ring group comprising the specified number of carbon atoms in the ring. For example, the term "$C_{3-6}$ cycloalkyl" refers to a cyclic group having from three to six ring carbon atoms. Exemplary "$C_{3-6}$ cycloalkyl" groups include cyclopropyl, cyclobutyl, cyclopentyl, and cyclohexyl.

The term "aryl", as used herein, refers to a group with aromaticity, including "conjugated" or multicyclic systems with one or more aromatic rings, which does not contain any heteroatom in the ring structure. The term aryl includes both monovalent species and divalent species. Examples of aryl groups include, but are not limited to, phenyl, biphenyl, naphthyl and the like. In some embodiments, an aryl is phenyl.

The term "heterocyclic group or moiety", as used herein, refers to a cyclic group or moiety having, as ring members, atoms of at least two different elements, which cyclic group or moiety may be saturated, partially unsaturated (non-aromatic) or fully unsaturated (aromatic).

The term "heteroatom", as used herein, refers to a nitrogen, sulfur, or oxygen atom, for example a nitrogen atom or an oxygen atom.

The term "heterocycloalkyl", as used herein, refers to a non-aromatic, monocyclic or bicyclic group comprising 3-10 ring atoms and comprising one or more (generally one or two) heteroatom ring members independently selected from oxygen, sulfur, and nitrogen. The point of attachment of a heterocycloalkyl group may be by any suitable carbon or nitrogen atom.

The term "heteroaryl", as used herein, refers to an aromatic monocyclic or bicyclic group comprising 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups comprising either a phenyl ring fused to a heterocyclic moiety or a heteroaryl ring moiety fused to a carbocyclic moiety. The point of attachment of a heteroaryl group may be by any suitable carbon or nitrogen atom.

The terms "halogen" and "halo", as used herein, refers to a halogen radical, for example, a fluoro, chloro, bromo, or iodo substituent.

The term "oxo", as used herein, refers to a double-bonded oxygen moiety; for example, if attached directly to a carbon atom forms a carbonyl moiety (C═O).

The term "hydroxy" or "hydroxyl", as used herein, is intended to mean the radical —OH.

The term "cyano", as used herein, refers to a nitrile group, —C≡N.

The term "optionally substituted", as used herein, indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s). In the case where groups may be selected from a number of alternative groups, the selected groups may be the same or different. Suitable substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "independently", as used herein, means that where more than one substituent is selected from a number of possible substituents, those substituents may be the same or different.

The term "pharmaceutically acceptable", as used herein, refers to those compounds, conjugates, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "preventing," "prevent," or "protecting against" describes reducing or eliminating the onset of the symptoms or complications of such disease, condition or disorder.

The term "subject" refers to an animal, preferably a mammal, most preferably a human, who has been the object of treatment, observation or experiment.

The term "therapeutically effective amount" refers to an amount of an active compound or pharmaceutical agent, including a conjugate of the disclosure, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

A therapeutically "effective amount" is intended to mean that amount of a conjugate that, when administered to a patient in need of such treatment, is sufficient to effective treat or prevent, as defined herein. The amount of a given conjugate that will correspond to such an amount will vary depending upon factors such as the particular conjugate (e.g., the potency (pIC$_{50}$), efficacy (EC$_{50}$), and the biological half-life of the particular conjugate), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the conjugate will vary according to the identity of the mammal in need of treatment (e.g., weight), the particular conjugate and its properties (e.g., pharmacokinetic properties), disease or disorder and its severity and the specific composition and method being used, but can nevertheless be determined by one of skill in the art.

The term "composition" refers to a product that includes the specified ingredients in therapeutically effective amounts, as well as any product that results, directly, or indirectly, from combinations of the specified ingredients in the specified amounts.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

In some embodiments, conjugates of the disclosure, or an enantiomer, diastereomer, solvate or pharmaceutically acceptable salt form thereof are useful for treating or ameliorating diseases, syndromes, conditions, or disorders such as melanoma, colon cancer, breast cancer, prostate cancer, lung cancer, fibrosarcoma, and hepatitis B.

The terms "conjugate(s) of the disclosure" or "conjugate(s) of the present disclosure", as used herein, mean a conjugate as defined herein, in any form, i.e., any tautomeric form, any isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present disclosure are the conjugates as disclosure herein, in any salt or non-salt form and any physical form thereof, and mixtures of various forms. While such are included within the present disclosure, it will be understood that the conjugates of the present disclosure, in any salt or non-salt form, and in any physical form thereof, may have varying levels of activity, different bioavailabilities and different handling properties for formulation purposes.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

When used herein in the context of two or more antibodies, the term "competes with" or "cross-competes with" indicates that the two or more antibodies compete for binding to B7-H4, e.g., compete for B7-H4 binding in the assay described in Examples 5 or 8. An antibody "blocks" or "cross-blocks" one or more other antibodies from binding to B7-H4 if the antibody competes with the one or more other antibodies 25% or more, with 25%-74% representing "partial block" and 75%-400% representing "full block", preferably as determined using the assay of Examples 5 and 8. For some pairs of antibodies, competition or blocking in the assay of the Examples 5 or 8 is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

Antibody-Drug Conjugates and Scaffolds

In some aspects, the present disclosure provides an B7-H4 antibody-drug conjugate. In some embodiments, the B7-H4 antibody-drug conjugate is with site-specificity. In some embodiments, the B7-H4 antibody-drug conjugate is without site-specificity. In some embodiments, the B7-H4 antibody-drug conjugate is biodegradable and biocompatible, and/or exhibits high drug load and strong binding to a target antigen.

In some embodiments, the present disclosure provides a B7-H4 antibody-drug conjugate, comprising a B7-H4 targeting moiety (e.g., an antibody) and one or more Linker-Drug moieties, wherein the targeting moiety is covalently linked to the one or more Linker-Drug moieties.

In some embodiments, the B7-H4 targeting moiety is an antibody, a cysteine engineered antibody, or a modified antibody.

In some embodiments, the B7-H4 targeting moiety is a B7-H4 antibody, a cysteine engineered B7-H4 antibody, or a modified B7-H4 antibody.

In some embodiments, the B7-H4 targeting moiety is a B7-H4 antibody.

In some embodiments, the B7-H4 targeting moiety is a cysteine engineered B7-H4 antibody.

In some embodiments, the B7-H4 targeting moiety is a modified B7-H4 antibody.

In some aspects, the present disclosure provides a B7-H4 antibody-drug conjugate, comprising a B7-H4 targeting moiety (e.g., an antibody) and one or more Linker-Drug moieties covalently linked to the targeting moiety, wherein:

each Linker-Drug moiety comprises a Multifunctional Linker that connects the targeting moiety to one or more Drug Units (e.g., one or more therapeutic agents (D)) through intermediacy of a Releasable Assembly Unit for each Drug Unit, and connects a hydrophilic group to the Drug Units of each Linker-Drug moiety;

the Releasable Assembly unit is capable of releasing free drug in proximity to a target site targeted by the targeting moiety; and the Multifunctional Linker comprises a peptide moiety between the targeting moiety and the hydrophilic group, wherein the peptide moiety comprises at least two amino acids.

In some aspects, the present disclosure provides a B7-H4 antibody-drug conjugate, comprising a B7-H4 targeting moiety (e.g., an antibody) and one or more Linker-Drug moieties covalently linked to the targeting moiety, wherein:

each Linker-Drug moiety comprises a Multifunctional Linker that connects the B7-H4 targeting moiety to one or more Drug Units (e.g., one or more therapeutic agents (D)) through intermediacy of a Releasable Assembly Unit for each Drug Unit, and connects a hydrophilic group to the Drug Units of each Linker-Drug moiety; and the Releasable Assembly unit is capable of releasing free drug in proximity to a target site targeted by the targeting moiety.

In some aspects, the present disclosure provides a B7-H4 antibody-drug conjugate of Formula (I'):

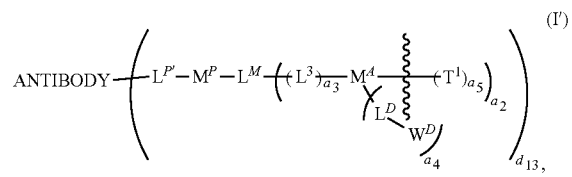

wherein
- $a_2$ is an integer from 1 to 3;
- $a_3$ is an integer from 0 to 1;
- $a_4$ is an integer from 1 to about 5;
- $a_5$ is an integer from 1 to 3;
- $d_{13}$ is an integer from 1 to about 12;
- ANTIBODY is a B7-H4 antibody, a cysteine engineered B7-H4 antibody, or a modified B7-H4 antibody;
- $L^{P'}$ is a divalent linker moiety connecting the modified antibody to $M^P$; of which the corresponding monovalent moiety $L^P$ comprises a functional group $W^P$ that is capable of forming a covalent bond with a reactive moiety of the antibody;
- $M^P$ is a Stretcher unit;
- $L^M$ is a bond, or a trivalent or tetravalent linker, and when $L^M$ is a bond, $a_2$ is 1, when $L^M$ is trivalent linker, $a_2$ is 2, or when $L^M$ is a tetravalent linker, $a_2$ is 3;
- $L^3$, when present, is a carbonyl-containing moiety;
- $M^4$ comprises a peptide moiety that comprises at least two amino acids;
- $T^1$ comprises a hydrophilic group and the

between $T^1$ and $M^4$ denotes direct or indirect attachment of $T^1$ and $M^4$;

each occurrence of D independently is a therapeutic agent having a molecular weight ≤about 5 kDa; and each occurrence of $L^D$ independently is a divalent linker moiety connecting D to $M^4$ and comprises at least one cleavable bond such that when the bond is broken, D is released in an active form for its intended therapeutic effect.

In some embodiment, D is a cytotoxic drug moiety or a STING agonist drug moiety.

In some embodiment, D is a cytotoxic drug moiety.

In some embodiment, D is a STING agonist drug moiety.

In some embodiments, the antibody-drug conjugate is of Formula (II') or (III'):

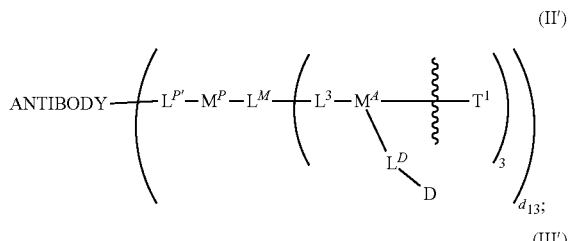

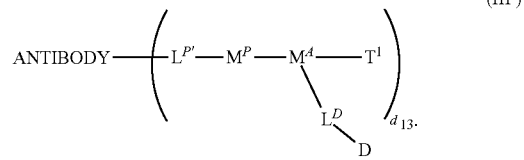

In some aspects, the present disclosure provides a B7-H4 antibody scaffold, comprising a B7-H4 targeting moiety (e.g., an antibody) and one or more Linker moieties covalently linked to the B7-H4 targeting moiety.

In some embodiments, the present disclosure provides a B7-H4 antibody scaffold of any one of Formulae (II)-(V):

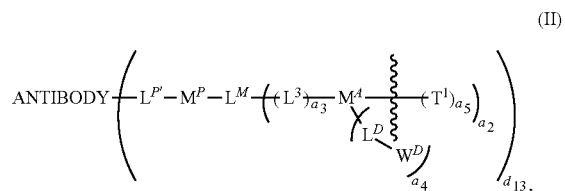

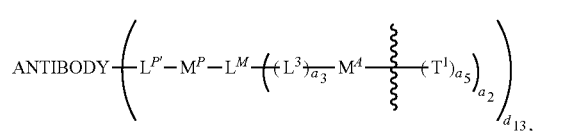

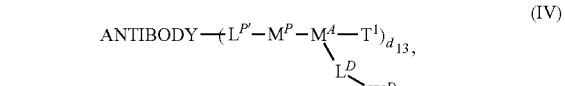

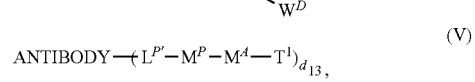

wherein:
- $a_2$ is an integer from 1 to 3;
- $a_3$, when present, is an integer from 0 to 1;
- $a_4$ is an integer from 1 to about 5;
- $a_5$ is an integer from 1 to 3;
- $d_{13}$ is an integer from 1 to about 12;
- ANTIBODY is a B7-H4 antibody, a cysteine engineered B7-H4 antibody, or a modified B7-H4 antibody;

$L^{P'}$ is a divalent linker moiety connecting the antibody to $M^P$; of which the corresponding monovalent moiety $L^P$ comprises a functional group $W^P$ that is capable of forming a covalent bond with a functional group of the antibody;

$M^P$ is a Stretcher unit;

$L^M$, when present, is a bond, or a trivalent or tetravalent linker, and when $L^M$ is a bond, $a_2$ is 1, when $L^M$ is trivalent linker, $a_2$ is 2, or when $L^M$ is a tetravalent linker, $a_2$ is 3;

$L^3$, when present, is a carbonyl-containing moiety;

$M^4$ comprises a peptide moiety that comprises at least two amino acids;

$T^1$ comprises a hydrophilic group and the

between $T^1$ and $M^4$ denotes direct or indirect attachment of $T^1$ and $M^4$;

each occurrence of $W^D$, when present, independently is a functional group that is capable of forming a covalent bond with a functional group of a therapeutic agent ("D") having a molecular weight ≤about 5 kDa; and each occurrence of $L^D$ independently is a divalent linker moiety connecting $W^D$ or D to $M^4$ and $L^D$ comprises at least one cleavable bond such that when the bond is broken, D is released in an active form for its intended therapeutic effect.

The conjugates and scaffolds of the disclosure can include one or more of the following features when applicable.

In some embodiments, $d_{13}$ is an integer from 2 to 12, from 2 to 10, from 2 to 8, from 2 to 6, from 2 to 4, from 1 to 2, from 4 to 10, from 4 to 8, from 4 to 6, from 6 to 12, from 6 to 10, from 6 to 8, from 8 to 14, from 8 to 12, or from 8 to 10.

In some embodiments, $d_{13}$ is an integer ranging from 1 to 2 (e.g., $d_{13}$ is 1 or 2). In some embodiments, $d_{13}$ is an integer ranging from 2 to 4 (e.g., $d_{13}$ is 2, 3, or 4). In some embodiments, $d_{13}$ is an integer ranging from 4 to 6 (e.g., $d_{13}$ is 4, 5, or 6). In some embodiments, $d_{13}$ is an integer ranging from 6 to 8 (e.g., $d_{13}$ is 6, 7, or 8). In some embodiments, $d_{13}$ is an integer ranging from 6 to 10 (e.g., $d_{13}$ is 6, 7, 8, 9, or 10). In some embodiments, $d_{13}$ is 6. In some embodiments, $d_{13}$ is 7.

In some embodiments, $d_{13}$ is 8. In some embodiments, $d_{13}$ is 1 or 2. In some embodiments, $d_{13}$ is 1. In some embodiments, $d_{13}$ is 2.

In some embodiments, $L^3$ is absent.

In some embodiments, each $L^3$, when present, independently is *—$C_{1-12}$ alkyl-C(O)—**, *—NH—$C_{1-12}$ alkyl-C(O)—**, or *—$C_{1-12}$ alkyl-C(O)—NH—$C_{1-12}$ alkyl-C(O)—**, wherein * indicates attachment to another $L^3$ when present, or to $L^M$; and ** indicates attachment to another $L^3$ when present, or to $M^4$.

In some embodiments, at least one $L^3$ is *—$CH_2CH_2$—C(O)—** or is *—NH—$CH_2CH_2$—C(O)—** wherein * indicates attachment to another $L^3$ when present, or to $L^M$; and ** indicates attachment to another $L^3$ when present, or to $M^4$.

In some embodiments, $a_3$ is 2 or greater, at least one $L^3$ is *—$C_{1-12}$ alkyl-C(O)—**, and at least one $L^3$ is *—NH—$C_{1-12}$ alkyl-C(O)—**.

In some embodiments, each $L^3$ is *—$CH_2CH_2$—C(O)—NH—$CH_2CH_2$—C(O)—** or *NH—$CH_2CH_2$—C(O)—$CH_2CH_2$—C(O)—**, wherein * indicates attachment to $L^M$; and ** indicates attachment to $M^4$.

In some embodiments, $a_4$ is 1. In some embodiments, $a_4$ is 2. In some embodiments, $a_4$ is 3.

Variable $L^P$ and $L^{P'}$ for Conjugation to the B7-H4 Antibody or Cysteine Engineered B7-H4 Antibody In some embodiments, $L^{P'}$ is a divalent linker moiety. In some embodiments, $L^{P'}$ is a divalent linker moiety connecting the cysteine of the B7-H4 antibody or cysteine engineered B7-H4 antibody to $M^P$. In some embodiments, $L^{P'}$ is a divalent linker moiety connecting the cysteine of the B7-H4 antibody to $M^P$. In some embodiments, $L^{P'}$ is a divalent linker moiety connecting the cysteine engineered B7-H4 antibody to $M^P$.

In some embodiments, $L^P$ is the corresponding monovalent moiety. In some embodiments, $L^P$ is the corresponding monovalent moiety of $L^{P'}$ when not connected to the cysteine of the B7-H4 antibody or the cysteine of the cysteine engineered B7-H4 antibody. In some embodiments, $L^P$ is the corresponding monovalent moiety of $L^{P'}$ when not connected to the cysteine of the B7-H4 antibody. In some embodiments, $L^P$ is the corresponding monovalent moiety of $L^{P'}$ when not connected to the cysteine of the cysteine engineered B7-H4 antibody.

In some embodiments, each $L^P$, when not connected to cysteine of the B7-H4 antibody or cysteine of the cysteine engineered B7-H4 antibody, comprises a terminal group $W^P$.

In some embodiments, $L^P$ comprises a terminal group $W^P$, in which each $W^P$ independently is:

(1)

(2)

(3)
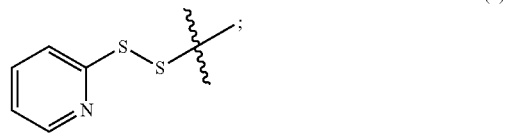

(4)
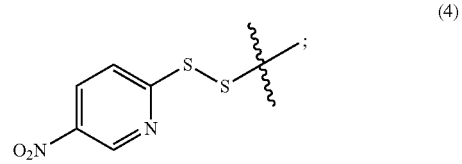

(5)
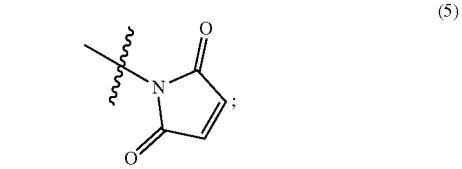

(6)
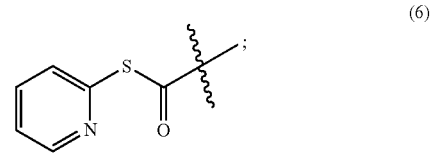

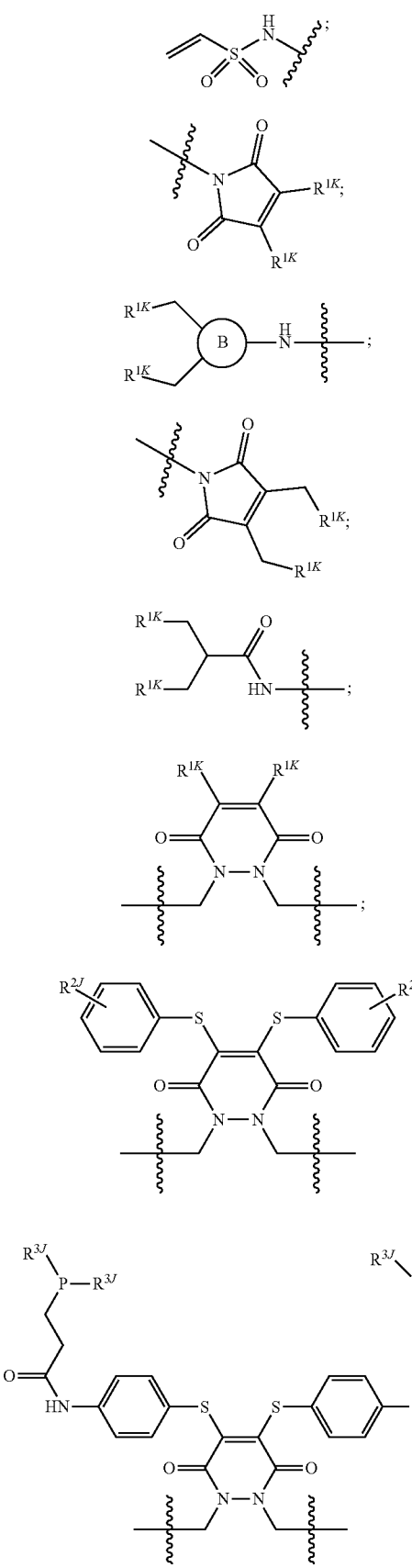

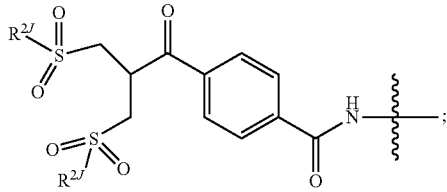

wherein ring B is cycloalkyl, heterocycloalkyl, aryl, or heteroaryl;

$R^{1K}$ is a leaving group;

$R^{1A}$ is a sulfur protecting group;

$R^{2J}$ is hydrogen, an aliphatic, aryl, heteroaliphatic, or carbocyclic moiety; and $R^{3J}$ is $C_{1-6}$ alkyl and each of $Z_1$, $Z_2$, $Z_3$, and $Z_7$ is independently a carbon or nitrogen atom.

In some embodiments, each $R^{1K}$ is halo or RC(O)O—, in which R is hydrogen, an aliphatic, heteroaliphatic, carbocyclic, or heterocycloalkyl moiety.

In some embodiments, each $R^{1A}$ independently is

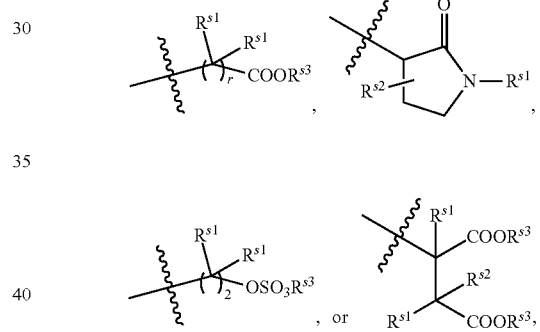

in which r is 1 or 2 and each of $R^{s1}$, $R^{s2}$, and $R^{s3}$ is independently hydrogen, an aliphatic, heteroaliphatic, carbocyclic, or heterocycloalkyl moiety.

In some embodiments, $W^P$ is

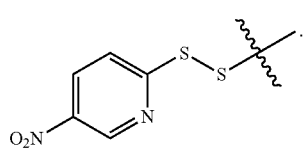 [SMILES: *SSc1ccc([N+](=O)[O-])cn1]

In some embodiments, $W^P$ is

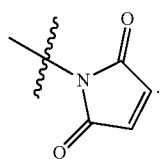 [SMILES: *N1C(=O)C=CC1=O]

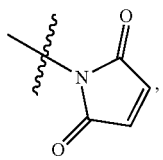 [SMILES: *N1C(=O)C=CC1=O]

wherein L<sup>P'</sup> comprises

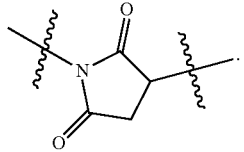 [SMILES: *C1CC(=O)N(*)C1=O]

Variable $L^P$ and $L^{P'}$ for Conjugation to the Modified B7-H4 Antibody

In some embodiments, $L^{P'}$ is formed by the reaction between a functional group (e.g., $W^P$) of $L^P$ and a reactive moiety (e.g., the modified-GlcNAc moiety of *-GlcNAc-S"-A") of the modified antibody.

In some embodiments, $L^{P'}$ comprises a triazolyl formed between the functional group (e.g., $W^P$) of $L^P$ and the reactive moiety (e.g., the modified-GlcNAc moiety of *-GlcNAc-S"-A") of the modified antibody.

In some embodiments, each $L^P$, when not connected to the modified B7-H4 antibody, comprises a terminal group $W^P$.

In some embodiments, at least one $W^P$ is

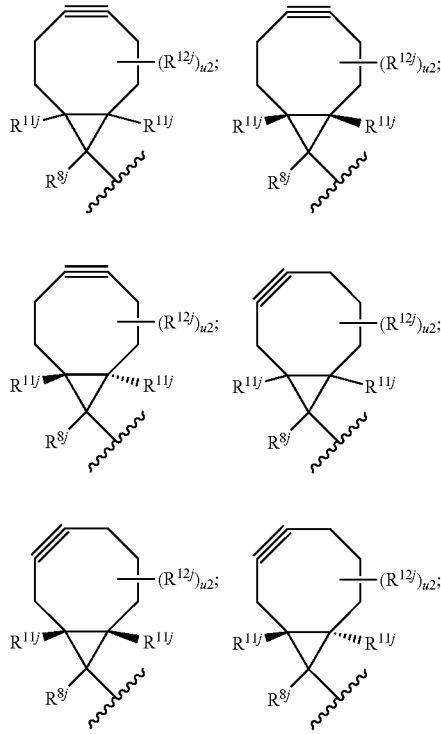

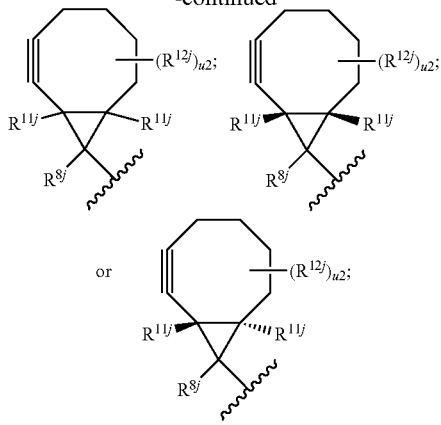

wherein
$R^{8j}$ is hydrogen, halogen, $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, —($C_{1-24}$ alkyl)-($C_{6-24}$ cycloalkyl), —($C_{1-24}$ alkyl)-(6- to 24-membered heterocycloalkyl), —($C_{1-24}$ alkyl)-($C_{6-24}$ aryl), or —($C_{1-24}$ alkyl)-(6- to 24-membered heteroaryl), wherein the $C_{1-24}$ alkyl is optionally interrupted by one of more O, N or S, and wherein the $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, —($C_{1-24}$ alkyl)-($C_{6-24}$ cycloalkyl), —($C_{1-24}$ alkyl)-(6- to 24-membered heterocycloalkyl), —($C_{1-24}$ alkyl)-($C_{6-24}$ aryl), or —($C_{1-24}$ alkyl)-(6- to 24-membered heteroaryl) is optionally substituted with one or more $C_1$-$C_{12}$ alkyl, $C_2$-$C_{12}$ alkenyl, $C_2$-$C_{12}$ alkynyl, $C_3$-$C_{12}$ cycloalkyl, —O($C_1$-$C_{12}$ alkyl), —O($C_2$-$C_{12}$ alkenyl), —O($C_2$-$C_{12}$ alkynyl), —O($C_3$-$C_{12}$ cycloalkyl), halogen, amino, oxo, or silyl, wherein the $C_1$-$C_{12}$ alkyl, $C_2$-$C_{12}$ alkenyl, $C_2$-$C_{12}$ alkynyl, $C_3$-$C_{12}$ cycloalkyl, —O($C_1$-$C_{12}$ alkyl), —O($C_2$-$C_{12}$ alkenyl), —O($C_2$-$C_{12}$ alkynyl), —O($C_3$-$C_{12}$ cycloalkyl) is optionally substituted, and wherein the $C_1$-$C_{12}$ alkyl, $C_3$-$C_{12}$ cycloalkyl, —O($C_1$-$C_{12}$ alkyl), or —O($C_3$-$C_{12}$ cycloalkyl) is optionally interrupted by one one of more O, N, or S;

$R^{10j}$ is hydrogen, halogen, $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, —($C_{1-24}$ alkyl)-($C_{6-24}$ cycloalkyl), —($C_{1-24}$ alkyl)-(6- to 24-membered heterocycloalkyl), —($C_{1-24}$ alkyl)-($C_{6-24}$ aryl), or —($C_{1-24}$ alkyl)-(6- to 24-membered heteroaryl), wherein the $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, —($C_{1-24}$ alkyl)-($C_{6-24}$ cycloalkyl), —($C_{1-24}$ alkyl)-(6- to 24-membered heterocycloalkyl), —($C_{1-24}$ alkyl)-($C_{6-24}$ aryl), or —($C_{1-24}$ alkyl)-(6- to 24-membered heteroaryl) is optionally substituted;

each $R^{11j}$ independently is hydrogen, $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, —($C_{1-24}$ alkyl)-($C_{6-24}$ cycloalkyl), —($C_{1-24}$ alkyl)-(6- to 24-membered heterocycloalkyl), —($C_{1-24}$ alkyl)-($C_{6-24}$ aryl), or —($C_{1-24}$ alkyl)-(6- to 24-membered heteroaryl);

each $R^{12j}$ independently is halogen, $-OR^{10j}$, $-NO_2$, $-CN$, $-S(O)_2R^{10j}$, $C_{1-24}$ alkyl (e.g., $C_{1-6}$ alkyl), $C_{6-24}$ cycloalkyl, 6- to 24-membered heterocycloalkyl, $C_{6-24}$ aryl, 6- to 24-membered heteroaryl, $-(C_{1-24}$ alkyl)-$(C_{6-24}$ cycloalkyl), $-(C_{1-24}$ alkyl)-(6- to 24-membered heterocycloalkyl), $-(C_{1-24}$ alkyl)-$(C_{6-24}$ aryl), or $-(C_{1-24}$ alkyl)-(6- to 24-membered heteroaryl); and $u_2$ is an integer ranging from 0 to 8.

In some embodiments, at least one $W^P$ is

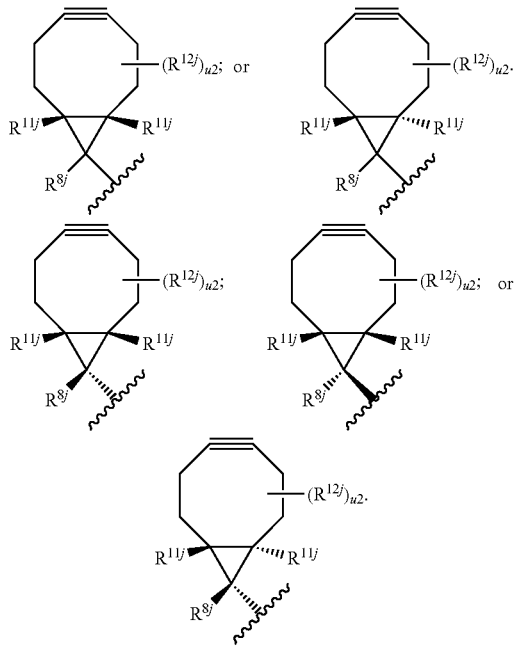

In some embodiments, at least one $W^P$ is
In some embodiments, each $R^{11j}$ is hydrogen. In some embodiments, $u_2$ is 0. In some embodiments, $R^{8j}$ is hydrogen.

In some embodiments, at least one $W^P$ is

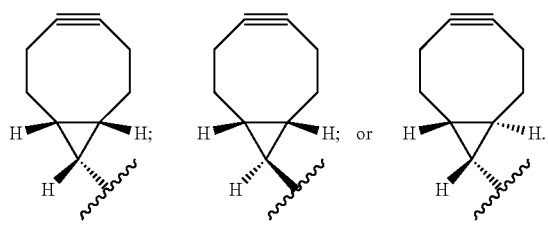

In some embodiments, at least one $W^P$ is

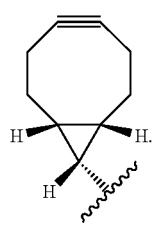

In some embodiments, at least one $R^{12j}$ is an electron-withdrawing group (e.g., a group with a positive value for the Hammett substituent constant σ). In some embodiments, suitable electron-withdrawing groups are known in the art. In some embodiments, at least one $R^{12j}$ is halogen (e.g., F or Cl), $-OR^{10j}$, $-NO_2$, $-CN$, $-S(O)_2R^{7j}$, substituted $C_1-C_{12}$ alkyl, or substituted $C_6-C_{12}$ aryl, wherein at least one of the substituents is an electron-withdrawing group. In some embodiments, at least one $R^{12j}$ is fluorinated $C_1-C_{12}$ alkyl (e.g., $-CF_3$), fluorinated $C_5-C_{12}$ aryl (e.g., $-C_6F_5$), or haloalkylated $C_5-C_{12}$ aryl (e.g., -[3,5-$(CF_3)_2(C_6H_3)$]).

In some embodiments, at least one $W^P$ is

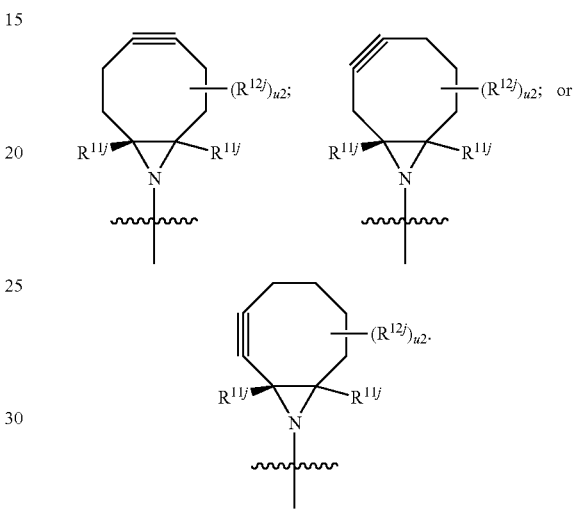

In some embodiments, at least one $W^P$ is

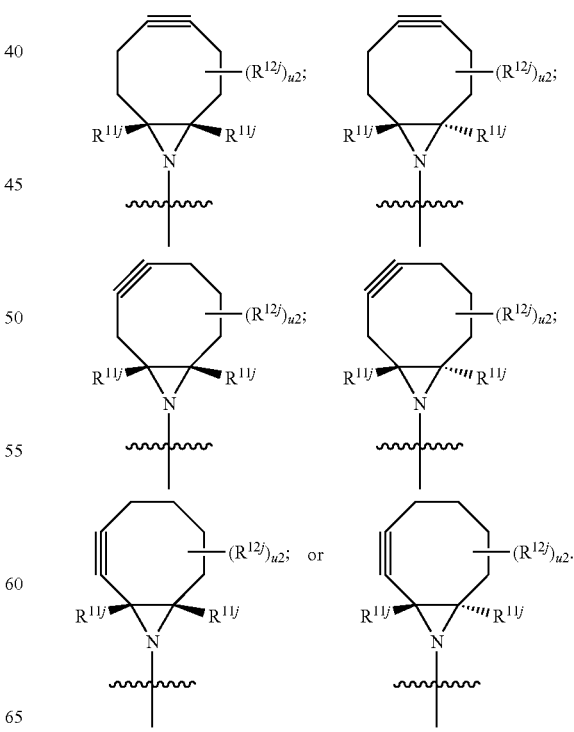

In some embodiments, at least one $W^P$ is

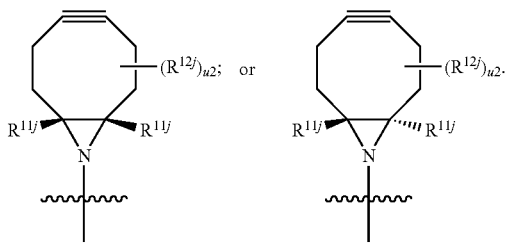

In some embodiments, each $R^{11j}$ is hydrogen. In some embodiments, $u_2$ is 0.

In some embodiments, at least one $W^P$ is

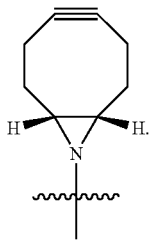

In some embodiments, each $W^P$, when present, independently is:

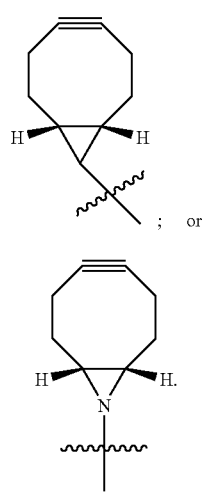

In some embodiments, each $W^P$ is:

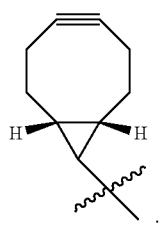

In some embodiments, each $L^{P'}$, when connected to a B7-H4 modified antibody, comprises a linking group $W^{P'}$.

In some embodiments, at least one $W^{P'}$ is

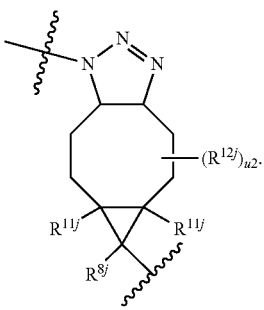

In some embodiments, at least one $W^{P'}$ is

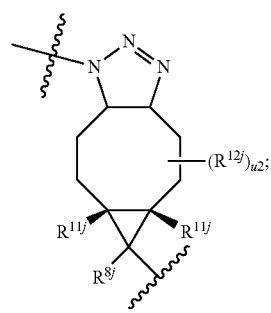

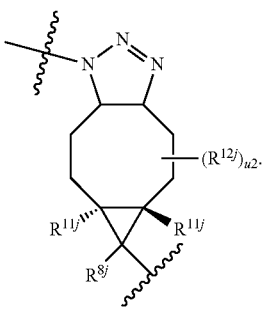

In some embodiments, at least one $W^{P'}$ is
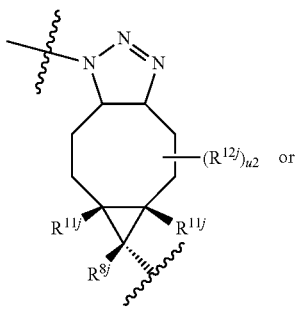
or
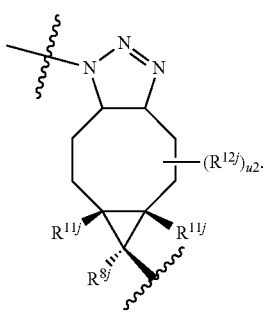
In some embodiments, at least one $W^{P'}$ is
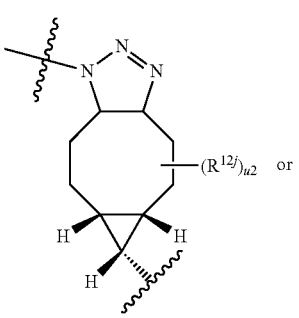
or
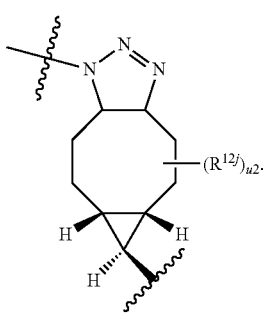
In some embodiments, at least one $W^{P'}$ is
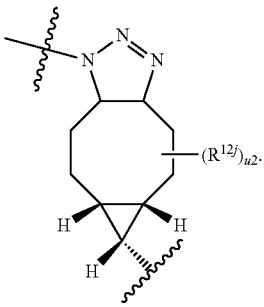
Stretcher Unit $M^P$
In some embodiments, $M^P$ is
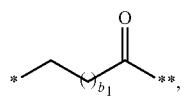 (1)
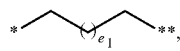 (2)
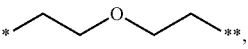 (3)
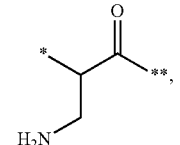 (4)
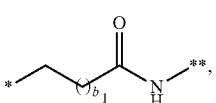 (5)
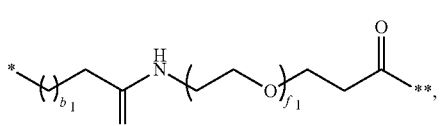 (6)
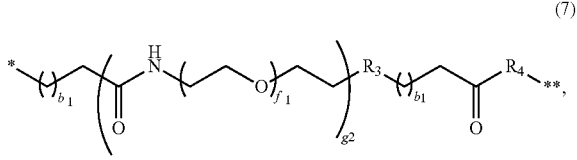 (7)
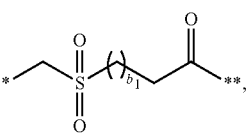 (8)
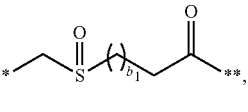 (9)
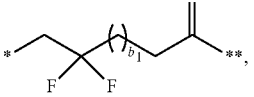 (10)

-continued

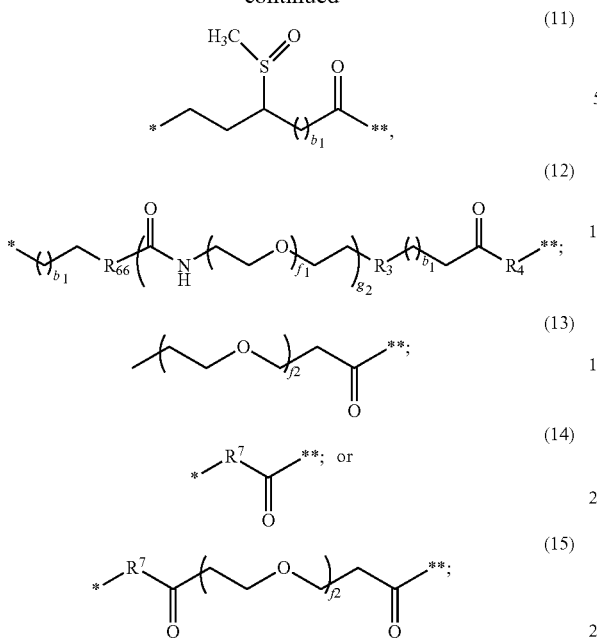

wherein * denotes attachment to $L^{P'}$ or $L^P$ and ** denotes attachment to $L^M$ or $M^A$; each $R_{66}$ independently is NH or O;

each $R_3$ independently is —C(O)—$NR_5$— or —$NR_5$—C(O)—;

each $R_5$ independently is hydrogen, $C_{1-6}$ alkyl, $C_{6-10}$ aryl, $C_{3-8}$ cycloalkyl, COOH, or COO—$C_{1-6}$ alkyl;

$R_4$ is a bond or —$NR_5$—($CR_{20}R_{21}$)—C(O)—;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

each $R^7$ independently is —O—, —$NR^8$, —($C_1$-$C_{10}$ alkyl)-, —($C_3$-$C_8$ cycloalkyl)-, -aryl-, —O—($C_1$-$C_8$ alkyl)-, —($C_1$-$C_{10}$ alkyl)-aryl-, -aryl-($C_1$-$C_{10}$ alkyl)-, —($C_1$-$C_{10}$ alkyl)-($C_3$-$C_8$ cycloalkyl)-, —($C_3$-$C_8$ cycloalkyl)-($C_1$-$C_{10}$ alkyl)-, -(3- to 8-membered heterocycloalkyl)-, -(5- to 8-membered heteroaryl)-, —($C_1$-$C_{10}$ alkyl)-(3- to 8-membered heterocycloalkyl)-, —($C_1$-$C_{10}$ alkyl)-(5- to 8-membered heteroaryl)-, -(3- to 8-membered heterocycloalkyl)-($C_1$-$C_{10}$ alkyl)-, -(5- to 8-membered heteroaryl)-($C_1$-$C_{10}$ alkyl)-, —O—C(O)—($CH_2CH_2O$)$_r$—($CH_2$)$_2$—, —($CH_2CH_2O$)$_r$—, or —($CH_2CH_2O$)$_r$—($CH_2$)$_2$—;

each $b_1$ independently is an integer ranging from 0 to 6;
each $e_1$ independently is an integer ranging from 0 to 8;
each $f_1$ independently is an integer ranging from 1 to 6;
each $f_2$ independently is an integer ranging from 1 to 12; and
each $g_2$ independently is an integer ranging from 1 to 4.

In some embodiments, $b_1$ is 0. In some embodiments, $b_1$ is 1.

In some embodiments, each $f_1$ independently is 1 or 2. In some embodiments, $f_1$ is 1. In some embodiments, $f_1$ is 2.

In some embodiments, $g_2$ is 1 or 2. In some embodiments, $g_2$ is 1. In some embodiments, $g_2$ is 2.

In some embodiments, $f_2$ is an integer ranging from 4 to 6.

In some embodiments, $R^7$ is —($C_1$-$C_{10}$ alkyl)-, —O—($C_1$-$C_8$ alkyl)-, —($CH_2CH_2O$)$_r$—, —O—C(O)—($CH_2CH_2O$)$_r$—($CH_2$)$_2$— or —($CH_2CH_2O$)$_r$—($CH_2$)$_2$—.

In some embodiments, $R^7$ is —O—, —NH, —N($CH_3$), —$CH_2$—, —($CH_2$)$_2$—, —($CH_2$)$_5$—, —O—C(O)—($CH_2CH_2O$)$_6$—($CH_2$)$_2$—, —($CH_2CH_2O$)—($CH_2$)$_2$—, —($CH_2CH_2O$)$_2$—($CH_2$)$_2$—, —($CH_2CH_2O$)$_4$—($CH_2$)$_2$—, or —($CH_2CH_2O$)$_6$—($CH_2$)$_2$—.

It is understood that for embodiments of $M^P$, * denotes attachment to $L^{P'}$ or $L^P$ and ** denotes attachment to $L^M$ or $M^A$.

In some embodiments, $M^P$ is:

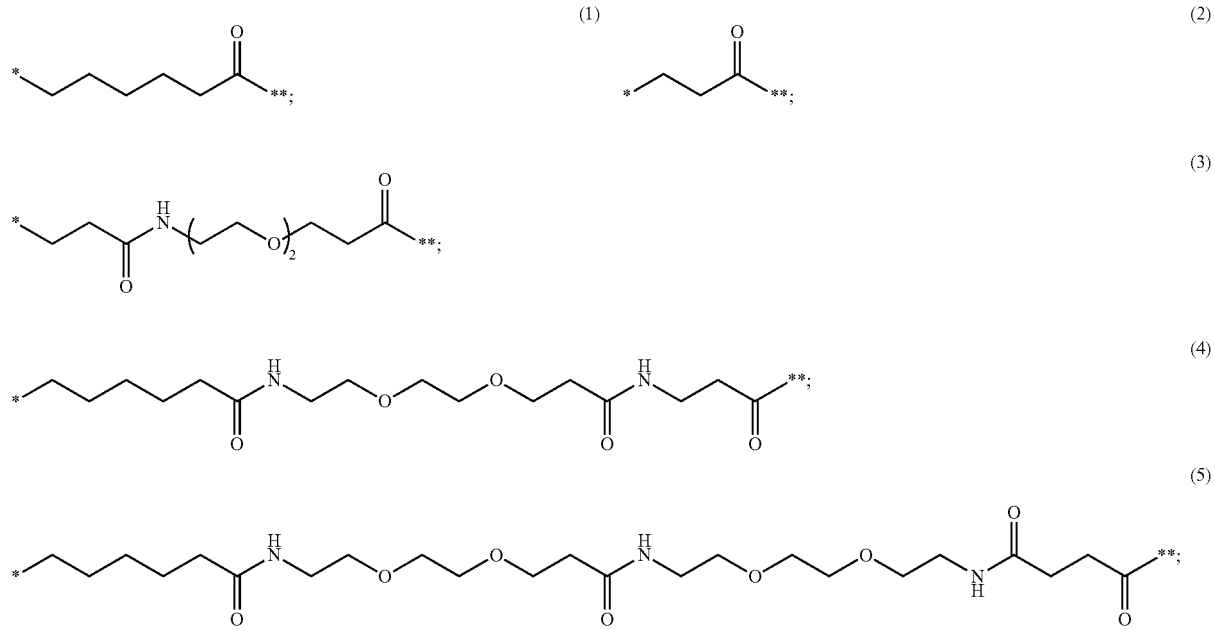

-continued (6)
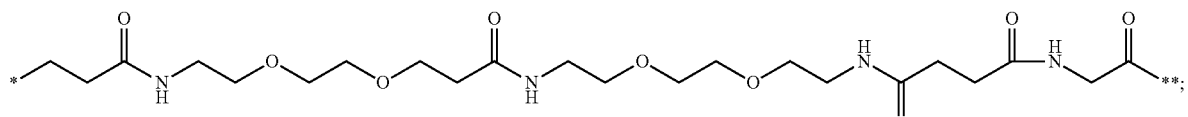

(7)
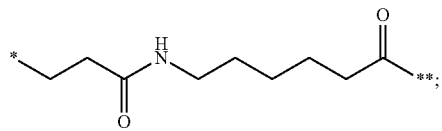

(8)
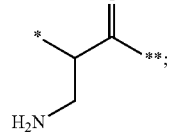

(9)
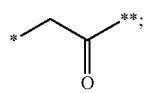

(10)
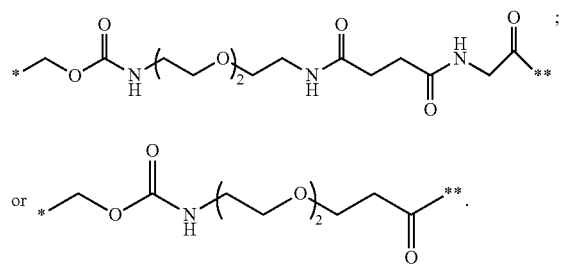

(11)
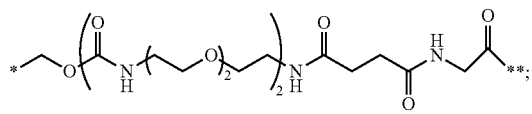

(12)

In some embodiments, $M^P$ is:

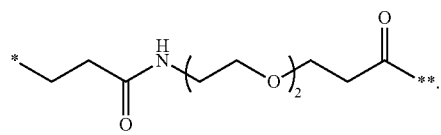

In some embodiments, $M^P$ is:

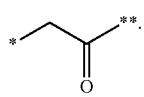

In some embodiments, $M^P$ is:

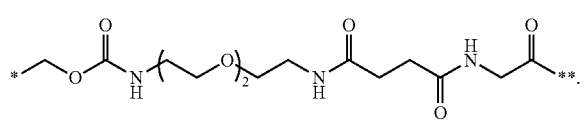

In some embodiments, $M^P$ is:

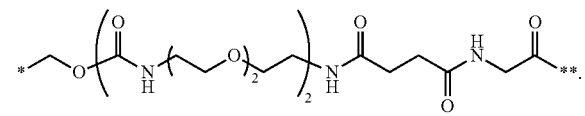

In some embodiments, $M^P$ is:

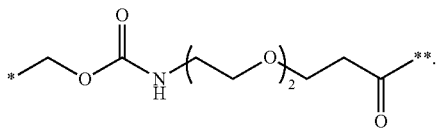

In some embodiments, $M^P$ is:

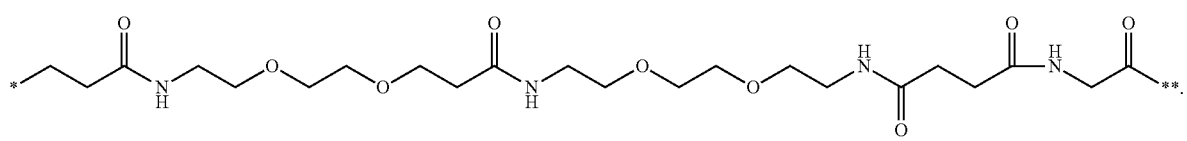

In some embodiments, $M^P$ is:

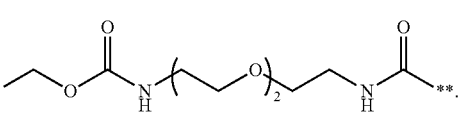

Variable $L^M$

In some embodiments, $L^M$ is a bond (e.g., a divalent linker or having 2 arms) or a multi-armed linker (e.g., trivalent or tetravalent or having 3 or 4 arms), wherein each arm may be the same or different.

In some embodiments, $L^M$ is a bond (e.g., a divalent linker or having 2 arms) or a multi-armed linker (e.g., tetravalent or having 4 arms; trivalent having 3 arms), wherein each arm may be the same or different.

It is understood that the term "arm", as used herein, refers to a portion of $L^M$ which is (1) attached to $M^P$ when present, or (2) attached to $L^3$ when present or attached to $M^A$ when $L^3$ is absent.

In some embodiments, $L^M$ is a bond (e.g., a divalent linker or having 2 arms).

In some embodiments, $L^M$ is a multi-armed linker (e.g., trivalent or tetravalent or having 3 or 4 arms), wherein each arm may be the same or different. In some embodiments, $L^M$ is a multi-armed linker (e.g., trivalent or tetravalent or having 3 or 4 arms).

In some embodiments, $L^M$ is a trivalent linker having 3 arms, wherein each arm may be the same or different. In some embodiments, $L^M$ is a trivalent linker having 3 arms, wherein each arm may be the same. In some embodiments, $L^M$ is a trivalent linker having 3 arms, wherein each arm may be different.

In some embodiments, $L^M$ is a tetravalent linker having 4 arms, wherein each arm may be the same or different. In some embodiments, $L^M$ is a tetravalent linker having 4 arms, wherein each arm may be the same. In some embodiments, $L^M$ is a tetravalent linker having 4 arms, wherein each arm may be different.

In some embodiments, $a_2$ is 2 and $L^M$ is

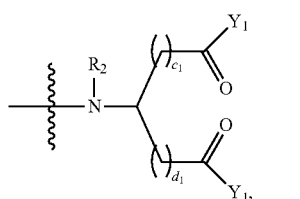
(1)

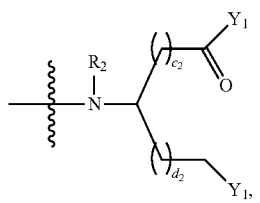
(2)

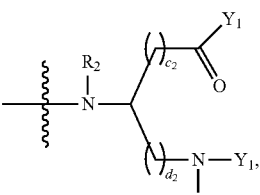
(3)

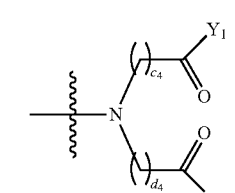
(4)

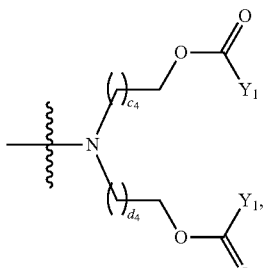
(5)

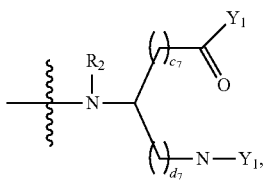
(6)

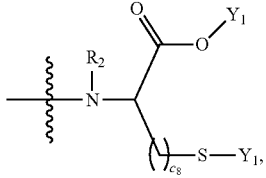
(7)

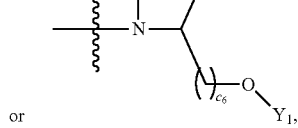
(8)

or wherein:

denotes attachment to $M^P$ when present, or attachment to $L^P$ or $L^{P'}$ when $M^P$ is absent;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_7$, and $c_8$, when present, is an integer independently ranging between 0 and 10; and each of $d_1$, $d_2$, $d_3$, $d_4$, $d_5$, and $d_7$, when present, is an integer independently ranging between 0 and 10.

In some embodiments, $a_2$ is 2 and $L^M$ is

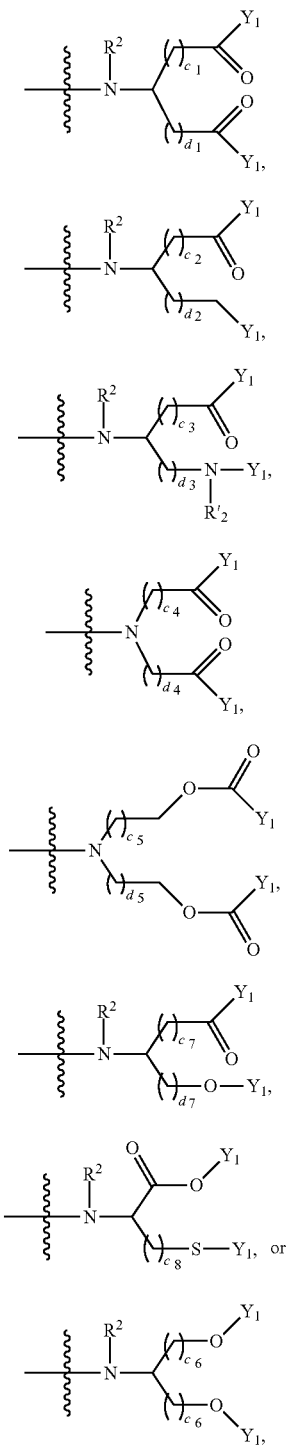

(1)
(2)
(3)
(4)
(5)
(6)
(7)
(8)

wherein:

denotes attachment to $M^P$;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_7$, and $c_8$, when present, is an integer independently ranging between 0 and 10; and each of $d_1$, $d_2$, $d_3$, $d_4$, $d_5$, and $d_7$, when present, is an integer independently ranging between 0 and 10.

In some embodiments, $a_2$ is 2 and $L^M$ is

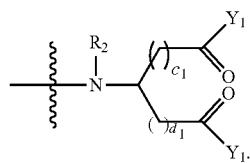

In some embodiments, $a_2$ is 2 and $L^M$ is

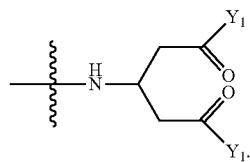

In some embodiments, $c_1$, $c_2$, $c_3$, $c_4$, $c_5$, $c_7$, and $c_8$, when present, are each independently 1, 2, 3, 4, 5, 6, 7, 8, 9, or 10. In some embodiments, $c_1$, $c_2$, $c_3$, $c_4$, $c_5$, $c_7$, and $c_8$ are each independently 0 or 1. In some embodiments, $c_1$, $c_2$, $c_3$, $c_4$, $c_5$, $c_7$, and $c_8$ are each independently 1, 2, 3, 4, 5, 6, 7, 8, 9, or 10. In some embodiments, $c_1$, $c_2$, $c_3$, $c_4$, $c_5$, $c_7$, and $c_8$ are each independently 0, 1 or 2. In some embodiments, $c_1$, $c_2$, $c_3$, $c_4$, $c_5$, $c_7$, and $c_8$ are each independently 0. In some embodiments, $c_1$, $c_2$, $c_3$, $c_4$, $c_5$, $c_7$, and $c_8$ are each independently 1. In some embodiments, $c_1$, $c_2$, $c_3$, $c_4$, $c_5$, $c_7$, and $c_8$ are each independently 2.

In some embodiments, $d_1$, $d_2$, $d_3$, $d_4$, $d_5$, and $d_7$, when present, are each independently 1, 2, 3, 4, 5, 6, 7, 8, 9, or 10. In some embodiments, $d_1$, $d_2$, $d_3$, $d_4$, $d_5$, and $d_7$ are each independently 0 or 1. In some embodiments, $d_1$, $d_2$, $d_3$, $d_4$, $d_5$, and $d_7$ are each independently 1, 2, 3, 4, 5, 6, 7, 8, 9, or 10. In some embodiments, $d_1$, $d_2$, $d_3$, $d_4$, $d_5$, and $d_7$ are each independently 1, 2, 3, or 4. In some embodiments, $d_1$, $d_2$, $d_3$, $d_4$, $d_5$, and $d_7$ are each independently 1. In some embodiments, $d_1$, $d_2$, $d_3$, $d_4$, $d_5$, and $d_7$ are each independently 2. In some embodiments, $d_1$, $d_2$, $d_3$, $d_4$, $d_5$, and $d_7$ are each independently 3. In some embodiments, $d_1$, $d_2$, $d_3$, $d_4$, $d_5$, and $d_7$ are each independently 4.

In some embodiments, $R_2$ and $R'_2$ are each independently hydrogen, $C_{1-6}$ alkyl, $C_{6-10}$ aryl, $C_{3-8}$ cycloalkyl, —COOH, or —COO—$C_{1-6}$ alkyl. In some embodiments, $R_2$ and $R'_2$ are each independently hydrogen or $C_{1-6}$ alkyl. In some embodiments, $R_2$ and $R'_2$ are each independently hydrogen. In some embodiments, $R_2$ and $R'_2$ are each independently $C_{1-6}$ alkyl.

In some embodiments, $L^M$ is:
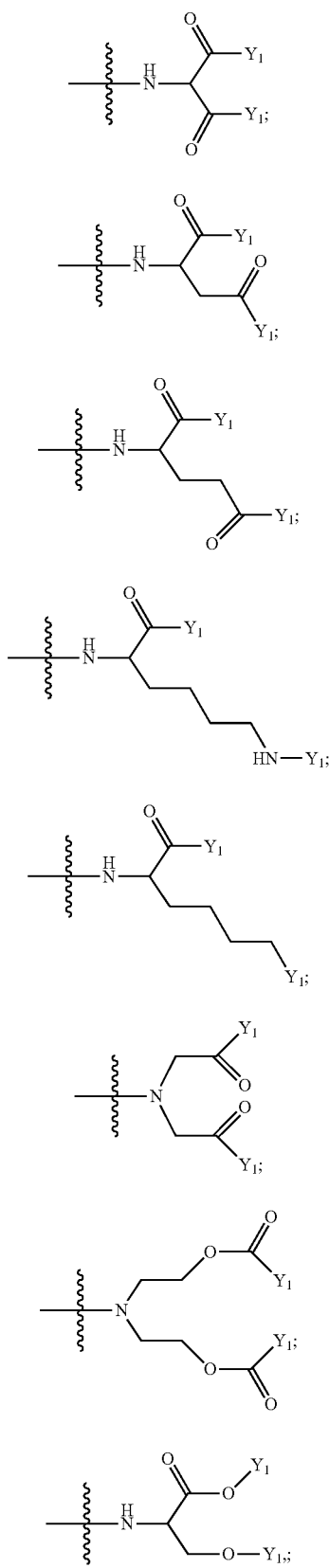
(1)
(2)
(3)
(4)
(5)
(6)
(7)
(8)
-continued
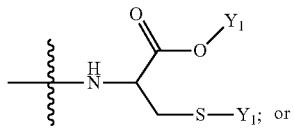
(9)
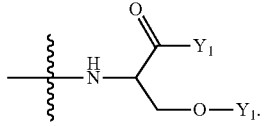
(10)
In some embodiments, $a_2$ is 3 and $L^M$ is
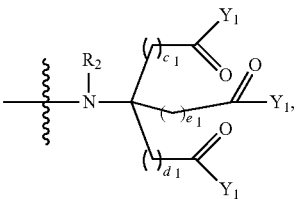
(1)
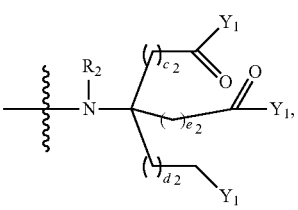
(2)
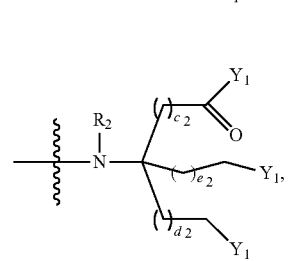
(3)
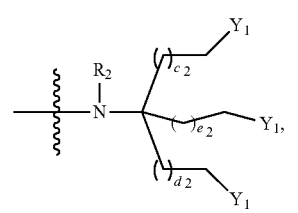
(4)
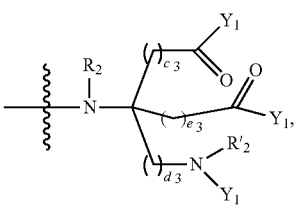
(5)

-continued

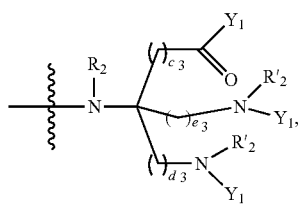
(6)

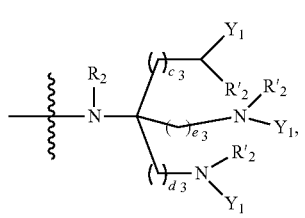
(7)

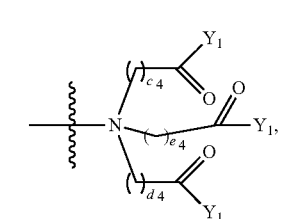
(8)

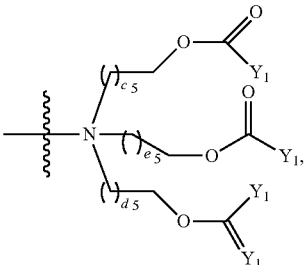
(9)

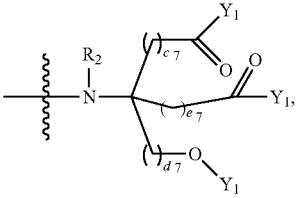
(10)

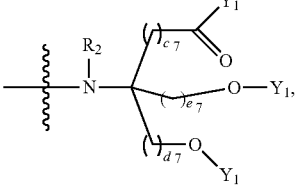
(11)

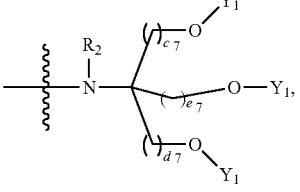
(12)

-continued

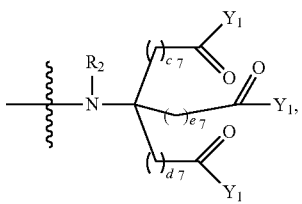
(13)

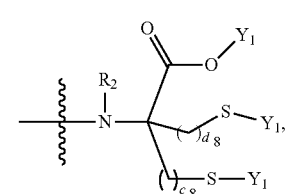
(14)

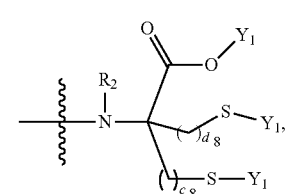
(15)

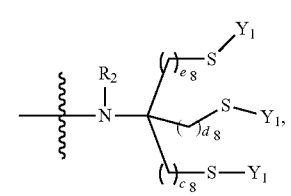
(16)

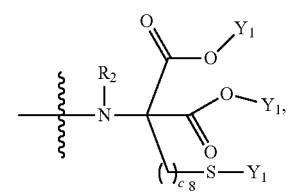
(17)

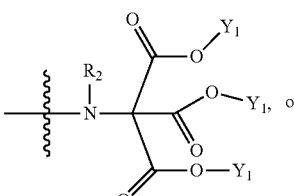
(18)

wherein:

denotes attachment to $M^P$ when present, or attachment to $L^P$ or $L^{P'}$ when $M^P$ is absent;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_6$, $c_7$, and $c_8$ is an integer independently ranging between 0 and 10;

each of $d_1$, $d_2$, $d_3$, $d_4$, $d_5$, $d_6$, $d_7$ and $d_8$ is an integer independently ranging between 0 and 10; and each of $e_1$, $e_2$, $e_3$, $e_4$, $e_5$, $e_6$, $e_7$, and $e_8$ is an integer independently ranging between 0 and 10.

In some embodiments, $a_2$ is 3 and $L^M$ is

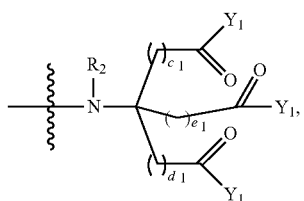

(1)

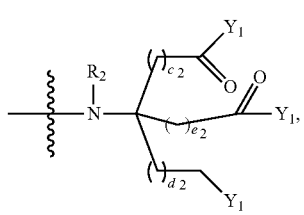

(2)

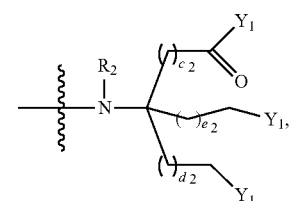

(3)

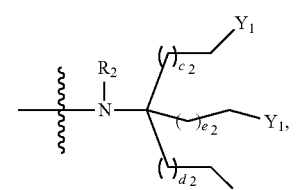

(4)

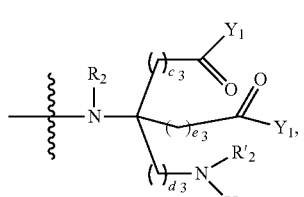

(5)

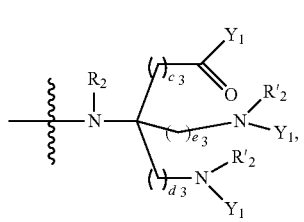

(6)

-continued

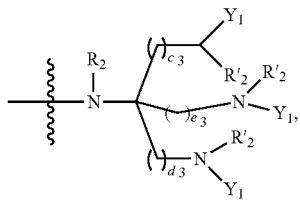

(7)

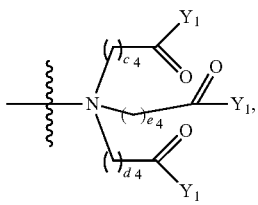

(8)

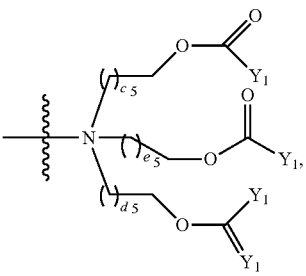

(9)

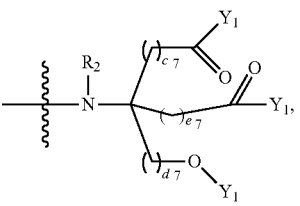

(10)

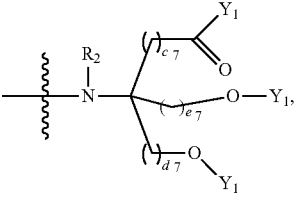

(11)

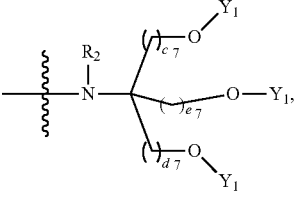

(12)

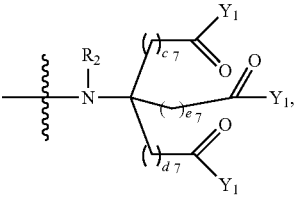

(13)

-continued

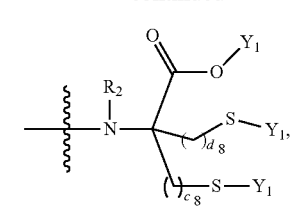 (14)

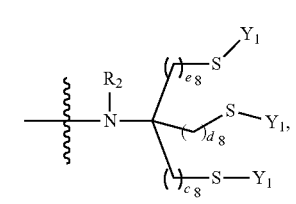 (15)

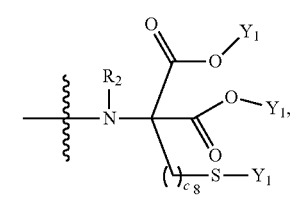 (16)

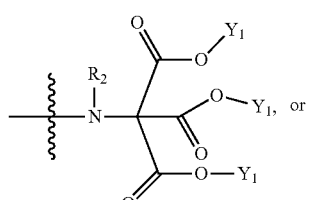 (17)

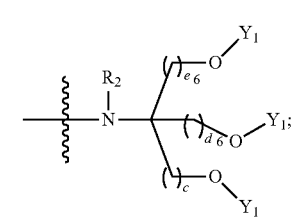 (18)

wherein:

denotes attachment to $M^P$;
  $Y_1$ denotes attachment to $L^3$ when present, or attachment to $M^A$ when $L^3$ is absent;
  $R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;
  each of $c_1$, $c_2$, $c_3$, $c_4$, $c_5$, $c_6$, $c_7$, and $c_8$ is an integer independently ranging between 0 and 10;
  each of $d_1$, $d_2$, $d_3$, $d_4$, $d_5$, $d_6$, $d_7$ and $d_8$ is an integer independently ranging between 0 and 10; and
  each of $e_1$, $e_2$, $e_3$, $e_4$, $e_5$, $e_6$, $e_7$, and $e_8$ is an integer independently ranging between 0 and 10.

In some embodiments, $a_2$ is 3 and $L^M$ is

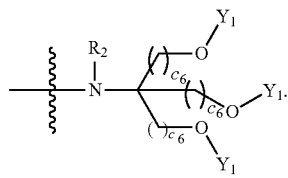

In some embodiments, $a_2$ is 3 and $L^M$ is

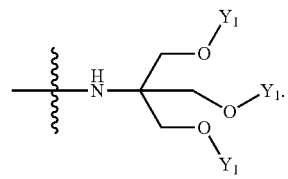

In some embodiments, $-L^M-(L^3)_{a2}-$ is:

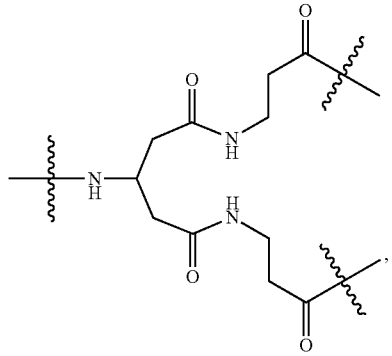

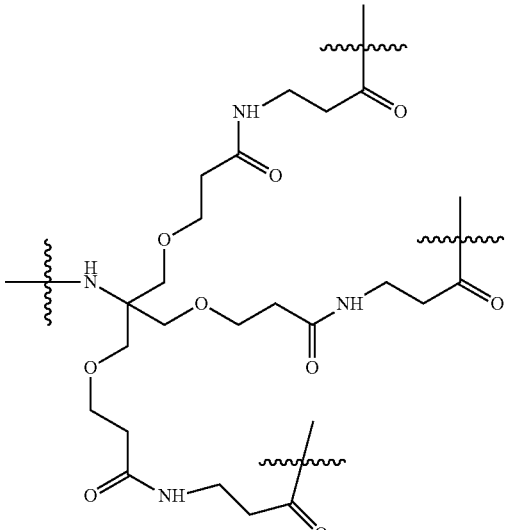, or

-continued

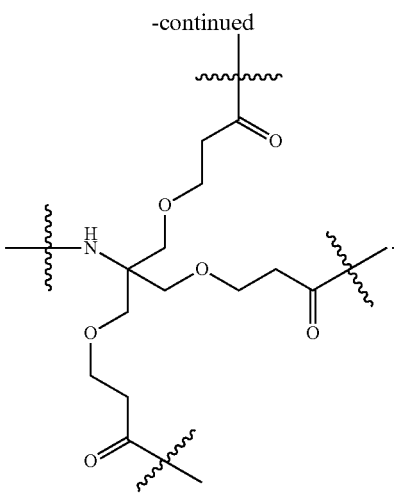

In some embodiments, wherein an amino acid unit has two attachment sites (i.e., a terminal drug unit) one of the attachment sites shown above can be replaced, for example, by H, OH, or a $C_{1-3}$ unsubstituted alkyl group.

In some embodiments, when $L^M$ is a multi-armed linker and not yet connected to the Stretcher unit $M^P$, $W^M$ is a terminus of $L^M$ and each occurrence of $W^M$ independently is hydrogen, a protecting group, a leaving group, or a functional group that is capable of connecting $L^M$ to $M^P$ by forming a covalent bond.

In some embodiments, $W^M$ is an amine protecting group. In some embodiments, $W^M$ is BOC.

In some embodiments, $W^M$ is an amine protecting group and $L^M$ is

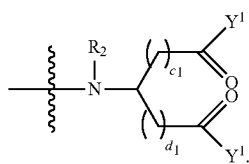

In some embodiments, $W^M$ is an amine protecting group and $L^M$ is

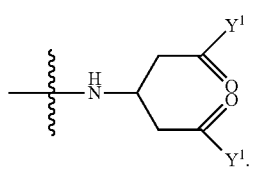

In some embodiments, $W^M$ is BOC, and $L^M$ is

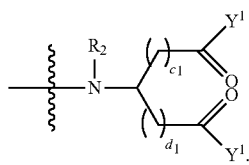

In some embodiments, $W^M$ comprises an amine group. In some embodiments, $W^M$ comprises $-C(O)-(CH_2)_w-$ $NH_2$, wherein w is an integer from 1 to 6. In some embodiments, $W^M$ is $-C(O)-CH_2-NH_2$.

In some embodiments, $W^M$ is $-C(O)-CH_2-NH_2$ and $L^M$ is

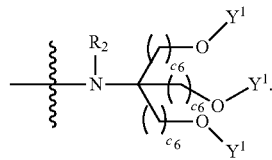

In some embodiments, $W^M$ is $-C(O)-CH_2-NH_2$ and $L^M$ is

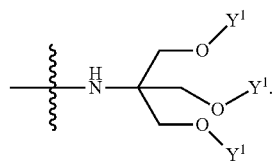

In some embodiments, $W^M$ is H.

Variable $L^3$

In some embodiments, each $L^3$ is absent. In some embodiments, each $L^3$ is a carbonyl-containing moiety.

It is understood that for embodiments of $L^3$, * indicates attachment to another $L^3$ when present, or to $L^M$; and ** indicates attachment to another $L^3$ when present, or to $M^A$.

In some embodiments, each $L^3$, when present, independently is *$-C_{1-12}$ alkyl-C(O)$-$**, *$-NH-C_{1-12}$ alkyl-C(O)$-$** or *$-C_{1-12}$ alkyl-C(O)$-NH-C_{1-12}$ alkyl-C(O)$-$**.

In some embodiments, at least one $L^3$ is *$-C_{1-12}$ alkyl-C(O)$-$**.

In some embodiments, at least one $L^3$ is *$-CH_2CH_2-C(O)-$**.

In some embodiments, $L^3$ is *$-CH_2CH_2-C(O)-$**.

In some embodiments, $(L^3)_{a3}$ is *$-CH_2CH_2-C(O)-$**.

In some embodiments, at least one $L^3$ is *$-NH-C_{1-12}$ alkyl-C(O)$-$**.

In some embodiments, at least one $L^3$ is *$-NH-CH_2CH_2-C(O)-$**.

In some embodiments, $L^3$ is *$-NH-CH_2CH_2-C(O)-$**.

In some embodiments, $(L^3)_{a3}$ is *$-NH-CH_2CH_2-C(O)-$**.

In some embodiments, at least one $L^3$ is *$-C_{1-12}$ alkyl-C(O)$-NH-C_{1-12}$ alkyl-C(O)$-$**.

In some embodiments, at least one $L^3$ is *$-CH_2CH_2-C(O)-NH-CH_2CH_2-C(O)-$**.

In some embodiments, $L^3$ is *$-CH_2CH_2-C(O)-NH-CH_2CH_2-C(O)-$**.

In some embodiments, $(L^3)_{a3}$ is *$-CH_2CH_2-C(O)-NH-CH_2CH_2-C(O)-$**.

In some embodiments, $a_3$ is 2 or greater, at least one $L^3$ is *$-C_{1-12}$ alkyl-C(O)$-$**, and at least one $L^3$ is *$-NH-C_{1-12}$ alkyl-C(O)$-$**.

In some embodiments, $(L^3)_{a3}$ is *$-CH_2CH_2-C(O)-NH-CH_2CH_2-C(O)-$**.

In some embodiments, $(L^3)_{a3}$ is *$NH-CH_2CH_2-C(O)-CH_2CH_2-C(O)-$**.

Variable $M^A$

In some embodiments, $M^A$ is a linker moiety that is capable of connecting one or more drugs and one or more hydrophilic group to $L^P$ or $L^{P'}$. In some embodiments, $M^A$ comprises a peptide moiety of at least two amino acids. In some embodiments, amino acid is referred to herein as "AA" and amino acids as "AA's".

In some embodiments, the peptide moiety is a moiety that is capable of forming a covalent bond with a -$L^D$-D unit and allows for the attachment of multiple drugs. In some embodiments, the peptide moiety comprises a single AA unit or has two or more AA units (e.g., from 2 to 10, from 2 to 6, or 2, 3, 4, 5 or 6) wherein the AA units are each independently a natural or non-natural amino acid, an amino alcohol, an amino aldehyde, a diamine, a polyamine, or combinations thereof. In some embodiments, in order to have the requisite number of attachments, at least one of the AA units will have a functionalized side chain to provide for attachment of the -$L^D$-D unit. In some embodiments, exemplary functionalized AA units (e.g., amino acids, amino alcohols, or amino aldehydes) include, for example, azido or alkyne functionalized AA units (e.g., amino acid, amino alcohol, or amino aldehyde modified to have an azide group or alkyne group). In some embodiments, the azide group or alkyne group is for attachment using click chemistry.

In some embodiments, the peptide moiety has 2 to 12 AA units. In some embodiments, the peptide moiety has 2 to 10 AA units. In some embodiments, the peptide moiety has 2 to 6 AA units. In some embodiments, the peptide moiety has 2, 3, 4, 5, or 6 AA units.

In some embodiments, the peptide moiety has 2 AA units. In some embodiments, the peptide moiety has 3 AA units. In some embodiments, the peptide moiety has 4 AA units. In some embodiments, the peptide moiety has 5 AA units. In some embodiments, the peptide moiety has 6 AA units.

In some embodiments, attachment within the peptide moiety or with the other components of the conjugate, intermediate thereof, or scaffold, can be, for example, via amino, carboxy, or other functionalities. In some embodiments, each amino acid of the peptide moiety can be independently D or L isomer of a thiol containing amino acid. In some embodiments, each amino acid of the peptide moiety can be independently a D isomer of a thiol containing amino acid. In some embodiments, each amino acid of the peptide moiety can be independently an L isomer of a thiol containing amino acid. In some embodiments, the thiol containing amino acid can be, for example, cysteine, homocysteine, or penicillamine.

In some embodiments, each amino acid that comprises the peptide moiety can be independently the L or D isomer of the following amino acids: alanine (including β-alanine), arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, stereoisomers thereof, or derivatives thereof.

In some embodiments, each amino acid that comprises the peptide moiety is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, alanine, or a stereoisomers thereof.

In some embodiments, the peptide moiety comprises a monopeptide, a dipeptide, tripeptide, tetrapeptide, or pentapeptide. In some embodiments, the peptide moiety comprises a pentapeptide.

In some embodiments, the peptide moiety comprises at least about five amino acids (e.g., 5, 6, 7, 8, 9, or 10 amino acids). In some embodiments, the peptide moiety comprises at most about ten amino acids.

In some embodiments, each amino acid that comprises the peptide moiety independently is glycine, serine, glutamic acid, lysine, aspartic acid, and cysteine.

In some embodiments, the peptide moiety comprises at least four glycines and at least one serine, e.g., (glycine)$_4$ and serine wherein the serine is at any position along the peptide chain, such as, for example, (serine)-(glycine)$_4$; (glycine)-(serine)-(glycine)$_3$; (glycine)$_2$-(serine)-(glycine)$_2$; (glycine)$_3$-(serine)-(glycine); or (glycine)$_4$-(serine).

In some embodiments, the peptide moiety comprises (glycine)$_4$-(serine) or (serine)-(glycine)$_4$. In some embodiments, the peptide moiety comprises (glycine)$_4$-(serine). In some embodiments, the peptide moiety comprises (serine)-(glycine)$_4$.

In some embodiments, the peptide moiety comprises at least four glycines and at least one glutamic acid e.g., (glycine)$_4$ and glutamic acid, wherein the glutamic acid is at any position along the peptide chain.

In some embodiments, the peptide moiety comprises (glutamic acid)-(glycine)$_4$ or (glycine)$_4$-(glutamic acid).

In some embodiments, the peptide moiety comprises (β-alanine)-(glycine)$_4$-(serine) wherein the serine is at any position along the peptide chain.

In some embodiments, the peptide moiety comprises (glycine)$_4$-(serine)-(glutamic acid) wherein the serine is at any position along the peptide chain. In some embodiments, the peptide moiety comprises (β-alanine)-(glycine)$_4$-(serine)-(glutamic acid) wherein the serine is at any position along the peptide chain.

In some embodiments, the peptide moiety comprises (glycine)$_{1-4}$-(serine), wherein the peptide moiety is attached to $L^3$ when present, or to $L^M$ when $L^3$ is absent, via one of the glycine; the peptide moiety is attached to $T^1$ when present, via the serine; and the peptide moiety is attached to $L^D$ when present, via the serine.

In some embodiments, the peptide moiety comprises (serine)-(glycine)$_{1-4}$, wherein the peptide moiety is attached to $L^3$ when present, or to $L^M$ when $L^3$ is absent, via the serine; the peptide moiety is attached to $T^1$ when present, via the glycine; and the peptide moiety is attached to $L^D$ when present, via the serine.

It is understood that for embodiments of the peptide moiety, * indicates attachment to $L^3$ when present, or to $L^M$ when $L^3$ is absent. In some embodiments,  indicates attachment to $T^1$ when present, or —OH when $T^1$ is absent. In some embodiments, * indicates attachment to $L^D$ when present, or hydrogen when $L^D$ is absent.

In some embodiments, the peptide moiety comprises

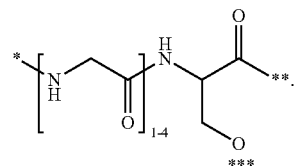

In some embodiments, the peptide moiety comprises (glycine)-(serine), wherein the peptide moiety is attached to $L^3$ when present, or to $L^M$ when $L^3$ is absent, via the glycine;

the peptide moiety is attached to $T^1$ when present, via the serine; and the peptide moiety is attached to $L^D$ when present, via the serine.

In some embodiments, the peptide moiety comprises (glycine)-(serine), wherein the peptide moiety is attached to $L^3$ when present, or to $L^M$ when $L^3$ is absent, via the serine; the peptide moiety is attached to $T^1$ when present, via the glycine; and the peptide moiety is attached to $L^D$ when present, via the serine.

In some embodiments, the peptide moiety comprises

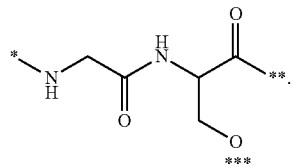

In some embodiments, the peptide moiety comprises (glycine)$_4$-(serine), wherein the peptide moiety is attached to $L^3$ when present, or to $L^M$ when $L^3$ is absent, via one of the glycine; the peptide moiety is attached to $T^1$ when present, via the serine; and the peptide moiety is attached to $L^D$ when present, via the serine.

In some embodiments, the peptide moiety comprises

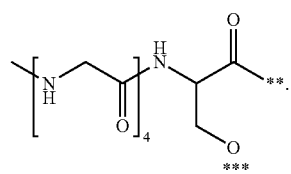

In some embodiments, the peptide moiety comprises (serine)-(glycine)$_4$, wherein the peptide moiety is attached to $L^3$ when present, or to $L^M$ when $L^3$ is absent, via the serine; the peptide moiety is attached to $T^1$ when present, via one of the glycine; and the peptide moiety is attached to $L^D$ when present, via the serine.

In some embodiments, the peptide moiety comprises

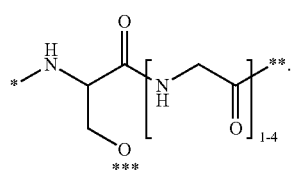

In some embodiments, the peptide moiety comprises

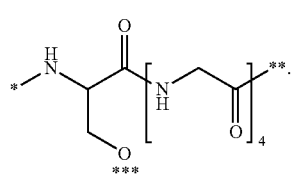

In some embodiments, the peptide moiety comprises (β-alanine)-(glycine)$_{1-4}$-(serine), wherein the peptide moiety is attached to $L^3$ when present, or to $L^M$ when $L^3$ is absent, via the β-alanine; the peptide moiety is attached to $T^1$ when present, via the serine; and the peptide moiety is attached to $L^D$ when present, via the serine.

In some embodiments, the peptide moiety comprises

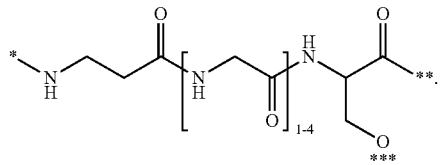

In some embodiments, the peptide moiety comprises (β-alanine)-(glycine)$_4$-(serine), wherein:
the peptide moiety is attached to $L^3$ when present, or to $L^M$ when $L^3$ is absent, via the β-alanine; the peptide moiety is attached to $T^1$ when present, via the serine; and the peptide moiety is attached to $L^D$ when present, via the serine.

In some embodiments, the peptide moiety comprises

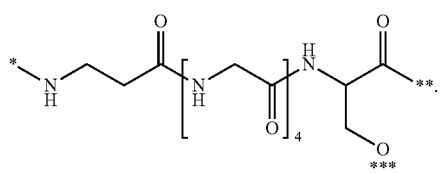

In some embodiments, the peptide moiety comprises (glycine)$_{1-4}$-(glutamic acid), wherein the peptide moiety is attached to $L^3$ when present, or to $L^M$ when $L^3$ is absent, via one of the glycine; the peptide moiety is attached to $T^1$ when present, via the glutamic acid; and the peptide moiety is attached to $L^D$ when present, via the glutamic acid.

In some embodiments, the peptide moiety comprises (glycine)$_{1-4}$-(glutamic acid, wherein: the peptide moiety is attached to $L^3$ when present, or to $L^M$ when $L^3$ is absent, via the glutamic acid; the peptide moiety is attached to $T^1$ when present, via the glycine; and the peptide moiety is attached to $L^D$ when present, via the glutamic acid.

In some embodiments, the peptide moiety comprises

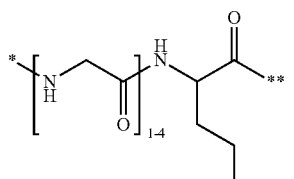

In some embodiments, the peptide moiety comprises (glycine)-(glutamic acid), wherein: the peptide moiety is attached to $L^3$ when present, or to $L^M$ when $L^3$ is absent, via the glycine; the peptide moiety is attached to $T^1$ when present, via the glutamic acid; and the peptide moiety is attached to $L^D$ when present, via the glutamic acid.

In some embodiments, the peptide moiety comprises

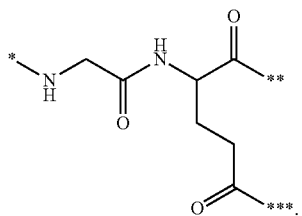

In some embodiments, the peptide moiety comprises (glycine)$_4$-(glutamic acid), wherein: the peptide moiety is attached to $L^3$ when present, or to $L^M$ when $L^3$ is absent, via one of the glycine; the peptide moiety is attached to $T^1$ when present, via the glutamic acid; and the peptide moiety is attached to $L^D$ when present, via the glutamic acid.

In some embodiments, the peptide moiety comprises

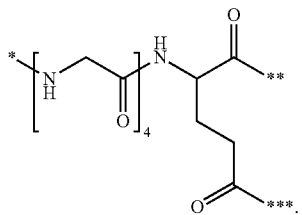

In some embodiments, the peptide moiety comprises (glutamic acid)-(glycine)$_{1-4}$, wherein: the peptide moiety is attached to $L^3$ when present, or to $L^M$ when $L^3$ is absent, via the glutamic acid; the peptide moiety is attached to $T^1$ when present, via one of the glycine; and the peptide moiety is attached to $L^D$ when present, via the glutamic acid.

In some embodiments, the peptide moiety comprises

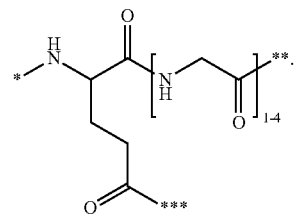

In some embodiments, the peptide moiety comprises

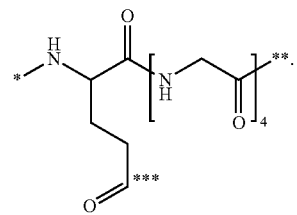

In some embodiments, the peptide moiety comprises (glutamic acid)-(glycine)$_4$, wherein: the peptide moiety is attached to $L^3$ when present, or to $L^M$ when $L^3$ is absent, via the glutamic acid; the peptide moiety is attached to $T^1$ when present, via one of the glycine; and the peptide moiety is attached to $L^D$ when present, via the glutamic acid.

In some embodiments, the peptide moiety comprises

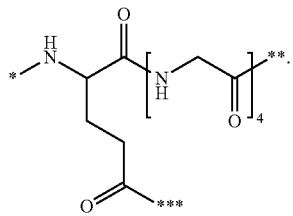

In some embodiments, the peptide moiety comprises (glutamic acid)-(glycine), wherein: the peptide moiety is attached to $L^3$ when present, or to $L^M$ when $L^3$ is absent, via the glutamic acid; the peptide moiety is attached to $T^1$ when present, via one of the glycine; and the peptide moiety is attached to $L^D$ when present, via the glutamic acid.

In some embodiments, the peptide moiety comprises

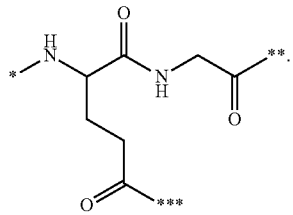

In some embodiments, the peptide moiety comprises (β-alanine)-(glycine)$_{1-4}$-(glutamic acid), wherein: the peptide moiety is attached to $L^3$ when present, or to $L^M$ when $L^3$ is absent, via the β-alanine; the peptide moiety is attached to $T^1$ when present, via the glutamic acid; and the peptide moiety is attached to $L^D$ when present, via the glutamic acid.

In some embodiments, the peptide moiety comprises

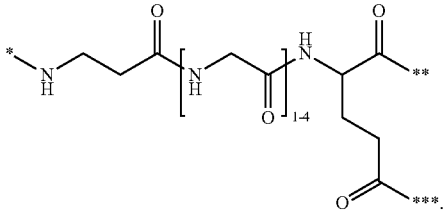

In some embodiments, the peptide moiety comprises (β-alanine)-(glycine)$_4$-(glutamic acid), wherein: the peptide moiety is attached to $L^3$ when present, or to $L^M$ when $L^3$ is absent, via the 0-alanine; the peptide moiety is attached to $T^1$ when present, via the glutamic acid; and the peptide moiety is attached to $L^D$ when present, via the glutamic acid.

In some embodiments, the peptide moiety comprises

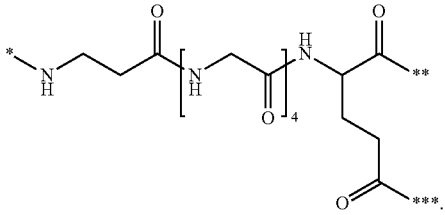

It is understood that for embodiments of $M^A$, * indicates attachment to $L^3$ when present, or to $L^M$ when $L^3$ is absent,  indicates attachment to $T^1$, and * indicates attachment to $L^D$.

In some embodiments, the peptide moiety comprises (β-alanine)-(glycine)-(glutamic acid), wherein:
the peptide moiety is attached to $L^3$ when present, or to $L^M$ when $L^3$ is absent, via the β-alanine; the peptide moiety is attached to $T^1$ when present, via the glutamic acid; and the peptide moiety is attached to $L^D$ when present, via the glutamic acid.

In some embodiments, the peptide moiety comprises

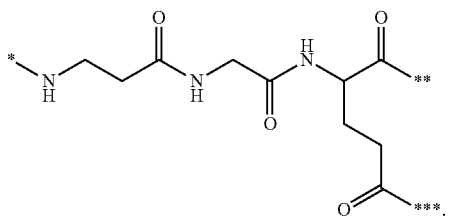

Variable $L^D$

In some embodiments, each $L^D$ independently is a divalent linker moiety connecting D to $M^A$. In some embodiments, each $L^D$ comprises at least one cleavable bond such that when the bond is cleaved, D is released in an active form for its intended therapeutic effect.

In some embodiments, $L^D$ comprises one cleavable bond. In some embodiments, $L^D$ comprises multiple cleavage sites or bonds.

It is understood that each $L^D$, prior to being connected to D, independently corresponds to a monovalent moiety $L^{D'}$.

In some embodiments, $L^{D'}$ comprises a functional group capable of forming the cleavable bond. Functional groups capable of forming the cleavable bond can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds.

In some embodiments, each $L^D$ comprises a disulfide bond that is cleavable through disulfide exchange, an acid-labile bond that is cleavable at acidic pH, and/or bonds that are cleavable by hydrolases. In some embodiments, $L^D$ comprises a carbamate bond (i.e., —O—C(O)—NR—, wherein R is hydrogen or alkyl or the like).

In some embodiments, the structure and sequence of the cleavable bond in $L^D$ can be such that the bond is cleaved by the action of enzymes present at the target site. In some embodiments, the cleavable bond can be cleavable by other mechanisms.

In some embodiments, the structure and sequence of the cleavable bonds in $L^D$ can be such that the bonds are cleaved by the action of enzymes present at the target site. In some embodiments, the cleavable bonds can be cleavable by other mechanisms.

In some embodiments, the cleavable bond(s) can be enzymatically cleaved by one or more enzymes, including a tumor-associated protease, to liberate the Drug unit or D, wherein the conjugate of the present disclosure, or intermediate, or scaffold thereof, is protonated in vivo upon release to provide a Drug unit or D.

In some embodiments, each $L^D$ independent is

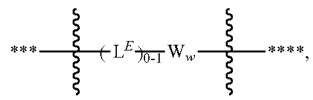

wherein:
$L^E$, when present, is —NH—[(CH$_2$CH$_2$O)$_p$—(CH$_2$)$_{0\text{-}2}$]$_q$—C(O)—, —NH—(C$_1$-C$_6$ alkyl)-O—C(O)—, or —NH—[(CH$_2$CH$_2$O)$_p$—(CH$_2$)$_{0\text{-}2}$]$_q$—C(O)—NH—(C$_1$-C$_6$ alkyl)-O—C(O)—, wherein p is an integer ranging from about 1 to about 20, and q is an integer ranging from about 1 to about 10;
each W independently is a natural or unnatural amino acid unit;
w is an integer ranging from about 0 to about 12;
** denotes attachment to $M^A$; and
*** denotes attachment to D.

In some embodiments, each $L^D$ independent is

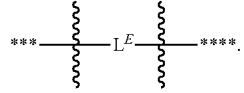

In some embodiments, each $L^D$ independent is

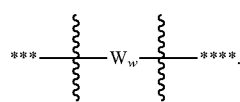

In some embodiments, each $L^D$ independent is

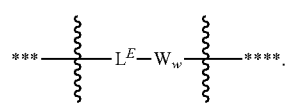

In some embodiments, $L^E$ comprises at least one PEG unit.

In some embodiments, the PEG unit comprises at least 1 subunit, at least 2 subunits, at least 3 subunits, at least 4 subunits, at least 5 subunits, or at least 6 subunits. In some embodiments, the PEG unit comprises at least 4 subunits, at least 3 subunits, at least 2 subunits, or at least 1 subunit.

In some embodiments, the PEG unit comprises at least 1 subunit.

In some embodiments, the PEG unit comprises at least 2 subunits.

In some embodiments, p is an integer ranging from about 1 to about 15, from about 1 to about 10, from about 1 to about 9, from about 1 to about 8, from about 1 to about 7, from about 1 to about 6, or from about 1 to about 5.

In some embodiments, p is an integer ranging from about 1 to about 6. In some embodiments, p is an integer ranging from about 1 to about 4. In some embodiments, p is an integer ranging from about 1 to about 2.

In some embodiments, p is 2.

In some embodiments, q is an integer ranging from about 1 to about 15, from about 1 to about 10, from about 1 to about 9, from about 1 to about 8, from about 1 to about 7, from about 1 to about 6, or from about 1 to about 5.

In some embodiments, q is 1, 2, 3, 4, or 5. In some embodiments, q is 2.

In some embodiments, $L^E$, when present, is —NH—$(CH_2CH_2O)_{1-4}$—$(CH_2)_2$—C(O)—. In some embodiments, $L^E$, when present, is —NH—$(CH_2CH_2O)_2$—$(CH_2)_2$—C(O)—. In some embodiments, $L^E$, when present, is —NH—$(CH_2CH_2O)_3$—$(CH_2)_{0-2}$—C(O)—. In some embodiments, $L^E$, when present, is —NH—$(CH_2CH_2O)_3$—$(CH_2)$—C(O)—. In some embodiments, $L^E$, when present, is —NH—$(CH_2CH_2O)_3$—$(CH_2)_2$—C(O)—. In some embodiments, $L^E$, when present, is —NH—$(CH_2CH_2O)$—$(CH_2)_{0-2}$—C(O)—. In some embodiments, $L^E$, when present, is —NH—$CH_2CH_2O$—C(O)—. In some embodiments, $L^E$, when present, is —NH—$(C_1$-$C_6$ alkyl)-O—C(O)—. In some embodiments, $L^E$, when present, is —NH—$CH_2$—CH$(CH_3)$—O—C(O)—. In some embodiments, $L^E$, when present, is —NH—$[(CH_2CH_2O)_{1-4}$—$(CH_2)_2$—C(O)—NH—$(C_1$-$C_6$ alkyl)-O—C(O)—. In some embodiments, $L^E$, when present, is —NH—$CH_2CH_2O$—$(CH_2)_2$—C(O)—NH—$(CH_2)_2$—O—C(O)—.

In some embodiments, w is an integer ranging from about 1 to about 12 (e.g., 1 to 6, or 1 to 4, or 1 to 3, or 1, 2, 3, 4, 5, 6, 7, 8, 9, 10, 11, or 12).

In some embodiments, w is 0, 1, 2, 3, 4, or 5. In some embodiments, w is 1, 2, 3, 4, or 5.

In some embodiments, w is 1. In some embodiments, w is 2. In some embodiments, w is 3.

In some embodiments, each W independently is a natural or unnatural amino acid and/or a D or L isomer.

In some embodiments, each W independently is an alpha, beta, or gamma amino acid that is natural or non-natural.

In some embodiments, at least one W is a natural amino acid. In some embodiments, at least one W is a non-natural amino acid.

In some embodiments, $W_w$ does not comprise natural amino acids. In some embodiments, $W_w$ does not comprise non-natural amino acids.

In some embodiments, $W_w$ comprises a natural amino acid linked to a non-natural amino acid.

In some embodiments, $W_w$ comprises a natural amino acid linked to a D-isomer of a natural amino acid.

In some embodiments, $W_w$ is a dipeptide, e.g., -Val-Cit-, -Phe-Lys-, -Val-Ala- or Glu-Ala.

In some embodiments, $W_w$ is a monopeptide, a dipeptide, a tripeptide, a tetrapeptide, a pentapeptide, a hexapeptide, a heptapeptide, an octapeptide, a nonapeptide, a decapeptide, an undecapeptide, or a dodecapeptide unit.

In some embodiments, $W_w$ is a peptide (e.g., a peptide of 1 to 12 amino acids), which is conjugated directly to D. In some embodiments, the peptide is a single amino acid. In some embodiments, the peptide is a dipeptide. In some embodiments, the peptide is a tripeptide.

In some embodiments, each amino acid in $W_w$ is independently selected from alanine, 3-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, each amino acid in $W_w$ is independently selected from alanine, 3-alanine, arginine, aspartic acid, asparagine, histidine, glycine, glutamic acid, glutamine, phenylalanine, lysine, leucine, serine, tyrosine, threonine, isoleucine, proline, tryptophan, valine, citrulline, and derivatives thereof.

In some embodiments, each amino acid in $W_w$ is independently selected from the proteinogenic and the non-proteinogenic amino acids.

In some embodiments, each amino acid in $W_w$ is independently selected from L or D isomers of the following amino acids: alanine, β-alanine, arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, valine, citrulline, and derivatives thereof.

In some embodiments, each amino acid in $W_w$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, citrulline, or alanine.

In some embodiments, each amino acid in $W_w$ is independently selected from L-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $W_w$ is independently selected from D-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $W_w$ is alanine, β-alanine, glycine, glutamine, glutamic acid, isoglutamic acid, isoaspartic acid, valine citrulline, or aspartic acid.

In some embodiments, $W_w$ comprises β-alanine. In some embodiments, $W_w$ comprises (β-alanine)-(alanine). In some embodiments, $W_w$ comprises (β-alanine) and optionally glutamic acid, glutamine, isoglutamic acid, aspartic acid, isoaspartic acid, valine, (valine)-(alanine), (alanine)-(alanine), or (valine)-(citruline).

In some embodiments, $W_w$ comprises (glutamic acid)-(alanine).

In some embodiments, $W_w$ comprises (β-alanine)-(glutamine).

In some embodiments, $W_w$ comprises (β-alanine)-(glutamine))-(alanine).

In some embodiments, $W_w$ comprises glutamic acid and optionally alanine, glycine, isoglutamic acid, aspartic acid, isoaspartic acid, valine, (valine)-(alanine), (alanine)-(alanine), or (valine)-(citruline).

In some embodiments, $W_w$ comprises 2,3-diaminopropanoic acid. In some embodiments, $W_w$ comprises (R)-2,3-diaminopropanoic acid. In some embodiments, $W_w$ comprises glutamic acid. In some embodiments, $W_w$ comprises (glutamic acid)-(alanine). In some embodiments, $W_w$ comprises (glutamic acid)-(glycine)-(alanine).

In some embodiments, $W_w$ comprises L-glutamic acid, D-glutamic acid, (L-glutamic acid)-(L-alanine), (L-glutamic acid)-(D-alanine), (D-glutamic acid)-(L-alanine), (D-glutamic acid)-(D-alanine), (L-glutamic acid)-(glycine)-(L-alanine), D-glutamic acid)-(glycine)-(D-alanine), (L-glutamic acid)-(glycine)-(D-alanine), or (D-glutamic acid)-(glycine)-(L-alanine).

In some embodiments, $W_w$ comprises a carbamate bond in addition to one or more amino acids.

In some embodiments, $L^P$ (e.g., $W_w$) is selective for enzymatic cleavage (e.g., by a particular enzyme). In some embodiments, the particular enzyme is a tumor-associated protease.

In some embodiments, $L^P$ (e.g., $W_w$) comprises a bond whose cleavage is catalyzed by cathepsin B, C, and D, or a plasmin protease.

In some embodiments, $L^P$ comprises a sugar cleavage site.

In some embodiments, $L^P$ comprises a sugar moiety (Su) linked via an oxygen glycosidic bond to a self-immolative group.

In some embodiments, a "self-immolative group" can be a tri-functional chemical moiety that is capable of covalently linking together three spaced chemical moieties (i.e., the sugar moiety (via a glycosidic bond), a drug unit (directly or indirectly), and $M^A$ (directly or indirectly) when $M^A$ is present or $A^1$ when $M^A$ is absent.

In some embodiments, the glycosidic bond can be cleaved at the target site to initiate a self-immolative reaction sequence that leads to a release of the drug.

In some embodiments, each $L^P$, when present, independently is:

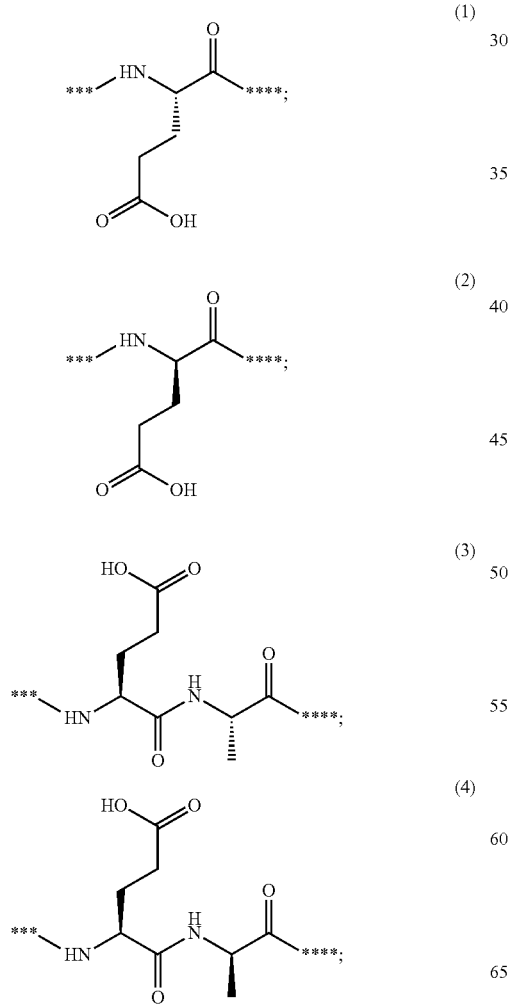

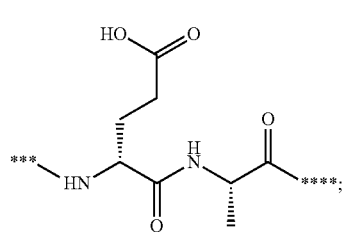

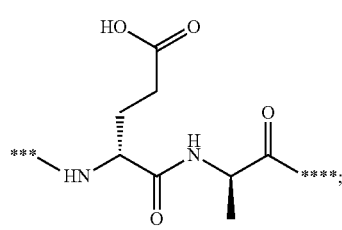

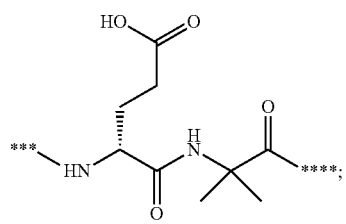

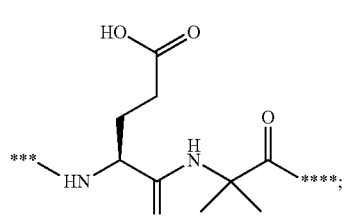

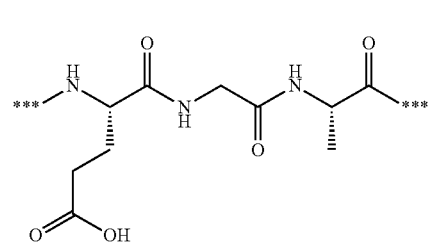

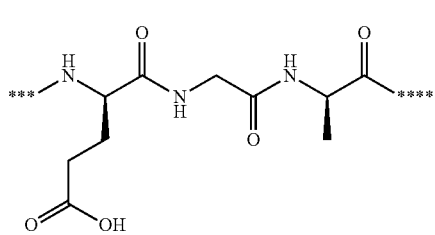

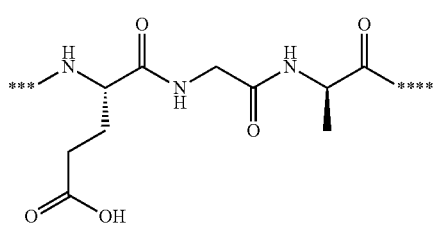

(12)
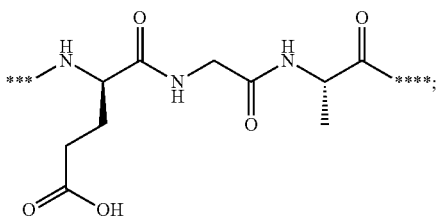
(13)
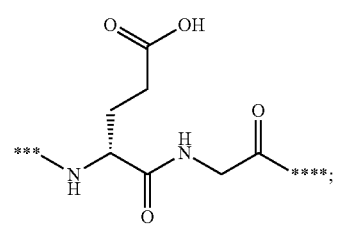
(14)
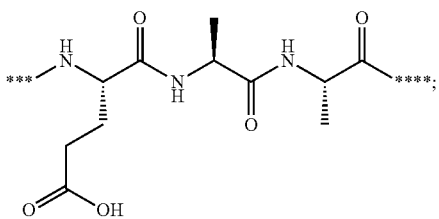
(15)
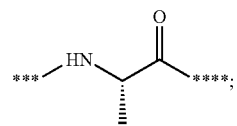
(16)
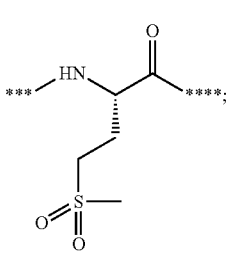
(17)
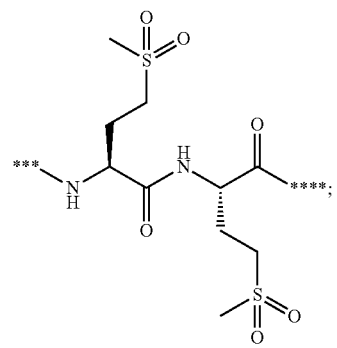
(18)
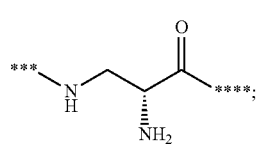
(19)
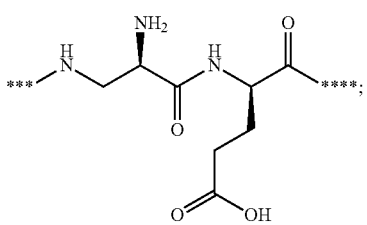
(20)
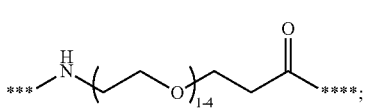
(21)
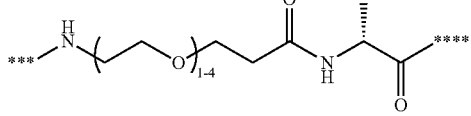
(22)
(23)
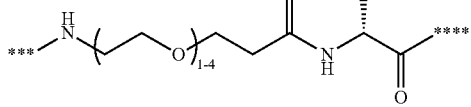
(24)
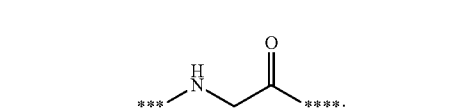
(25)
(26)
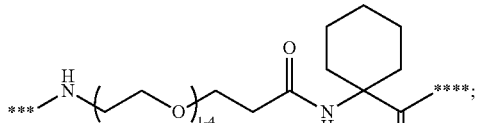
(27)

-continued
(28)
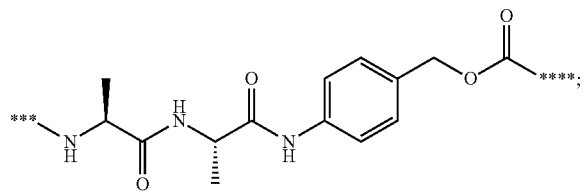
(29)
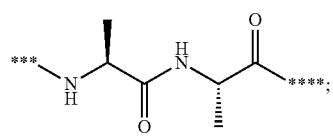
(30)
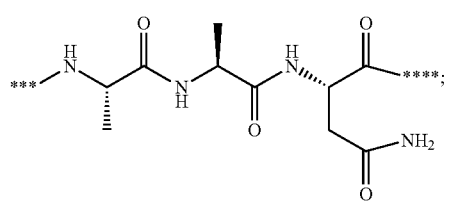
(31)
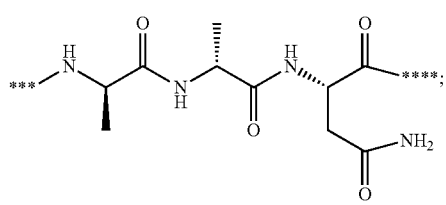
(32)
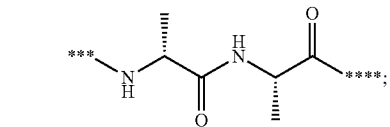
(33)
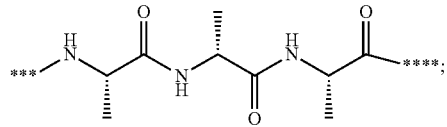
(34)
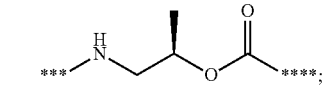
(35)
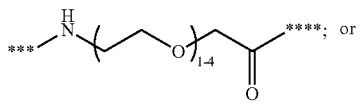
(36)
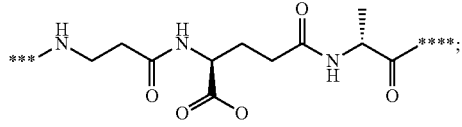
wherein:
\*\*\*denotes attachment to $M^A$; and
\*\*\*\*denotes attachment to D.
In some embodiments, each $L^D$, when present, independently is:
(1)
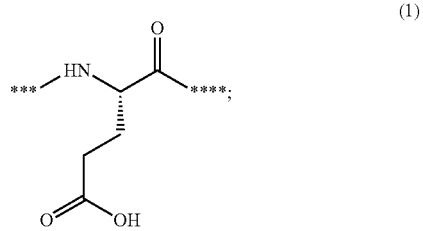
(2)
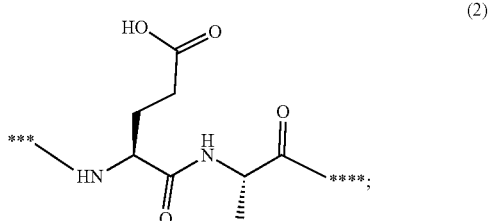
(3)
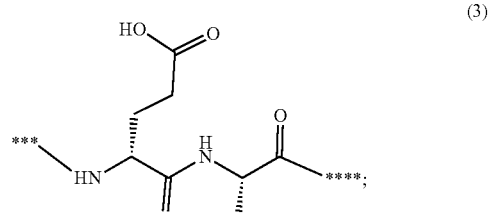
(4)
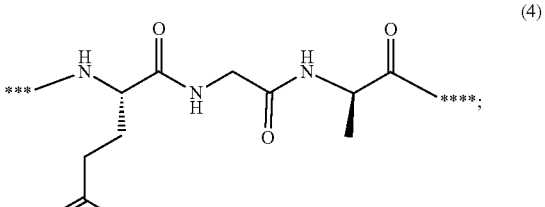
(5)
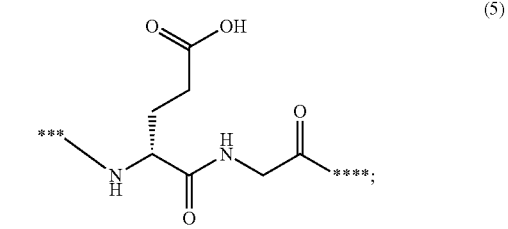
(6)
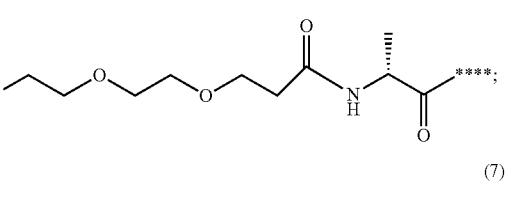
(7)
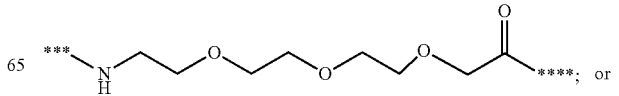; or (8)

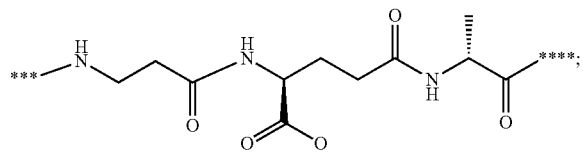

wherein:
***denotes attachment to $M^A$; and
****denotes attachment to D.

In some embodiments, each $L^D$, when present, independently is:

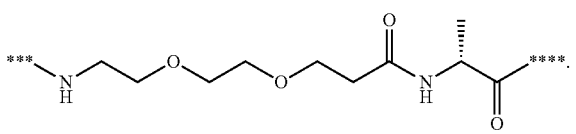

Therapeutic Agents, Drug Unit, or Variable D

In some embodiments, the therapeutic agent is a cytotoxic drug moiety. In some embodiments, the therapeutic agent is a STING agonist drug moiety In some embodiments, the cytotoxic drug moiety is a small molecule.

In some embodiments, the therapeutic agent has a molecular weight ≤about 5 kDa (e.g., having a molecular weight ≤about 4 kDa, ≤about 3 kDa, ≤about 1.5 kDa, or ≤about 1 kDa).

In some embodiments, the therapeutic agent has an $IC_{50}$ of about less than 1 nM. In some embodiments, the cytotoxic drug moiety or STING agonist drug moiety has an $IC_{50}$ of less than 1 nM.

In some embodiments, the therapeutic agent has an $IC_{50}$ of about greater than 1 nM, (e.g., the cytotoxic drug moiety or STING agonist drug moiety has an $IC_{50}$ of about 1 to 50 nM). In some embodiments, the therapeutic agent has an $IC_{50}$ of about greater than 1 nM. In some embodiments, the therapeutic agent has an $IC_{50}$ of greater than 1 nM, (e.g., the cytotoxic drug moiety or STING agonist drug moiety has an $IC_{50}$ of 1 to 50 nM). In some embodiments, the therapeutic agent has an $IC_{50}$ of greater than 1 nM.

In some embodiments, the therapeutic agent having an $IC_{50}$ of greater than about 1 nM (e.g., "less potent drugs") is unsuitable for conjugation with an antibody using art-recognized conjugation techniques. Without wishing to be bound by theory, such therapeutic agents (i.e., cytotoxic agents drug moieties or STING agonist drug moieties) have a potency that is insufficient for use in targeted antibody-drug conjugates using conventional techniques as sufficient copies of the drug (i.e., more than 8) cannot be conjugated using art-recognized techniques without resulting in diminished pharmacokinetic and physiochemical properties of the conjugate. In some embodiments, sufficiently high loadings of these less potent drugs can be achieved using the conjugation strategies described herein thereby resulting in high loadings of the therapeutic agent while maintaining the desirable pharmacokinetic and physiochemical properties. In some embodiments, the disclosure relates to an antibody-drug conjugate which includes an antibody, a scaffold, and at least eight therapeutic agents (i.e., cytotoxic agents drug moieties or STING agonist drug moieties), wherein the therapeutic agent has an $IC_{50}$ of greater than about 1 nM.

Cytotoxic Drug Moiety (Variable D)

In some embodiments, the therapeutic agent is a cytotoxic drug moiety. In some embodiments, the cytotoxic drug moiety is a derivative of (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase; (q) a PARP inhibitor; (r) a NAMPT inhibitor; (s) a topoisomerase inhibitor; (t) a protein synthesis inhibitor; (u) a DNA-binding drug; (v) a DNA intercalation drug; or (w) an immunomodulatory compound, as described in US 2018/0154018, the contents of which is hereby incorporated by reference in its entirety.

In some embodiments, the cytotoxic drug moiety is auristatin F-hydroxypropylamide-L-alanine.

In some embodiments, the auristatin is a compound of Formula (X):

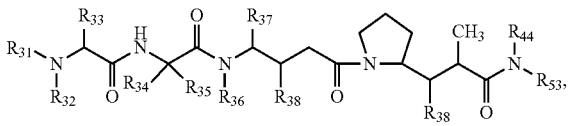

(X)

wherein:
each of $R_{31}$ and $R_{32}$ independently is hydrogen or $C_{1-8}$ alkyl and at most one of $R_{31}$ and $R_{32}$ is H;
$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle, or $X^1$—($C_{3-8}$ heterocycle);
$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle, or $X^1$—($C_{3-8}$ heterocycle);
$R_{35}$ is hydrogen or methyl;
or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;
$R_{36}$ is hydrogen or $C_{1-8}$ alkyl;
$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);
each $R_{38}$ independently is hydrogen, OH, $C_{1-8}$ alkyl, $C_{3-8}$ carbocycle or O—($C_{1-8}$ alkyl);
$R_{53}$ is:

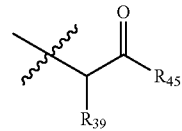

or $R_{54}$;
$R_{39}$ is hydrogen, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-NH$_2$, or $(CH_2)_2SCH_3$; each $X^1$ independently is $C_{1-10}$ alkylene or $C_{3-10}$ cycloalkylene;
$R_{44}$ is hydrogen or $C_{1-8}$ alkyl;
$R_{45}$ is $X^3$—$R_{42}$ or NH—$R_{19}$;
$X^3$ is O or S;
$R_{19}$ is hydrogen, OH, amino group, $C_{1-8}$ alkyl amino, or —$[C(R_{20}R_{21})]_a$—$R_{22}$;

$R_{42}$ is an amino group, $C_{1-6}$ alkyl amino, or $-[C(R_{20}R_{21})]_a-R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid; $R_{22}$ is $-OH$, $-NHR_{23}$, $-COOH$, $-R_{82}-C(O)(CH_2)_c-C(H)(R_{23})-N(H)(R_{23})$, $-R_{82}-C(O)(CH_2)_d-(O\ CH_2-CH_2)_f-N(H)(R_{23})$ or $-R_{82}-(C(O)-CH(X^2)-NH)_d-R_{77}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is $-NR_{23}$ or oxygen;

$R_{54}$ is $-C(R_{56})_2-C(R_{56})_2-C_{6-10}$ aryl, $-C(R_{56})_2-C(R_{56})_2-C_{3-8}$ heterocycle, or $-C(R_{56})_2-C(R_{56})_2-C_{3-8}$ carbocycle;

$R_{56}$ independently is H, OH, $C_{1-8}$ alkyl, $C_{3-8}$ carbocycle, $-O-C_{1-8}$ alkyl, $-O-C(O)-R_{29}$, or $-O-R_{23}-O-C_{1-6}$ alkyl-$NH_2$;

$R_{29}$ is an amino group, 5 to 12-membered heterocycloalkyl, $-R_{28}-C_{1-6}$ alkyl-$R_{22}$, $R_{28}-C_{5-12}$ heterocycloalkyl-$C_{1-6}$ alkyl-$R_{22}$, $-[C(R_{20}R_{21})]_a-R_{22}$, or $-R_{28}-C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments, in the auristatin compound of Formula (X): $R_{39}$ is benzyl or

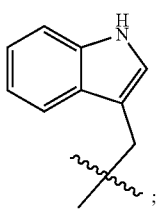 [SMILES: *Cc1c[nH]c2ccccc12]

and $R_{44}$ is hydrogen.

In some embodiments, the auristatin is a compound of Formula (Xa):

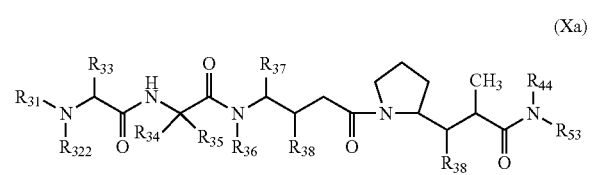

(Xa)

wherein:

$R_{33}$ through $R_{38}$, and $R_{44}$ are as defined herein, one of $R_{31}$ and $R_{32}$ is hydrogen or $C_{1-8}$ alkyl and the other is:

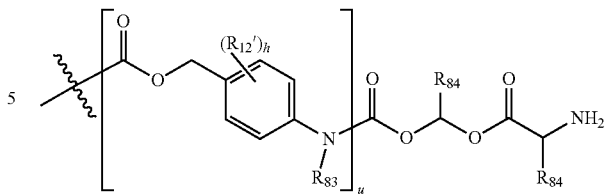

wherein:

$R_{83}$ is hydrogen or $CH_3$;

$R_{84}$ is $C_{1-6}$ alkyl or $C_{6-10}$ aryl;

each $R_{12}'$ independently is halogen, $-C_{1-8}$ alkyl, $-O-C_{1-8}$ alkyl, nitro, or cyano;

h is an integer from 0 to 4;

u is an integer 0 or 1;

$R_{53}$ is:

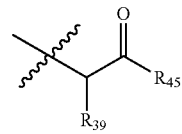

or $R_{54}$ $R_{39}$ is hydrogen, $C_{1-8}$ alkyl, $C_{6-10}$ aryl, $-X^1-C_{6-10}$ aryl, $C_{3-8}$ carbocycle, $C_{3-8}$ heterocycle, $-X^1-C_{3-8}$ heterocycle, $-C_{1-8}$ alkylene-$NH_2$, or $(CH_2)_2SCH_3$, each $X^1$ independently is $C_{1-10}$ alkylene or $C_{3-10}$ cycloalkylene;

$R_{45}$ is $X^3-R_{42}$ or $NH-R_{19}$;

$X^3$ is O or S;

$R_{19}$ is hydrogen, OH, amino group, $C_{1-8}$ alkyl amino, or $-[C(R_{20}R_{21})]_a-R_{22}$;

$R_{42}$ is hydrogen, an amino group, $C_{1-6}$ alkyl amino, or $-[C(R_{20}R_{21})]_a-R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

$R_{22}$ is $-OH$, $-NHR_{23}$, $-COOH$, $-R_{82}-C(O)(CH_2)_c-C(H)(R_{23})-N(H)(R_{23})$, $-R_{82}-C(O)(CH_2)_d-(O-CH_2-CH_2)_f-N(H)(R_{23})$, or $-R_{82}-(C(O)-CH(X^2)-NH)_a-R_{77}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is $-NR_{23}$ or oxygen;

$R_{54}$ is $-C(R_{56})_2-C(R_{56})_2-C_{6-10}$ aryl, $-C(R_{56})_2-C(R_{56})_2-C_{3-8}$ heterocycle, or $-C(R_{56})_2-C(R_{56})_2-C_{3-8}$ carbocycle;

$R_{56}$ independently is hydrogen, OH, $C_{1-8}$ alkyl, $C_{3-8}$ carbocycle, $-O-C_{1-8}$ alkyl, $-O-C(O)-R_{29}$, or $-O-R_{23}-O-C_{1-6}$ alkyl-$NH_2$;

$R_{29}$ is an amino group, 5 to 12-membered heterocycloalkyl, $-R_{28}-C_{1-6}$ alkyl-$R_{22}$, $R_{28}-C_{5-12}$ heterocycloalkyl-$C_{1-6}$ alkyl-$R_{22}$, $-[C(R_{20}R_{21})]_a-R_{22}$, or $-R_{28}-C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments, the auristatin compound of Formula (Xa) is a compound of Formula (XIa) or Formula (XIb):

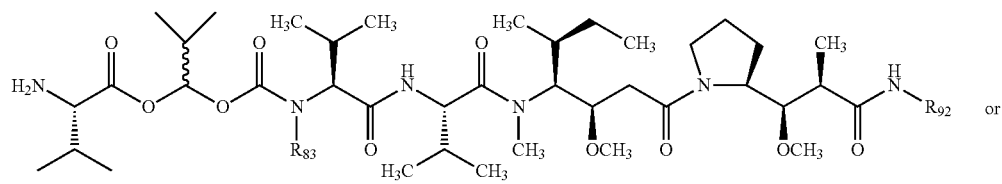
(XIa)
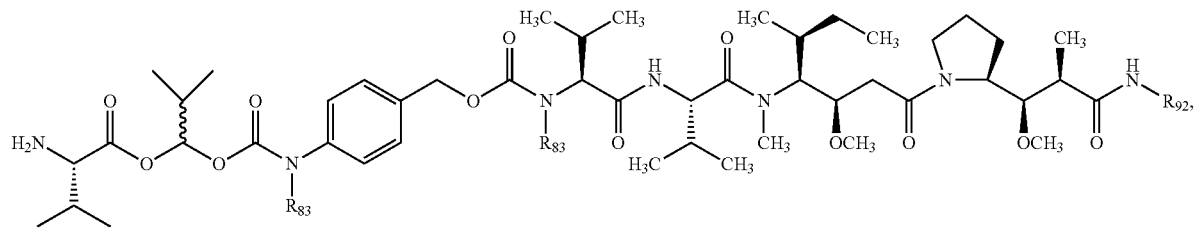
(XIb)
wherein:
$R_{92}$ is:
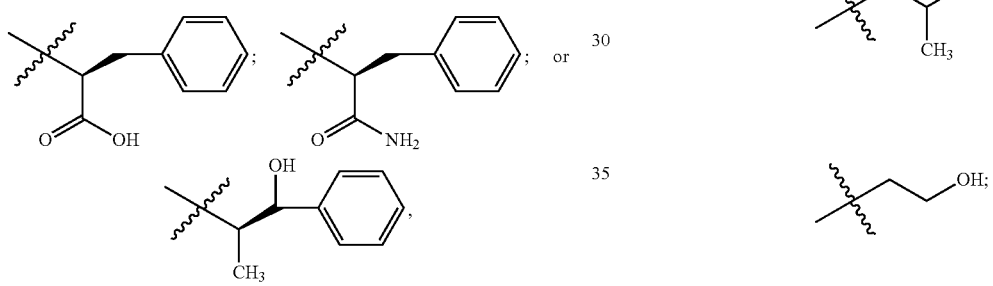
and
$R_{83}$ is hydrogen or $CH_3$.
In some embodiments, the auristatin of Formula (X) is a compound of Formula (XI), Formula (XII), or Formula (XIII):
wherein the compound of Formula (XI) is:
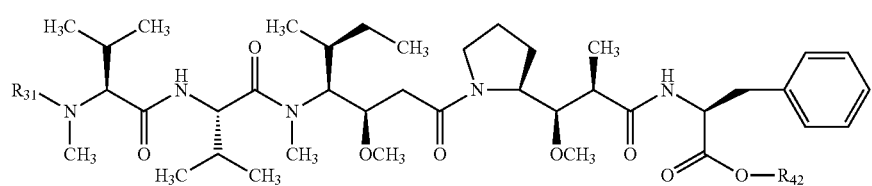
(XI)
wherein $R_{31}$ is hydrogen or $CH_3$ and $R_{42}$ is —$CH_3$ or any one of the following structures:
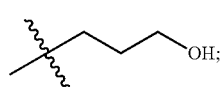
(1)
-continued
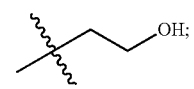
(2)
(3)
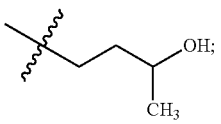
(4)
-continued
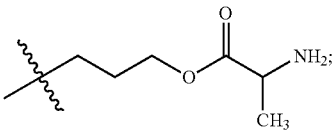
(5)

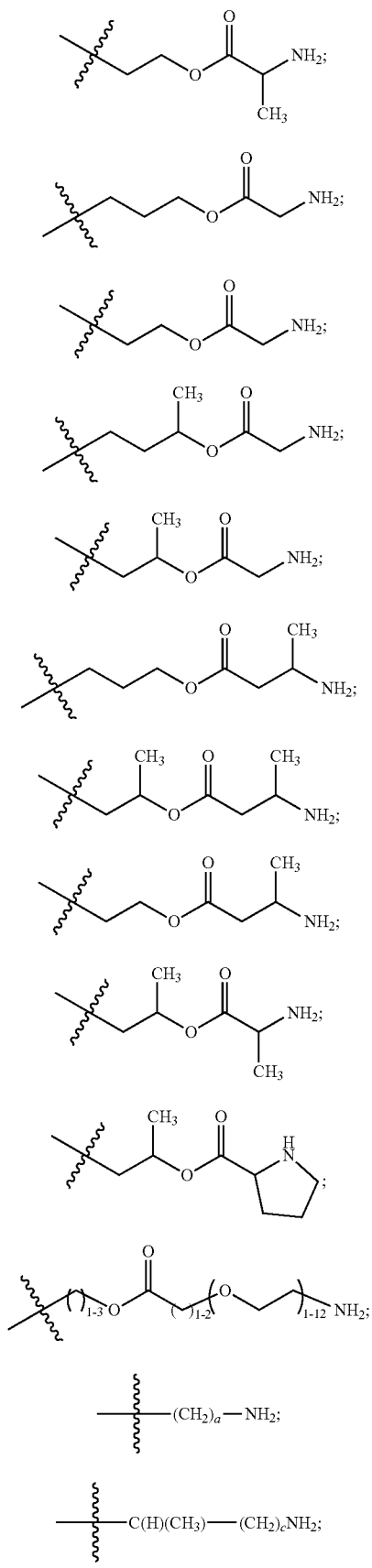
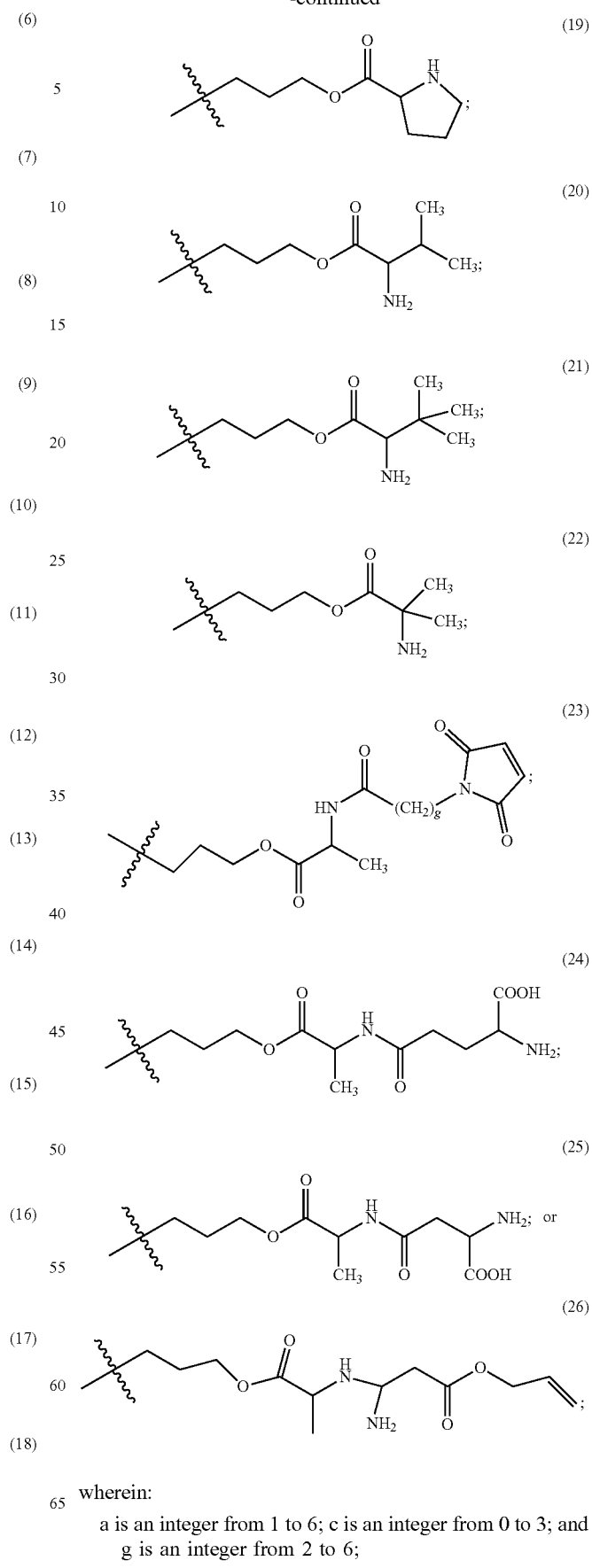
wherein:
a is an integer from 1 to 6; c is an integer from 0 to 3; and
g is an integer from 2 to 6;

wherein the compound of Formula (XII) is:
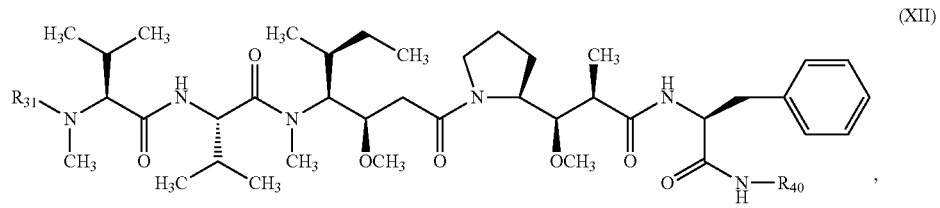
(XII)
wherein R$_{31}$ is hydrogen or CH$_3$ and R$_{40}$ is hydrogen, —OH, —NH$_2$, or any of the following structures:
(1)
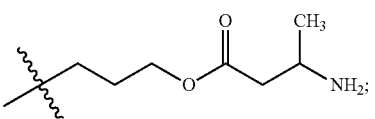
(2)
(3)
(4)
(5)
(6)
(7)
(8)
(9)
(10)
-continued
(11)
(12)
(13)
(14)
(15)
(16)
(17) —(CH$_2$)$_a$—NH$_2$;
(18) —C(H)(CH$_3$)—(CH$_2$)$_c$NH$_2$;
(19)
(20)

-continued

(21) 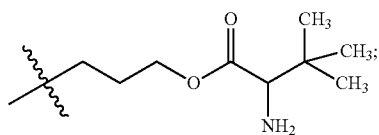

(22) 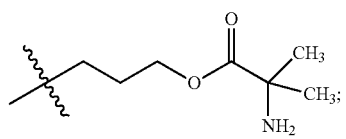

(23) 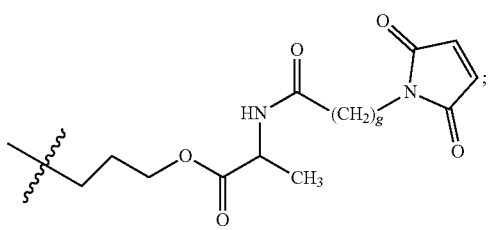

(24) 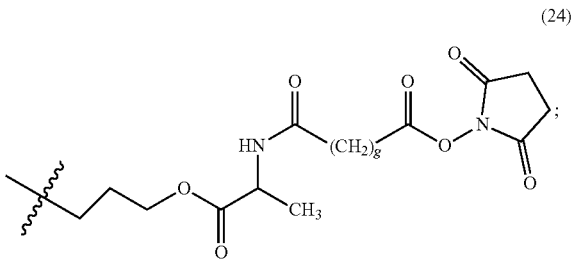

(25) 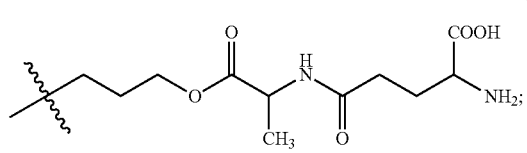

-continued

(26) 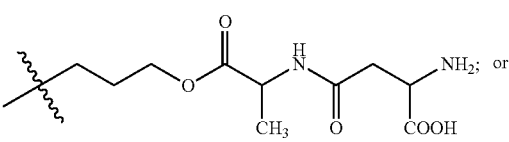

(27) 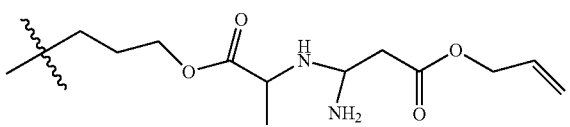

wherein:

a is an integer from 1 to 6; g is an integer from 2 to 6; and c is an integer from 0 to 3;

wherein the compound of Formula (XIII) is:

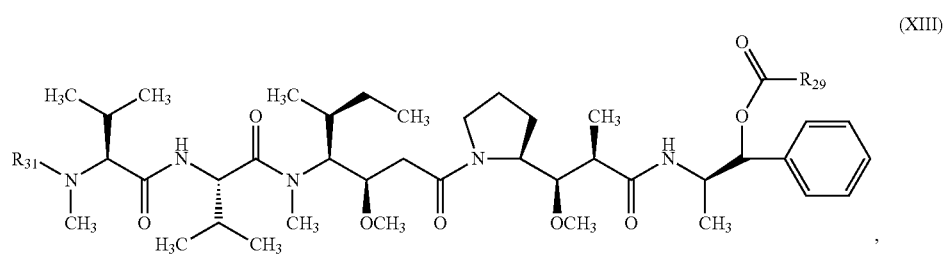

(XIII)

wherein:

$R_{31}$ is hydrogen or $CH_3$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—[$C(R_{20}R_{21})$]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid; $R_{22}$ is —OH, —NH$R_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(O CH$_2$—CH$_2$)$_f$—N(H)(R$_{23}$), or —$R_{82}$—(C(O)—CH(X$^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments of the Formula (XII), $R_{40}$ is
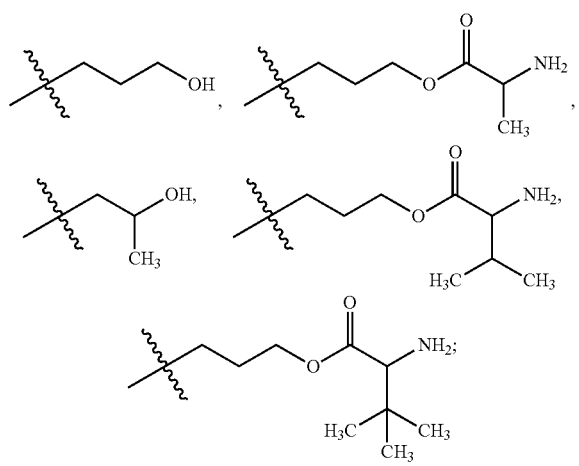
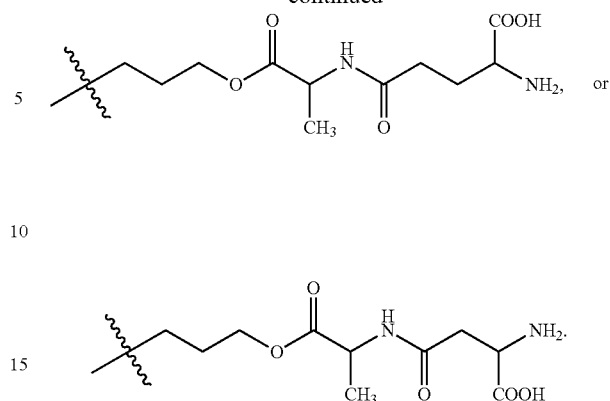
In some embodiments, the compound of Formula (XII) is a compound of Formula (XIIa), (XIIb), (XIIc), (XIId), (XIIe), (XIIf), (XIIg) or (XIIh):
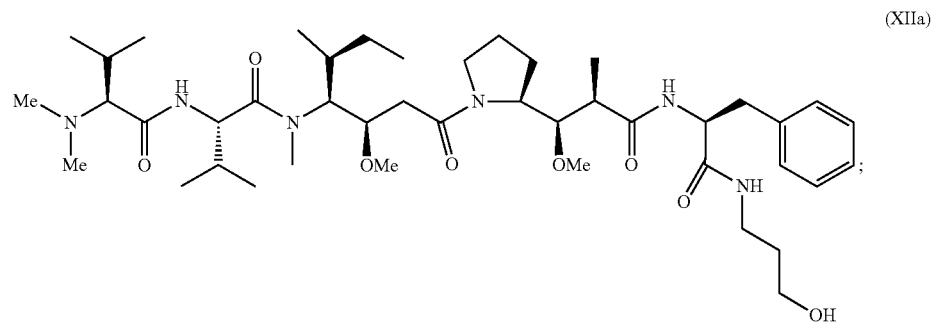
(XIIa)
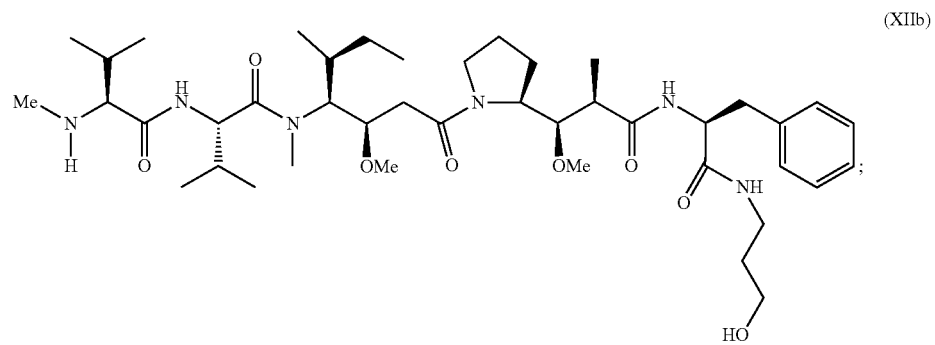
(XIIb)
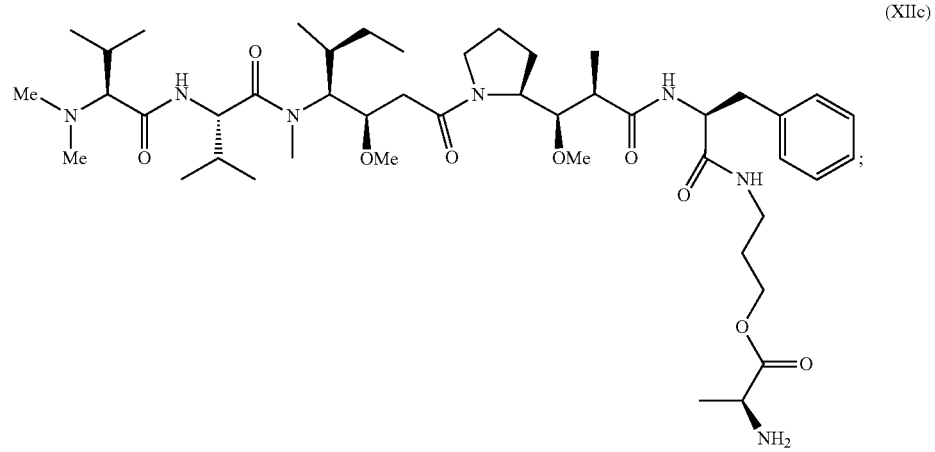
(XIIc)

(XIId)
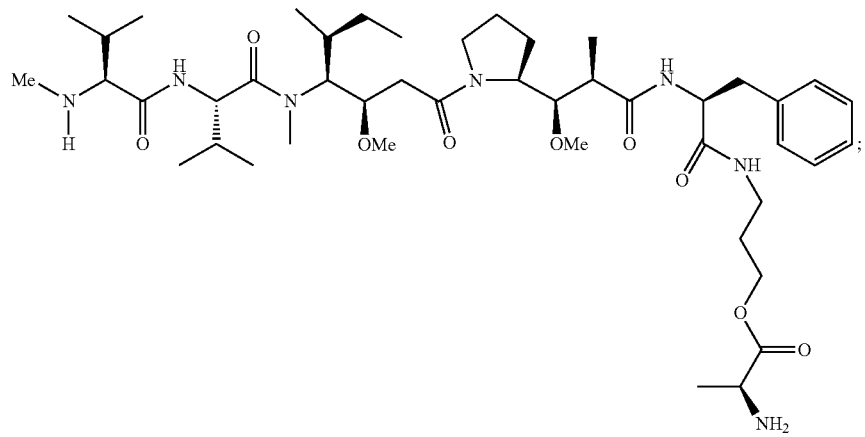
(XIIe)
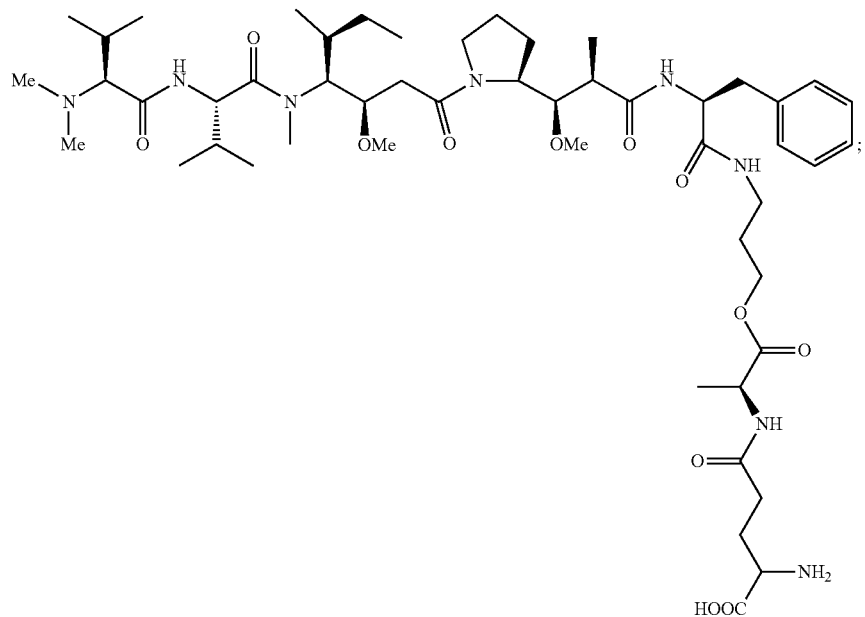
(XIIf)
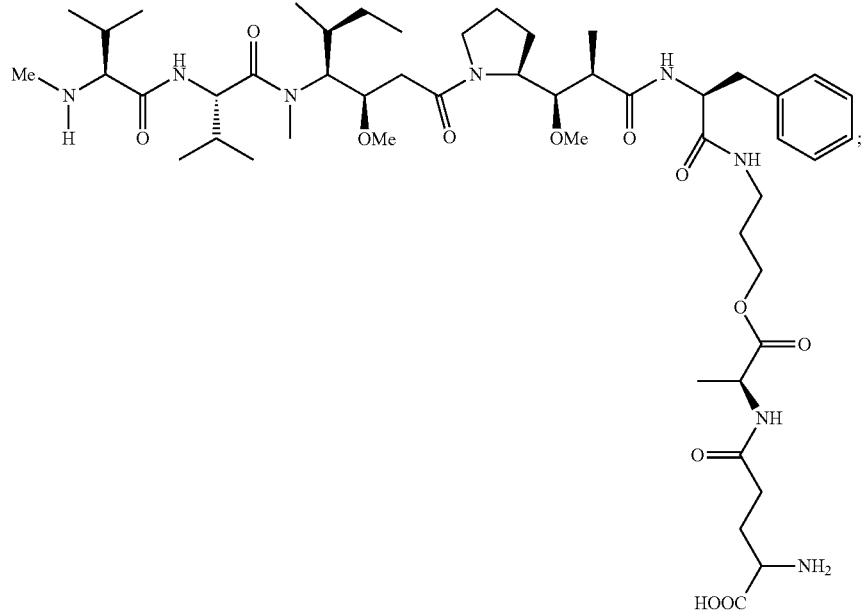

(XIIg)

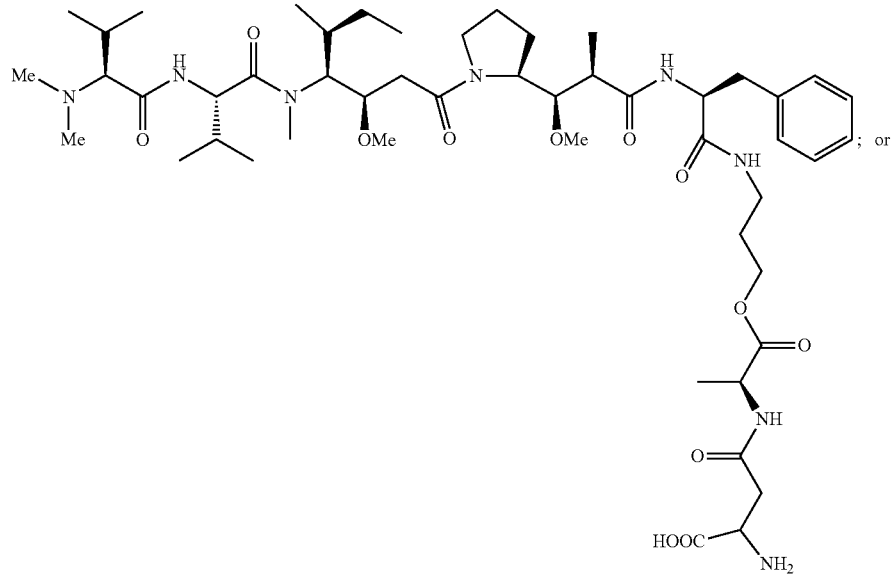

(XIIh)

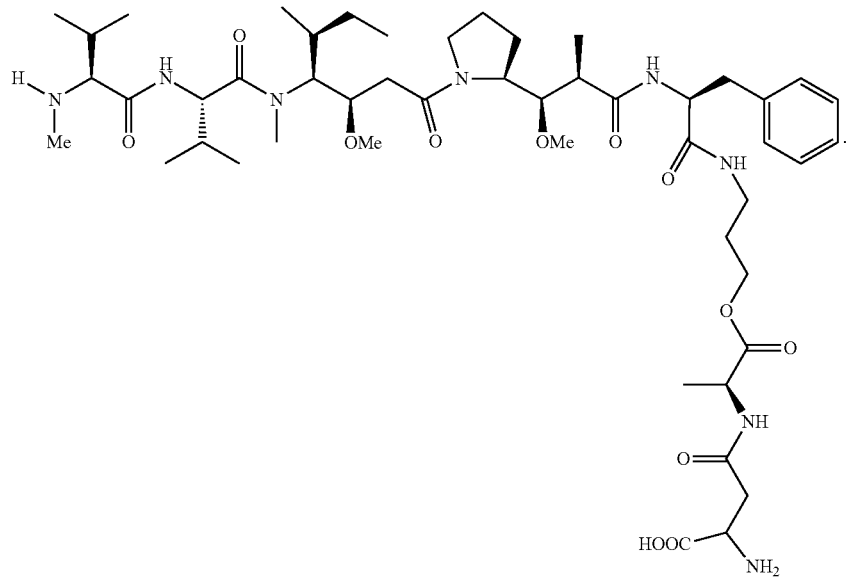

In some embodiments of the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$, or oxygen;

$R_{22}$ is —OH, —$NHR_{23}$, —COOH, —$R_{82}$—C(O)(CH$_2$)$_c$—C(H)($R_{23}$)—N(H)($R_{23}$), —$R_{82}$—C(O)(CH$_2$)$_d$—(O CH$_2$—CH$_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

c is an integer from 0 to 3; d is an integer from 1 to 3; and f is an integer from 1 to 12.

In some embodiments, $R_{29}$ is:

(1)

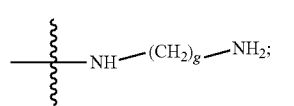

(2)

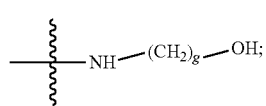

-continued
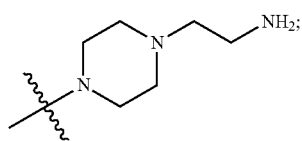 (3)
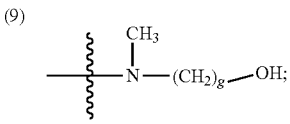 (4)
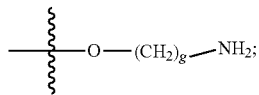 (5)
(6)
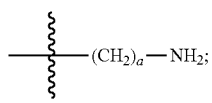 (7)
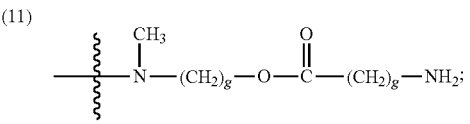 (8)
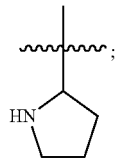 (9)
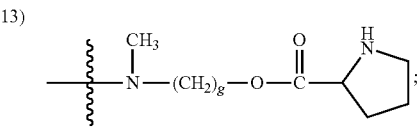 (10)
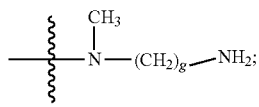 (11)
(12)
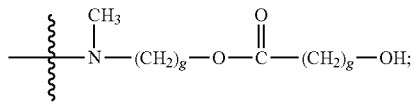 (13)
(14)
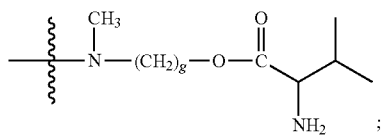 (15)
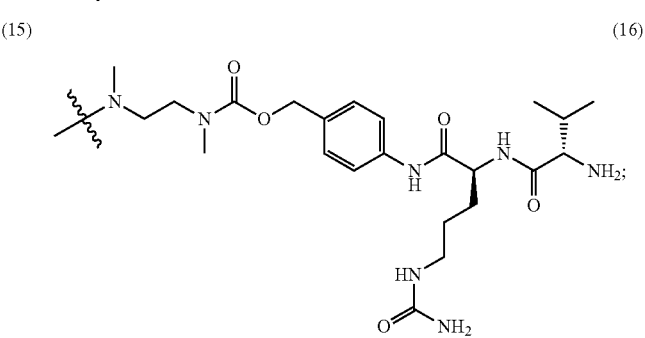 (16)
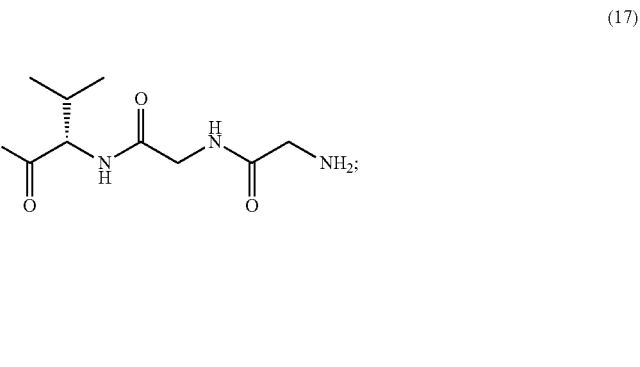 (17)

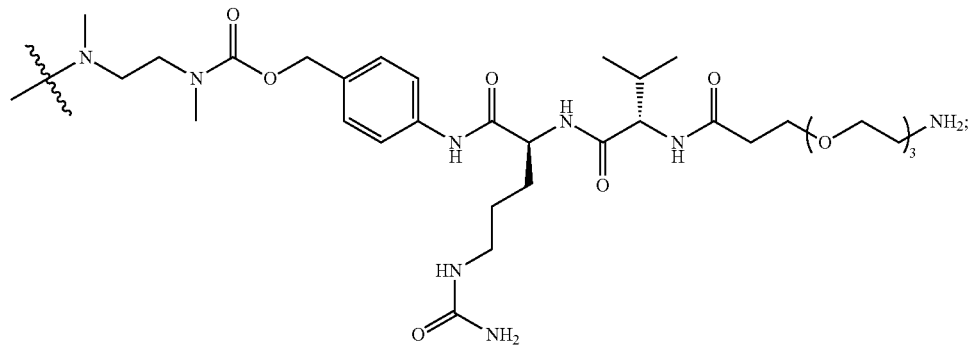
(18)
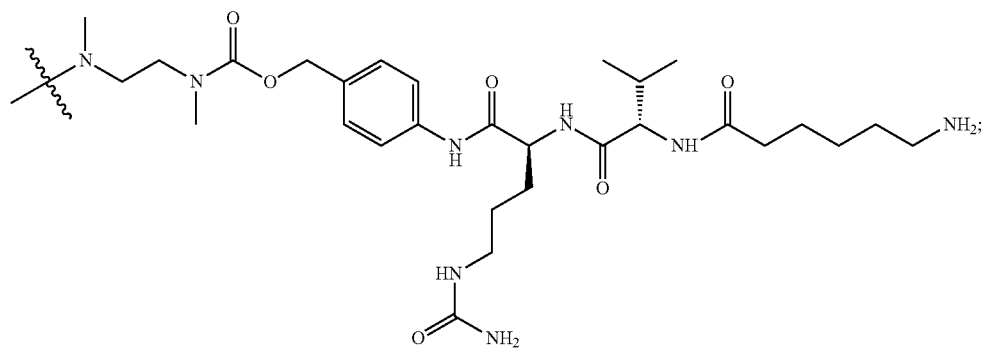
(19)
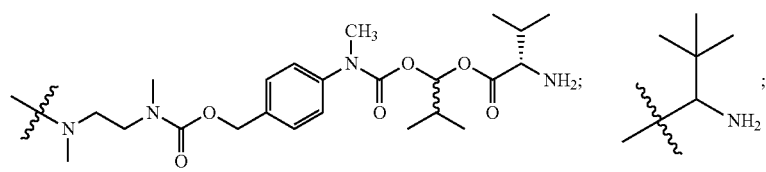
(20)
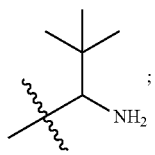
(21)
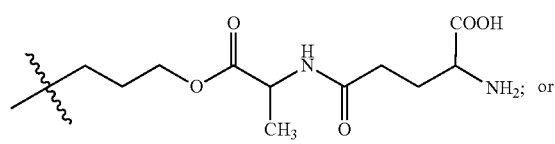
(22)
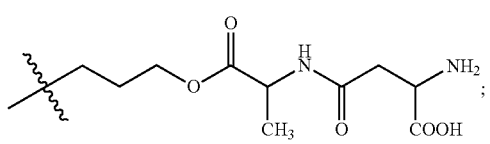
(23)
wherein:
a is an integer from 1 to 6; c is an integer from 0 to 3; and
g is an integer from 2 to 6.
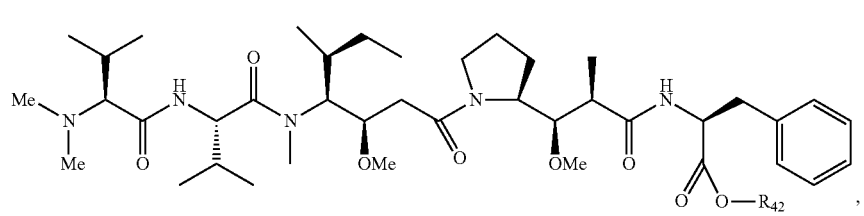
(XI)

wherein $R_{42}$ is H, —$CH_3$
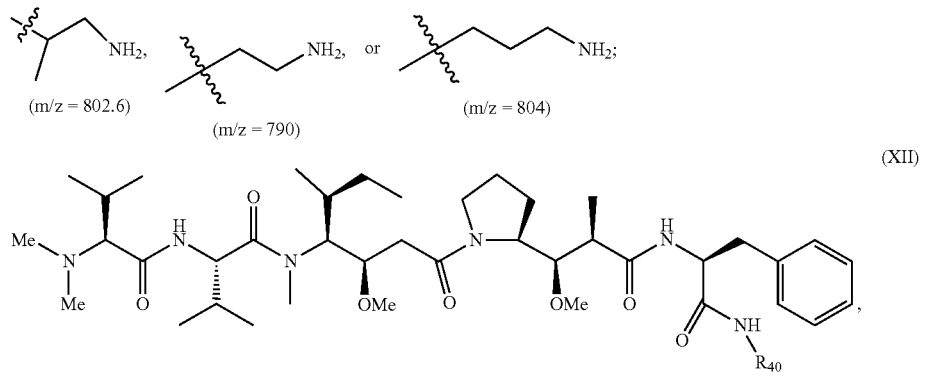
wherein R40 is H
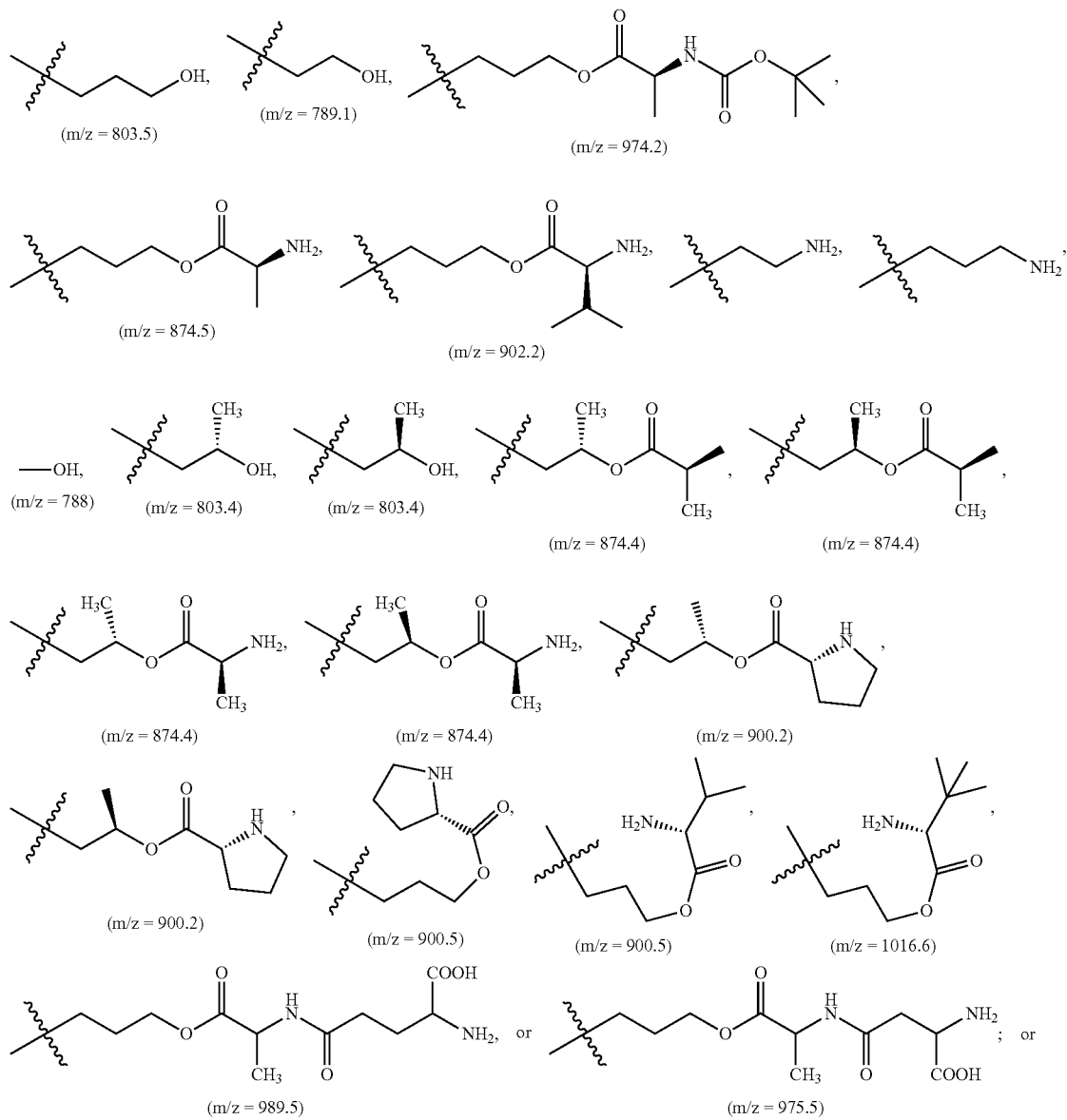

-continued

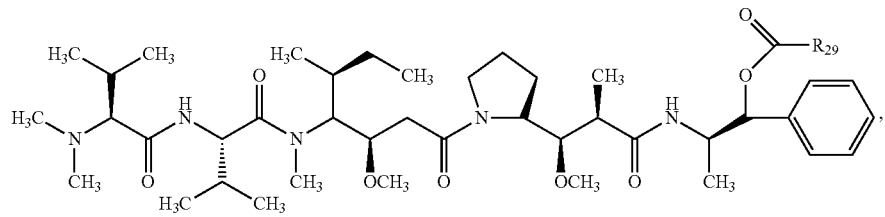
(XIII)

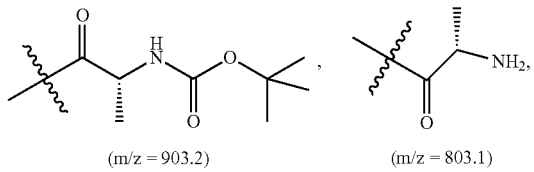

(m/z = 903.2)   (m/z = 803.1)

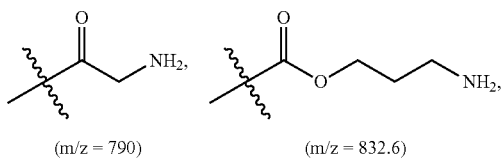

(m/z = 790)   (m/z = 832.6)

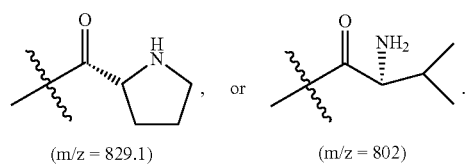

(m/z = 829.1)   (m/z = 802)

In some embodiments, the cytotoxic drug moiety (D) is:

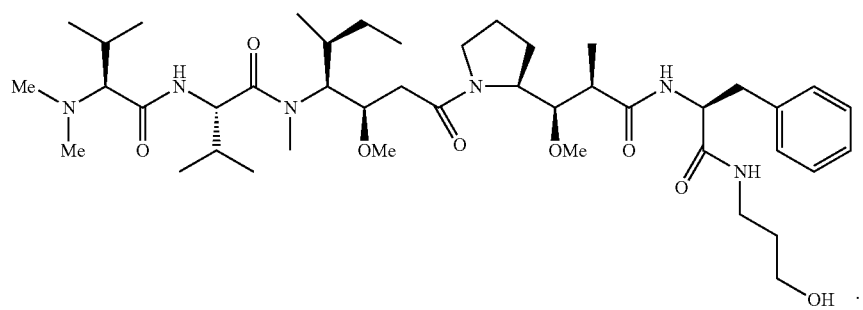 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCO)OC)N(C)C(=O)[C@@H](NC(=O)[C@H](C(C)C)N(C)C)C(C)C]

STING Agonist Drug Moiety (Variable D)

In some embodiments, the STING agonist drug moiety (D) is a compound of Formula (A):

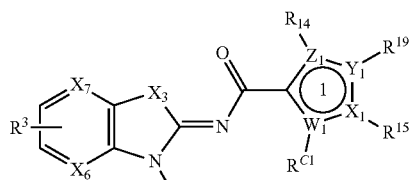

(A)

or a prodrug, solvate, pharmaceutically acceptable salt, or tautomer thereof, wherein:

$Y_1$, $Y_2$, $Z_1$ and $Z_2$ are each independently O, S, C or N;

$X_1$, $X_2$, $W_1$ and $W_2$ are each independently C or N;

$X_3$ and $X_4$ are each independently S or $NR^f$;

$X_5$ is N or $CR^{A2}$;

$X_6$ is N or $CR^{A1}$;

$X_7$ is N or $CR^4$;

R$^3$ and R$^5$ are each independently —CON(R$^d$)(R$^f$), —CH$_2$N(R$^d$)(R$^f$), —N(R$^d$)(R$^f$), —N(R$^d$)CO(R$^f$), —CH$_2$N(R$^d$)CO(R$^f$) or one of R$^3$ and R$^5$ is —CON(R$^d$)(R$^f$), —CH$_2$N(R$^d$)(R$^f$), —N(R$^d$)(R$^f$), —N(R$^d$)CO(R$^f$) or —CH$_2$N(R$^d$)CO(R$^f$), and the other of R$^3$ and R$^5$ is H, —COOH, or —CO$_2$(R$^c$);

R$^c$ is C$_{1-4}$ alkyl;

R$^{A2}$, R$^{A1}$, and R$^4$ are each independently H, halogen, hydroxy, amino, amino(C$_{1-4}$ alkyl)-, optionally substituted (C$_{1-6}$ alkyl), or optionally substituted (C$_{1-6}$ alkyl)oxy-, wherein C$_{1-6}$ alkyl of said optionally substituted (C$_{1-6}$ alkyl), or optionally substituted (C$_{1-6}$ alkyl)oxy- is optionally substituted with 1-4 substituents each independently selected from the group comprising hydroxyl, C$_{1-4}$ alkoxyl, —N(R$^e$)(R$^f$), —CO$_2$(R$^f$), —CON(R$^e$)(R$^f$), and —COOH;

each R$^d$ is independently H, hydroxy, or C$_{1-4}$ alkyl;

R$^e$ is selected from H, (C$_{1-4}$ alkyl), —CO(C$_{1-4}$ alkyl), —OCO(C$_{1-4}$ alkyl), and —CO$_2$(C$_{1-4}$ alkyl);

each R$^f$ is independently H, hydroxy, or (C$_{1-4}$ alkyl);

R$^{14}$ and R$^{C2}$ are each independently absent or C$_{1-4}$ alkyl, wherein C$_{1-4}$ alkyl is optionally substituted by a substituent selected from halogen, —OR$^c$, —NR$^c$R$^d$, —CO$_2$R$^c$, —CONR$^c$R$^d$, —SO$_2$NR$^c$R$^d$, and —OCONR$^c$R$^d$;

R$^{16}$ and R$^{C1}$ are each independently absent, H or C$_{1-4}$ alkyl; and

R$^{15}$, R$^{17}$, R$^{18}$, or R$^{19}$ are each independently absent, H, or C$_{1-4}$ alkyl, wherein C$_{1-4}$ alkyl is optionally substituted by a substituent selected from halogen, —OR$^c$, —NR$^c$R$^d$, —CO$_2$R, —CONR$^c$R$^d$, —SO$_2$NR$^c$R$^d$, and —OCONR$^c$R$^d$;

wherein: (i) at least one of R$^{A2}$ and R$^{A1}$ is present, and wherein at least one of R$^{A2}$ and R$^{A1}$ is directly or indirectly connected to L$^C$ when L$^C$ is present, or to A$^1$ when L$^C$ is absent, via at least one functional group of the R$^{A2}$ and/or R$^{A1}$; or (ii) at least one of R$^{C2}$ and R$^{C1}$ is present, and wherein at least one of R$^{C2}$ and R$^{C1}$ is directly or indirectly connected to L$^C$ when L$^C$ is present, or to A$^1$ when L$^C$ is absent, via at least one functional group of the R$^{C2}$ and/or R$^{C1}$.

In some embodiments, the STING agonist drug moiety (D) is a compound of Formula (A'):

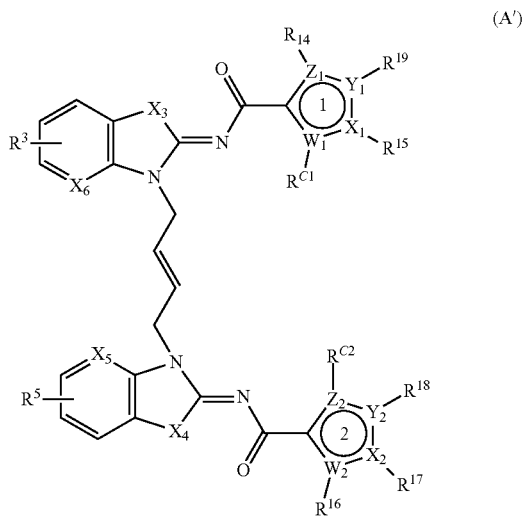

(A')

or a prodrug, solvate, pharmaceutically acceptable salt, or tautomer thereof, wherein Y$_1$, Y$_2$, Z$_1$, Z$_2$, X$_1$, X$_2$, W$_1$, W$_2$, X$_3$, X$_4$, X$_5$, X$_6$, R$^3$, R$^5$, R$^c$, R$^{A1}$, R$^{A2}$, R$^d$, R$^e$, R$^f$, R$^{14}$, R$^{C2}$, R$^{16}$, R$^{C1}$, R$^{15}$, R$^{17}$, R$^{18}$, and R$^{19}$ are as defined in Formula (A).

In some embodiments, the STING agonist drug moiety is a compound of Formula (A-a):

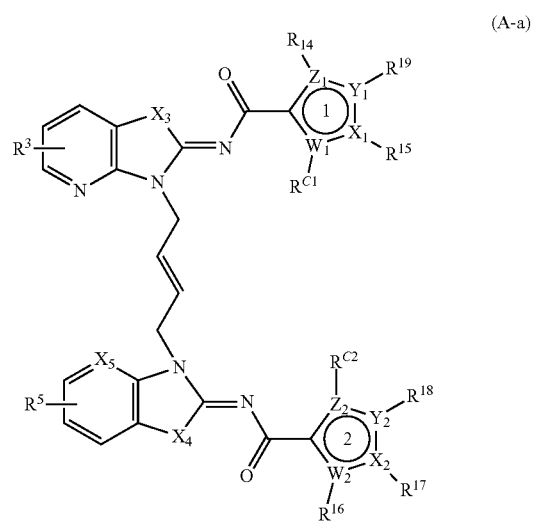

(A-a)

or a prodrug, solvate, pharmaceutically acceptable salt, or tautomer thereof, wherein:

Y$_1$, Y$_2$, Z$_1$, Z$_2$, X$_1$, X$_2$, W$_1$, W$_2$, X$_3$, X$_4$, R$^3$, R$^5$, R$^c$, R$^d$, R$^e$, R$^f$, R$^{14}$, R$^{C2}$, R$^{16}$, R$^{C1}$, R$^{15}$, R$^{17}$, R$^{18}$, and R$^{19}$ are as defined in Formula (A);

X$_5$ is CR$^{A2}$; and

R$^{A2}$ is halogen, hydroxyl, optionally substituted (C$_{1-6}$ alkyl), substituted (C$_{1-6}$ alkyl)oxy-, optionally substituted (C$_{1-6}$ alkyl)amino-, or optionally substituted (C$_{1-6}$ alkyl)(C$_{1-4}$ alkyl)amino-, wherein C$_{1-6}$ alkyl of said optionally substituted (C$_{1-6}$ alkyl) or substituted (C$_{1-6}$ alkyl)oxy- is optionally substituted with 1-4 substituents each independently selected from the group comprising hydroxyl, C$_{1-4}$ alkoxyl, —N(R$^e$)(R$^f$), —CO$_2$(R$^f$), —CON(R$^e$)(R$^f$), and —COOH;

wherein: (i) R$^{A2}$ is connected to L$^D$ via a functional group of R$_{A2}$; or (ii) at least one of R$^{C2}$ and R$^{C1}$ is present, and wherein at least one of R$^{C2}$ and R$^{C1}$ is connected to L$^D$ via at least one functional group of the R$^{C2}$ and/or R$^{C1}$.

In some embodiments, the STING agonist drug moiety is a compound is of Formula (A-b):

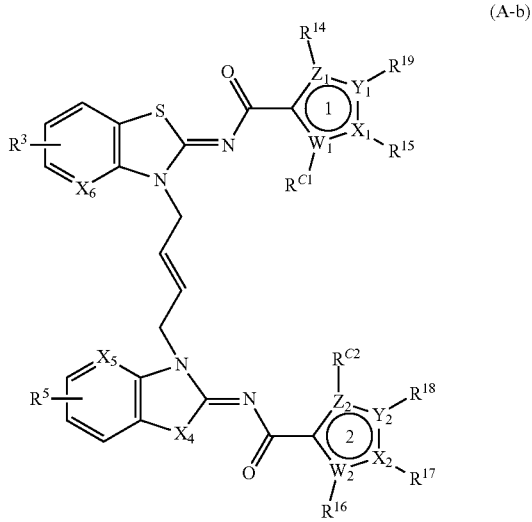

(A-b)

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_4$, $X_5$, $X_6$, $R^3$, $R^5$, $R^c$, $R^{A2}$, $R^{A1}$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$;

or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-c):

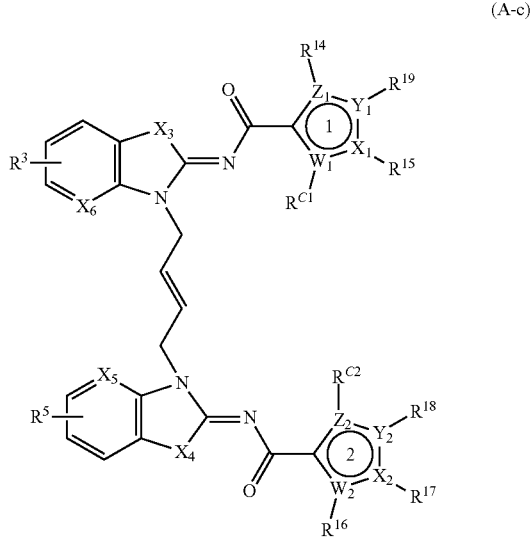

(A-c)

or a prodrug, solvate, pharmaceutically acceptable salt, or tautomer thereof, wherein:

$Y_2$, $Z_2$, $X_2$, $W_2$, $X_3$, $X_4$, $X_5$, $X_6$, $R^3$, $R^5$, $R^c$, $R^{A2}$, $R^{A1}$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

wherein one of $W_1$, $X_1$, $Y_1$, and $Z_1$ is N and the additional $W_1$, $X_1$, $Y_1$, and $Z_1$ are O, S, or C;

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$;

or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-d):

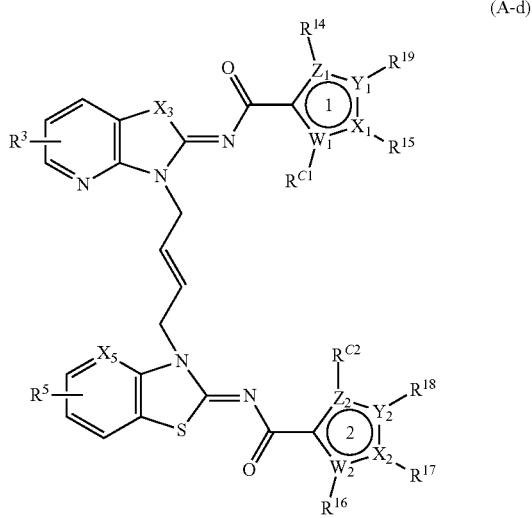

(A-d)

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_3$, $R^3$, $R^5$, $R^c$, $R^d$, $R^e$, $R^f$, $R^{14}$, $R^{A2}$, $R^{C2}$, $R^{16}$, $R^{C1}$, $R^{15}$, $R^{17}$, $R^{18}$, and $R^{19}$ are as defined in Formula (A);

$X_5$ is $CR^{A2}$; and wherein: (i) $R^{A2}$ is connected to $L^D$ via a functional group of $R_{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-e):

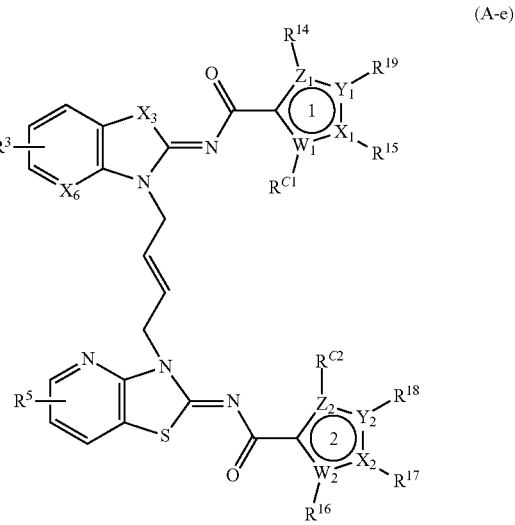

(A-e)

or a prodrug, solvate, pharmaceutically acceptable salt, or tautomer thereof, wherein:

$Y_1$, $Y_2$, $Z_1$, $Z_2$, $X_1$, $X_2$, $X_3$, $W_1$, $W_2$, $R^{A1}$, $R^3$, $R^5$, $R^c$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

$X_6$ is $CR^{A1}$; and wherein: (i) $R^{A1}$ is connected to $L^D$ via a functional group of $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f):

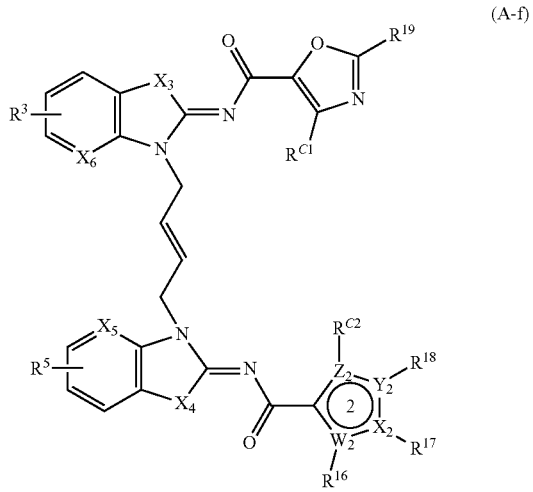

(A-f)

or a prodrug, solvate, pharmaceutically acceptable salt, or tautomer thereof, wherein:

$X_2$, $X_3$, $X_4$, $X_5$, $X_6$, $W_2$, $Y_2$, $Z_2$ $R^3$, $R^5$, $R^c$, $R_{A2}$, $R^{A1}$, $R^d$, $R^e$, $R^f$, $R^{16}$, $R^{17}$, $R^{18}$, $R^{19}$, $R^{C2}$, and $R^{C1}$, are as defined in Formula (A), and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f1):

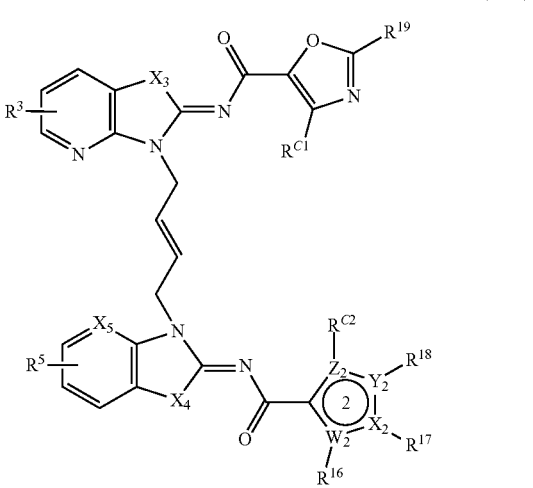

(A-f1)

or a prodrug, solvate, pharmaceutically acceptable salt, or tautomer thereof, wherein:

$X_2$, $X_3$, $X_4$, $W_2$, $Y_2$, $Z_2$, $R^3$, $R^5$, $R^c$, $R^d$, $R^e$, $R^f$, $R^{16}$, $R^{42}$, $R^{17}$, $R^{18}$, $R^{19}$, $R^{C2}$, and $R^{C1}$, are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f2):

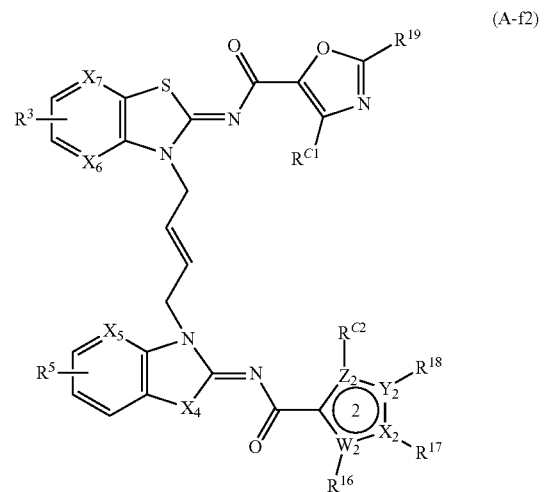

(A-f2)

or a prodrug, solvate, pharmaceutically acceptable salt, or tautomer thereof, wherein:

$X_2$, $X_4$, $X_5$, $X_6$, $X_7$, $W_2$, $Y_2$, $Z_2$ $R^3$, $R^5$, $R^c$, $R_{A2}$, $R^{A1}$, $R^4$, $R^d$, $R^e$, $R^{C1}$, $R^{C2}$, $R^{16}$, $R^{17}$, $R^{18}$, $R^{19}$, and $R^f$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f3):

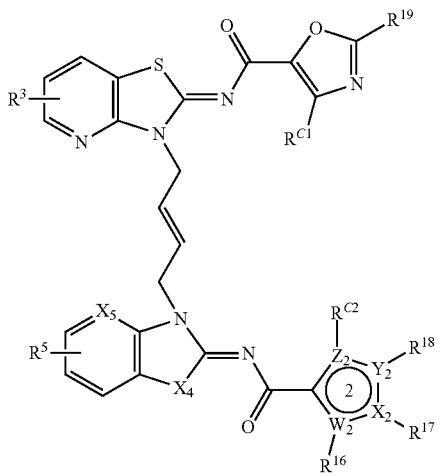

(A-f3)

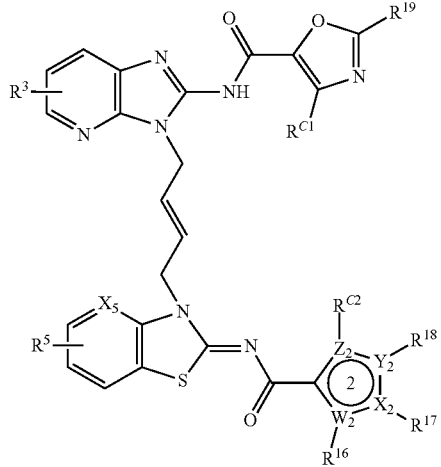

(A-f5)

or a prodrug, solvate, pharmaceutically acceptable salt, or tautomer thereof, wherein:
$X_2$, $X_4$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);
$X_5$ is $CR^{A2}$; and
wherein: (i) $R^{A2}$ is connected to $L^D$ via a functional group of $R_{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f4):

or a prodrug, solvate, pharmaceutically acceptable salt, or tautomer thereof, wherein:
$X_2$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);
$X_5$ is $CR^{A2}$; and
wherein: (i) $R^{A2}$ is connected to $L^D$ via a functional group of $R_{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f6):

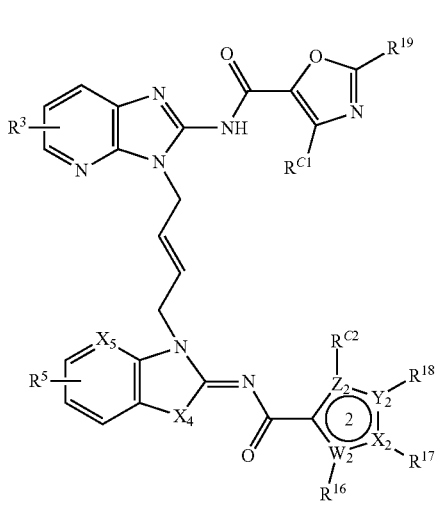

(A-f4)

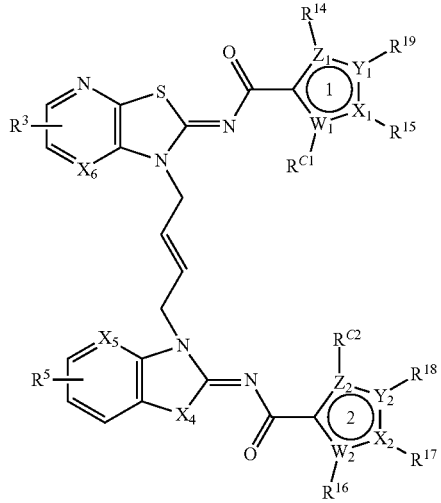

(A-f6)

or a prodrug, solvate, pharmaceutically acceptable salt, or tautomer thereof, wherein:
$X_2$, $X_4$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);
$X_5$ is $CR^{A2}$; and
wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f5):

or a prodrug, solvate, pharmaceutically acceptable salt, or tautomer thereof, wherein:
$Y_1$, $Y_2$, $Z_1$, $Z_2$, $X_1$, $X_2$, $W_1$, $W_2$, $X_4$, $X_5$, $X_6$, $R^3$, $R^5$, $R^c$, $R^{A2}$, $R^{A1}$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);
wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f7):

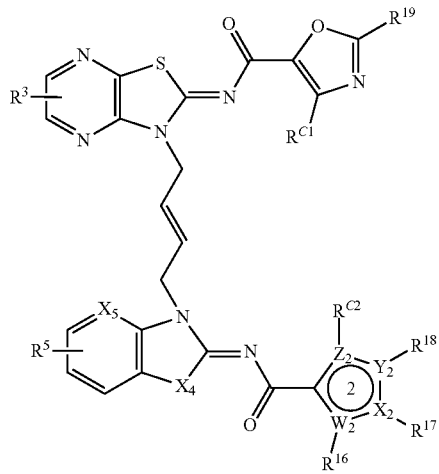
(A-f7)

or a prodrug, solvate, pharmaceutically acceptable salt, or tautomer thereof, wherein:
$X_2$, $X_4$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);
$X_5$ is $CR^{A2}$; and
wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g):

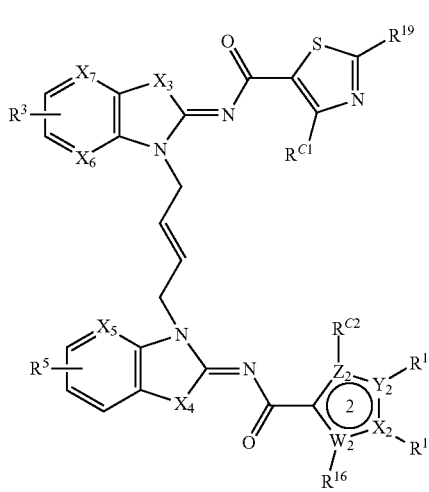
(A-g)

or a prodrug, solvate, pharmaceutically acceptable salt, or tautomer thereof, wherein:
$X_3$, $X_4$, $X_5$, $X_6$, $X_7$, $R^3$, $R^5$, $R^c$, $R_{A2}$, $R^{A1}$, $R^4$, $R^{C2}$, $R^{17}$, $R^{18}$, $R^{19}$, $R^d$, $R^e$, $R^f$, $R^{16}$, and $R^{C1}$ are as defined in Formula (A);
$Y_2$ and $Z_2$ are each independently O, S, C or N;
$X_2$ and $W_2$ are each independently C or N;
wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$;
or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g1):

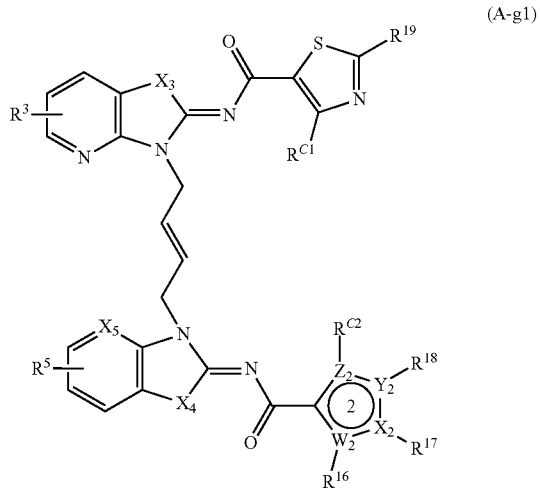
(A-g1)

or a prodrug, solvate, pharmaceutically acceptable salt, or tautomer thereof, wherein:
$X_2$, $W_2$, $Y_2$, $Z_2$, $X_3$, $X_4$, $X_5$, $R^3$, $R^5$, $R^c$, $R^d$, $R^f$, $R^{A2}$, $R^{C2}$, $R^{17}$, $R^{18}$, $R^{19}$, $R^{16}$, and $R^{C1}$ are as defined in Formula (A); wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g2):

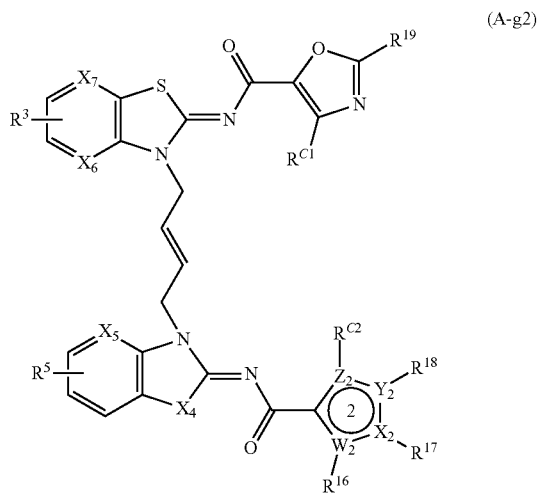
(A-g2)

or a prodrug, solvate, pharmaceutically acceptable salt, or tautomer thereof, wherein:
$X_2$, $X_4$, $X_5$, $X_6$, $X_7$, $W_2$, $Y_2$, $Z_2$, $R^3$, $R^5$, $R^c$, $R^{A2}$, $R^{A1}$, $R^4$, $R^{C2}$, $R^{17}$, $R^{18}$, $R^{19}$, $R^d$, $R^e$, $R^f$, $R^{16}$, and $R^{C1}$ are as defined in Formula (A);
wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$;
or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g3):

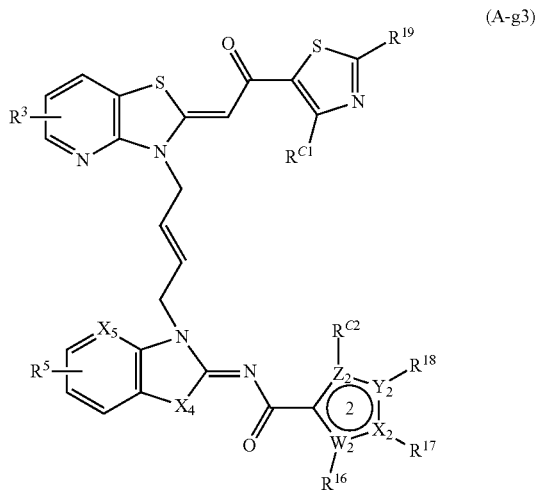

(A-g3)

or a prodrug, solvate, pharmaceutically acceptable salt, or tautomer thereof, wherein:
$X_2$, $X_4$, $W_2$, $Y_2$, $Z_2$, $R^3$, $R^5$, $R^c$, $R^{A2}$, $R^{C2}$, $R^{17}$, $R^{18}$, $R^{19}$, $R^{16}$, and $R^{C1}$ are as defined in Formula (A);
$X_5$ is $CR^{A2}$; and
wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$; and
optionally, wherein $R^{A2}$ is connected to $L^D$ via a functional group of $R^{A2}$.

In some embodiments, the STING agonist drug moiety is a compound is of Formula (A-g4):

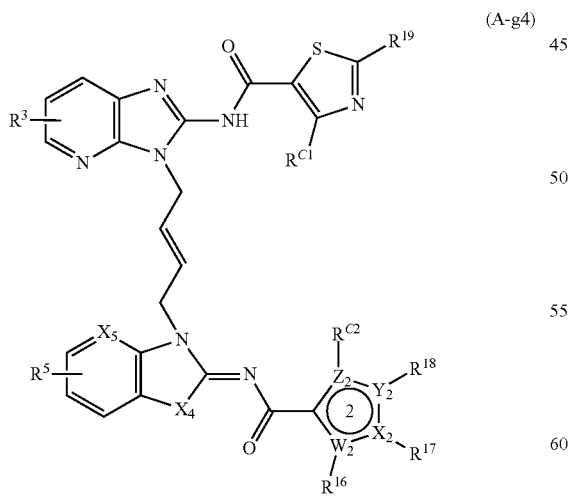

(A-g4)

or a prodrug, solvate, pharmaceutically acceptable salt, or tautomer thereof, wherein:
$X_2$, $X_4$, $W_2$, $Y_2$, $Z_2$ $R^3$, $R^5$, $R^c$, $R^d$, $R^e$, $R^f$, $R^{A2}$, $R^{C2}$, $R^{17}$, $R^{18}$, $R^{19}$, $R^{16}$, and $R^{C1}$ are as defined in Formula (A);

$X_5$ is $CR^{A2}$; and
wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g5):

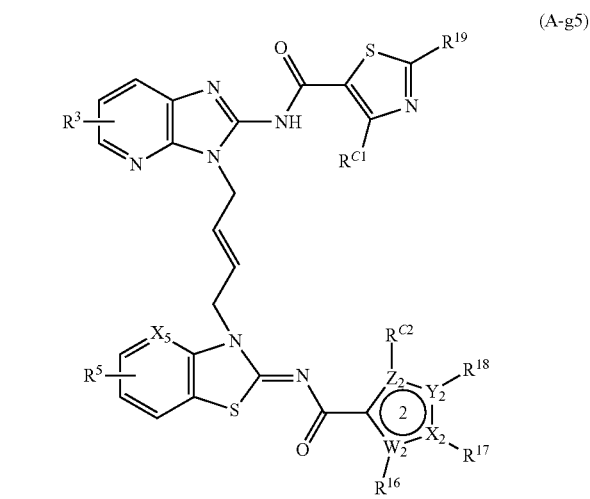

(A-g5)

or a prodrug, solvate, pharmaceutically acceptable salt, or tautomer thereof, wherein:
$X_2$, $W_2$, $Y_2$, $Z_2$, $R^3$, $R^5$, $R^c$, $R^d$, $R^e$, $R^f$, $R^{A2}$, $R^{C2}$, $R^{17}$, $R^{18}$, $R^{19}$, $R^{16}$, and $R^{C1}$ are as defined in Formula (A);
$X_5$ is $CR^{A2}$; and
wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g6):

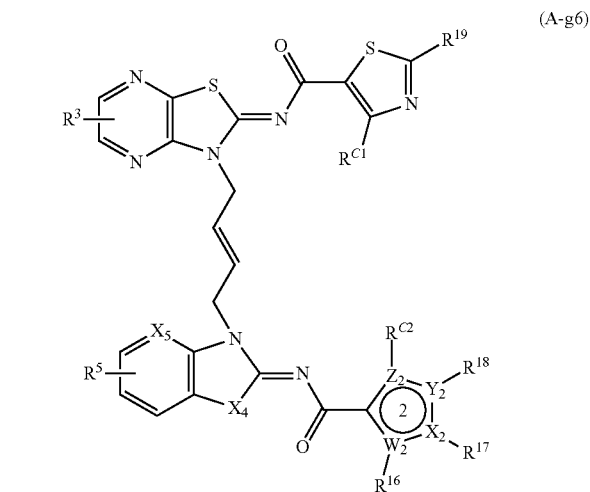

(A-g6)

or a prodrug, solvate, pharmaceutically acceptable salt, or tautomer thereof, wherein:
$X_2$, $X_4$, $W_2$, $Y_2$, $Z_2$, $R^3$, $R^5$, $R^c$, $R^{A2}$, $R^{C2}$, $R^{17}$, $R^{18}$, $R^{19}$, $R^{16}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$; and optionally, wherein $R^{A2}$ is connected to $L^D$ via a functional group of $R^{A2}$.

In some embodiments, the STING agonist drug moiety is a compound is of Formula (A-h):

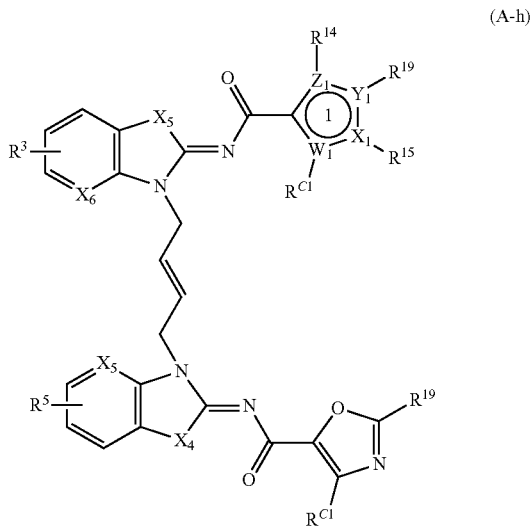

(A-h)

or a prodrug, solvate, pharmaceutically acceptable salt, or tautomer thereof, wherein:

$X^1$, $W_1$, $Y_1$, $Z_1$, $X_3$, $X_4$, $X_5$, $X_6$, $R^3$, $R^5$, $R^c$, $R^{A2}$, $R^{A1}$, $R^d$, $R^e$, $R^f$, $R^{14}$, $R^{15}$, $R^{18}$, $R^{19}$, $R^{16}$, and $R^{C1}$ are as defined in Formula (A); wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-h1):

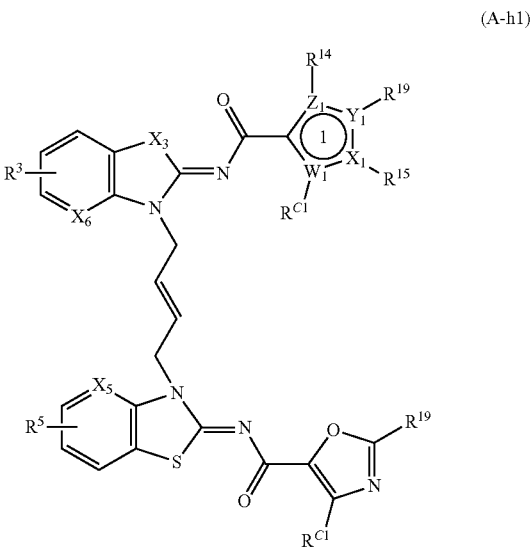

(A-h1)

or a prodrug, solvate, pharmaceutically acceptable salt, or tautomer thereof, wherein:

$X_1$, $X_3$, $W_1$, $Y_1$, $Z_1$, $X_5$, $X_6$, $R^3$, $R^5$, $R^c$, $R^{A2}$, $R^{A1}$, $R^d$, $R^e$, $R^f$, $R^{14}$, $R^{15}$, $R^{18}$, $R^{19}$, $R^{16}$, and $R^{C1}$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-h2):

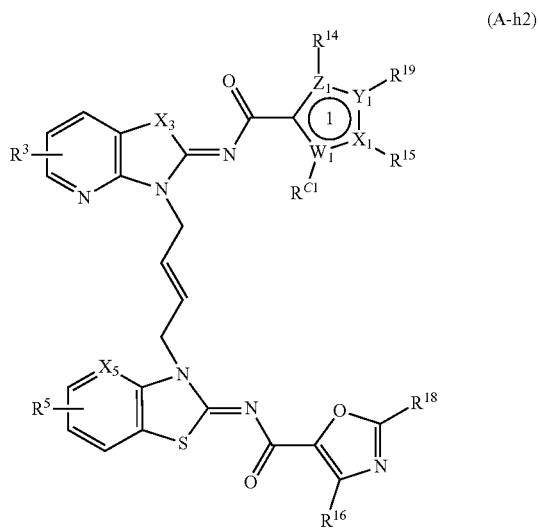

(A-h2)

or a prodrug, solvate, pharmaceutically acceptable salt, or tautomer thereof, wherein:

$X_1$, $X_3$, $W_1$, $Y_1$, $Z_1$, $R^3$, $R^5$, $R^c$, $R^d$, $R^e$, $R^f$, $R^{A2}$, $R^{14}$, $R^{15}$, $R^{18}$, $R^{19}$, $R^{16}$, and $R^{C1}$ are as defined in Formula (A);

$X_5$ is $CR^{A2}$; and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety (D) is a compound of Formula (A), wherein the compound is of Formula (A-i):

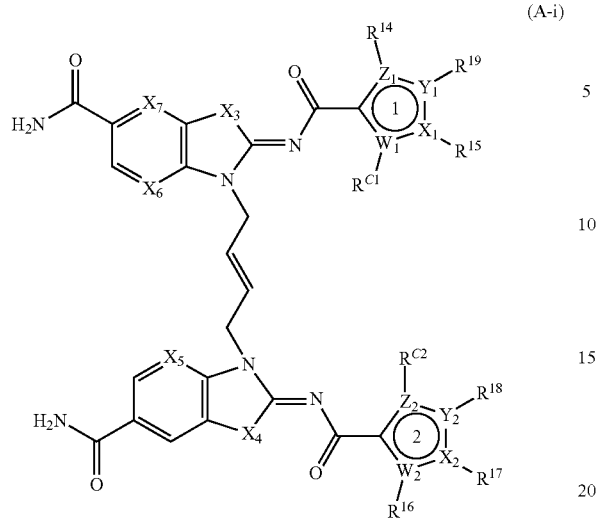

(A-i)

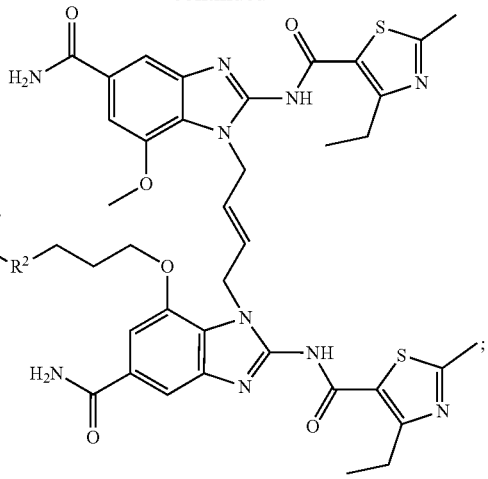

-continued or a prodrug, solvate, pharmaceutically acceptable salt, or tautomer thereof, wherein:

$Y_1$, $Y_2$, $Z_1$, $Z_2$, $X_1$, $X_2$, $X_3$, $X_6$, $X_7$, $W_1$, $W_2$, $R^{A1}$, $R^{A2}$, $R^4$, $R^c$, $R^d$, $R^e$, $R^f$, $R^{14}$, $R^{C2}$, $R^{16}$, $R_{C1}$, $R^{15}$, $R^{17}$, $R^{18}$, and $R^{19}$ are as defined in Formula (A); and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, each STING agonist drug moiety (D) independently is:

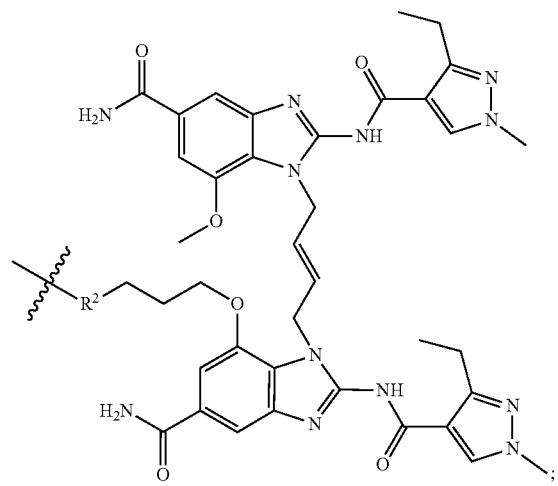

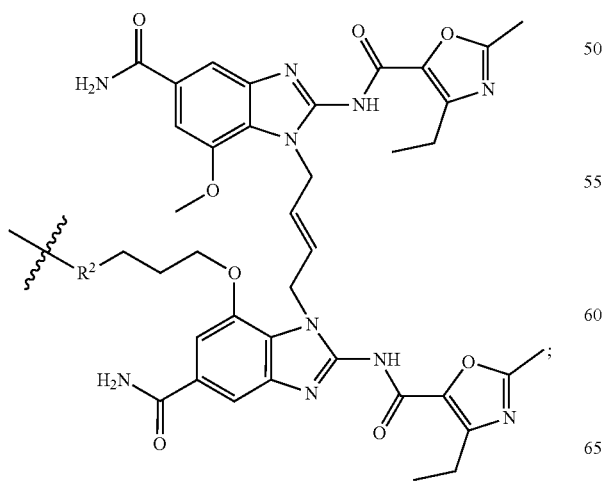

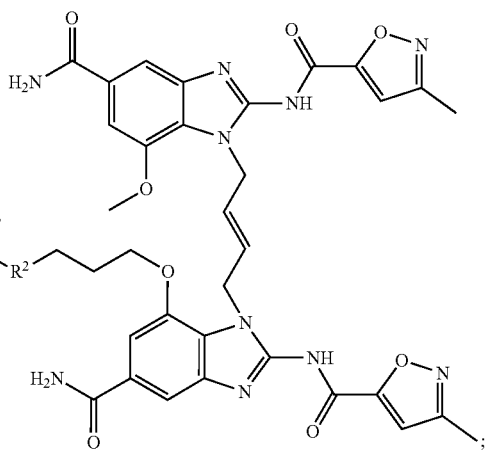

105
-continued
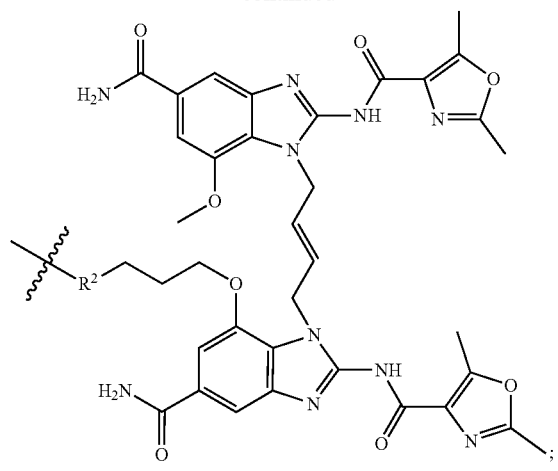
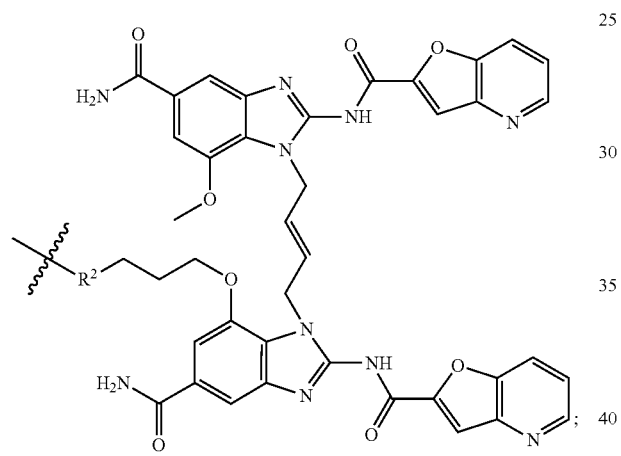
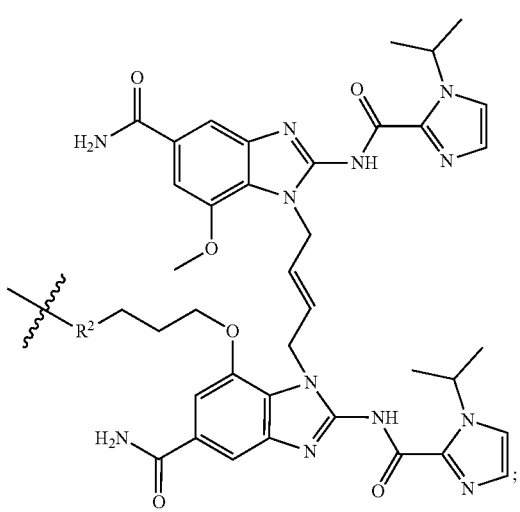
106
-continued
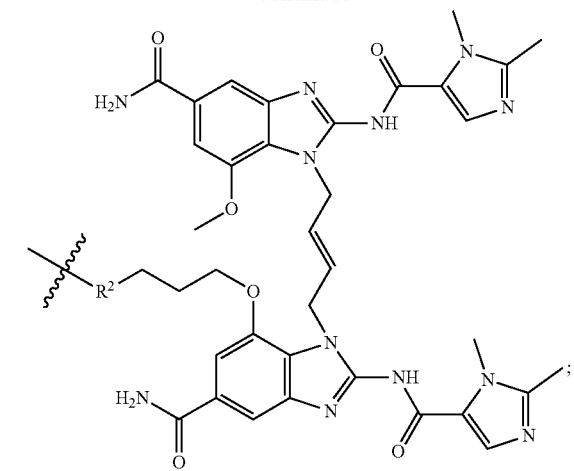
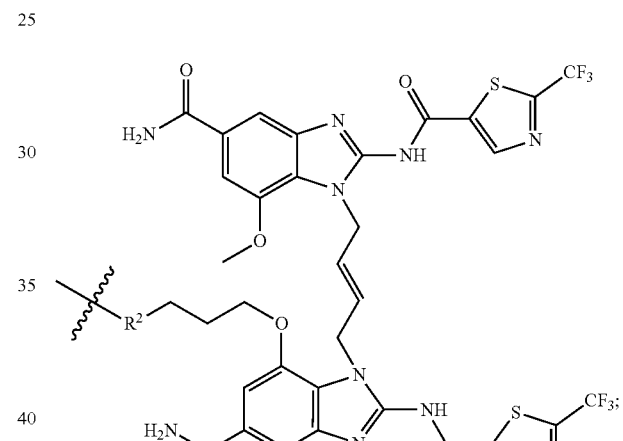
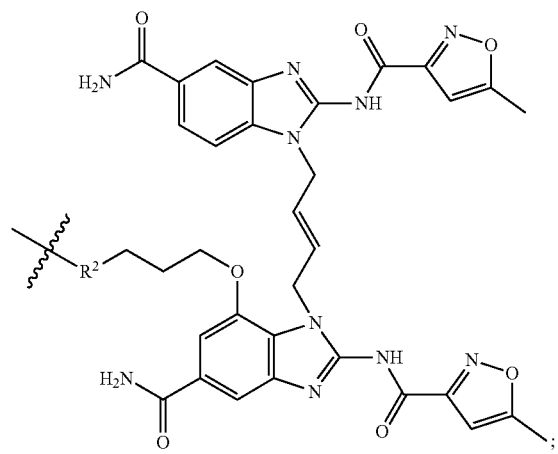

107
-continued
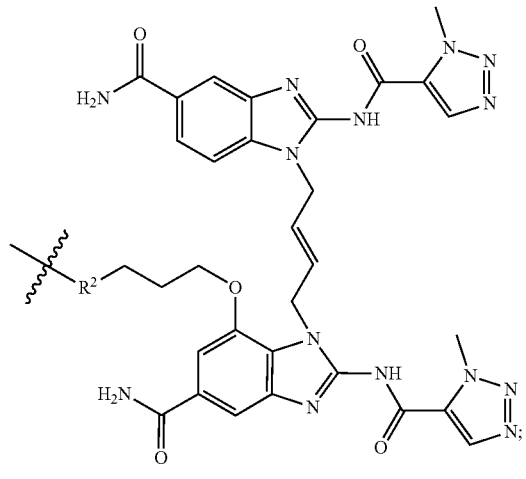
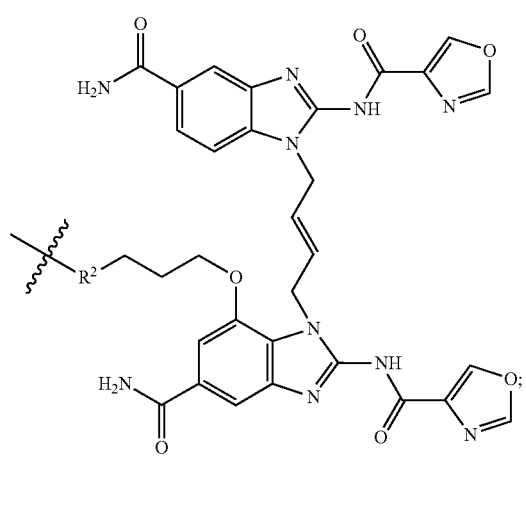
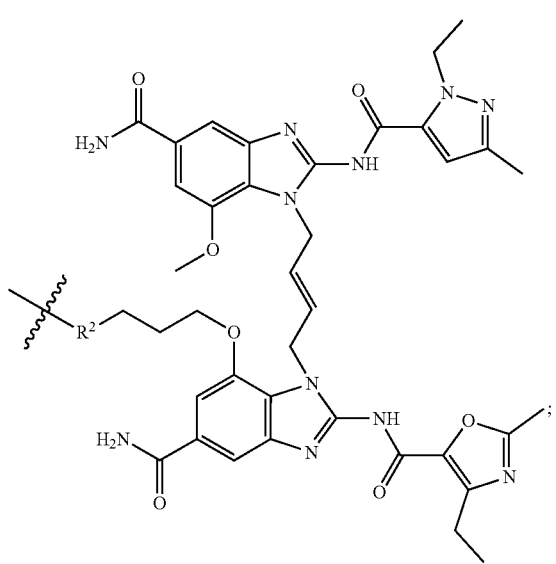
108
-continued
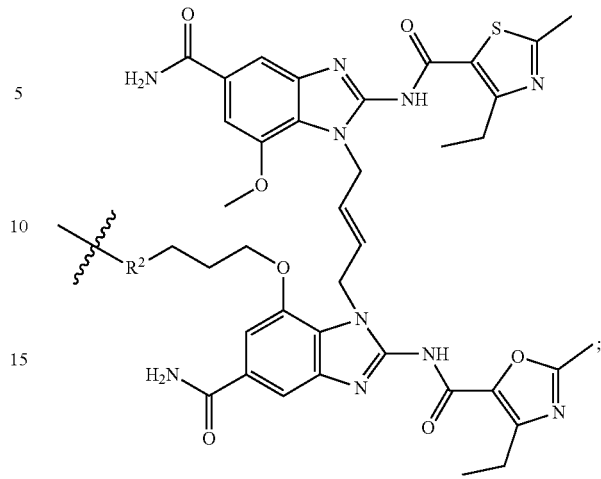
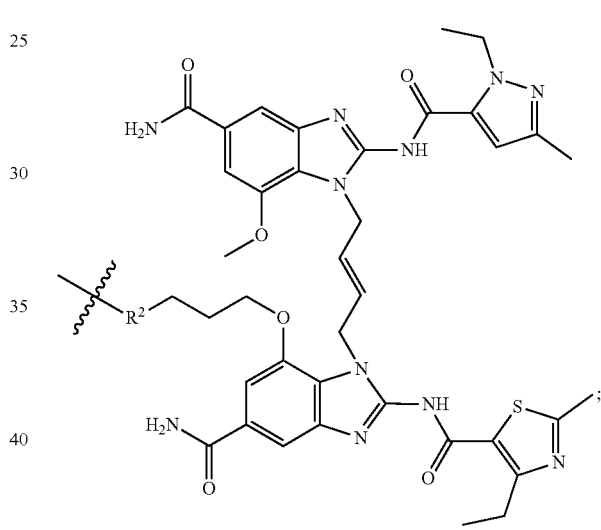
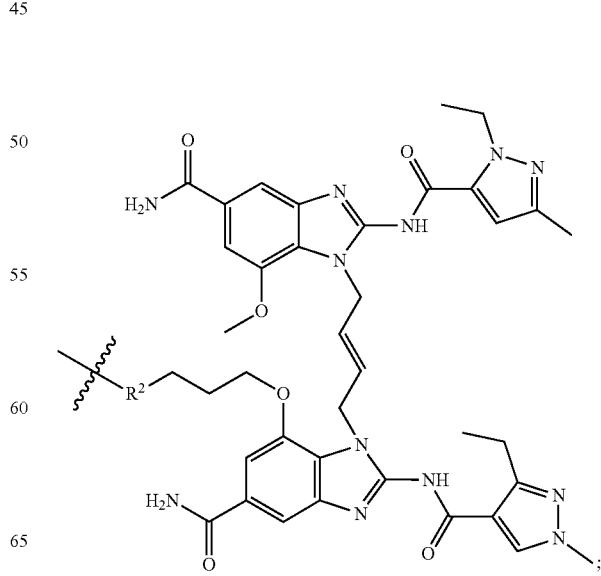

109
-continued
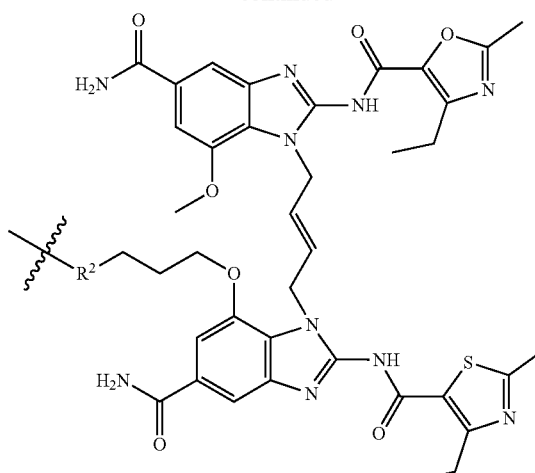
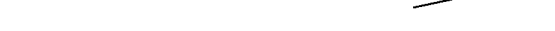
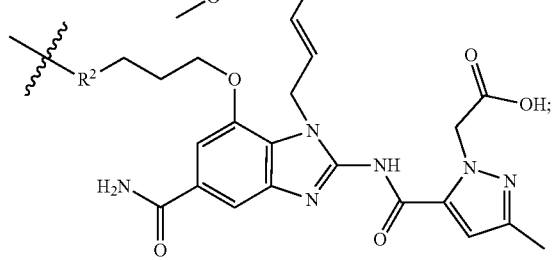
110
-continued
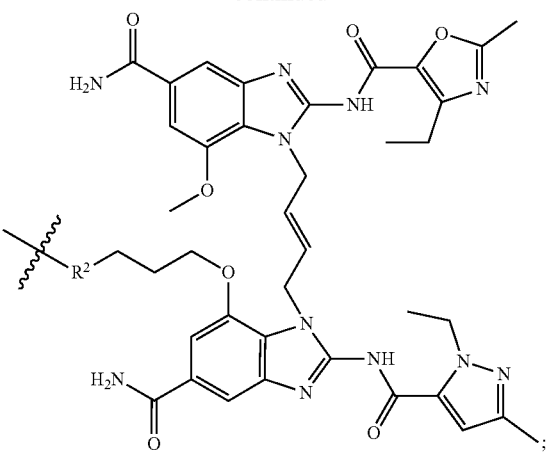
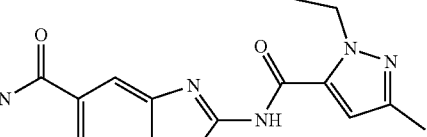
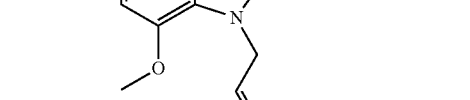
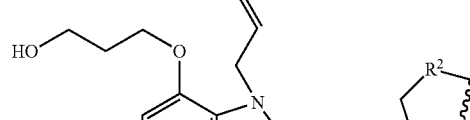
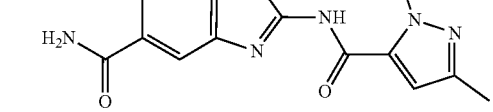
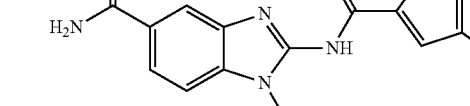
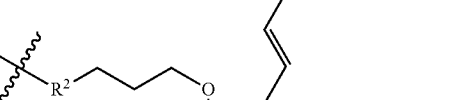
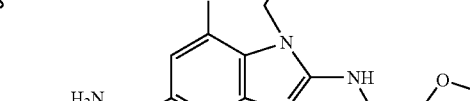

111
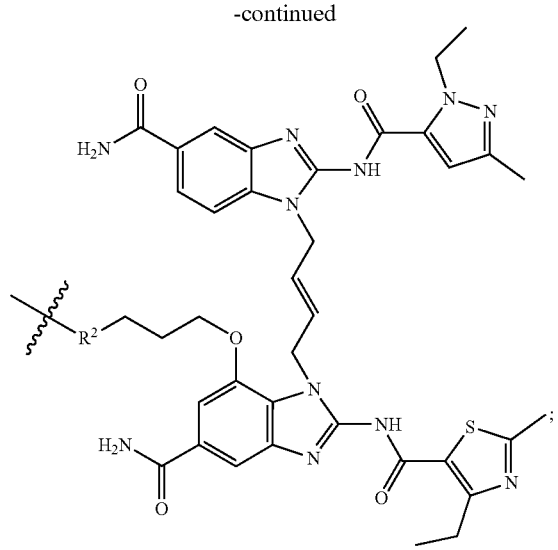
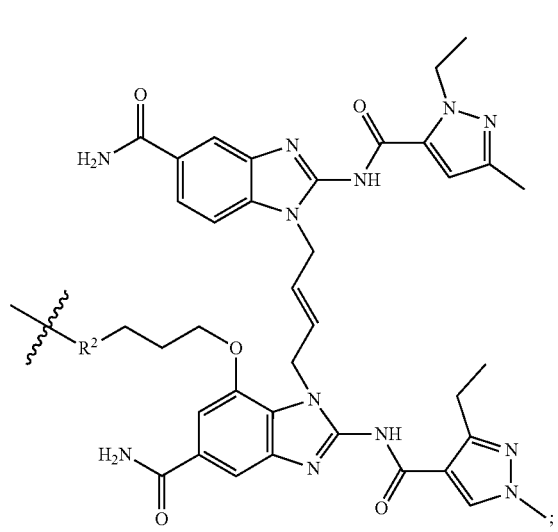
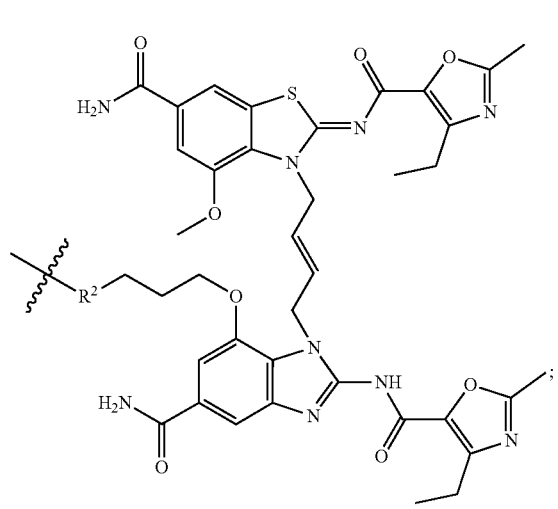
112
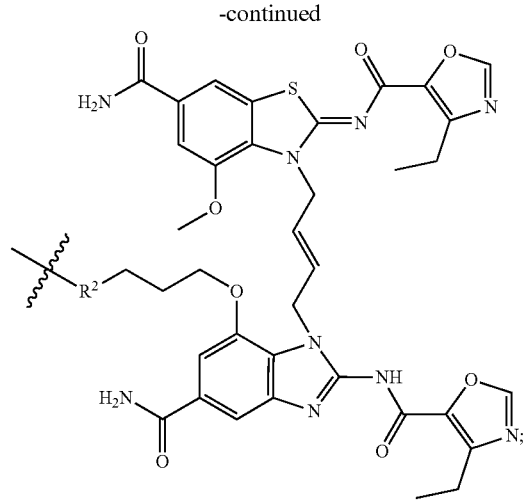
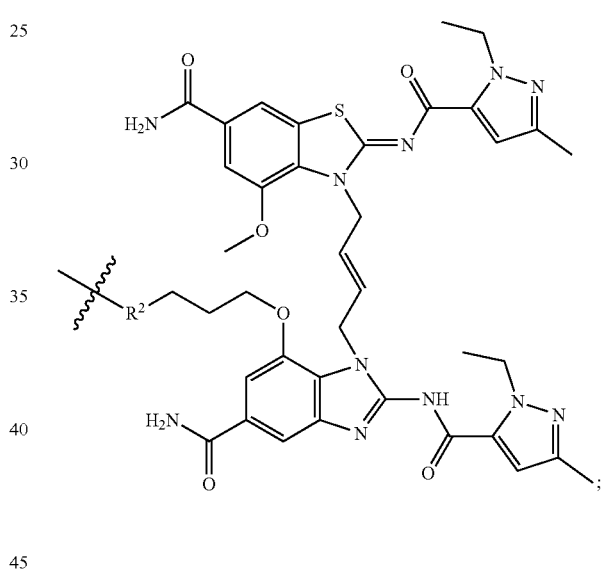
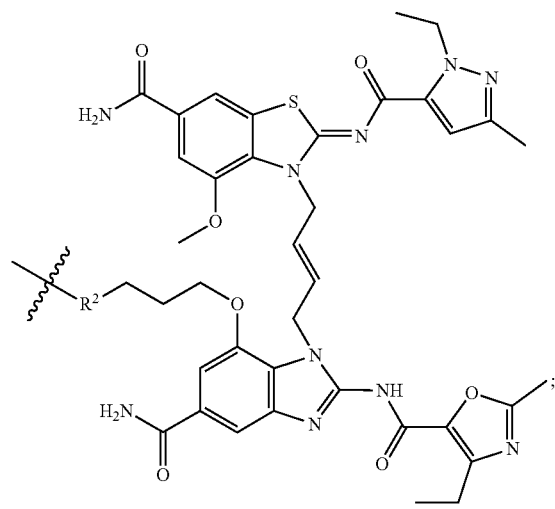

113
-continued
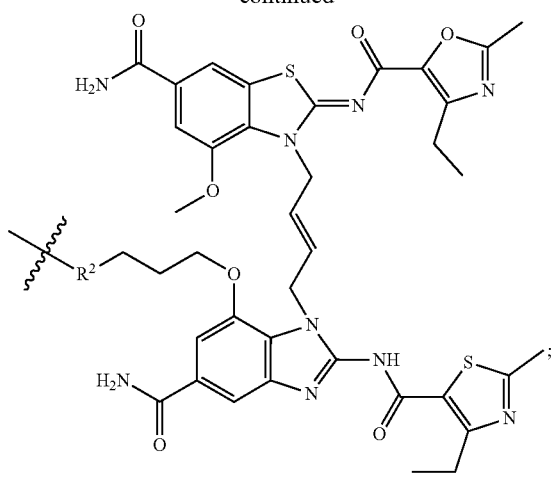
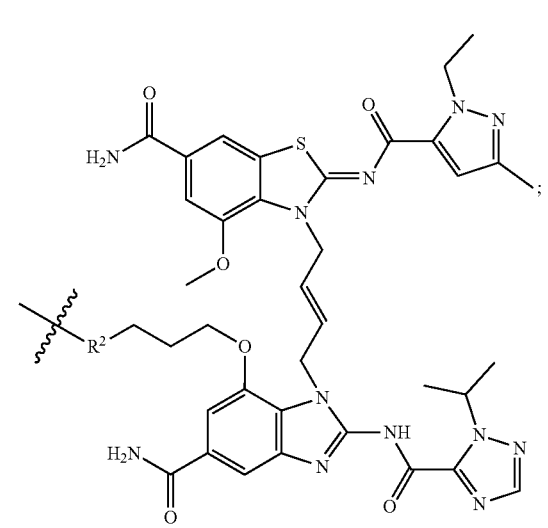
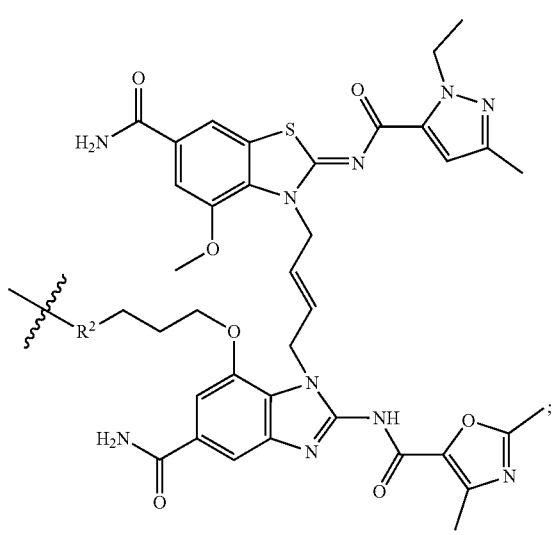
114
-continued
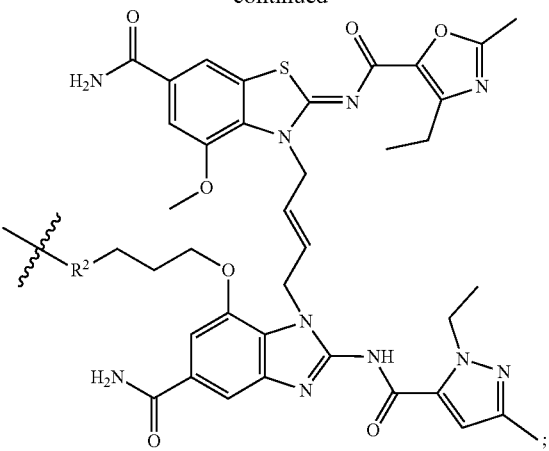
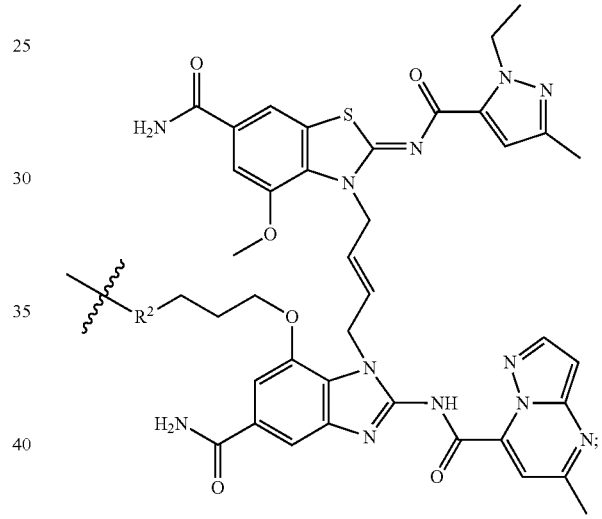
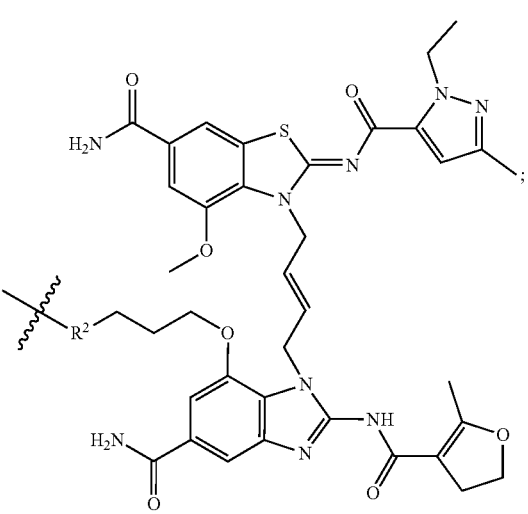

115
-continued
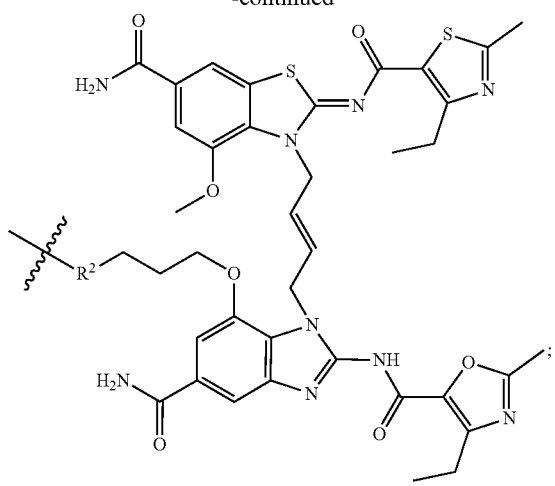
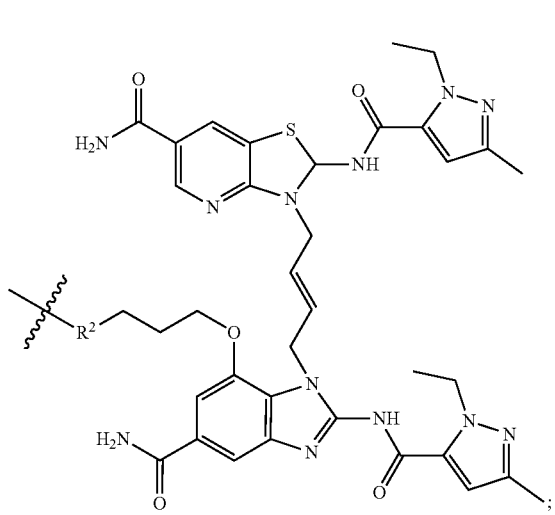
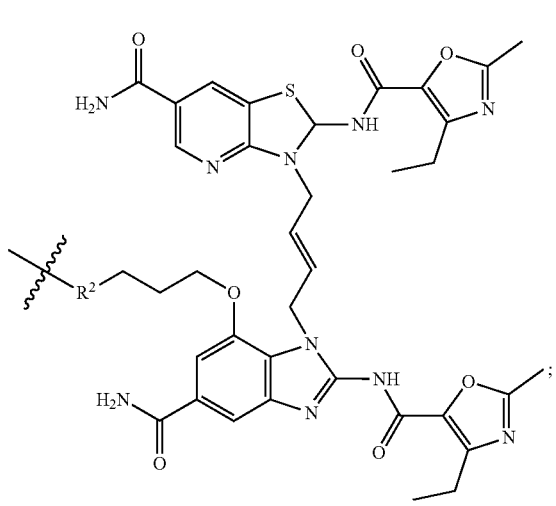
116
-continued
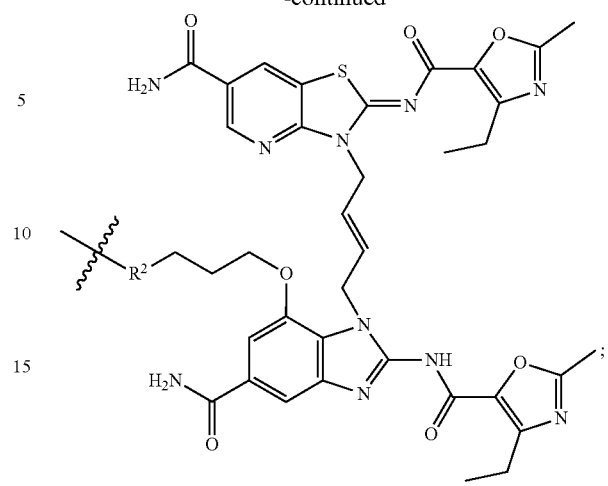
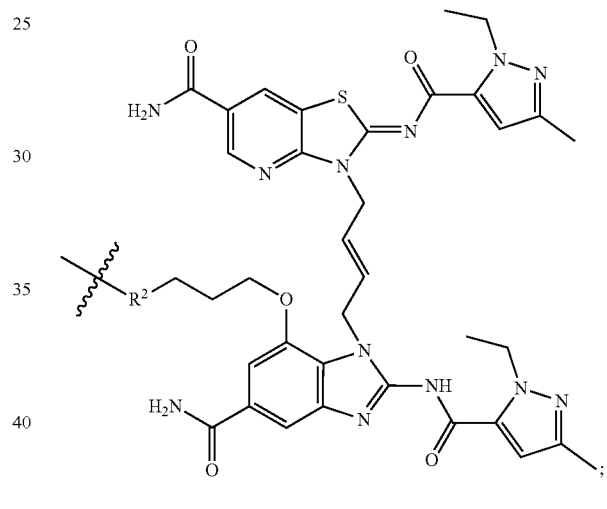
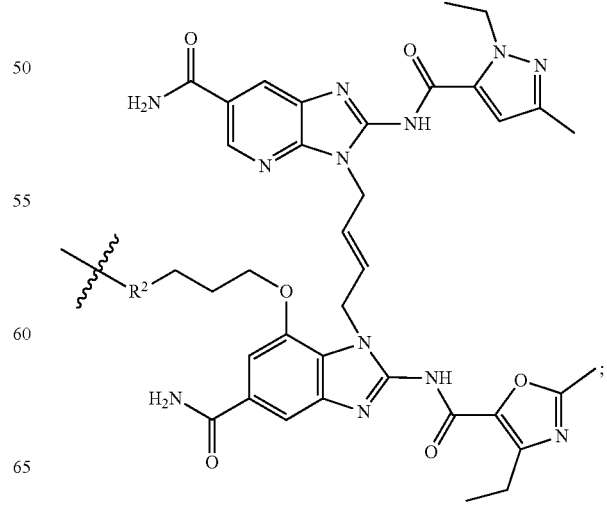

117
-continued
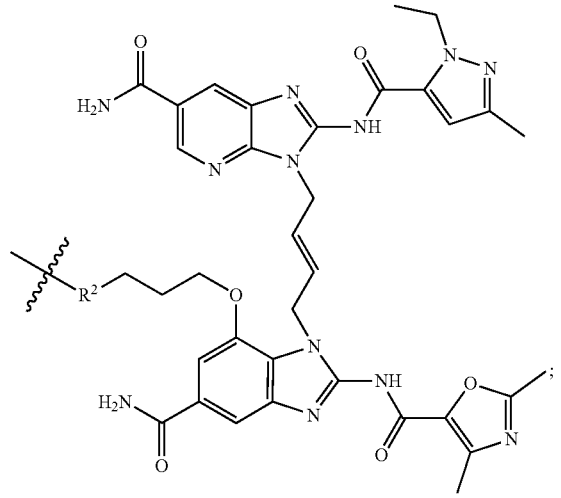
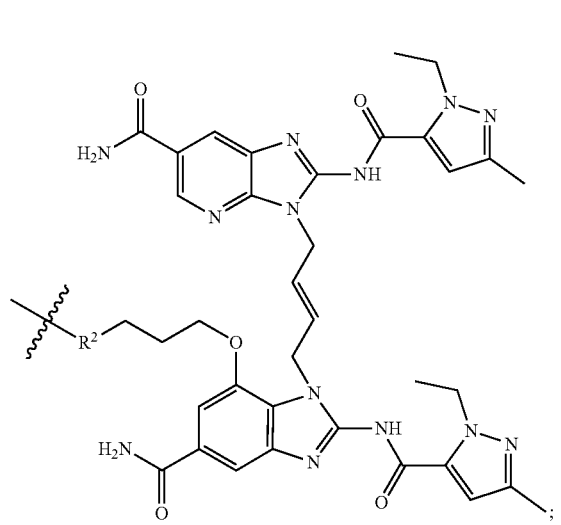
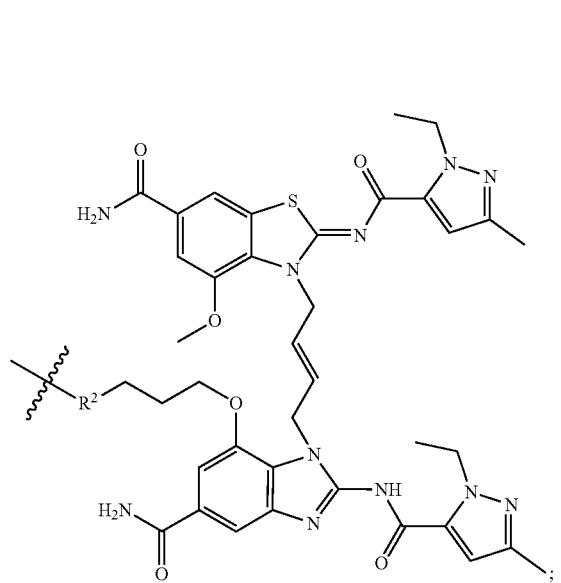
118
-continued
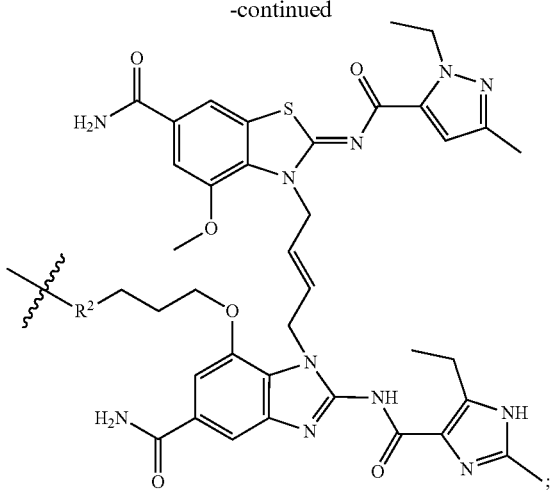
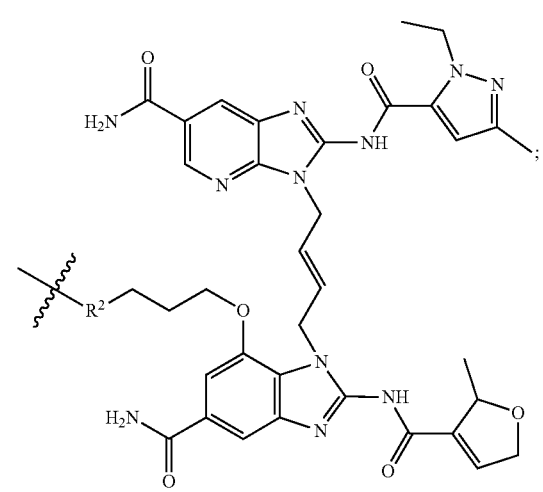
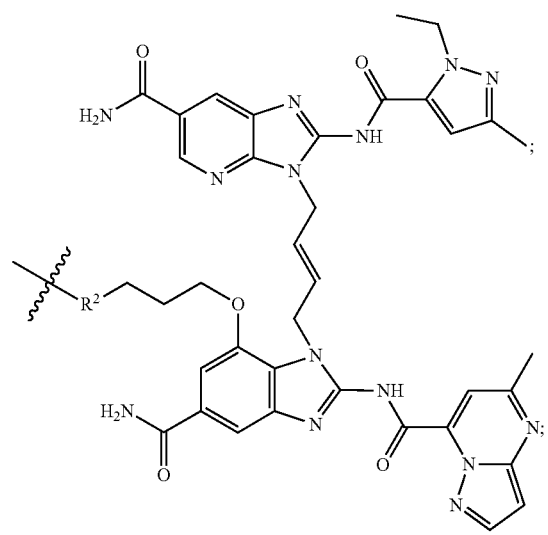

119
-continued
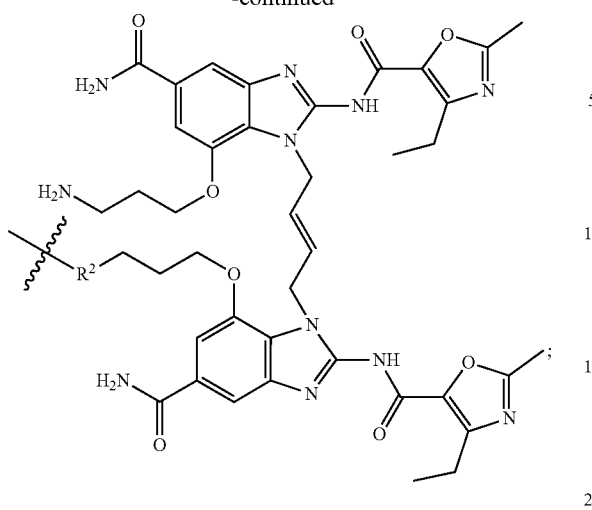
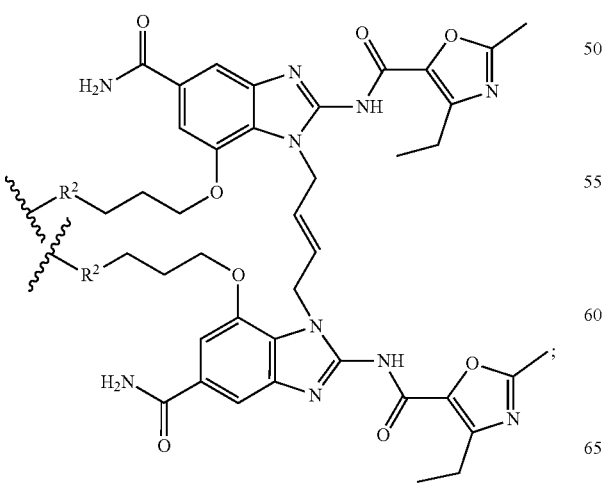
120
-continued
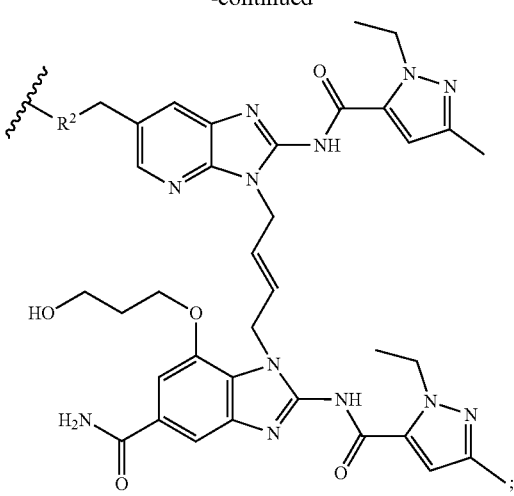
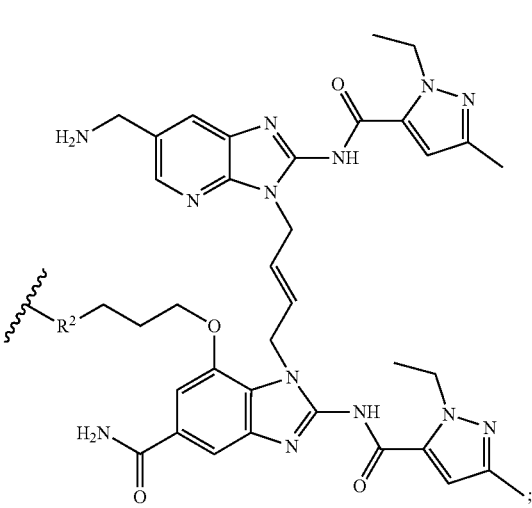
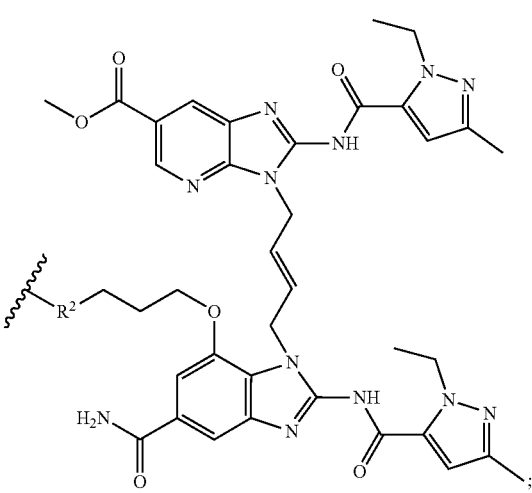

121
-continued
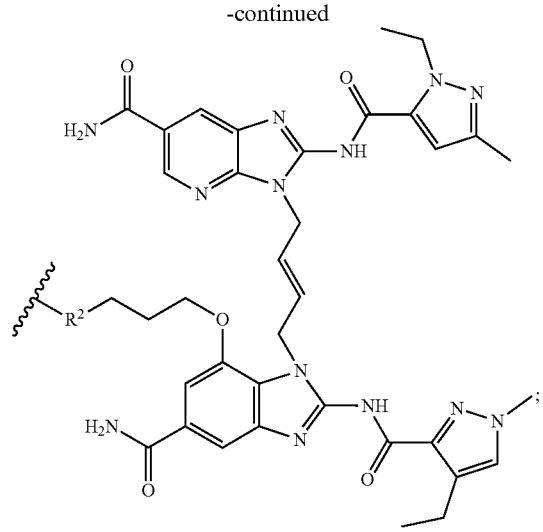
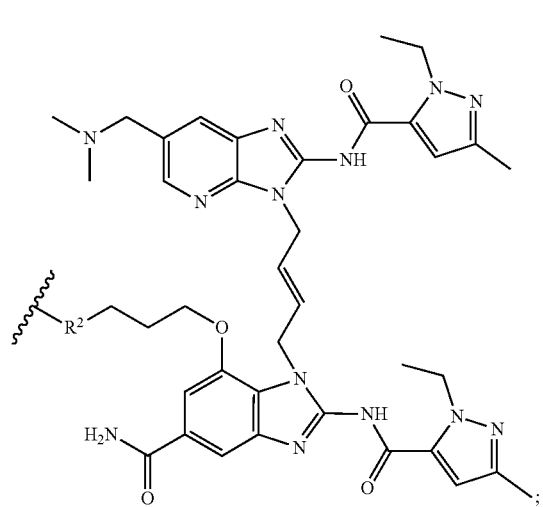
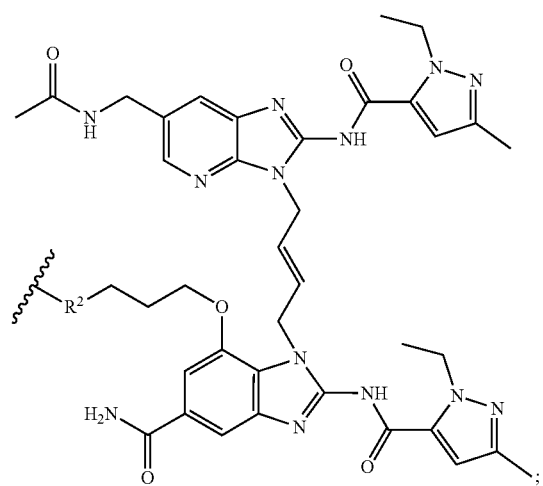
122
-continued
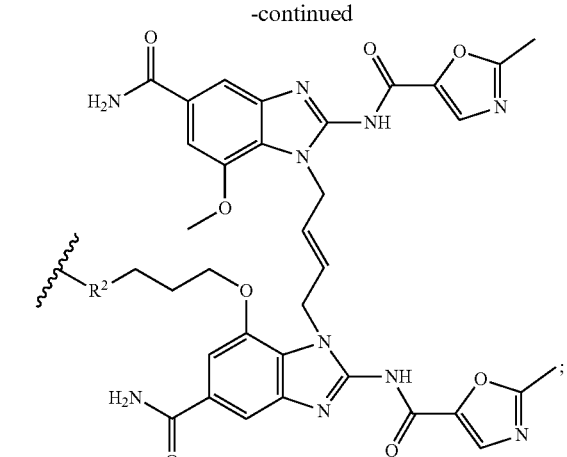
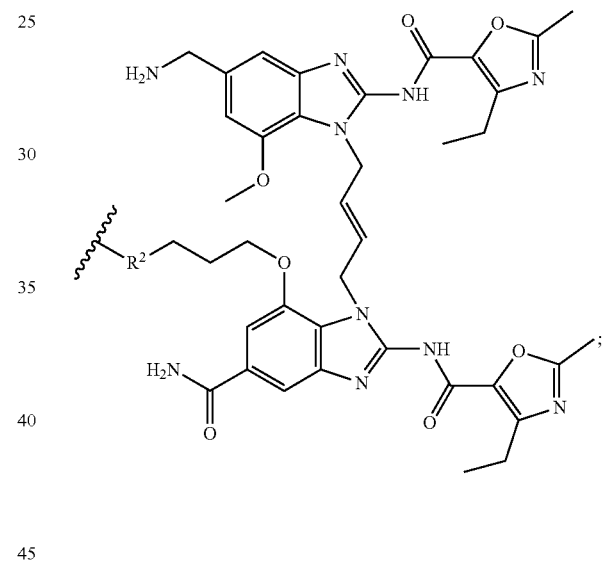
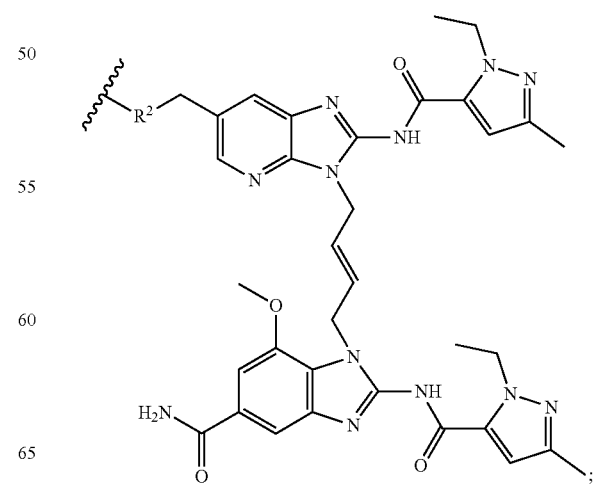

123
-continued
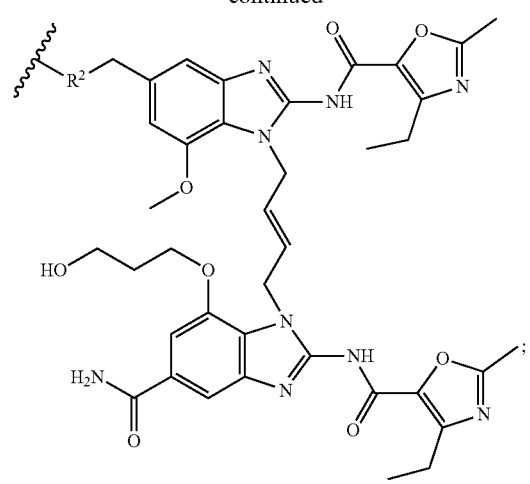
124
-continued
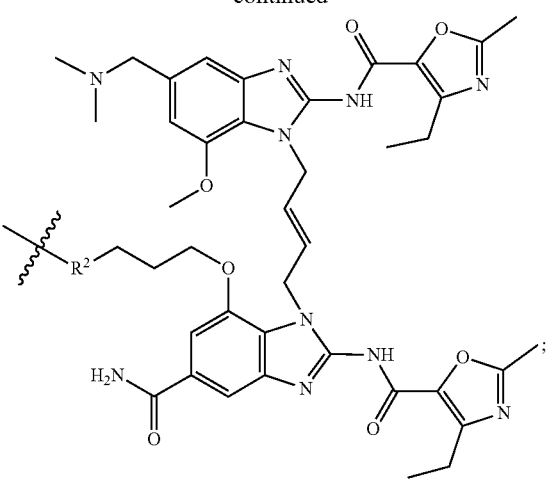
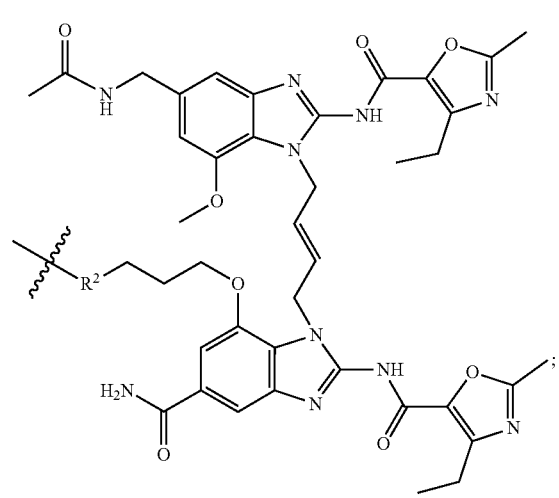
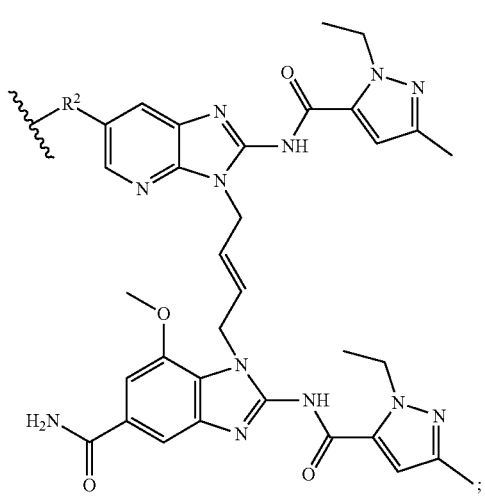
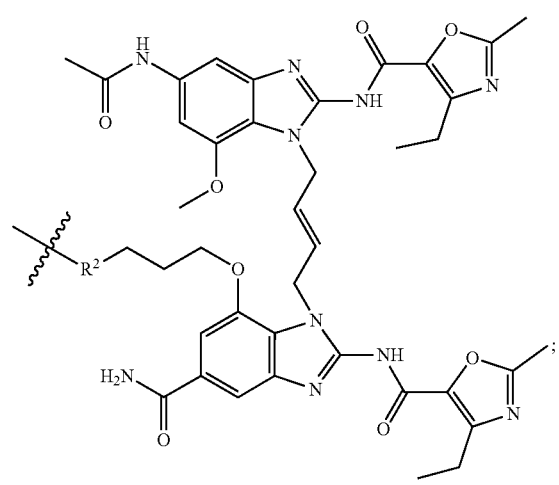
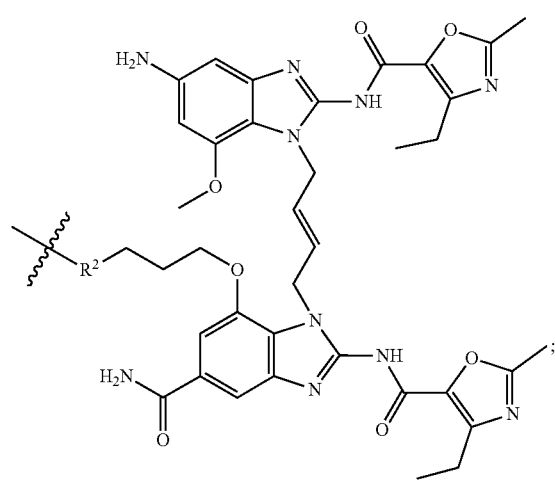

125
-continued
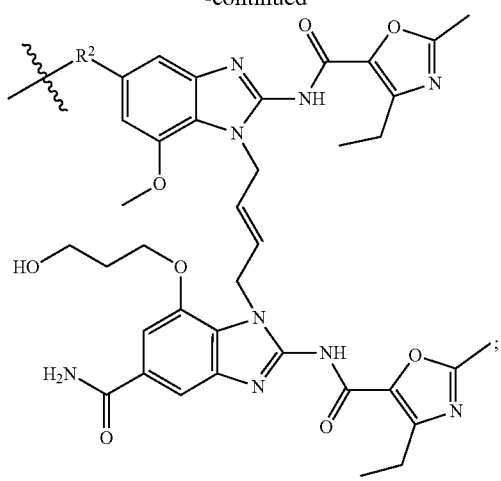
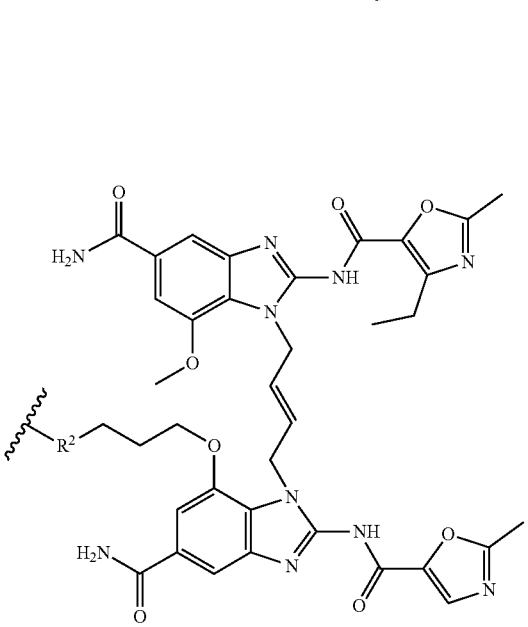
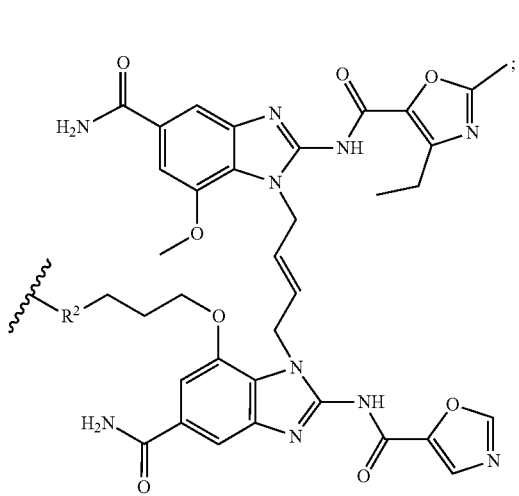
126
-continued
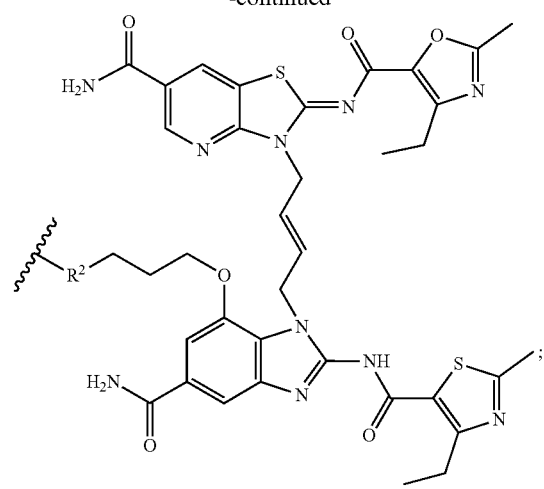
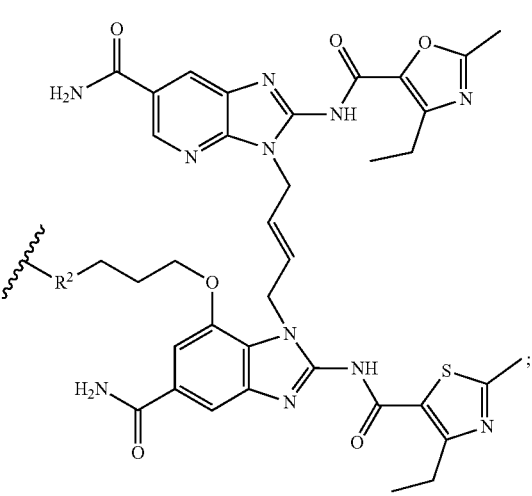
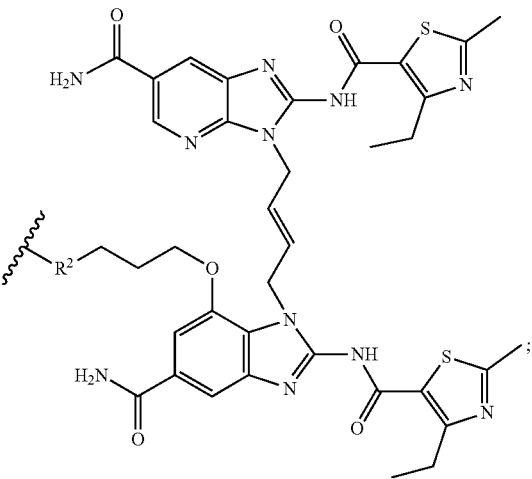

127
-continued
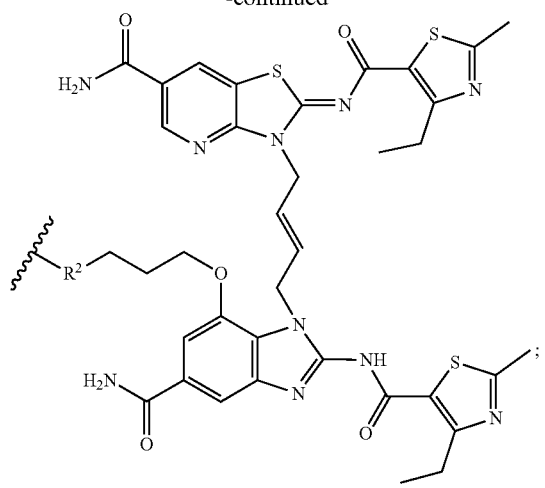
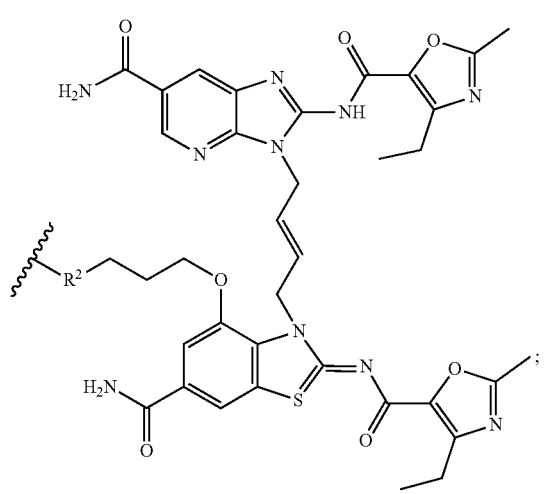
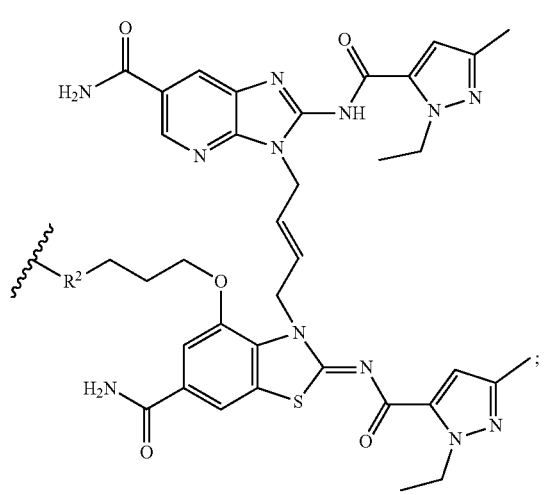
128
-continued
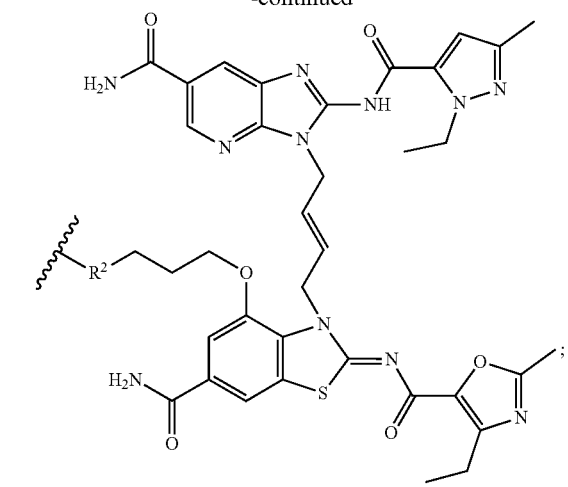
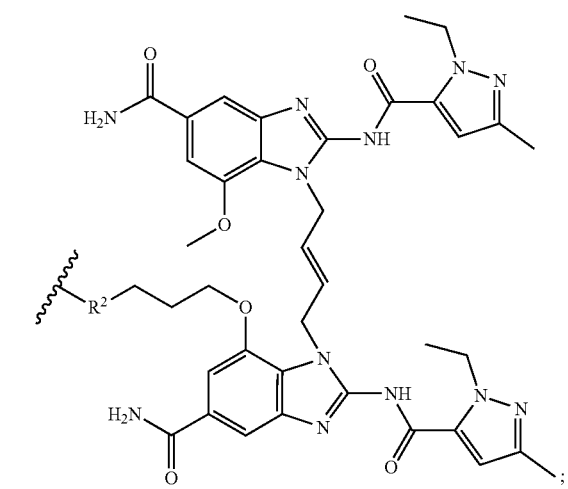
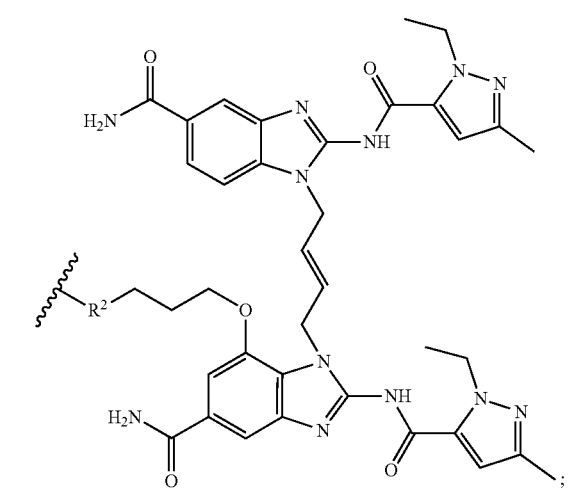

129
-continued
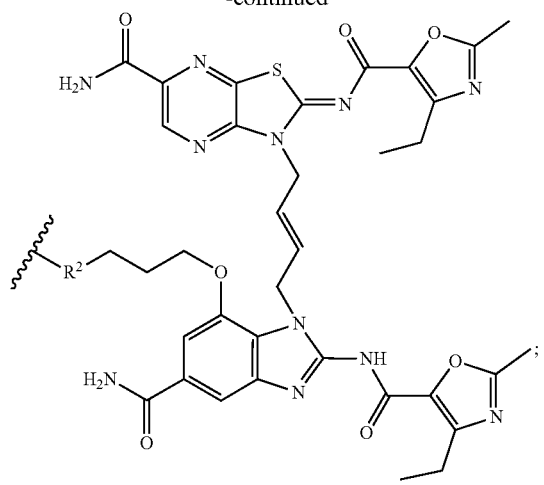
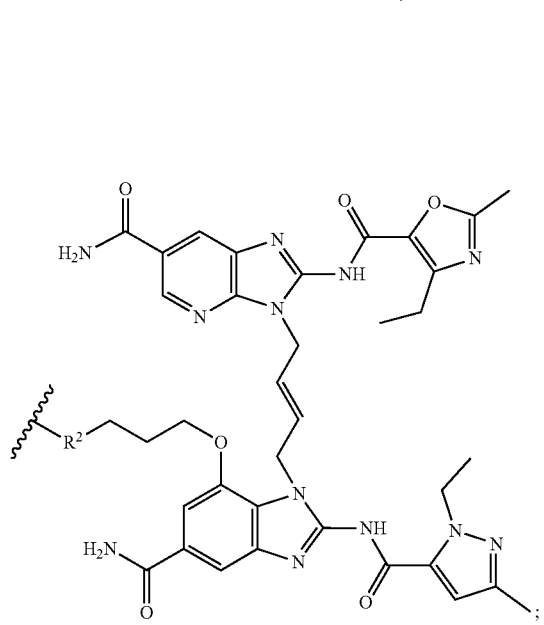
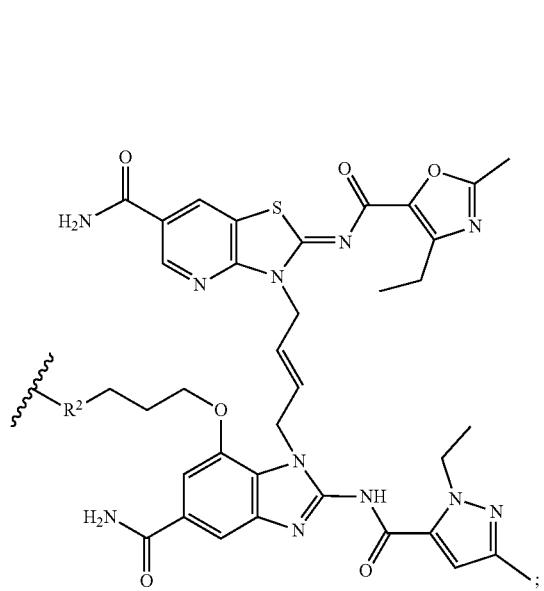
130
-continued
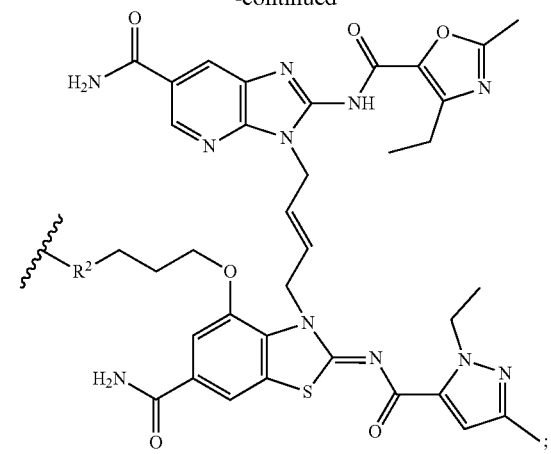
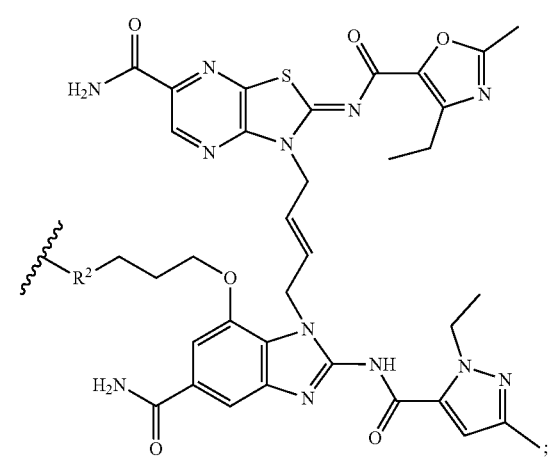
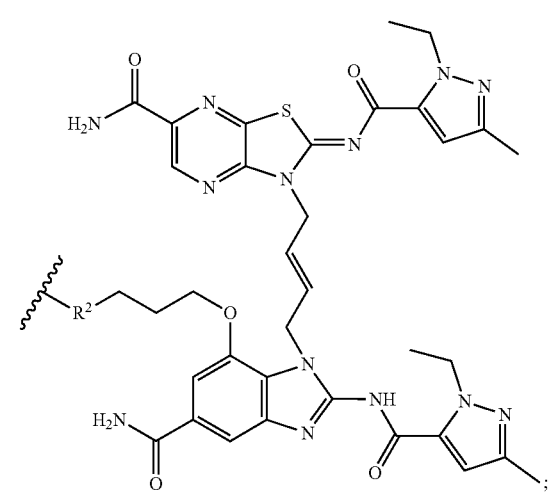

131
-continued
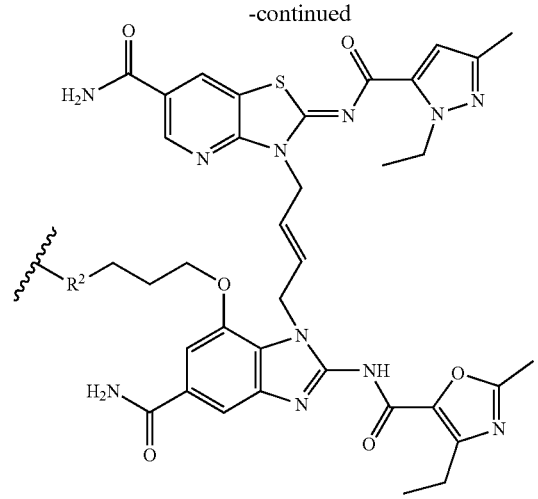
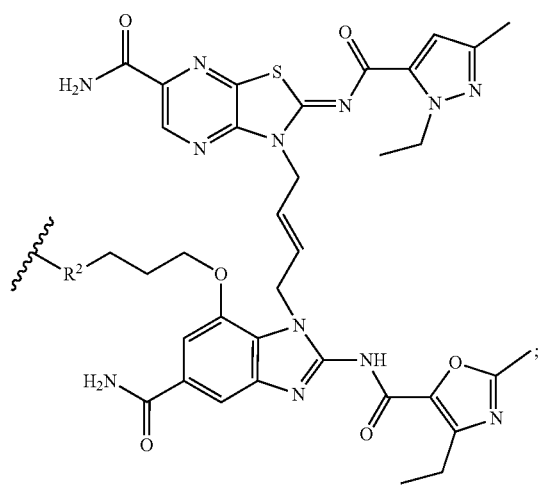
wherein:
R² is absent, —O— or —NR₄—; R⁴ is H or C₁₋₃ alkyl; and
denotes attachment to $L^D$.
132
In some embodiments, each STING agonist drug moiety (D) independently is:
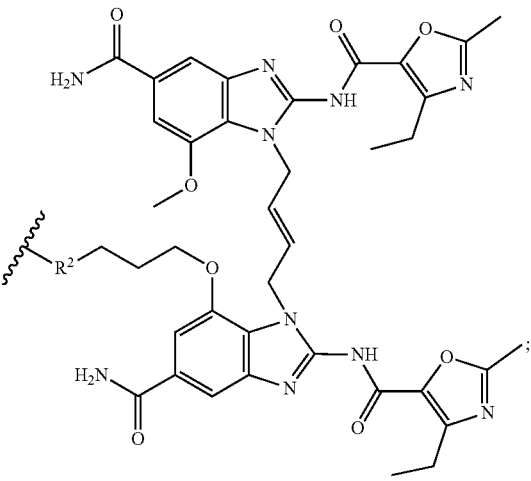
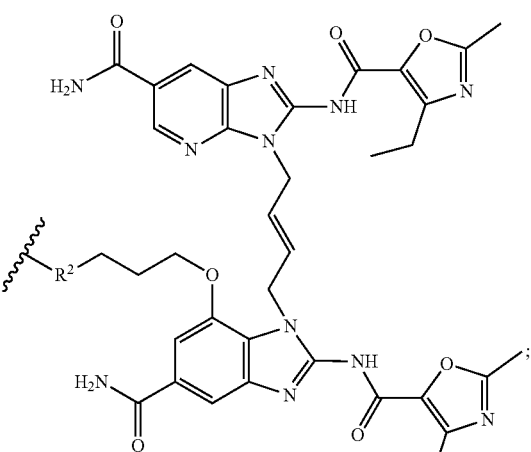
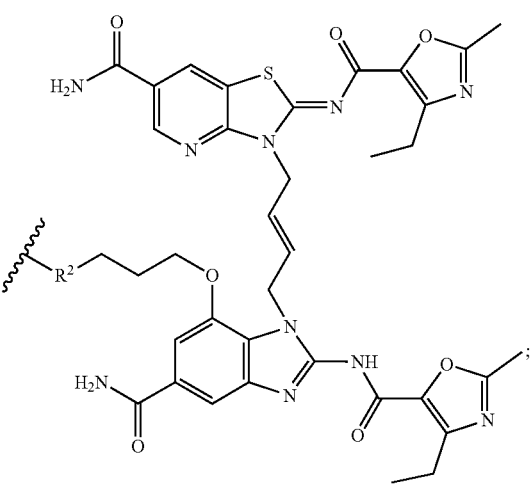

133
-continued
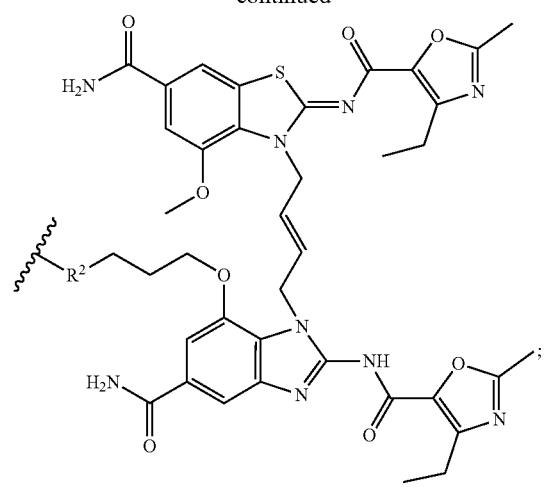
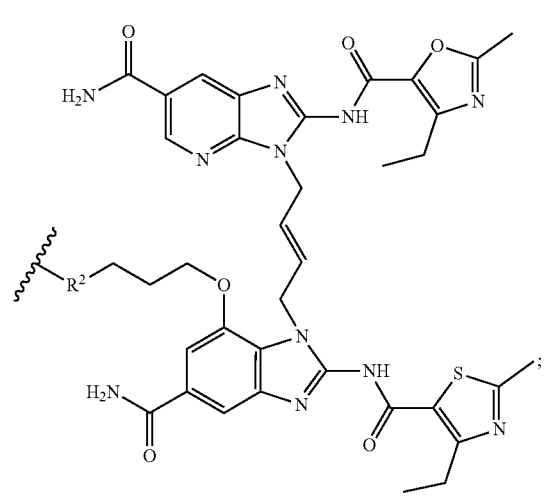
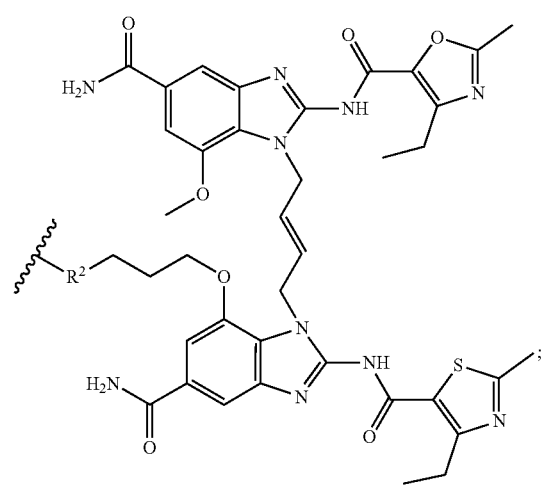
134
-continued
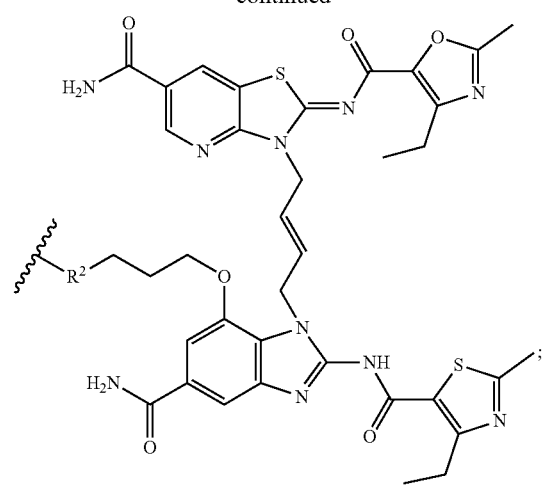
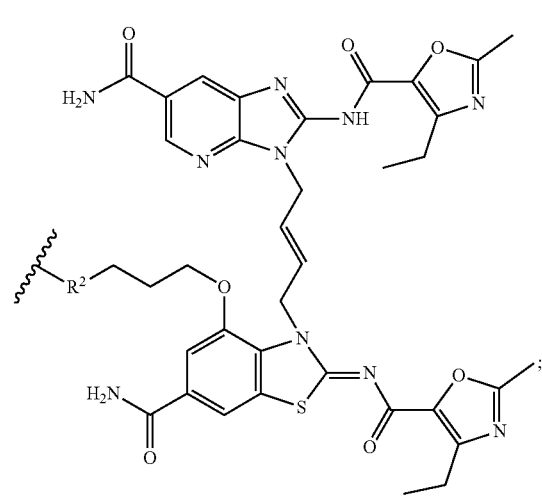
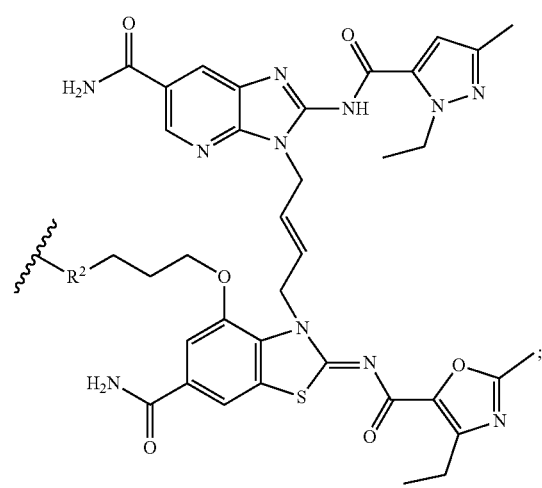

135
-continued
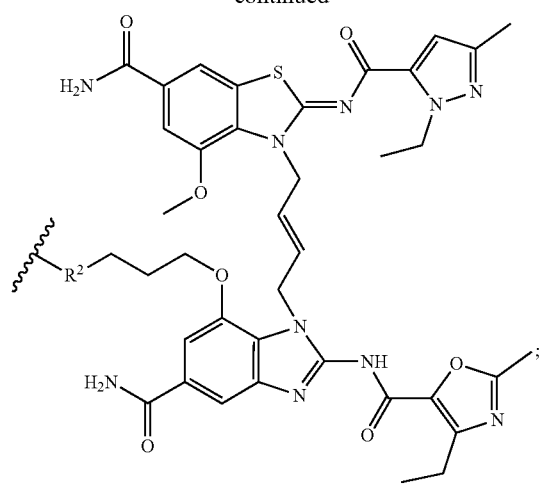
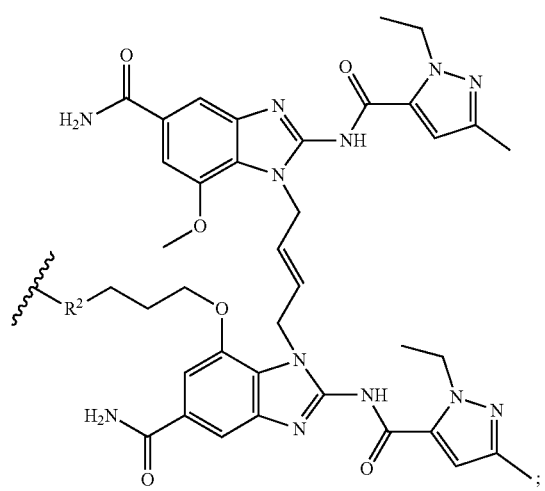
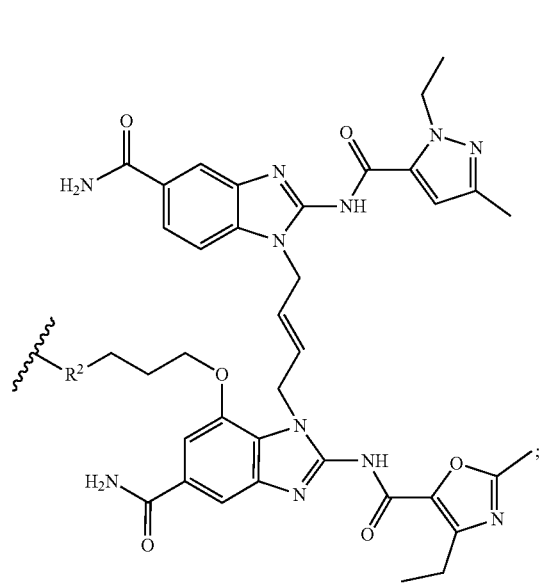
136
-continued
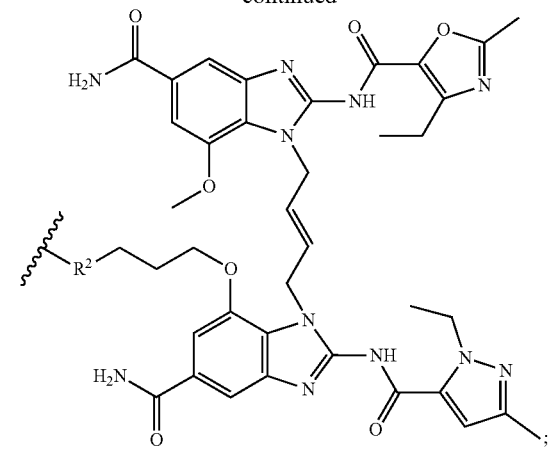
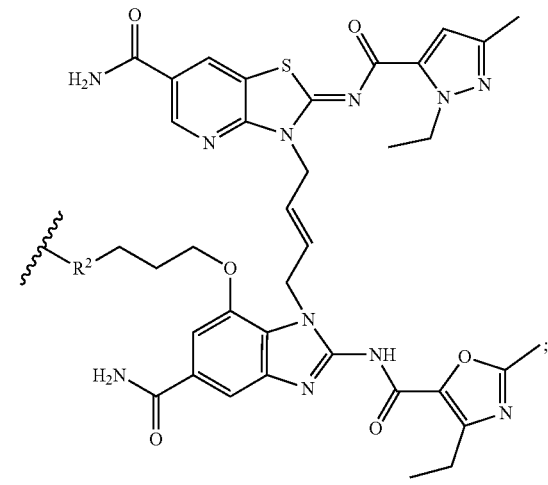
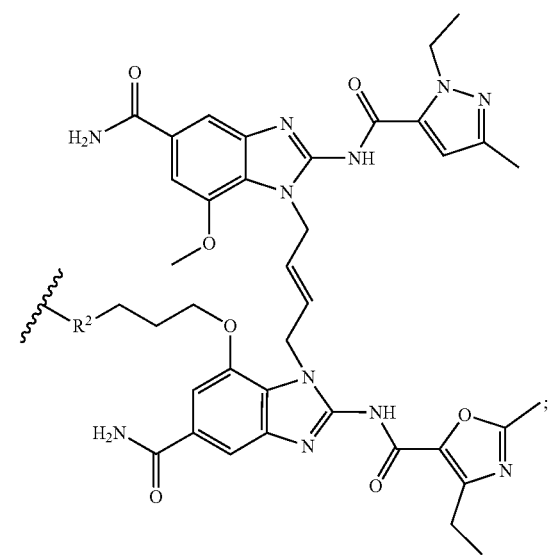

137
-continued
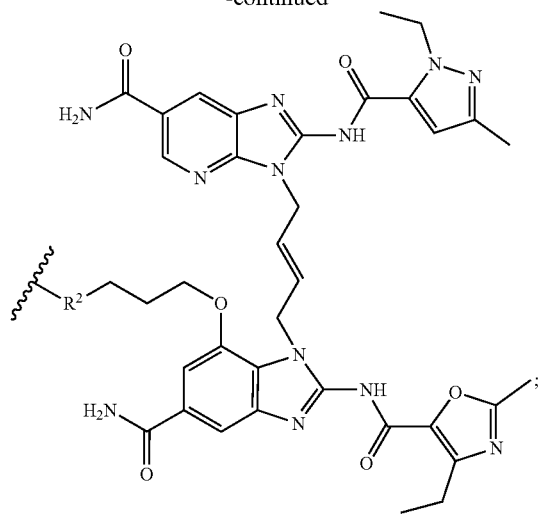
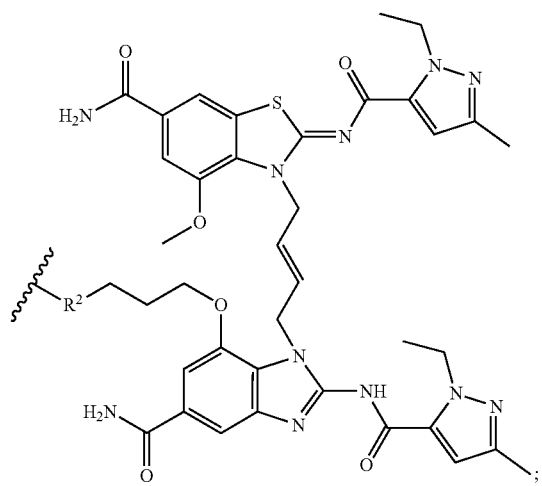
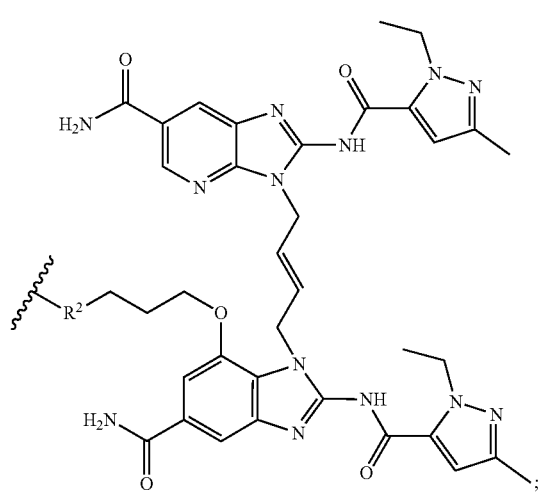
138
-continued
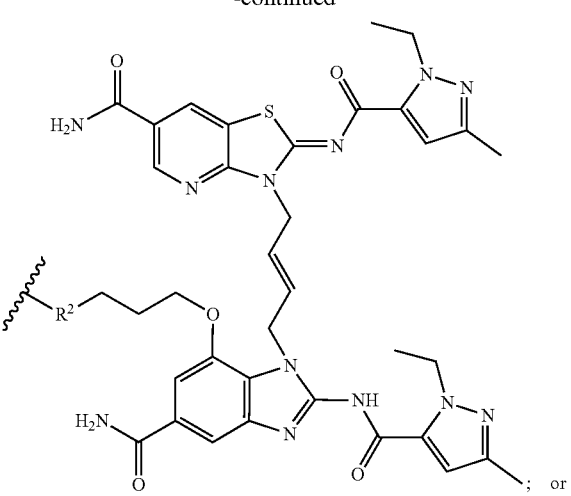
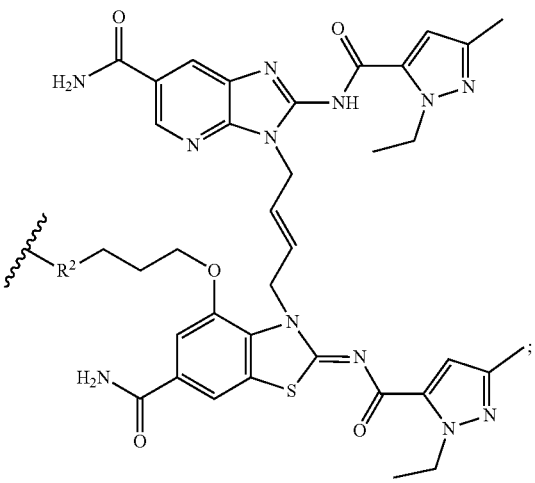
wherein:
R² is absent, —O— or —NR⁴—; R⁴ is H or $C_{1-3}$ alkyl; and
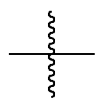
denotes attachment to $L^D$.

In some embodiments, each STING agonist drug moiety (D) independently is:
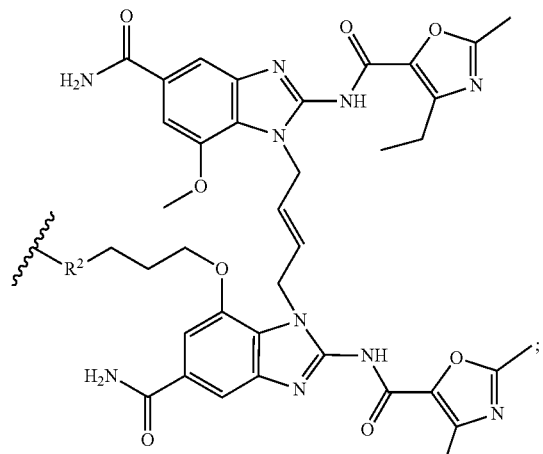
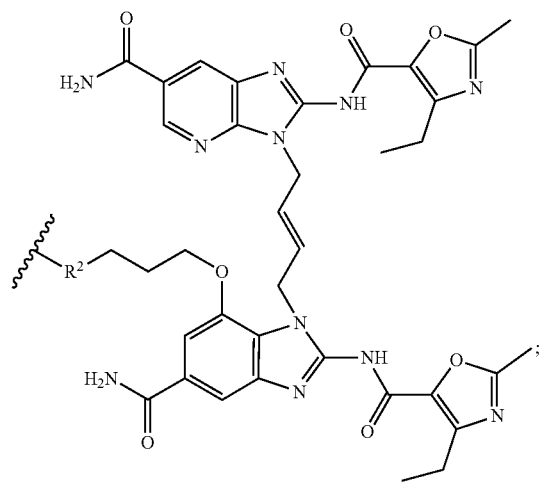
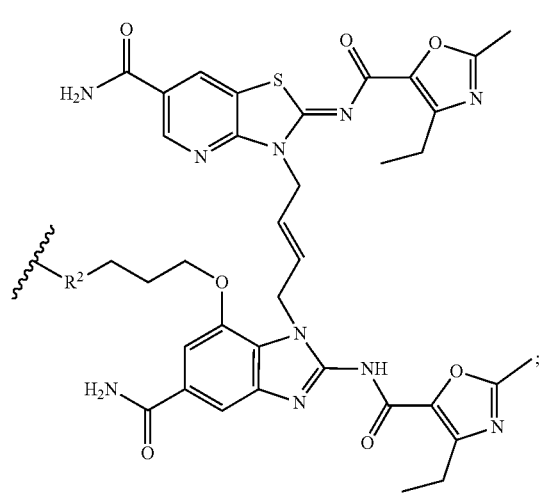
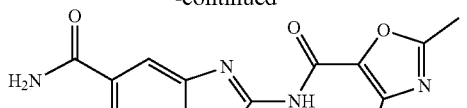
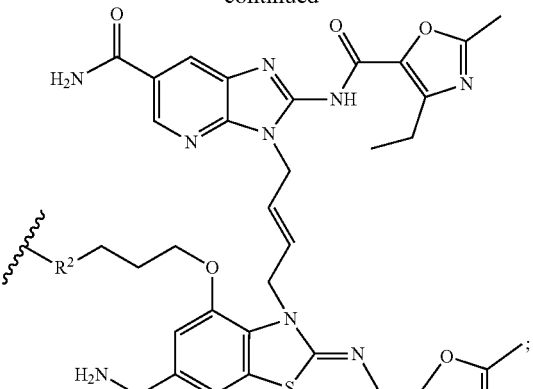
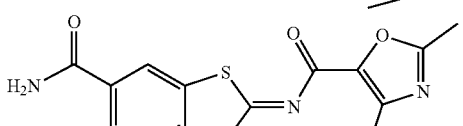
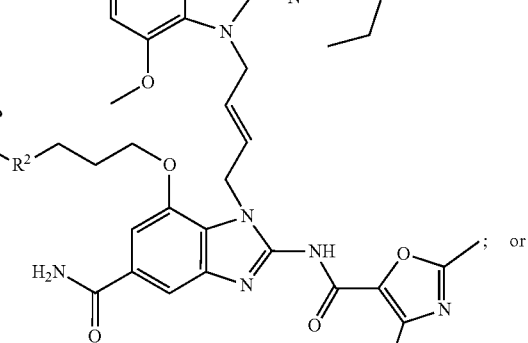
; or
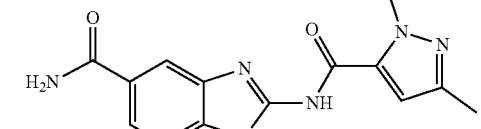
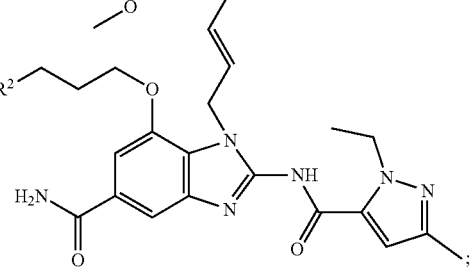
wherein:
R² is absent, —O— or —NR⁴—; R⁴ is H or C$_{1-3}$ alkyl; and
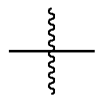
denotes attachment to L$^D$.

In some embodiments, each STING agonist drug moiety (D) independently is:
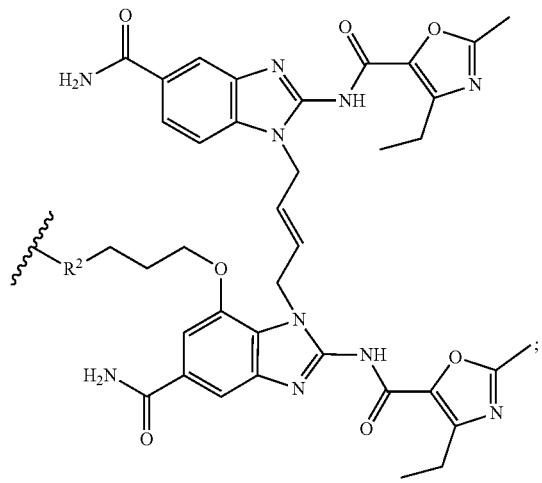
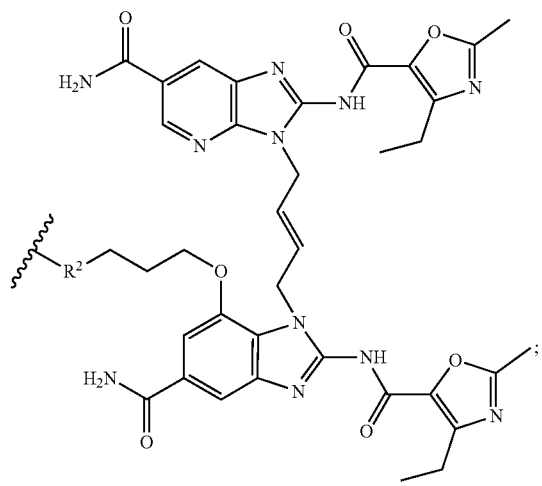
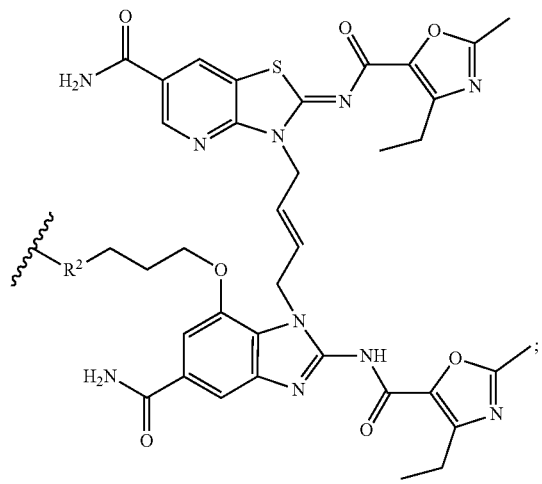
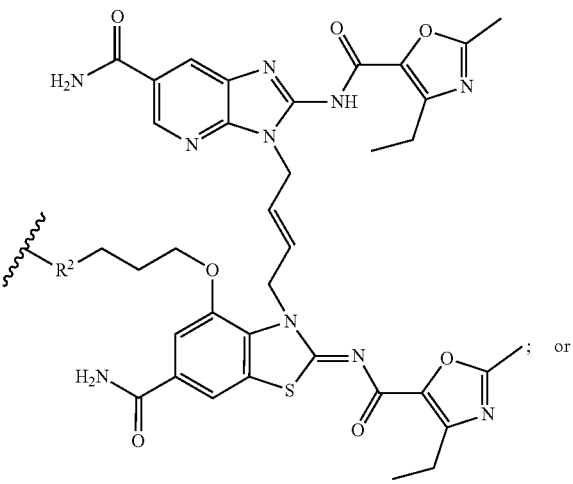
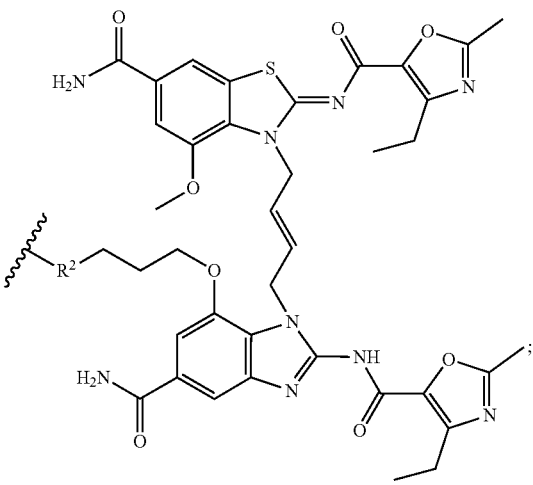
wherein:
R² is absent, —O— or —NR⁴—; R⁴ is H or C$_{1-3}$ alkyl; and
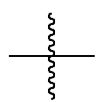
denotes attachment to L$^D$.

In some embodiments, each STING agonist drug moiety (D) independently is:

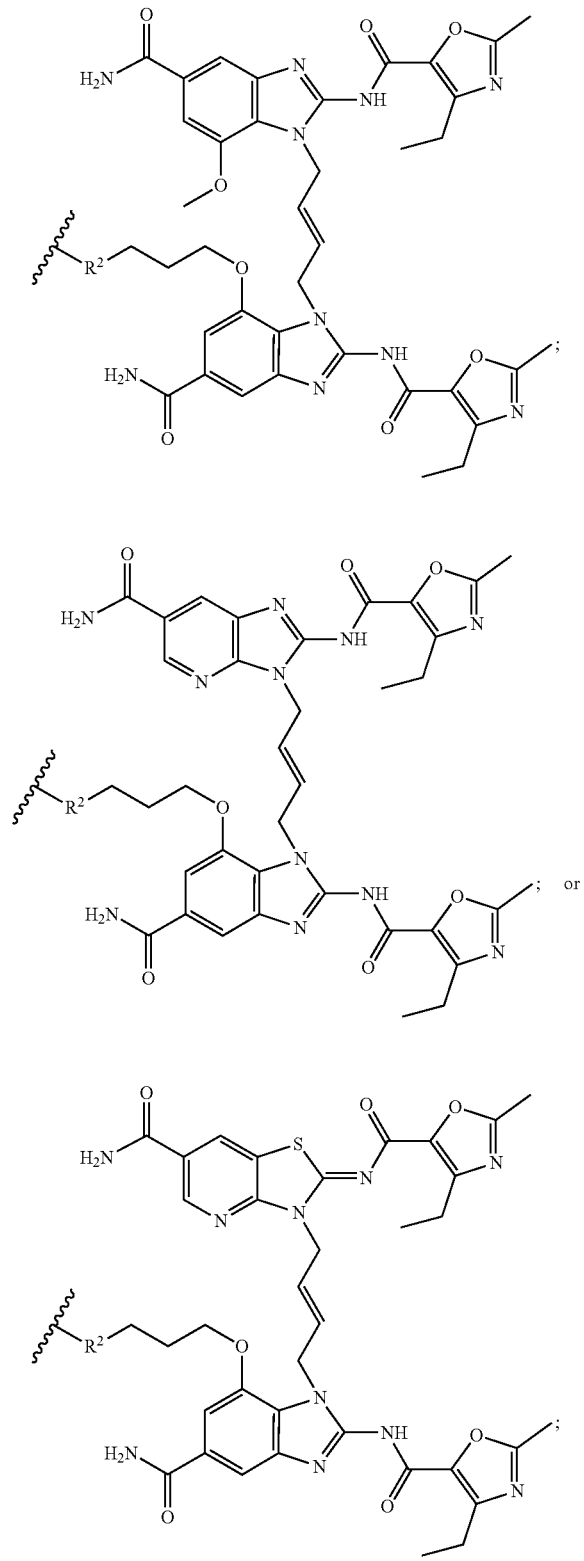

denotes attachment to $L^P$.

Hydrophilic Group (Variable $T^1$)

In some embodiments, the hydrophilic group included in the conjugates or scaffolds of the disclosure is a water-soluble and substantially non-antigenic polymer. Examples of the hydrophilic group, include, but are not limited to, polyalcohols, polyethers, polyanions, polycations, polyphosphoric acids, polyamines, polysaccharides, polyhydroxy compounds, polylysines, and derivatives thereof. In some embodiments, one end of the hydrophilic group can be functionalized so that it can be covalently attached to the $M^A$ linker (e.g., to an amino acid in the $M^A$ linker) by means of a non-cleavable linkage or via a cleavable linkage. In some embodiments, functionalization can be, for example, via an amine, thiol, NHS ester, maleimide, alkyne, azide, carbonyl, or other functional group. In some embodiments, the other terminus (or termini) of the hydrophilic group will be free and untethered. In some embodiments, by "untethered", it is meant that the hydrophilic group will not be attached to another moiety, such as D or a Drug Unit, or other components of the conjugates or scaffolds of the disclosure. In some embodiments, the free and untethered end of the hydrophilic group may include a methoxy, carboxylic acid, alcohol or other suitable functional group. In some embodiments, the methoxy, carboxylic acid, alcohol, or other suitable functional group acts as a cap for the terminus or termini of the hydrophilic group.

In some embodiments, a cleavable linkage refers to a linkage that is not substantially sensitive to cleavage while circulating in the plasma but is sensitive to cleavage in an intracellular or intratumoral environment. In some embodiments, a non-cleavable linkage is one that is not substantially sensitive to cleavage in any biological environment. In some embodiments, chemical hydrolysis of a hydrazone, reduction of a disulfide, and enzymatic cleavage of a peptide bond or glycosidic linkage are examples of cleavable linkages. In some embodiments, exemplary attachments of the hydrophilic group are via amide linkages, ether linkages, ester linkages, hydrazone linkages, oxime linkages, disulfide linkages, peptide linkages, or triazole linkages. In some embodiments, the attachment of the hydrophilic group to the $M^A$ linker (e.g., to an amino acid in the $M^A$ linker) is via an amide linkage.

In some embodiments wherein the conjugate or scaffold of the disclosure comprises more than one hydrophilic groups, the multiple hydrophilic groups may be the same or different chemical moieties (e.g., hydrophilic groups of different molecular weight, number of subunits, or chemical structure). In some embodiments, the multiple hydrophilic groups can be attached to the $M^A$ linker at a single attachment site or different sites.

In some embodiments, the addition of the hydrophilic group may have two potential impacts upon the pharmacokinetics of the resulting conjugate. In some embodiments, the desired impact is the decrease in clearance (and consequent in increase in exposure) that arises from the reduction in non-specific interactions induced by the exposed hydrophobic elements of the drug or drug-linker. In some embodiments, the undesired impact is the decrease in volume and rate of distribution that may arise from the increase in the molecular weight of the conjugate. In some embodiments, increasing the molecular weight of the hydrophilic group increases the hydrodynamic radius of a conjugate, resulting in decreased diffusivity that may diminish the ability of the conjugate to penetrate into a tumor. Because of these two competing pharmacokinetic effects, it may be desirable to use a hydrophilic group that is sufficiently large to decrease wherein:
$R^2$ is absent, —O— or —$NR^4$—; $R^4$ is H or $C_{1-3}$ alkyl; and the conjugate clearance thus increasing plasma exposure, but not so large as to greatly diminish its diffusivity, which may reduce the ability of the conjugate to reach the intended target cell population.

In some embodiments, the hydrophilic group, includes, but is not limited to, a sugar alcohol (also known as polyalcohol, polyhydric alcohol, alditol or glycitol, such as inositol, glycerol, erythritol, threitol, arabitol, xylitol, ribitol, galactitol, mannitol, sorbitol, and the like) or a derivative thereof (e.g., amino polyalcohol), carbohydrate (e.g., a saccharide), a polyvinyl alcohol, a carbohydrate-based polymer (e.g., dextrans), a hydroxypropylmethacrylamide (HPMA), a polyalkylene oxide, and/or a copolymer thereof.

In some embodiments, $T^1$ comprises a plurality of hydroxyl ("—OH") groups, such as moieties that incorporate monosaccharides, oligosaccharides, polysaccharides, and the like.

In some embodiments, $T^1$ comprises a plurality of —$(CR_{58}OH)$— groups, wherein $R^{58}$ is —H or $C_{1-8}$ alkyl.

In some embodiments, $T^1$ is —OH or

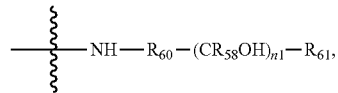

wherein:
  $n_1$ is an integer from 0 to about 6;
  each $R_{58}$ is independently —H or $C_{1-8}$ alkyl;
  $R_{60}$ is a bond, a $C_{1-6}$ alkyl linker, or —$CHR_{59}$— wherein $R_{59}$ is —H, $C_{1-8}$ alkyl, cycloalkyl, or arylalkyl;
  $R_{61}$ is $CH_2OR_{62}$, $COOR_{62}$, —$(CH_2)_{n2}COOR_{62}$, or a heterocycloalkyl substituted with one or more hydroxyl;
  $R_{62}$ is —H or $C_{1-8}$ alkyl; and
  $n_2$ is an integer from 1 to about 5.

In some embodiments, $T^1$ is —OH.
In some embodiments, $T^1$ is

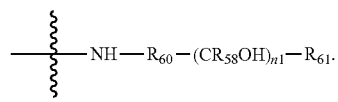

In some embodiments, $R_{58}$ is —H; $R_{60}$ is a bond or a $C_{1-6}$ alkyl linker; $n_1$ is an integer from 1 to about 6; and $R_{61}$ is $CH_2OH$ or COOH.

In some embodiments, $R^{58}$ is —H; $R_{60}$ is —$CHR_{59}$—; $n_1$ is 0; and $R_{61}$ is a heterocycloalkyl substituted with one or more hydroxyl, e.g., a monosaccharide.

In some embodiments, $T^1$ comprises a glucosyl-amine, a di-amine, or a tri-amine.

In some embodiments, $T^1$ comprises one or more of the following fragments or a stereoisomer thereof:

(1)
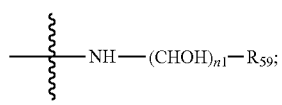

(2)
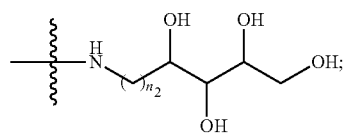

(3)
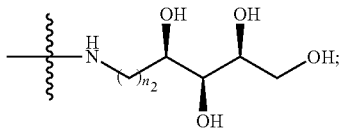

(4)
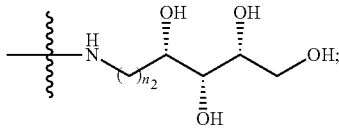

(5)
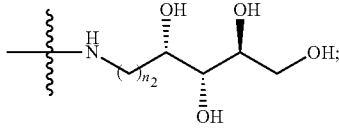

(6)
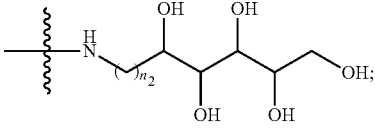

(7)
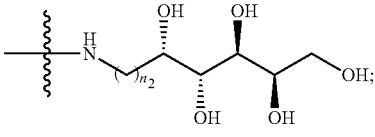

(8)
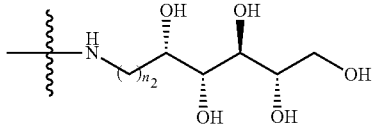

(9)
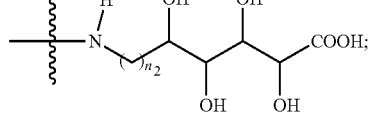

(10)
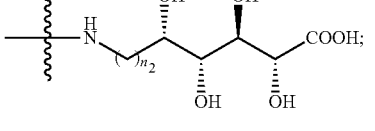

(11)
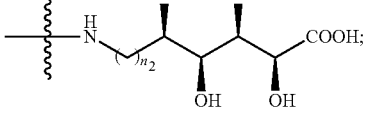

(12)
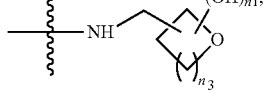

(13)
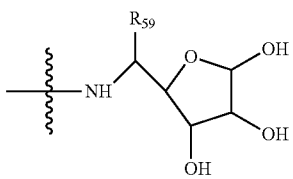

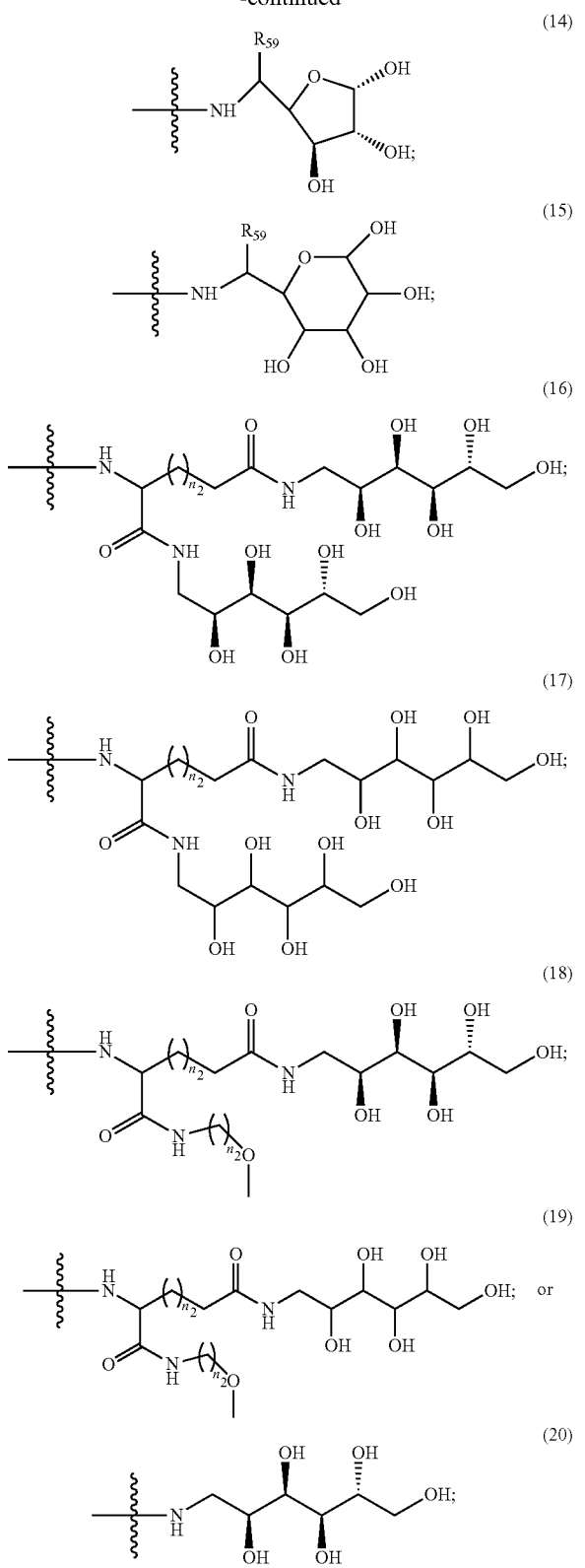

wherein:
R$_{59}$ is —H, C$_{1-8}$ alkyl, cycloalkyl, or arylalkyl;
n$_1$ is an integer from 1 to about 6;
n$_2$ is an integer from 1 to about 5; and
n$_3$ is an integer from about 1 to about 3.

It is understood that all stereochemical forms of the hydrophilic groups are contemplated herein. For example, in the above formula, the hydrophilic group may be derived from ribose, xylose, glucose, mannose, galactose, or other sugar and retain the stereochemical arrangements of pendant hydroxyl and alkyl groups present on those molecules.

It is to be understood that in the foregoing formulae, various deoxy compounds are also contemplated. Illustratively, one or more of the following features are contemplated for the hydrophilic groups when applicable.

In some embodiments, n$_3$ is 2 or 3.
In some embodiments, n$_1$ is 1, 2, or 3.
In some embodiments, n$_2$ is 1.
In some embodiments, R$^{59}$ is hydrogen.
In some embodiments, T$^1$ is

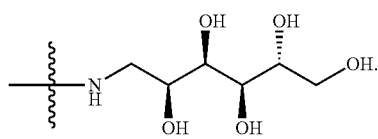 [SMILES: *NC[C@H](O)[C@@H](O)[C@H](O)[C@H](O)CO]

In some embodiments, T$^1$ is

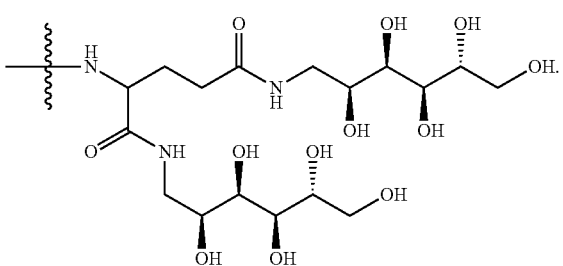 [SMILES: *NC(CCC(=O)NC[C@H](O)[C@@H](O)[C@H](O)[C@H](O)CO)C(=O)NC[C@H](O)[C@@H](O)[C@H](O)[C@H](O)CO]

In some embodiments, T$^1$ is

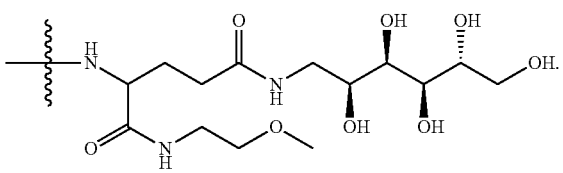

wherein

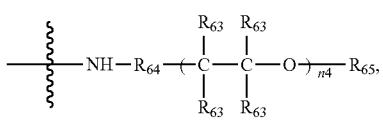

n$_4$ is an integer from 1 to about 25;
each R$_{63}$ is independently —H or C$_{1-8}$ alkyl;
R$_{64}$ is a bond or a C$_{1-8}$ alkyl linker;

$R_{65}$ is —H, $C_{1-8}$ alkyl, —$(CH_2)_{n2}COOR_{62}$, or —$(CH_2)_{n2}COR_{66}$;
$R_{62}$ is H or $C_{1-8}$ alkyl;
$R_{66}$ is H,

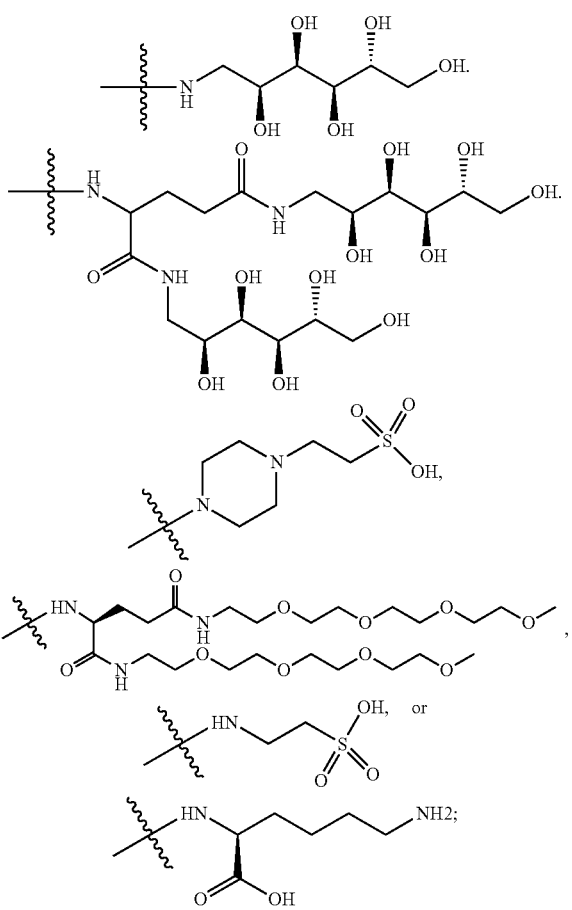

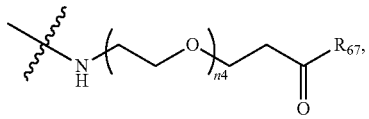

and
$n_2$ is an integer from 1 to about 5.
In some embodiments, $T^1$ is:

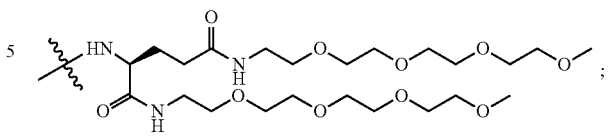

wherein $R_{67}$ is: (1) OH (2)

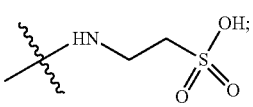

(3)

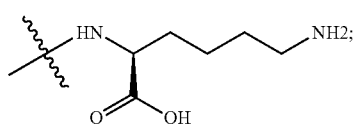

(4)

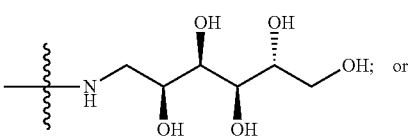

(5)

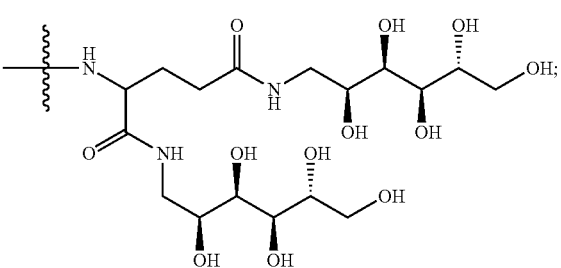

(6)

(7)

wherein $n_4$ is an integer from about 2 to about 20, from about 4 to about 16, from about 6 to about 12, from about 8 to about 12.

In some embodiments, $T^1$ is

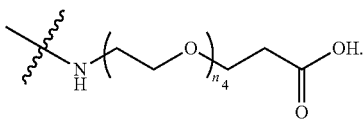

In some embodiments, $n_4$ is an integer from about 2 to about 20, from about 4 to about 16, from about 6 to about 12, from about 8 to about 12.

In some embodiments, $n_4$ is 6, 7, 8, 9, 10, 11, or 12.

In some embodiments, $n_4$ is 8 or 12.

In some embodiments, $T^1$ is

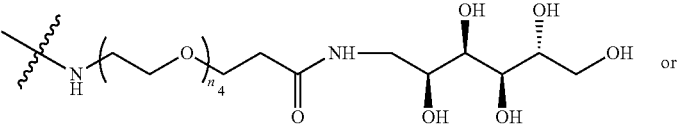

-continued

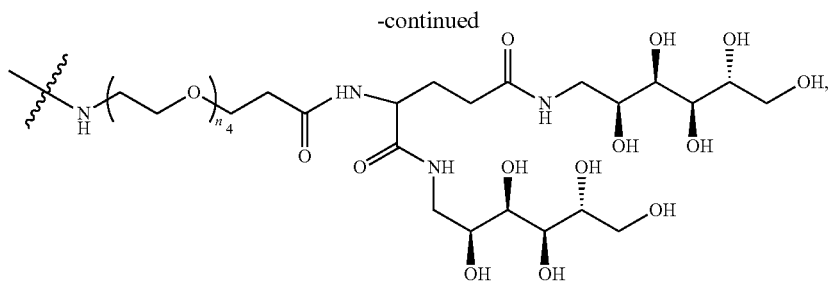

wherein $n_4$ is an integer from about 2 to about 24, from about 4 to about 16, from about 6 to about 12, from about 8 to about 12.

In some embodiments, $n_4$ is 6, 7, 8, 9, 10, 11, or 12.

In some embodiments, $n_4$ is 8. In some embodiments, $n_4$ is 12.

In some embodiments, $T^1$ is

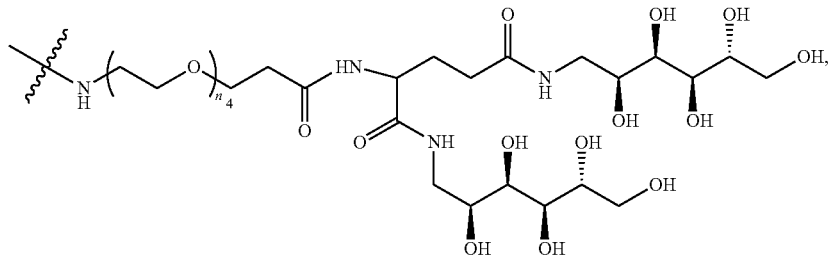

wherein $n_4$ is 8.

In some embodiments, $T^1$ comprises a polyether, e.g., a polyalkylene glycol (PAO). PAO includes but is not limited to, polymers of lower alkylene oxides, in particular polymers of ethylene oxide, such as, for example, propylene oxide, polypropylene glycols, polyethylene glycol (PEG), polyoxyethylenated polyols, copolymers thereof, and block copolymers thereof.

In some embodiments, the polyalkylene glycol is a polyethylene glycol (PEG) including, but not limited to, polydisperse PEG, monodisperse PEG, and discrete PEG. Polydisperse PEGs are a heterogeneous mixture of sizes and molecular weights whereas monodisperse PEGs are typically purified from heterogeneous mixtures and are therefore provide a single chain length and molecular weight. In some embodiments, the PEG units are discrete PEGs provide a single molecule with defined and specified chain length. In some embodiments, the polyethylene glycol is mPEG.

In some embodiments, $T^1$ comprises a PEG unit which comprises one or multiple PEG chains. The PEG chains can be linked together, for example, in a linear, branched or star shaped configuration. The PEG unit, in addition to comprising repeating PEG subunits, may also comprise non-PEG material (e.g., to facilitate coupling of multiple PEG chains to each other or to facilitate coupling to the amino acid). Non-PEG material refers to the atoms in the PEG chain that are not part of the repeating —$CH_2CH_2O$— subunits. In some embodiments, the PEG chain can comprise two monomeric PEG chains linked to each other via non-PEG elements. In some embodiments, the PEG Unit can comprise two linear PEG chains attached to a central core that is attached to the amino acid (i.e., the PEG unit itself is branched).

The PEG unit may be covalently bound to the $M^A$ linker (e.g., to an amino acid in the $M^A$ linker) via a reactive group. Reactive groups are those to which an activated PEG molecule may be bound (e.g., a free amino or carboxyl group). In some embodiments, N-terminal amino acids and lysines (K) have a free amino group; and C-terminal amino acid residues have a free carboxyl group. Sulfhydryl groups (e.g., as found on cysteine residues) may also be used as a reactive group for attaching PEG.

In some embodiments, the PEG unit may be attached to the $M^A$ linker (e.g., to an amino acid in the $M^A$ linker) by using methoxylated PEG ("mPEG") having different reactive moieties, including, but not limited to, succinimidyl succinate (SS), succinimidyl carbonate (SC), mPEG-imidate, para-nitrophenylcarbonate (NPC), succinimidyl propionate (SPA), and cyanuric chloride. Examples of mPEGs include, but are not limited to, mPEG-succinimidyl succinate (mPEG-SS), $mPEG_2$-succinimidyl succinate ($mPEG_2$-SS), mPEG-succinimidyl carbonate (mPEG-SC), $mPEG_2$-succinimidyl carbonate ($mPEG_2$-SC), mPEG-imidate, mPEG-para-nitrophenylcarbonate (mPEG-NPC), mPEG-imidate, $mPEG_2$-para-nitrophenylcarbonate ($mPEG_2$-NPC), mPEG-succinimidyl propionate (mPEG-SPA), $mPEG_2$-succinimidyl propionate ($mPEG_2$-SPA), mPEG-N-hydroxy-succinimide (mPEG-NHS), $mPEG_2$-N-hydroxy-succinimide ($mPEG_2$-NHS), mPEG-cyanuric chloride, $mPEG_2$-cyanuric chloride, $mPEG_2$-Lysinol-NPC, and $mPEG_2$-Lys-NHS. A wide variety of PEG species can be used, and substantially any suitable reactive PEG reagent can be used. In some embodiments, the reactive PEG reagent will result in formation of a carbamate or amide bond upon attachment to the Multifunctional Linker or $M^A$ linker (e.g., to an amino acid in the $M^A$ linker). The reactive PEG reagents include, but are not limited to, $mPEG_2$-N-hydroxy-succinimide ($mPEG_2$-NHS), bifunctional PEG propionaldehyde ($mPEG_2$-ALD), multi-Arm PEG, maleimide-containing PEG (mPEG(MAL)$_2$, $mPEG_2$(MAL)), mPEG-NH2, mPEG-succinimidyl propionate (mPEG-SPA), succinimide of mPEG butanoate acid (mPEG-SBA), mPEG-thioesters, mPEG-double Esters, mPEG-BTC, mPEG-ButyrALD, mPEG-acetaldehyde diethyl acetal (mPEG-ACET), heterofunctional PEGs (e.g., NH2-PEG-COOH, Boc-PEG-NHS, Fmoc-PEG-NHS, NHS-PEG-vinylsulfone (NHS-PEG-VS), or NHS-PEG-MAL), PEG acrylates (ACRL-PEG-NHS), PEG-phospholipids (e.g., mPEG-DSPE), multi-armed PEGs of the SUNBRITE™ series including the glycerine-based PEGs activated by a chemistry chosen by those skilled in the art, any SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some such embodiments, the PEG unit comprises no more than about 72 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, or at least 20 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, or at least 18 subunits.

In some embodiments, the PEG unit comprises at least 6 subunits, at least 7 subunits, at least 8 subunits, at least 9 subunits, at least 10 subunits, at least 11 subunits, or at least 12 subunits.

In some embodiments, the PEG unit comprises at least 8 subunits, at least 9 subunits, at least 10 subunits, at least 11 subunits, or at least 12 subunits.

In some embodiments, the PEG unit comprises at least 6 subunits, at least 7 subunits, or at least 8 subunits.

In some embodiments, a linear PEG unit is:

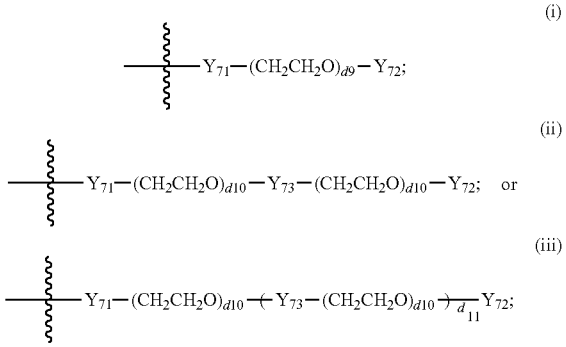

wherein;

indicates site of attachment to the $M^A$ linker (e.g., to an amino acid in the $M^A$ linker);

$Y_{71}$ is a PEG attachment unit;

$Y_{72}$ is a PEG capping unit;

$Y_{73}$ is an PEG coupling unit (i.e., for coupling multiple PEG subunit chains together);

$d_9$ is an integer from 2 to 72;

each $d_{10}$ is independently an integer from 1 to 72; and $d_{11}$ is an integer from 2 to 5.

In some embodiments, $d_9$ is an integer from 2 to 24. In some embodiments, $d_9$ is an integer from 4 to 24. In some embodiments, $d_9$ is an integer from 6 to 24, from 8 to 24, from 10 to 24, or from 12 to 24.

In some embodiments, there are at least 6 PEG subunits in the PEG unit. In some embodiments, there are at least 8 PEG subunits in the PEG unit. In some embodiments, there are at least 10 PEG subunits in the PEG unit. In some embodiments, there are at least 12 PEG subunits in the PEG unit.

In some embodiments, $d_9$ is 8 or about 8, 12 or about 12, 24 or about 24.

In some embodiments, each $Y_{72}$ is independently —$C_{1-10}$ alkyl, —$C_{2-10}$ alkyl-$CO_2H$, —$C_{2-10}$ alkyl-OH, —$C_{2-10}$ alkyl-$NH_2$, —$C_{2-10}$ alkyl-NH($C_{1-3}$ alkyl), or $C_{2-10}$ alkyl-N ($C_{1-3}$ alkyl)$_2$.

In some embodiments, $Y_{72}$ is —$C_{1-10}$ alkyl, —$C_{2-10}$ alkyl-$CO_2H$, —$C_{2-10}$ alkyl-OH, or —$C_{2-10}$ alkyl-$NH_2$.

In some embodiments, the PEG coupling unit is part of the PEG unit and is non-PEG material that acts to connect two or more chains of repeating $CH_2CH_2O$— subunits. In some embodiments, the PEG coupling unit $Y_{73}$ is —$C_{2-10}$ alkyl-C(O)—NH—, —$C_{2-10}$ alkyl-NH—C(O)—, —$C_{2-10}$ alkyl-NH—, —$C_{2-10}$ alkyl-C(O)—, —$C_{2-10}$ alkyl-O—, or —$C_{2-10}$ alkyl-S—.

In some embodiments, each $Y_{73}$ is independently —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$ alkyl-S—, or —$C_{1-10}$ alkyl-NH—.

In some embodiments, the PEG attachment unit is part of the PEG unit and acts to link the PEG unit to the $M^A$ linker (e.g., to an amino acid in the $M^A$ linker). In some embodiments, the amino acid has a functional group that forms a bond with the PEG Unit. In some embodiments, the functional groups for attachment of the PEG unit to the amino acid include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. In some embodiments, the PEG unit can be attached to the amino acid, for example, via a disulfide, thioether, hydrazone, oxime, peptide, ester, sulfonamide, carbamate, or amide bond. In some embodiments, the reaction for attaching the PEG unit can be a cycloaddition, addition, addition/elimination or substitution reaction, or a combination thereof when applicable.

Examples of linear PEG units include:

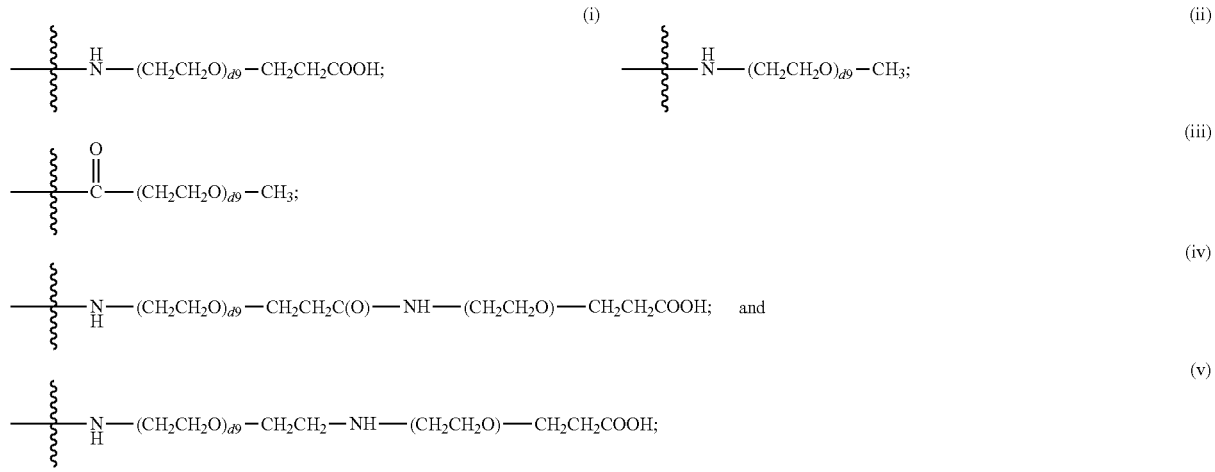

wherein

indicates site of attachment to the Multifunctional Linker or $M^4$ linker (e.g., to an amino acid in the $M^4$ linker), and each $d_9$ is independently an integer from 4 to 24, 6 to 24, 8 to 24, 10 to 24, 12 to 24, 14 to 24, or 16 to 24.

In some embodiments, $d_9$ is about 8, about 12, or about 24.

In some embodiments, $d_9$ is about 8.

In some embodiments, the PEG unit is from about 300 Da to about 5 kDa; from about 300 Da to about 4 kDa; from about 300 Da to about 3 kDa; from about 300 Da to about 2 kDa; or from about 300 Da to about 1 kDa. In some embodiments, the PEG unit has at least 6 subunits or at least 8, 10 or 12 subunits. In some embodiments, the PEG unit has at least 6 subunits or at least 8, 10 or 12 subunits but no more than 24 subunits.

In some embodiments, suitable polyethylene glycols may have a free hydroxy group at each end of the polymer molecule, or may have one hydroxy group etherified with a lower alkyl, e.g., a methyl group. In some embodiments suitable polyethylene glycols are derivatives of polyethylene glycols having esterifiable carboxy groups. In some embodiments, polyethylene glycols are commercially available under the trade name PEG, usually as mixtures of polymers characterized by an average molecular weight. In some embodiments, polyethylene glycols having an average molecular weight from about 300 to about 5000. In some embodiments, polyethylene glycols having an average molecular weight from about 600 to about 1000.

In some embodiments, examples of hydrophilic groups that are suitable for the conjugates, scaffolds, and methods disclosed herein can be found in e.g., U.S. Pat. No. 8,367,065 column 13; U.S. Pat. No. 8,524,696 column 6; WO2015/057699 and WO 2014/062697, the contents of each of which are hereby incorporated by reference in their entireties.

Antibodies

In some embodiments, the glycoprotein comprising a core-N-acetylglucosamine substituent (core-GlcNAc moiety) is an antibody comprising a core-N-acetylglucosamine substituent (core-GlcNAc moiety). In some embodiments, the glycoprotein is a monoclonal antibody (mAb) IgA, IgD, IgE, IgG, or IgM antibodies. In some embodiments, the antibody is an IgG antibody. In some embodiments, the antibody is an IgG1 antibody. In some embodiments, when said antibody is a whole antibody, the antibody comprises one or more (e.g., one) core-GlcNAc moiety on each heavy chain, said core-GlcNAc moiety being optionally fucosylated. In some embodiments, the whole antibody comprises two or more (e.g., two) optionally fucosylated, core-GlcNAc moieties. In some embodiments, when said antibody is a single chain antibody or an antibody fragment, e.g. a Fab or Fc fragment, the antibody comprises one or more core-GlcNAc moieties, which are optionally fucosylated. In some embodiments in the antibody comprising a core-GlcNAc moiety, said core-GlcNAc moiety may be situated anywhere on the antibody, provided that said substituent does not hinder the antigen-binding site of the antibody. In some embodiments, said core-GlcNAc moiety is present at a native N-glycosylation site of the antibody. In some embodiments, the antibody comprises, or is engineered to comprise, at least one chemically reactive group or a chemically reactive amino acid moiety or side chains.

In some embodiments, the antibody is capable of directing the conjugate to specific tissues, cells, or locations in a cell. In some embodiments, the antibody is capable of directing the conjugate in culture or in a whole organism, or both. In some embodiments, the antibody comprises a ligand that is present on the cell surface of the targeted cell(s) to which it binds with an effective specificity, affinity, and avidity. In some embodiments, the antibody directs the conjugate to tissues other than the liver. In some embodiments, the antibody directs the conjugate to a specific tissue such as the liver, kidney, lung, or pancreas. In some embodiments, the antibody directs the conjugate to a target cell (e.g., a cancer cell), a receptor expressed on a cell (e.g., a cancer cell), a matrix tissue, or a protein associated with cancer (e.g., tumor antigen). In some embodiments, cells comprising the tumor vasculature may be targeted. In some embodiments, the antibody is capable of directing the conjugate to specific types of cells, e.g., specific targeting to hepatocytes in the liver as opposed to Kupffer cells. In some embodiments, the antibody is capable of directing the conjugate to cells of the reticular endothelial or lymphatic system, or to professional phagocytic cells such as macrophages or eosinophils. In some embodiments, the conjugate itself is an effective delivery system, without the need for specific targeting.

In some embodiments, the antibody is capable of directing the conjugate to a location within the cell (e.g., the nucleus, the cytoplasm, or the endosome). In some embodiments, the antibody enhances cellular binding to receptors, or cytoplasmic transport to the nucleus and nuclear entry or release from endosomes or other intracellular vesicles.

In some embodiments, the conjugate comprises a B7-H4 antibody or modified B7-H4 antibody of the present disclosure.

B7-H4 Antibodies

Provided by the disclosure are isolated antibodies that bind to B7-H4, a Type I transmembrane protein found, for example, on the surface of antigen presenting cells (APC). The B7-H4 antibodies include, but are not limited to, humanized antibodies, chimeric antibodies, mouse antibodies, human antibodies, and antibodies comprising the heavy chain and/or light chain CDRs discussed herein.

In some embodiments, B7-H4 antibodies of the disclosure specifically bind to an epitope on the full-length human B7-H4 protein comprising the amino acid sequence:

```
                                       (SEQ ID NO: 59)
MASLGQILFWSIISIIIILAGAIALIIGFGISGRHS

ITVTTVASAGNIGEDGILSCTFEPDIKLSDIVIQW

LKEGVLGLVHEFKEGKDELSEQDE1VIFRGRTAVF

ADQVIVGNASLRLKNVQLTDAGTYKCYIITSKGKG

NANLEYKTGAFSMPEVNVDYNASSETLRCEAPRWF

PQPTVVWASQVDQGANFSEVSNTSFELNSENVTMK

VVSVLYNVTINNTYSCMIENDIAKATGDIKVTESE

IKRRSHLQLLNSKASLCVSSFFAISWALLPLSPYL

MLK.
```

In some embodiments, a B7-H4 antibody is a human antibody. In some embodiments, a B7-H4 antibody modulates B7-H4 activity. In some embodiments, the antibody is one that induces an ADCC response in a subject that receives the antibody. In some embodiments, a B7-H4 antibody does not inhibit T-Cell suppression activity of B7-H4. The B7-H4 antibodies of this disclosure can be, for example, full-length antibodies. Alternatively, the antibodies can be antibody fragments, such as Fab, Fab' or Fab' 2 fragments or single chain antibodies (e.g., scFv). In some embodiments, the antibody is an IgG1 antibody.

In some embodiments, a B7-H4 antibody comprises a heavy chain variable region and a light chain variable region. In some embodiments, a B7-H4 antibody comprises at least one heavy chain comprising a heavy chain variable region and at least a portion of a heavy chain constant region, and at least one light chain comprising a light chain variable region and at least a portion of a light chain constant region. In some embodiments, a B7-H4 antibody comprises two heavy chains, wherein each heavy chain comprises a heavy chain variable region and at least a portion of a heavy chain constant region, and two light chains, wherein each light chain comprises a light chain variable region and at least a portion of a light chain constant region.

In some embodiments, a human B7-H4 antibody comprises one or more human constant regions. In some embodiments, the human heavy chain constant region is of an isotype selected from IgA, IgG (for example, an IgG1, IgG2, IgG3, or IgG4, and IgD. In some embodiments, the human light chain constant region is of an isotype selected from kappa (κ) and lambda (λ). In some embodiments, a human antibody described herein comprises a human IgG constant region.

In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human B7-H4 antibody comprising a human IgG1 heavy chain constant region or a human IgG3 heavy chain constant region is selected. In some embodiments, when effector function is not desirable, a human B7-H4 antibody comprising a human IgG4 or IgG2 heavy chain constant region is selected.

In some embodiments, the antibodies of this disclosure are characterized by particular functional features or properties of the antibodies. For example, the antibodies bind specifically to human B7-H4. Typically, an antibody of this disclosure binds to B7-H4 with high affinity, for example with a $K_D$ of $1\times10^{-7}$ M or less. The anti-B7-H4 antibodies of this disclosure typically exhibit one or more of the following characteristics:

(a) binds to human B7-H4 with a $K_D$ of $1\times10^{-7}$ M or less; and/or (b) binds to human CHO cells transfected with B7-H4 (e.g. human B7-H4).

In some embodiments, the antibody binds to human B7-H4 with a $K_D$ of $5\times10^{-8}$ M or less, bind to human B7-H4 with a $K_D$ of $2\times10^{-8}$ M or less, binds to human B7-H4 with a $K_D$ of $5\times10^{-9}$ M or less, binds to human B7-H4 with a $K_D$ of $4\times10^{-9}$ M or less, binds to human B7-H4 with a $K_D$ of $3\times10^{-9}$ M or less, binds to human B7-H4 with a $K_D$ of $2\times10^{-9}$ M or less or binds to human B7-H4 with a $K_D$ of $1\times10^{-9}$ M or less.

Standard assays to evaluate the binding ability of the antibodies toward B7-H4 are known in the art, including for example, ELISAs, Western blots, RIAs and flow cytometry analysis. The binding kinetics (e.g., binding affinity) of the antibodies also can be assessed by standard assays known in the art, such as by ELISA, Scatchard and Biacore® system analysis.

A potential therapeutic mAbs must not only bind to their target but must also be free from "developability issues" such as poor stability or high levels of aggregation. We describe guideline values for five metrics thought to be implicated in poor developability: the total length of the complementarity-determining regions (CDRs), the extent and magnitude of surface hydrophobicity, positive charge and negative charge in the CDRs, and asymmetry in the net heavy- and light-chain surface charges. The guideline cut-offs for each property were derived from the values seen in CSTs, and a flagging system is proposed to identify non-conforming candidates.

An exemplary B7-H4 antibody of the disclosure include B7-H4_2F9 (also referred to herein in as the "B7-H4_2F9 parental antibody", "2F9 parental antibody" or "parental antibody" which was disclosed in U.S. Pat. No. 8,609,816, the contents of which is hereby incorporated by reference in its entirety.

A potential therapeutic mAbs must not only bind to their target but must also be free from "developability issues" such as poor stability, high levels of aggregation, low-level expression, low solubility, covalent integrity, conformational and colloidal instability, high polyspecificity, and high immunogenicity.

According the B7-H4_2F9 parental antibody sequence was analyzed for metrics thought to be implicated in poor developability, such as for example, the total length of the complementarity-determining regions (CDRs), the extent and magnitude of surface hydrophobicity, positive charge and negative charge in the CDRs, asymmetry in the net heavy- and light-chain surface charges and post-translational modifications (PTMs). This developability analysis of the B7-H4_2F9 parental antibody sequence revealed three potential sequence liabilities. In particular, the B7-H4_2F9 parental antibody sequence had an unpaired cysteine residue, an aspartate isomerization sequence, and a methionine oxidation site. Each of these three sequence liabilities could create potential development such as stability, potency, and homogeneity of an antibody, and can result in a complicated process in downstream development.

In order to address the potential sequence liabilities of the B7-H4_2F9 parental antibody, twenty (20) variants of B7-H4_2F9 were designed and generated that addressed these potential developability concerns. These variant antibodies included B7-H4_2F9V1, B7-H4_2F9V2, B7-H4_2F9V3, B7-H4_2F9V4, B7-H4_2F9V5, B7-H4_2F9V6, B7-H4_2F9V7, B7-H4_2F9V8, B7-H4_2F9V9, B7-H4_2F9V10, B7-H4_2F9V11, B7-H4_2F9V12, B7-H4_2F9V13, B7-H4_2F9V14, B7-H4_2F9V15, B7-H4_2F9V16, B7-H4_2F9V17, B7-H4_2F9V18, B7-H4_2F9V19, and B7-H4_2F9V20. Each of the 20 variants were characterized for B7-H4 binding, polyspecificity, and other properties.

The nucleic acid and amino acid sequence of the monoclonal B7-H4 antibodies of the disclosure are provided below. The complementarity determining regions (CDRs) of the heavy chain and the light chain are underlined in the amino acid sequences presented below. The amino acids encompassing the complementarity determining regions (CDR) as shown below are defined in accordance to the IMGT numbering system (See IMGT®, the international ImMunoGeneTics information System®. Available online: http://www.imgt.org/).

B7-H4_2F9 Variable Regions

All of the twenty B7-H4_2F9 parental variants (i.e., B7-H4_2F9V1 through B7-H4_2F9V20) share a common light chain variable region. (referred to herein as the B7-H4_2F9 $V_L$)

In some embodiments, all the antibodies of the disclosure comprise a light chain variable region comprising or consisting of the amino acid sequence of SEQ ID NO: 50.

The $V_L$ chain of B7-H4_2F9_$V_L$ (SEQ ID NO:50) comprises or consists of the amino acid sequence:

```
                                        (SEQ ID NO: 50)
EIVLTQSPGTLSLSPGERATLSCRASQSVSSSYLA

WYQQKPGQAPRLLIYGASSRATGIPDRFSGSGSGT

DFTLTISRLEPEDFAVYYCQQYGSSPLYTFGQGTK

LEIK.
```

The VH chain of B7-H4_2F9_parental (SEQ ID NO:1) comprises or consists of the amino acid sequence:

```
                                        (SEQ ID NO: 1)
EVQLVESGGGLIQPGGSLRLSCAASGFIVSRNYMNWVRQAPGKGLEWVSVIYGSGRTD

CADSVKGRFTISRDNSKNTLYLQMNSLRAEDTAVYYCARDGDYGMDVWGQGTTVTVS

S.
```

The VH chain of B7-H4_2F9V1 (SEQ ID NO: 5) comprises or consists of the amino acid sequence:

```
                                        (SEQ ID NO: 5)
EVQLVESGGGLIQPGGSLRLSCAASGFIVSRNYMNWVRQAPGKGLEWVSVIYGSGRTY

YADSVKGRFTISRDNSKNTLYLQMNSLRAEDTAVYYCARDGDYGMDVWGQGTTVTVS

S.
```

The VH chain of B7-H4_2F9V2 (SEQ ID NO: 8) comprises or consists of the amino acid sequence:

```
                                        (SEQ ID NO: 8)
EVQLVESGGGLIQPGGSLRLSCAASGFIVSRNYMNWVRQAPGKGLEWVSVIYGSGRTY

YADSVKGRFTISRDNSKNTLYLQMNSLRAEDTAVYYCARDADYGMDVWGQGTTVTVS

S.
```

The VH chain of B7-H4_2F9V3 (SEQ ID NO: 11) comprises or consists of the amino acid sequence:

```
                                        (SEQ ID NO: 11)
EVQLVESGGGLIQPGGSLRLSCAASGFIVSRNYMNWVRQAPGKGLEWVSVIYGSGRTY

YADSVKGRFTISRDNSKNTLYLQMNSLRAEDTAVYYCARDTYAMDVWGQGTTVTVSS.
```

-continued

The VH chain of B7-H4_2F9V4 (SEQ ID NO: 14)
comprises or consists of the amino
acid sequence:

(SEQ ID NO: 14)
EVQLVESGGGLIQPGGSLRLSCAASGFIVSRNYMNWVRQAPGKGLEWVSVIYGSGRTY

YADSVKGRFTISRDNSKNTLYLQMNSLRAEDTAVYYCARDADYGLDVWGQGTTVTVS

S.

The VH chain of B7-H4_2F9V5 (SEQ ID NO: 17)
comprises or consists of the amino
acid sequence:

(SEQ ID NO: 17)
EVQLVESGGGLIQPGGSLRLSCAASGFIVSRNYMNWVRQAPGKGLEWVSVIYGSGRTY

YADSVKGRFTISRDNSKNTLYLQMNSLRAEDTAVYYCARDTYALDVWGQGTTVTVSS.

The VH chain of B7-H4_2F9V6 (SEQ ID NO: 20)
comprises or consists of the amino acid
sequence comprises or consists of the
amino acid sequence:

(SEQ ID NO: 20)
EVQLVESGGGLIQPGGSLRLSCAASGFIVSRNYMNWVRQAPGKGLEWVSVIYGSGRTD

YADSVKGRFTISRDNSKNTLYLQMNSLRAEDTAVYYCARDGDYGMDVWGQGTTVTVS

S.

The VH chain of B7-H4_2F9V7 (SEQ ID NO: 22)
comprises or consists of the amino
acid sequence:

(SEQ ID NO: 22)
EVQLVESGGGLIQPGGSLRLSCAASGFIVSRNYMNWVRQAPGKGLEWVSVIYGSGRTD

YADSVKGRFTISRDNSKNTLYLQMNSLRAEDTAVYYCARDADYGMDVWGQGTTVTVS

S.

The B7-H4_2F9V7 variable heavy chain is also
referred to herein as the XMT-1603
variable heavy chain.
The VH chain of B7-H4_2F9V8 (SEQ ID NO: 24)
comprises or consists of the amino
acid sequence:

(SEQ ID NO: 24)
EVQLVESGGGLIQPGGSLRLSCAASGFIVSRNYMNWVRQAPGKGLEWVSVIYGSGRTD

YADSVKGRFTISRDNSKNTLYLQMNSLRAEDTAVYYCARDADYGLDVWGQGTTVTVS

S.

The VH chain of B7-H4_2F9V9 (SEQ ID NO: 26)
comprises or consists of the amino
acid sequence:

(SEQ ID NO: 26)
EVQLVESGGGLIQPGGSLRLSCAASGFIVSRNYMNWVRQAPGKGLEWVSVIYGSGRTD

YADSVKGRFTISRDNSKNTLYLQMNSLRAEDTAVYYCARDTYAMDVWGQGTTVTVSS.

The VH chain of B7-H4_2F9V10 (SEQ ID NO: 28)
comprises or consists of the amino
acid sequence:

(SEQ ID NO: 28)
EVQLVESGGGLIQPGGSLRLSCAASGFIVSRNYMNWVRQAPGKGLEWVSVIYGSGRTD

YADSVKGRFTISRDNSKNTLYLQMNSLRAEDTAVYYCARDTYALDVWGQGTTVTVSS.

The VH chain of B7-H4_2F9V11 (SEQ ID NO: 30)
comprises or consists of the amino
acid sequence:

(SEQ ID NO: 30)
EVQLVESGGGLIQPGGSLRLSCAASGFIVSRNYMNWVRQAPGKGLEWVSVIYGSGRTD

AADSVKGRFTISRDNSKNTLYLQMNSLRAEDTAVYYCARDGDYGMDVWGQGTTVTVS

S.

The VH chain of B7-H4_2F9V12 (SEQ ID NO: 32) comprises or consists of the amino acid sequence:

(SEQ ID NO: 32)
EVQLVESGGGLIQPGGSLRLSCAASGFIVSRNYMNWVRQAPGKGLEWVSVIYGSGRTD

AADSVKGRFTISRDNSKNTLYLQMNSLRAEDTAVYYCARDADYGMDVWGQGTTVTVS

S.

The VH chain of B7-H4_2F9V13 (SEQ ID NO: 34) comprises or consists of the amino acid sequence:

(SEQ ID NO: 34)
EVQLVESGGGLIQPGGSLRLSCAASGFIVSRNYMNWVRQAPGKGLEWVSVIYGSGRTD

AADSVKGRFTISRDNSKNTLYLQMNSLRAEDTAVYYCARDADYGLDVWGQGTTVTVS

S.

The VH chain of B7-H4_2F9V14 (SEQ ID NO: 36) comprises or consists of the amino acid sequence:

(SEQ ID NO: 36)
EVQLVESGGGLIQPGGSLRLSCAASGFIVSRNYMNWVRQAPGKGLEWVSVIYGSGRTD

AADSVKGRFTISRDNSKNTLYLQMNSLRAEDTAVYYCARDTYAMDVWGQGTTVTVSS.

The VH chain of B7-H4_2F9V15 (SEQ ID NO: 38) comprises or consists of the amino acid sequence:

(SEQ ID NO: 38)
EVQLVESGGGLIQPGGSLRLSCAASGFIVSRNYMNWVRQAPGKGLEWVSVIYGSGRTD

AADSVKGRFTISRDNSKNTLYLQMNSLRAEDTAVYYCARDTYALDVWGQGTTVTVSS.

The VH chain of B7-H4_2F9V16 (SEQ ID NO: 40) comprises or consists of the amino acid sequence:

(SEQ ID NO: 40)
EVQLVESGGGLIQPGGSLRLSCAASGFIVSRNYMNWVRQAPGKGLEWVSVIYGSGRTDS

ADSVKGRFTISRDNSKNTLYLQMNSLRAEDTAVYYCARDGDYGMDVWGQGTTVTVSS.

The VH chain of B7-H4_2F9V17 (SEQ ID NO: 42) comprises or consists of the amino acid sequence:

(SEQ ID NO: 42)
EVQLVESGGGLIQPGGSLRLSCAASGFIVSRNYMNWVRQAPGKGLEWVSVIYGSGRTDS

ADSVKGRFTISRDNSKNTLYLQMNSLRAEDTAVYYCARDADYGMDVWGQGTTVTVSS.

The VH chain of B7-H4_2F9V18 (SEQ ID NO: 44) (also referred to herein as the XMT-1604 VH) comprises or consists of the amino acid sequence:

(SEQ ID NO: 44)
EVQLVESGGGLIQPGGSLRLSCAASGFIVSRNYMNWVRQAPGKGLEWVSVIYGSGRTDS

ADSVKGRFTISRDNSKNTLYLQMNSLRAEDTAVYYCARDADYGLDVWGQGTTVTVSS.

The B7-H4_2F9V18 variable heavy chain is also referred to herein as the XMT-1604 variable heavy chain.

The VH chain of B7-H4_2F9V19 (SEQ ID NO: 46) comprises or consists of the amino acid sequence:

(SEQ ID NO: 46)
EVQLVESGGGLIQPGGSLRLSCAASGFIVSRNYMNWVRQAPGKGLEWVSVIYGSGRTDS

ADSVKGRFTISRDNSKNTLYLQMNSLRAEDTAVYYCARDTYAMDVWGQGTTVTVSS.

The VH chain of B7-H4_2F9V20 (SEQ ID NO: 48) comprises or consists of the amino acid sequence:

(SEQ ID NO: 48)
EVQLVESGGGLIQPGGSLRLSCAASGFIVSRNYMNWVRQAPGKGLEWVSVIYGSGRTDS

ADSVKGRFTISRDNSKNTLYLQMNSLRAEDTAVYYCARDTYALDVWGQGTTVTVSS.

CDRs

Table I below summarizes the CDRs of the B7-H4 antibodies of the disclosure.

TABLE I

AMINO ACID SEQUENCES OF THE COMPLEMENTARY DETERMINING REGIONS OF THE HEAVY AND LIGHT CHAINS.

| Antibody | CDR1 | SEQ ID NO: | CDR2 | SEQ ID NO: | CDR3 | SEQ ID NO: |
|---|---|---|---|---|---|---|
| B7-H4_2F9 parental_vH | GFIVSRNY | 2 | IYGSGRT | 3 | ARDGDYGMDV | 4 |
| B7-H42F9V1 | GFIVSRNY | 2 | IYGSGRT | 3 | ARDGDYGMDV | 4 |
| B7-H42F9V2 | GFIVSRNY | 2 | IYGSGRT | 3 | ARDADYGMDV | 10 |
| B7-H4_2F9V3 | GFIVSRNY | 2 | IYGSGRT | 3 | ARDTYAMDV | 13 |
| B7-H4_2F9V4 | GFIVSRNY | 2 | IYGSGRT | 3 | ARDADYGLDV | 16 |
| B7-H4_2F9V5 | GFIVSRNY | 2 | IYGSGRT | 3 | ARDTYALDV | 19 |
| B7-H4_2F9V6 | GFIVSRNY | 2 | IYGSGRT | 3 | ARDGDYGMDV | 4 |
| XMT-1603 B7-H4_2F9V7 | GFIVSRNY | 2 | IYGSGRT | 3 | ARDADYGMDV | 10 |
| B7-H4_2F9V8 | GFIVSRNY | 2 | IYGSGRT | 3 | ARDADYGLDV | 16 |
| B7-H4_2F9V9 | GFIVSRNY | 2 | IYGSGRT | 3 | ARDTYAMDV | 13 |
| B7-H42F9V10 | GFIVSRNY | 2 | IYGSGRT | 3 | ARDTYALDV | 19 |
| B7-H42F9V11 | GFIVSRNY | 2 | IYGSGRT | 3 | ARDGDYGMDV | 4 |
| B7-H4_2F9V12 | GFIVSRNY | 2 | IYGSGRT | 3 | ARDADYGMDV | 10 |
| B7-H4_2F9V13 | GFIVSRNY | 2 | IYGSGRT | 3 | ARDADYGLDV | 16 |
| B7-H4_2F9V14 | GFIVSRNY | 2 | IYGSGRT | 3 | ARDTYAMDV | 13 |
| B7-H42F9V15 | GFIVSRNY | 2 | IYGSGRT | 3 | ARDTYALDV | 19 |
| B7-H42F9V16 | GFIVSRNY | 2 | IYGSGRT | 3 | ARDGDYGMDV | 4 |
| B7-H42F9V17 | GFIVSRNY | 2 | IYGSGRT | 3 | ARDADYGMDV | 10 |
| XMT-1604 B7-H4_2F9V18 | GFIVSRNY | 2 | IYGSGRT | 3 | ARDADYGLDV | 16 |
| B7-H42F9V19 | GFIVSRNY | 2 | IYGSGRT | 3 | ARDTYAMDV | 13 |
| B7-H4_2F9V20 | GFIVSRNY | 2 | IYGSGRT | 3 | ARDTYALDV | 19 |
| B7-H4_2F9 parental_vL | QSVSSSY | 53 | GAS | 54 | QQYGSSPLYT | 55 |

It is well known in the art that the CDR3 domain, independently from the CDR1 and/or CDR2 domain(s) alone can determine the binding specificity of a B7-H4 antibody for a cognate antigen and that multiple antibodies can predictably be generated having the same binding specificity based on a common CDR3 sequence.

In some embodiments, the antibodies comprise one or more heavy and/or light chain CDR3 domain from a non-human antibody, such as a mouse or rat antibody, wherein the monoclonal antibody is capable of specifically binding to B7-H4. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

In some embodiments, the monoclonal antibodies comprising one or more heavy and/or light chain CDR3 domain from a first human antibody, such as, for example, a human antibody obtained from a non-human animal, wherein the first human antibody is capable of specifically binding to B7-H4 and wherein the CDR3 domain from the first human antibody replaces a CDR3 domain in a human antibody that is lacking binding specificity for B7-H4 to generate a second human antibody that is capable of specifically binding to B7-H4. In some embodiments, the antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

B7-H4_2F9 Constant Regions

The B7-H4_2F9 parental antibody and the twenty variants of the disclosure have light chain constant region comprises or consists of the amino acid sequence:

(SEQ ID NO: 51)
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC.

The B7-H4_2F9 light chain constant region (SEQ ID NO:51) is also referred to herein as B7-H4_2F9 LC.

In some embodiments, antibodies of the disclosure comprise a light chain comprising or consisting of a light chain variable region amino acid sequence and a light chain constant region amino acid sequence. Antibody light chains (variable and constant regions) of the disclosure comprising or consisting of the amino acid sequence of SEQ ID NO: 52.

The B7-H4_2F9 parental antibody and the twenty variants of the disclosure have a IgG1 heavy chain constant region comprises or consisting of the amino acid sequence:

```
                                     (SEQ ID NO: 6)
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLEPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPG.
```

The B7-H4_2F9 IgG1 heavy chain constant region (SEQ ID NO:6) is also referred to herein as B7-H4_2F9 HC.

In some embodiments, the IgG1 heavy chain constant region comprising or consisting of SEQ ID NO: 6 further comprises one or more amino acids at the N-terminus or C-terminus. In some embodiments, the IgG1 heavy chain constant region comprises a C-terminal lysine (SEQ ID NO: 61).

In some embodiments, antibodies of the disclosure comprise a heavy chain comprising or consisting of a heavy chain variable region amino acid sequence and a heavy chain constant region amino acid sequence. Antibody heavy chains (variable and constant regions) of the disclosure are described in Table II and the sequence listing filed herewith.

In some embodiments, antibodies of the disclosure can comprise an IgG2 heavy chain constant region that comprises or consisting of the amino acid sequence:

```
                                     (SEQ ID NO: 57)
ASTKGPSVFPLAPCSRSTSESTAALGCLVKDYFPE

PVTVSWNSGALTSGVHTFPAVLQSSGLYSLSSVVT

VPSSNFGTQTYTCNVDHKPSNTKVDKTVERKCCVE

CPPCPAPPVAGPSVFLFPPKPKDTLMISRTPEVTC

VVVDVSHEDPEVQFNWYVDGVEVHNAKTKPREEQF

NSTFRVVSVLTVVHQDWLNGKEYKCKVSNKGLPAP

IEKTISKTKGQPREPQVYTLPPSREEMTKNQVSLT

CLVKGFYPSDISVEWESNGQPENNYKTTPPMLDSD

GSFFLYSKLTVDKSRWQQGNVFSCSVMHEALHNHY

TQKSLSLSPGK.
```

In some embodiments, antibodies of the disclosure can comprise an IgG4 heavy chain constant region that comprises or consisting of the amino acid sequence:

```
                                     (SEQ ID NO: 58)
ASTKGPSVFPLAPCSRSTSESTAALGCLVKDYFPE

PVTVSWNSGALTSGVHTFPAVLQSSGLYSLSSVVT
```

-continued
```
VPSSSLGTKTYTCNVDHKPSNTKVDKRVESKYGPP

CPSCPAPEFLGGPSVFLEPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFELYSRLTVDKSRWQEGNVFSCSVMHEALHNH

YTQKSLSLSLGK.
```

TABLE II

Antibody Heavy Chain Amino Acid Sequences
(Heavy chain variable region + IgG1
Heavy chain constant region)

| Heavy Chain | SEQ ID NO: |
|---|---|
| B7-H4_2F9 parental_vH | 56 |
| B7-H4_2F9V1 | 7 |
| B7-H4_2F9V2 | 9 |
| B7-H4_2F9V3 | 12 |
| B7-H4_2F9V4 | 15 |
| B7-H4_2F9V5 | 18 |
| B7-H4_2F9V6 | 21 |
| B7-H4_2F9V7 | 23 |
| B7-H4_2F9V8 | 25 |
| B7-H4_2F9V9 | 27 |
| B7-H4_2F9V10 | 29 |
| B7-H4_2F9V11 | 31 |
| B7-H4_2F9V12 | 33 |
| B7-H4_2F9V13 | 35 |
| B7-H4_2F9V14 | 37 |
| B7-H4_2F9V15 | 39 |
| B7-H4_2F9V16 | 41 |
| B7-H4_2F9V17 | 43 |
| XMT-1604 B7-H4_2F9V18 | 45 |
| B7-H4_2F9V19 | 47 |
| B7-H4_2F9V20 | 49 |

Specific Embodiments

In yet another embodiment, a B7-H4 antibody of this disclosure comprises heavy and light chain variable regions comprising amino acid sequences that are homologous to the amino acid sequences of the preferred antibodies described herein and wherein the antibodies retain the desired functional properties of the anti-B7-H4 antibodies of this disclosure. For example, this disclosure provides an isolated monoclonal antibody or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 44, 22, 30, 40, and 42;

(b) the light chain variable region comprises an amino acid sequence that is at least 80% homologous to an amino acid sequence of SEQ ID NO: 50;

(c) the antibody binds to human B7-H4 with a $K_D$ of $1 \times 10^{-7}$ M or less; and (d) the antibody binds to human CHO cells transfected with B7-H4.

In various embodiments, the antibody can be, for example, a human antibody, a humanized antibody or a chimeric antibody.

In other embodiments, the VH and/or VL amino acid sequences may be 85%, 90%, 95%, 96%, 97%, 98% or 99% homologous to the sequences set forth above. A B7-H4 antibody having VH and VL regions having high (i.e. 80% or greater) homology to the VH and VL regions of the sequences set forth above, can be obtained by mutagenesis (e.g., site-directed or PCR-mediated mutagenesis) of nucleic acid molecules encoding the amino acid sequences set forth in SEQ ID NOs: 44, 22, 30, 40, and 42 followed by testing of the encoded altered antibody for retained function (i.e., the functions set forth in (c) and (d) above), using the functional assays described herein.

In a preferred embodiment, the heavy chain variable region CDR2 sequence comprises an amino acid sequence selected from the group consisting of amino acid sequences of SEQ ID NOs: 44, 22, 30, 40 and 42 and conservative modifications thereof, and the light chain variable region CDR2 sequence comprises an amino acid sequence SEQ ID NO: 54 and conservative modifications thereof. In another preferred embodiment, the heavy chain variable region CDR1 sequence comprises an amino acid sequence selected from the group consisting of amino acid sequences of SEQ ID NOs: 44, 22, 30, 40 and 42 and conservative modifications thereof, and the light chain variable region CDR1 sequence comprises an amino acid sequence SEQ ID NO: 50 and conservative modifications thereof.

In various embodiments, the antibody can be, for example, human antibodies, humanized antibodies or chimeric antibodies.

In some embodiment, the antibodies bind to the same epitope on human B7-H4 as any of the B7-H4 monoclonal antibodies of this disclosure (i.e. antibodies that have the ability to cross-compete for binding to B7-H4 with any of the monoclonal antibodies of this disclosure).

Accordingly, another embodiment of this disclosure pertains to an isolated monoclonal antibody or antigen binding portion thereof, comprising a heavy chain variable region comprising CDR1, CDR2 and CDR3 sequences comprising an amino acid sequence selected from the group consisting of SEQ ID NOs: 44, 22, 30, 40, and 42 respectively and a light chain variable region comprising CDR1, CDR2 and CDR3 sequences comprising an amino acid sequence of SEQ ID NOs: 53, 54 and 55 respectively Accordingly, in another embodiment, this disclosure provides isolated anti-B7-H4 monoclonal antibodies or antigen binding portions thereof, comprising a heavy chain variable region comprising: (a) a VH CDR1 region comprising an amino acid sequence comprising SEQ ID NO: 2; or an amino acid sequence having one, two, three, four or five amino acid substitutions, deletions or additions as compared to SEQ ID NO: 2; (b) a VH CDR2 region comprising an amino acid sequence comprising SEQ ID NO: 3; or an amino acid sequence having one, two, three, four or five amino acid substitutions, deletions or additions as compared to SEQ ID NO: 3; (c) a VH CDR3 region comprising an amino acid sequence selected from the group consisting of SEQ ID NOs: 16, 10, or 4; or an amino acid sequence having one, two, three, four or five amino acid substitutions, deletions or additions as compared to SEQ ID NOs: 16, 10, or 4.

In some embodiments, the antibodies disclosed herein contain a heavy chain having an amino acid sequence at least 90%, 91%, 92%, 93%, 94%, 95%, 96%, 97% 98%, 99% or more identical to a sequence selected from the group consisting of SEQ ID NOs: 45, 23, 31, 41, or 43 and a light chain having an amino acid sequence at least 90%, 91%, 92%, 93%, 94%, 95%, 96%, 97% 98%, 99% or more identical to a sequence selected from the group consisting of SEQ ID No: 52.

In some embodiments, the antibodies disclosed herein contain a combination of heavy chain and light chain amino acid sequences selected from the group consisting of (i) a heavy chain amino acid sequence at least 90%, 91%, 92%, 93%, 94%, 95%, 96%, 97% 98%, 99% or more identical to the amino acid sequence of SEQ ID NO: 45 and a light chain amino acid sequence at least 90%, 91%, 92%, 93%, 94%, 95%, 96%, 97% 98%, 99% or more identical to the amino acid sequence of SEQ ID NO: 52; (ii) a heavy chain amino acid sequence at least 90%, 91%, 92%, 93%, 94%, 95%, 96%, 97% 98%, 99% or more identical to the amino acid sequence of SEQ ID NO: 23 and a light chain amino acid sequence at least 90%, 91%, 92%, 93%, 94%, 95%, 96%, 97% 98%, 99% or more identical to the amino acid sequence of SEQ ID NO: 52; (iii) a heavy chain amino acid sequence at least 90%, 91%, 92%, 93%, 94%, 95%, 96%, 97% 98%, 99% or more identical to the amino acid sequence of SEQ ID NO: 31 and a light chain amino acid sequence at least 90%, 91%, 92%, 93%, 94%, 95%, 96%, 97% 98%, 99% or more identical to the amino acid sequence of SEQ ID NO: 52; (iv) a heavy chain amino acid sequence at least 90%, 91%, 92%, 93%, 94%, 95%, 96%, 97% 98%, 99% or more identical to the amino acid sequence of SEQ ID NO: 41 and a light chain amino acid sequence at least 90%, 91%, 92%, 93%, 94%, 95%, 96%, 97% 98%, 99% or more identical to the amino acid sequence of SEQ ID NO: 50; and (v) a heavy chain amino acid sequence at least 90%, 91%, 92%, 93%, 94%, 95%, 96%, 97% 98%, 99% or more identical to the amino acid sequence of SEQ ID NO: 43 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 45 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 23 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 31 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 41 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 43 and a light chain amino acid sequence at least 90%, 91%, 92%, 93%, 94%, 95%, 96%, 97% 98%, 99% or more identical to the amino acid sequence of SEQ ID NO: 52.

In some embodiments, the antibodies disclosed herein contain a heavy chain having an amino acid sequence selected from the group consisting of SEQ ID NOs: 45, 23, 31, 41, or 43 and a light chain having an amino acid sequence of SEQ ID NOs: 52.

In some embodiments, the antibodies disclosed herein contain a combination of heavy chain and light chain amino acid sequences selected from the group consisting of (i) the heavy chain amino acid sequence of SEQ ID NO: 45 and the light chain amino acid sequence of SEQ ID NO: 52; (ii) the heavy chain amino acid sequence of SEQ ID NO: 23 and the light chain amino acid sequence of SEQ ID NO: 52; (iii) the heavy chain amino acid sequence of SEQ ID NO: 31 and the light chain amino acid sequence of SEQ ID NO: 52; (iv) the heavy chain amino acid sequence of SEQ ID NO: 41 and the light chain amino acid sequence of SEQ ID NO: 52; and (v) the heavy chain amino acid sequence of SEQ ID NO: 43 and the light chain amino acid sequence of SEQ ID NO: 52.

In some embodiments, the antibodies disclosed herein contain the heavy chain amino acid sequence of SEQ ID NO: 45 and the light chain amino acid sequence of SEQ ID NO: 52.

In some embodiments, the antibodies disclosed herein contain the heavy chain amino acid sequence of SEQ ID NO: 23 and the light chain amino acid sequence of SEQ ID NO: 52.

In some embodiments, the antibodies disclosed herein contain the heavy chain amino acid sequence of SEQ ID NO: 31 and the light chain amino acid sequence of SEQ ID NO: 52.

In some embodiments, the antibodies disclosed herein contain the heavy chain amino acid sequence of SEQ ID NO: 41 and the light chain amino acid sequence of SEQ ID NO: 52.

In some embodiments, the antibodies disclosed herein contain the heavy chain amino acid sequence of SEQ ID NO: 43 and the light chain amino acid sequence of SEQ ID NO: 52.

The antibodies disclosed herein contain a heavy chain variable region having an amino acid sequence at least 90%, 91%, 92%, 93%, 94%, 95%, 96%, 97% 98%, 99% or more identical to a sequence selected from the group consisting of SEQ ID NOs: 44, 22, 30, 40, or 42 and a light chain variable region having an amino acid sequence at least 90%, 91%, 92%, 93%, 94%, 95%, 96%, 97% 98%, 99% or more identical to a sequence consisting of SEQ ID NOs: 50.

In some embodiments, the three heavy chain CDRs of the antibodies disclosed herein include a heavy chain complementarity determining region 1 (CDRH1) that includes an amino acid sequence at least 90%, 91%, 92%, 93%, 94%, 95%, 96%, 97% 98%, 99% or more identical to a sequence comprising SEQ ID NO: 2; a heavy chain complementarity determining region 2 (CDRH2) that includes an amino acid sequence at least 90%, 91%, 92%, 93%, 94%, 95%, 96%, 97% 98%, 99% or more identical to a sequence comprising SEQ ID NO: 3; and a heavy chain complementarity determining region 3 (CDRH3) that includes an amino acid sequence at least 90%, 91%, 92%, 93%, 94%, 95%, 96%, 97% 98%, 99% or more identical to a sequence selected from the group consisting of SEQ ID NOs: 16, 10, or 4; and a heavy chain amino acid sequence at least 90%, 91%, 92%, 93%, 94%, 95%, 96%, 97% 98%, 99% or more identical to the amino acid sequence of SEQ ID NO: 45, 23, 31, 41, or 43.

The three light chain CDRs of the antibodies disclosed herein include a light chain complementarity determining region 1 (CDRL1) that includes an amino acid sequence at least 90%, 91%, 92%, 93%, 94%, 95%, 96%, 97% 98%, 99% or more identical to a sequence comprising SEQ ID NO. 53; a light chain complementarity determining region 2 (CDRL2) that includes an amino acid sequence at least 90%, 91%, 92%, 93%, 94%, 95%, 96%, 97% 98%, 99% or more identical to a sequence comprising SEQ ID NO: 54; and a light chain complementarity determining region 3 (CDRL3) that includes an amino acid sequence at least 90%, 91%, 92%, 93%, 94%, 95%, 96%, 97% 98%, 99% or more identical to a sequence comprising SEQ ID NO: 55.

The antibodies include a combination of heavy chain CDR and light chain CDR sequences that include a CDRH1 that includes an amino acid sequence at least 90%, 91%, 92%, 93%, 94%, 95%, 96%, 97% 98%, 99% or more identical to a sequence comprising SEQ ID NO: 2; a CDRH2 that includes an amino acid sequence at least 90%, 91%, 92%, 93%, 94%, 95%, 96%, 97% 98%, 99% or more identical to a sequence comprising SEQ ID NO: 3; a CDRH3 that includes an amino acid sequence at least 90%, 91%, 92%, 93%, 94%, 95%, 96%, 97% 98%, 99% or more identical to a sequence selected from the group consisting of SEQ ID NOs: 16, 10, or 4; a CDRL1 that includes an amino acid sequence at least 90%, 91%, 92%, 93%, 94%, 95%, 96%, 97% 98%, 99% or more identical to a sequence selected from the group consisting of SEQ ID NO: 53; a CDRL2 that includes an amino acid sequence at least 90%, 91%, 92%, 93%, 94%, 95%, 96%, 97% 98%, 99% or more identical to a sequence of SEQ ID NO: 54; and a CDRL3 that includes an amino acid sequence at least 90%, 91%, 92%, 93%, 94%, 95%, 96%, 97% 98%, 99% or more identical to a of SEQ ID NO: 55; and a heavy chain amino acid sequence at least 90%, 91%, 92%, 93%, 94%, 95%, 96%, 97% 98%, 99% or more identical to the amino acid sequence of SEQ ID NO: 45, 23, 31, 41, or 43.

The three heavy chain CDRs of the antibodies disclosed herein include a CDRH1 that includes an amino acid sequence selected from the group comprising SEQ ID NO: 2 a CDRH2 that includes an amino acid sequence comprising SEQ ID NO: 3; and a CDRH3 that includes an amino acid sequence selected from the group consisting of SEQ ID NOs: 10 or 16; and a heavy chain amino acid sequence selected from the group consisting of SEQ ID NO: 45 or 23.

The three light chain CDRs of the antibodies disclosed herein include a CDRL1 that has an amino acid sequence of SEQ ID NO: 53; a CDRL2 that has an amino acid sequence of SEQ ID NO: 54; and a CDRL3 that has an amino acid sequence of SEQ ID NO: 55. The antibodies disclosed herein include a combination of heavy chain CDR and light chain CDR sequences that include a CDHR1 that includes an amino acid sequence selected comprising SEQ ID NO: 2; a CDRH2 that includes an amino acid sequence comprising SEQ ID NO: 3; a CDRH3 that includes an amino acid sequence comprising SEQ ID NOs: 10 or 16; a CDRL1 that has an amino acid sequence of SEQ ID NO: 53; a CDRL2 that has an amino acid sequence of SEQ ID NO: 54; and a CDRL3 that has an amino acid sequence of SEQ ID NO: 55; and a heavy chain amino acid sequence of SEQ ID NO: 45 or 23 The antibodies disclosed herein contain a combination of heavy chain complementarity determining region and light chain complementarity determining region amino acid sequences selected from the group consisting of (i) the CDRH1 amino acid sequence of SEQ ID NO: 2, the CDRH2 amino acid sequence of SEQ ID NO: 3, the CDRH3 amino acid sequence of SEQ ID NO: 16, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 45; (ii) the CDRH1 amino acid sequence of SEQ ID NO: 2, the CDRH2 amino acid sequence of SEQ ID NO: 3, the CDRH3 amino acid sequence of SEQ ID NO: 10, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 23; (iii) the CDRH1 amino acid sequence of SEQ ID NO: 2, the CDRH2 amino acid sequence of SEQ ID NO: 3, the CDRH3 amino acid sequence of SEQ ID NO: 4, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 31; (iv) the CDRH1 amino acid sequence of SEQ ID NO: 2, the CDRH2 amino acid sequence of SEQ ID NO: 3 the CDRH3 amino acid sequence of SEQ ID NO: 4, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 41 and (v) the CDRH1 amino acid sequence of SEQ ID NO: 2, the CDRH2 amino acid sequence of SEQ ID NO: 3, the CDRH3 amino acid sequence of SEQ ID NO: 10, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 43.

In some embodiments, the antibodies disclosed herein contain the CDRH1 amino acid sequence of SEQ ID NO: 2, the CDRH2 amino acid sequence of SEQ ID NO: 3, the CDRH3 amino acid sequence of SEQ ID NO: 16, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 45.

In some embodiments, the antibodies disclosed herein contain the CDRH1 amino acid sequence of SEQ ID NO: 2, the CDRH2 amino acid sequence of SEQ ID NO: 3, the CDRH3 amino acid sequence of SEQ ID NO: 10, the CDRL1 amino acid sequence of SEQ ID NO: 53, the CDRL2 amino acid sequence of SEQ ID NO: 54, the CDRL3 amino acid sequence of SEQ ID NO: 55, and a heavy chain amino acid sequence of SEQ ID NO: 23.

In some embodiments, the antibodies disclosed herein contain the CDRH1 amino acid sequence of SEQ ID NO: 2, the CDRH2 amino acid sequence of SEQ ID NO: 3, the CDRH3 amino acid sequence of SEQ ID NO: 4, the CDRL1 amino acid sequence of SEQ ID NO: 53, the CDRL2 amino acid sequence of SEQ ID NO: 54, and the CDRL3 amino acid sequence of SEQ ID NO: 55.

In some embodiments, the antibodies disclosed herein contain the CDRH1 amino acid sequence of SEQ ID NO: 2, the CDRH2 amino acid sequence of SEQ ID NO: 3, the CDRH3 amino acid sequence of SEQ ID NO: 4, the CDRL1 amino acid sequence of SEQ ID NO: 53, the CDRL2 amino acid sequence of SEQ ID NO: 54, and the CDRL3 amino acid sequence of SEQ ID NO: 55.

In some embodiments, the antibodies disclosed herein contain the CDRH1 amino acid sequence of SEQ ID NO: 2, the CDRH2 amino acid sequence of SEQ ID NO: 3, the CDRH3 amino acid sequence of SEQ ID NO: 10, the CDRL1 amino acid sequence of SEQ ID NO: 53, the CDRL2 amino acid sequence of SEQ ID NO: 54, and the CDRL3 amino acid sequence of SEQ ID NO: 55.

Preferred antibodies disclosed herein include, for example, the B7-H4-2F9V7 (also referred to herein as the XMT 1603 antibody), and the B7-H4-2F9V18 (also referred to herein as the XMT 1604 antibody). These antibodies show specificity for human B7-H4 and they have been shown to inhibit the functional activity of B7-H4 in vitro.

Production of B7-H4 Antibodies

B7-H4 antibodies are generated, for example, using the methods described in the Examples provided herein. Alternatively, or in addition, various procedures known within the art may be used for the production of monoclonal antibodies directed against B7-H4, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, NY; Kozbor, et al., 1983 Immunol Today 4: 72); Cole, et al., 1985 In: Monoclonal Antibodies and Cancer Therapy, Alan R. Liss, Inc., pp. 77-96; Cote, et al., 1983. Proc Natl Acad Sci USA 80: 2026-2030; Cole, et al., 1985 In: Monoclonal Antibodies and Cancer Therapy, Alan R. Liss, Inc., pp. 77-96; each of which are incorporated herein by reference in their entirety).

Monoclonal antibodies disclosed herein include fully human antibodies or humanized antibodies. These antibodies are suitable for administration to humans without engendering an immune response by the human against the administered immunoglobulin. A humanized or fully human B7-H4 antibody is developed, for example, using phage-display methods using antibodies containing only human sequences. Such approaches are well-known in the art, e.g., in WO92/01047 and U.S. Pat. No. 6,521,404, which are hereby incorporated by reference.

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28; incorporated herein by reference)

The invention also includes $F_v$, $F_{ab}$, $F_{ab'}$ and $F_{(ab')2}$ anti-B7-H4 fragments or anti-B7-H4 fragments, single chain anti-B7-H4 antibodies, multispecific antibodies in which at least one arm binds B7-H4, and heteroconjugate anti-B7-H4 antibodies.

Bispecific antibodies are antibodies that have binding specificities for at least two different antigens. In the present case, one of the binding specificities is for B7-H4. The second binding target is any other antigen, including a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)).

Bispecific antibodies can be prepared as full length antibodies or antibody fragments (e.g., F(ab')$_2$ bispecific antibodies). Techniques for generating bispecific antibodies from antibody fragments have been described in the literature.

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen disclosed herein. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody disclosed herein with respect to effector function, so as to enhance, e.g., the effectiveness of the antibody in treating diseases and disorders associated with aberrant B7-H4 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

Cysteine Engineered B7-H4 Antibodies

In some embodiments, the cysteine engineered B7-H4 antibody directs the conjugates comprising a peptide linker to specific tissues, cells, or locations in a cell. In some embodiments, the cysteine engineered B7-H4 antibody comprises an engineered cysteine.

In some embodiments, the B7-H4 cysteine engineered antibody or antibody fragment is a B7-H4 antibody or antibody fragment in which one or more amino acids of the corresponding parent antibody or antibody fragment (e.g., the corresponding wild type B7-H4 antibody or antibody fragment) are substituted with cysteines (e.g., engineered cysteine). In some embodiments, the parent B7-H4 antibody or antibody fragment are those described herein.

In some embodiments, the B7-H4 antibody is engineered to form the cysteine engineered antibody. In some embodiments, the cysteine engineered B7-H4 antibody or antibody fragment retains the antigen binding capability of its corresponding wild type B7-H4 antibody or antibody fragment. In some embodiments, the cysteine engineered antibody or antibody fragment is capable of binding to the one or more antigens for its corresponding wild type B7-H4 antibody or antibody fragment.

In some embodiments, the engineered cysteine is not a part of an intrachain or interchain disulfide unit. In some embodiments, the engineered cysteine contains a free thiol group that is reactive with an electrophilic functionality. In some embodiments, the engineered cysteine (e.g., the free thiol group thereof) on the B7-H4 antibody or antibody fragment surface may allow for conjugation of the B7-H4 antibody or antibody fragment with a Linker-Drug moiety comprising a thiol-reactive group (e.g., a maleimide or a haloacetyl).

It is understood that substituting one or more non-cysteine amino acids in a B7-H4 antibody or antibody fragment with cysteines may create one or more engineered cysteines as available sites for conjugation. In some embodiments, by substituting a non-cysteine amino acid in a B7-H4 antibody or antibody fragment with cysteine, a reactive thiol group is positioned as an accessible site of the antibody or antibody fragment and may be used to conjugate the antibody or antibody fragment to other moieties (e.g., drug moieties, or Linker-Drug moieties), and to create the conjugate of the present disclosure. In some embodiments, the amino acid at V205 (Kabat or EU numbering) of the light chain, or A118 or S442 of the heavy chain (EU numbering) of a parent B7-H4 antibody or antibody fragment is substituted with cysteine. In some embodiments, cysteine engineered antibodies may be generated as described, e.g., in U.S. Pat. No. 7,521,541.

In some embodiments, the cysteine engineered B7-H4 antibody is conjugated to the Linker-Drug moiety by forming a covalent bond via the sulfhydryl group of the engineered cysteine and a functional group of the Linker-Drug moiety.

Modified B7-H4 Antibodies

In some embodiments, the B7-H4 antibody is a modified B7-H4 antibody.

In some embodiments of the modified B7-H4 antibody, * denotes a direct or indirect attachment to the rest of the modified B7-H4 antibody. In some embodiments, S" is a sugar or a derivatized sugar. In some embodiments, A" is a functional group being capable of forming a covalent bond with a functional group of the Linker-Drug moiety, In some embodiments, the modified B7-H4 antibody, prior to conjugation, comprises a sugar-derivative moiety of *-S"-A".

In some embodiments, the modified B7-H4 antibody comprises an asparagine group in the region 290-305 (e.g., at N297; EU numbering). In some embodiments, the sugar-derivative moiety is directly or indirectly attached to the asparagine group (e.g., at N297).

In some embodiments, the modified B7-H4 antibody, prior to conjugation, comprises a modified-GlcNAc moiety, *-GlcNAc-S" A", wherein GlcNAc is N-acetylglucosamine.

In some embodiments, the modified-GlcNAc moiety is connected to the rest of the modified B7-H4 antibody via the C1 position of the GlcNAc. In some embodiments, the modified-GlcNAc moiety further comprises a fucose.

In some embodiments, the modified-GlcNAc moiety is directly or indirectly attached to the asparagine group (e.g., at N297).

In some embodiments, the modified B7-H4 antibody is conjugated to the Linker-Drug moiety via a covalent bond formed between A" and a functional group of the Linker-Drug moiety.

In some embodiments, the modified B7-H4 antibody of the present disclosure is obtained by a process comprising:
(a) contacting a glycoprotein (e.g., a B7-H4 antibody glycan) comprising a B7-H4 antibody and a core-GlcNAc moiety with an endoglycosidase, thereby forming an intermediate antibody comprising the antibody and a terminal-GlcNAc moiety and, optionally, the terminal-GlcNAc moiety further comprises a fucose; and
(b) contacting the intermediate antibody with a compound having the structure of P'''-S''-A'', in the presence of a glycosyltransferase, thereby forming the modified B7-H4 antibody comprising the antibody and the modified-GlcNAc moiety, *-GlcNAc-S''-A'', and, optionally, the modified-GlcNAc moiety is attached to the rest of the modified B7-H4 antibody the C1 position of the GlcNAc; wherein
GlcNAc is N-acetylglucosamine;
S'' is a sugar or a derivatized sugar;
A'' is azido, keto, or alkynyl; and
P''' is uridine diphosphate (UDP), guanosine diphosphate (GDP) or cytidine diphosphate (CDP).

In some embodiments, steps (a) and (b) are conducted sequentially. In some embodiments, steps (a) and (b) are conducted concurrently.

In some embodiments, the antibody glycan comprises a mixture of glycoforms G0, G1, G2, G0F, G1F, G2F, and M5 (e.g., the glycoforms shown in FIG. 1).

In some embodiments, the antibody is a monoclonal antibody (mAb).

In some embodiments, the antibody is a IgA, IgD, IgE, IgG, or IgM antibody.

In some embodiments, the antibody is an IgG antibody, e.g., an IgG1, IgG2, IgG3, or IgG4 antibody. In some embodiments, the antibody is an IgG1 antibody.

In some embodiments, the antibody is a full-length antibody, and the antibody glycan comprises one or more core-GlcNAc moiety.

In some embodiments, the antibody is a full-length antibody, and the antibody glycan comprises one or more core-GlcNAc moiety connected to each heavy chain of the antibody.

In some embodiments, the core-GlcNAc moiety further comprises a fucose.

In some embodiments, the antibody is a full-length antibody, and the antibody glycan comprises two or more core-GlcNAc moiety connected to the full-length antibody.

In some embodiments, the antibody is a full-length antibody, and the antibody glycan comprises two core-GlcNAc moieties connected to the full-length antibody.

In some embodiments, at least one of the two or more core-GlcNAc moieties further comprises a fucose.

In some embodiments, each of the two or more core-GlcNAc moiety further comprises a fucose.

In some embodiments, the antibody is a single chain antibody or a B7-H4 antibody fragment (e.g., a Fab or Fc fragment), the antibody glycan comprises one or more core-GlcNAc moiety (which optionally further comprises fucose) connected to the antibody.

In some embodiments, the core-GlcNAc moiety is connected to a position of the antibody, wherein the core-GlcNAc moiety does not substantially hinder the antigen-binding site of the antibody.

In some embodiments, the core-GlcNAc moiety is connected to the Fc fragment of the antibody. In some embodiments, the core-GlcNAc moiety is connected to the CH domain. In some embodiments, the core-GlcNAc moiety is connected to the Fab or Fc fragment of the antibody. In some embodiments, the core-GlcNAc moiety is connected to the antibody via an N-glycosidic bond to the amide nitrogen atom in the side chain of an asparagine amino acid of the antibody. In some embodiments, the core-GlcNAc moiety is connected to a native N-glycosylation site of the antibody.

In some embodiments, the antibody is an IgG, antibody and the core-GlcNAc moiety is connected to a native N-glycosylation site of the IgG.

In some embodiments, the antibody is an IgG, antibody and the core-GlcNAc moiety is connected to a native N-glycosylation site of the IgG (e.g., the N297 N-glycosylation site of IgG). In some embodiments, the N297 N-glycosylation site is present in the conserved Fc region of the heavy chain of an IgG antibody at asparagine in the region 290-305 (e.g., at N297).

In some embodiments, the intermediate antibody is of Formula (XXII):

(XXII)

wherein:
Ab is a B7-H4 antibody; GlcNAc is N-acetylglucosamine;
Fuc is fucose; $u_3$ is 0 or 1; and $u_4$ is an integer ranging from is 1 to 16.

In some embodiments, $u_4$ is an integer ranging from 1 to 10. In some embodiments, $u_4$ is 1, 2, 3, 4, 5, 6, 7 or 8. In some embodiments, $u_4$ is 1, 2, 3, 4, 5 or 6. In some embodiments, $u_4$ is 1, 2, 3 or 4. In some embodiments, $u_4$ is 2 or 4. In some embodiments, $u_4$ is 1 or 2. In some embodiments, $u_4$ is 1. In some embodiments, $u_4$ is 2.

In some embodiments, the antibody comprises one core-GlcNAc moiety (e.g., $u_4$ is 1). In some embodiments, the antibody comprises two core-GlcNAc moieties (e.g., $u_4$ is 2).

In some embodiments, the modified B7-H4 antibody is obtained by the process outlined in Scheme 1. As shown below, contacting an intermediate antibody of Formula (XXIII) comprising one terminal-GlcNAc moiety with a compound having the structure of P'''-S''-A'', in the presence of a glycosyltransferase, provides a modified B7-H4 antibody comprising one modified-GlcNAc moiety (e.g., the modified B7-H4 antibody of Formula (XXIIIa)).

In some embodiments, the modified B7-H4 antibody is obtained by contacting an intermediate antibody of Formula (XXIV) comprising two terminal-GlcNAc moieties with a compound having the structure of P'''-S''-A'', in the presence of a glycosyltransferase, provides a modified B7-H4 antibody comprising two modified-GlcNAc moieties (e.g., the modified B7-H4 antibody of Formula (XXIVa)).

Scheme 1

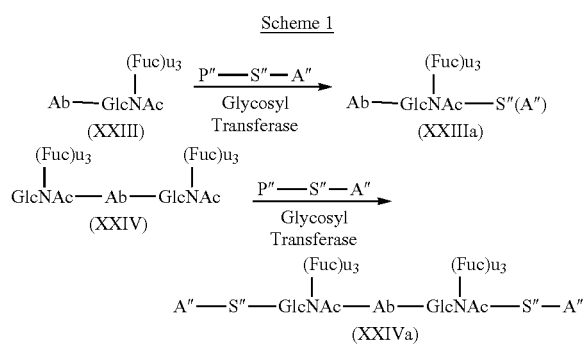

wherein $u_3$, Ab, S", A", and P" are as defined herein.

In some embodiments, the antibody glycan to be modified in the process according to the present disclosure comprises a glycan, said glycan comprising a core-GlcNAc moiety, i.e., a GlcNAc moiety that is present at the non-reducing end of the glycan. In some embodiments, the glycan comprises one or more saccharide moieties and may be linear or branched.

In some embodiments, upon reacting with endoglycosidase, the intermediate antibody may be formed, which comprises a terminal GlcNAc moiety (e.g., the intermediate antibody of Formula (XXIII) or (XXIV)).

Figure 2:
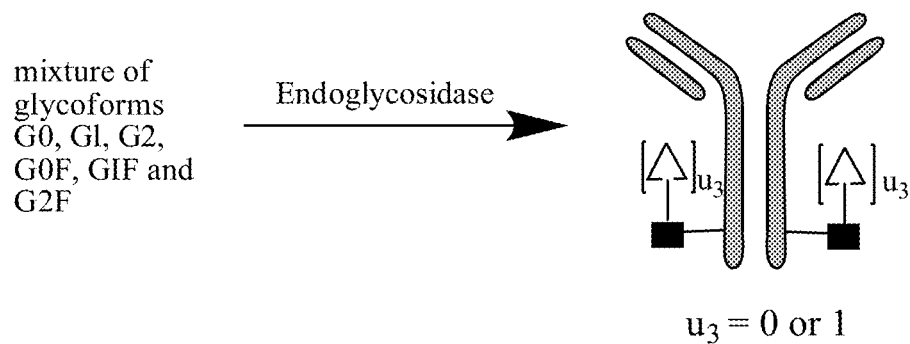
FIG. 2 is a scheme showing the deglycosylation of a mixture of glycoforms G0, G1, G2, G0F, G1F, G2F, and M5 in the presence of the endoglycosidase.

In some embodiments, step (a) of the process (the deglycosylation or trimming) is as shown in FIG. 2, wherein a mixture of antibody glycoforms G2F, G1F, G0F, G2, G1, G0, and M5 (e.g., see FIG. 1), and possibly additional glycoforms (e.g., triantennary glycans), is converted into intermediate antibodies comprising a terminal GlcNAc moiety which optionally comprises a fucose (e.g., $u_3$ is 0 or 1).

In some embodiments, the endoglycosidase is endoglycosidase Endo S, Endo SH, Endo S2, Endo S49, Endo F1, Endo F2, Endo F3, or a combination thereof.

In some embodiments, the endoglycosidase is Endo S, Endo SH, Endo S2, Endo S49, or a combination thereof.

In some embodiments the endoglycosidase is Endo S or Endo SH, or a combination thereof. In some embodiments the endoglycosidase is Endo SH.

Figure 3:
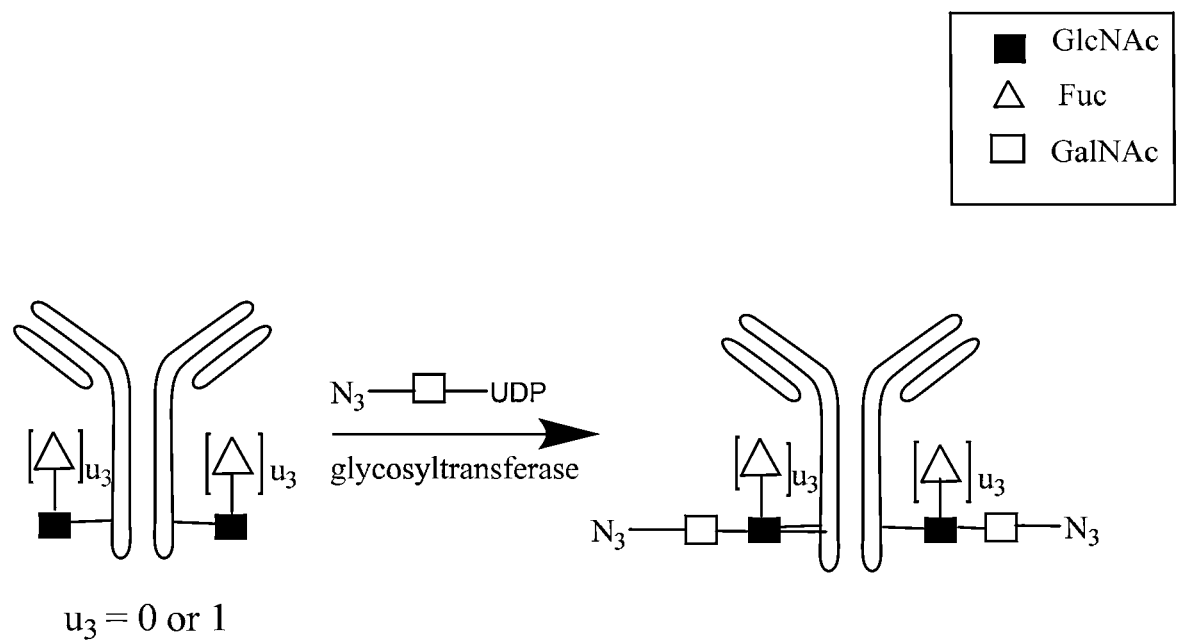
FIG. 3 is a scheme showing a process for preparing an azido-modified antibody, wherein an intermediate antibody comprising a terminal-GlcNAc moiety is reacted with an azido-modified UDP-GalNAc derivative molecule in the presence of a glycosyltransferase.

In some embodiments, step (b) of the process (the formation of the modified B7-H4 antibody) is as shown in FIG. 3, wherein the intermediate antibody comprises a monoclonal antibody (mAb) and a terminal GlcNAc moiety (which optionally comprises a fucose (e.g., $u_3$ is 0 or 1)) on each heavy chain of the monoclonal antibody (mAb). In some embodiments, in step (b), the terminal-GlcNAc moiety is converted into modified-GlcNAc moiety. In some embodiments, said conversion may be executed via reaction of the terminal GlcNAc moiety with the compound of P"-S"-A" in the presence of a glycosyltransferase.

In some embodiments, the compound of P"-S"-A" is GalNAz-UDP (e.g., 4-AzGalNAc-UDP). In some embodiments, the terminal-GlcNAc moiety is *-GlcNAc-GalNAz or *-GlcNAc(Fuc)-GalNAz, wherein * denotes the attachment to the rest of the modified B7-H4 antibody.

In some embodiments, the steps of the deglycosylation/trimming step and the formation of the modified B7-H4 antibody are conducted sequentially.

In some embodiments, the steps of the deglycosylation/trimming step and the formation of the modified B7-H4 antibody are conducted simultaneously.

In some embodiments, the process for the preparation of a modified B7-H4 antibody is performed in a suitable buffer solution, e.g., buffered saline (e.g. phosphate-buffered saline, Tris-buffered saline), citrate, HEPES, Tris and glycine. In some embodiments, the buffer solution is phosphate-buffered saline (PBS) or Tris buffered saline. In some embodiments, the buffer solution is phosphate-buffered saline (PBS).

In some embodiments, the process is performed at a temperature ranging from about 4 to about 50° C. In some embodiments, the process is performed at a temperature ranging from about 10 to about 45° C. In some embodiments, the process is performed at a temperature ranging from about 20 to about 40° C. In some embodiments, the process is performed at a temperature ranging from about 30 to about 37° C. In some embodiments, the process is performed at a temperature of about 30° C. In some embodiments, the process is performed at a temperature of 30° C.

In some embodiments, the process is performed at a pH value ranging from about 5 to about 9 (e.g., from about 5.5 to about 8.5, from about 6 to about 8, or from about 7 to about 8). In some embodiments, the process is performed at a pH value of about 7.4.

Figure 4:
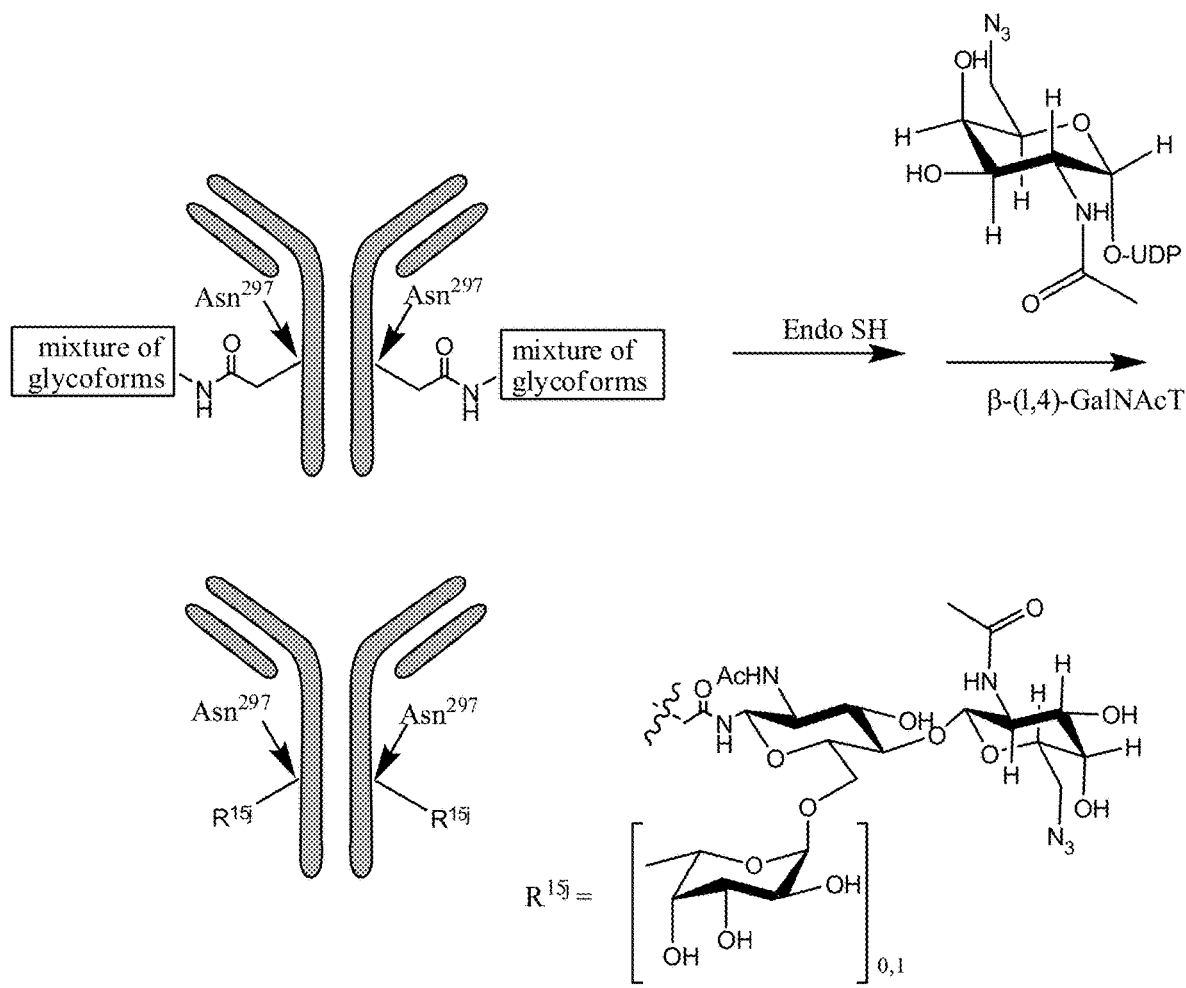
FIG. 4 is a scheme showing an embodiment of the process of preparing an azido-modified antibody.

In some embodiments, the process for the preparation of a modified B7-H4 antibody is as shown in FIG. 4.

In some embodiments, the process for the preparation of a modified B7-H4 antibody comprises:
(a) contacting a glycoprotein (e.g., a B7-H4 antibody glycan) comprising a B7-H4 antibody and core-GlcNAc moiety connected to site N297 of the antibody, with endoglycosidase Endo SH, thereby forming an intermediate antibody comprising a terminal GlcNAc moiety; and
(b) contacting the intermediate antibody with 4-AzGalNAc-UDP in the presence of a 0-(1,4)-GalNAcT enzyme, thereby forming the modified B7-H4 antibody comprising the modified-GlcNAc moiety;
wherein steps (a) and (b) are conducted concurrently.

In some embodiments, the endoglycosidase is Endo SH, a fusion between the two endoglycosidases, Endo S and Endo H, linked by a Gly-rich spacer comprising an internal 6×His tag resulting in an overall molecular weight of 139 kDa.

In some embodiments, the β-(1,4)-GalNAcT enzyme comprises an N-terminal 6×His tag and has an overall molecular weight of 45.7 kDa. In some embodiments, the β-(1,4)-GalNAcT enzyme containing an N-terminal 6×His tag is derived from *Trichopulsia ni*.

In some embodiments, the process is conducted in PBS buffer at pH value of about 7.4 and at a temperature of about 30° C.

Endoglycosidases

Endoglycosidases are enzymes that are capable of cleaving internal glycosidic linkages in glycan structures, thereby remodeling or trimming the glycan structure. For example, endoglycosidases can be used for the facile homogenization of heterogeneous glycan populations, when they cleave at predictable sites within conserved glycan regions. One class of endoglycosidases comprises the endo-β-N-acetylglucosaminidases (EC 3.2.1.96, commonly known as Endo S or ENGases), a class of hydrolytic enzymes that removes N-glycans from glycoproteins by hydrolyzing the β-1,4-glycosidic bond in the N,N'-diacetylchitobiose core (as described in Wong et al. Chem. Rev. 2011, 111, 4259, which is incorporated herein by reference in its entirety), leaving a single core N-linked GlcNAc residue. Endo-β-N-acetylglucosaminidases are widely found in nature with common chemoenzymatic variants including Endo D, which is specific for paucimannose; Endo A and Endo H, which are specific for high mannose; Endo F subtypes, which range from high mannose to biantennary complex; and Endo M, which can cleave most N-glycan structures (high mannose/complex-type/hybrid-type), except fucosylated glycans, and the hydrolytic activity for the high-mannose type oligosaccharides is significantly higher than that for the complex- and hybrid-type oligosaccharides. In some embodiments, these ENGases show specificity toward the distal N-glycan structure and not the protein displaying it, making them useful for cleaving most N-linked glycans from glycoproteins under native conditions.

In some embodiments, endoglycosidases F1, F2, and F3 are suitable for deglycosylation of native proteins. The linkage specificities of Endo F1, F2, and F3 suggest a general strategy for deglycosylation of proteins that may remove all classes of N-linked oligosaccharides without denaturing the protein. In some embodiments, biantennary and triantennary structures can be immediately removed by endoglycosidases F2 and F3, respectively. In some embodiments, oligo-mannose and hybrid structures can be removed by Endo F1.

Endo S is a secreted endoglycosidase from *Streptococcus pyogenes*, and also belongs to the glycoside hydrolase family 18, as disclosed by Collin et al. (EMBO J., 2001, 20, 3046), which is incorporated by reference herein in its entirety. In contrast to the ENGases mentioned above, Endo S has a more defined specificity and is specific for cleaving only the conserved N-glycan in the Fc domain of human IgGs (no other substrate has been identified to date), suggesting that a protein-protein interaction between the enzyme and IgG provides this specificity.

Endo S49, also known as Endo S2, is described in WO 2013/037824, incorporated by reference herein in its entirety, is isolated from *Streptococcus pyogenes* NZ131 and is a homologue of Endo S. Endo S49 has a specific endoglycosidase activity on native IgG and cleaves a larger variety of Fc glycans than Endo S.

Endo SH is a fusion between the two endoglycosidases, Endo S and Endo H linked by a Gly-rich spacer. Endo SH specifically cleaves the N-linked glycans between two N-acetylglucosame (GluNAc) moieties in the core region of the glycan chain.

In some embodiments, the endoglycosidase for deglycosylating the antibody is Endo S, Endo SH, Endo S2, Endo S49, Endo F1, Endo F2, Endo F3, Endo H, Endo M, Endo A, or a combination thereof. In some embodiments, the endoglycosidase for deglycosylating the antibody is Endo S, Endo SH, Endo S2, Endo S49, Endo F1, Endo F2, Endo F3, Endo H, or a combination thereof. In some embodiments, the endoglycosidase is Endo S, Endo SH, Endo S2, or Endo S49.

In some embodiments, when the glycan to be trimmed is a diantennary structure of the complex type, the endoglycosidase is Endo S, Endo SH, Endo S2, Endo S49, Endo F1, Endo F2, Endo F3, or a combination thereof.

In some embodiments, when the glycoprotein is a B7-H4 antibody and the oligosaccharide to be trimmed is a diantennary structure of the complex type and is present at the IgG conserved N-glycosylation site at N297, the endoglycosidase is Endo S, Endo SH, Endo S2, Endo S49, Endo F1, Endo F2, Endo F3, or a combination thereof. In some embodiments the endoglycosidase is Endo S, Endo SH, Endo S2, Endo S49, or a combination thereof.

In some embodiments, when the glycoprotein is a B7-H4 antibody and the glycan to be trimmed is a diantennary structure of the complex type, and is not present at the IgG conserved N-glycosylation site at N297, the endoglycosidase is Endo F1, Endo F2, Endo F3, or a combination thereof.

In some embodiments, when the glycan to be trimmed is a high mannose, the endoglycosidase is Endo H, Endo M, Endo A, Endo F1, or a combination thereof.

In some embodiments, when the glycoprotein is a B7-H4 antibody and the oligosaccharide to be trimmed is a high mannose in addition to having a diantennary structure of the complex type is present at the IgG conserved N-glycosylation site at N297, the endoglycosidase is Endo S, Endo SH, Endo S2, Endo S49, or a combination thereof. In some embodiments, the endoglycosidase is Endo S or Endo SH. In some embodiments, the endoglycosidase is Endo SH.

In some embodiments, the endoglycosidase enzyme as defined herein comprises a sequence encoding a tag for ease of purification. In some embodiments, said tag includes, but is not limited to, a FLAG-tag, poly(His)-tag, HA-tag, Myc-tag, SUMO-tag, GST-tag, MBP-tag, or a CBP-tag. In some embodiments, said tag is a 6×His tag. In some embodiments, said tag is covalently linked to the endoglycoside enzyme at the C-terminus of the enzyme or at an internal residue. In some embodiments, said tag is covalently linked to the endoglycoside enzyme at the N-terminus of the enzyme.

In some embodiments, the Endo SH is a fusion between the two endoglycosidases, Endo S and Endo H linked by a Gly-rich spacer comprising an internal 6×His tag resulting in an overall molecular weight of 139 kDa.

Glycosyltransferase

The process to form a modified B7-H4 antibody comprises treating the deglycosylated/trimmed antibody having an optionally fucosylated terminal N-acetylglucosamine (Gal-NAc) moiety with a compound of Formula S"(A")-P" in the presence of a glycosyltransferase to form the modified B7-H4 antibody having a GlcNAc-S"(A") substituent bonded to the antibody at C1 of the GalNAc moiety via a β-1,4-O-glycosidic bond.

In some embodiments, the glycosyltransferases is a β-1, 4-galactosyltransferases (4Gal-T), a β-(1,4)-Acetylgalactosaminyltransferase (β-(1,4)-GalNAcT or GalNAcT) or a mutant thereof.

β-(1,4)-Acetylgalactosaminyltransferases (β-(1,4)-GalNAcTs or GalNAcTs) have been identified in a number of organisms, including humans, *Caenorhabditis elegans* (Kawar et al, J. Biol. Chem. 2002, 277, 34924, incorporated by reference herein in its entirety), *Drosophila melanogaster* (Hoskins et al. Science 2007, 316, 1625, incorporated by reference herein in its entirety) and *Trichoplusia ni* (Vadaie et al, J. Biol. Chem. 2004, 279, 33501, incorporated by reference herein in its entirety).

β-(1,4)-N-Acetylgalactosaminyltransferases (β-(1,4)-GalNAcTs) are known in the art. In some embodiments, a β-(1,4)-GalNAcT is an enzyme that catalyzes the transfer of N-acetylgalactosamine (GalNAc) from uridine diphosphate-GalNAc (UDP-GalNAc, also referred to as GalNAc-UDP) to a terminal GlcNAc moiety of a glycoprotein glycan, wherein C1 of the GalNAc moiety is attached to the antibody via a β-1,4-O-glycosidic bond. In some embodiments, the terminal GlcNAc moiety is fucosylated In some embodiments, the β-(1,4)-GalNAcT enzyme used in the process of the invention is or is derived from an invertebrate β-(1,4)-GalNAcT enzyme, such as, for example, is or is derived from a β-(1,4)-GalNAcT that originates from invertebrate animal species. The β-(1,4)-GalNAcT enzyme can be or can be derived from any invertebrate β-(1,4)-GalNAcT enzyme known by one skilled in the art. In some embodiments, the β-(1,4)-GalNAcT enzyme is or is derived from a β-(1,4)-GalNAcT enzyme that originates from the phylum of Nematoda, such as, for example, of the class of Chromadorea or Secernentea, or of the phylum of Arthropoda, such as, for example, of the class of Insecta. In some embodiments, the β-(1,4)-GalNAcT enzyme is or is derived from a β-(1,4)-GalNAcT enzyme that originates from *Caenorhabditis elegans, Caenorhabditis remanei, Caenorhabditis briggsae, Ascaris suum, Trichoplusia ni, Drosophila melanogaster, Wuchereria bancrofti, Loa loa, Cerapachys biroi, Zootermopsis nevadensis, Camponotus floridanus, Crassostrea gigas* or *Danaus plexippus*, (e.g., from *Caenorhabditis elegans, Ascaris suum, Trichoplusia ni* or *Drosophila melanogaster*). In some embodiments, the β-(1,4)-GalNAcT enzyme is, or is derived from, a β-(1,4)-GalNAcT enzyme that originates from *Caenorhabditis elegans, Ascaris suum* or *Trichoplusia* $n_1$. In other embodiments, the β-(1,4)-GalNAcT enzyme is, or is derived from, a β-(1,4)-GalNAcT enzyme that originates from *Trichoplusia ni*.

The term "derived from" comprises e.g. truncated enzymes, mutant enzymes, enzymes comprising a tag for ease of purification or a combination of these modifications. Derived from thus refers to as having an amino acid sequence that is altered from a naturally occurring β-(1,4)-GalNAcT enzyme by substituting, inserting, deleting, or adding one or more, (e.g., 1, 2, 3, 4, 5, 6, 7, 8, 9, 10, 12, 14, 16, 18, 20 or more) amino acids, respectively. A β-(1,4)-GalNAcT enzyme that is derived from a β-(1,4)-GalNAcT enzyme is herein also referred to as a derived β-(1,4)-GalNAcT enzyme or a modified β-(1,4)-GalNAcT enzyme or a β-(1,4)-GalNAcT mutant enzyme.

In some embodiments, the derived β-(1,4)-GalNAcT enzyme is modified by adding additional N- or C-terminal amino acids or chemical moieties or by deleting N- or C-terminal amino acids to increase stability, solubility, activity and/or ease of purification.

In some embodiments, the β-(1,4)-GalNAcT enzyme is modified by deleting the N-terminal cytoplasmic domain and transmembrane domain, referred to as a truncated enzyme.

A β-(1,4)-GalNAcT enzyme wherein one or more amino acid has been substituted, added or deleted is herein also referred to as a mutant β-(1,4)-GalNAcT enzyme or a derived β-(1,4)-GalNAcT enzyme. In some embodiments, the β-(1,4)-GalNAcT enzyme is modified by deleting the N-terminal cytoplasmic domain and transmembrane domain and mutated by substituting one or more amino acids. A substitution of one or more amino acids is herein also referred to as a mutation. An enzyme comprising one or more substituted amino acids is also referred to as a mutant enzyme.

In some embodiments, when the glycosyltransferase is a β-(1,4)-GalNAcT enzyme or truncated β-(1,4)-GalNAcT enzyme, the enzyme further comprises one or more mutations. In some embodiments, these mutations include, but are not limited to, substitution of the isoleucine (Ile, also referred to as I) at position 257 by leucine (Leu, also referred to as L), methionine (Met, also referred to as M), or alanine (Ala, also referred to as A). In some embodiments, substitution of the methionine (Met, also referred to as M) at position 312 by histidine (His, also referred to as H) is also included. It should be noted that the numbering of amino acid position is herein based on the numbering of amino acid position in the wild-type β-(1,4)-GalNAcT enzyme. When a β-(1,4)-GalNAcT enzyme is, for example, a truncated enzyme, the number used herein to indicate the position of an amino acid substitution corresponds to the numbering of amino acid position in the corresponding wild-type β-(1,4)-GalNAcT enzyme.

In some embodiments, the glycosyltransferase is a β(1,4)-GalT enzyme comprising a mutant catalytic domain.

A catalytic domain may have an amino acid sequence as found in a wild-type enzyme or have an amino acid sequence that is different from that of a wild-type sequence. A catalytic domain having an amino acid sequence that is different from a wild-type sequence is herein referred to as a mutant catalytic domain. In some embodiments, the mutation may comprise a single amino acid change (for example, a point mutation), or multiple amino acids changes (for example, 1 to 10, or 1 to 6, or 1, 2, 3 or 4, or 1 or 2 amino acids), or a deletion or insertion of one or more amino acids (for example, 1 to 10, or 1 to 6, or 1, 2, 3 or 4, or 1 or 2) amino acids. In some embodiments, said mutant catalytic domain may be present in a full-length enzyme, for example, β(1,4)-galactosyltransferase or α(1,3)-N-galactosyltransferase, but also in a polypeptide fragment or a recombinant polypeptide comprising said mutant catalytic domain, optionally linked to additional amino acids.

β(1,4)-galactosyltransferase I is herein referred to as GalT. Such mutant GalT catalytic domains are disclosed in, for example, WO 2004/063344, which is incorporated by reference herein in its entirety. WO 2004/063344 also discloses Tyr-289 mutants of GalT and their methods of preparation. These mutants are referred to as Y289L, Y289N or Y289I.

In some embodiments, the GalT mutant catalytic domain is Y289L, Y289N, Y289I, Y284L, or R228K. In some embodiments, the GalT mutant catalytic domain is Y289L.

In some embodiments, the GalT Y289F, GalT Y289M, GalT Y289V, GalT Y289G, GalT Y289I, GalT Y289A, GalT Y289N, and GalT Y289L mutants may be produced via site-directed mutagenesis processes, described in, for example, WO2004063344, Qasba et al, Prot. Expr. Pur. 2003, 30, 219 and Qasba et al, J. Biol. Chem. 2002, 277, 20833 (all incorporated by reference herein in their entirety). In GalT Y289F the tyrosine amino acid (Y) at position 289 is replaced by a phenyl alanine (F) amino acid, in GalT Y289M said tyrosine is replaced by a methionine (M) amino acid, in GalT Y289V by a valine (V) amino acid, in GalT Y289G by a glycine (G) amino acid, in GalT Y289I by an isoleucine (I) amino acid and in Y289A by an analine (A) amino acid.

In some embodiments, the β-(1,4)-GalNAcT enzyme comprises a sequence encoding a tag for ease of purification. In some embodiments, said tag includes, but is not limited to, a FLAG-tag, poly(His)-tag, HA-tag, Myc-tag, SUMO-tag, GST-tag, MBP-tag, or a CBP-tag. In other embodiments, said tag is a 6×His tag. In some embodiments, said tag is covalently linked to the β-(1,4)-GalNAcT enzyme at the C-terminus of the enzyme. In some embodiments, said tag is covalently linked to the β-(1,4)-GalNAcT enzyme at the N-terminus of the enzyme.

In some embodiments, β-(1,4)-GalNAcT enzyme comprises an N-terminal 6×His tag and has an overall molecular weight of 45.7 kDa. In some embodiments, the β-(1,4)-GalNAcT enzyme containing an N-terminal 6×His tag is derived from *Trichopulsia ni*.

Molecules of P'''-S''-A''

In some embodiments, the molecule of P'''-S''-A'', for use in the process of preparing a modified B7-H4 antibody of the present disclosure, may be any sugar derivative nucleotide that is a substrate for a suitable galactosyltransferase catalyst.

In some embodiments, S"-A" is a sugar derivative moiety, wherein:

S" is a sugar or a derivatized sugar; and A" is a functional group being capable of forming a covalent bond with a functional group of the Linker-Drug moiety.

In some embodiments, A" is an azido, keto, or alkynyl moiety. In some embodiments, A" is an azido or keto moiety. In some embodiments, A" is an azido moiety. In some embodiments, A" is $-N^3$. In some embodiments, A" is a keto moiety.

In some embodiments, A" is $-[C(R^{8k})_2]_{x2}C(O)R^{9k}$, wherein:

$R^{9k}$ is methyl or optionally substituted $C_{2-24}$ alkyl;
each $R^{8k}$ independently is a hydrogen, halogen, or $R^{9k}$; and
$x_2$ is an integer ranging from 0 to 24.

In some embodiments, $x_2$ is an integer ranging from 0 to 10. In some embodiments, $x_2$ is 0, 1, 2, 3, 4, 5, or 6.

In some embodiments, each $R^{8k}$ is hydrogen.

In some embodiments, A" is an alkynyl moiety. In some embodiments, A" is terminal alkynyl, cycloalkynyl, or heterocycloalkynyl moiety. In some embodiments, A" is terminal alkynyl moiety. In some embodiments, A" is cycloalkynyl moiety. In some embodiments, A" is heterocycloalkynyl moiety.

In some embodiments, A" is $-[C(R^{8k})_2]_{x2}-C\equiv C-R^{8k}$ group, wherein $R^{8k}$ and $x_2$ are as defined herein. In some embodiments, A" is $-[CH_2]_{x2}-C\equiv CH$.

In some embodiments, S"-A" is derived from a sugar or a derivatized sugar, e.g., an amino sugar or an otherwise derivatized sugar. In some embodiments, examples of sugars and derivatized sugars include, but are not limited to, galactose (Gal), mannose (Man), glucose (Glc), glucuronic acid (Gcu), and fucose (Fuc). It is understood that an amino sugar is a sugar wherein a hydroxyl (OH) group is replaced by an amine group. Examples of amino sugars include, but are not limited to, N-acetylglucosamine (GlcNAc), and N-acetylgalactosamine (GalNAc). Examples of otherwise derivatized sugars include, but are not limited to, glucuronic acid (Gcu), and N-acetylneuraminic acid (sialic acid).

In some embodiments, S"-A" is derived from galactose (Gal), mannose (Man), N-acetylglucosamine (GlcNAc), glucose (Glc), N-acetylgalactosamine (GalNAc), glucuronic acid (Gcu), fucose (Fuc), or N-acetylneuraminic acid (sialic acid). In some embodiments, S"-A" is derived from GlcNAc, Glc, Gal, or GalNAc. In some embodiments, S"-A" is derived from GlcNAc. In some embodiments, S"-A" is derived from Glc. In some embodiments, S"-A" is derived from Gal or GalNAc. In some embodiments, S"-A" is derived from Gal. In some embodiments, S"-A" is derived from GalNAc.

In some embodiments, the functional group A" may be attached to S" in various ways.

In some embodiments, A" is directly attached to the carbon atom at C2, C3, C4, or C6 position of the sugar or derivatized sugar of S" (e.g., instead of the hydroxyl at the corresponding position).

In some embodiments, S" is a fucose or a derivatized fucose, which lacks any hydroxyl C6 position. In some embodiments, when A" is attached to C6 position of the fucose or derivatized fucose, A" is directly attached to the carbon atom at the C6 position.

In some embodiments, A" is an azido moiety, and A" is attached to C2, C4, or C6 position of the sugar or derivatized sugar of S".

In some embodiments, A" is an azido moiety, and A" is directly attached to the carbon atom at C2, C3, C4 or C6 position of the sugar or derivatized sugar of S" (e.g., instead of the hydroxyl at the corresponding position). In some embodiments, S"-A" is 6-azidofucose (6-AzFuc). In some embodiments, A" is an azido moiety, and A" is attached to the N-acetyl moiety of an amino sugar or a derivatized amino sugar (e.g., by replacing the acetyl moiety with an azidoacetyl moiety). In some embodiments, S"-A" is 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc), or 6-azido-6-deoxy-2-azidoacetamidoglucose (6-AzGlcNAz). In some embodiments, S"-A" is GalNAz, 4-AzGalNAc, GlcNAz, or 6-AzGlcNAc.

In some embodiments, P"-S"-A" is a compound of Formula (XXIVb), (XXXIVc), or (XXIVd), or a salt thereof.

In some embodiments, A" keto, and A" is directly attached to the carbon atom at C2 position of the sugar or derivatized sugar of S" (e.g., instead of the hydroxyl at the corresponding position).

In some embodiments, A" is attached to the nitrogen atom of an amino sugar or derivatized amino sugar, e.g., a C2-derivatized amino sugar. In some embodiments, the derivatized amino sugar comprises a moiety of $-NC(O)-R^{9k}$, wherein $R^{9k}$ is methyl or optionally substituted $C_{2-24}$ alkyl (e.g., ethyl).

In some embodiments, $R^{9k}$ is ethyl.

In some embodiments, S"-A" is 2-deoxy-(2-oxopropyl)-galactose (2-keto-Gal), 2-N-propionyl-galactosamine (2-N-propionylGal-NAc), 2-N-(4-oxopentanoyl)-galactosamine (2-N-Lev-Gal), or 2-N-butyryl-galactosamine (2-N-butyryl-GalNAc). In some embodiments, S"-A" is 2-ketoGalNAc or 2-N-propionyl-GalNAc.

In some embodiments, P"-S"-A" is a compound of Formula (XXIVe) or (XXIVf), or a salt thereof.

In some embodiments, A" is terminal alkynyl, cycloalkynyl, or heterocycloalkynyl. In some embodiments, A" is attached to a C2-derivatized amino sugar of S".

In some embodiments, S"-A" is 2-(but-3-ynoic acid amido)-2-deoxy-galactose.

In some embodiments, P"-S"-A" is a compound of Formula (XXIVg) or a salt thereof. In some embodiments, P"-S"-A" is a compound of Formula (XXIVd) or a salt thereof.

In some embodiments, compounds of P"-S"-A" may be synthesized according to various methods known in the art. In some embodiments, the compound is synthesized by linking a nucleoside monophosphate or a nucleoside diphosphate P" to a sugar derivative S"-A", e.g., as disclosed in Wang et al. (*Chem. Eur. J.* 16:13343-13345 (2010)), Piller et al. (*ACS Chem. Biol.* 7:753 (2012)), Piller et al. (*Bioorg. Med. Chem. Lett.* 15:5459-5462 (2005), and PCT Appl'n Pub. No. WO/2009/102820, each of which are incorporated by reference herein in their entireties.

In some embodiments, P" is a nucleoside mono- or diphosphate. In some embodiments, P" is uridine diphosphate (UDP), guanosine diphosphate (GDP), thymidine diphosphate (TDP), cytidine diphosphate (CDP), or cytidine monophosphate (CMP). In some embodiments, P" is uridine diphosphate (UDP).

In some embodiments, P"-S"-A" is a compound of Formula (XXIVb), (XXIVc), (XXIVd), (XXIVe), (XXIVf), or (XXIVg):

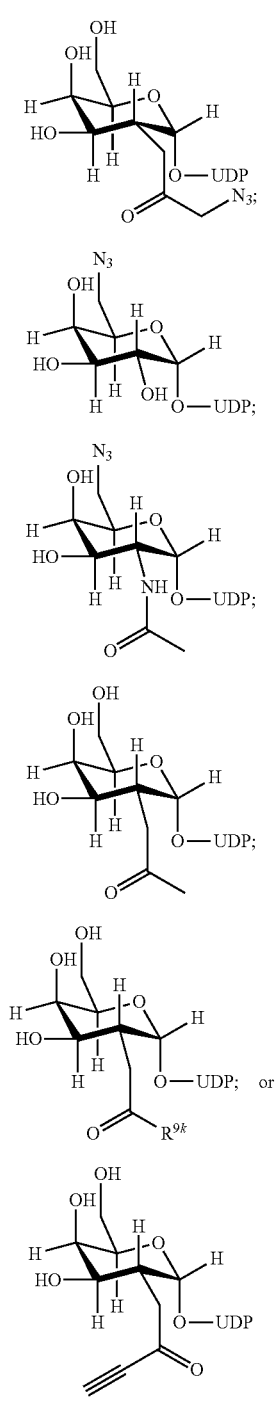

or a salt thereof, wherein: $R^{9k}$ is a $C_{2-24}$ alkyl group.

In some embodiments, P"-S"-A" is GalNAz-UDP (e.g., Formula (XXIVb)), 6-AzGal-UDP (e.g., Formula (XXIVc)), 6-AzGalNAc-UDP (e.g., Formula (XXIVd)), 4-AzGalNAz-UDP, 6-AzGalNAz-UDP, 6-AzGlc-UDP, 6-AzGlcNAz-UDP, 2-ketoGal-UDP (e.g., Formula (XXIVe)), 2-N-propionylGalNAc-UDP (e.g., Formula (XXIVf), wherein $R^{9k}$ is ethyl), or 2-(but-3-ynoic acid amido)-2-deoxy-galactose-UDP (e.g., Formula (XXIVg)).

In some embodiments, P"-S"-A" is GalNAz-UDP or 4-AzGalNAc-UDP. In some embodiments, P"-S"-A" is a compound of Formula (XXIVb) or (XXIVd). The syntheses of GalNAz-UDP (e.g., Formula (XXIVb)) and 6-AzGal-NAc-UDP (e.g., Formula (XXIVd)) are disclosed in Piller et al. (*Bioorg. Med. Chem. Lett.* 15:5459-5462 (2005)) and Wang et al. (*Chem. Eur. J.* 16:13343-13345 (2010)), each of which is incorporated by reference herein in its entirety.

In some embodiments, P"-S"-A" is 4-AzGalNAc-UDP. In some embodiments, P"-S"-A" is a compound of Formula (XXIVd) or a salt thereof. The synthesis of 2-ketoGal-UDP (XXIVe) is disclosed in Qasba et al. (*J. Am. Chem. Soc.* 125:16162 (2003)), and in the supporting information thereof, both of which are incorporated by reference herein in their entireties.

The synthesis of 2-(but-3-ynoic acid amido)-2-deoxy-galactose-UDP is disclosed in PCT Appl'n Pub. No. WO/2009/102820, which is incorporated by reference herein in its entirety.

Variable $d_{13}$

In some embodiments, $d_{13}$ is an integer ranging from about 2 to about 14, from about 2 to about 12, from about 2 to about 10, from about 2 to about 8, from about 2 to about 6, from about 2 to about 4, from about 4 to about 10, from about 4 to about 8, from about 4 to about 6, from about 6 to about 14, from about 6 to about 12, from about 6 to about 10, from about 6 to about 8, from about 8 to about 14, from about 8 to about 12, or from about 8 to about 10.

In some embodiments, $d_{13}$ is an integer ranging from about 2 to about 8.

In some embodiments, $d_{13}$ is 2, 4, 6, or 8. In some embodiments, $d_{13}$ is 2, 6 or 8. In some embodiments, $d_{13}$ is 8. In some embodiments, $d_{13}$ is 6. In some embodiments, $d_{13}$ is 2.

B7-H4 Antibody-Drug Conjugates

In some embodiments, conjugates of the disclosure comprise one or more occurrences of D, wherein D is a cytotoxic drug moiety or a STING agonist drug moiety, wherein the one or more occurrences of D may be the same or different.

In some embodiments, one or more occurrences of the B7-H4 antibody or B7-H4 modified antibody is attached to the Linker-Drug moiety, wherein the one or more occurrences of B7-H4 antibody or B7-H4 modified antibody may be the same or different. In some embodiments, one or more Linker-Drug moieties that comprises one or more occurrences of D are connected to one B7-H4 antibody or B7-H4 modified antibody.

In some embodiments, B7-H4 antibody is a B7-H4 antibody or a cysteine engineered B7-H4 antibody In some embodiments, the targeting ligands, the linkers and the drug or prodrug fragments described herein can be assembled into the conjugate or scaffold of the disclosure, for example according to the disclosed techniques and methods. Therapeutic and targeting conjugates of the disclosure, and methods for producing them, are described below by way of non-limiting example.

In some embodiments, the total number of sulfide bonds formed between the Linker-drug moieties and the B7-H4 antibody or the cysteine engineered B7-H4 antibody (or total number of attachment points) is 10 or less (e.g., 8, 6, 4, or 2).

In some embodiments, the total number of sulfide bonds formed between the Linker-Drug moiety and the B7-H4 antibody or the cysteine engineered B7-H4 antibody (or total number of attachment points) is 8 or less.

In some embodiments, the total number of sulfide bonds formed between the Linker-Drug moiety and the B7-H4 antibody or the cysteine engineered B7-H4 antibody (or total number of attachment points) is 8. In some embodiments, the total number of sulfide bonds formed between the Linker-Drug moiety and the B7-H4 antibody or the cysteine engineered B7-H4 antibody (or total number of attachment points) is 6. In some embodiments, the total number of sulfide bonds formed between the Linker-Drug moiety and the B7-H4 antibody or the cysteine engineered B7-H4 antibody or the cysteine engineered B7-H4 antibody (or total number of attachment points) is 5. In some embodiments, the total number of sulfide bonds formed between the Linker-Drug moiety and the B7-H4 antibody or the cysteine engineered B7-H4 antibody (or total number of attachment points) is 4. In some embodiments, the total number of sulfide bonds formed between the Linker-Drug moiety and the B7-H4 antibody or the cysteine engineered B7-H4 antibody (or total number of attachment points) is 3. In some embodiments, the total number of sulfide bonds formed between the Linker-Drug moiety and the B7-H4 antibody or the cysteine engineered B7-H4 antibody (or total number of attachment points) is 2.

In some embodiments, the ratio between Linker-Drug moiety and the B7-H4 antibody is between about 1:1 and about 8:1. In some embodiments, the ratio between Linker-Drug moiety and the B7-H4 antibody or the cysteine engineered B7-H4 antibody is between about 1:1 and about 6:1. In some embodiments, the ratio between Linker-Drug moiety and the B7-H4 antibody is between about 1:1 and about 4:1. In some embodiments, the ratio between Linker-Drug moiety and the B7-H4 antibody or the cysteine engineered B7-H4 antibody is between about 2:1 and about 2:1.

In some embodiments, the ratio between Linker-Drug moiety and the B7-H4 antibody or the cysteine engineered B7-H4 antibody is between about 6:1 and about 8:1.

In some embodiments, the ratio between Linker-Drug moiety and the B7-H4 antibody or the cysteine engineered B7-H4 antibody is about 8:1.

In some embodiments, the ratio between Linker-Drug moiety and the B7-H4 antibody is about 6:1.

In some embodiments, the disclosure also relates to a Linker-Drug moiety comprising or the cysteine engineered B7-H4 antibody at least two moieties, wherein each moiety is capable of conjugation to a thiol group in a B7-H4 antibody so as to form a protein-Linker-Drug conjugate.

In some embodiments, one or more thiol groups of the B7-H4 antibody or the cysteine engineered B7-H4 antibody are produced by reducing a protein. The one or more thiol groups of the B7-H4 antibody or the cysteine engineered B7-H4 antibody may then react with one or more Linker-Drug moieties that are capable of conjugation to a thiol group from the B7-H4 antibody or the cysteine engineered B7-H4 antibody with the Linker-Drug moiety. In some embodiments, the at least two moieties connected to the B7-H4 antibody or the cysteine engineered B7-H4 antibody are maleimide groups. In these embodiments, D is a cytotoxic drug moiety or a STING agonist drug moiety.

In some embodiments, the antibodies may be activated for conjugation with Linker-Drug moiety by treatment with a reducing agent such as DTT (Cleland's reagent, dithiothreitol) or TCEP (tris(2-carboxyethyl)phosphine hydrochloride). In some embodiments, full length, monoclonal antibodies can be reduced with an excess of TCEP to reduce disulfide bonds (e.g., between the cysteine present in the corresponding parent antibodies or the cysteine engineered antibody) to yield a reduced form of the antibody. The newly introduced and unpaired cysteine may remain available for reaction with Linker-Drug moiety to form the antibody conjugates of the present disclosure. In some embodiments, an excess of Linker-drug moiety is added to effect conjugation and form the antibody-drug conjugate, and the conjugation mixture is purified to remove excess Linker-drug intermediate and other impurities.

In some embodiments, the ratio of the B7-H4 antibody or the cysteine engineered B7-H4 per Linker-Drug moiety is between about 1:1 and about 1:8; between about 1:1 and about 1:6; between about 1:1 and about 1:5; between about 1:1 and about 1:4; between about 1:1 and about 1:3; or between about 1:1 and about 1:2.

Conjugates disclosed herein can be purified (i.e., removal of any starting materials) by extensive diafiltration. If necessary, additional purification by size exclusion chromatography can be conducted to remove any aggregated conjugates. In general, the conjugates as purified typically contain less than 5% (e.g., <2% w/w) aggregated conjugates as determined by SEC; less than 0.5% (e.g., <0.1% w/w) free (unconjugated) drug as determined by RP-HPLC; less than 1% drug carrying-peptide-containing scaffolds as determined by SEC and less than 2% (e.g., <1% w/w) unconjugated B7-H4 antibody as determined by HIC-HPLC.

In some embodiments, the B7-H4 antibody or the cysteine engineered B7-H4 conjugated to a STING agonist drug moiety is selected from the conjugates described in Table A1 and Table A2.

TABLE A1

Structure: (chemical structure of antibody-drug conjugate, labeled $d_{13}$)

TABLE A1-continued
Structure
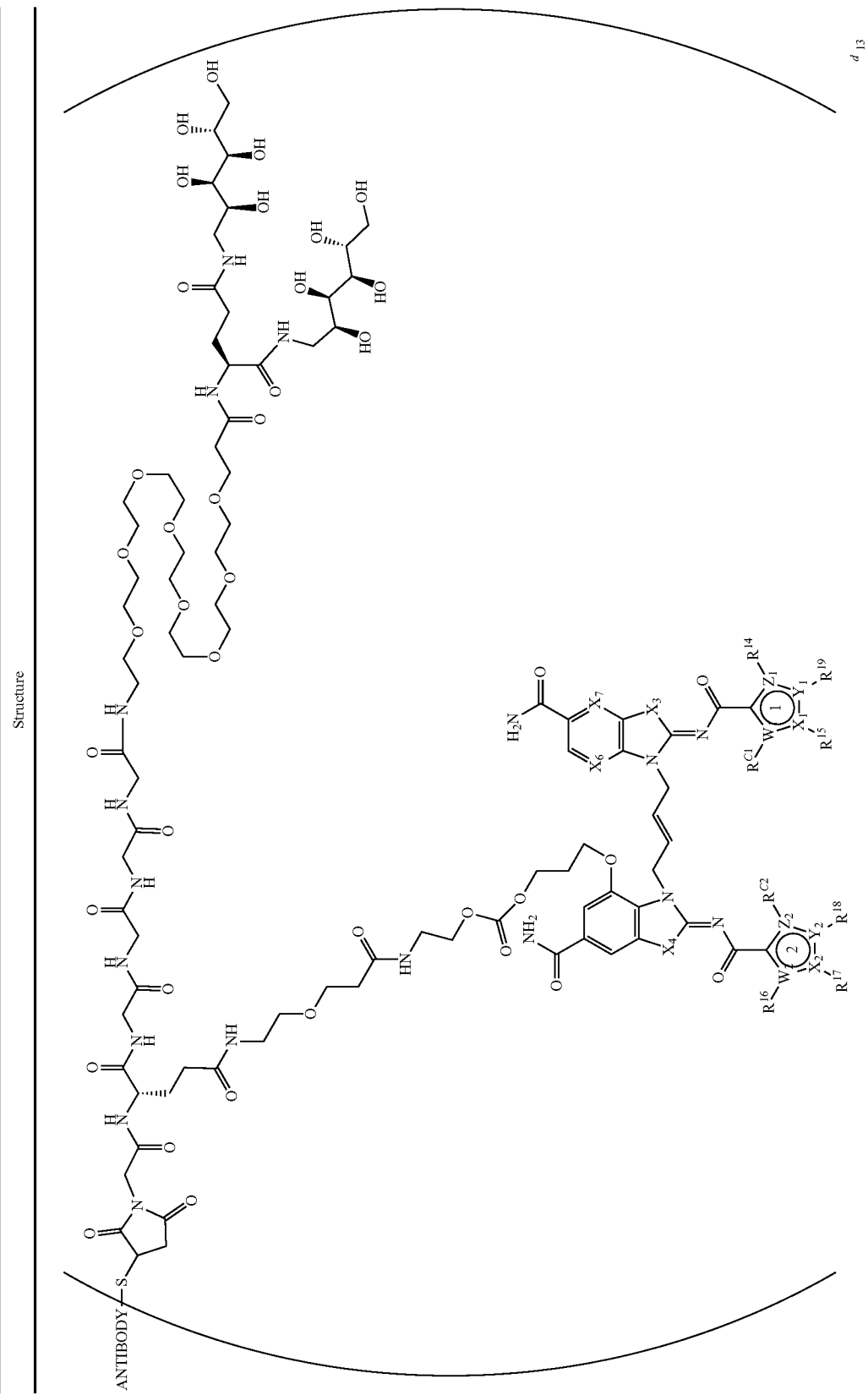

TABLE A1-continued
Structure
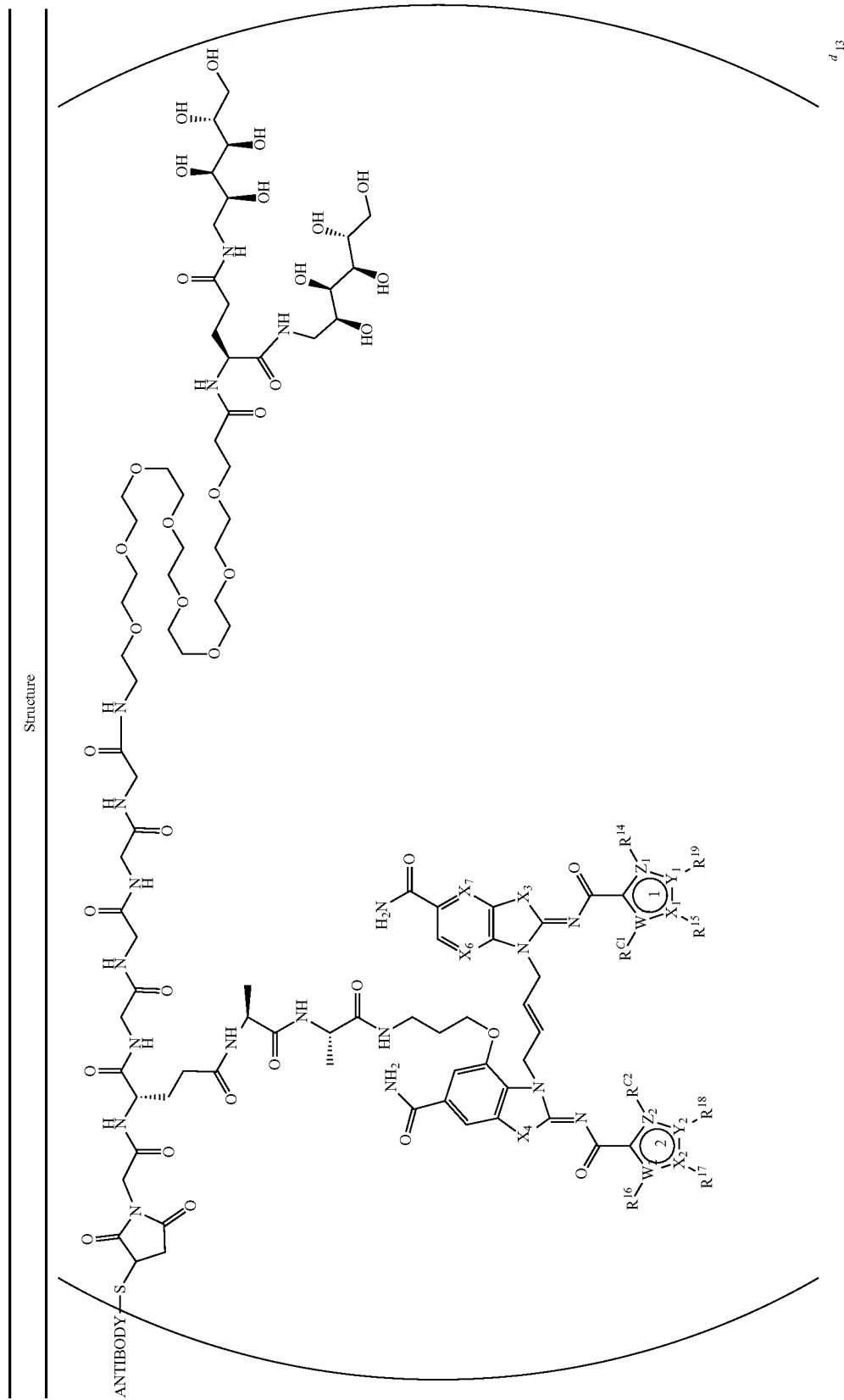

TABLE A1-continued
Structure
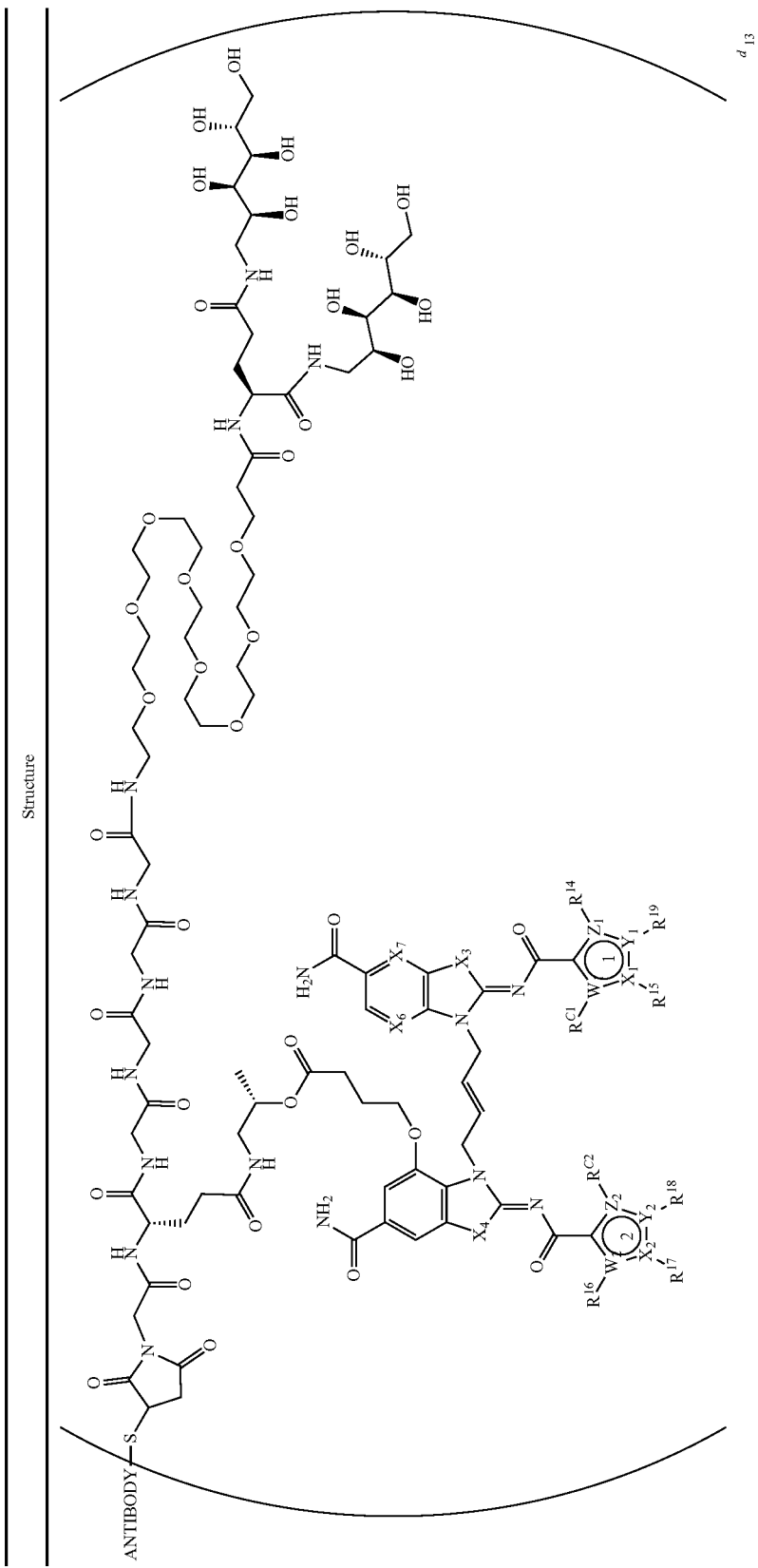

TABLE A1-continued
Structure
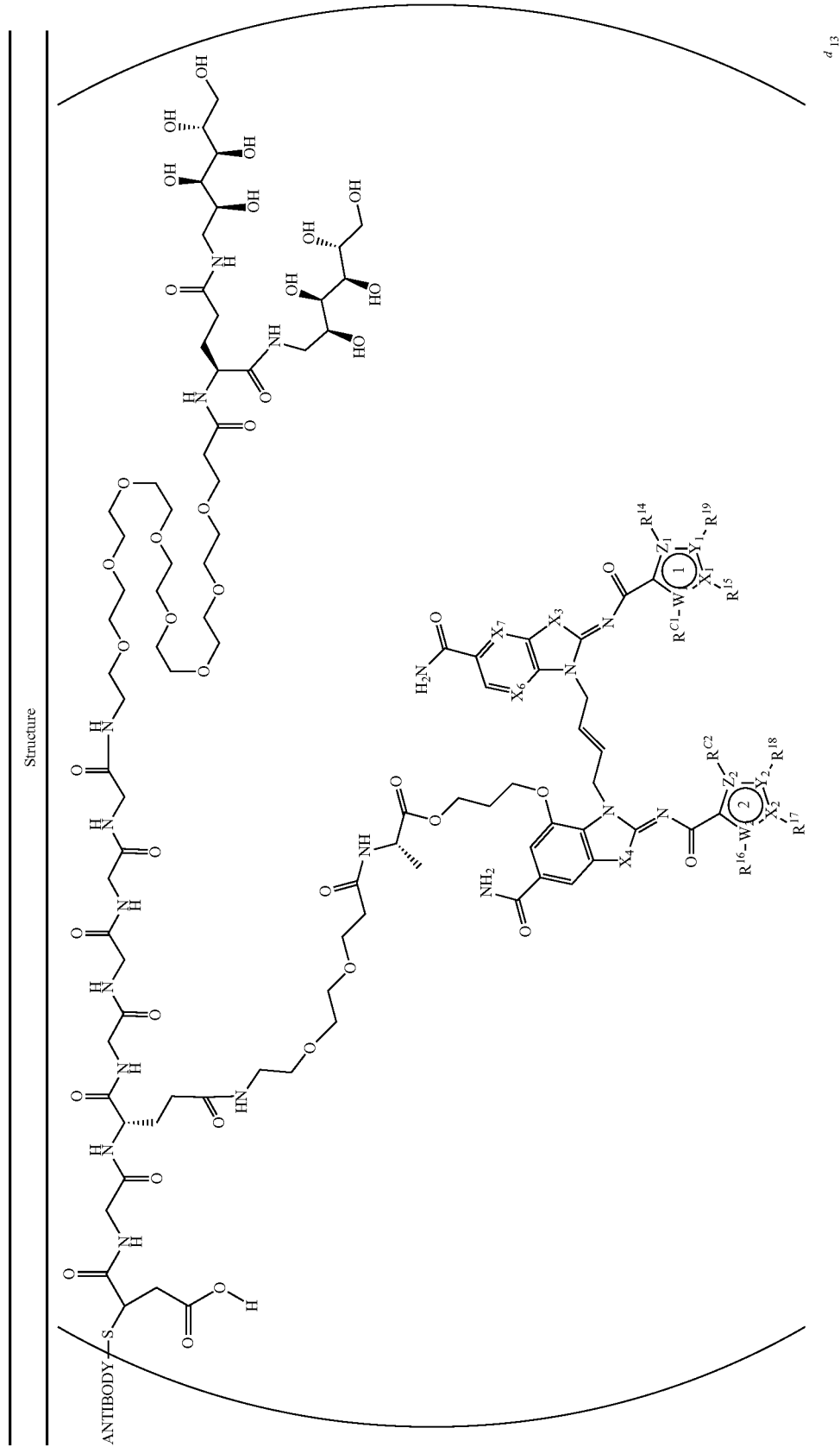

TABLE A1-continued
Structure
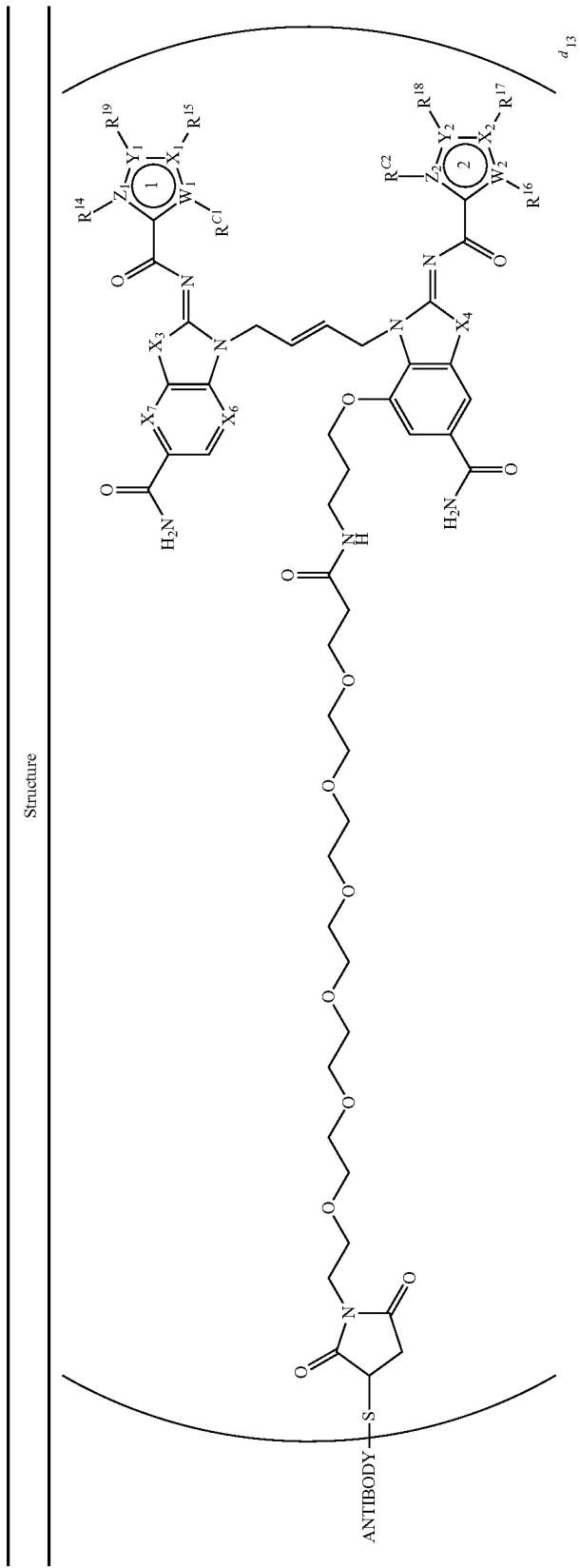

TABLE A1-continued
Structure

TABLE A1-continued
Structure

TABLE A1-continued
Structure
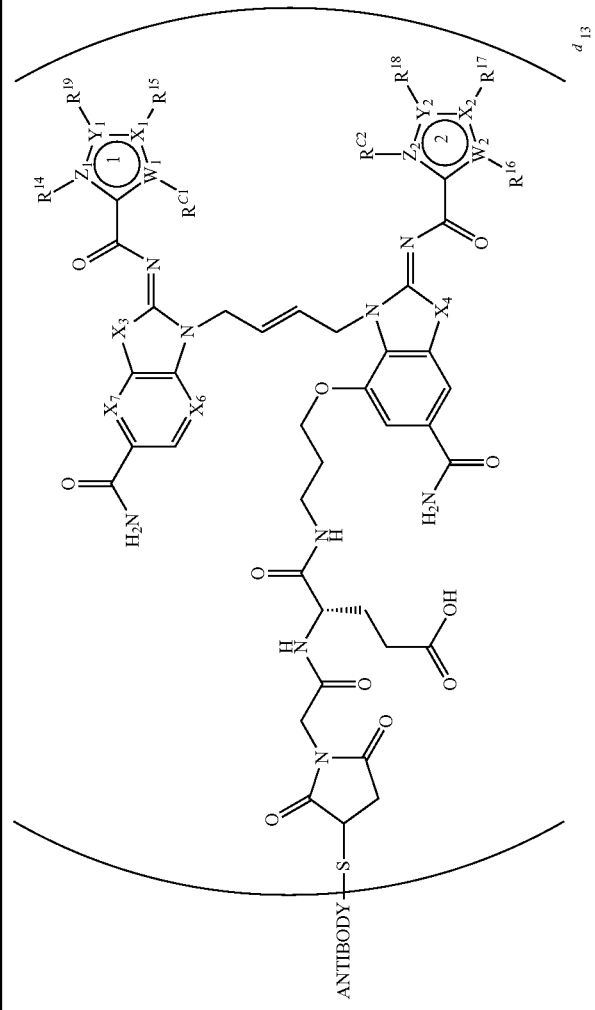

TABLE A1-continued
Structure

TABLE A1-continued
Structure

TABLE A1-continued
Structure

TABLE A1-continued
Structure

TABLE A1-continued
Structure

TABLE A1-continued
Structure
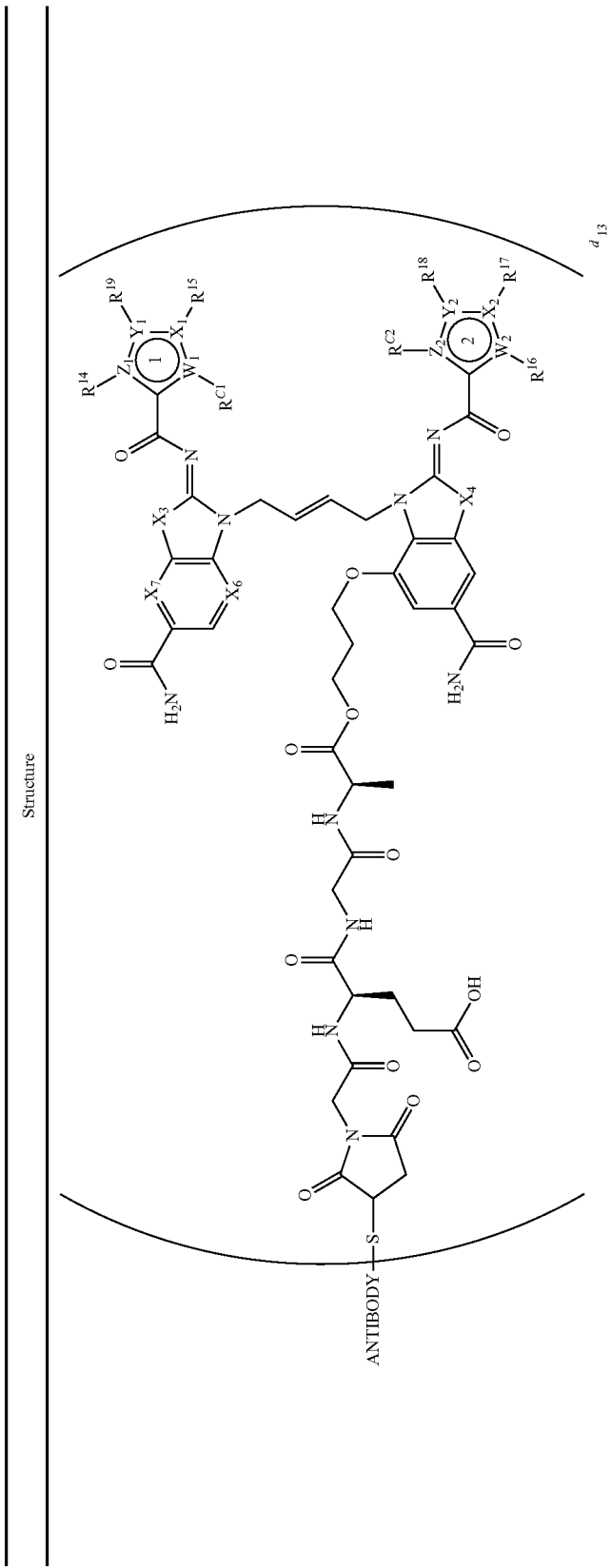

TABLE A1-continued
Structure
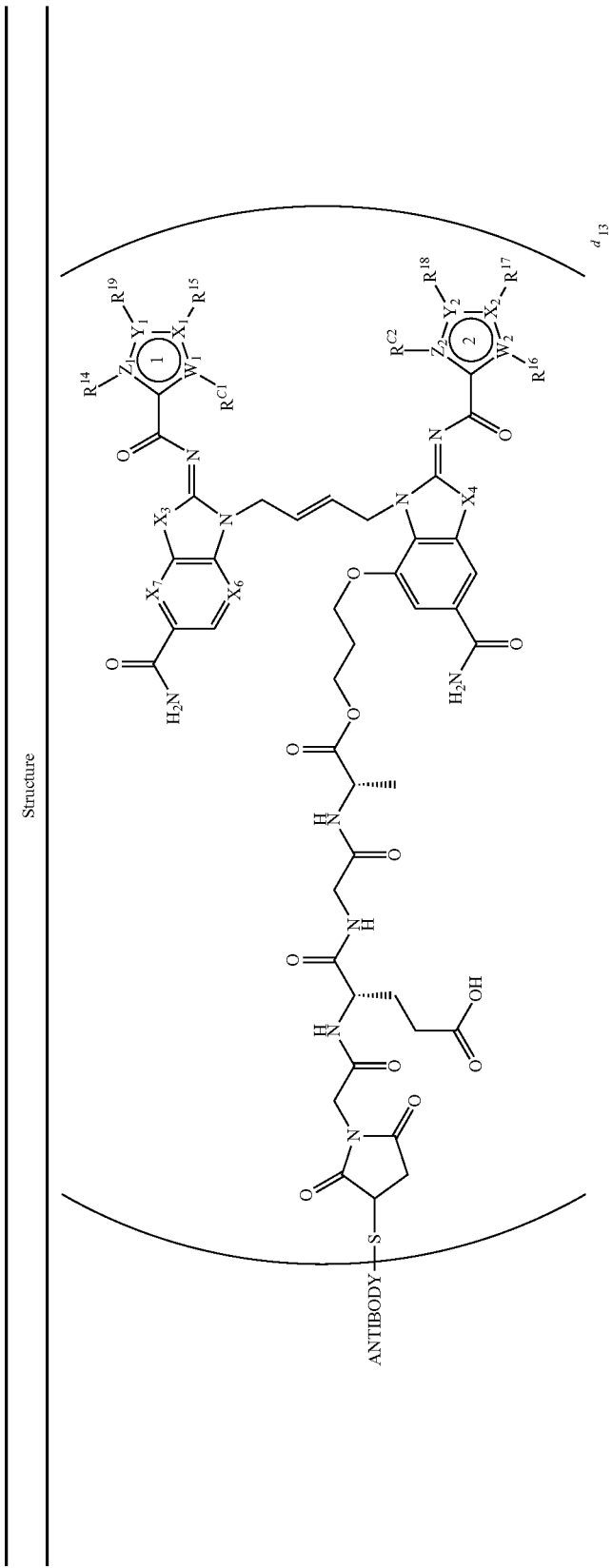

TABLE A1-continued
Structure
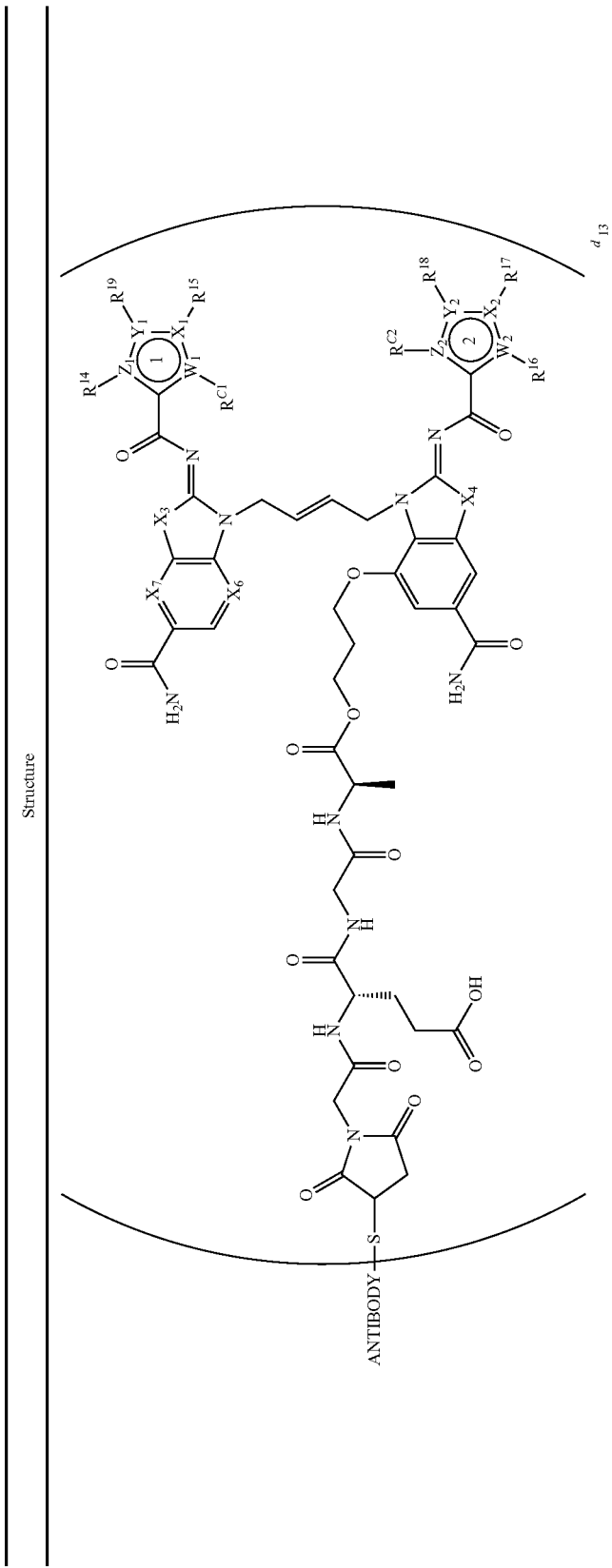

TABLE A1-continued
Structure
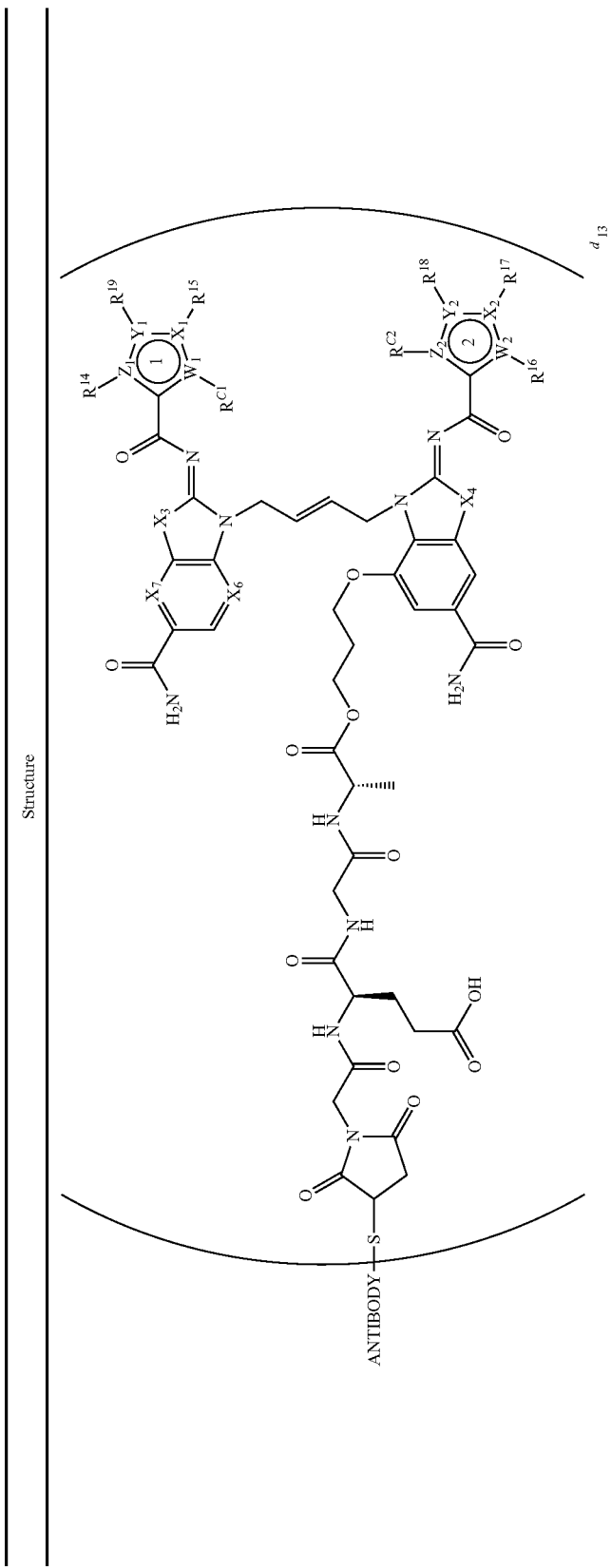

TABLE A1-continued
Structure
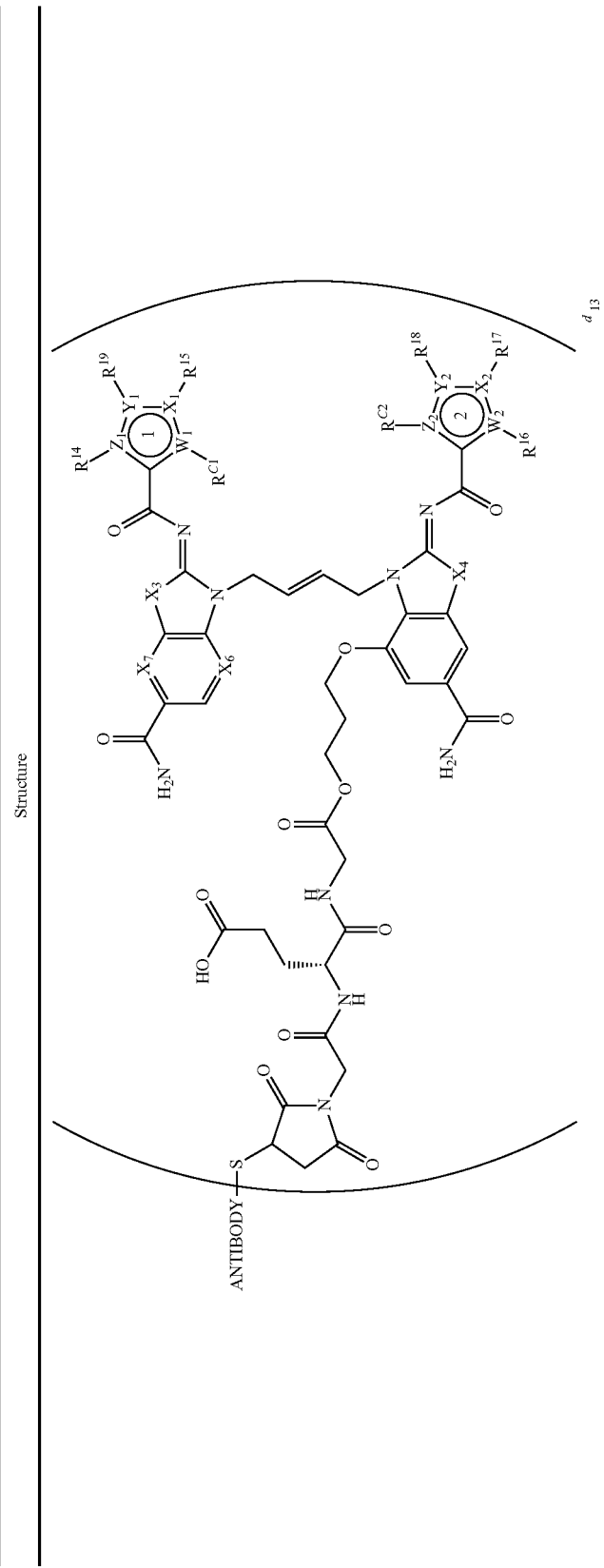

wherein $d_{13}$, $R^{14}$, $R^{15}$, $R^{16}$, $R^{17}$, $R^{18}$, $R^{19}$, $R^{C1}$, $R^{C2}$, $R^4$, $X_3$, $X_4$, $X_6$, $X_7$, $X^1$, $W_1$, $Y_1$, $Z_1$, $X_2$, $W_2$, $Y_2$, $Z_2$, are as defined herein and ANTIBODY is a B7-H4 antibody or a cysteine engineered B7-H4 antibody.

In some embodiments, for the conjugates in Table A1, $d_{13}$ is an integer from 6 to 8.

In some embodiments, for the conjugates in Table A1, $d_{13}$ is 8. In some embodiments, for the conjugates in Table A1, $d_{13}$ is 7. In some embodiments, for the conjugates in Table A1, $d_{13}$ is 6.

In some embodiments, for the conjugates in Table A1, $d_{13}$ is 8.

TABLE A2
Structure
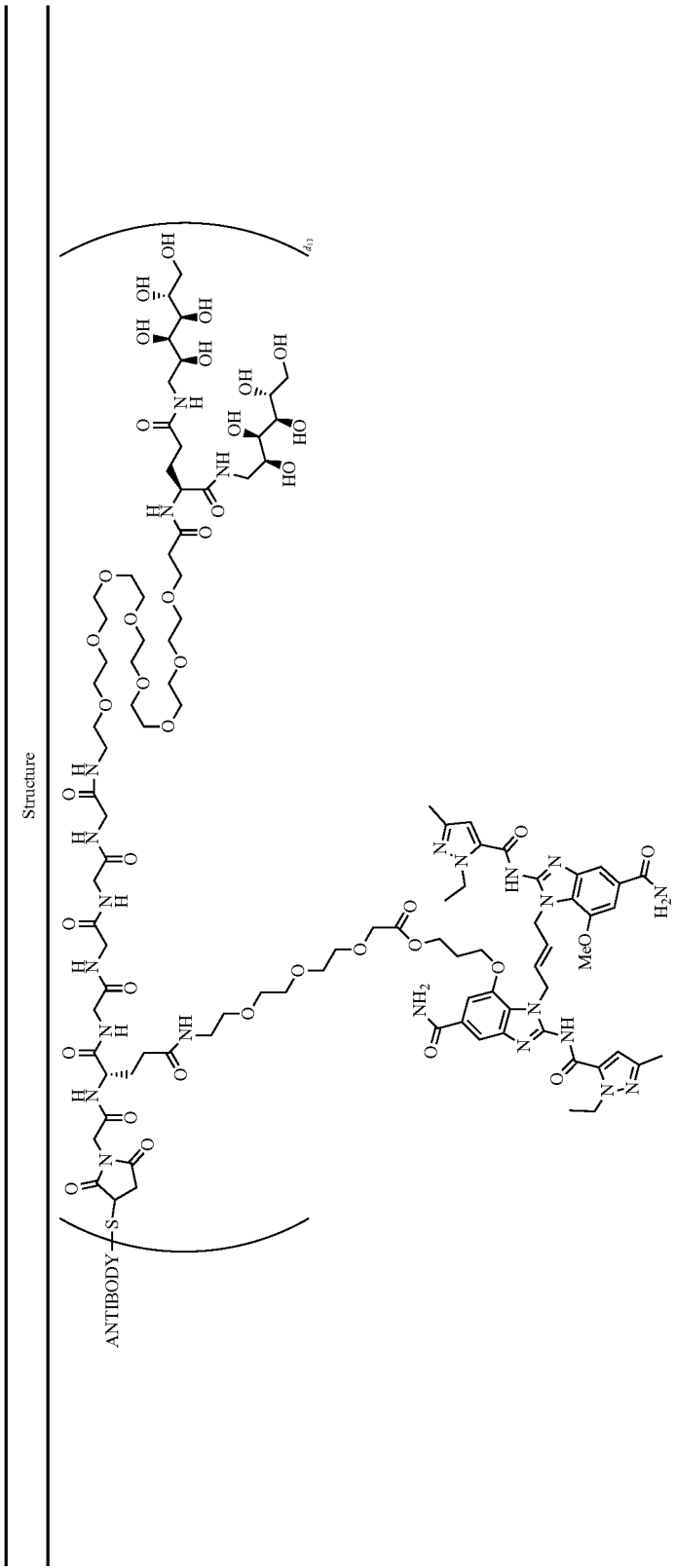

TABLE A2-continued
Structure
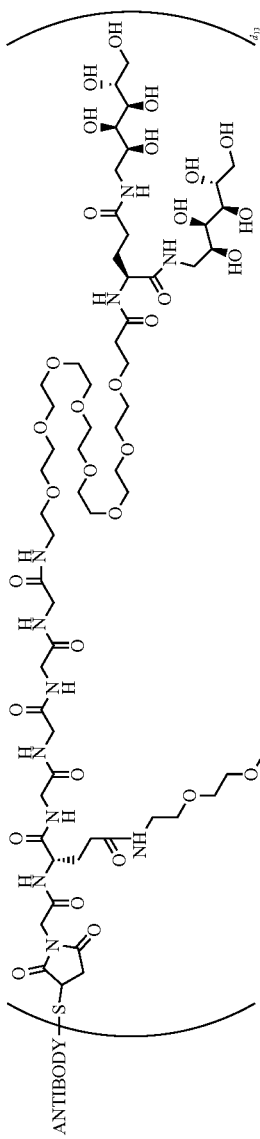

TABLE A2-continued
Structure

TABLE A2-continued
Structure

TABLE A2-continued
Structure

TABLE A2-continued
Structure
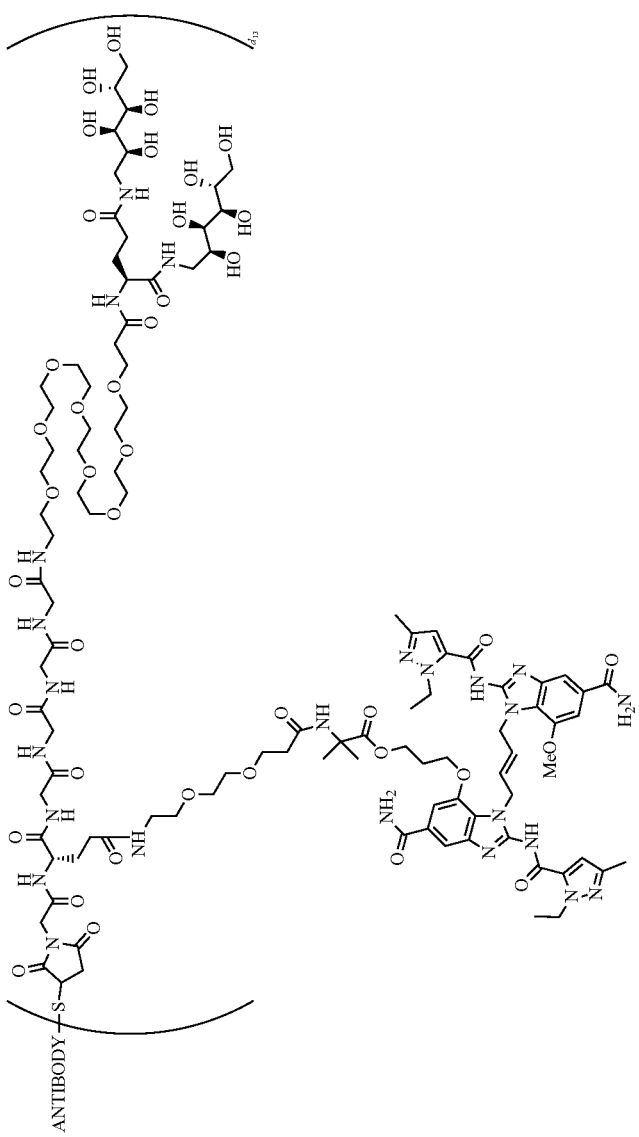

TABLE A2-continued
Structure
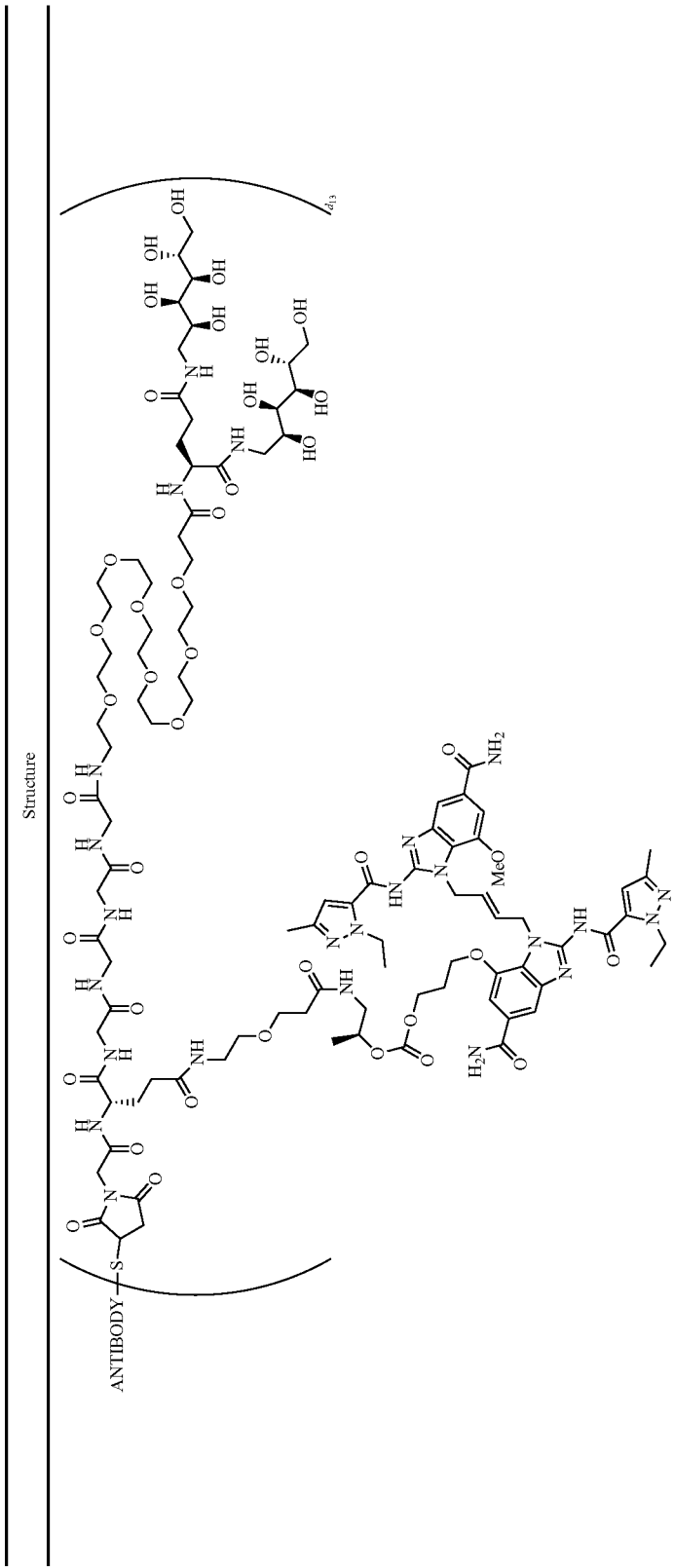

TABLE A2-continued
Structure
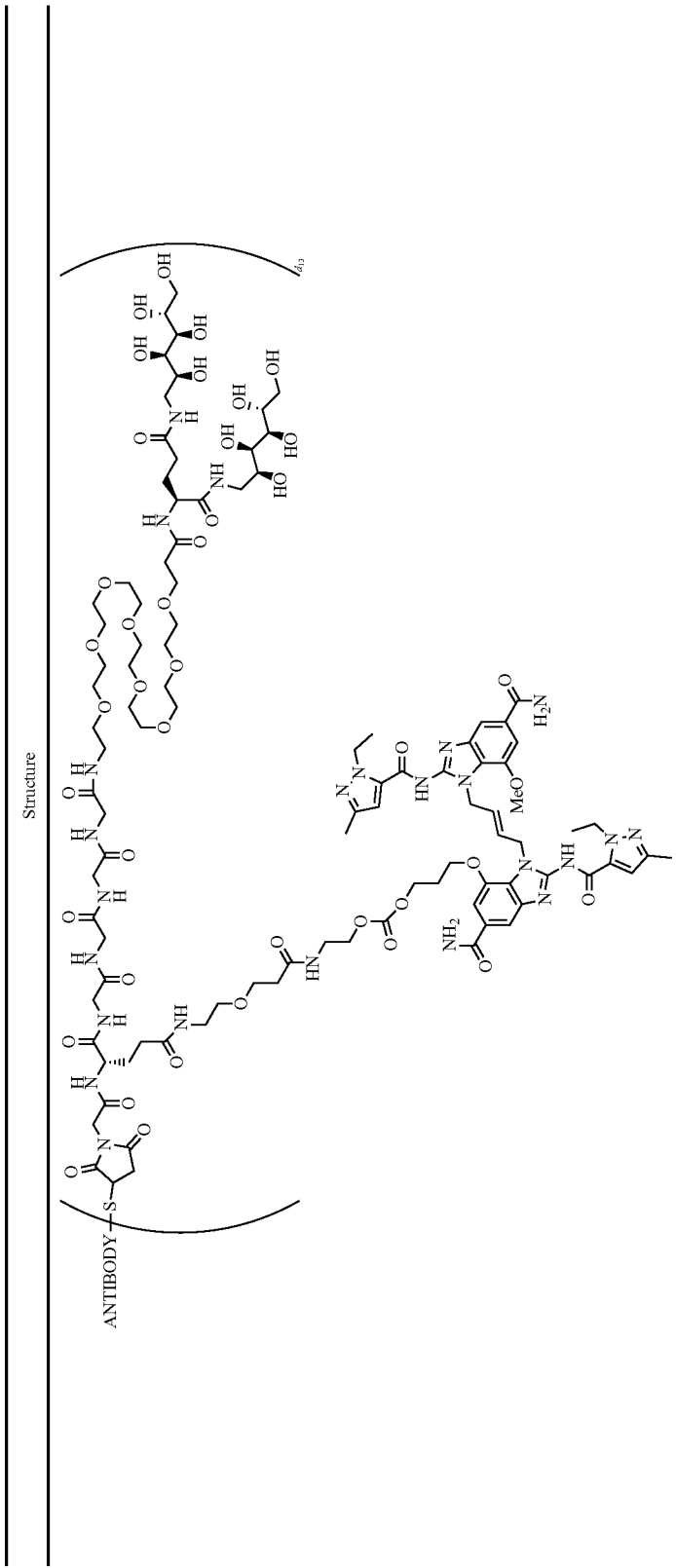

TABLE A2-continued
Structure
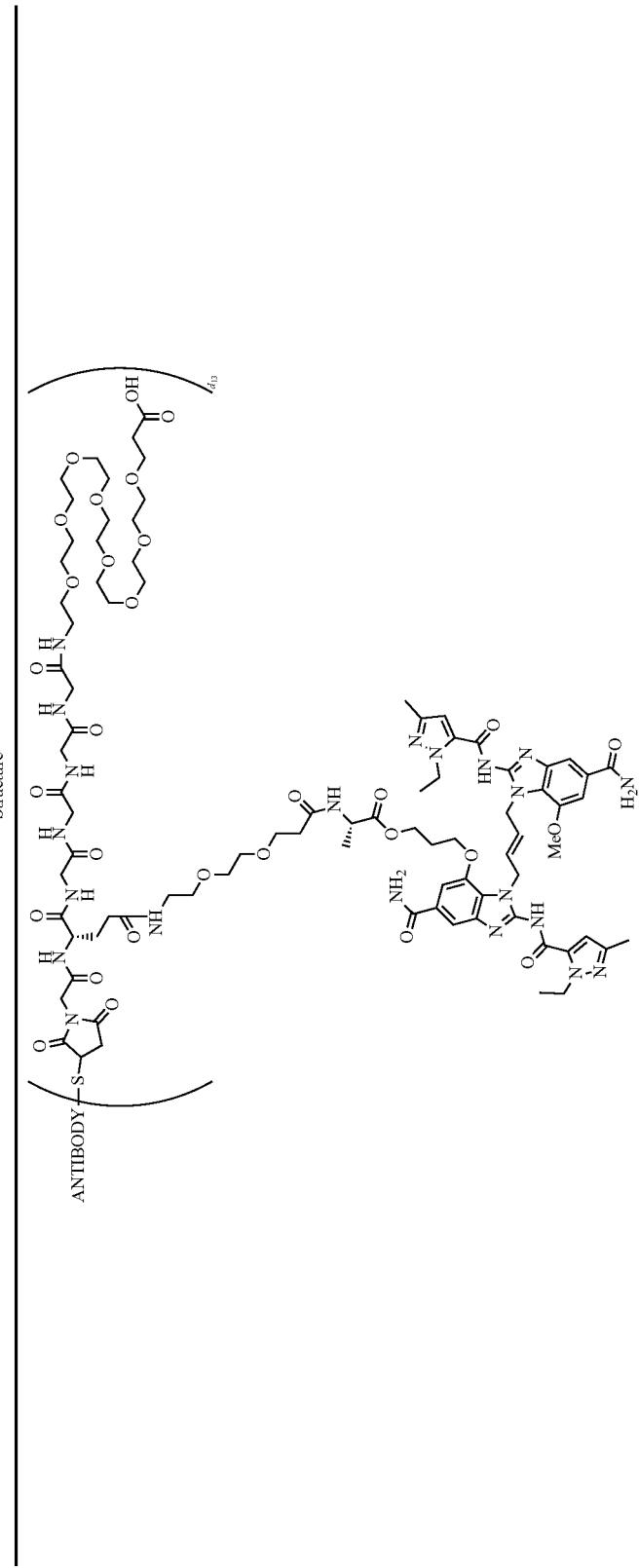

TABLE A2-continued

TABLE A2-continued
Structure
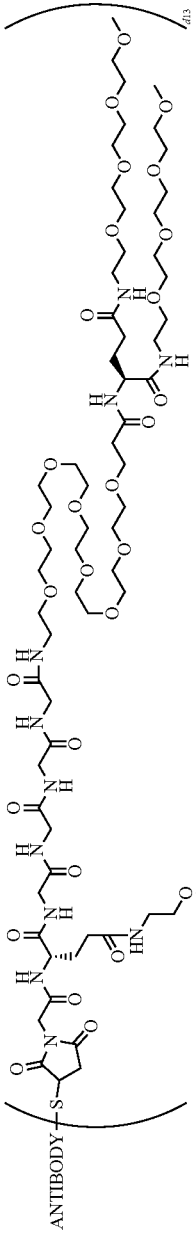

TABLE A2-continued
Structure
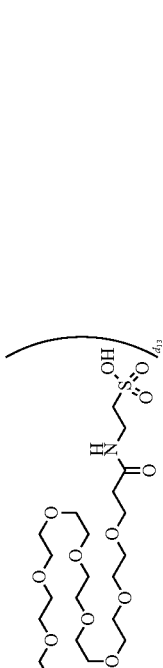

TABLE A2-continued

TABLE A2-continued

Structure

TABLE A2-continued

Structure

TABLE A2-continued
Structure

TABLE A2-continued
Structure

TABLE A2-continued
Structure
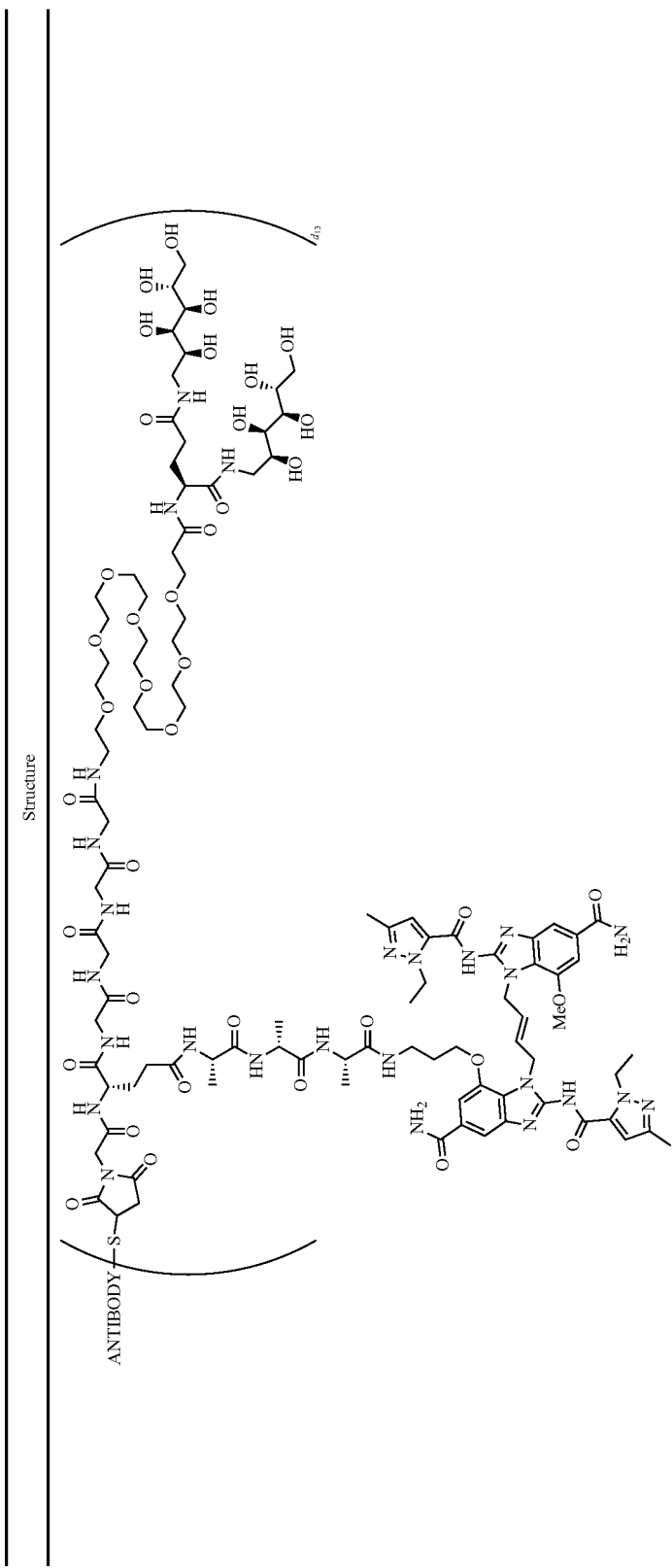

TABLE A2-continued
Structure
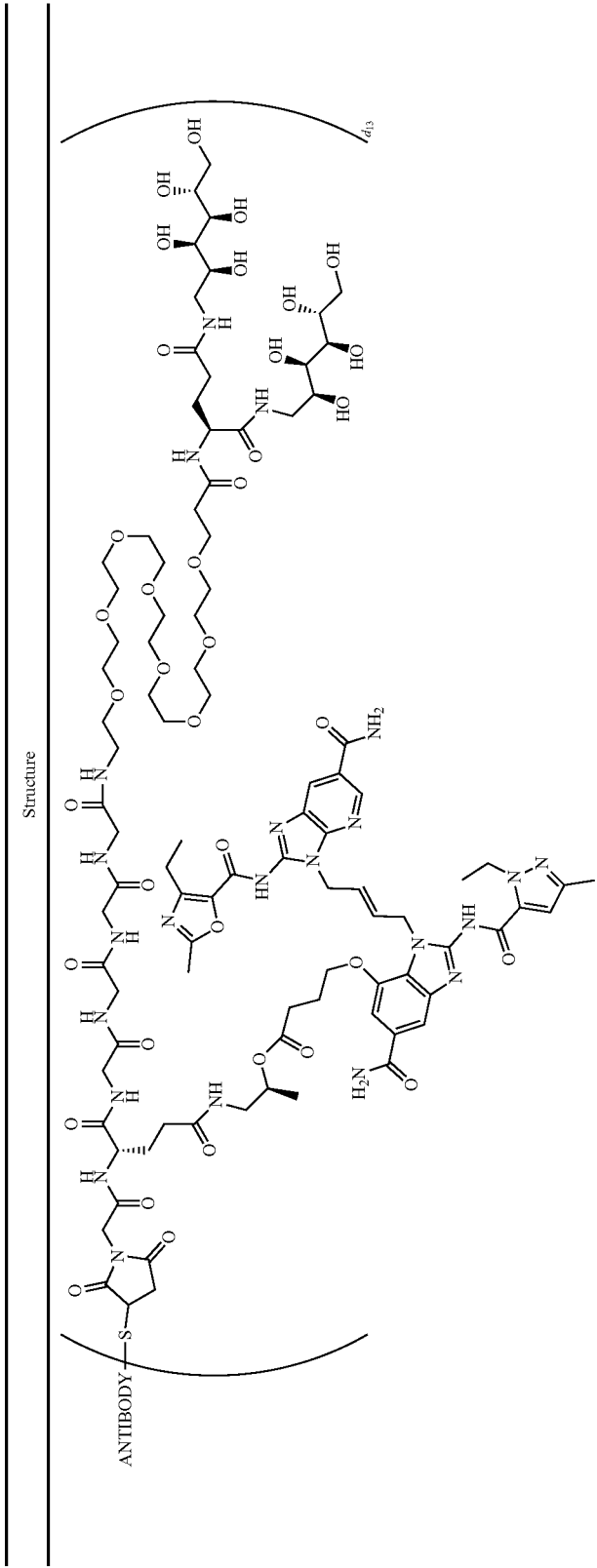

TABLE A2-continued
Structure
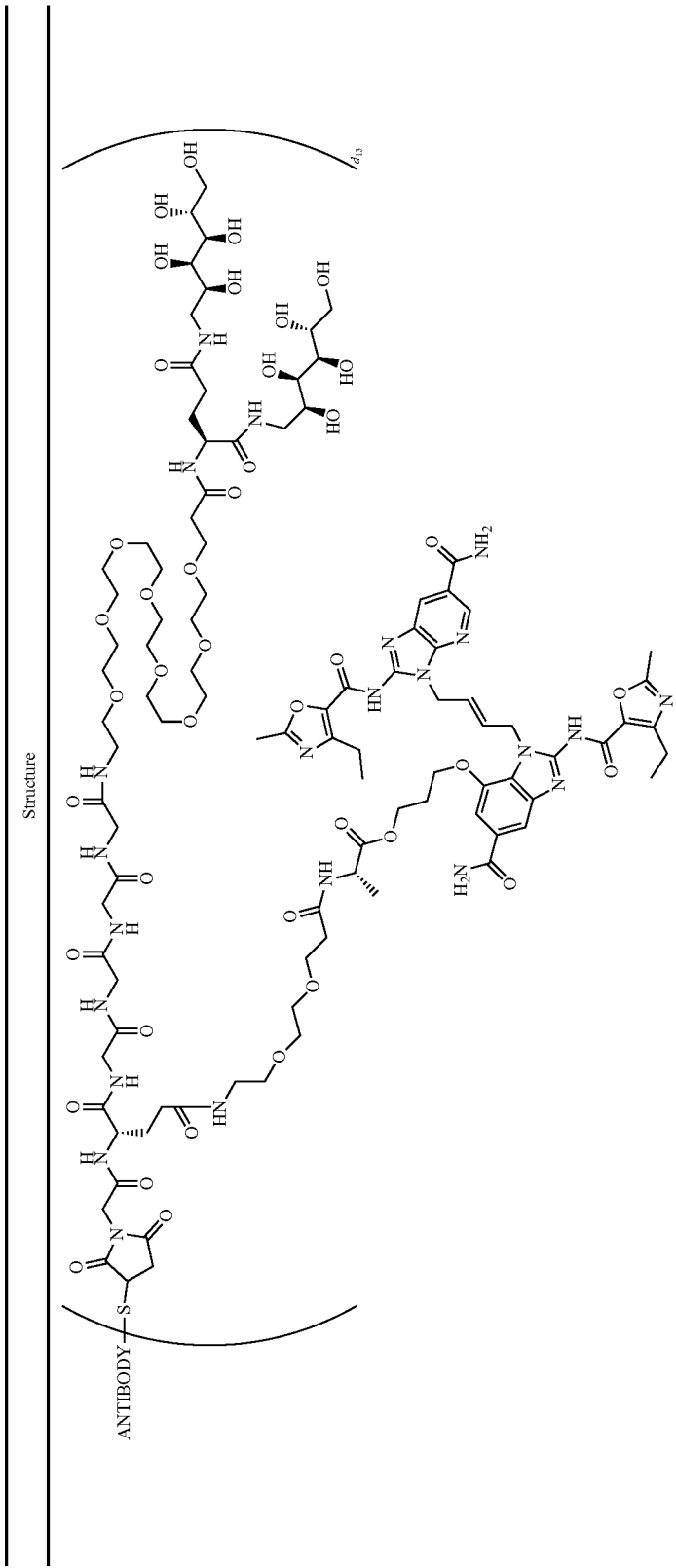

TABLE A2-continued
Structure
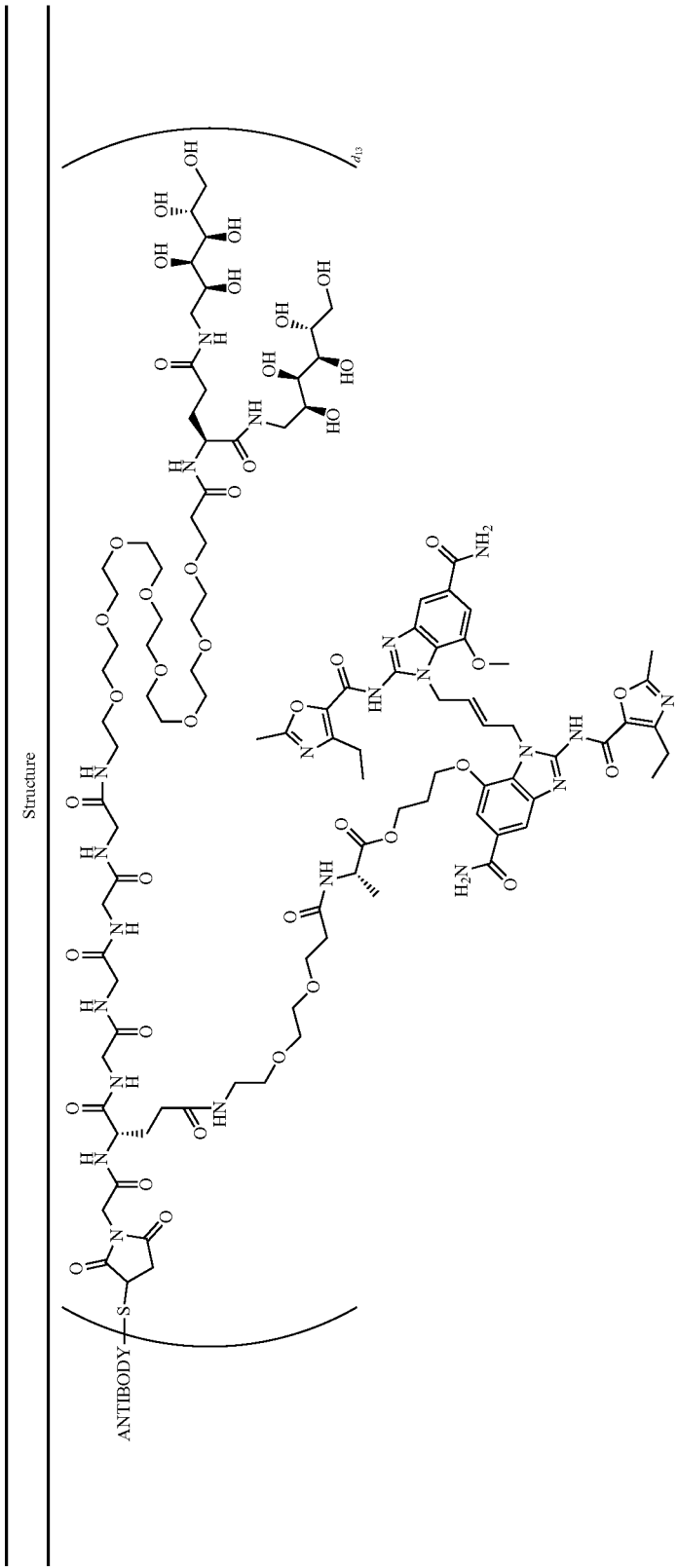

TABLE A2-continued
Structure
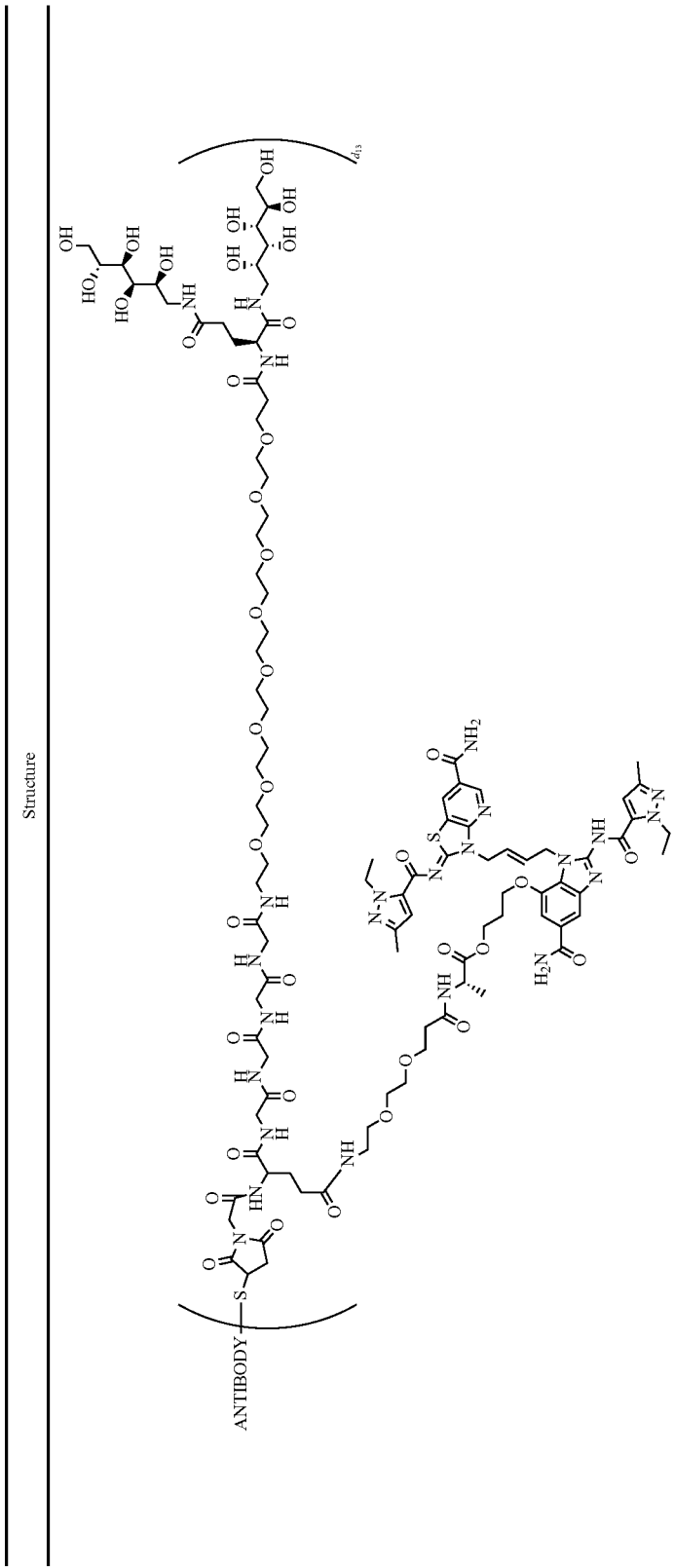

TABLE A2-continued
Structure
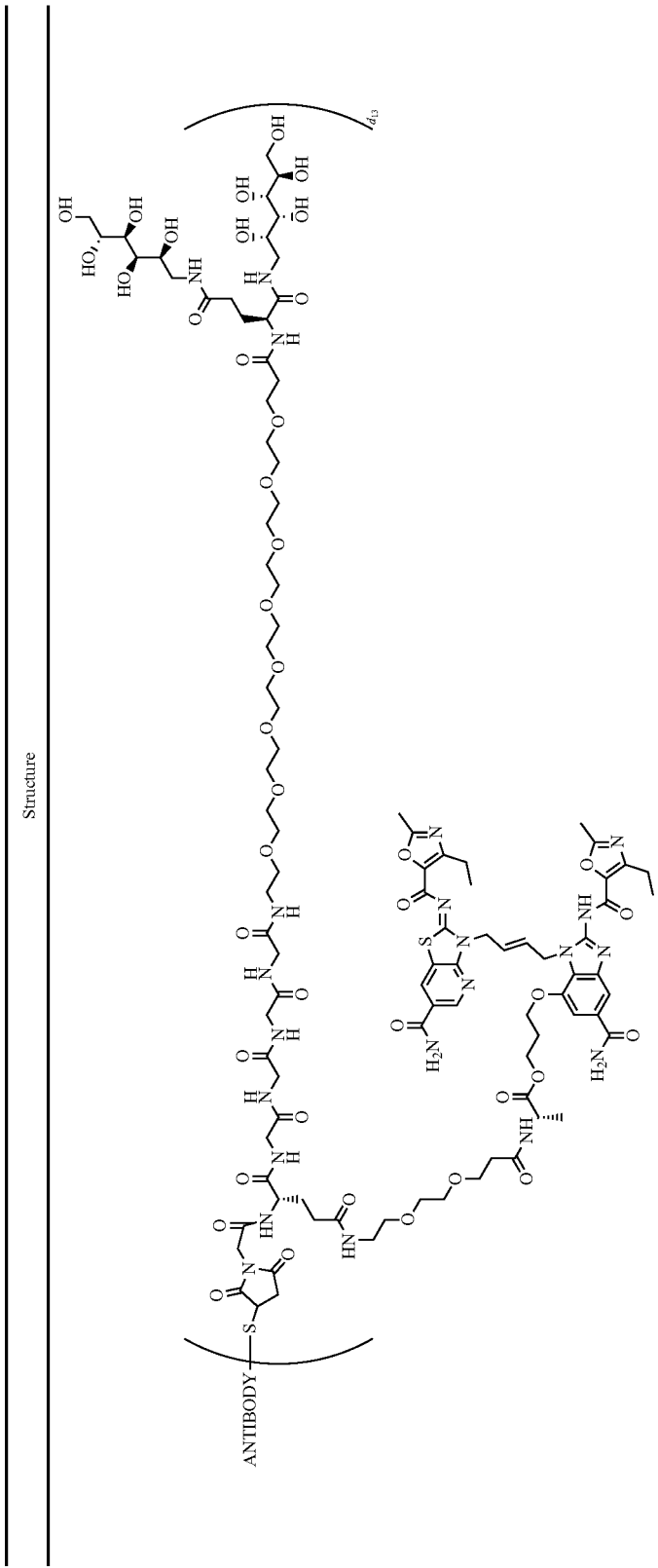

TABLE A2-continued
Structure
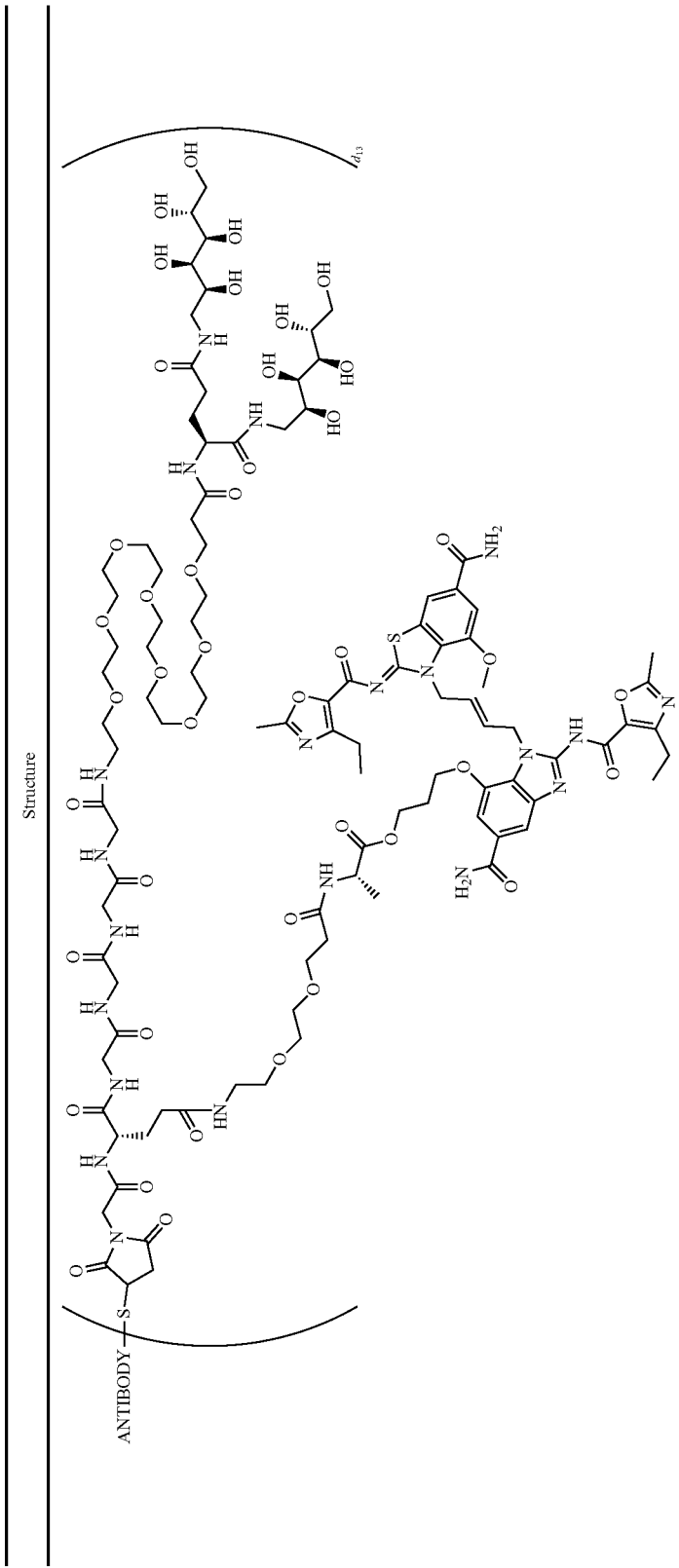

TABLE A2-continued
Structure
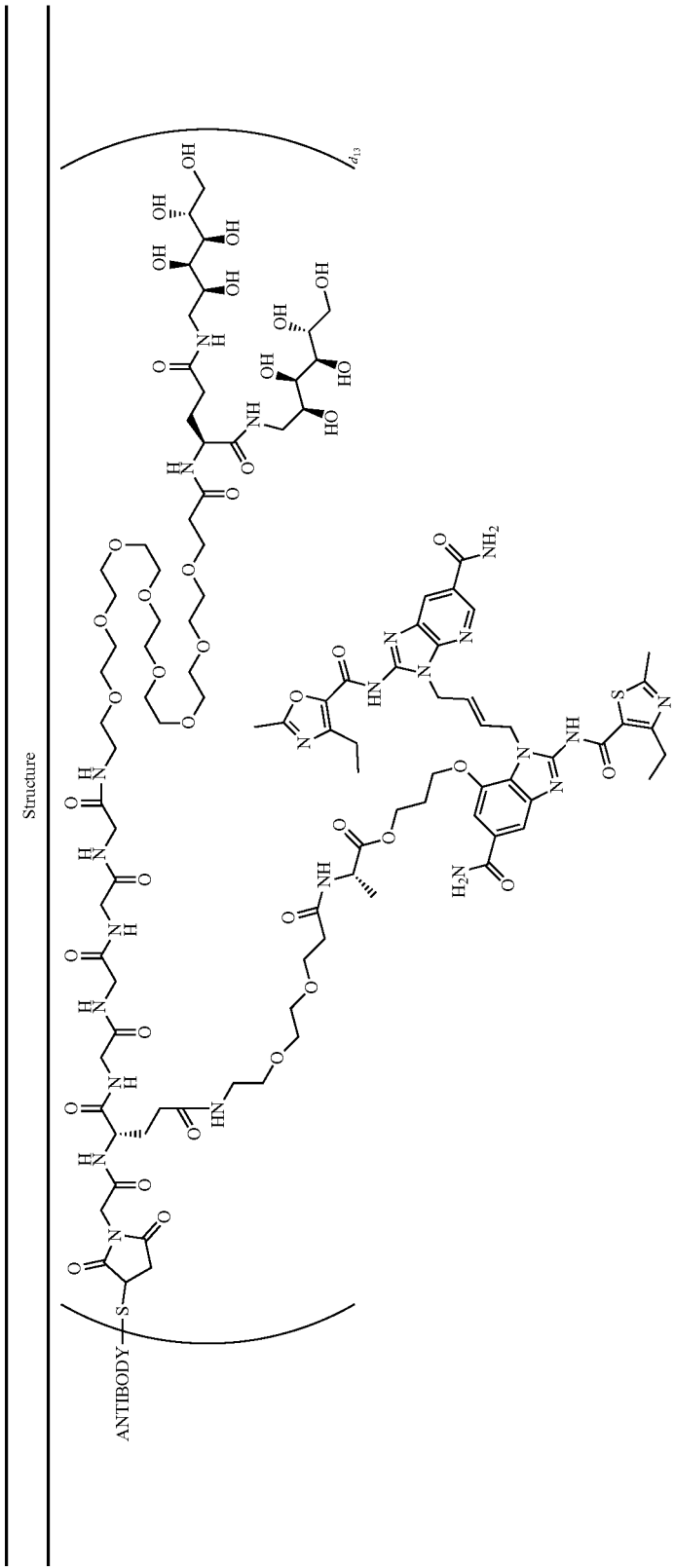

TABLE A2-continued
Structure
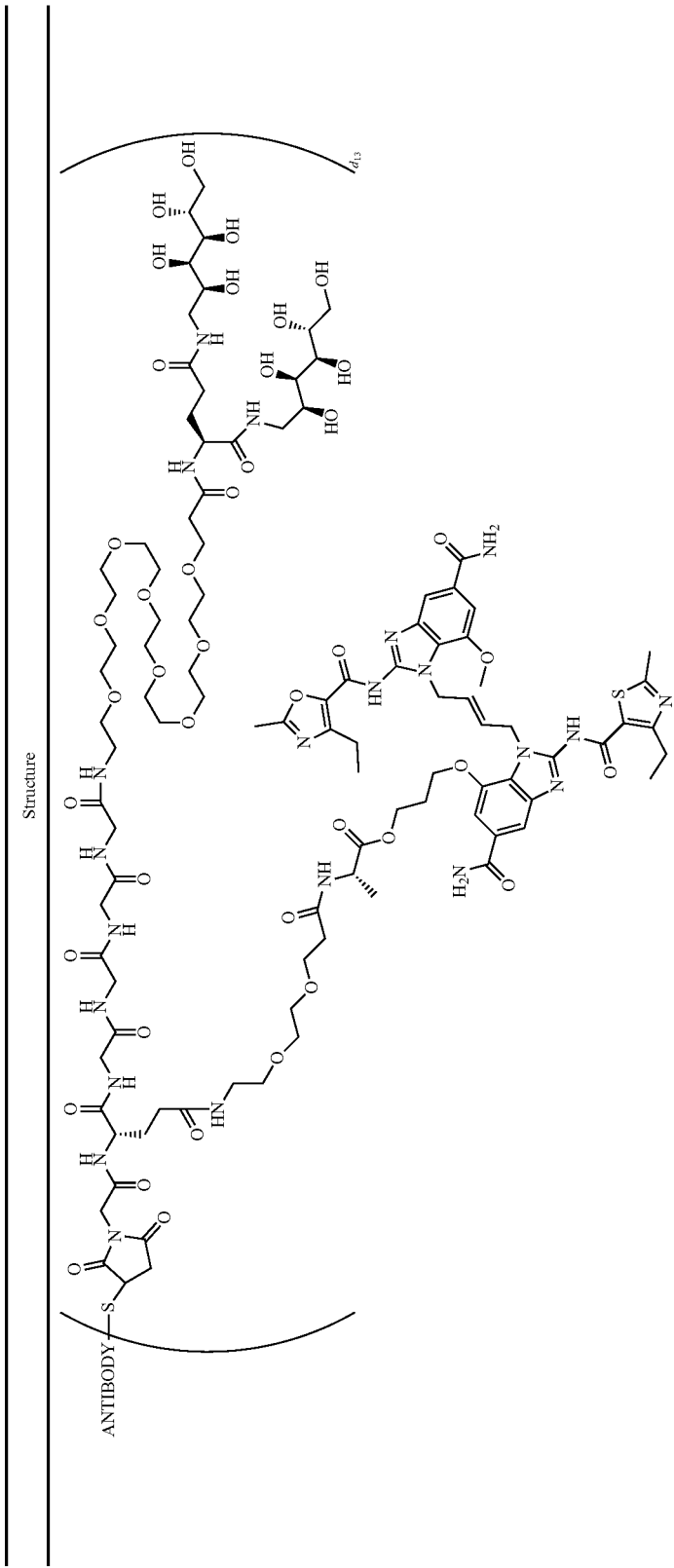

TABLE A2-continued
Structure

TABLE A2-continued
Structure
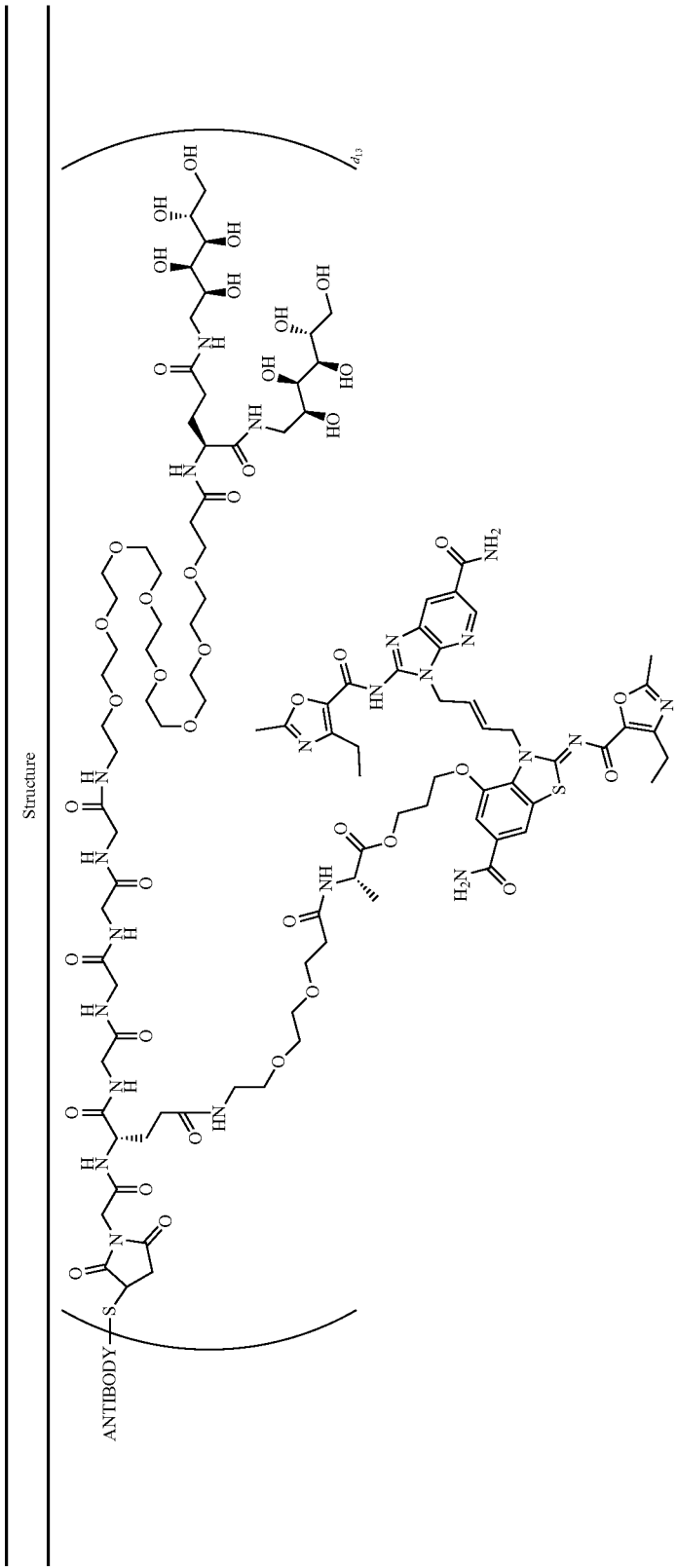

TABLE A2-continued
Structure
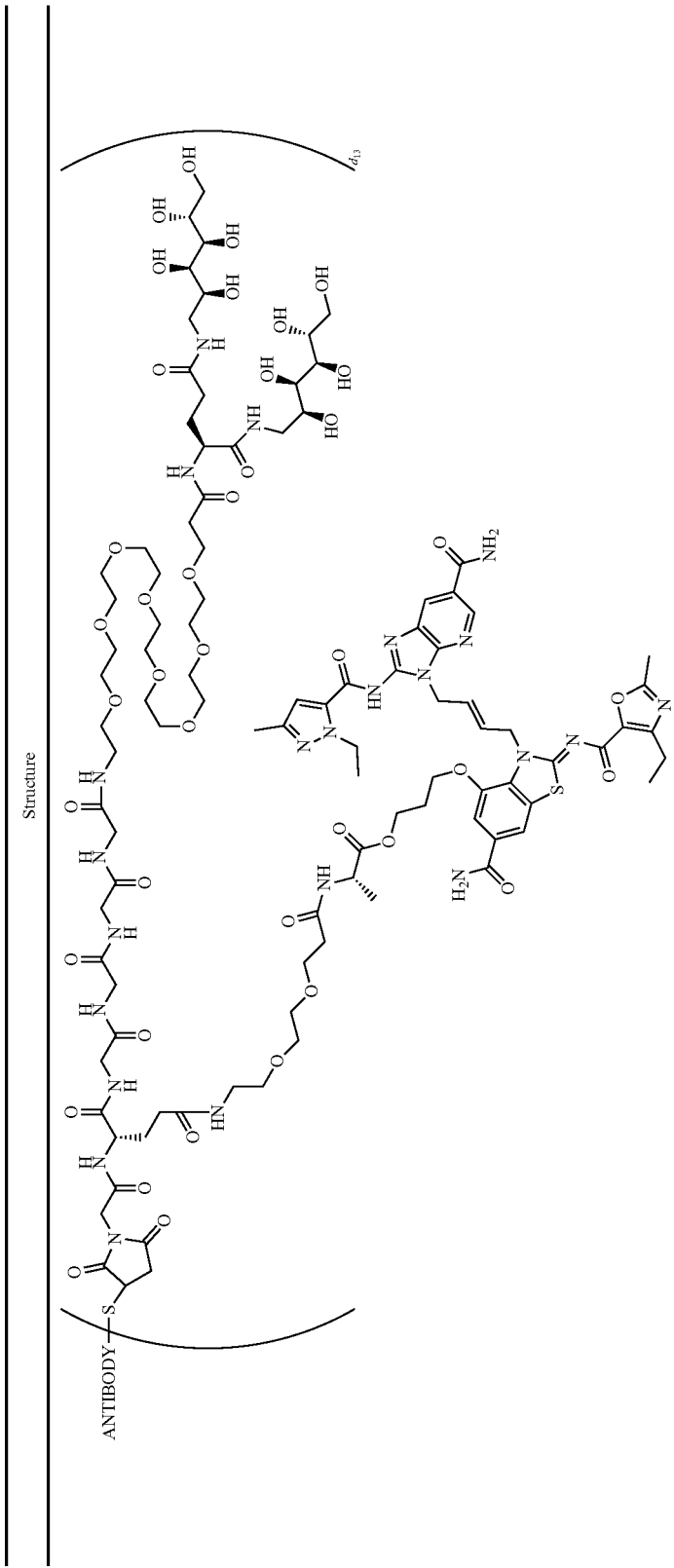

TABLE A2-continued
Structure
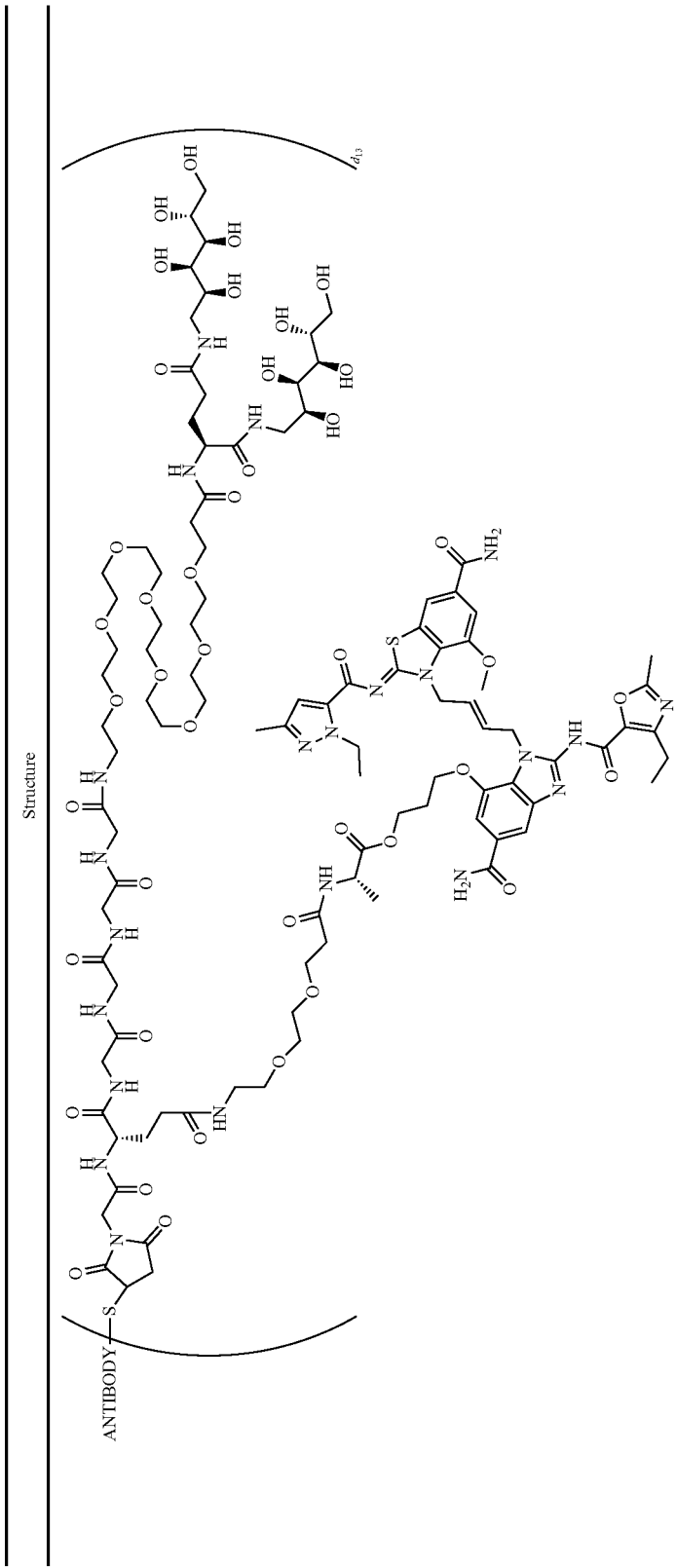

TABLE A2-continued
Structure
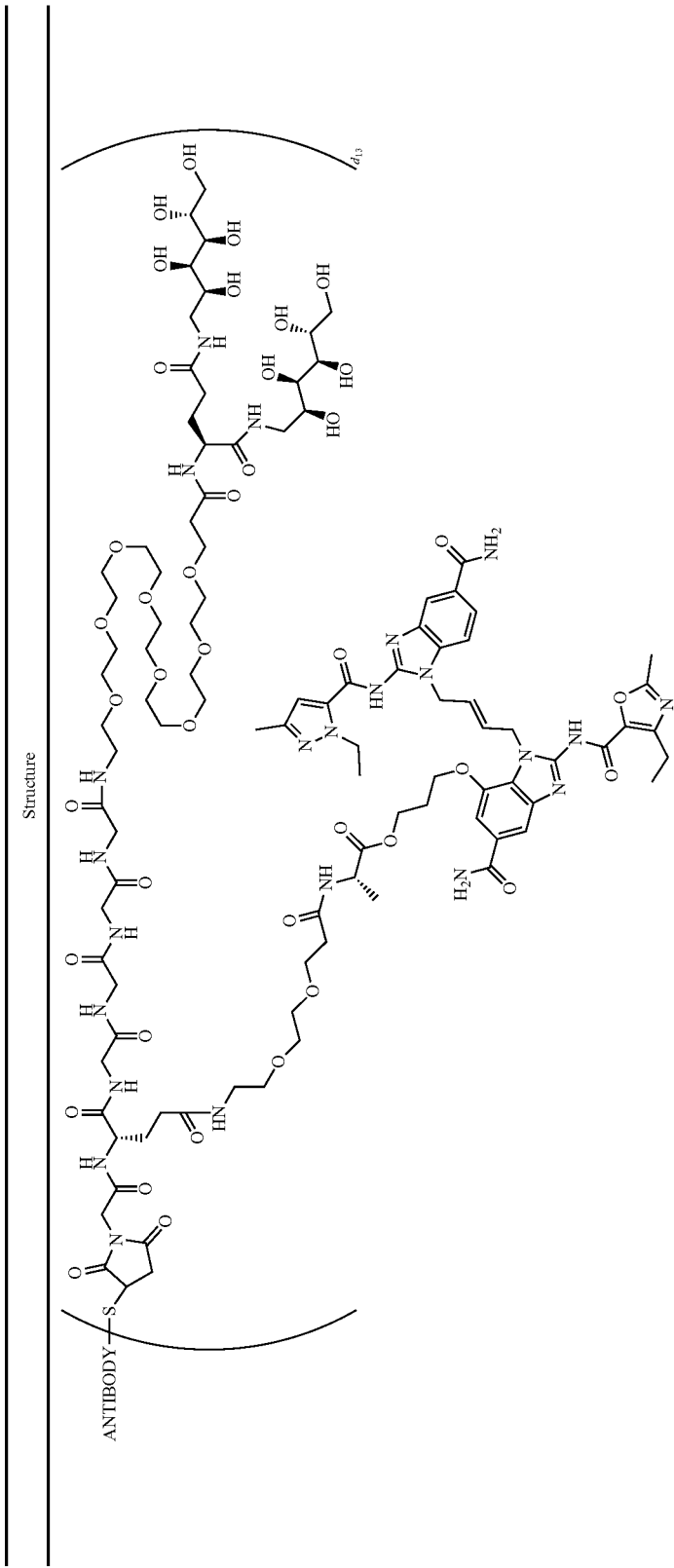

TABLE A2-continued
Structure

TABLE A2-continued
Structure

TABLE A2-continued
Structure
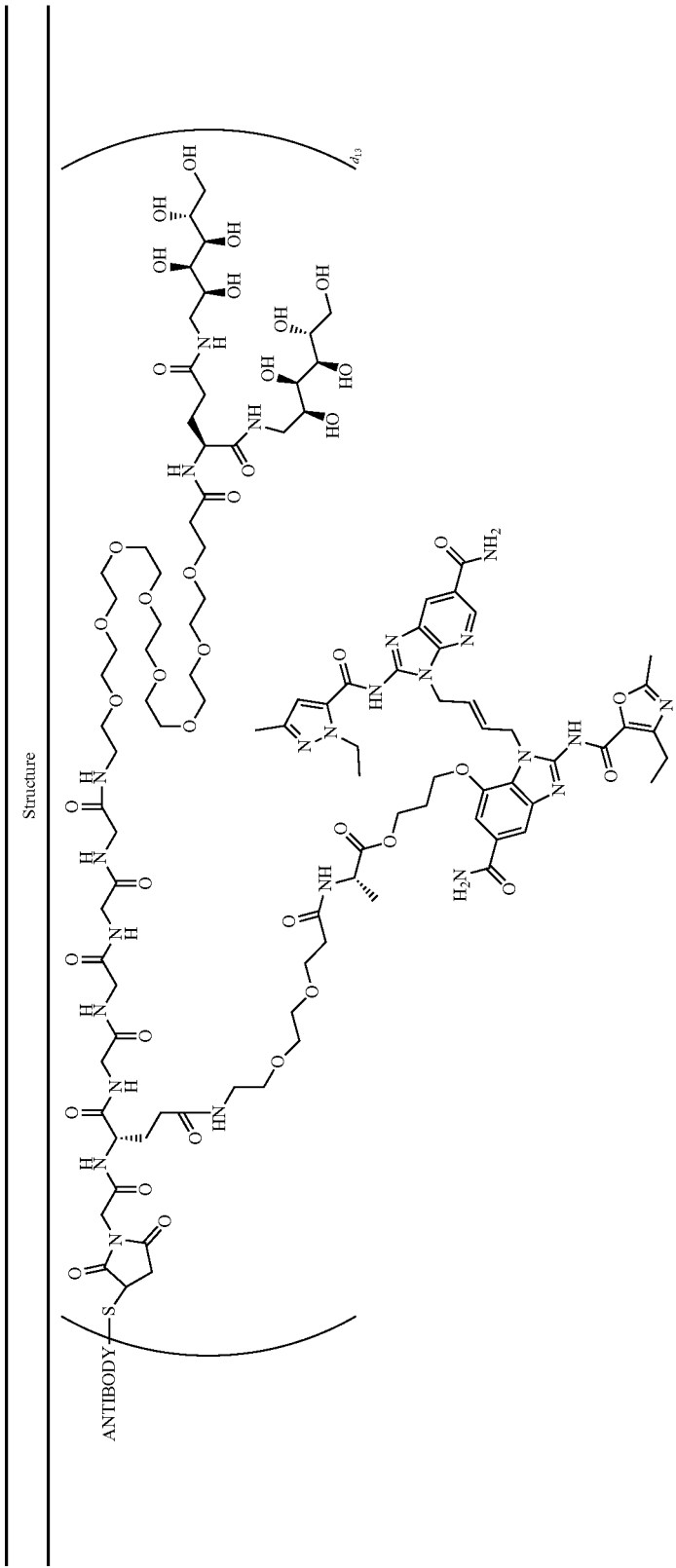

TABLE A2-continued
Structure

TABLE A2-continued
Structure
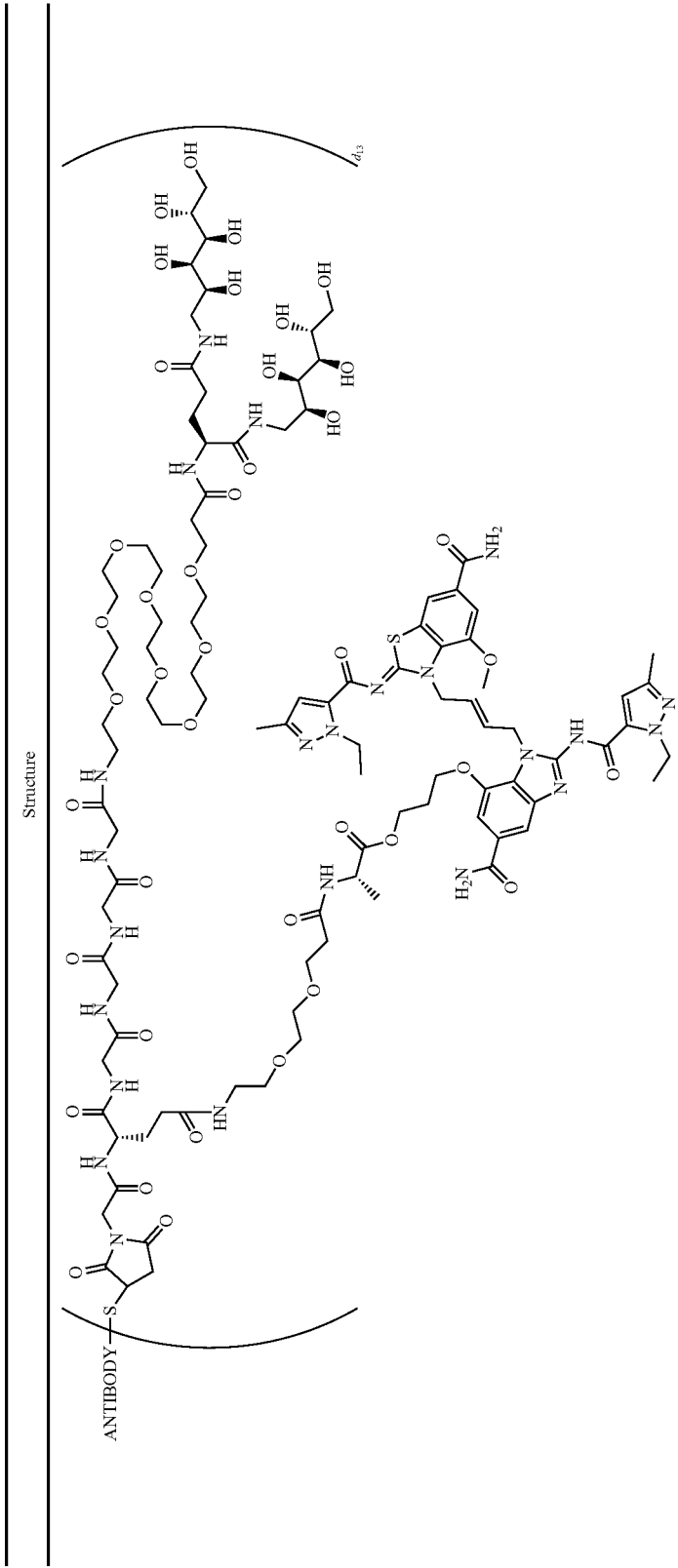

TABLE A2-continued
Structure
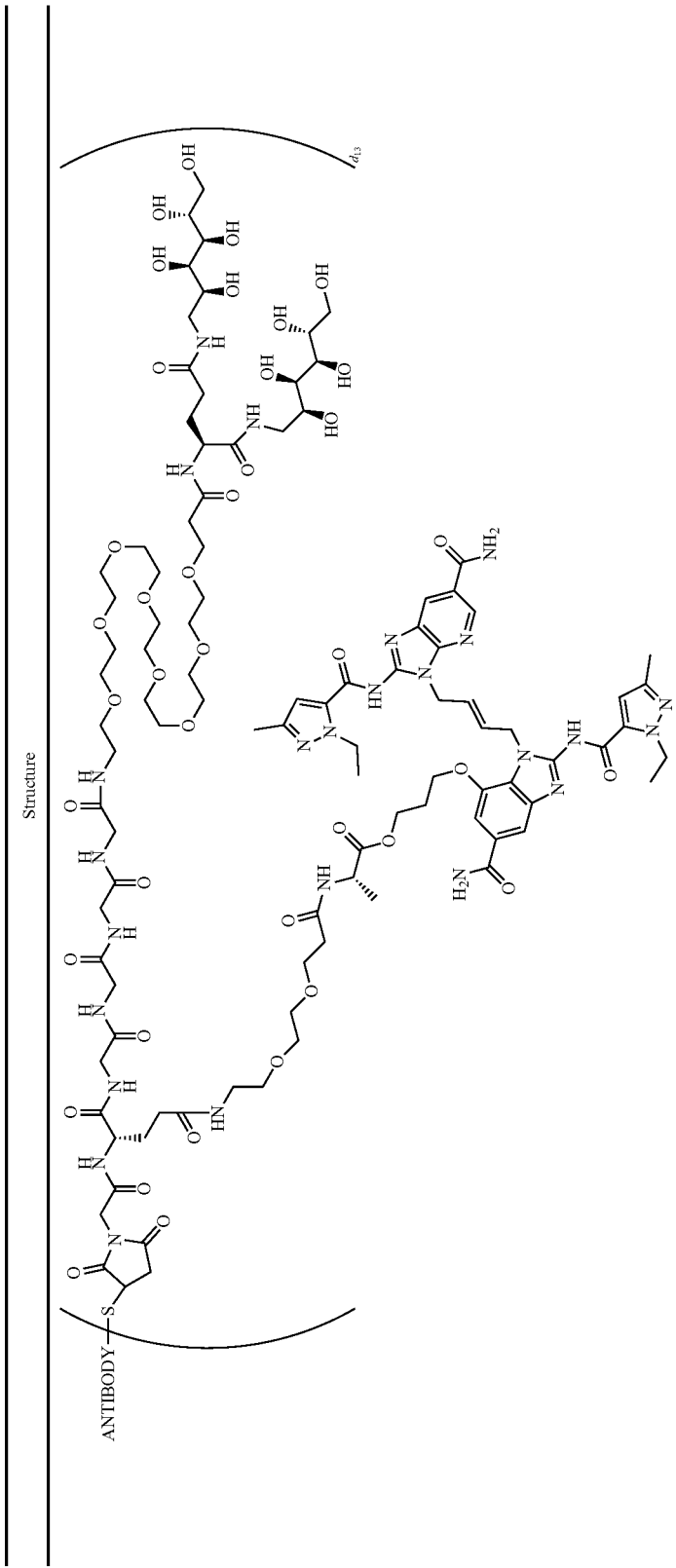

TABLE A2-continued
Structure

TABLE A2-continued
Structure
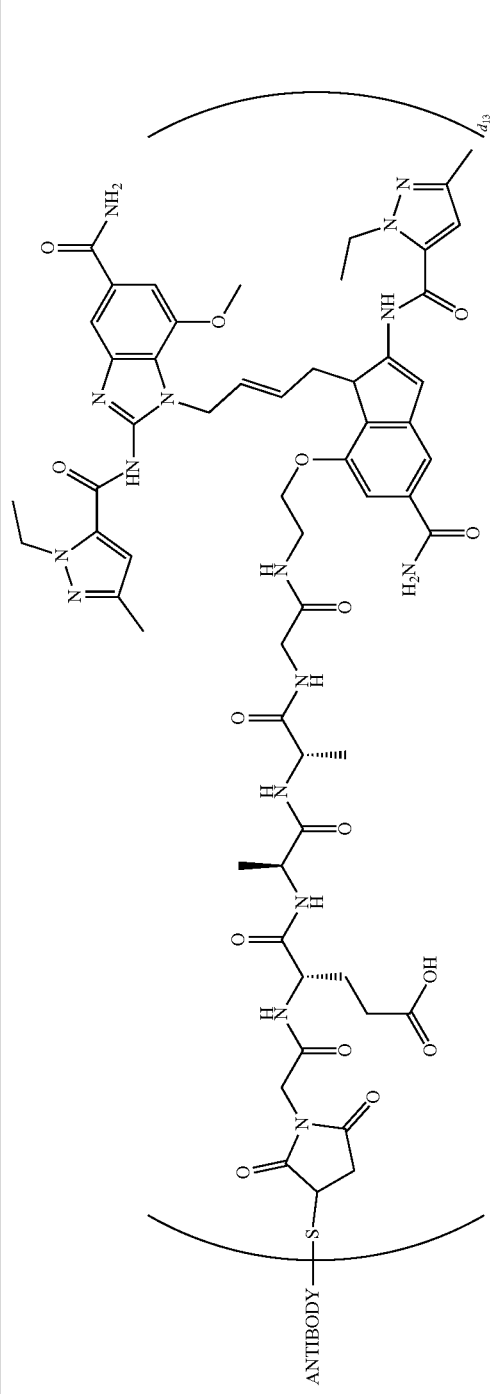
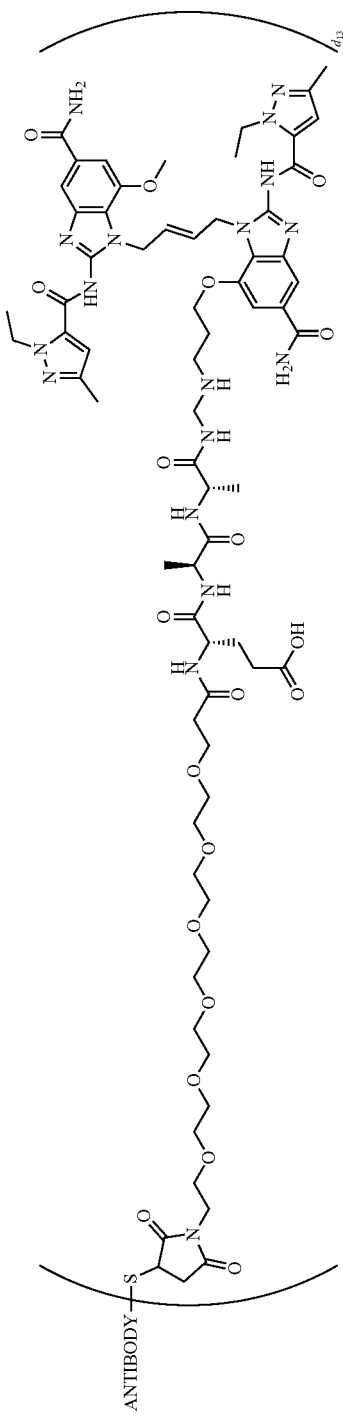

TABLE A2-continued
Structure
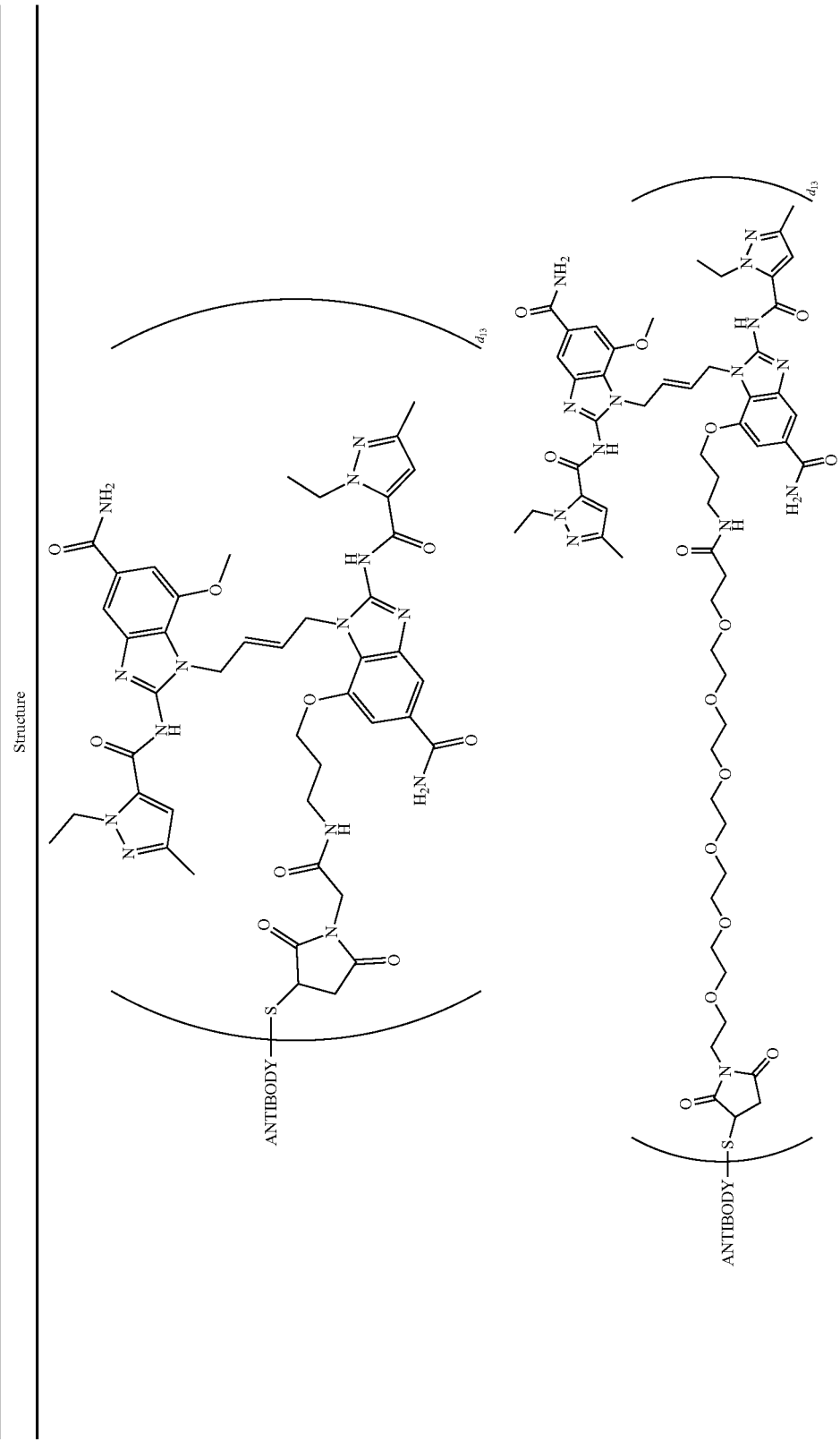

TABLE A2-continued
Structure
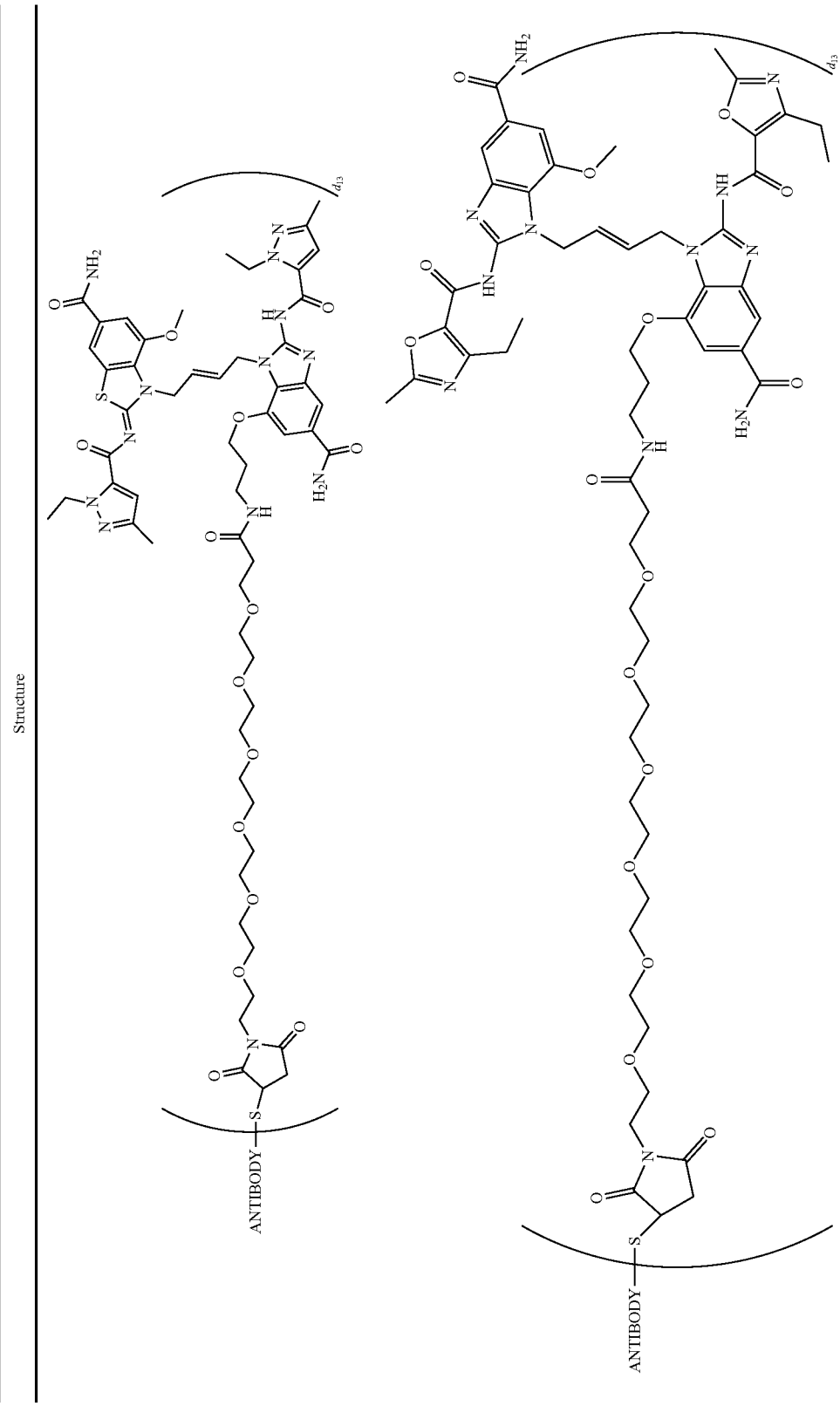

TABLE A2-continued
Structure
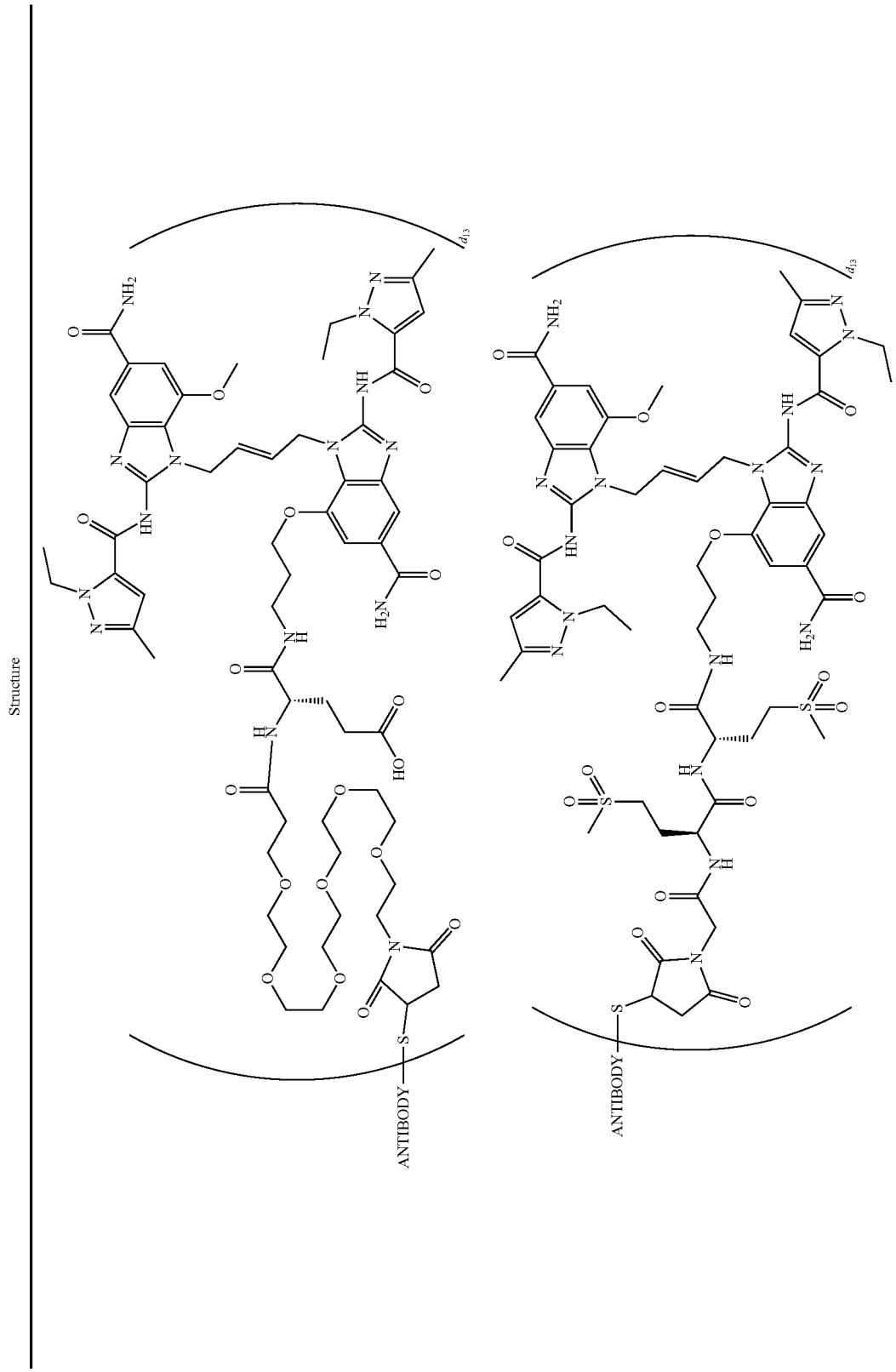

TABLE A2-continued
Structure
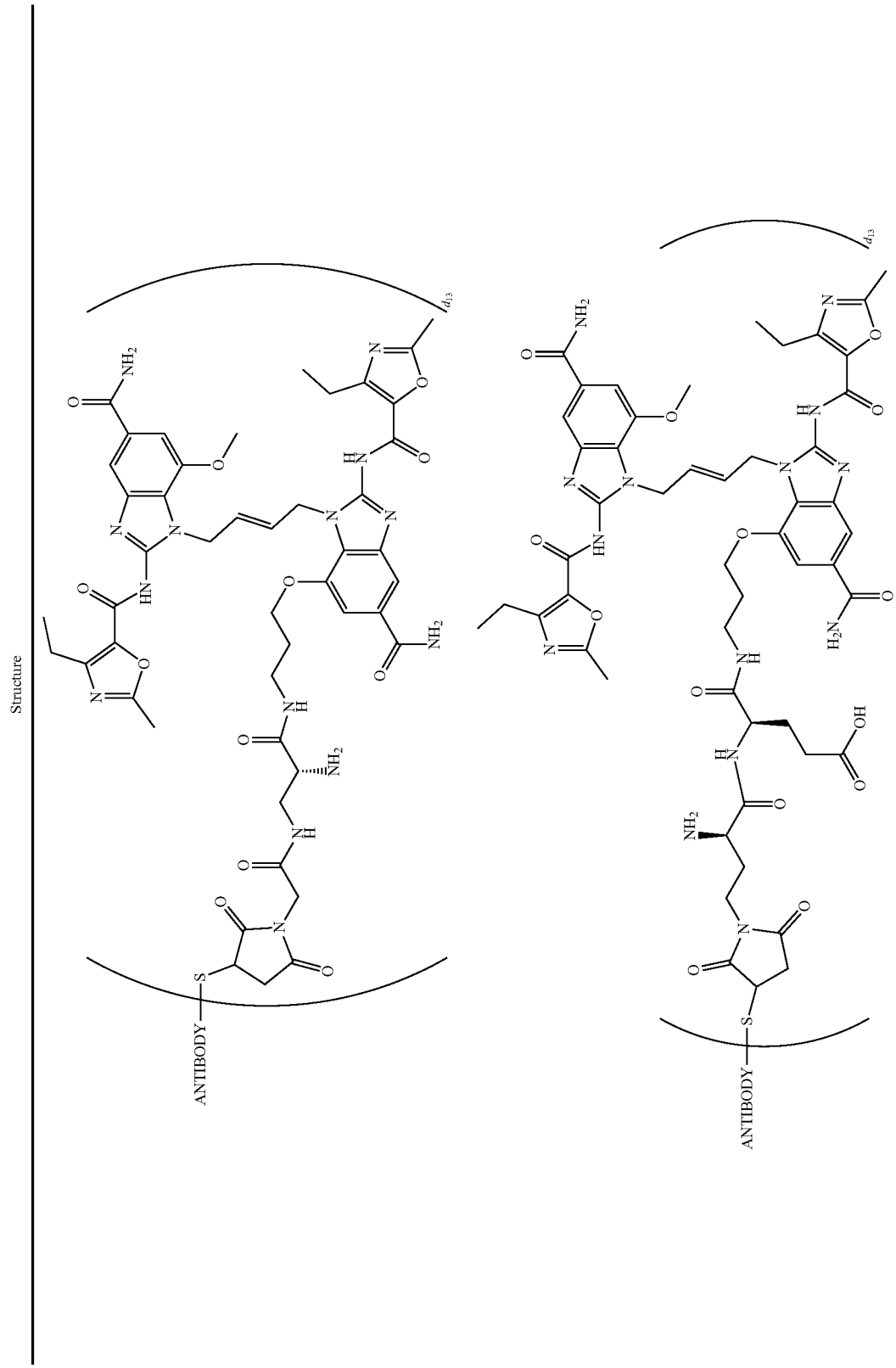

TABLE A2-continued
Structure
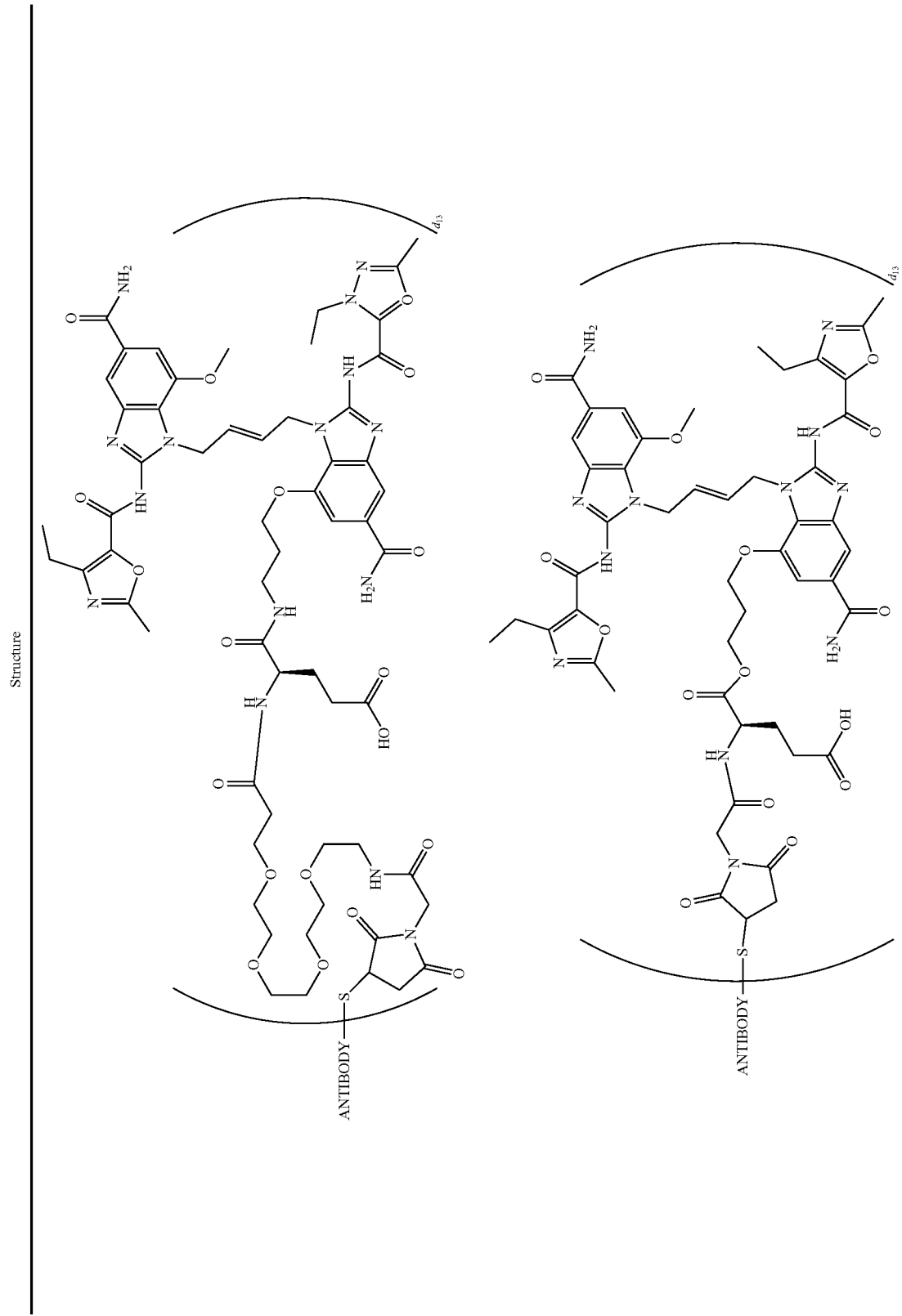

TABLE A2-continued
Structure
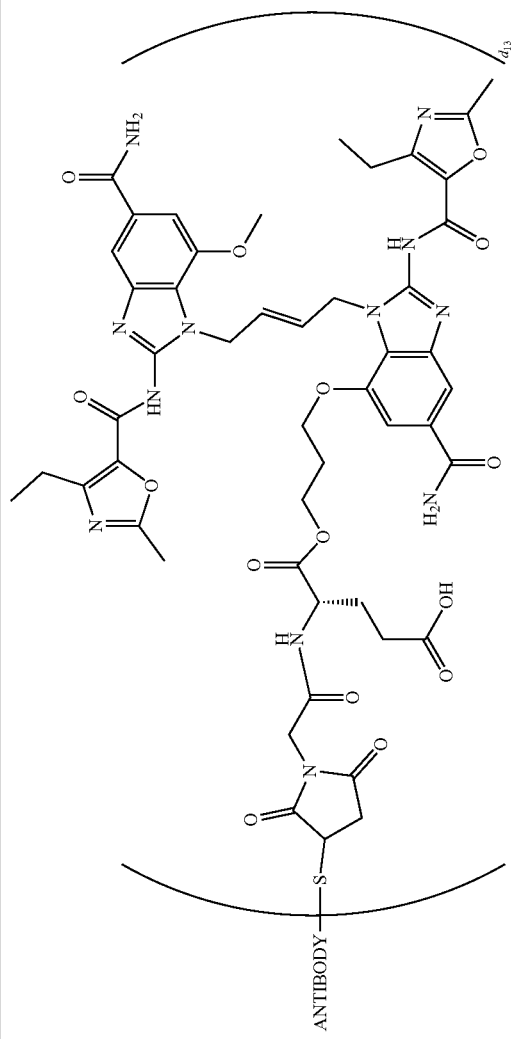
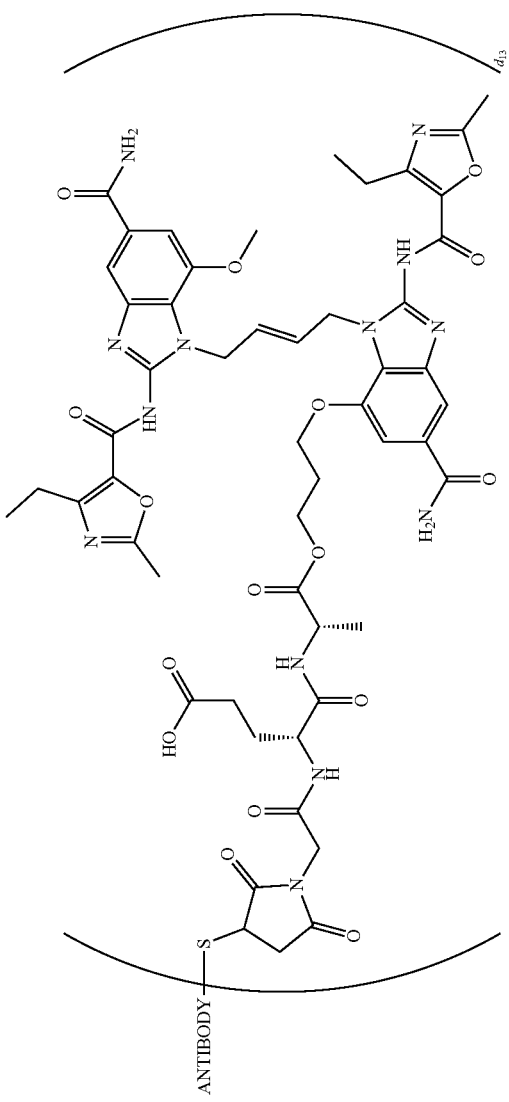

TABLE A2-continued
Structure
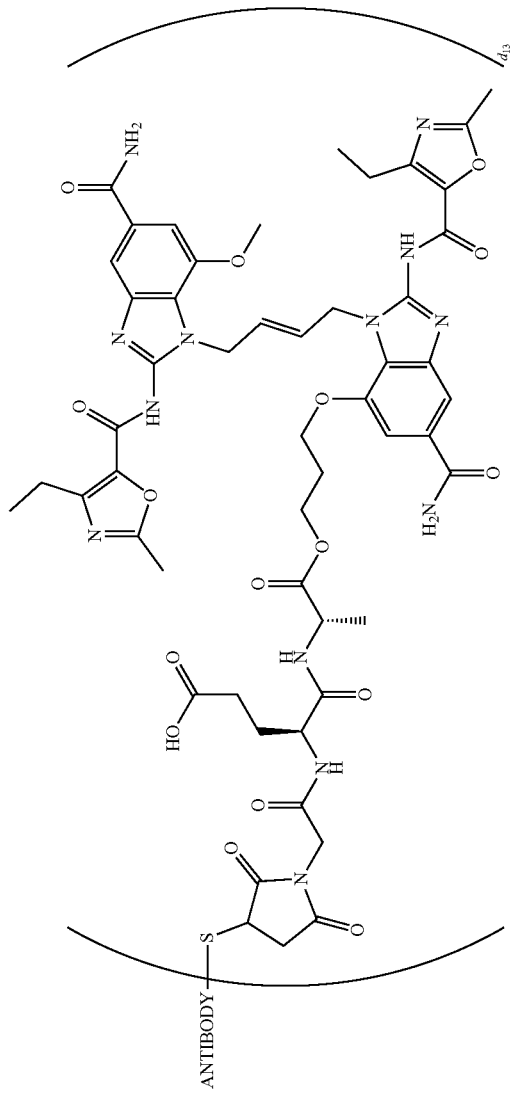

TABLE A2-continued
Structure
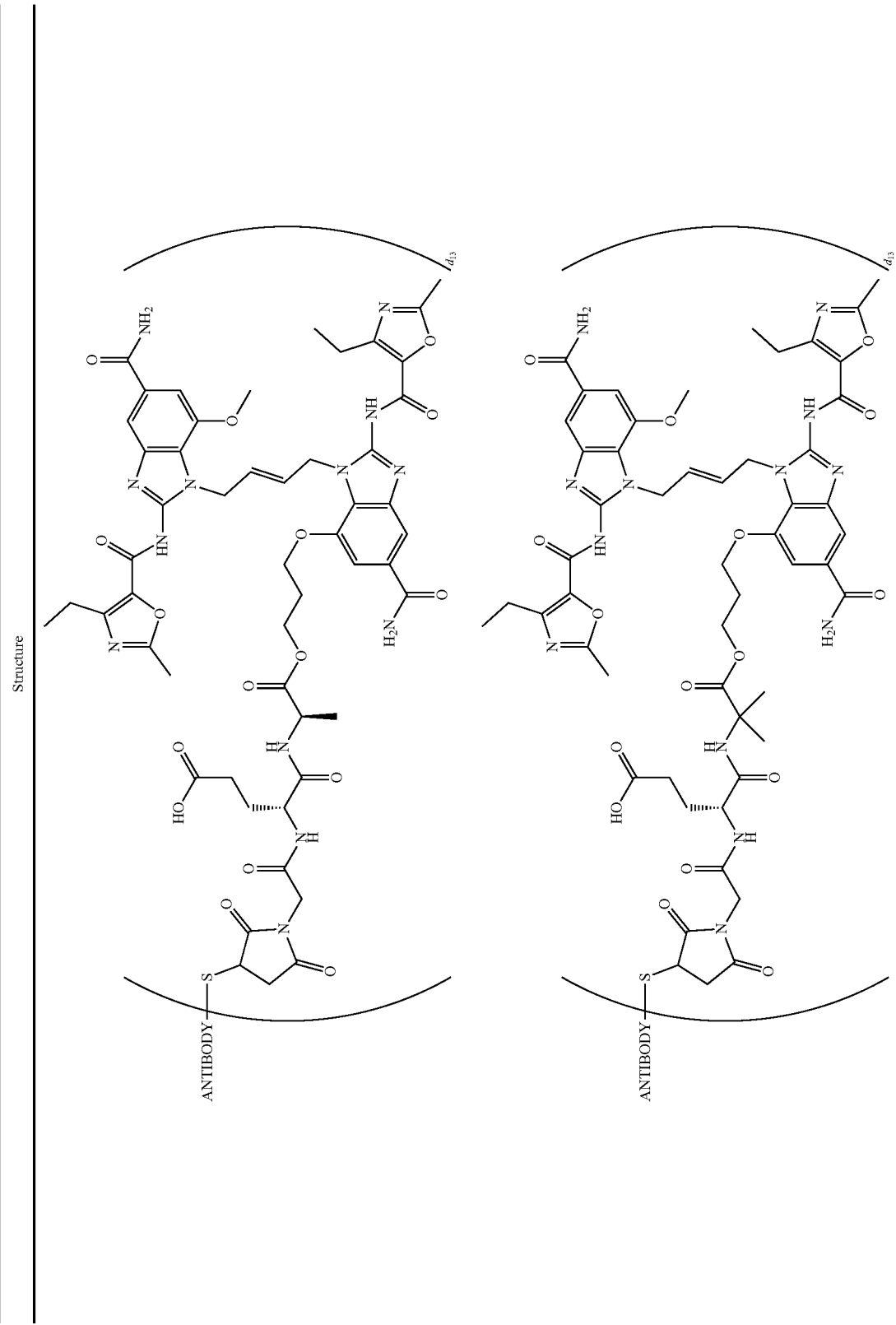

TABLE A2-continued
Structure
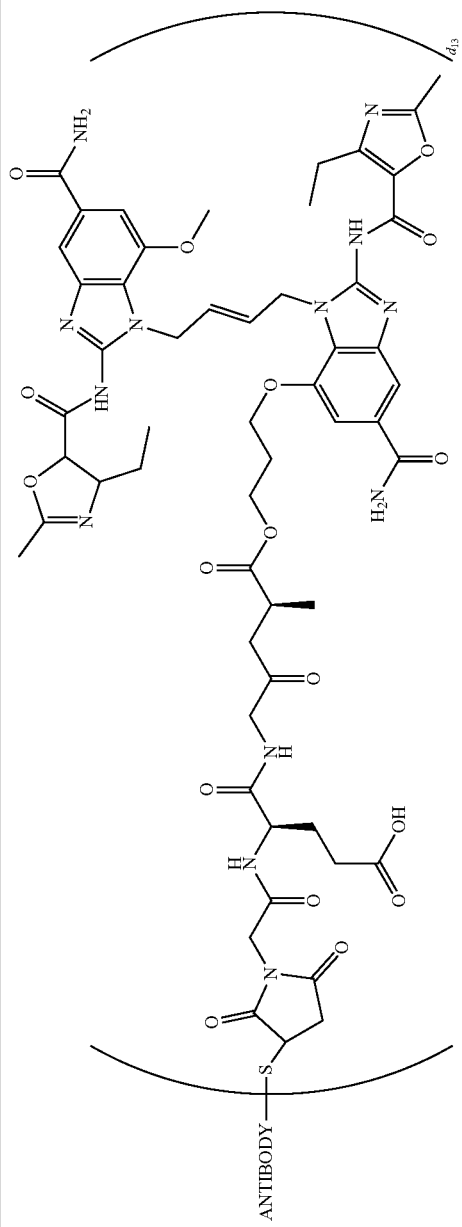
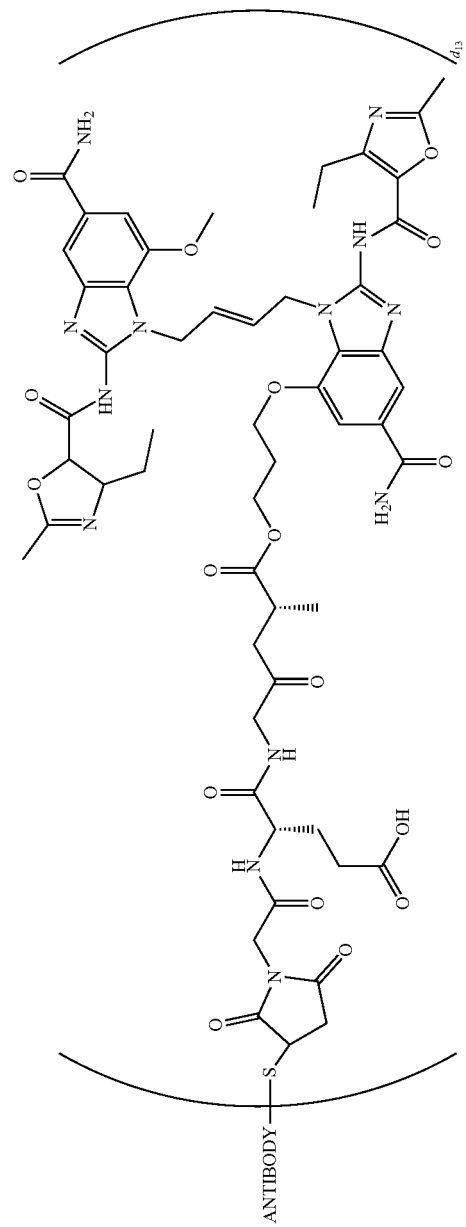

TABLE A2-continued
Structure
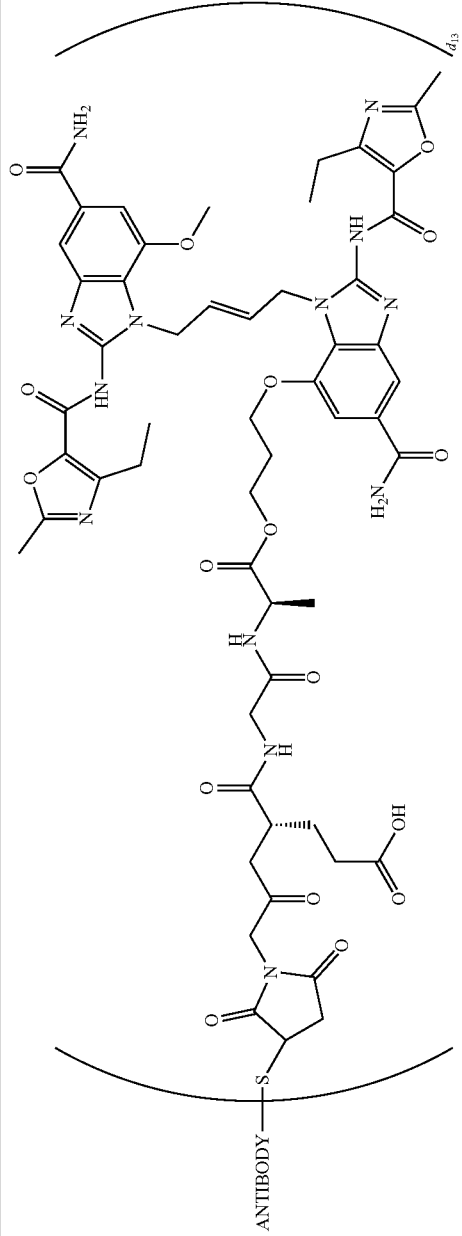
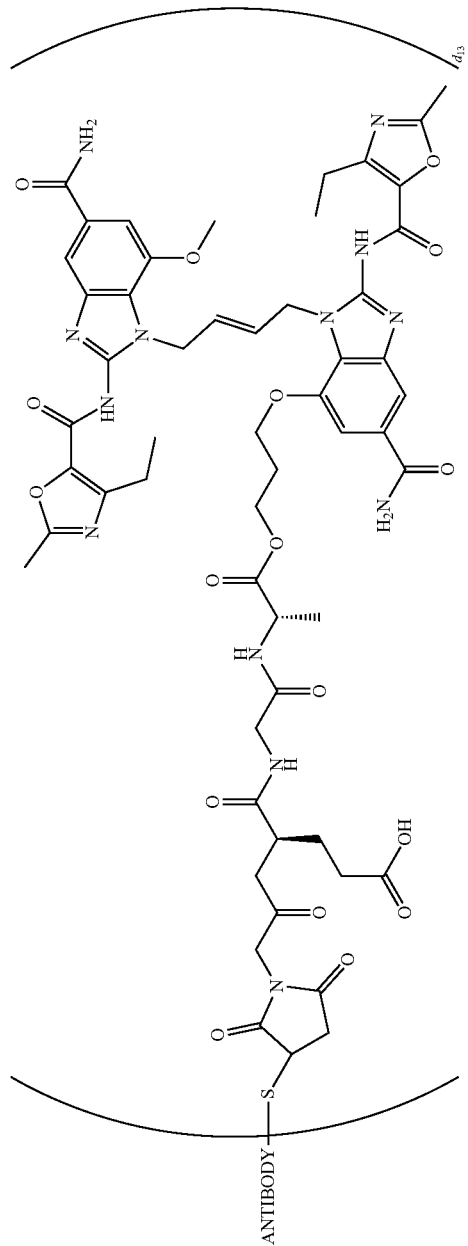

TABLE A2-continued
Structure
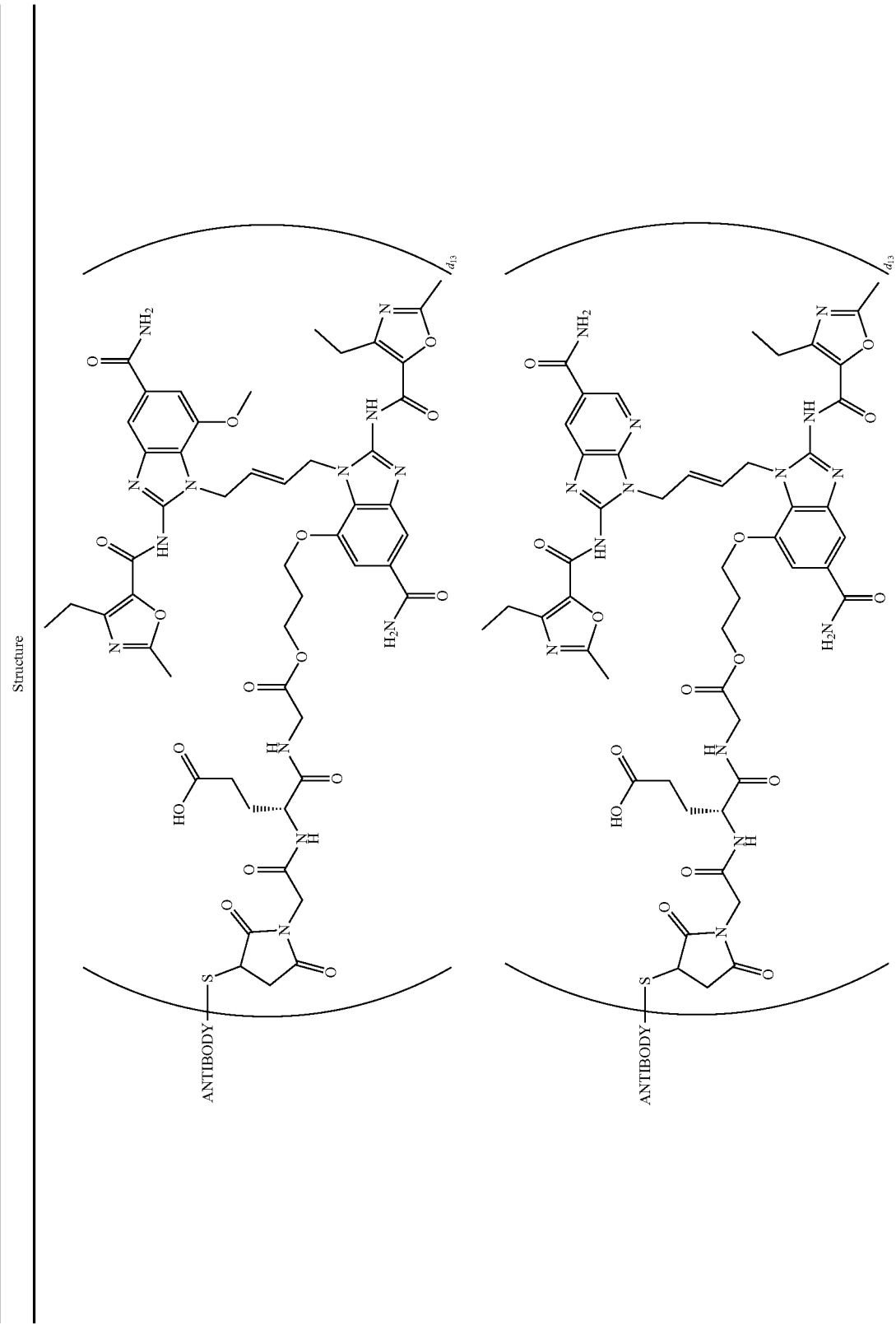

TABLE A2-continued
Structure
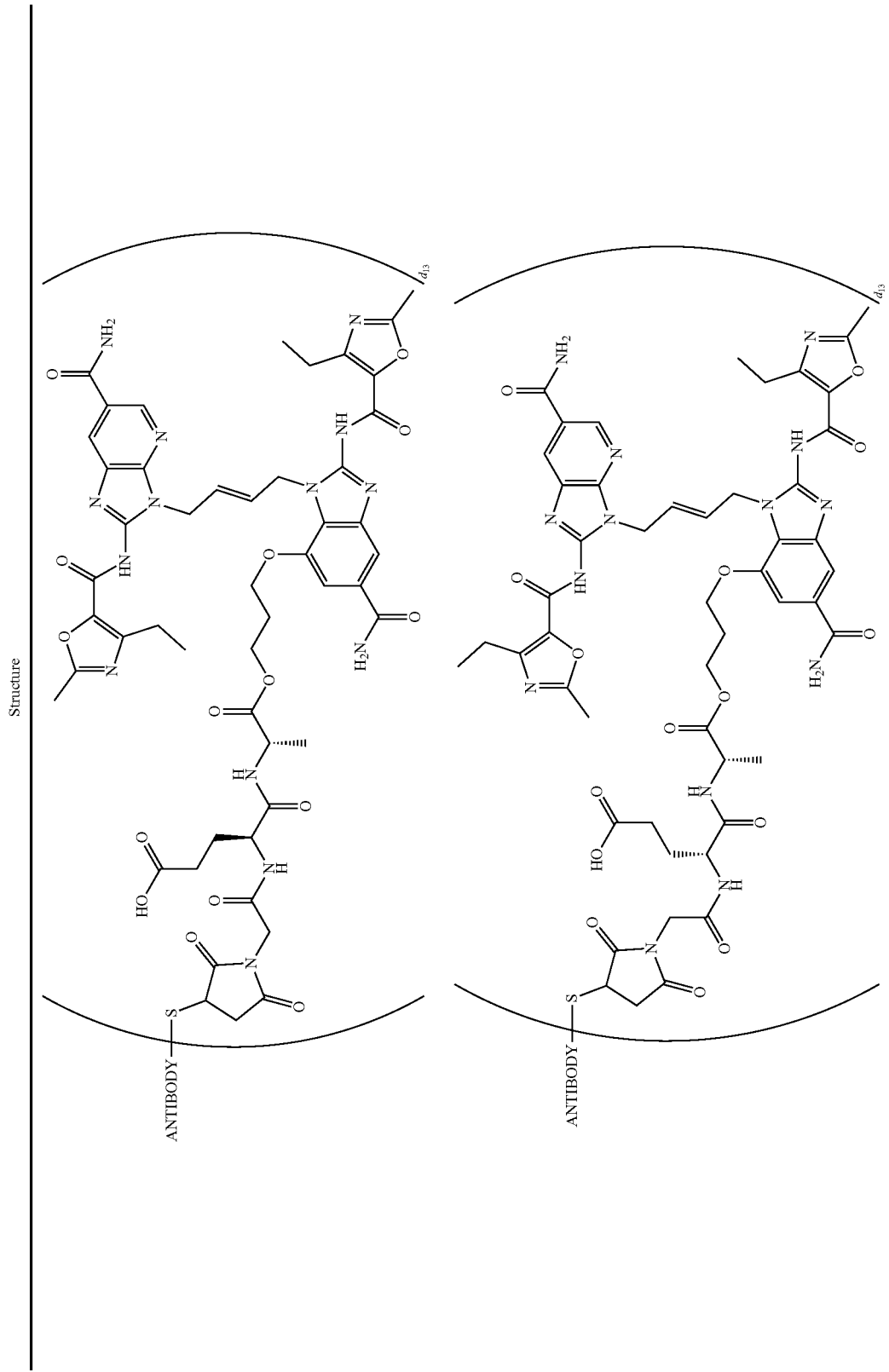

TABLE A2-continued
Structure
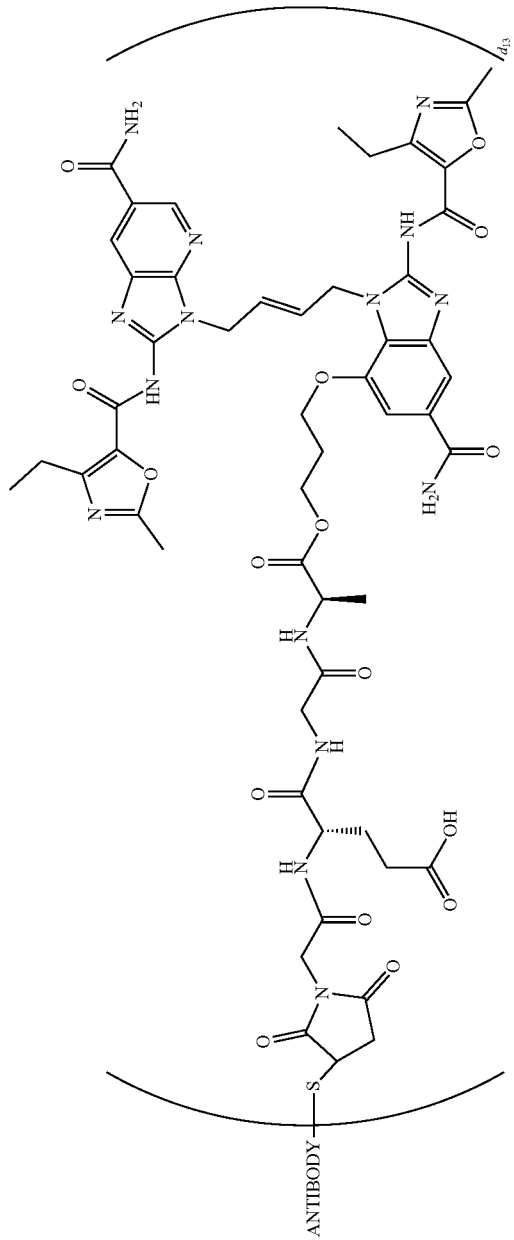
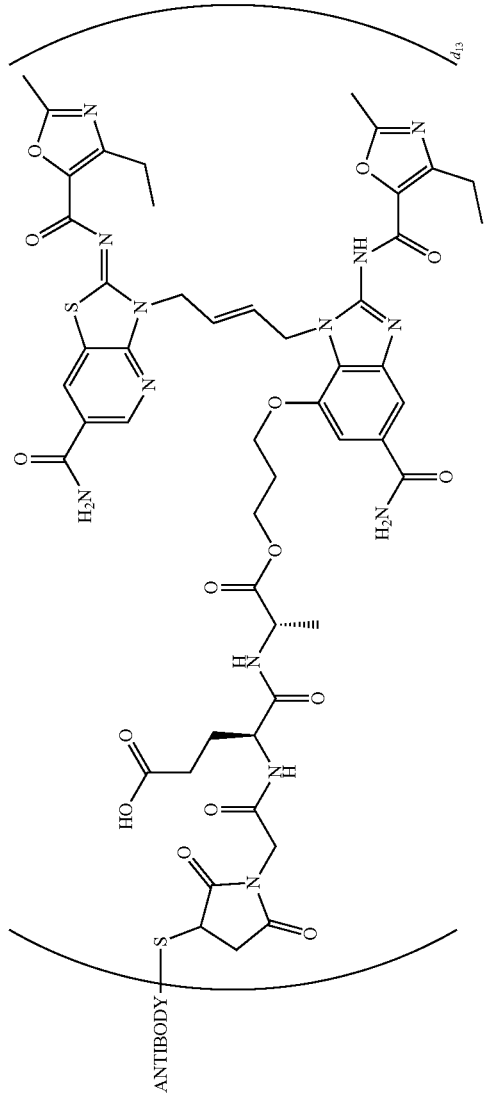

TABLE A2-continued
Structure
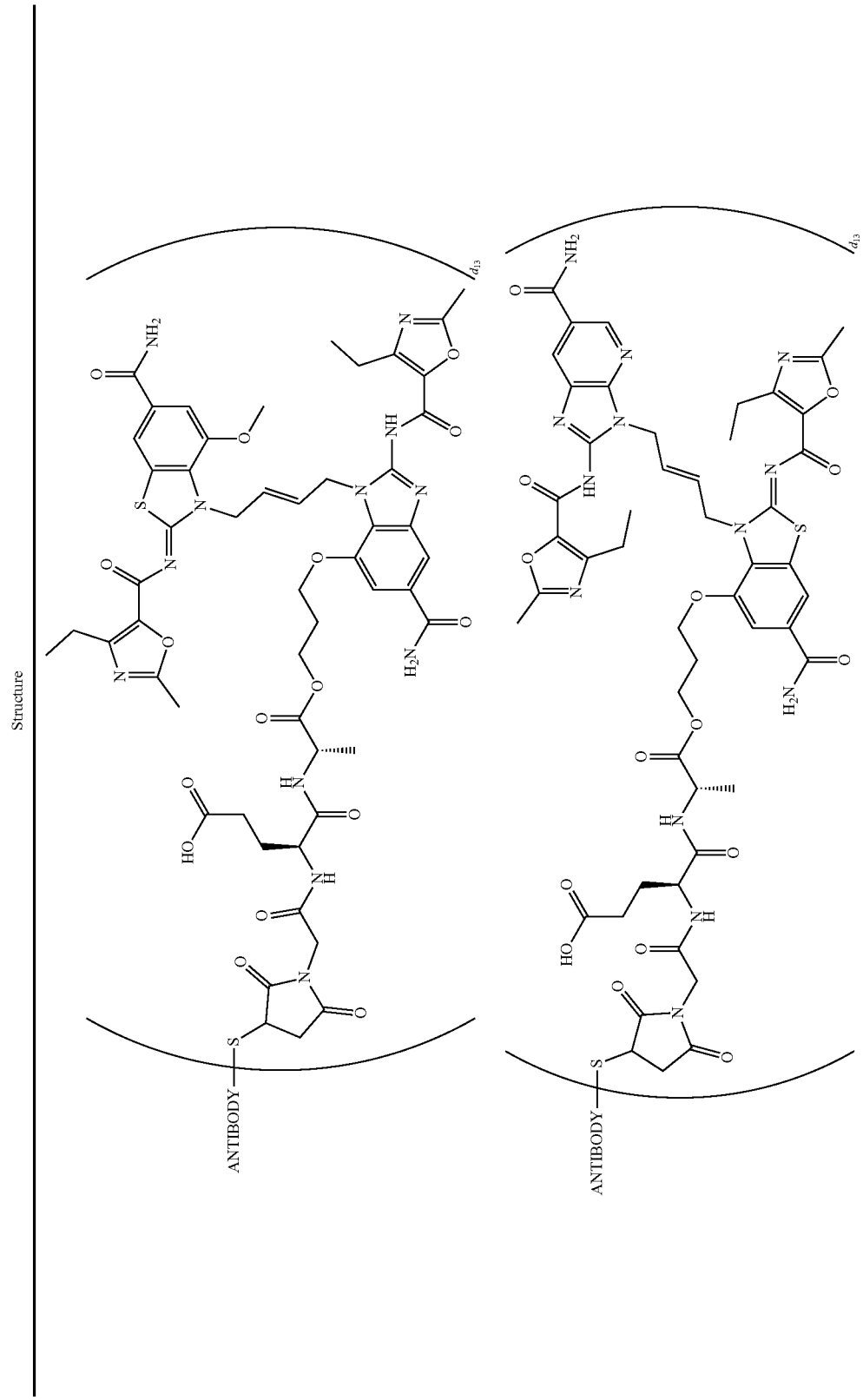

TABLE A2-continued
Structure
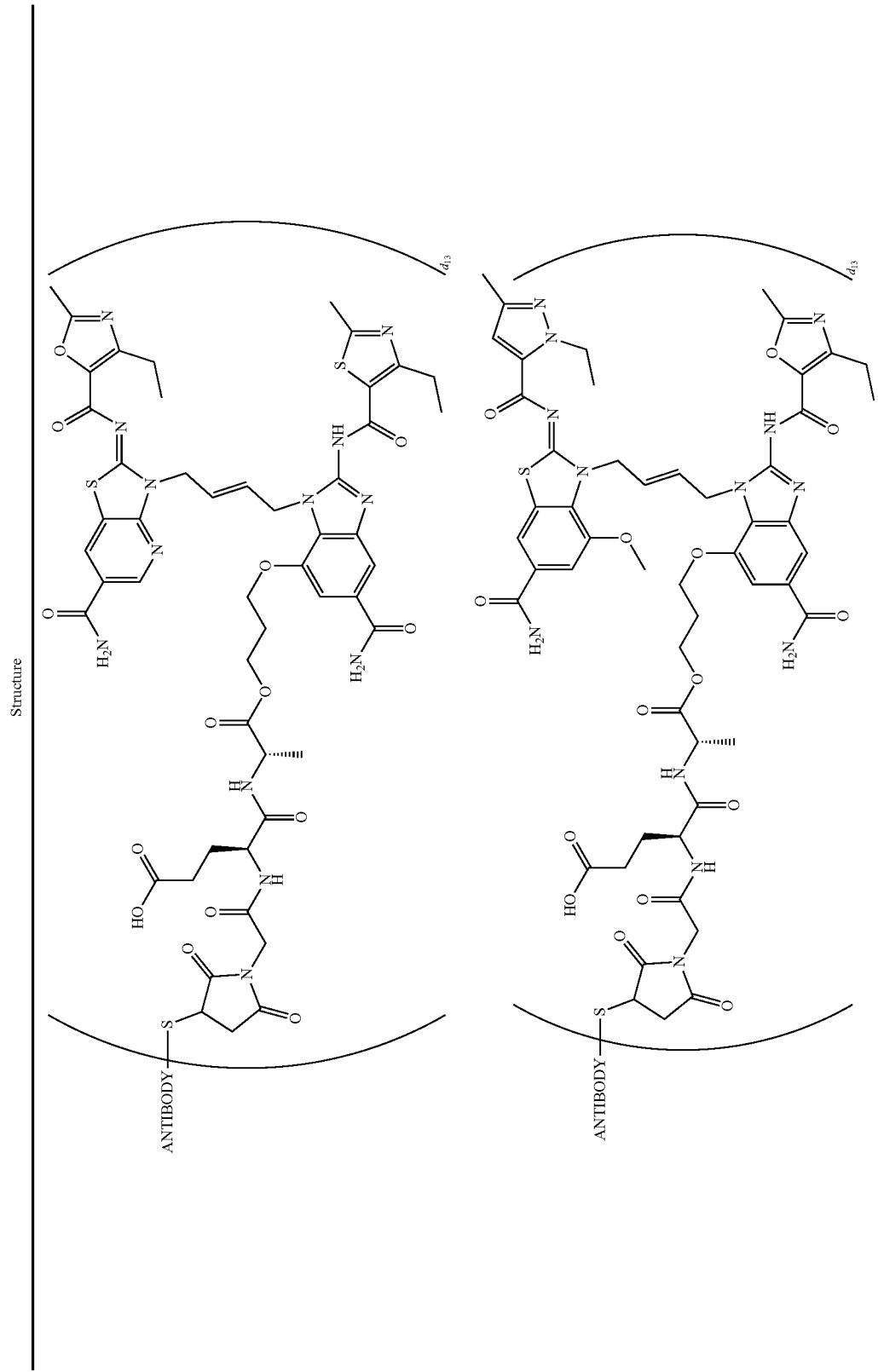

TABLE A2-continued
Structure
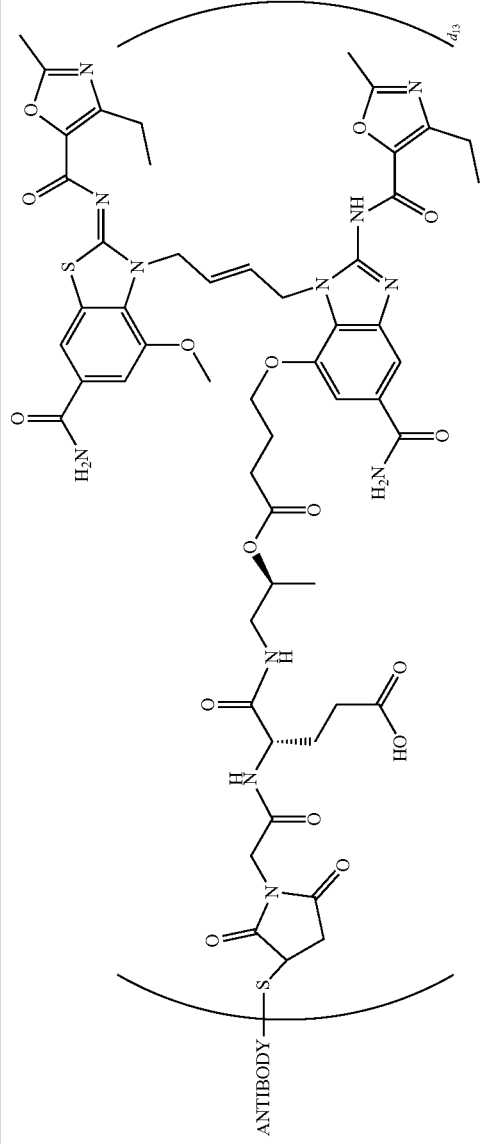
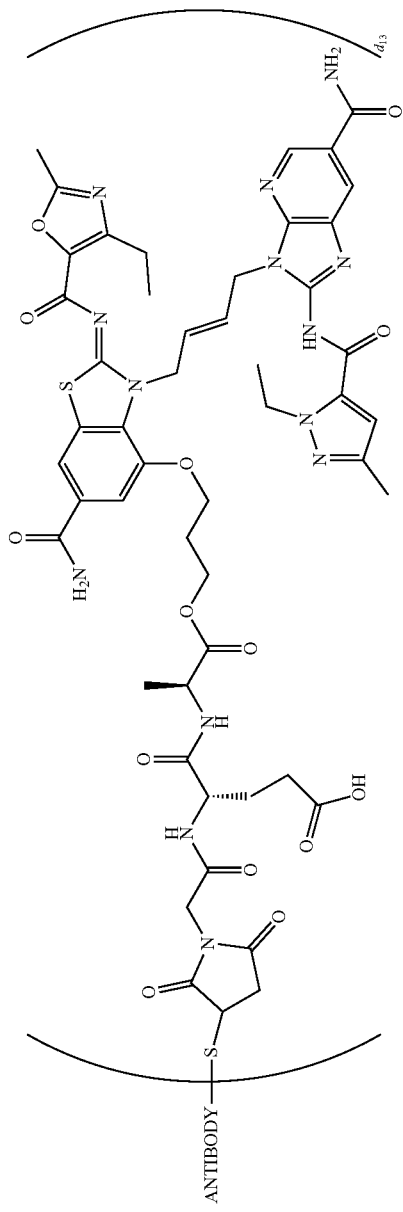

wherein $d_{13}$ is as defined herein and ANTIBODY is a B7-H4 antibody or a cysteine engineered B7-H4 antibody.

In some embodiments, for the conjugates in Table A2, $d_{13}$ is an integer from 6 to 8.

In some embodiments, for the conjugates in Table A2, $d_{13}$ is 8. In some embodiments, for the conjugates in Table A2, $d_{13}$ is 7. In some embodiments, for the conjugates in Table A2, $d_{13}$ is 6.

In some embodiments, for the conjugates in Table A2, $d_{13}$ is 8.

In some embodiments, the STING agonist drug conjugate is:

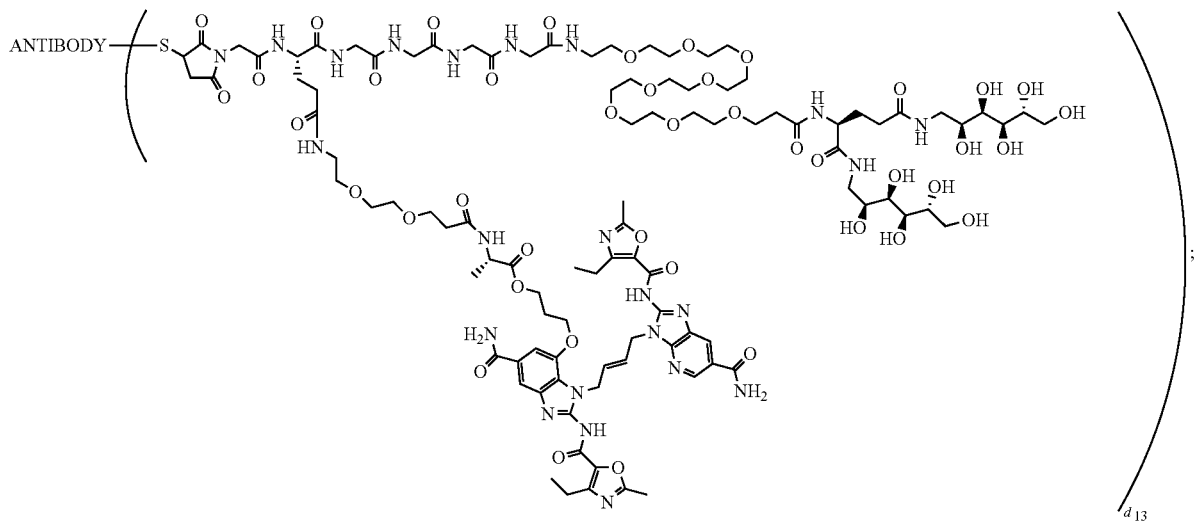

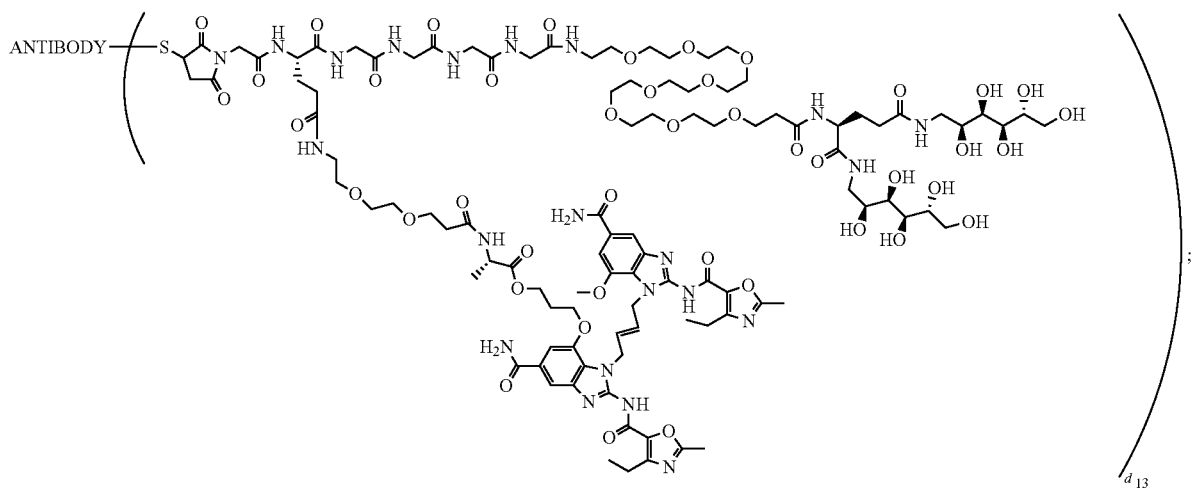

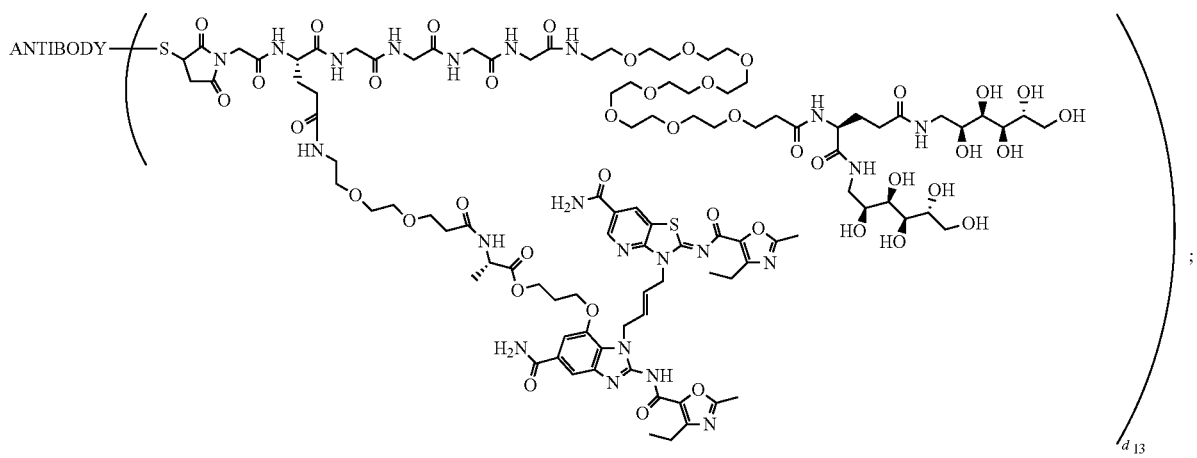

-continued

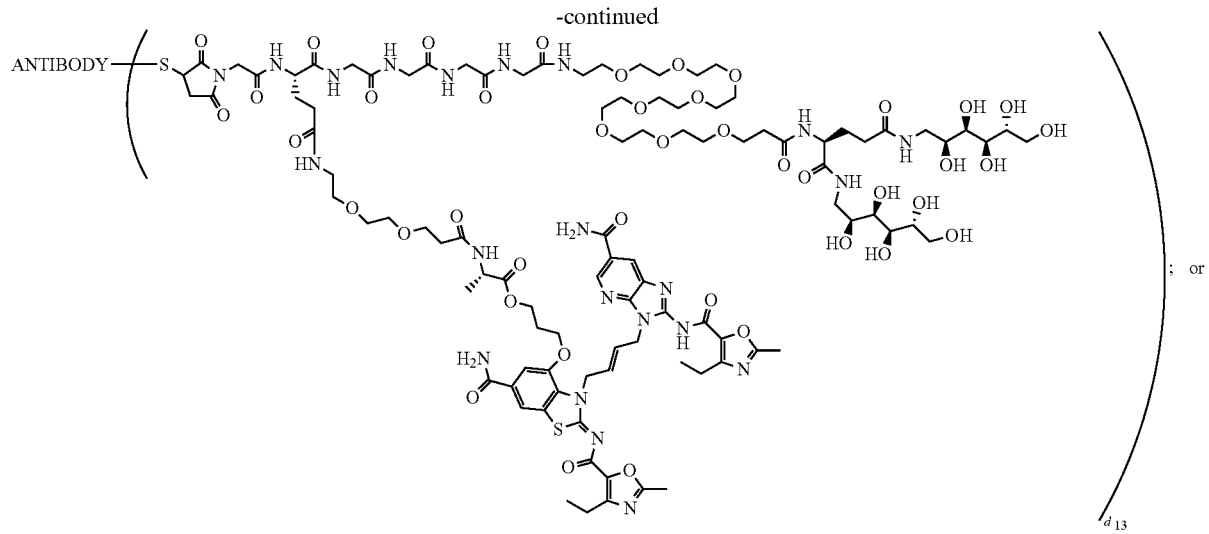

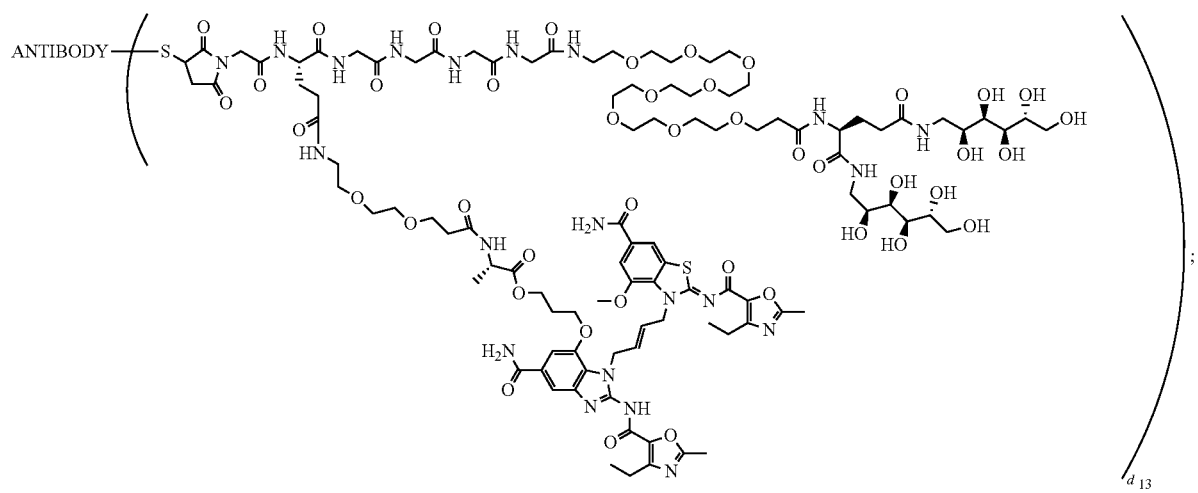

wherein $d_{13}$, is 8 and ANTIBODY is a B7-H4 antibody or a cysteine engineered 7-H4 antibody, wherein the B7-H4 antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ TD NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55).

In some embodiments, the STING agonist drug conjugate is:

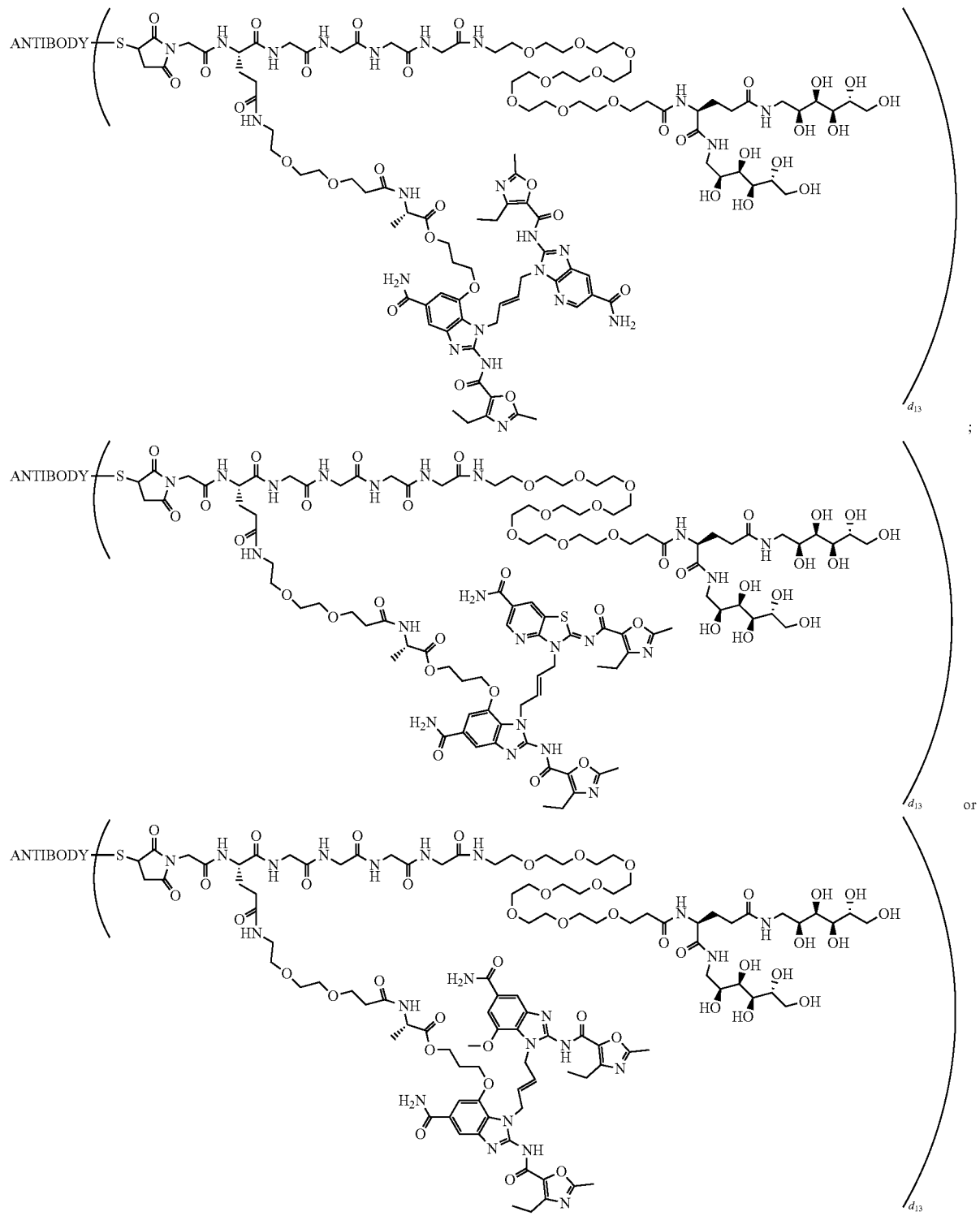

wherein $d_{13}$ is 8 and ANTIBODY is a B7-H4 antibody or a cysteine engineered B7-H4 antibody, wherein the B7-H4 antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1

(CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55).

In some embodiments, the STING agonist drug conjugate is:

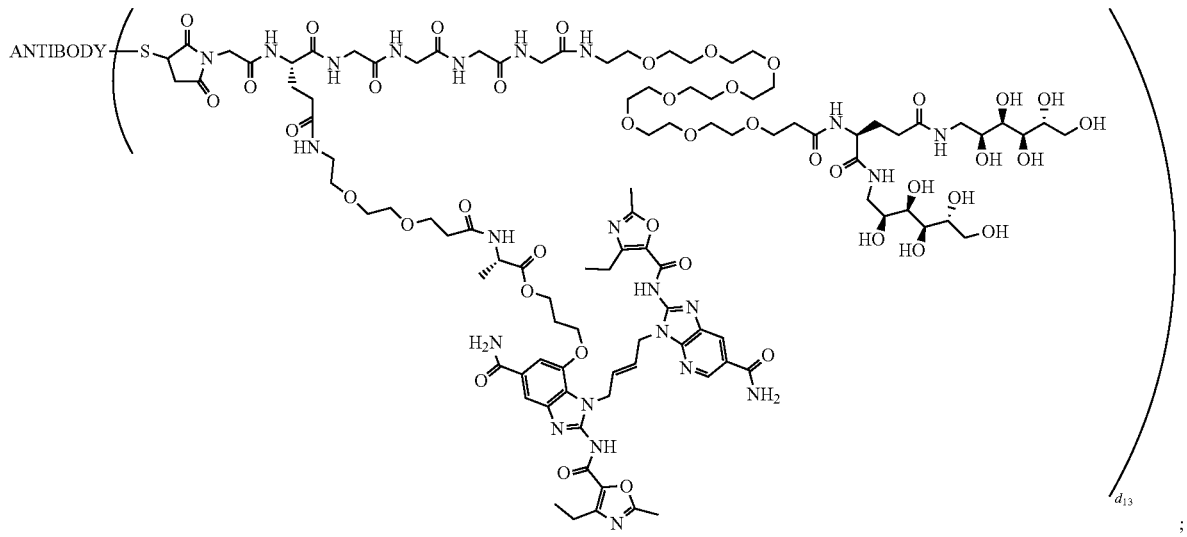

wherein $d_{13}$, is 8 and ANTIBODY is a B7-H4 antibody or $d_{13}$, is 2 and ANTIBODY is a cysteine engineered B7-H4 antibody, wherein the B7-H4 antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55)

In some embodiments, the B7-H4 antibody or the cysteine engineered B7-H4 conjugated to a cytotoxic drug moiety is selected from the conjugates described in Table BL.

TABLE B1

Structure

TABLE B1-continued
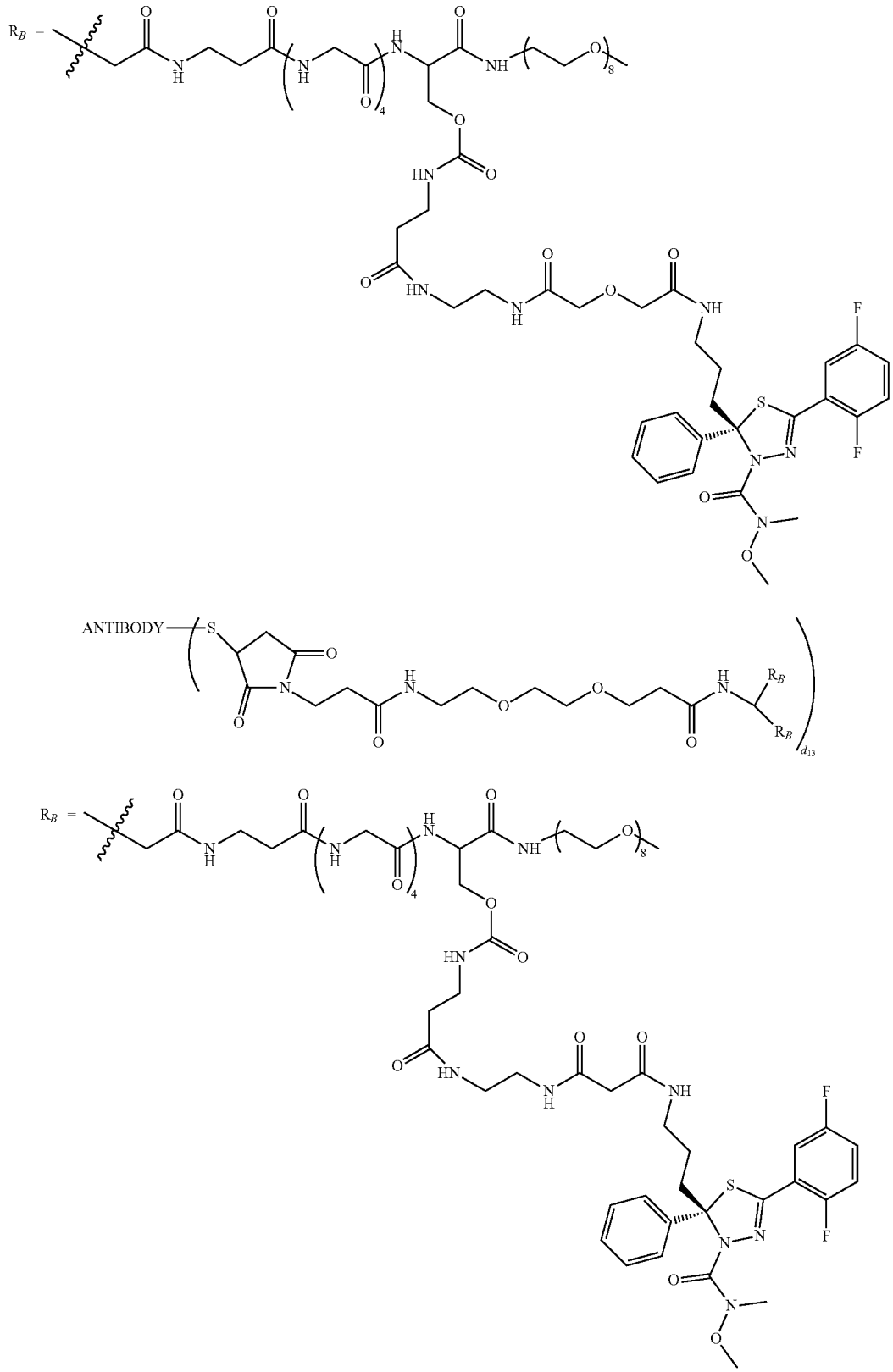

TABLE B1-continued
Structure
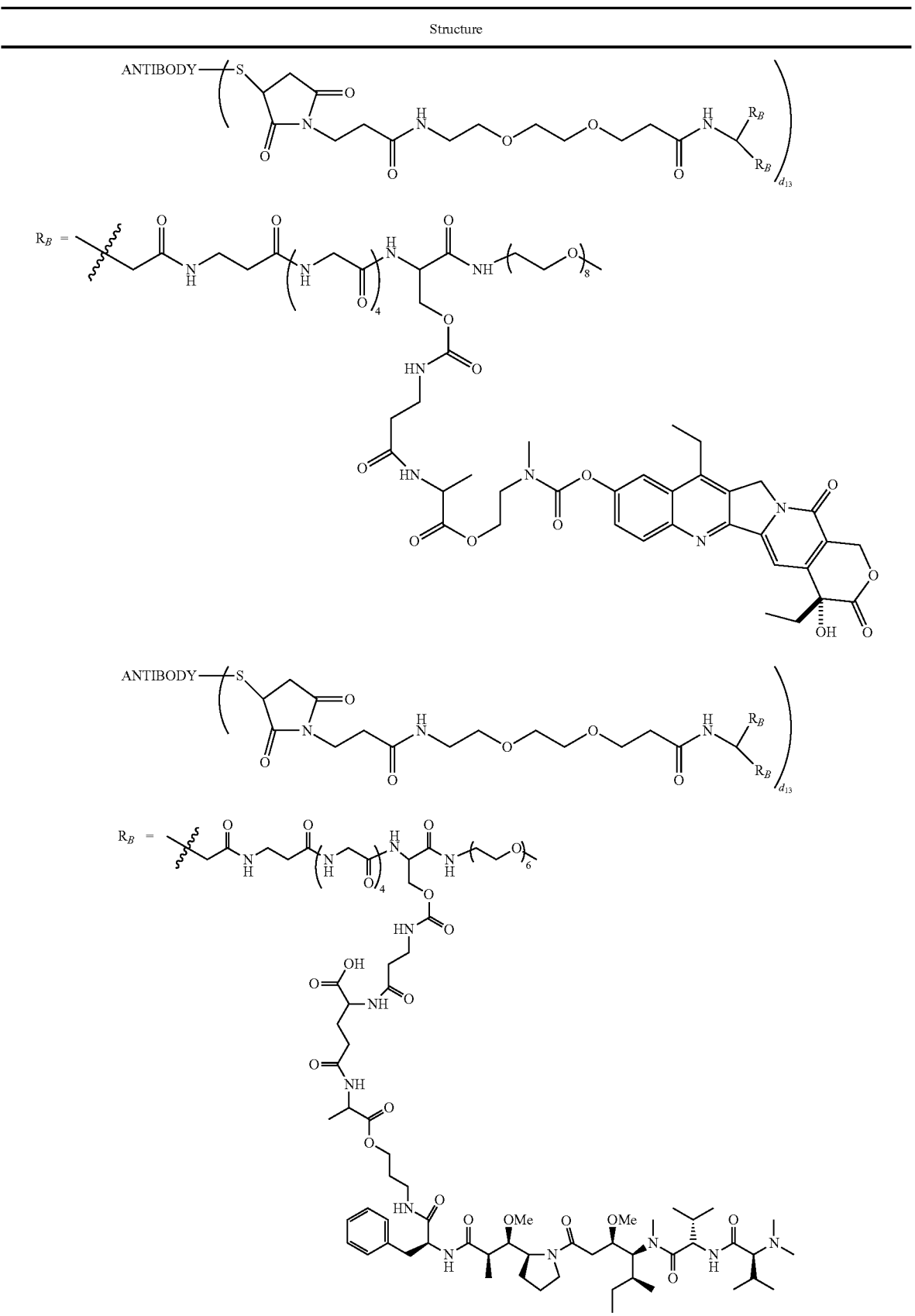

TABLE B1-continued
Structure
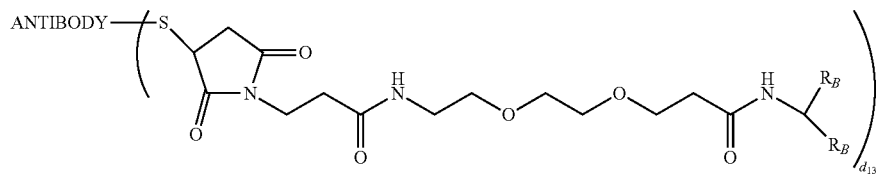
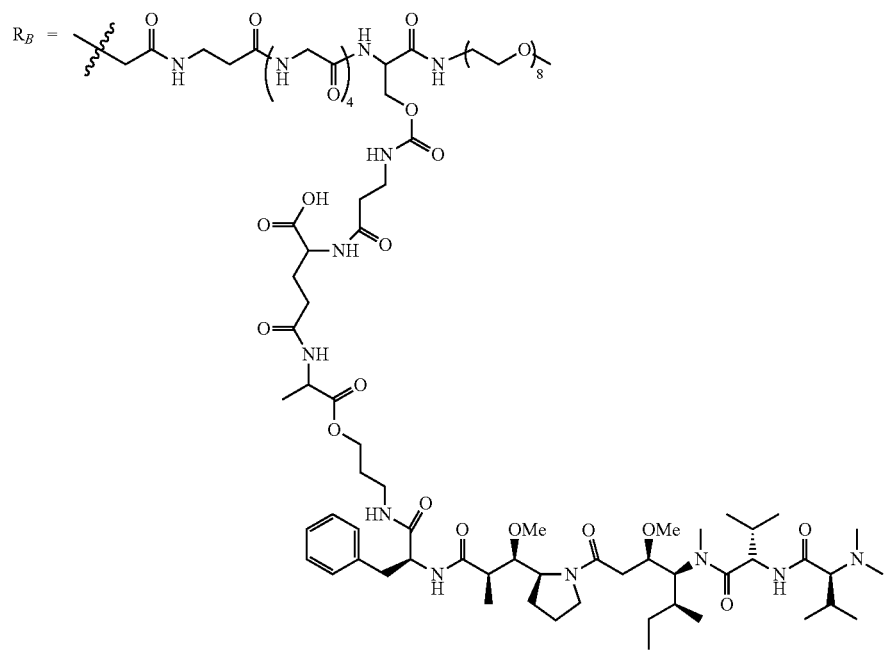
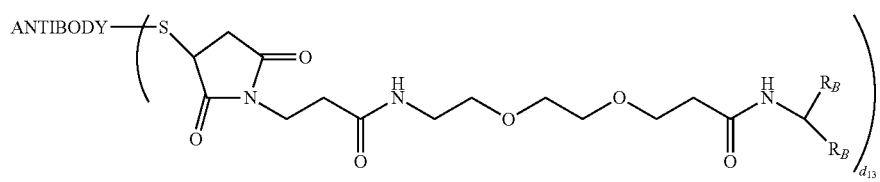

TABLE B1-continued
Structure
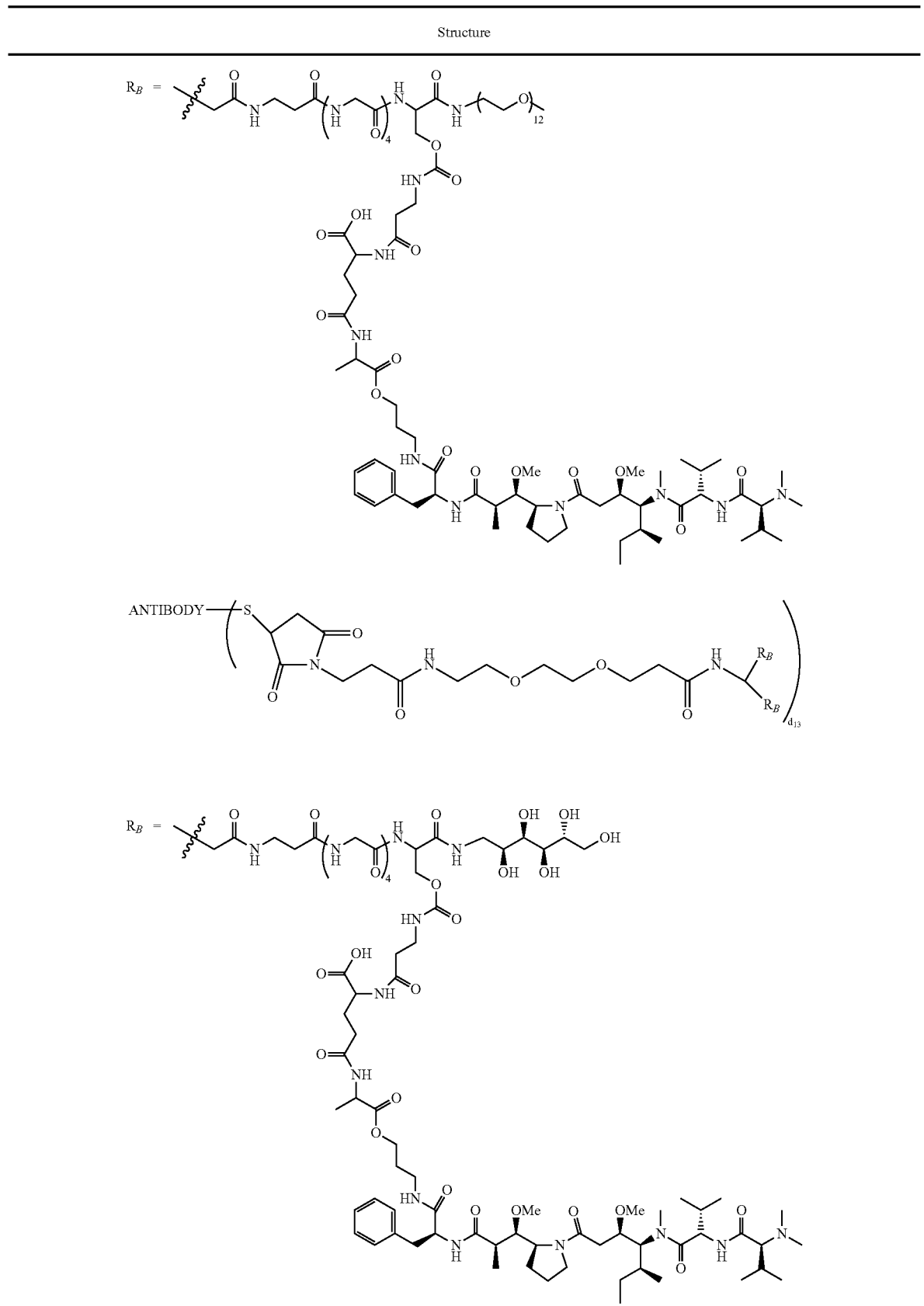

TABLE B1-continued
Structure
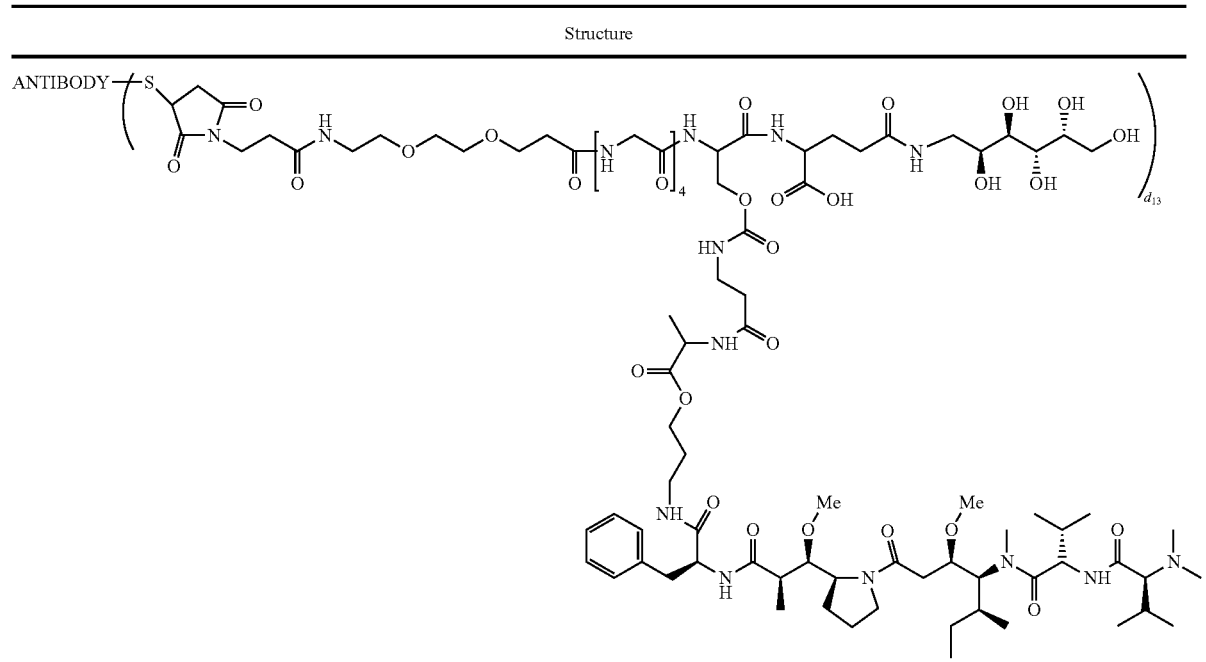
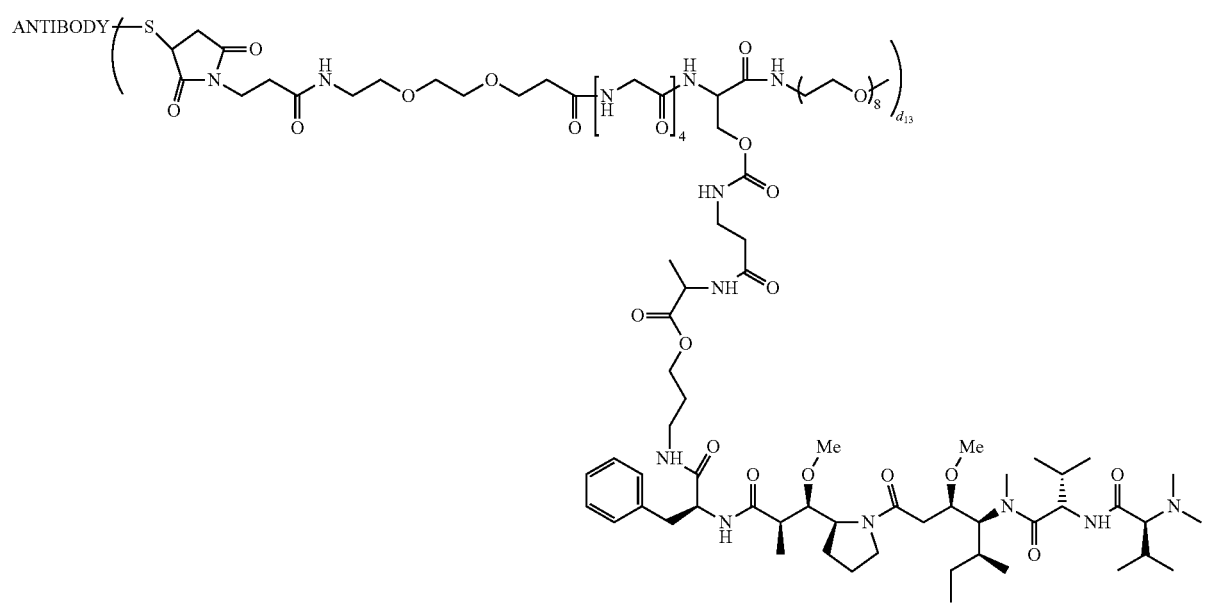

TABLE B1-continued
Structure
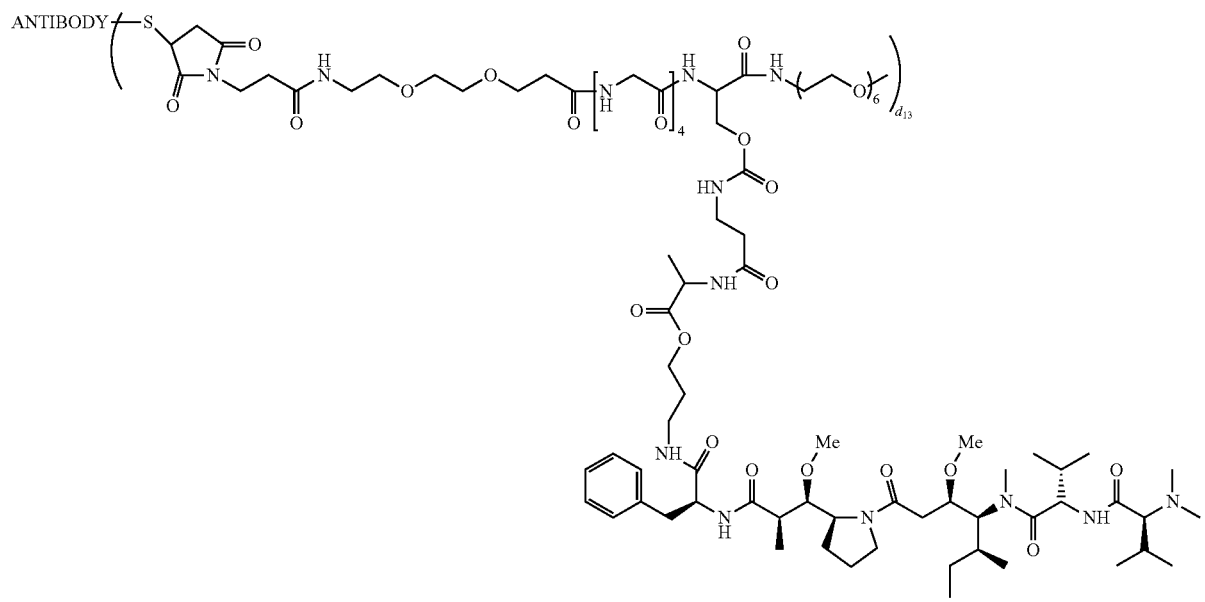
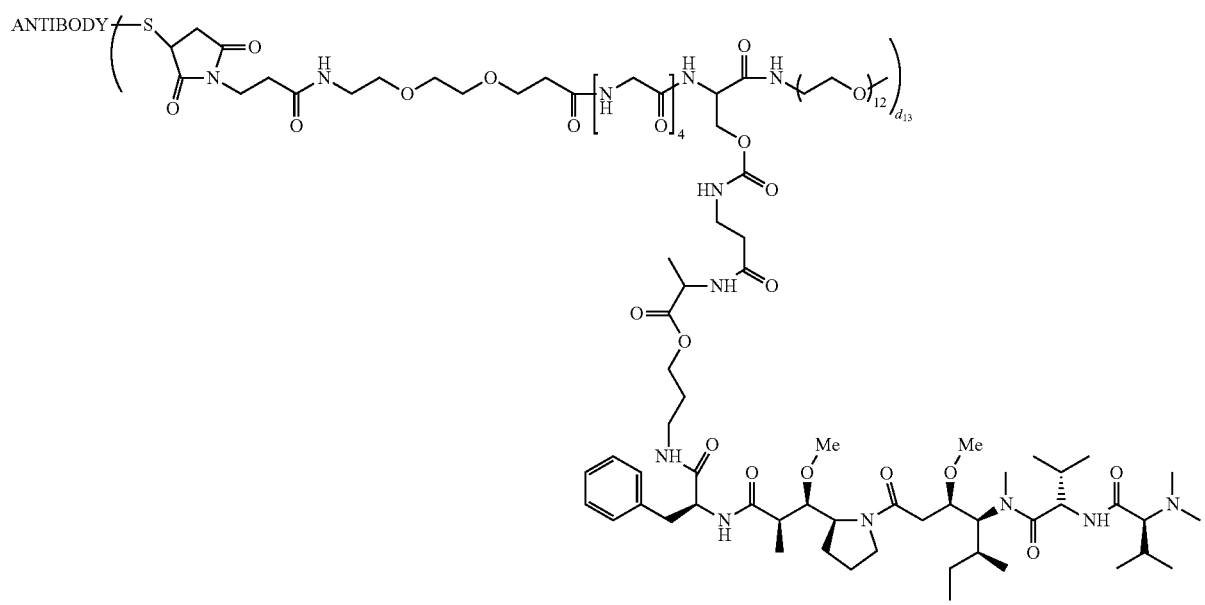

TABLE B1-continued

Structure

TABLE B1-continued
Structure
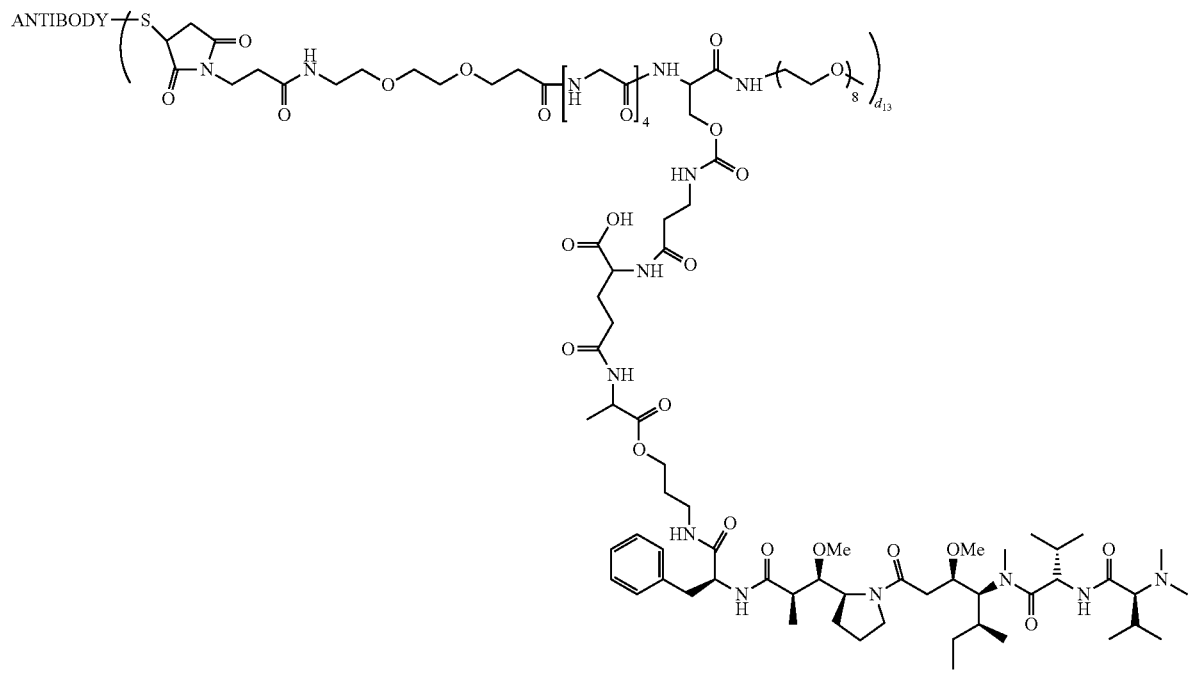
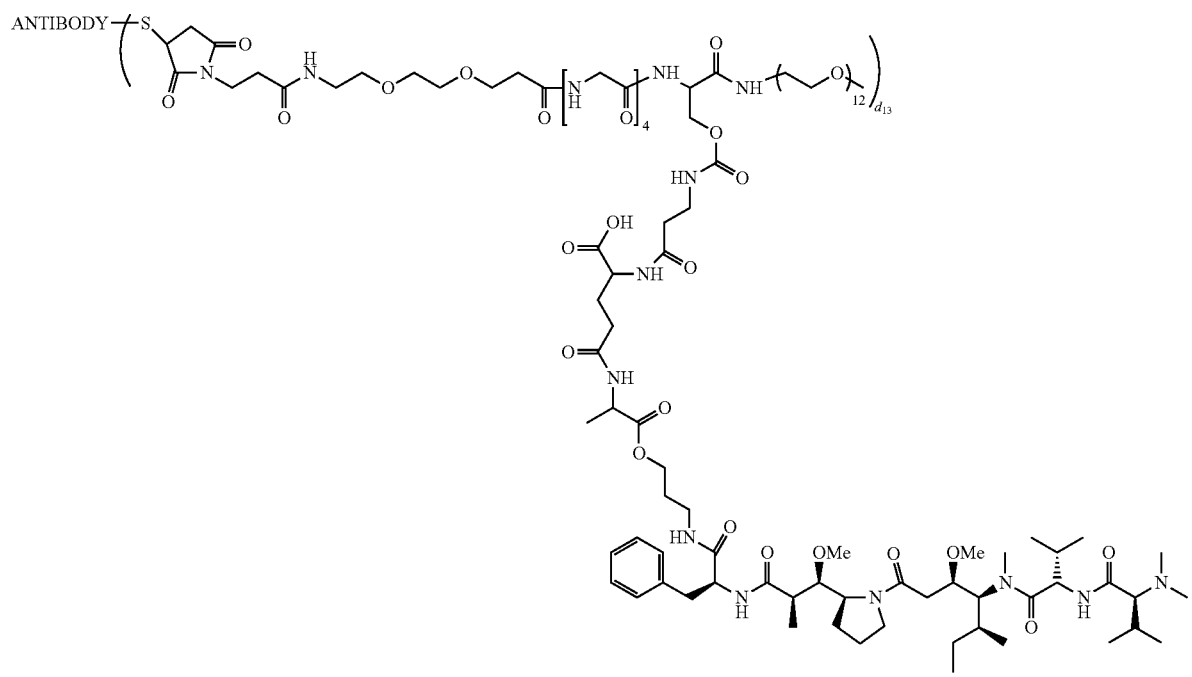

TABLE B1-continued
Structure
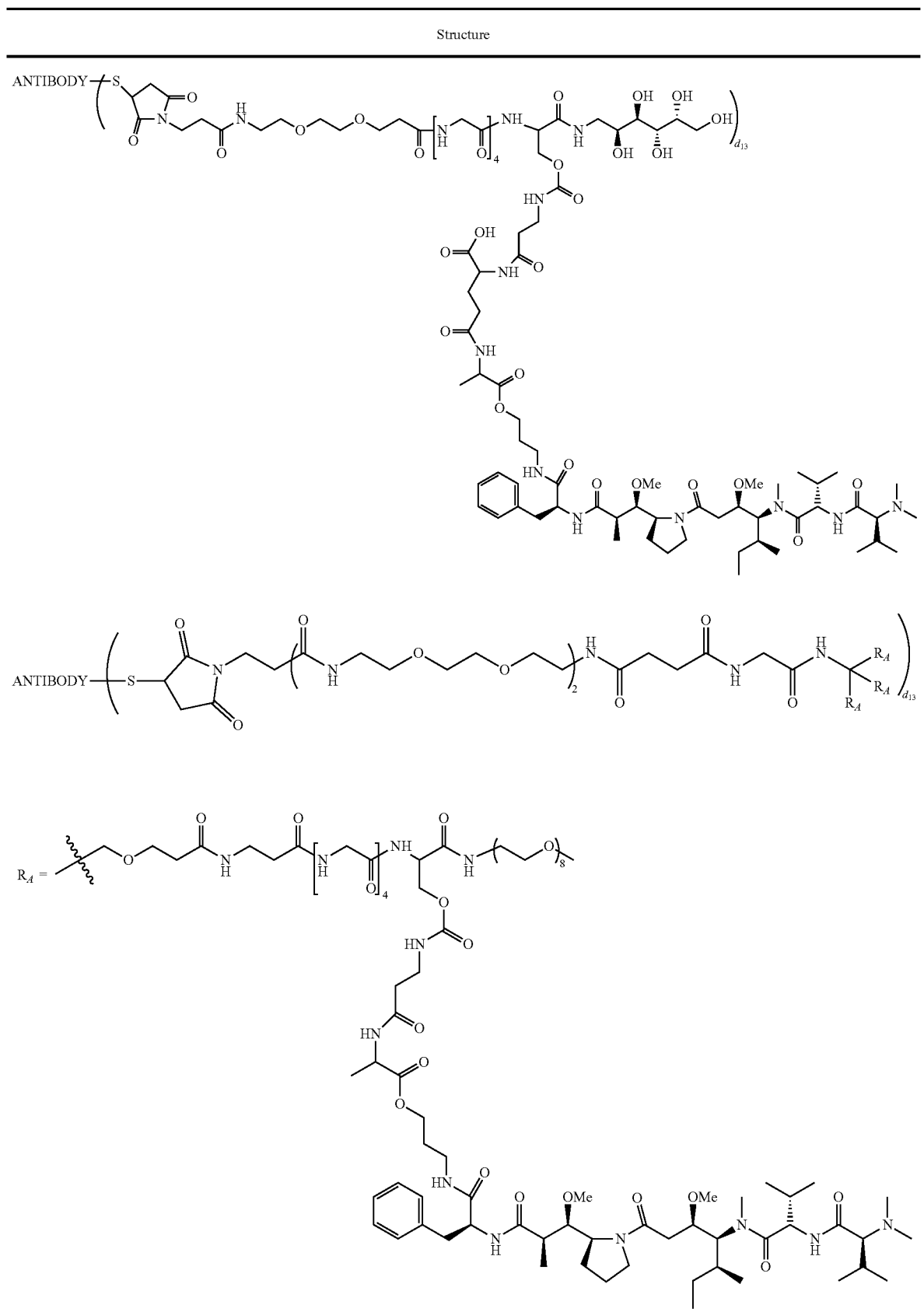

TABLE B1-continued
Structure
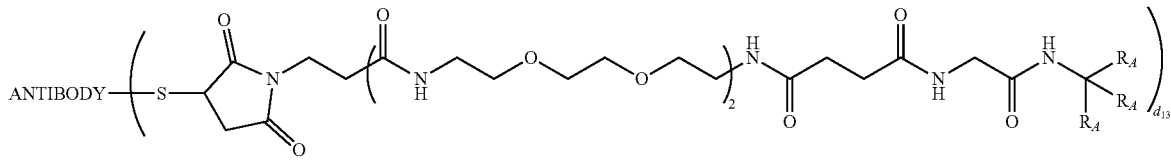
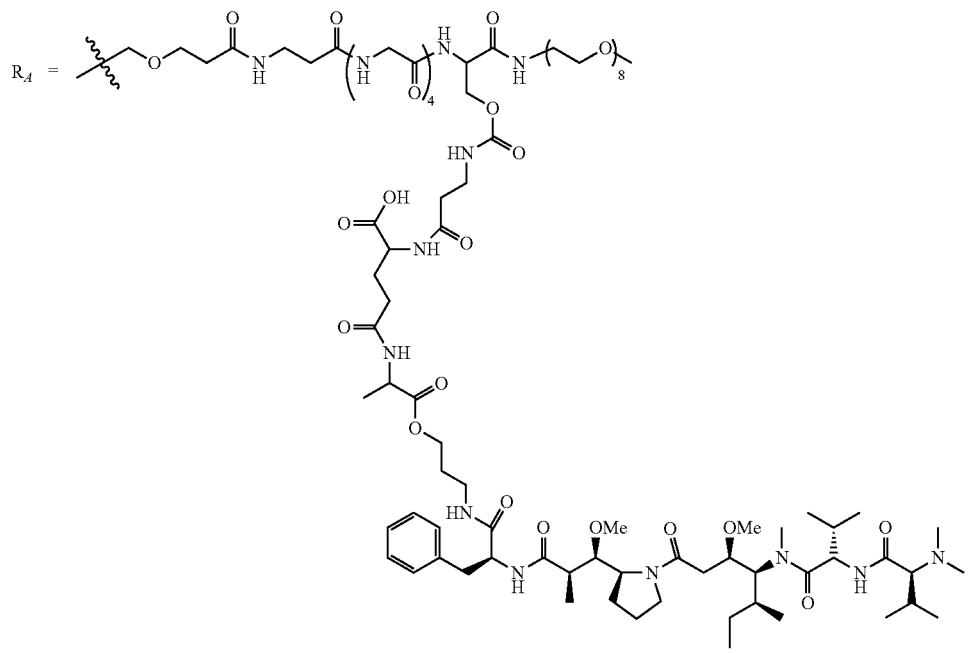
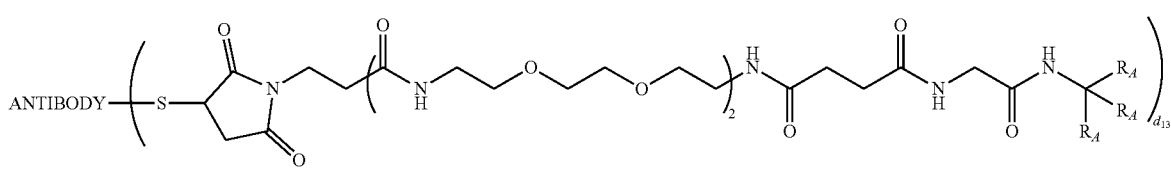

TABLE B1-continued
Structure
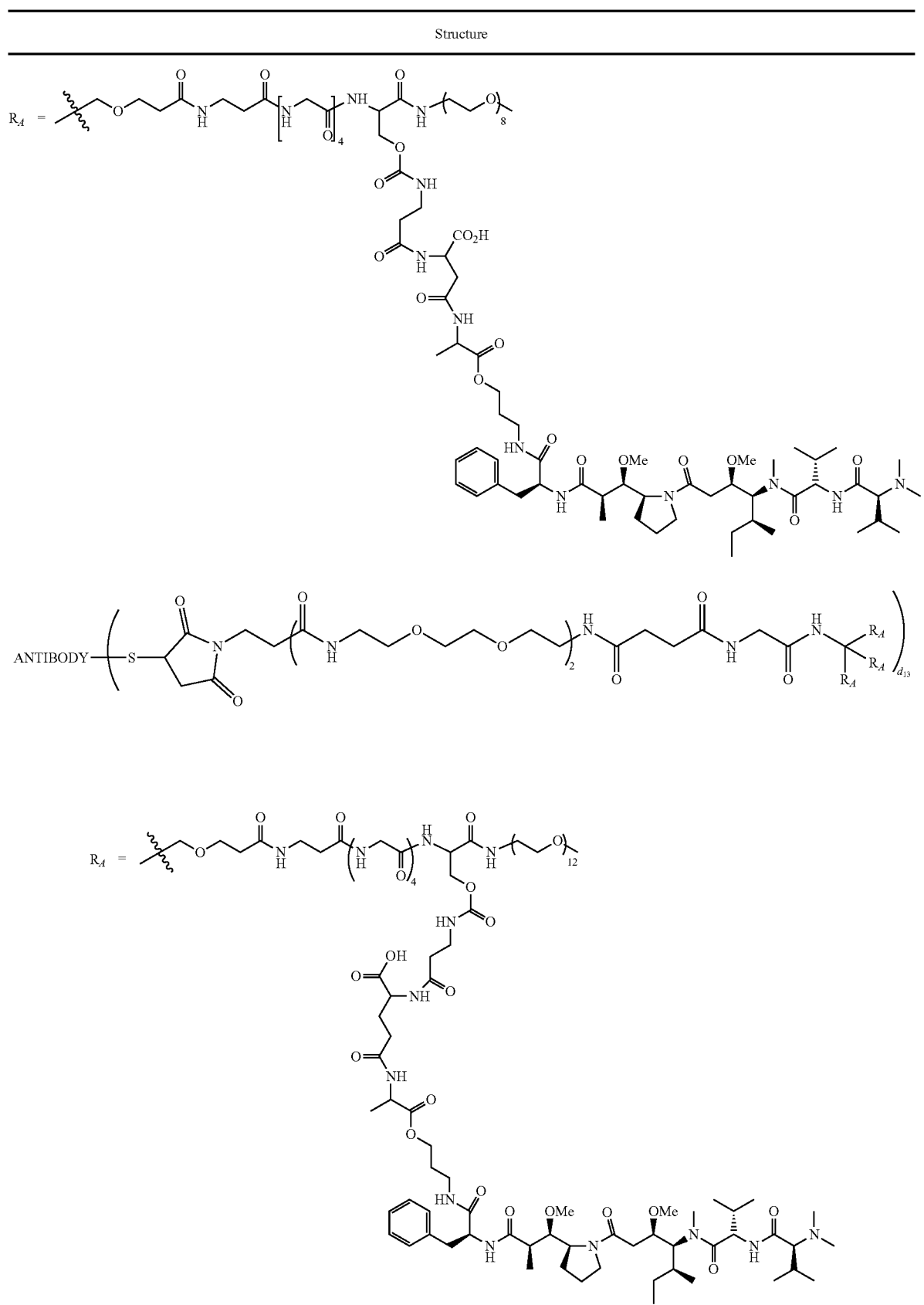

TABLE B1-continued

Structure

TABLE B1-continued
Structure
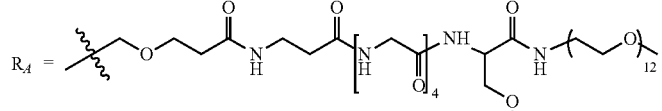

TABLE B1-continued
Structure
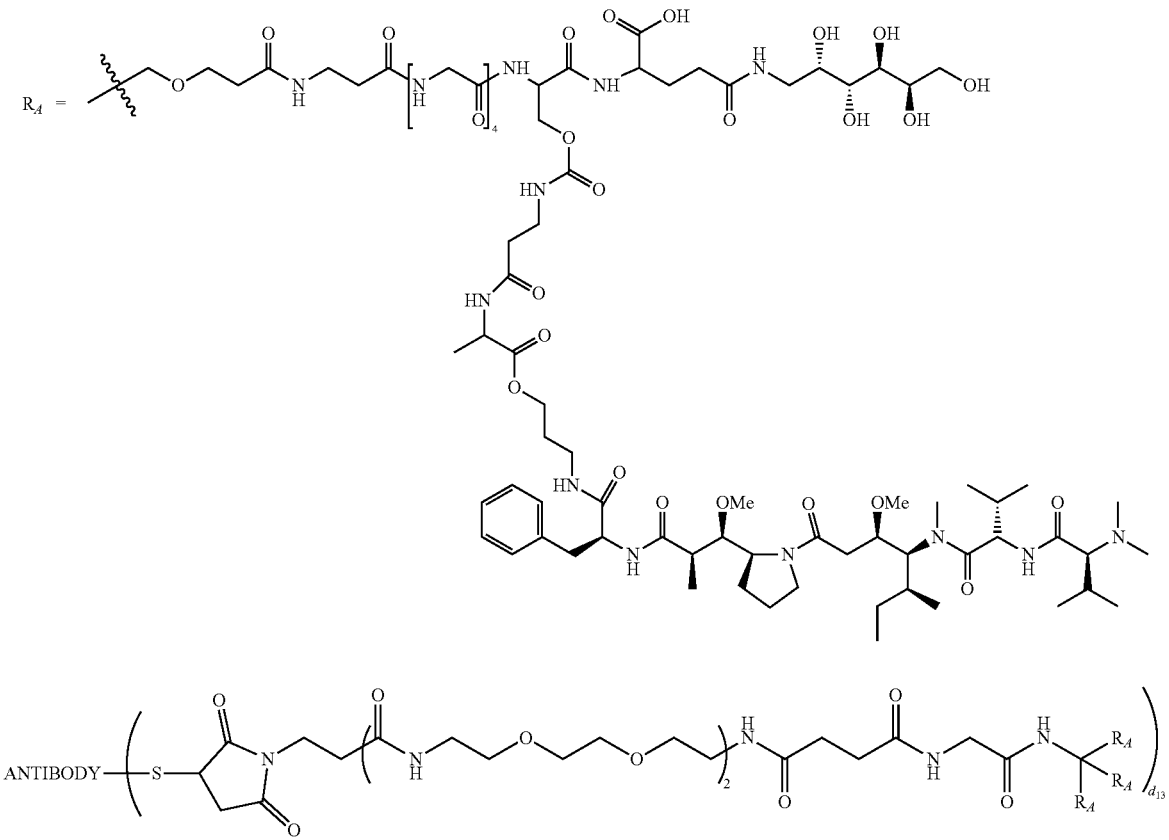
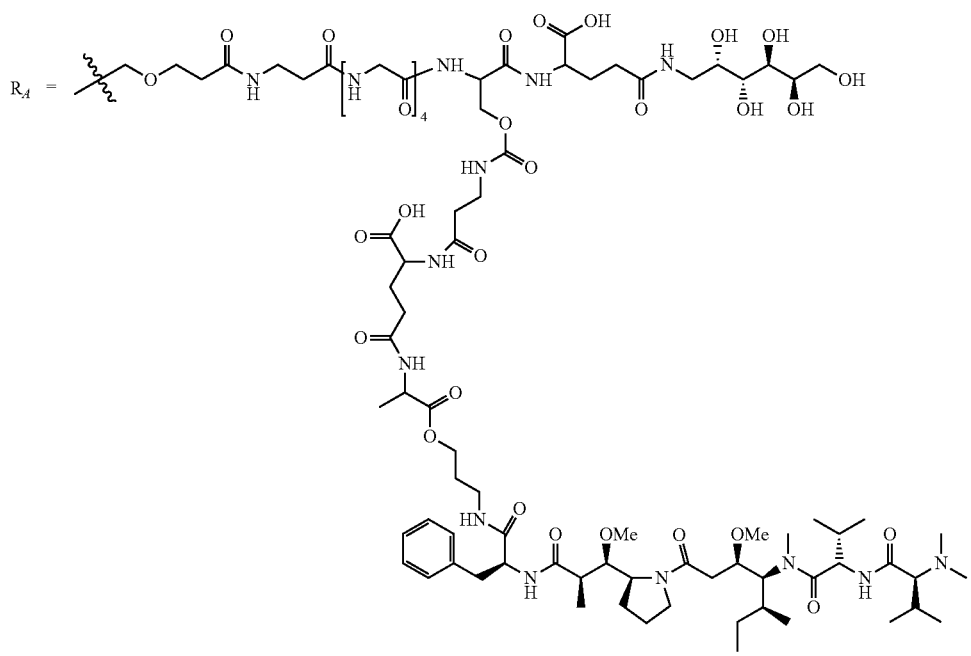

TABLE B1-continued
Structure
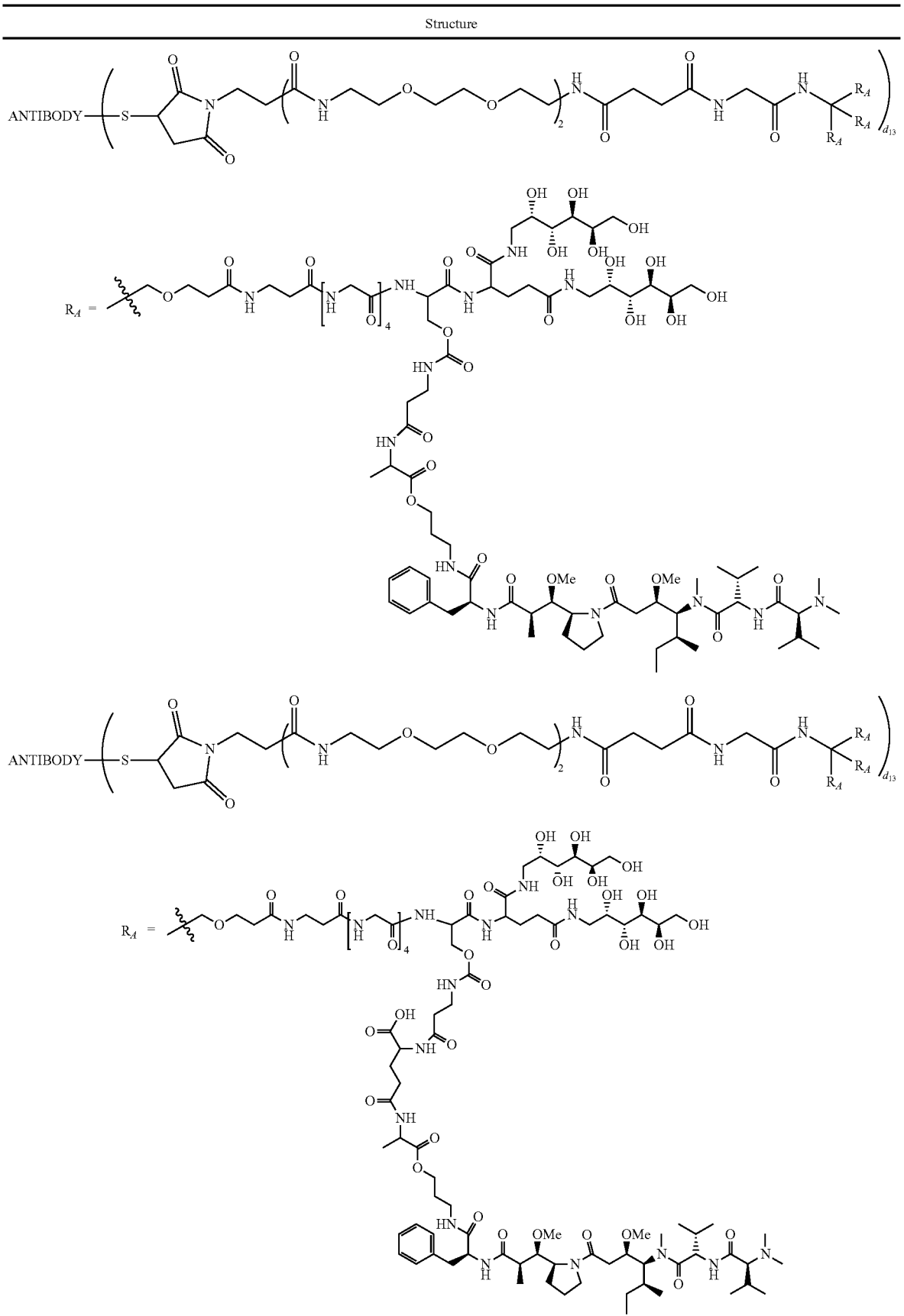

TABLE B1-continued
Structure
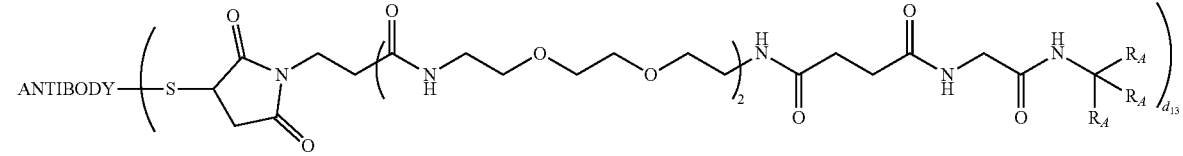
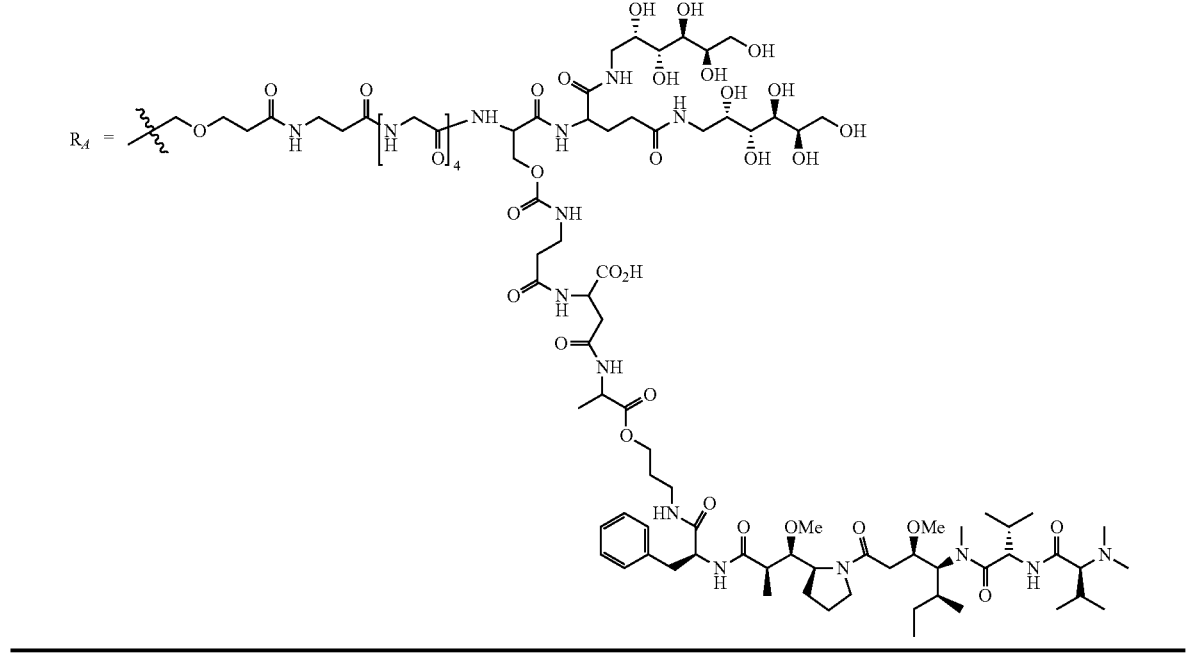
wherein $d_{13}$, is as defined herein and ANTIBODY is a B7-H4 antibody or a cysteine engineered B7-H4 antibody.
In some embodiments, the B7-H4 antibody or the cysteine engineered B7-H4 antibody conjugated to a cytotoxic drug moiety are conjugates of Formula (XXX):
(XXX)
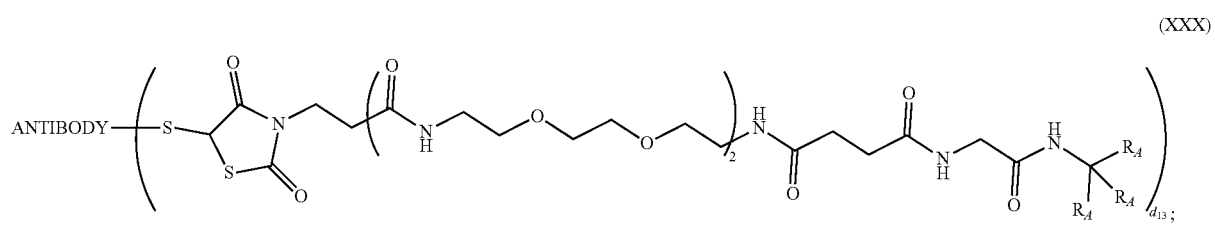

wherein each $R_A$ is:
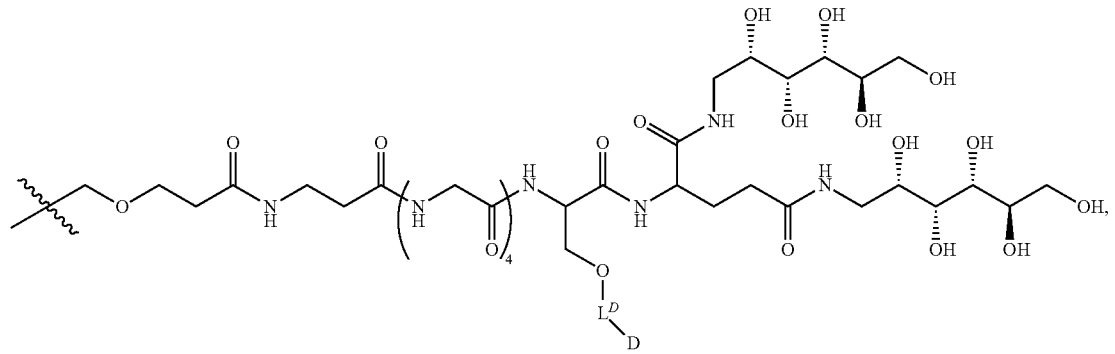
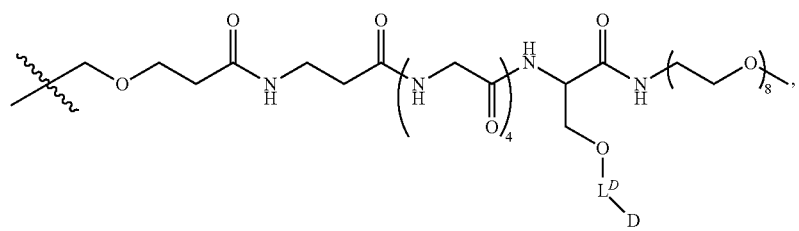
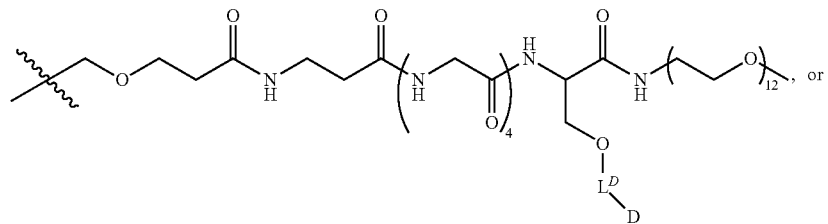
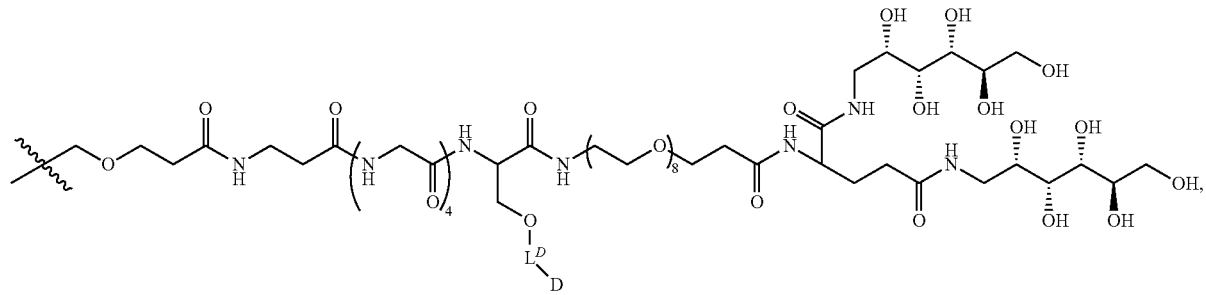
wherein: $d_{13}$ is 2, 4, 6 or 8.

In other embodiments, the B7-H4 antibody or the cysteine engineered B7-H4 antibody conjugated to a cytotoxic drug moiety are conjugates of Formula (XXX)] wherein each $R_A$ is
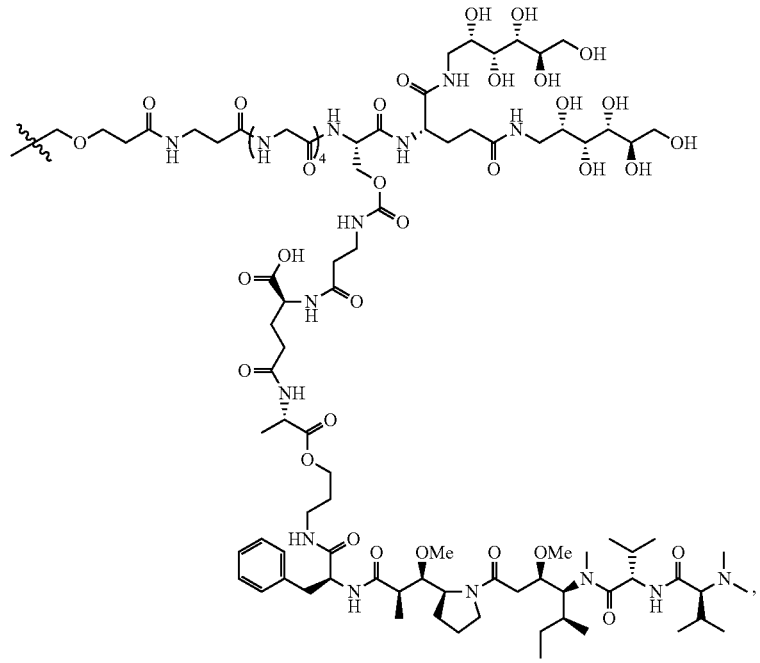
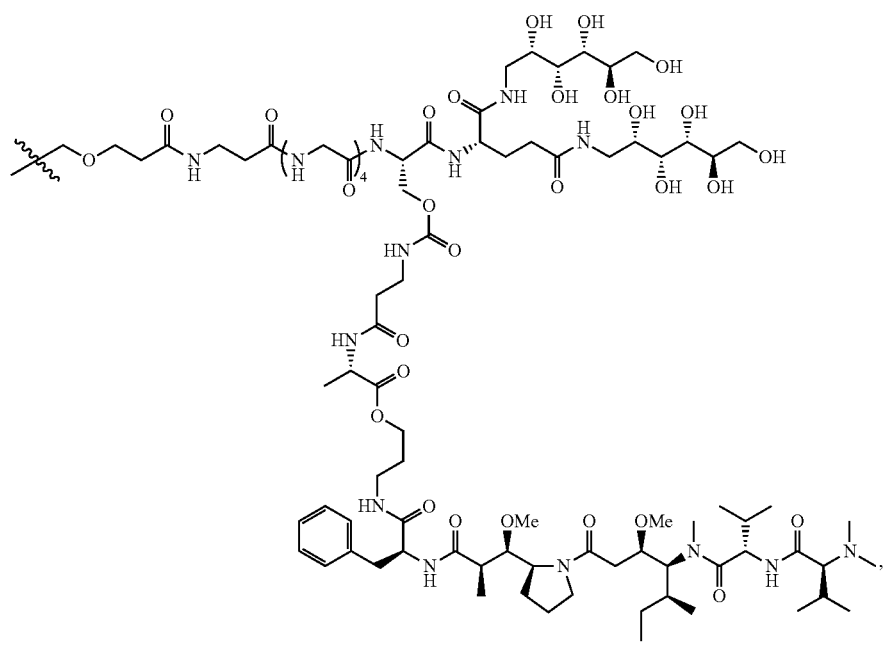

-continued
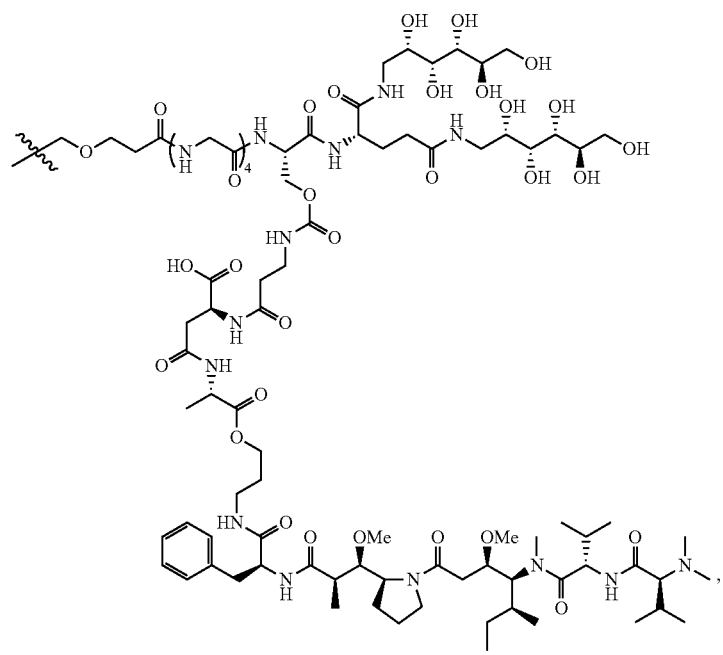
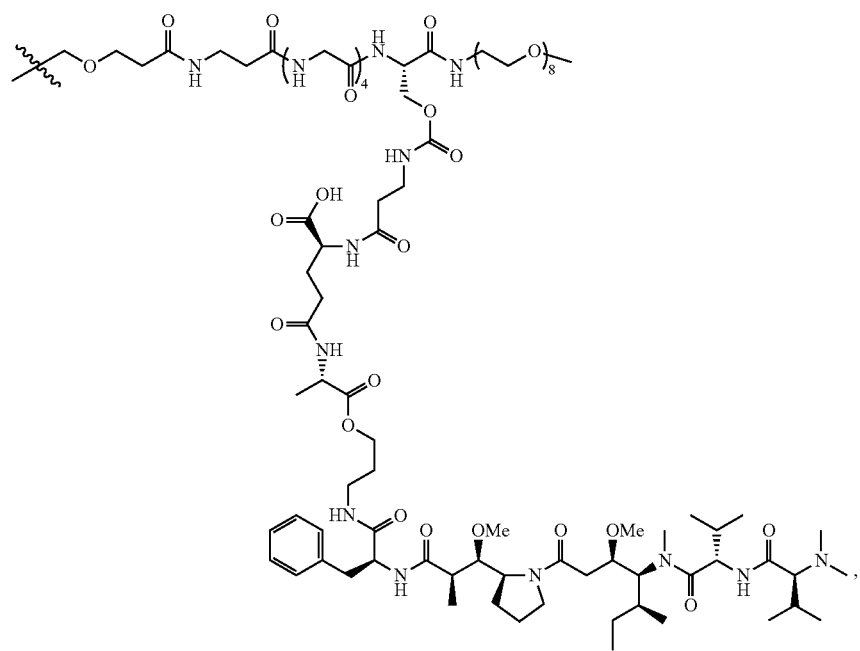

-continued
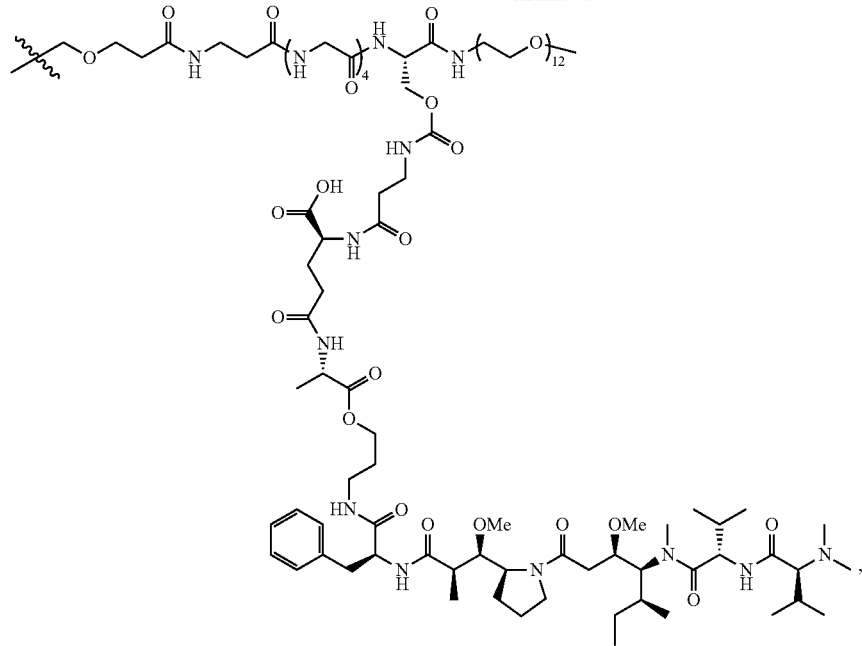
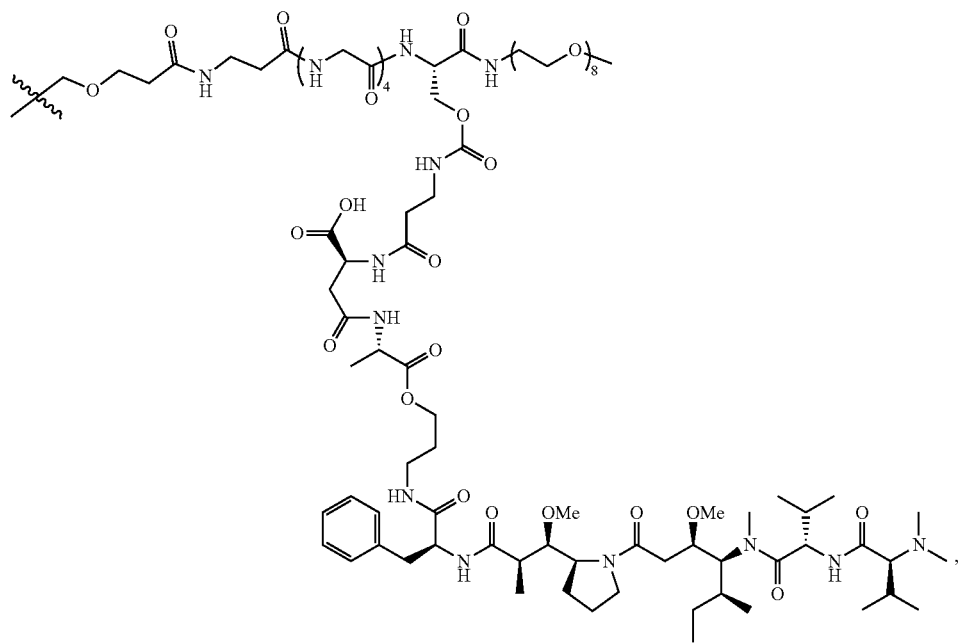

-continued
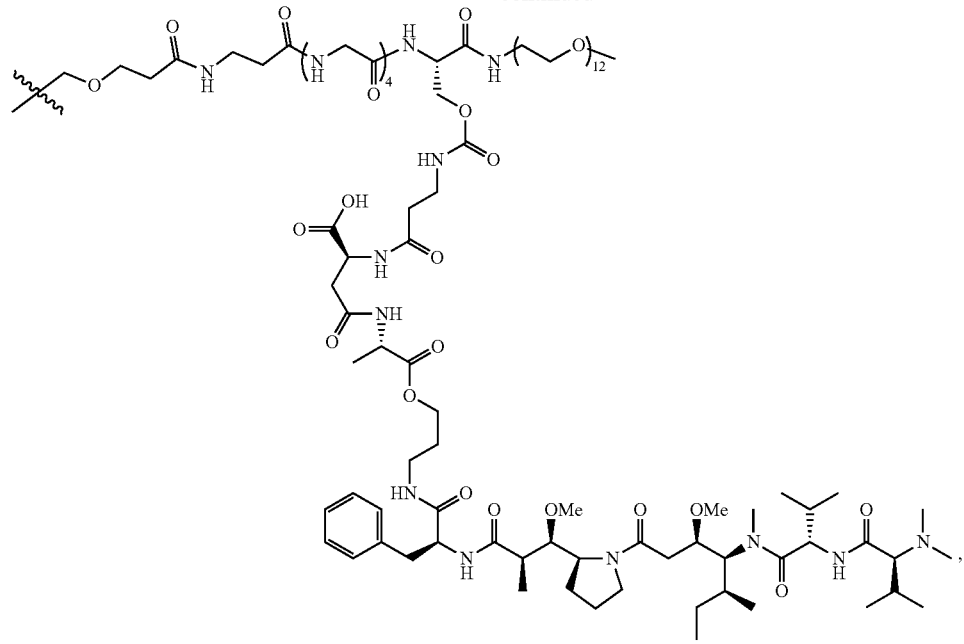
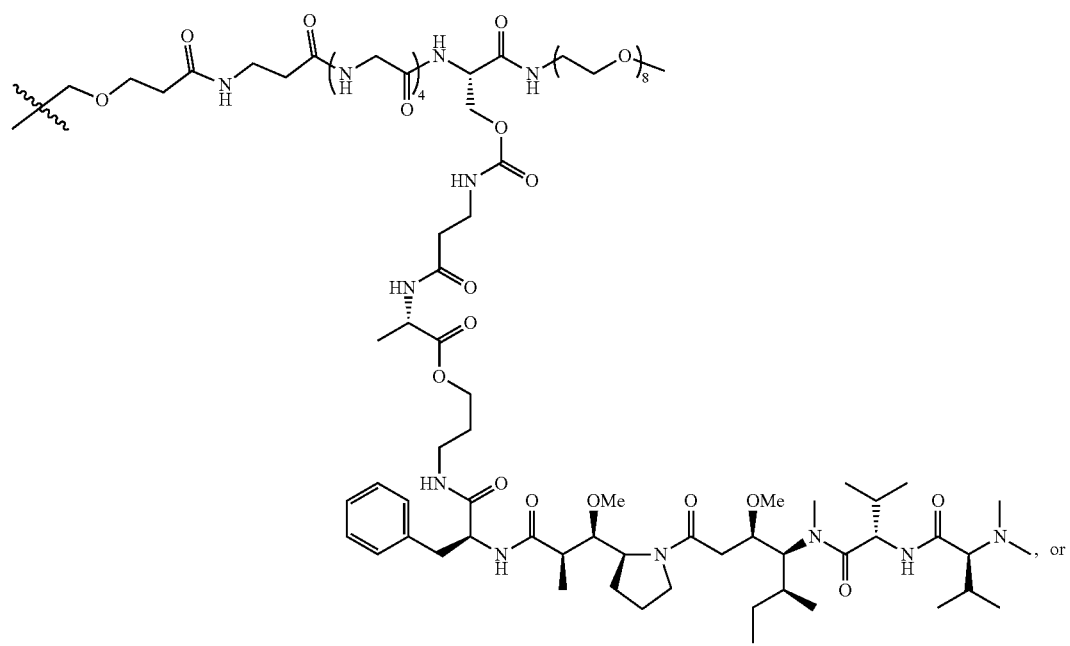

-continued
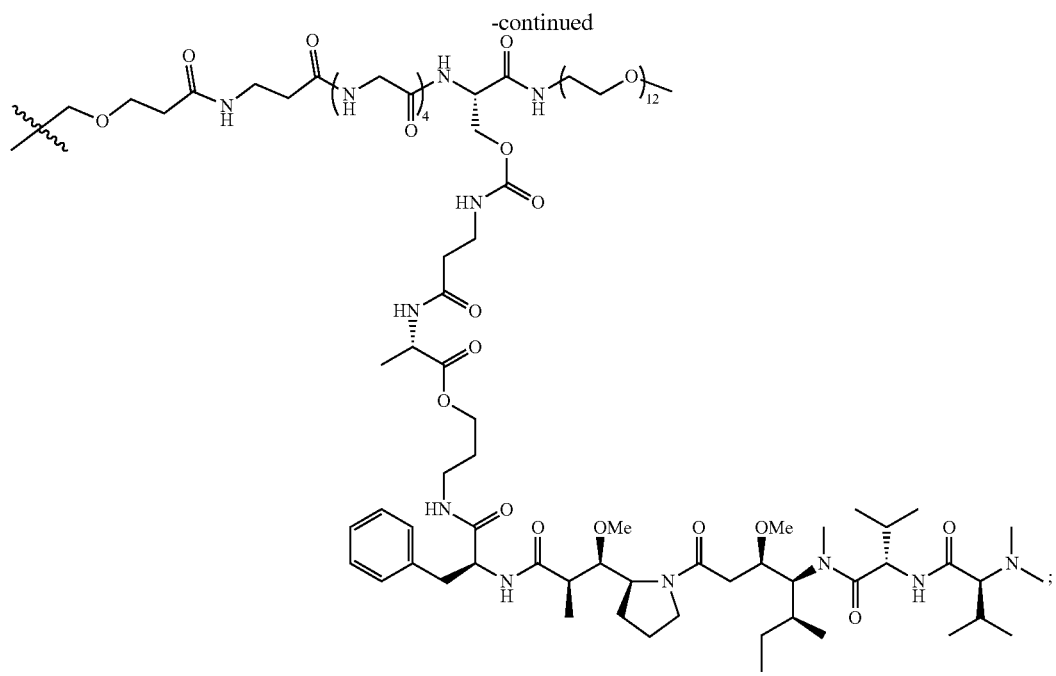
wherein:
$d_{13}$ is 2, 4, 6 or 8.
In some embodiments, the B7-H4 antibody or the cysteine engineered B7-H4 antibody conjugated to a cytotoxic drug moiety are conjugates of Formula (XXX), wherein each $R_A$ is:
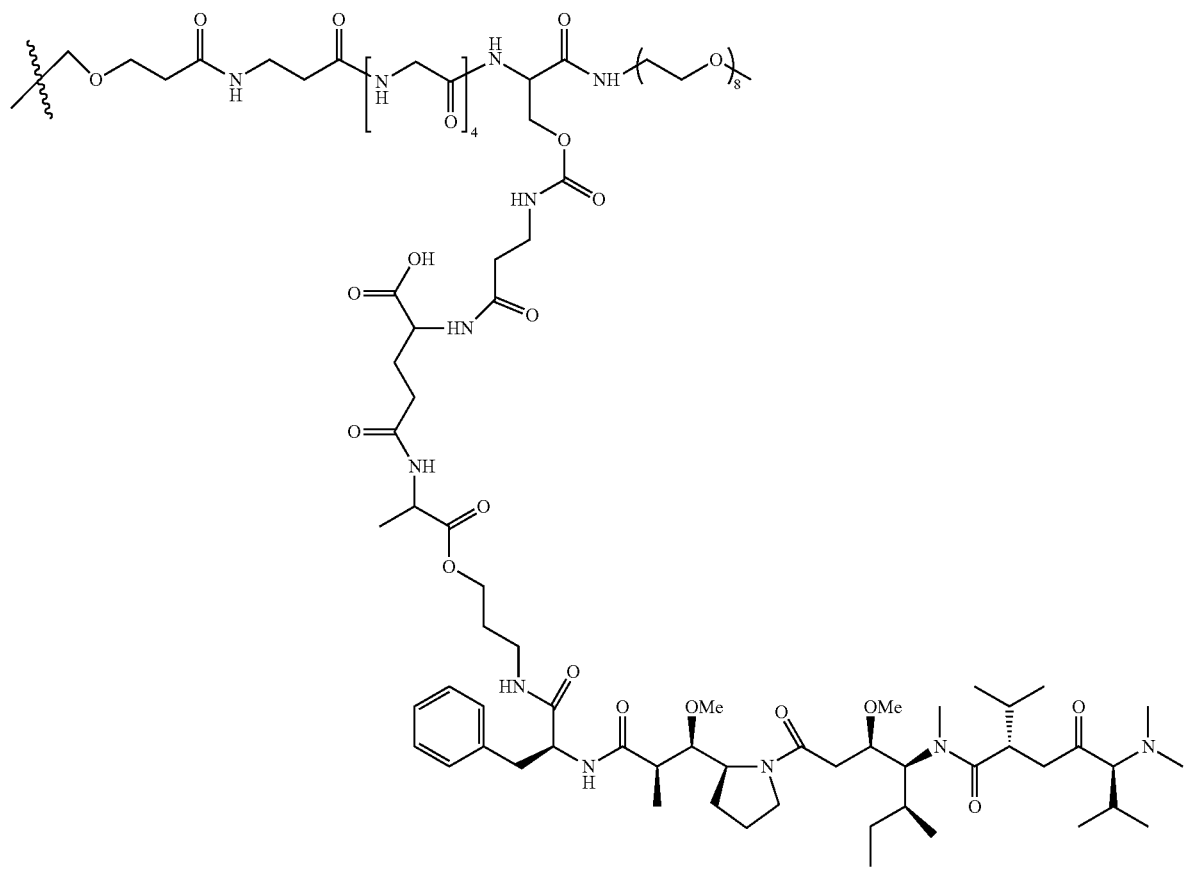

In some embodiments, the B7-H4 antibody or the cysteine engineered B7-H4 antibody conjugated to a cytotoxic drug moiety are conjugates of Formula (XXXI-1), (XXXI-2), (XXXI-3) or (XXXI-4):
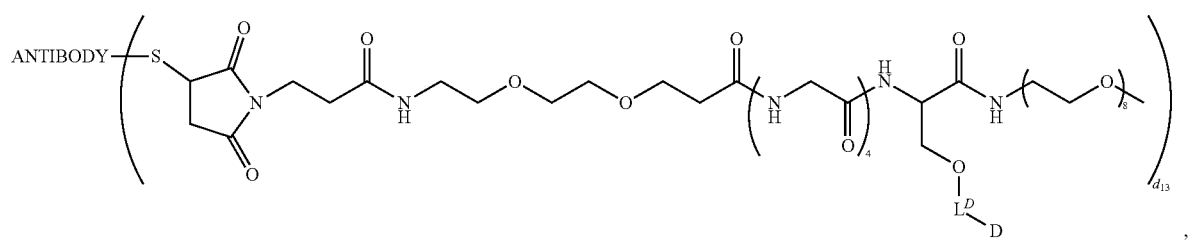
(XXXI-1)
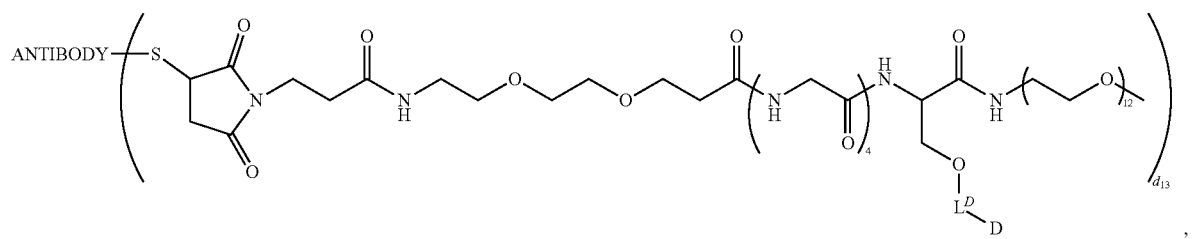
(XXXI-2)
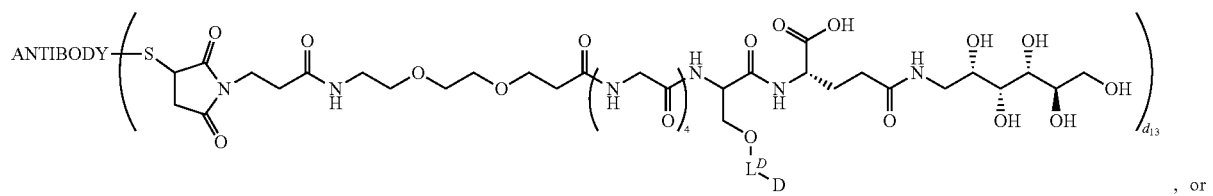
(XXXI-3)
, or
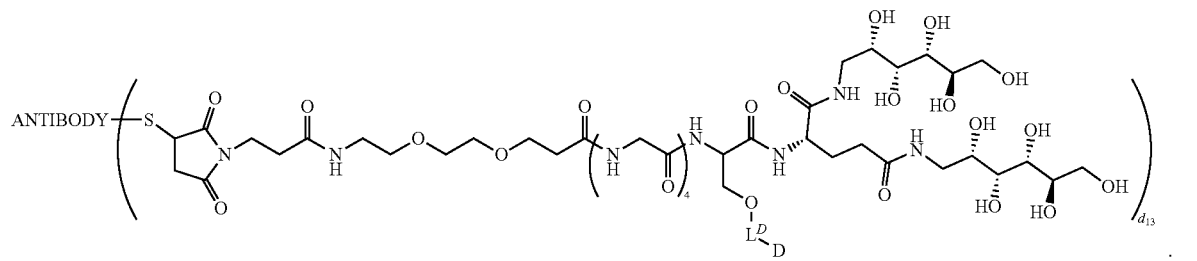
(XXXI-4)
.

In some embodiments, the B7-H4 antibody or the cysteine engineered B7-H4 antibody conjugated to a cytotoxic drug moiety are conjugates of Formula (XXXII):
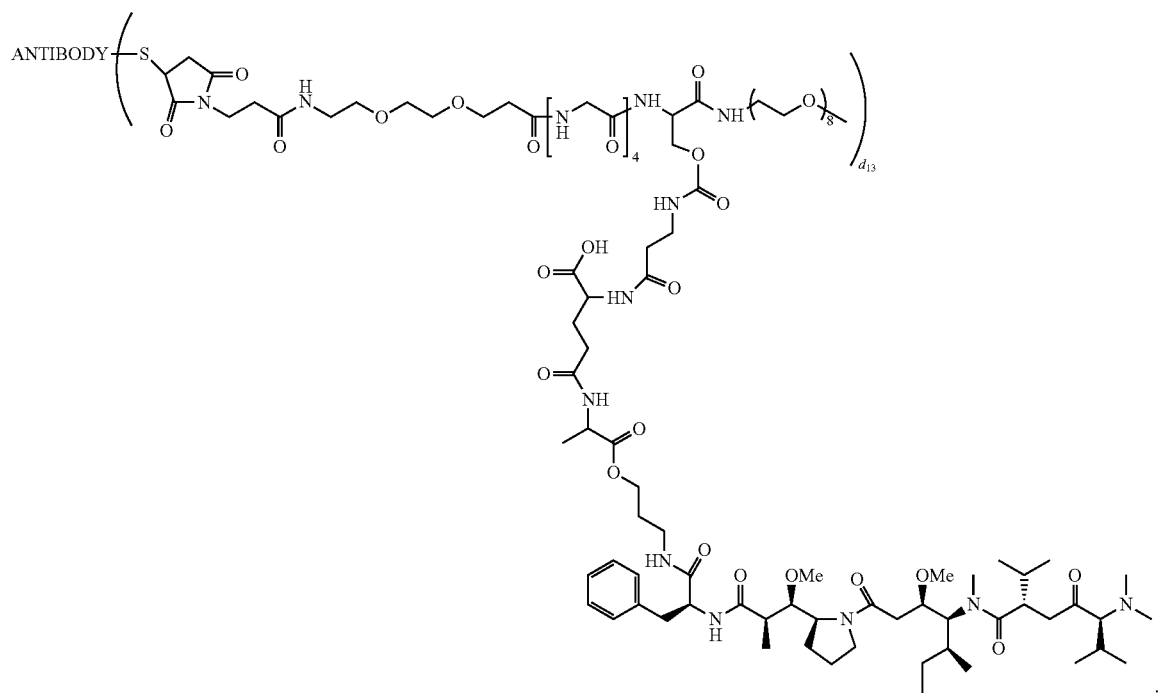
In some embodiments, the B7-H4 antibody or the cysteine engineered B7-H4 antibody conjugated to a cytotoxic drug moiety are conjugates of Formula (XXXII):
(XXXII)
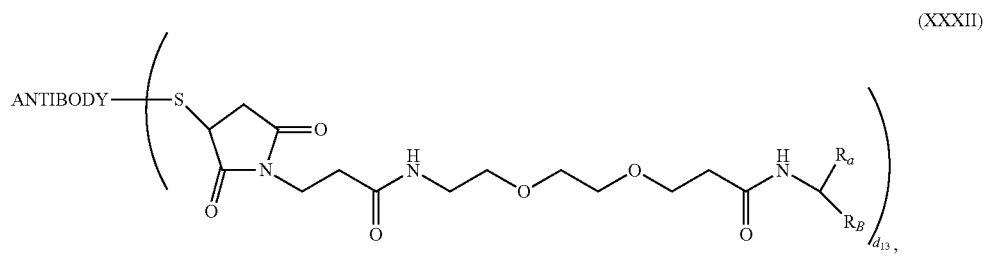
wherein each $R_B$ is:
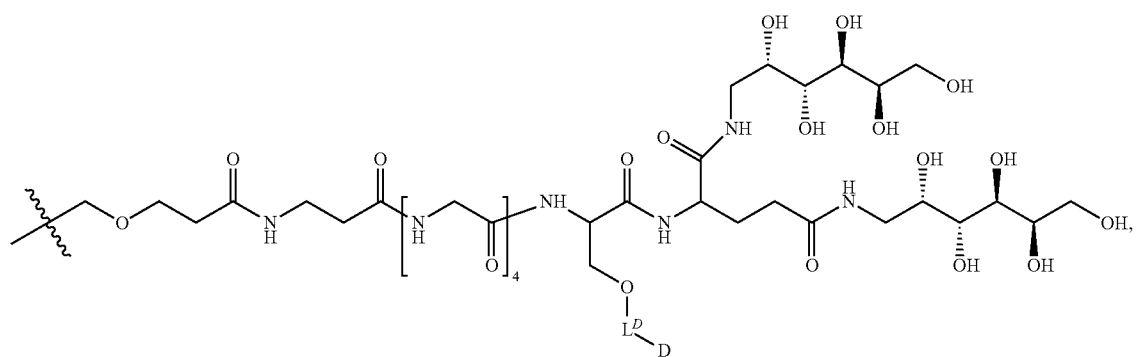

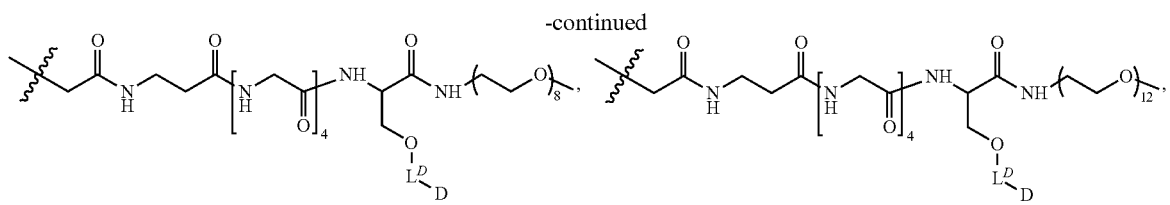
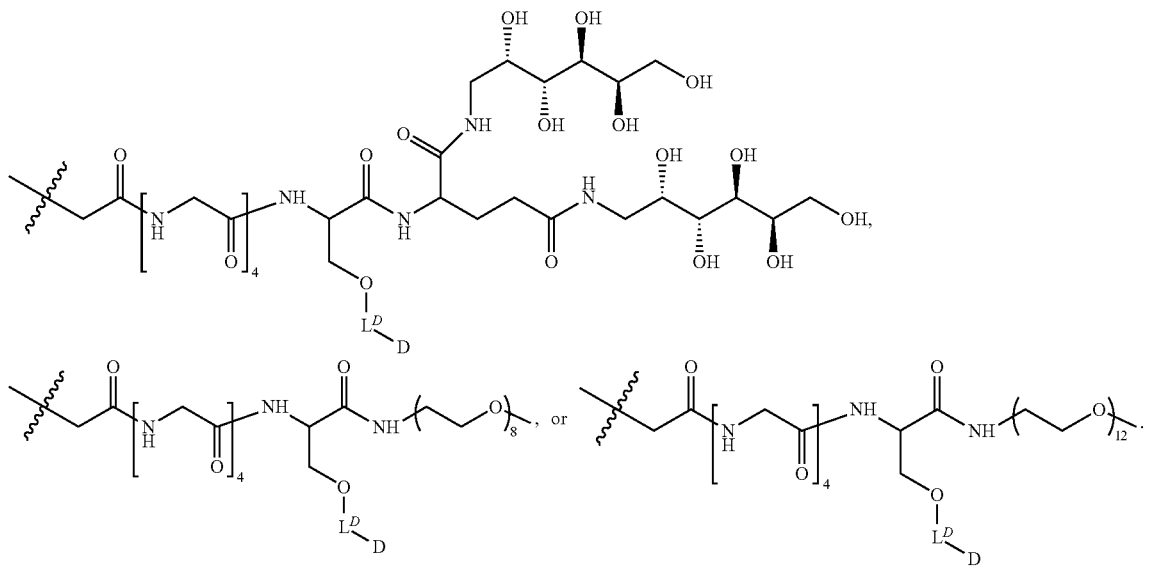
In some embodiments, the B7-H4 antibody or the cysteine engineered B7-H4 antibody conjugated to a cytotoxic drug moiety are conjugates of Formula (XXXI-1), (XXXI-2), (XXXI-3), (XXXI-4) or (XXXII), in which the variable -L$^D$-D is:
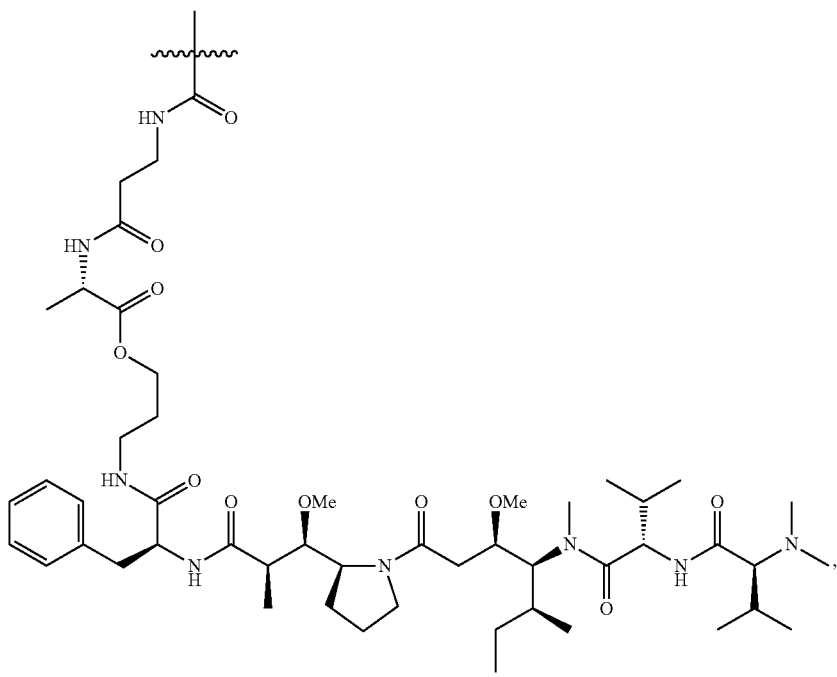

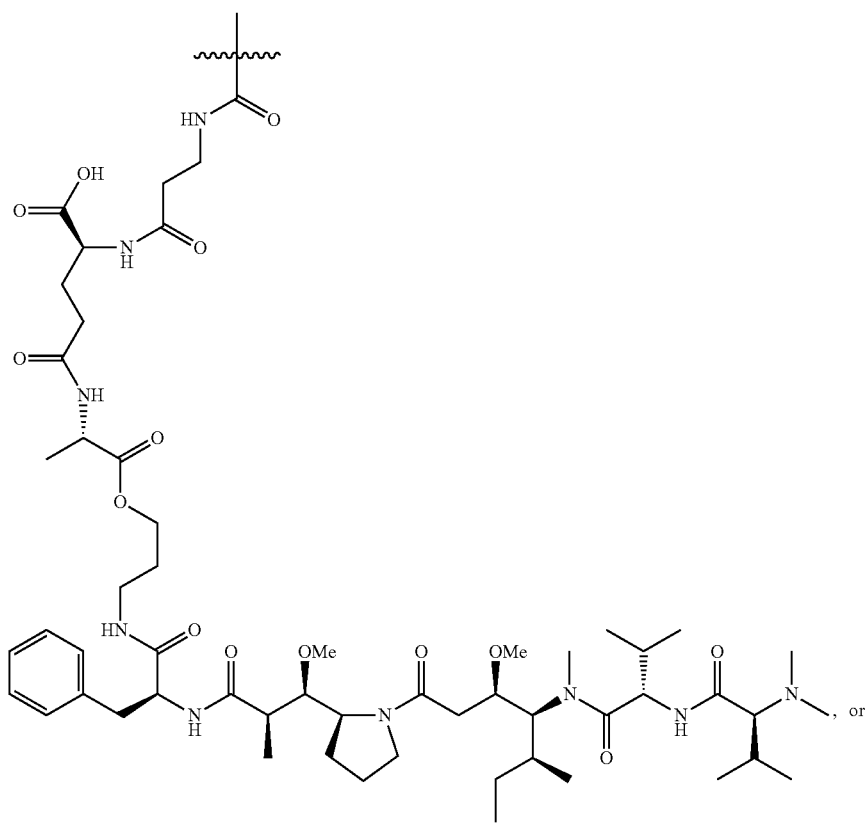
, or
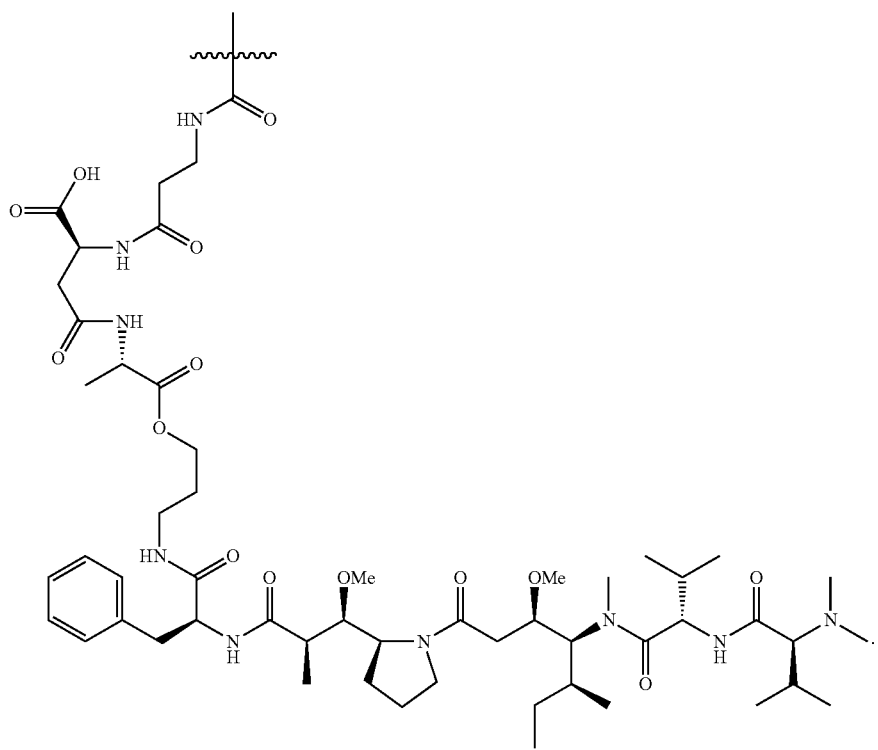 [SMILES: *C(=O)NCCC(=O)N[C@@H](CC(=O)N[C@@H](C)C(=O)OCCCNC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C)C(=O)O]
.

In some embodiments, the B7-H4 antibody or the cysteine engineered B7-H4 antibody conjugated to a cytotoxic drug moiety are conjugates of Formula (XXXI-1), (XXXI-2), (XXXI-3), (XXXI-4) or (XXXII), in which the variable -L$^D$-D is:
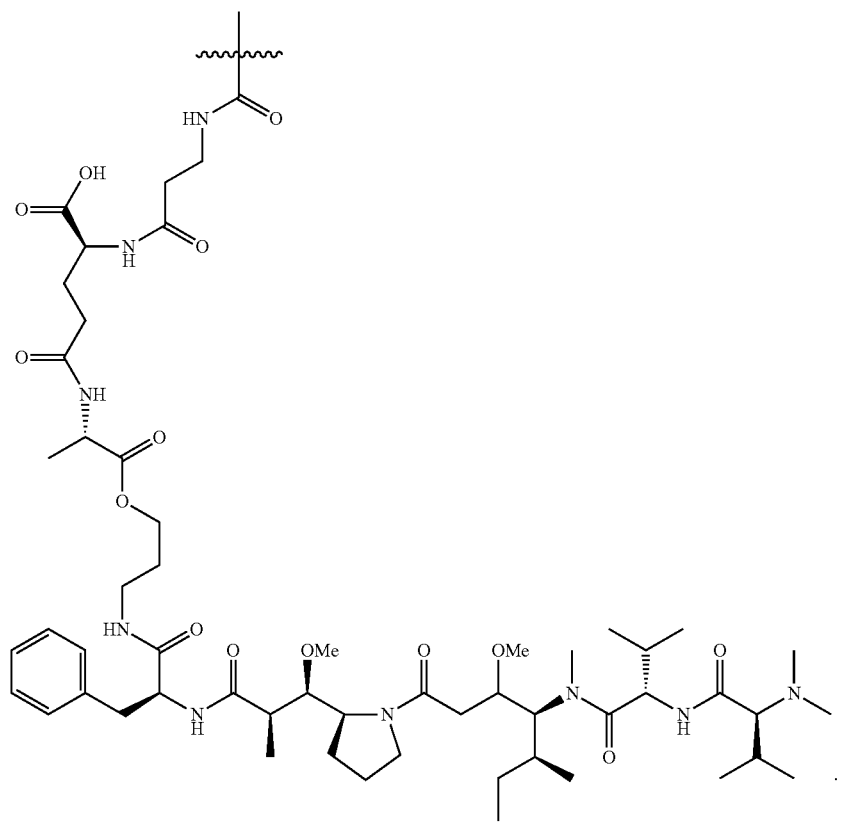 [SMILES: *C(=O)NCCC(=O)N[C@@H](CCC(=O)N[C@@H](C)C(=O)OCCCNC(=O)[C@H](Cc1ccccc1)NC(=O)[C@H](C)[C@@H](OC)[C@@H]1CCCN1C(=O)CC(OC)[C@H]([C@@H](C)CC)N(C)C(=O)[C@@H](NC(=O)[C@H](C(C)C)N(C)C)C(C)C)C(=O)O]
In some embodiments, the B7-H4 antibody or the cysteine engineered B7-H4 antibody conjugated to a cytotoxic drug moiety are conjugates of Formula (XXXXIII-3):
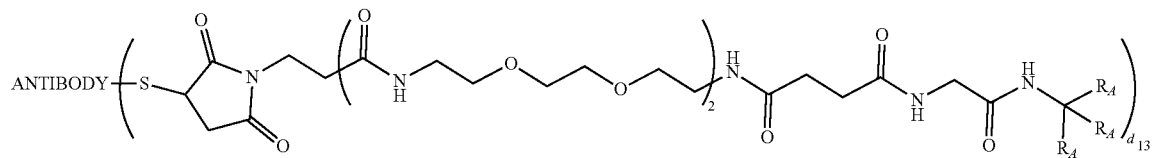

wherein each $R_A$ is:
(XXXIII-3)
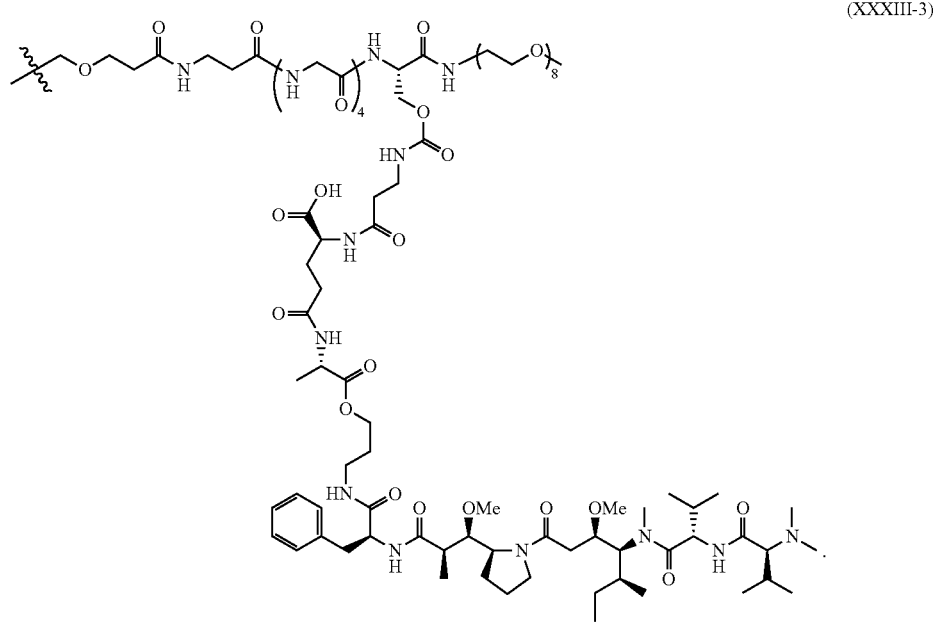
In some embodiments, the B7-H4 antibody or the cysteine engineered B7-H4 antibody conjugated to a cytotoxic drug moiety are conjugates of Formula (XXXXIII-8):
(XXXIII-8)
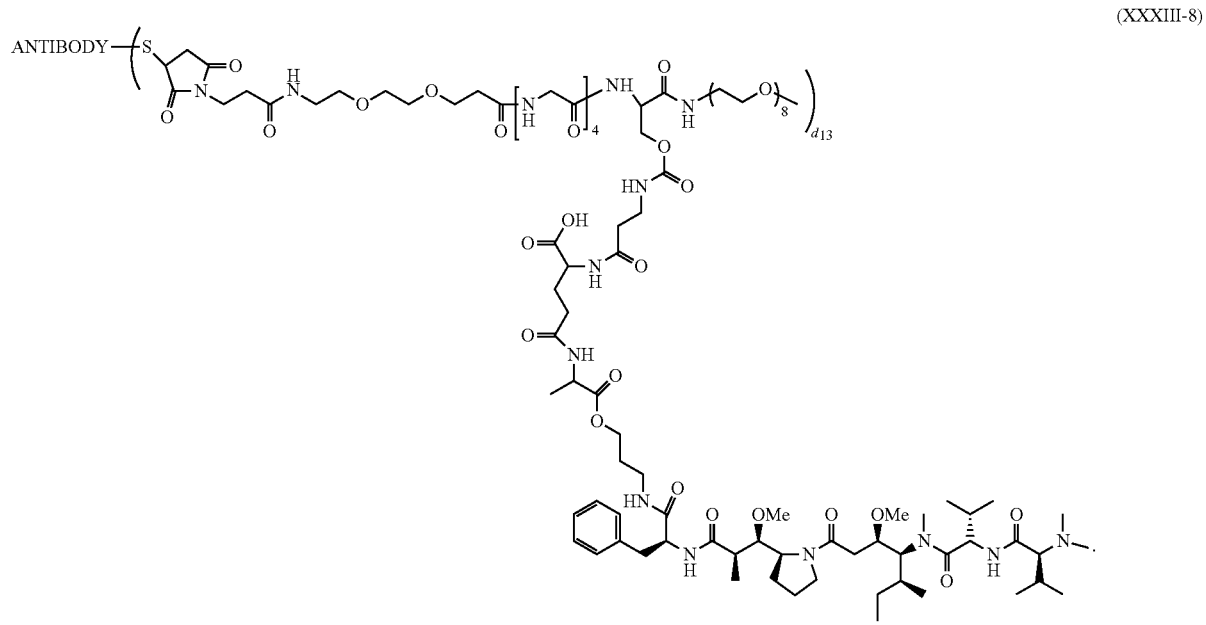
In some embodiments, the B7-H4 antibody or the cysteine engineered B7-H4 antibody conjugated to a cytotoxic drug moiety are conjugates of Formula (XXXIII-5):

(XXXIII-5)
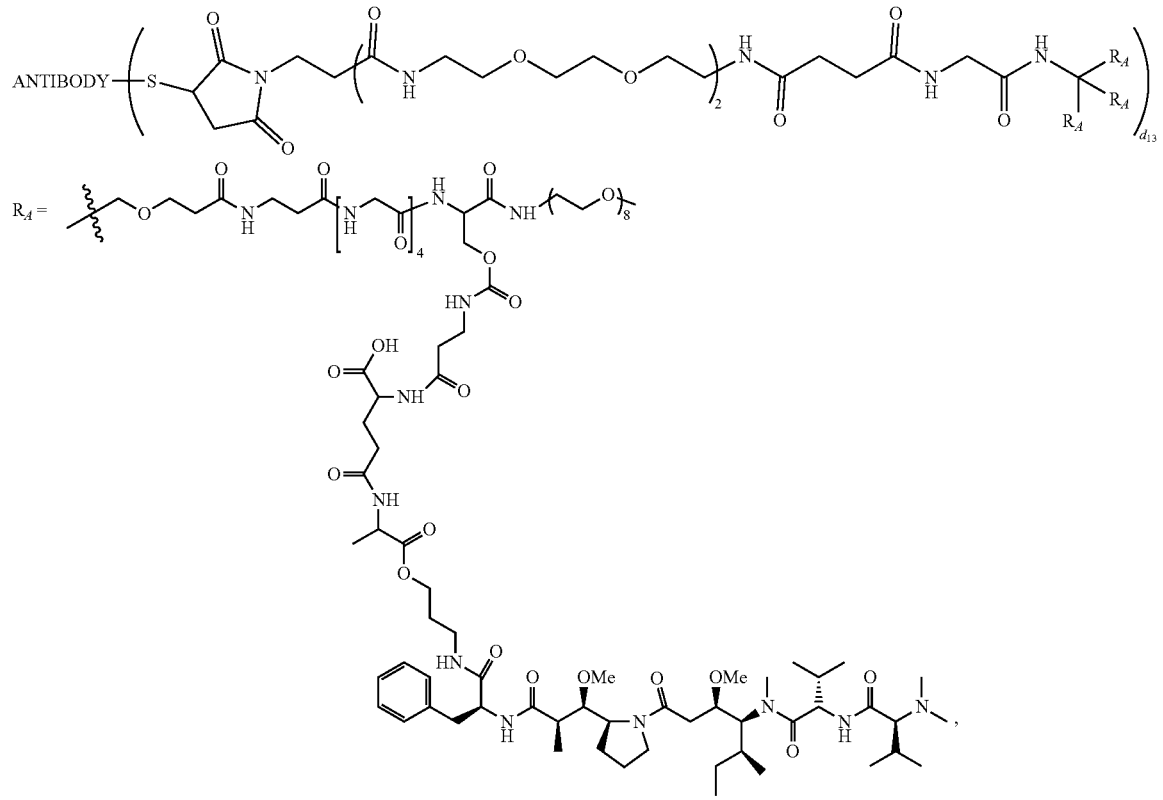
wherein $d_{13}$ is as defined herein.
In some embodiments, the B7-H4 antibody or the cysteine engineered B7-H4 antibody conjugated to a cytotoxic drug moiety are conjugates of Formula (XXXIII-8):
(XXXIII-8)
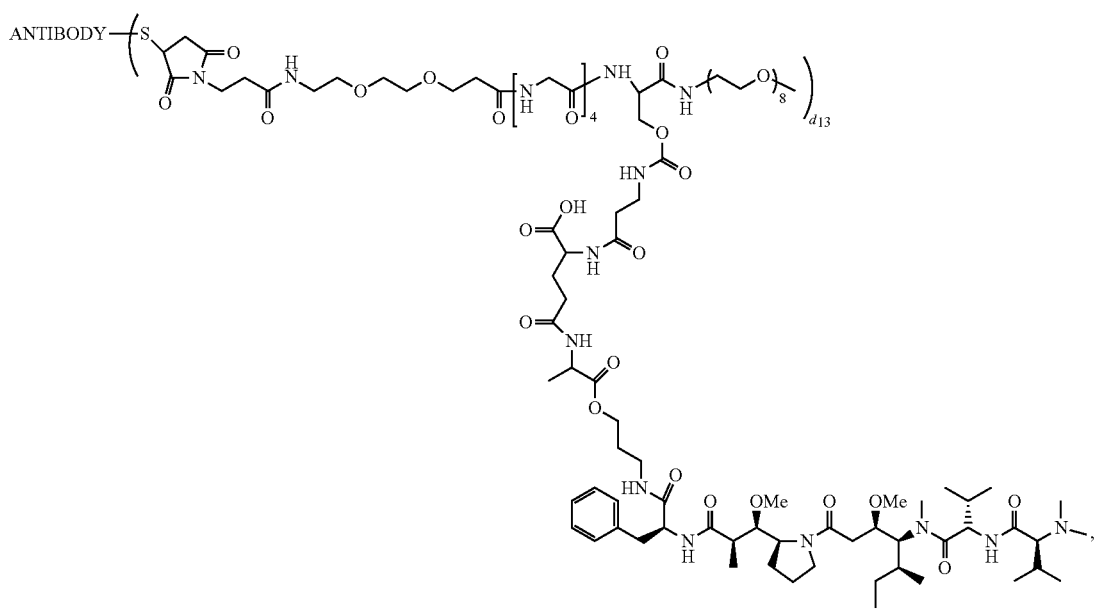
wherein $d_{13}$ is as defined herein.

Modified B7-H4 Antibody-Drug Conjugates

In some embodiments, modified B7-H4 antibody-drug conjugates of the present disclosure may be obtained by reacting the modified B7-H4 antibody of the present disclosure with a Linker-Drug moiety comprising a functional group (e.g., $W^P$), which is capable of forming a covalent bond with the functional group A" of the modified-GlcNAc moiety, *-GlcNAc-S"-A" in the modified B7-H4 antibody.

In some embodiments, $W^P$ comprises alkynyl e.g., cycloalkynyl, heterocycloalkynyl, or terminal alkynyl.

In some embodiments, the functional group A" of the modified B7-H4 antibody is azido, keto, or alkynyl. In some embodiments, the functional group A" of the modified B7-H4 antibody is azido. In some embodiments, the azido functional group A" of the modified B7-H4 antibody reacts with the alkynyl of $W^P$ (e.g., the cycloalkynyl, heterocycloalkynyl, or terminal alkynyl) of the Linker-Drug moiety to form a triazole moiety (e.g., via a cycloaddition reaction). The cycloaddition reaction of an azido group and an alkynyl group is known in the art as "click chemistry".

In some embodiments, $W^P$ of the Linker-Drug moiety comprises a terminal alkynyl, and the cycloaddition reaction may be performed in the presence of a catalyst (e.g., a Cu(I) catalyst).

In some embodiments, $W^P$ of the Linker-Drug moiety comprises cycloalkynyl or heterocycloalkynyl (e.g., strained cycloalkynyl or heterocycloalkynyl).

In some embodiments, $W^P$ of the Linker-Drug moiety comprises a strained cycloalkynyl or heterocycloalkynyl, and the cycloaddition reaction may be performed in the presence or absence of a catalyst. In some embodiments, the cycloaddition reaction may occur spontaneously by a reaction called strain-promoted azide-alkyne cycloaddition (SPAAC), which is known in the art as "metal-free click chemistry". In some embodiments, the strained cycloalkynyl or heterocycloalkynyl is as described herein.

In some embodiments, upon conjugation, the functional group A" of the modified B7-H4 antibody and $W^P$ of the Linker-Drug moiety forms a triazole moiety.

In some embodiments, upon conjugation, the functional group A" of the modified B7-H4 antibody and $W^P$ of the Linker-Drug moiety forms a triazole moiety of Formula (XXXV):

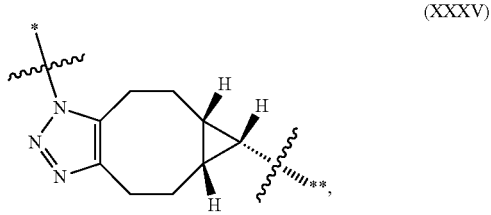

(XXXV)

wherein * denotes a direct or indirect attachment to the rest of the modified B7-H4 antibody; and ** indicates attachment to $M^P$ when present, or to $L^M$ or $M^A$.

In some embodiments, when an azide-modified B7-H4 antibody of the present disclosure is reacted with a Linker-Drug moiety comprising an alkynyl group to form an antibody-drug conjugate via a cycloaddition reaction, the formed triazole moiety in the antibody-drug conjugate may be resistant to hydrolysis and/or other degradation pathways.

In some embodiments, when an aldehyde or ketone-modified B7-H4 antibody of the present disclosure is reacted with a Linker-Drug moiety comprising a hydroxylamine or a hydrazine, the resulting oxime or hydrazone moiety in the modified B7-H4 antibody-drug conjugate may be relatively inert at neutral conditions.

In some embodiments, the modified B7-H4 antibody-drug conjugate of the present disclosure may be of high stability.

In some embodiments, the modified B7-H4 antibody and modified B7-H4 antibody-drug conjugate of the present disclosure may be synthesized by practical synthetic routes, as the process for introducing the functional group A" (e.g., azido, keto, or alkynyl) into the antibody is straightforward and generally applicable.

In some embodiments, a site-specific B7-H4 antibody-drug conjugate of the present disclosure is obtained by a process comprising reacting a modified B7-H4 antibody with a Linker-Drug moiety, wherein:
the Linker-Drug moiety comprises cycloalkynyl or heterocycloalkynyl,
the modified B7-H4 antibody, prior to conjugation, comprises a B7-H4 antibody and a modified GlcNAc moiety of *-GlcNAc-S"-A" attached to a B7-H4 antibody via the C1 position of the GlcNAc; GlcNAc is N-acetylglucosamine; S" is a sugar or a derivatized sugar; and A" is azido.

In some embodiments, A" is cycloalkynyl or heterocycloalkynyl. In some embodiments, A" is cycloalkynyl. In some embodiments, A" is heterocycloalkynyl.

In some embodiments, A" is strained cycloalkynyl or heterocycloalkynyl. In some embodiments, A" is strained cycloalkynyl. In some embodiments, A" is strained heterocycloalkynyl.

In some embodiments, a site-specific B7-H4 antibody-drug conjugate of the present disclosure is obtained by a process comprising the steps of:
(a) contacting an intermediate antibody of Formula (XXII):

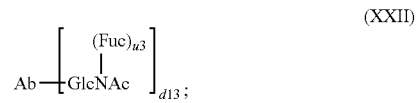

(XXII)

wherein:
Ab is an B7-H4 antibody; GlcNAc is N-acetylglucosamine; Fuc is fucose; $u_3$ is 0 or 1; and $d_{13}$ is an integer ranging from 1 to 12;
with a compound P"-S"-A", wherein:
S" is a sugar or a derivatized sugar; A" is azido; and P is uridine diphosphate (UDP), guanosine diphosphate (GDP), or cytidine diphosphate (CDP);
in the presence of an galactosyltransferase, thereby forming a modified B7-H4 antibody comprising the modified-GlcNAc moiety, *-GlcNAc-S"-A", (optionally, the modified-GlcNAc moiety is attached to the rest of the modified antibody the C1 position of the GlcNAc); and
(b) reacting the modified B7-H4 antibody with a Linker-Drug moiety comprising a strained cycloalkynyl or heterocycloalkynyl, thereby forming the antibody-drug conjugate.

Figure 5:
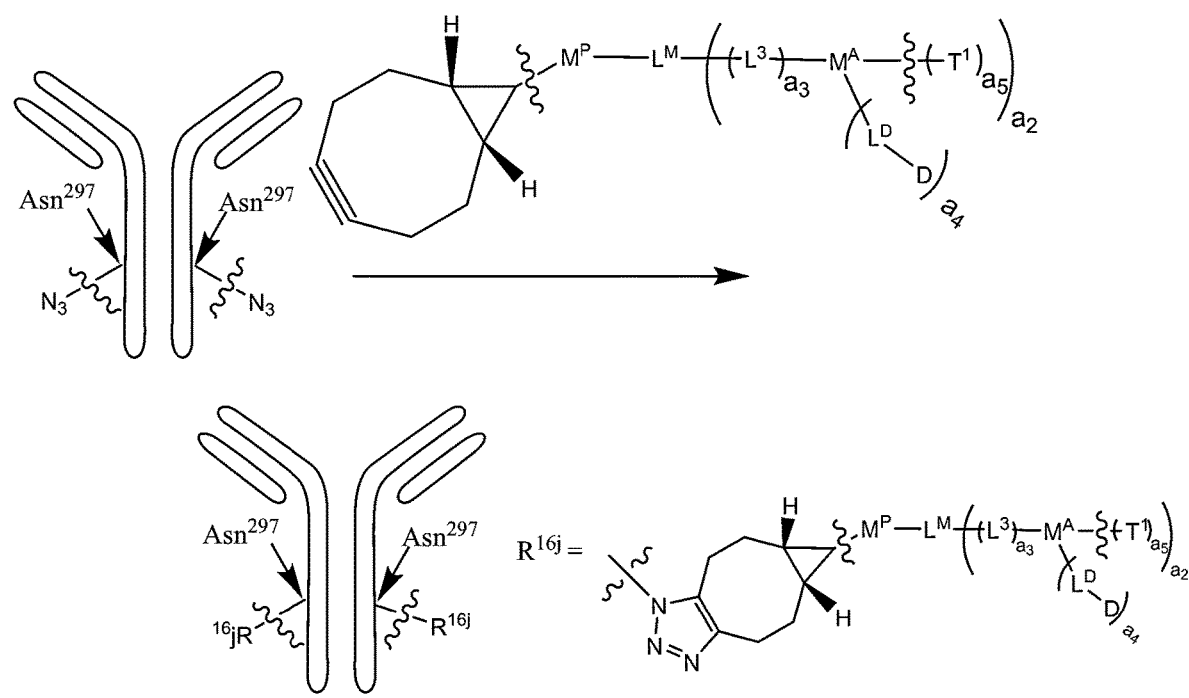
FIG. 5 is a scheme showing an embodiment of the process of preparing an antibody-drug conjugate, wherein an azido-modified antibody is conjugated to a Linker-Drug moiety comprising strained cycloalkynyl group.
Figure 6:
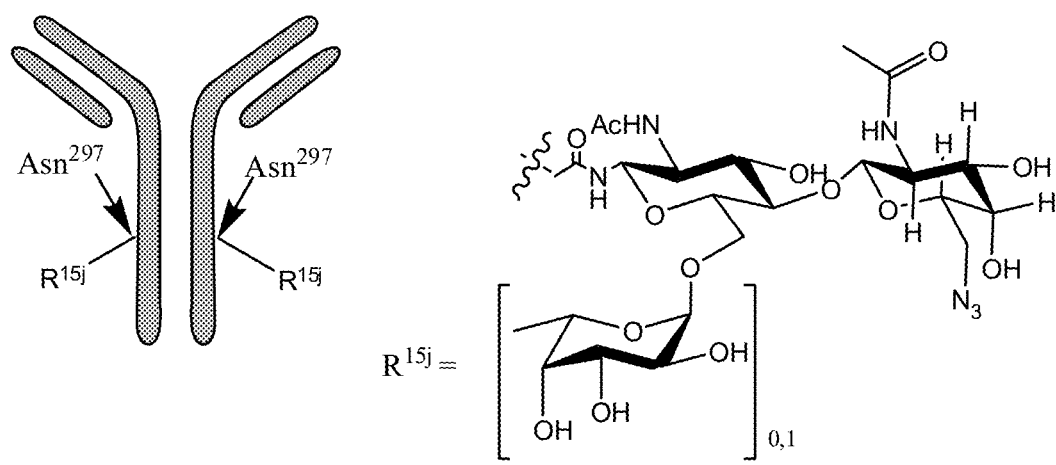
FIG. 6 is a graph showing a modified antibody.

In some embodiments, the process for preparing a site-specific B7-H4 antibody-drug conjugate is as depicted in FIG. 5.

In some embodiments, the modified B7-H4 antibody comprising an azido at each amino acid N297 of the antibody is conjugated with a Linker-drug moiety comprising strained cycloalkynyl or heterocycloalkynyl by metal-free click chemistry to form the site-specific antibody-drug conjugate of the present disclosure.

In some embodiments, when the modified B7-H4 antibody comprises at least one azido moiety and the Linker-drug moiety comprises a strained cycloalkynyl, the presence of a copper catalyst is not necessary for the cycloaddition reaction between the azido in the modified antibody and the strained cycloalkynyl or heterocycloalkynyl of the Linker-Drug moiety. In some embodiments, the cycloaddition reaction proceeds in the absence of a copper catalyst, which may alleviate several possible disadvantages of using a copper catalyst in the process.

In some embodiments, a Cu(I) catalyst is generally required in the cycloaddition of an azido moiety of an antibody and a terminal alkyne moiety. In some embodiments, extensive optimization and fine-tuning of conditions may be required to find the optimal parameters for efficient conversion. Nevertheless, even under such conditions, the concomitant formation of reactive oxygen species cannot always be fully avoided, which in turn may induce oxidative damage to the antibody/protein (e.g., oxidation of methionine, histidine, cysteine or disulfide bonds). Other protocols have employed Cu(I) sources such as CuBr for labeling fixed cells and synthesizing glycoproteins. In these cases, the instability of Cu(I) in air imposes a requirement for large excesses of Cu (e.g., greater than 4 mm) and ligand for efficient reactions, which could also raise the risk of antibody/protein damage or precipitation, plus the presence of residual metal after purification. Thus, the conjugation of an azido-containing antibody to a terminal alkyne in the presence of a copper catalyst can lead to extensive side-product formation by undesired amino acid oxidation.

In some embodiments, the modified B7-H4 antibody comprising an azido (e.g., at each amino acid N297 of the antibody) is conjugated with a Linker-Drug moiety comprising strained cycloalkynyl or heterocycloalkynyl (e.g., by metal-free click chemistry).

In some embodiments, upon conjugation, the azido moiety of the modified B7-H4 antibody and the strained cycloalkynyl or heterocycloalkynyl of the Linker-Drug moiety forms a triazole moiety of Formula (XXXV):

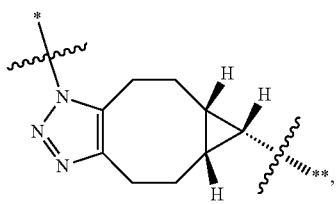

(XXXV)

wherein * denotes a direct or indirect attachment to the rest of the modified antibody; and ** indicates attachment to $M^P$ when present, or to $L^M$ or $M^A$.

In some embodiments, the B7-H4 antibody-drug conjugate of the present disclosure comprises one or more occurrences of D, wherein each D independently is a therapeutic agent (e.g., a cytotoxic drug moiety), wherein the one or more occurrences of D may be the same or different.

In some embodiments, one or more specific sites of the B7-H4 antibody is attached to the Linker-Drug moiety, wherein the Linker-Drug moieties attached to the one or more specific sites may be the same or different. In some embodiments, one or more Linker-Drug moieties that comprises one or more occurrences of D (i.e. a cytotoxic drug moiety) are attached to one B7-H4 antibody.

In some embodiments, D is a cytotoxic drug moiety wherein the cytotoxic drug moiety is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase; (q) a PARP inhibitor; (r) a NAMPT inhibitor; (s) a topoisomerase inhibitor; (t) a protein synthesis inhibitor; (u) a DNA-binding drug; (v) a DNA intercalation drug; or (w) an immunomodulatory compound.

In some embodiments, D, cytotoxic drug moiety, is (a) an auristatin compound; (b) a calicheamicin compound; (c) a duocarmycin compound; (d) a camptothecin compound, (e) a pyrrolobenzodiazepine compound; (f) a vinca compound; or an analog thereof.

In some embodiments, the auristatin compound is auristatin, dolastatin, monomethylauristatin E (MMAE), monomethylauristatin F (MMAF), auristatin F, AF-HPA, MMAF-HPA, or phenylenediamine (AFP).

In some embodiments, the duocarmycin or an analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

In some embodiments, the camptothecin compound is camptothecin, CPT-11 (irinotecan), SN-38, or topotecan.

In some embodiments, the pyrrolobenzodiazepine compound is a pyrrolobenzodiazepine monomer, a symmetrical pyrrolobenzodiazepine dimer, or an unsymmetrical pyrrolobenzodiazepine dimer.

In some embodiments, the modified B7-H4 antibody is modified at the amino acid N297.

In some embodiments, the total number of specific bonds formed between the Linker-Drug moiety and the modified B7-H4 antibody (or total number of attachment points) is 12 or less. In some embodiments, the total number of specific bonds formed between the Linker-Drug moiety and the modified B7-H4 antibody (or total number of attachment points) is 10 or less. In some embodiments, the total number of specific bonds formed between the Linker-Drug moiety and the modified B7-H4 antibody (or total number of attachment points) is 8 or less. In some embodiments, the total number of specific bonds formed between the Linker-Drug moiety and the modified B7-H4 antibody (or total number of attachment points) is 6 or less. In some embodiments, the total number of specific bonds formed between the Linker-Drug moiety and the modified B7-H4 antibody (or total number of attachment points) is 4 or less. In some embodiments, the total number of specific bonds formed between the Linker-Drug moiety and the modified B7-H4 antibody (or total number of attachment points) is 2 or less.

In some embodiments, the total number of specific bonds formed between the Linker-Drug moiety and the modified B7-H4 antibody (or total number of attachment points) is 2.

In some embodiments, the modified B7-H4 antibody, linker, or therapeutic agent described herein may be assembled into the conjugate or scaffold of the present disclosure according to various techniques and methods known in the art. The conjugate of the present disclosure, and method for producing the conjugate, are described herein (e.g., by way of non-limiting embodiments and examples).

In some embodiments, the total number of bonds formed between the Linker-Drug moiety and the modified B7-H4 antibody (or total number of attachment points) is 12 or less.

In some embodiments, the ratio between the Linker-Drug moiety and the modified B7-H4 antibody is greater than 1:1 and less than or equal to 12:1. In some embodiments, the ratio between Linker-Drug moiety and the modified B7-H4 antibody is about 12:1, about 11:1, about 10; 1, about 9:1, about 8:1, about 7:1, about 6:1, about 5:1, about 4:1, about 3:1, about 2:1, or about 1:1. In some embodiments, the ratio between Linker-Drug moiety and the modified B7-H4 antibody is between 2:1 and 10:1. In some embodiments, the ratio between Linker-Drug moiety and the modified B7-H4 antibody is about 10:1, about 9:1, about 8:1, about 7:1, about 6:1, about 5:1, about 4:1, about 3:1, or about 2:1. In some embodiments, the ratio between Linker-Drug moiety and the modified B7-H4 antibody is between about 2:1 and about 4:1. In some embodiments, the ratio between Linker-Drug moiety and the modified B7-H4 antibody is about 4:1, about 3:1, or about 2:1. In some embodiments, the ratio between Linker-Drug moiety and the modified B7-H4 antibody is about 2:1, or 1:1.

In some embodiments, $a_2$ is 3, the ratio between the Linker-Drug moiety and the modified B7-H4 antibody is 2:1, and the ratio between the therapeutic agent (D) and the modified B7-H4 antibody is about 8:1, about 7:1, about 6:1, about 5:1, about 4:1, about 3:1, about 2:1 or about 1:1. In some embodiments, $a_2$ is 3, the ratio between the Linker-Drug moiety and the modified B7-H4 antibody is 2:1, and the ratio between the therapeutic agent (D) and the modified B7-H4 antibody is about 6:1, about 5:1, about 4:1, about 3:1, about 2:1 or about 1:1. In some embodiments, $a_2$ is 3, the ratio between the Linker-Drug moiety and the modified B7-H4 antibody is 2:1, and the ratio between the therapeutic agent (D) and the modified B7-H4 antibody is about 6:1, about 5:1, about 4:1 or about 3:1. In some embodiments, $a_2$ is 3, the ratio between the Linker-Drug moiety and the modified B7-H4 antibody is 1:1, and the ratio between the therapeutic agent (D) and the modified B7-H4 antibody is about 3:1, about 2:1 or about 1:1.

In some embodiments, $a_2$ is 3, the ratio between the Linker-Drug moiety and the modified B7-H4 antibody is 2:1, and the ratio between the therapeutic agent (D) and the modified B7-H4 antibody is about 8:1. In some embodiments, $a_2$ is 3, the ratio between the Linker-Drug moiety and the modified antibody is 2:1, and the ratio between the therapeutic agent (D) and the modified B7-H4 antibody is about 6:1. In some embodiments, $a_2$ is 3, the ratio between the Linker-Drug moiety and the modified B7-H4 antibody is 2:1, and the ratio between the therapeutic agent (D) and the modified B7-H4 antibody is about 5:1. In some embodiments, $a_2$ is 3, the ratio between the Linker-Drug moiety and the modified B7-H4 antibody is 2:1, and the ratio between the therapeutic agent (D) and the modified B7-H4 antibody is about 4:1. In some embodiments, $a_2$ is 3, the ratio between the Linker-Drug moiety and the modified antibody is 2:1, and the ratio between the therapeutic agent (D) and the modified B7-H4 antibody is about 3:1. In some embodiments, $a_2$ is 3, the ratio between the Linker-Drug moiety and the modified antibody is 2:1, and the ratio between the therapeutic agent (D) and the modified B7-H4 antibody is about 2:1. In some embodiments, $a_2$ is 3, the ratio between the Linker-Drug moiety and the modified B7-H4 antibody is 2:1, and the ratio between the therapeutic agent (D) and the modified B7-H4 antibody is about 1:1.

In some embodiments, the ratio between Linker-Drug moiety and the modified B7-H4 antibody is about 2:1.

In some embodiments, the antibody comprises an asparagine group in the region 290-305 (e.g., at N297) attached to the sugar-derivative moiety, which comprises a functional group A"; and the modified B7-H4 antibody is conjugated to the Linker-Drug moiety by a covalent bond formed between A" and a functional group of the Linker-Drug moiety.

In some embodiments, the Linker-Drug moiety comprises at least two functional groups, each of which is capable of forming a covalent bond with a functional group A" of the sugar-derivative moiety of the modified B7-H4 antibody (e.g., at amino acid N297 of the antibody) to form an antibody-drug conjugate.

In some embodiments, the ratio between the modified B7-H4 antibody and the Linker-Drug moiety is between about 1:1 and about 1:2.

In some embodiments, the modified B7-H4 antibody drug conjugate and scaffold of the present disclosure can be purified (e.g., to remove any starting materials) by extensive diafiltration. If necessary, additional purification by size exclusion chromatography can be conducted to remove any aggregated conjugates. In some embodiments, the purified conjugate or scaffold comprises less than 5% w/w (e.g., <2% w/w) aggregated conjugates as determined by SEC; less than 0.5% w/w (e.g., <0.1% w/w) free (unconjugated) drug as determined by RP-HPLC; less than 1% w/w drug carrying-peptide-containing scaffolds as determined by SEC; and/or less than 2% w/w (e.g., <1% w/w) unconjugated antibodies as determined by HIC-HPLC.

In some embodiments, the modified B7-H4 antibody drug conjugate to a cytotoxic drug moiety is selected from the conjugates described in Table B2.

TABLE B2

Structure

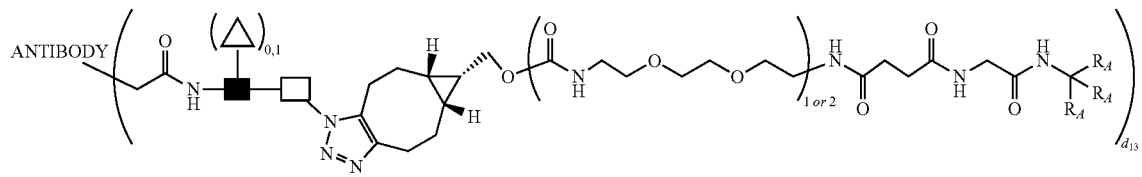

TABLE B2-continued
Structure
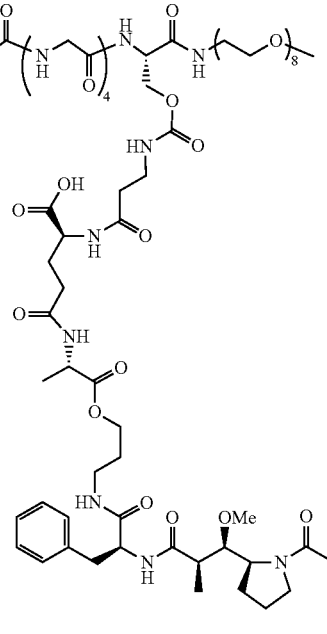
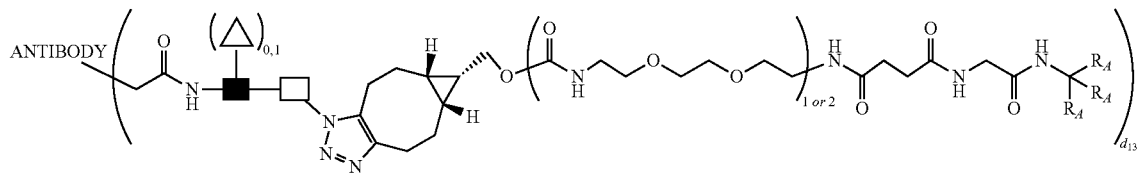

TABLE B2-continued
Structure
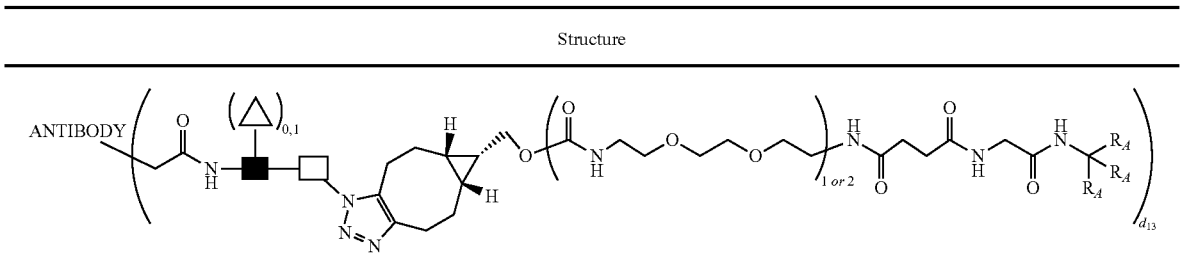
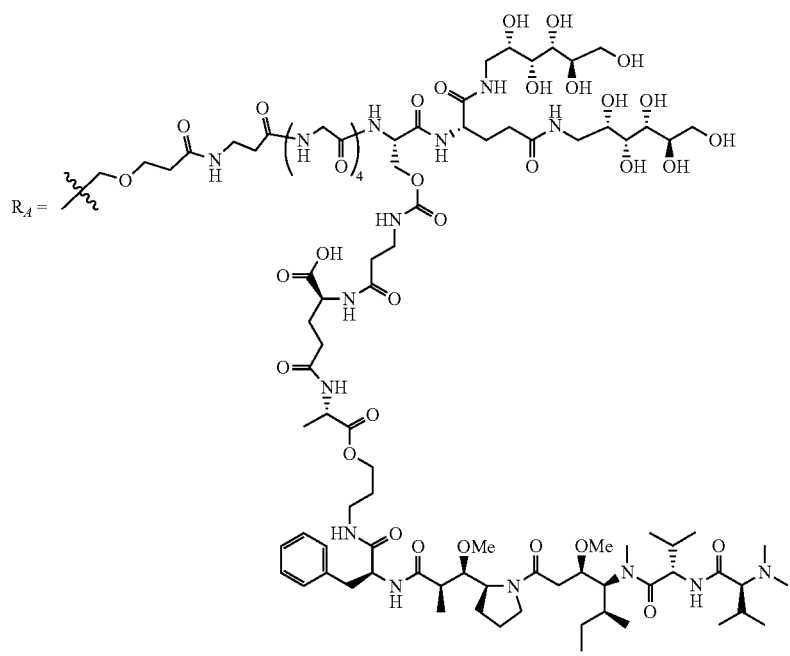
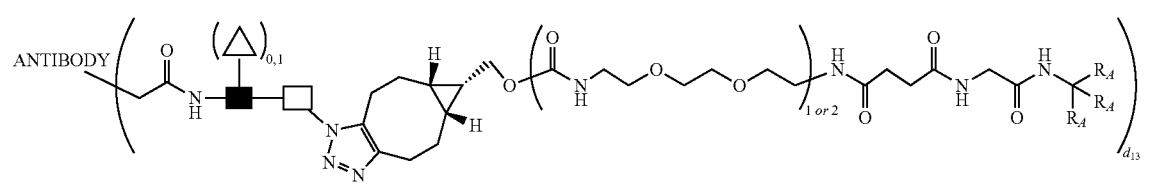

TABLE B2-continued
Structure
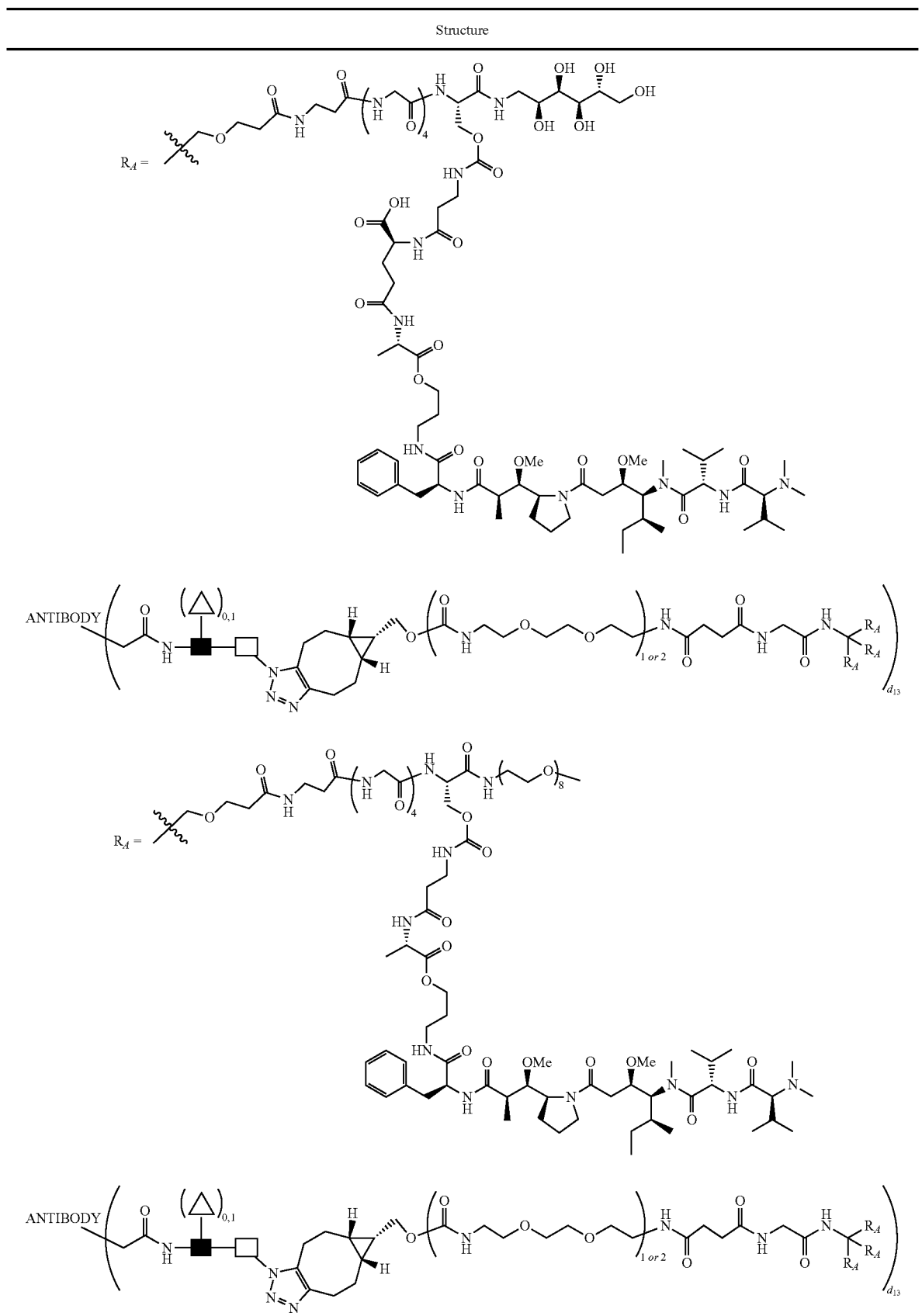

TABLE B2-continued
Structure
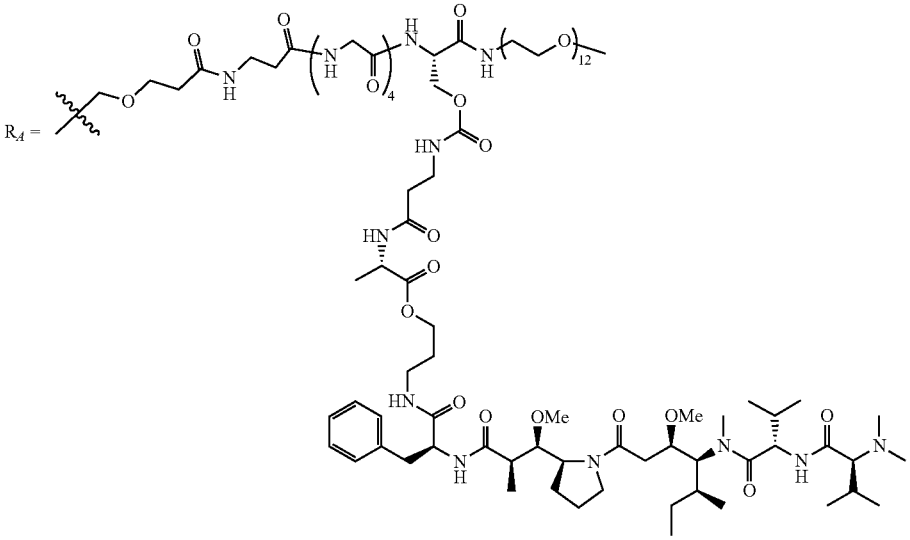
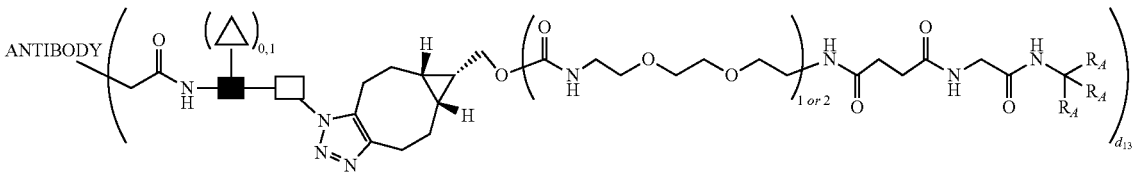
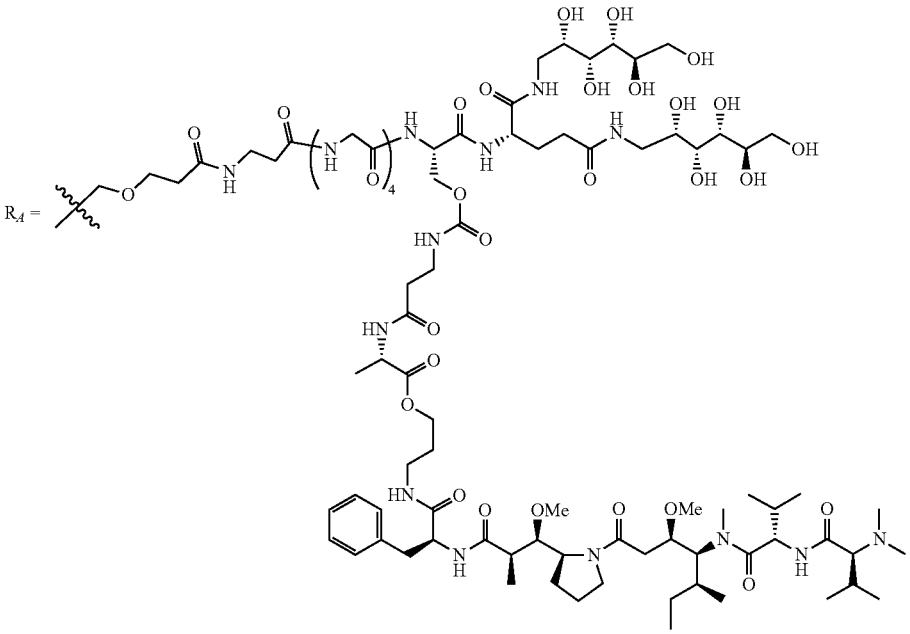
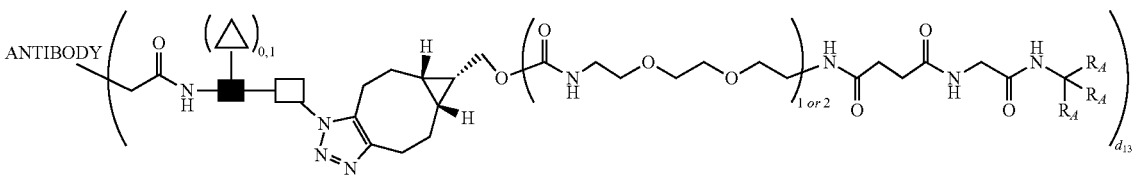

TABLE B2-continued
Structure
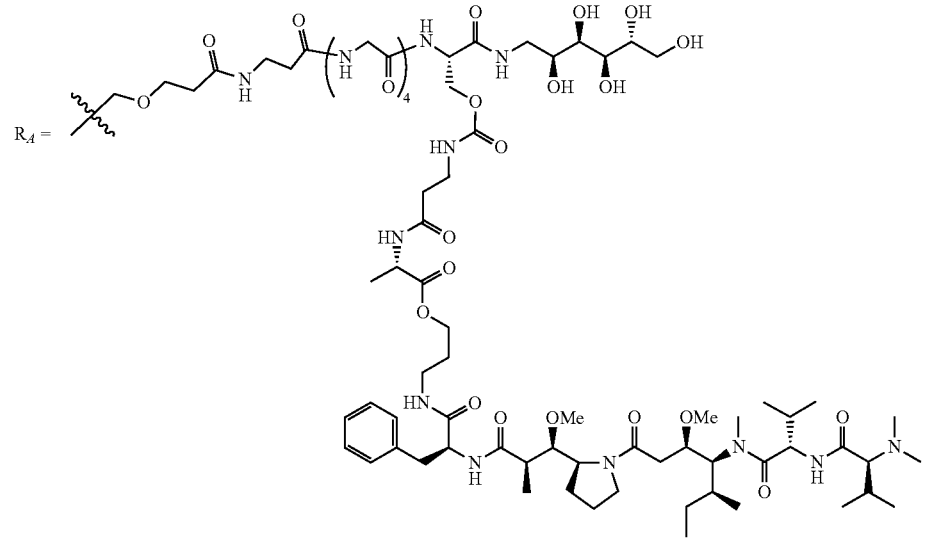
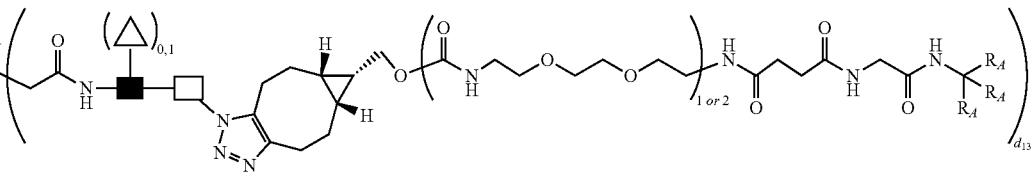
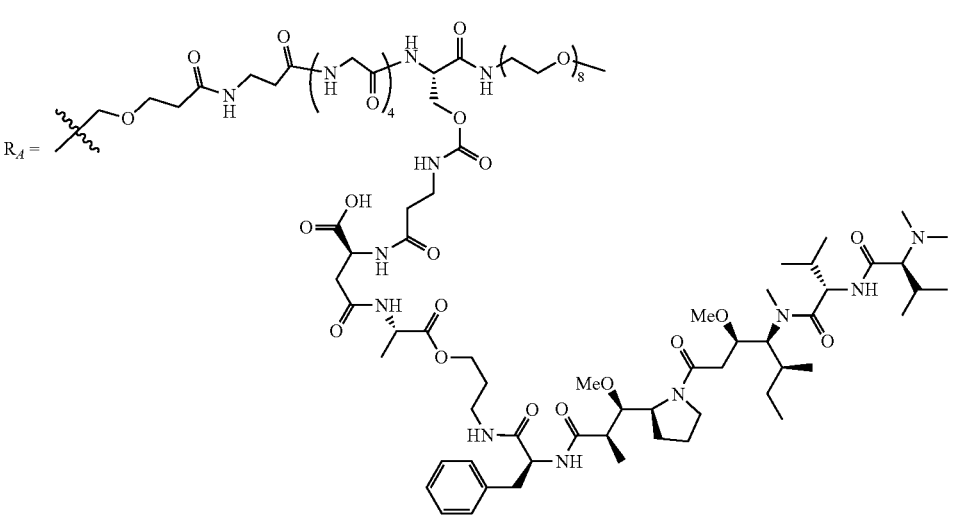
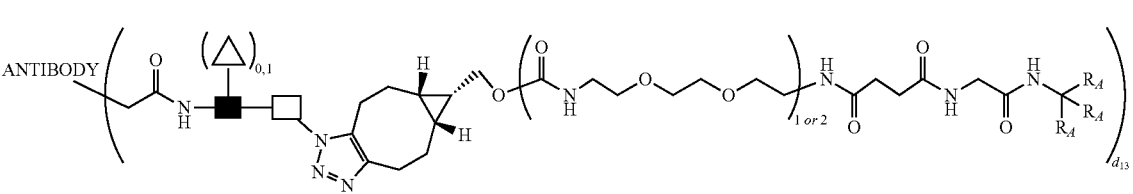

TABLE B2-continued

Structure

TABLE B2-continued
Structure
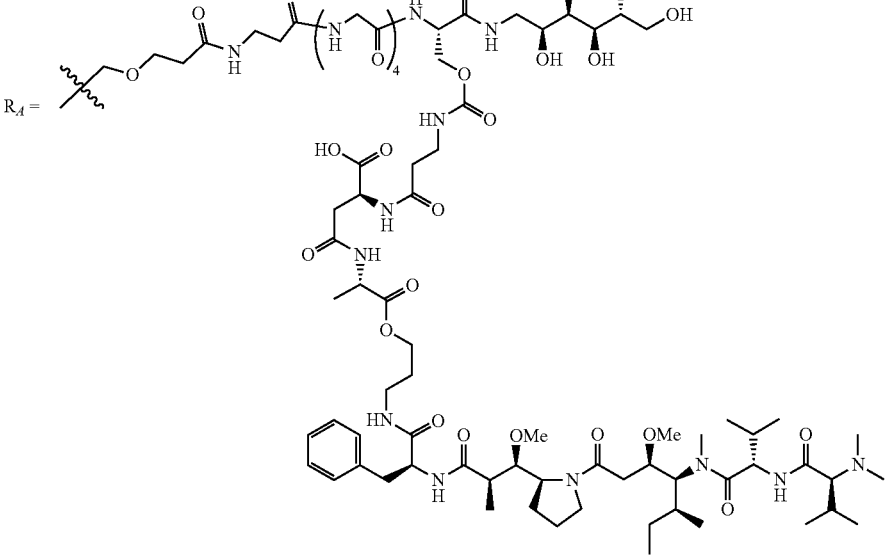
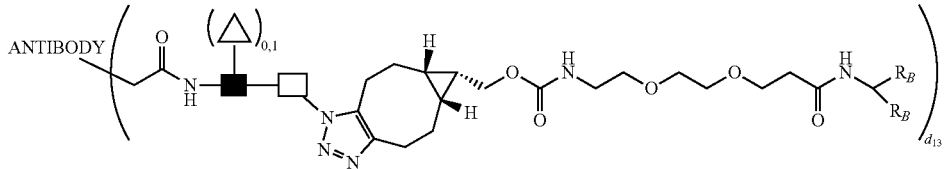
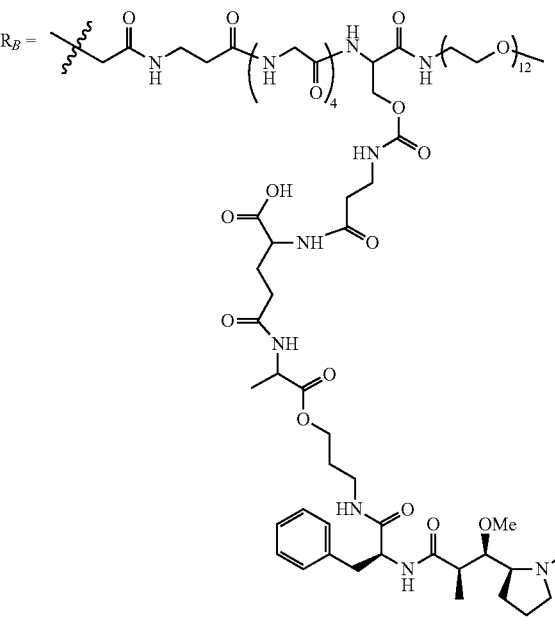
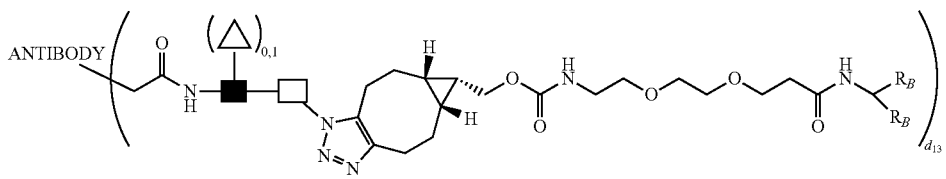

TABLE B2-continued
Structure
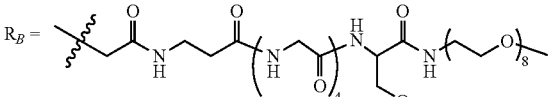
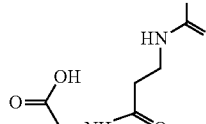
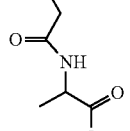

TABLE B2-continued
Structure
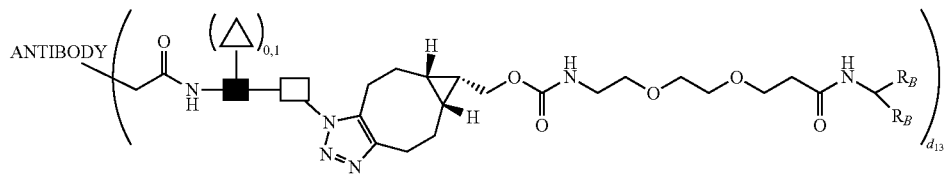
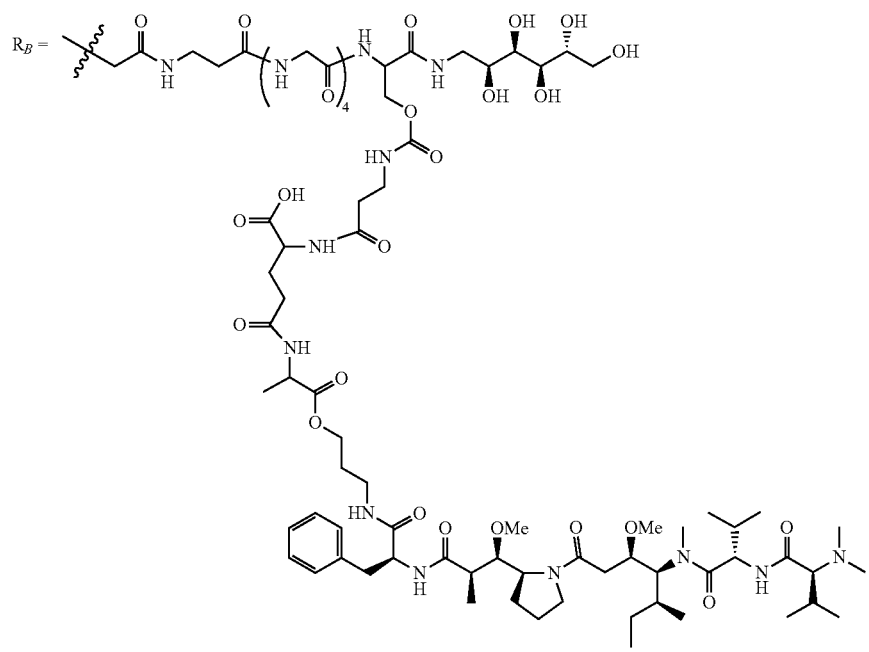
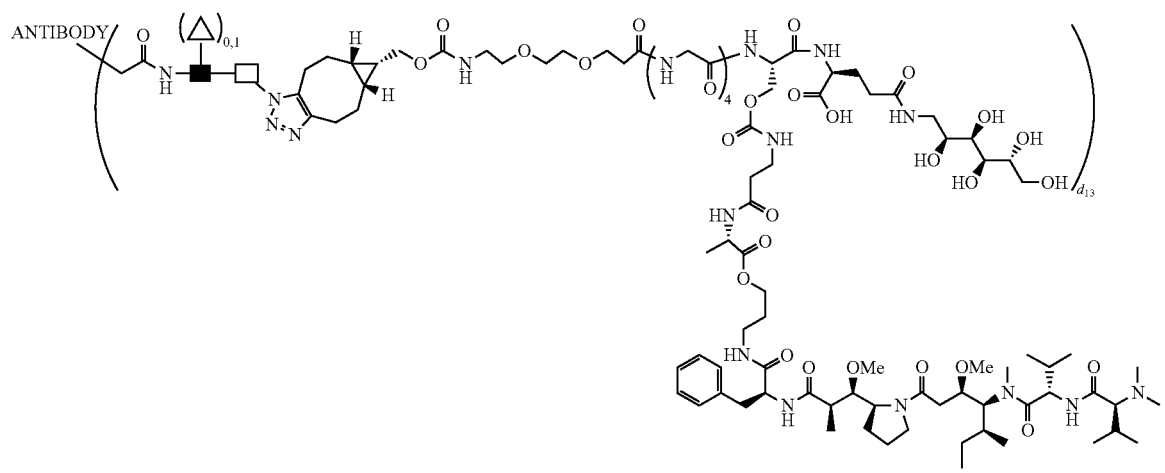

TABLE B2-continued
Structure
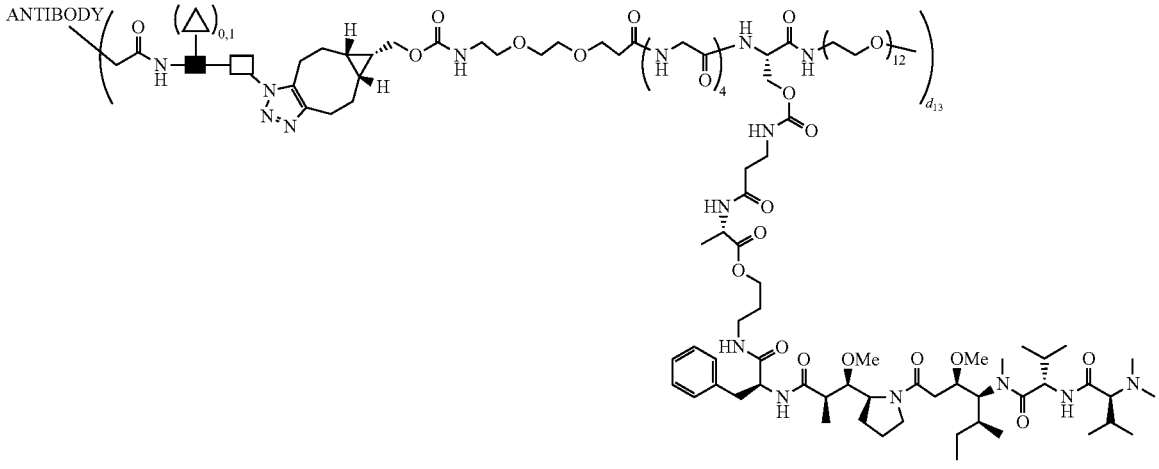
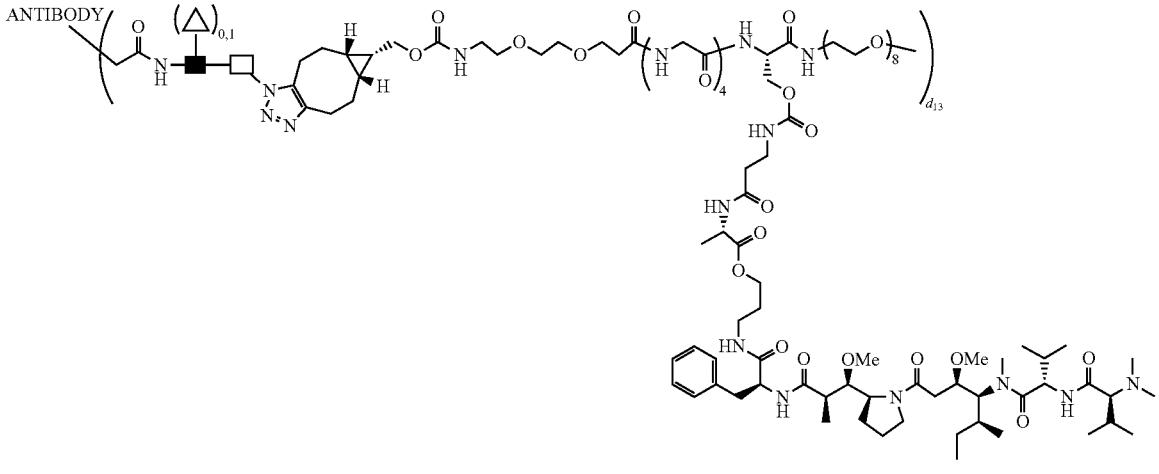
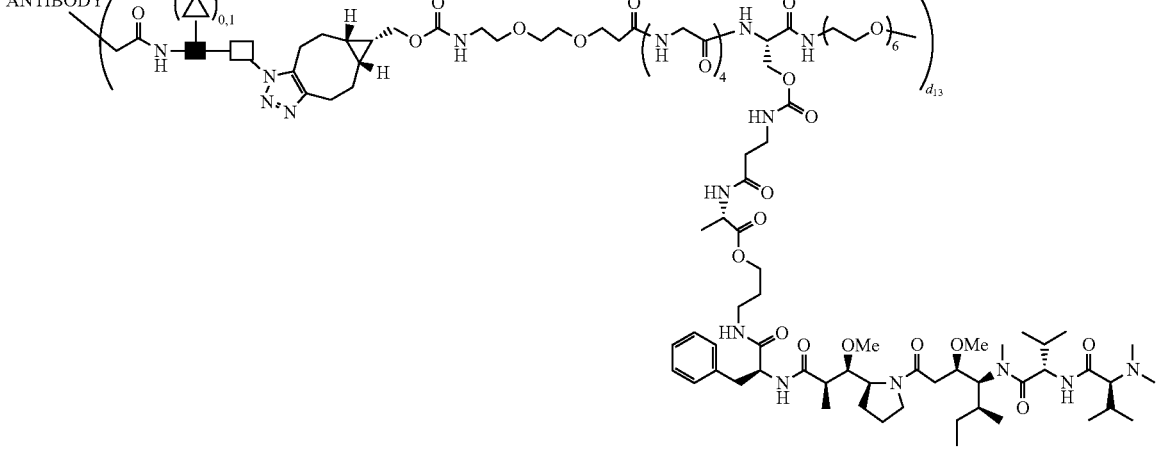

TABLE B2-continued

Structure wherein
Antibody is a modified B7-H4 antibody;
■ is GlcNAc; Δ is Fuc; □ is GalNAc; and $d_{13}$ is as defined herein.

It is understood that, unless stated otherwise, the symbol of ■ refers to GlcNAc in the present disclosure. It is understood that, unless stated otherwise, the symbol of Δ refers to fucose in the present disclosure. It is understood that, unless stated otherwise, the symbol of □ refers to GalNAc in the present disclosure.

In some embodiments, the modified B7-H4 antibody-drug conjugate is of Formula (XXXIV):

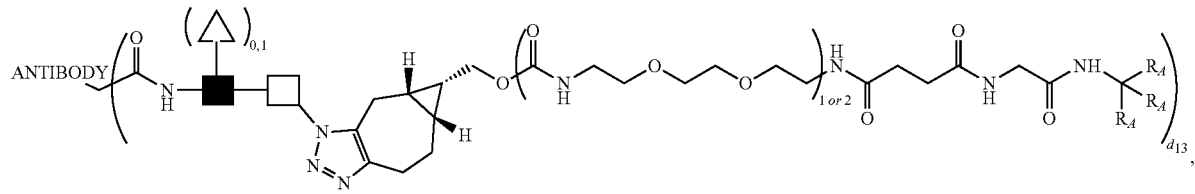

(XXX)

wherein:
each $R_A$ is

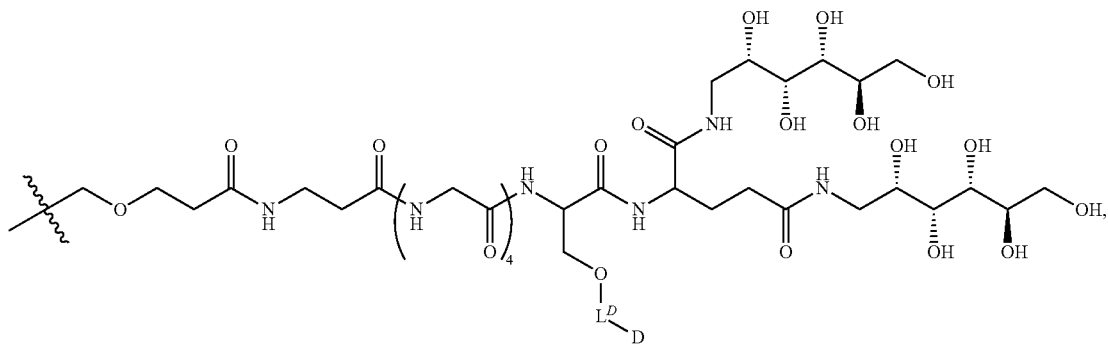

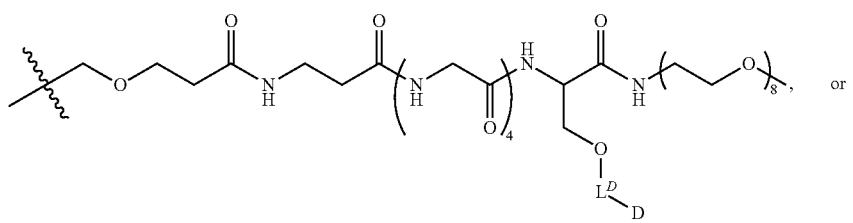

or

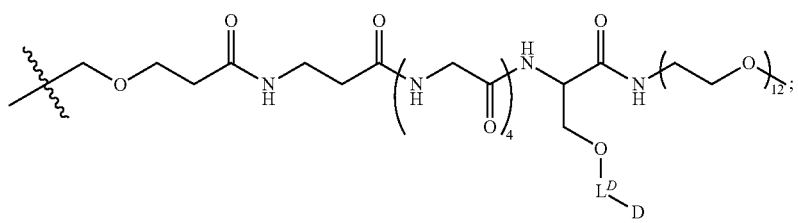

$d_{13}$ is 2; and the one or more Linker-Drug moiety is attached to the asparagine group at N297 of the antibody.

In some embodiments, the modified B7-H4 antibody-drug conjugate is of Formula (XXXIV) wherein each $R_A$ is:
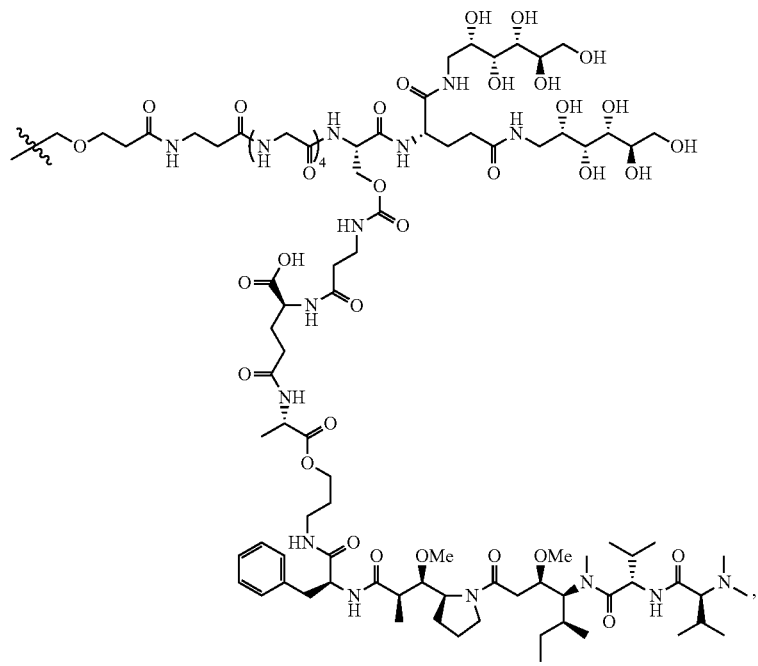
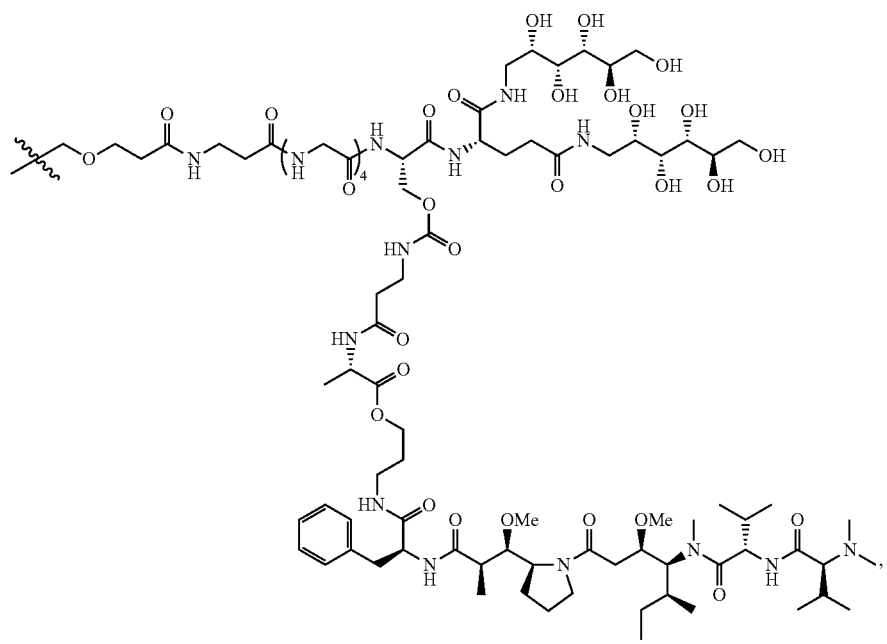

-continued
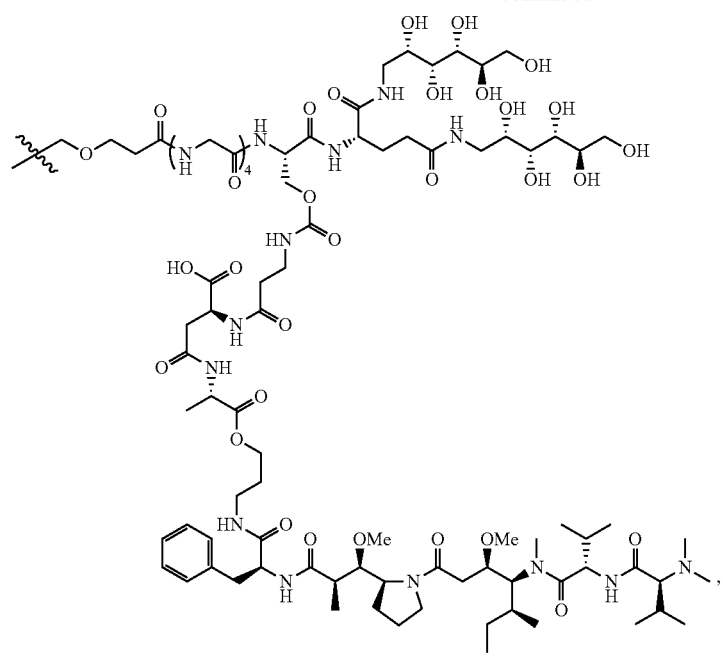
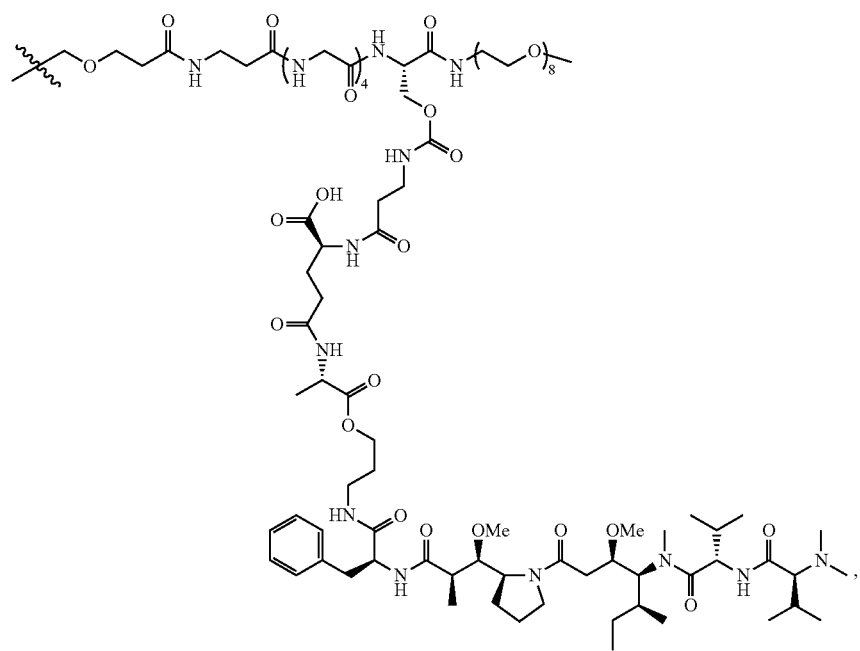

-continued
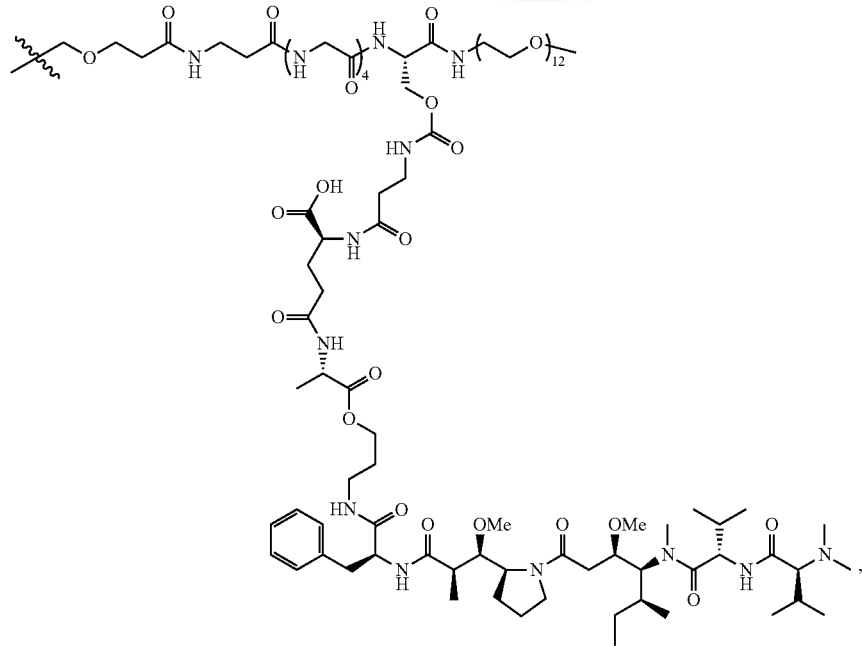
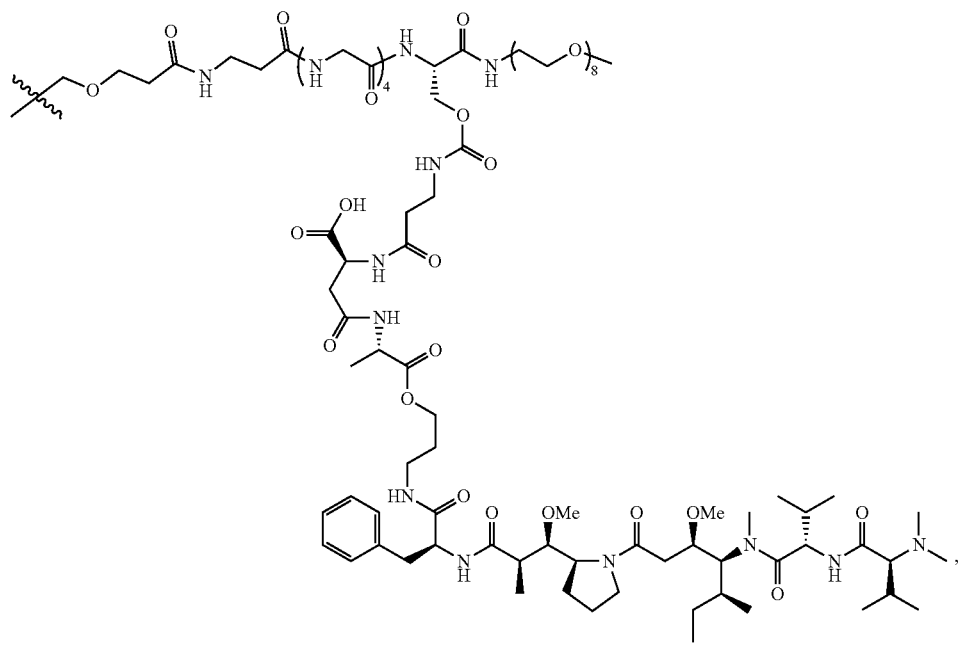

-continued
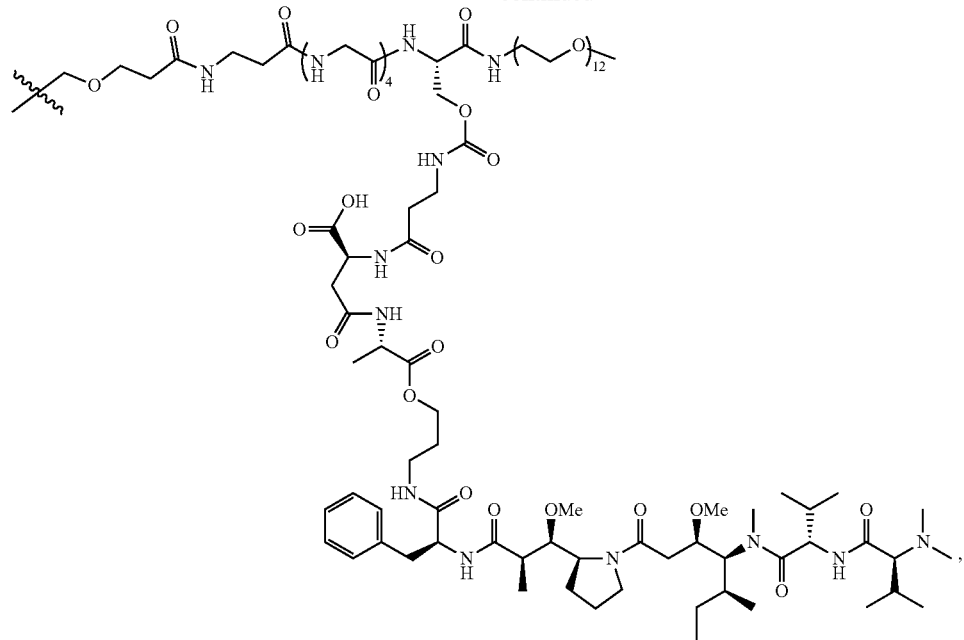
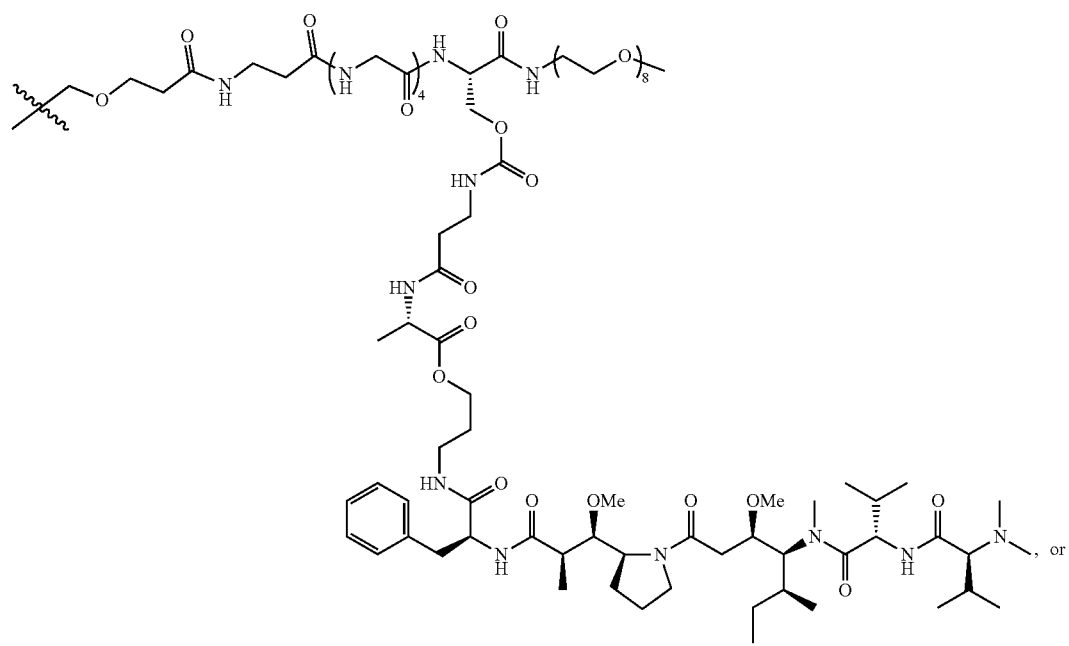

-continued
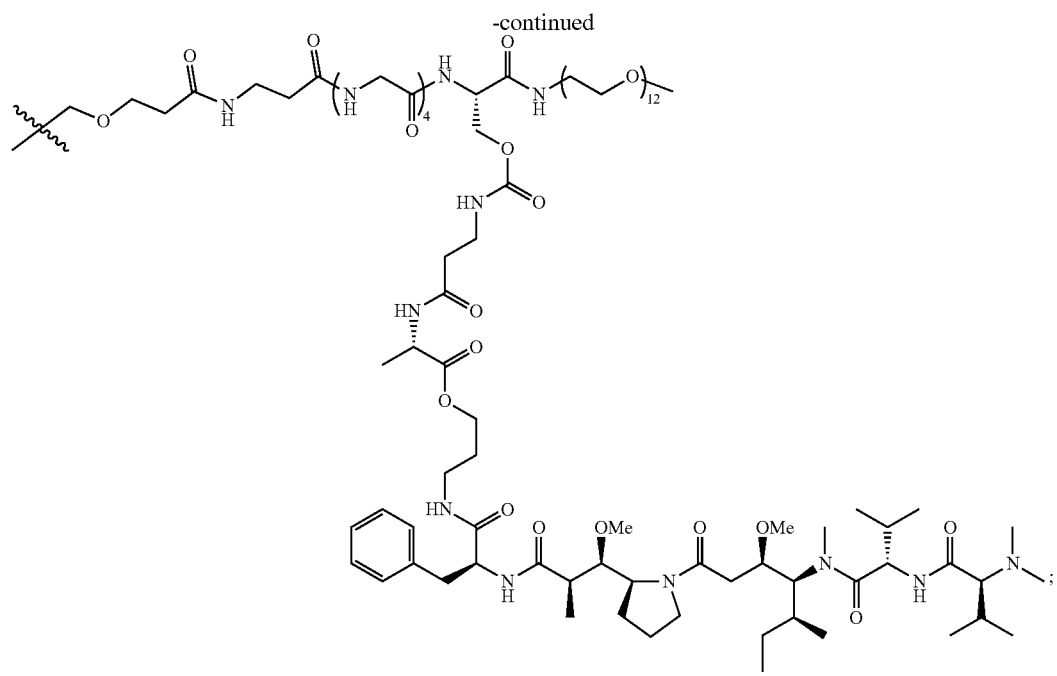
wherein $d_{13}$ is 2; and the modified B7-H4 antibody comprises one or more asparagine group at N297 being connected to the rest of the conjugate.
In some embodiments, the modified B7-H4 antibody-drug conjugate is of Formula (XXXIV), wherein each $R_A$ is
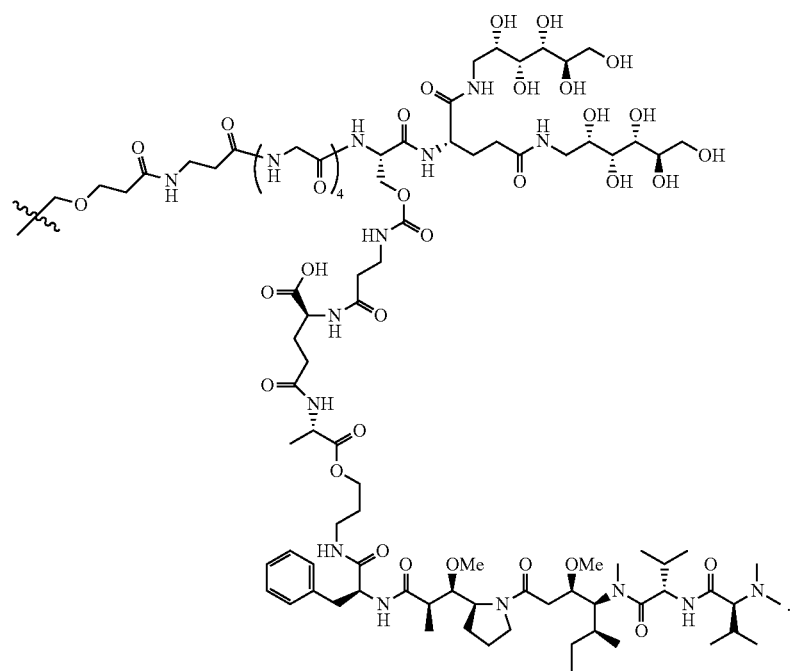

In some embodiments, the modified B7-H4 antibody-drug conjugate is of Formula (XXXIV), wherein each $R_A$ is
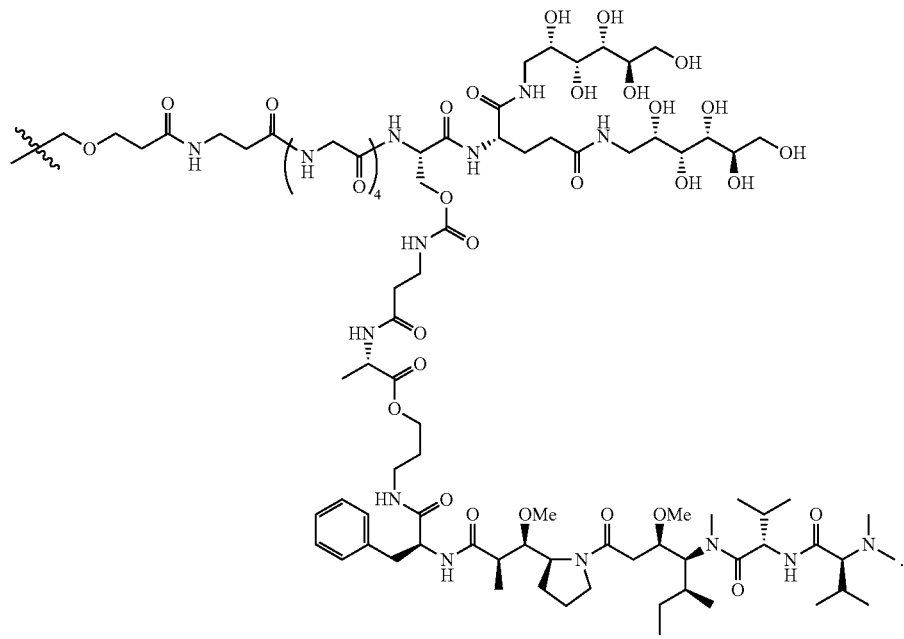
In some embodiments, the modified B7-H4 antibody-drug conjugate is of Formula (XXXIV), wherein each $R_A$ is
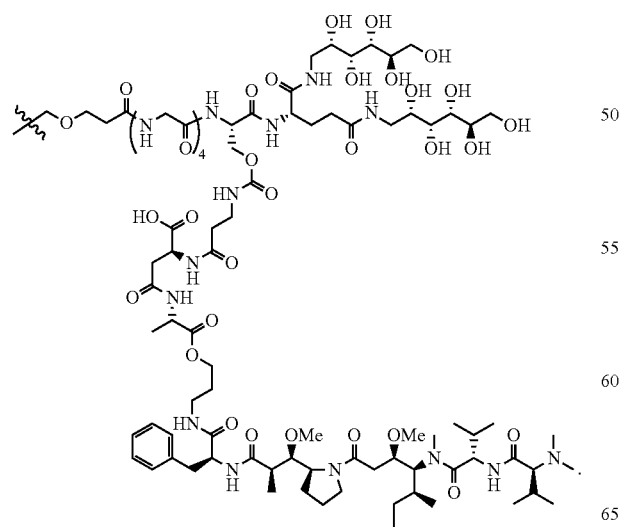

In some embodiments, the modified B7-H4 antibody-drug conjugate is of Formula (XXXIV), wherein each $R_A$ is
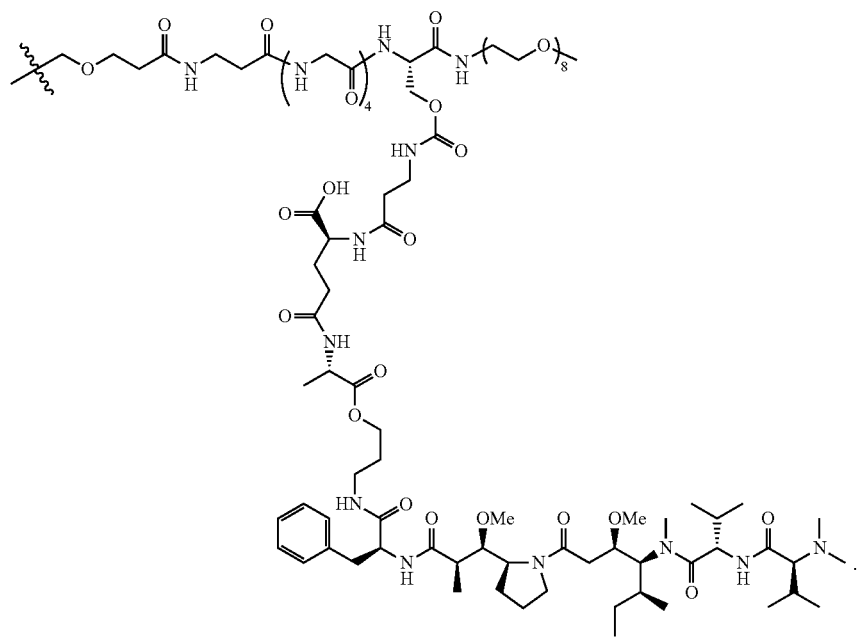
In some embodiments, the modified B7-H4 antibody-drug conjugate is of Formula (XXXIV), wherein each $R_A$ is
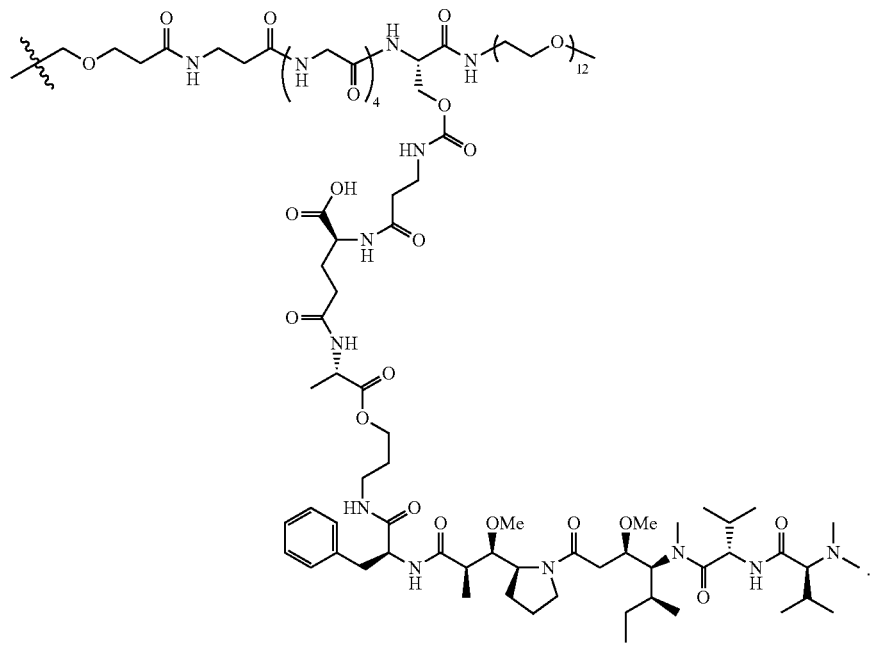

In some embodiments, the modified B7-H4 antibody-drug conjugate is of Formula (XXXIV), wherein each $R_A$ is
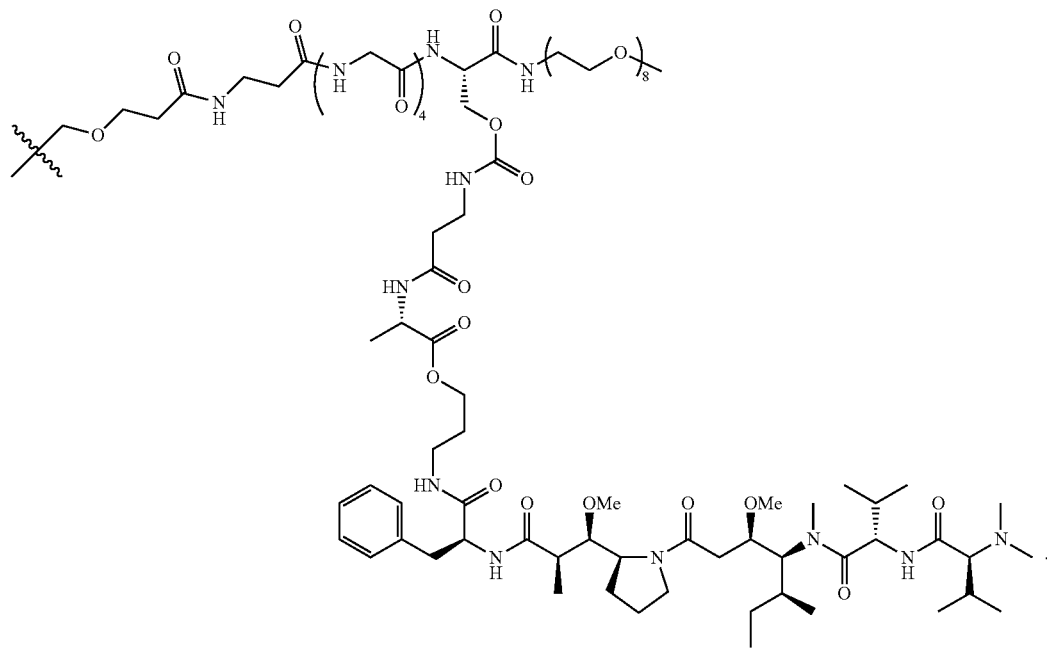
In some embodiments, the modified B7-H4 antibody-drug conjugate is of Formula (XXXIV), wherein each $R_A$ is
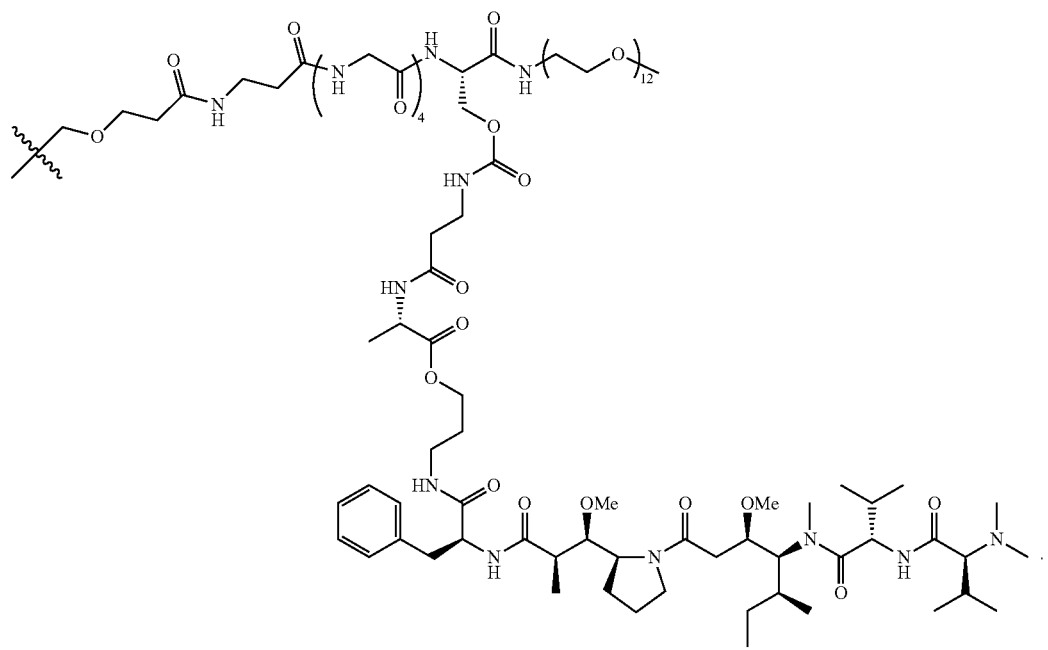

In some embodiments, the modified B7-H4 antibody-drug conjugate is of Formula (XXXIV), wherein each $R_A$ is:
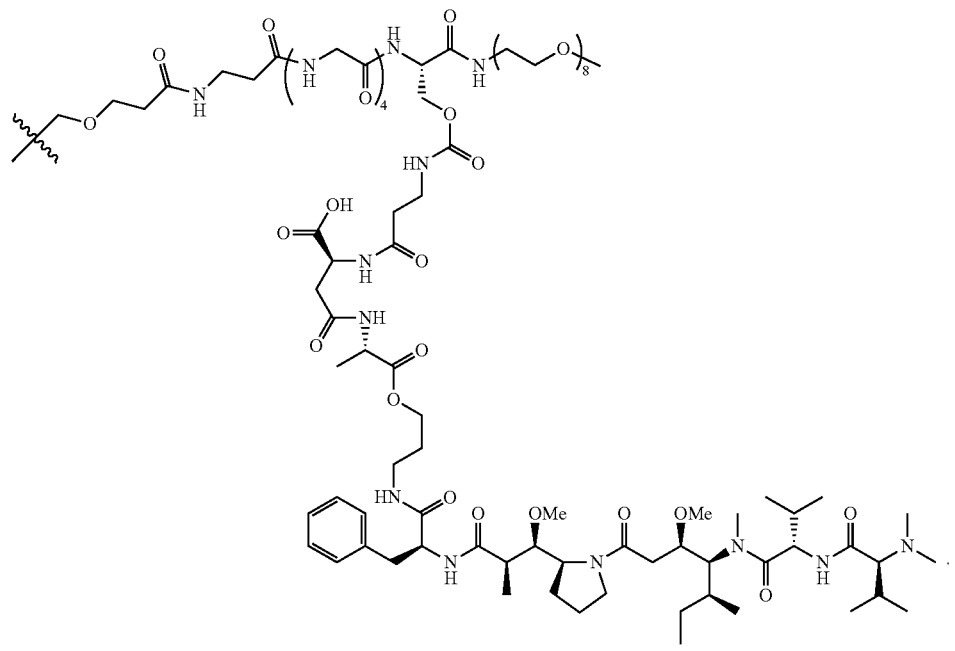
In some embodiments, the modified B7-H4 antibody-drug conjugate is of Formula (XXXIV), wherein each $R_A$ is
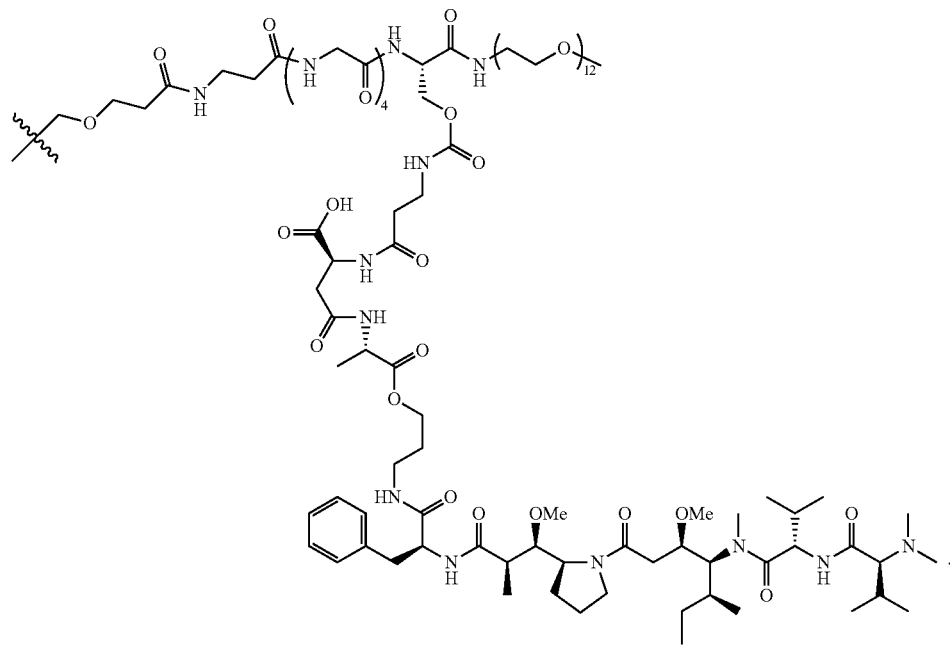

In some embodiments, the modified B7-H4 antibody-drug conjugate is of Formula (XXXIV-1), (XXXIV-2), (XXXIV-3), or (XXXIV-4):
(XXXIV-1)
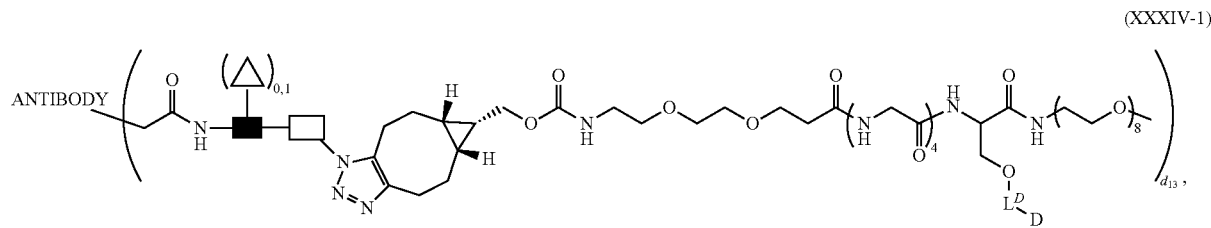
(XXXIV-2)
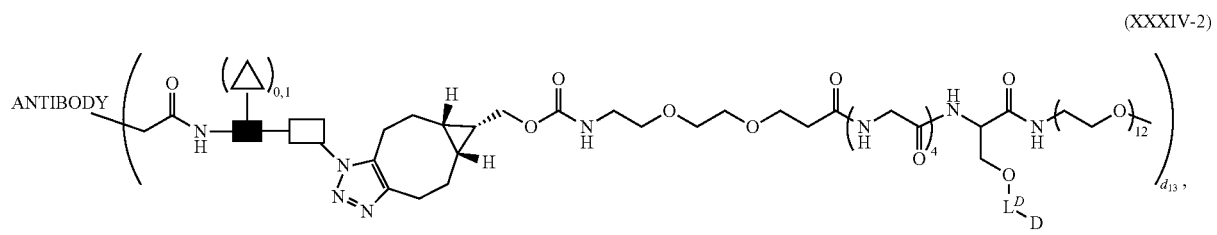
(XXXIV-3)
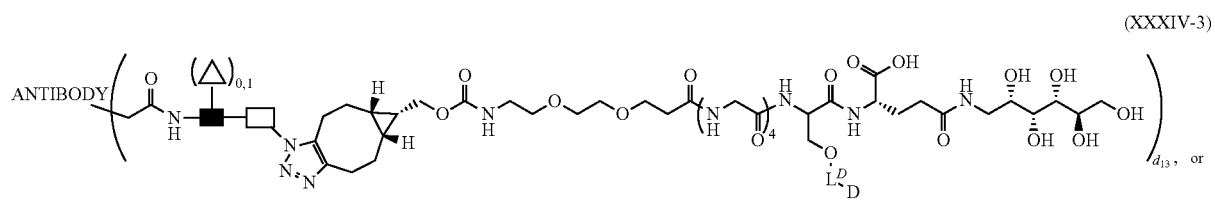
(XXXIV-4)
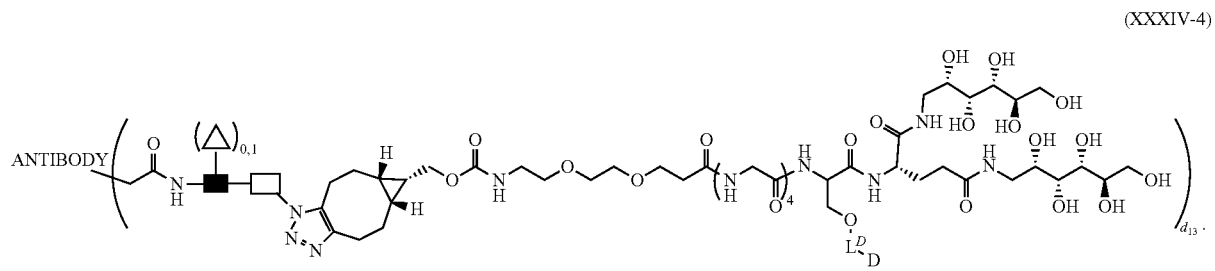
In some embodiments, the modified B37-H4 antibody-drug conjugate is of Formula (XXXV):
(XXXV)
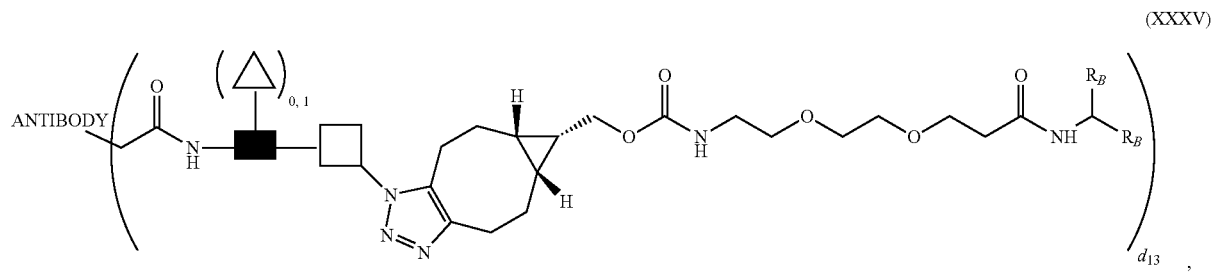

wherein each $R_B$ is:
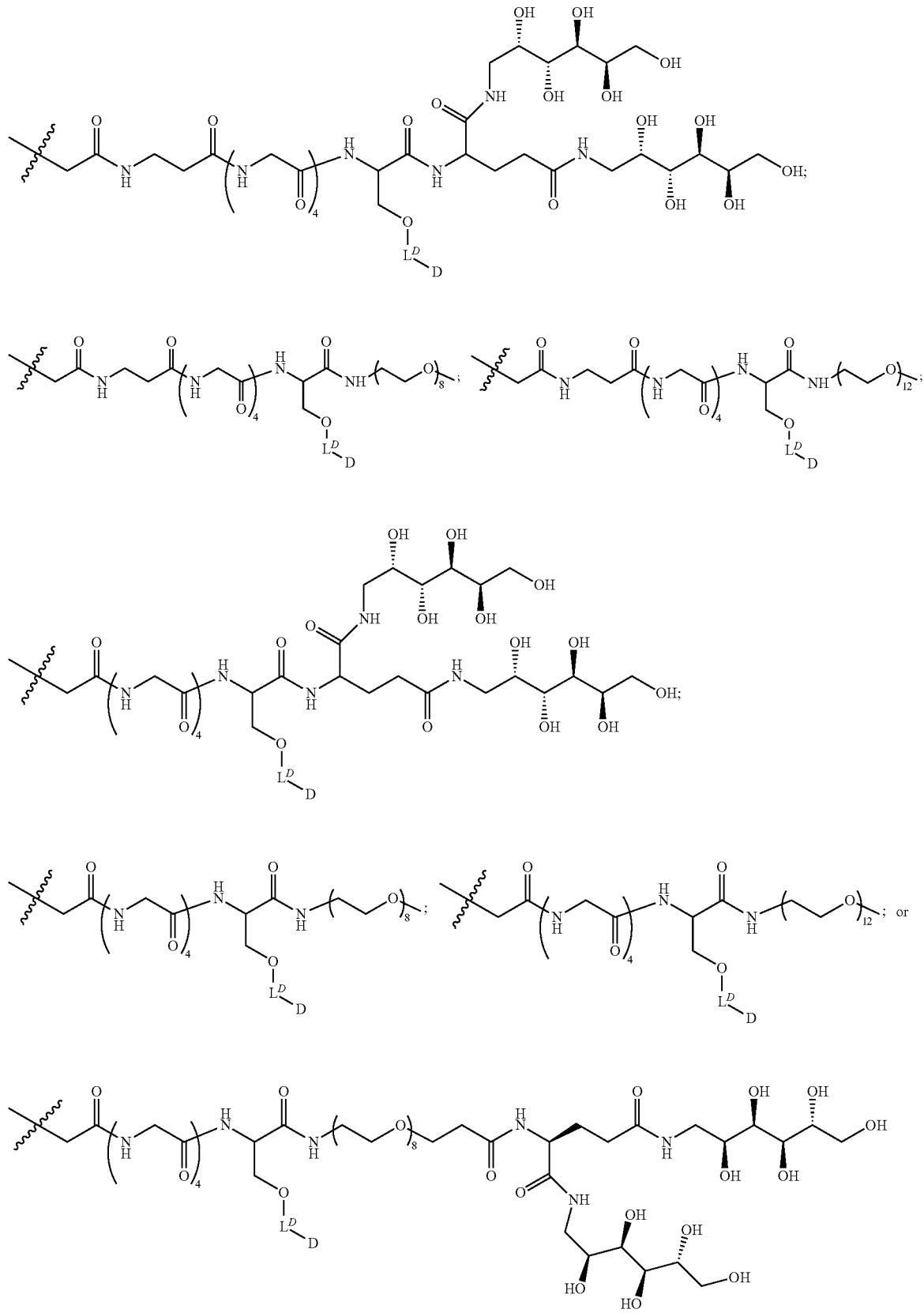

In some embodiments, the modified B7-H4 antibody-drug conjugate is of Formula (XXXIV-1), (XXXIV-2), (XXXIV-3), (XXXIV-4), or (XXXV), wherein the moiety of -L$^D$-D is:
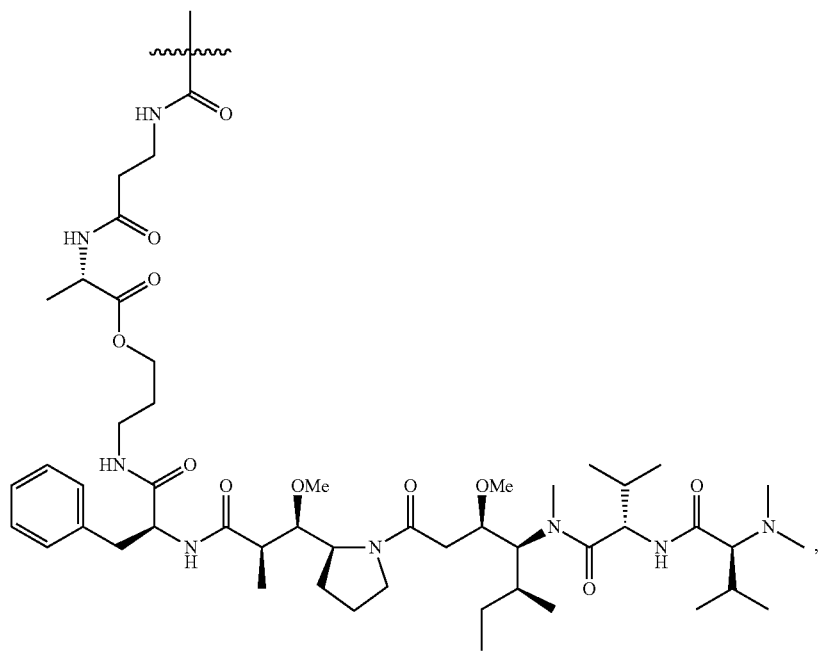
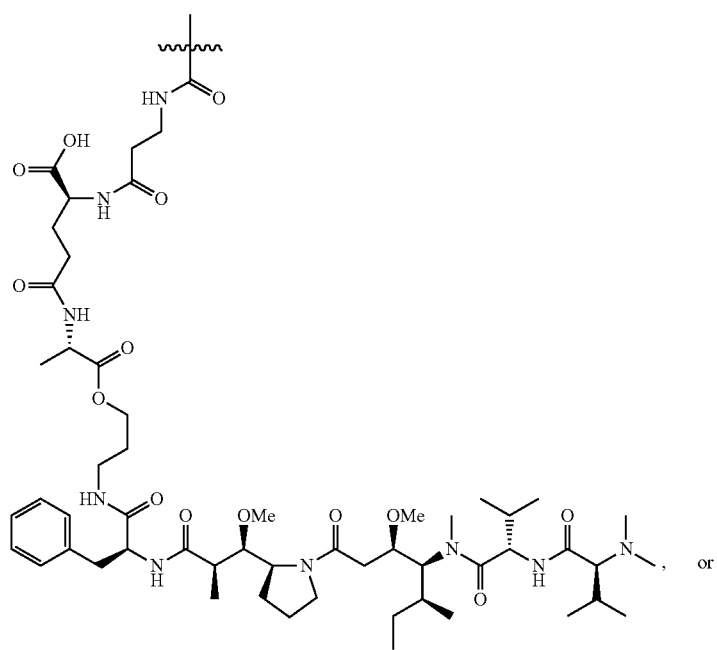
or

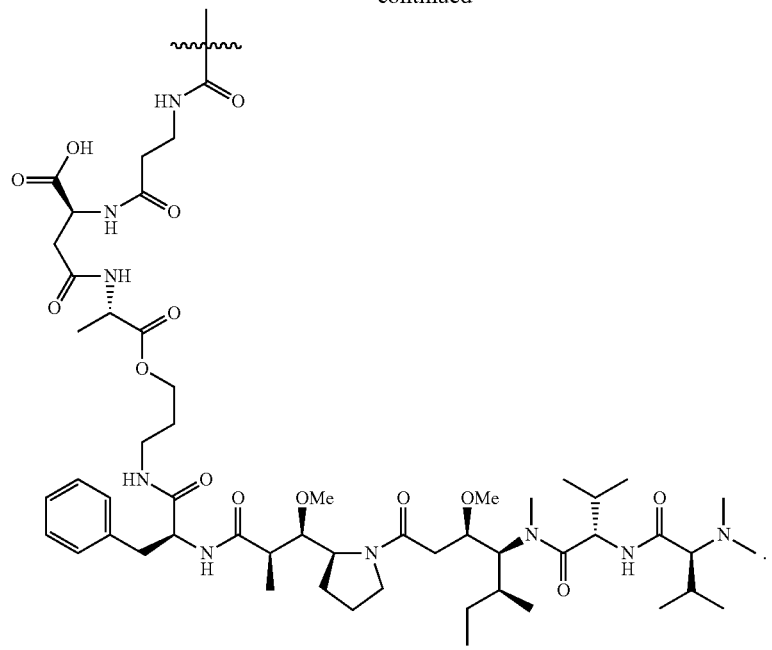
In some embodiments, the modified B7-H4 antibody-drug conjugate is of Formula (XXXIV-1), (XXXIV-2), (XXXIV-3), (XXXIV-4), or (XXXV), wherein the moiety of -L$^D$-D is:
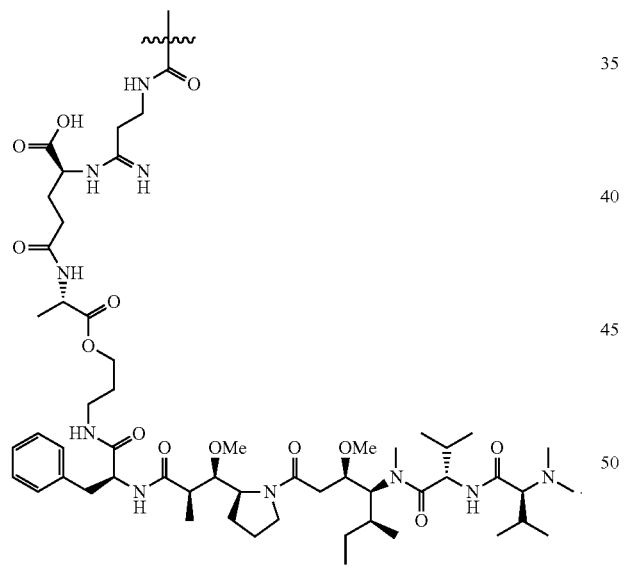
In some embodiments, the modified B7-H4 antibody-drug conjugate is of Formula (XXXVI):
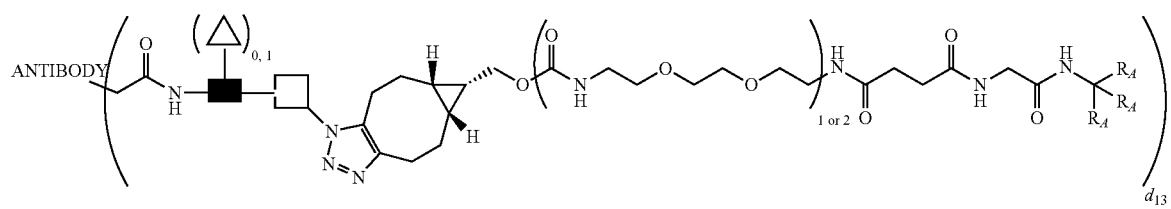

wherein each $R_A$ is
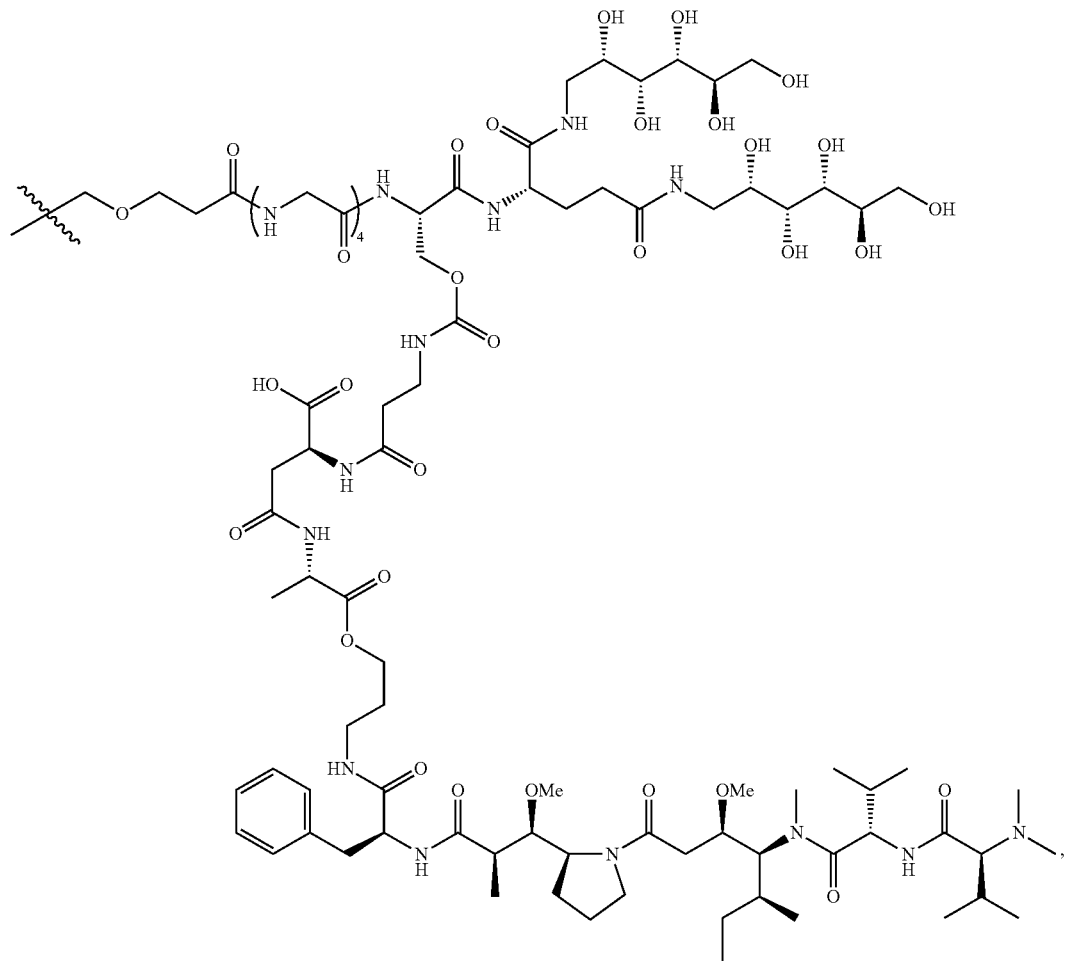
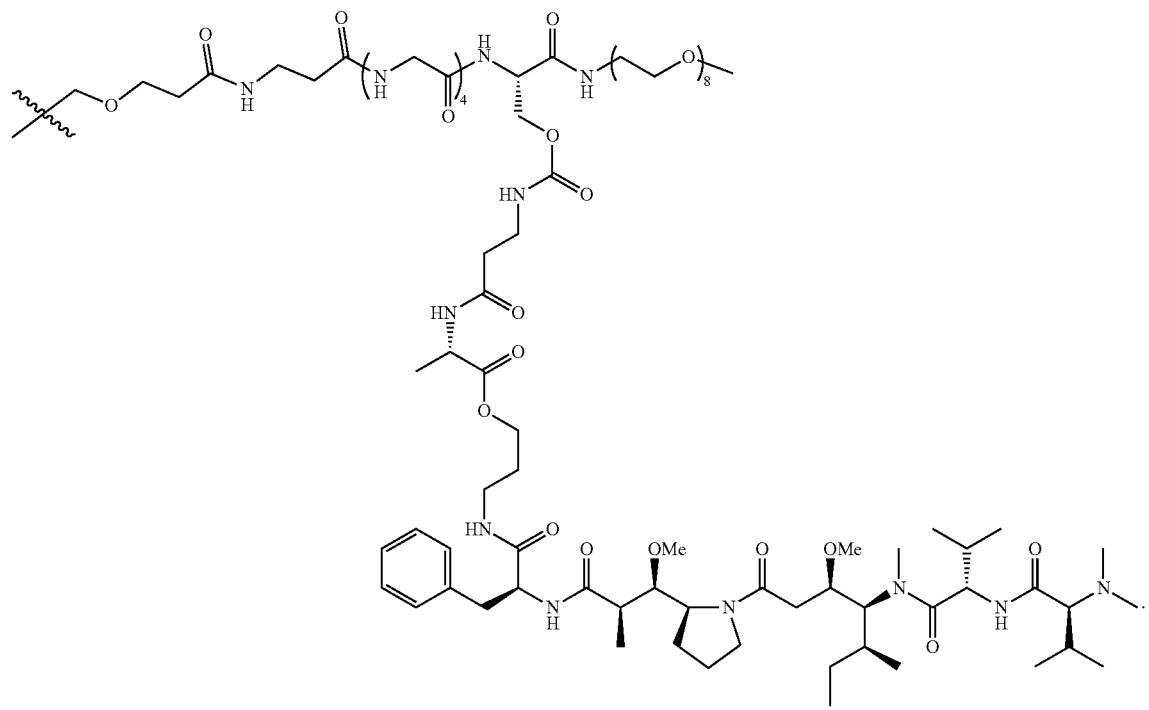

465
466
-continued
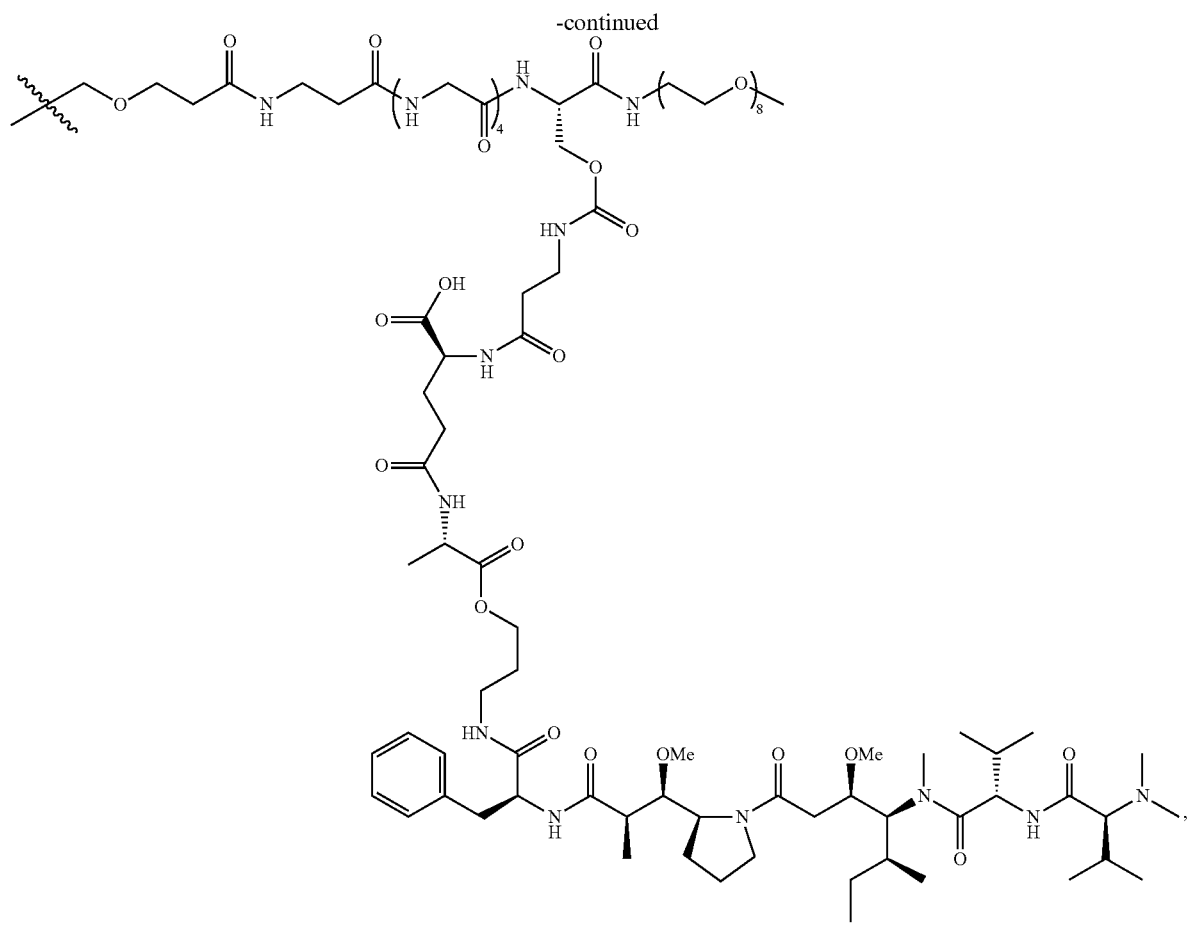
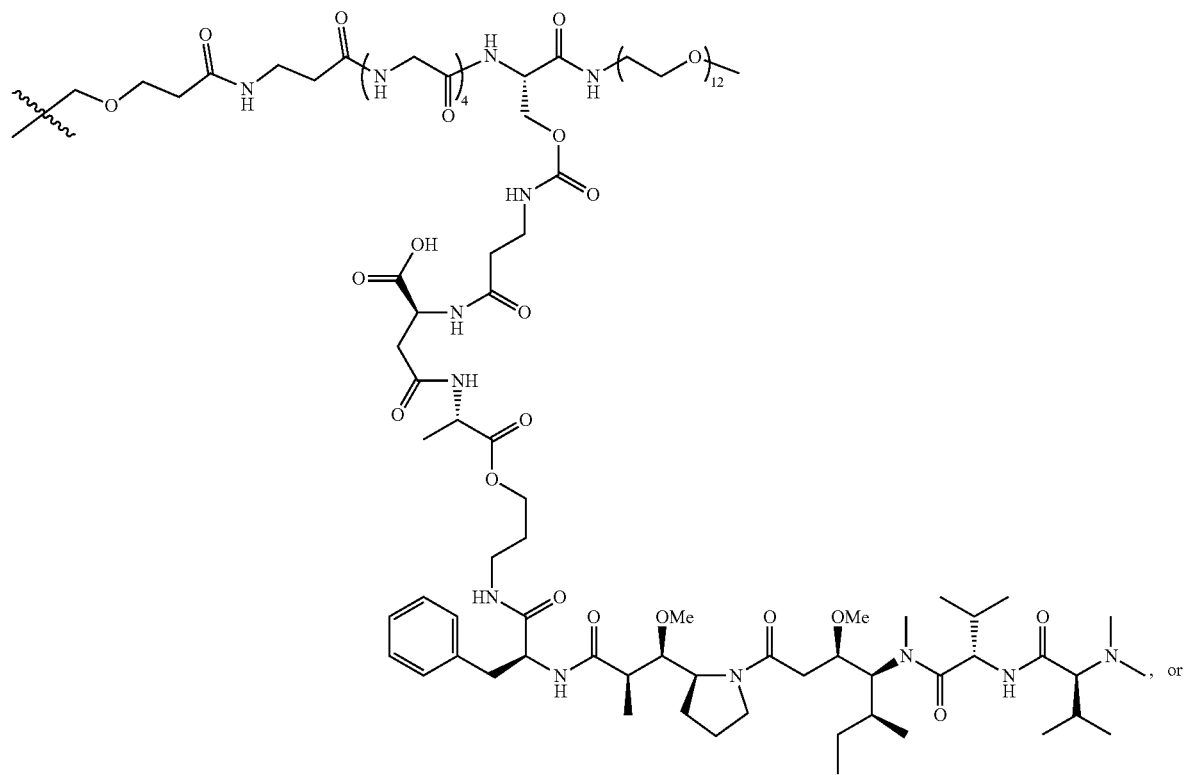

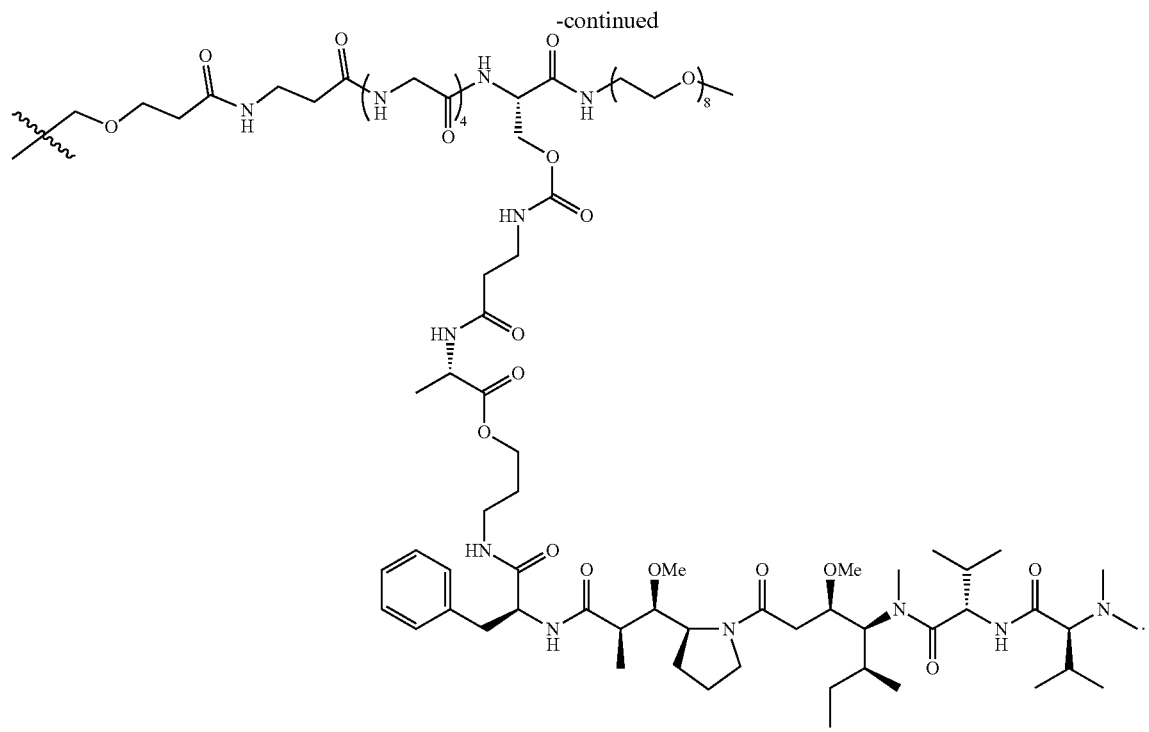
In some embodiments, the modified B7-H4 antibody-drug conjugate is a conjugate of Formula (XXXVI), wherein each $R_A$ is
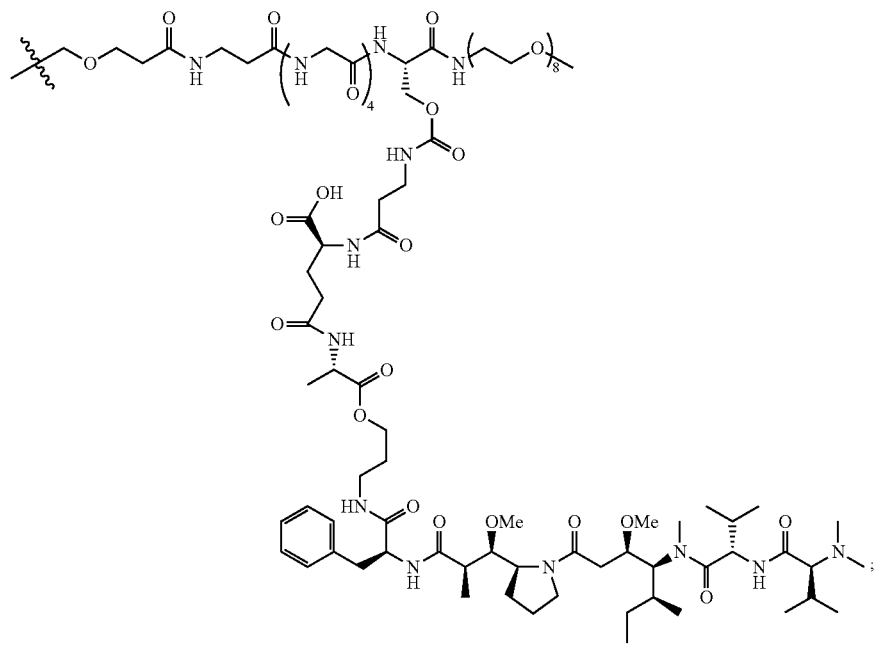
wherein, the modified B7-H4 antibody comprises one or more asparagine group at N297 being connected to the rest of the conjugate.

In some embodiments, the modified B7-H4 antibody-drug conjugate is a conjugate of Formula (XXXVII):

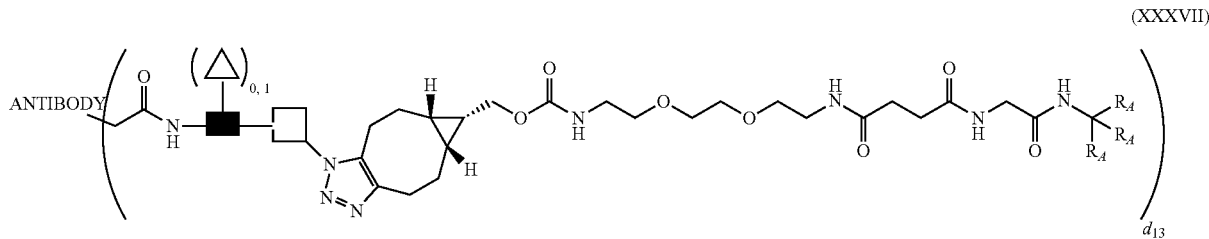

(XXXVII)

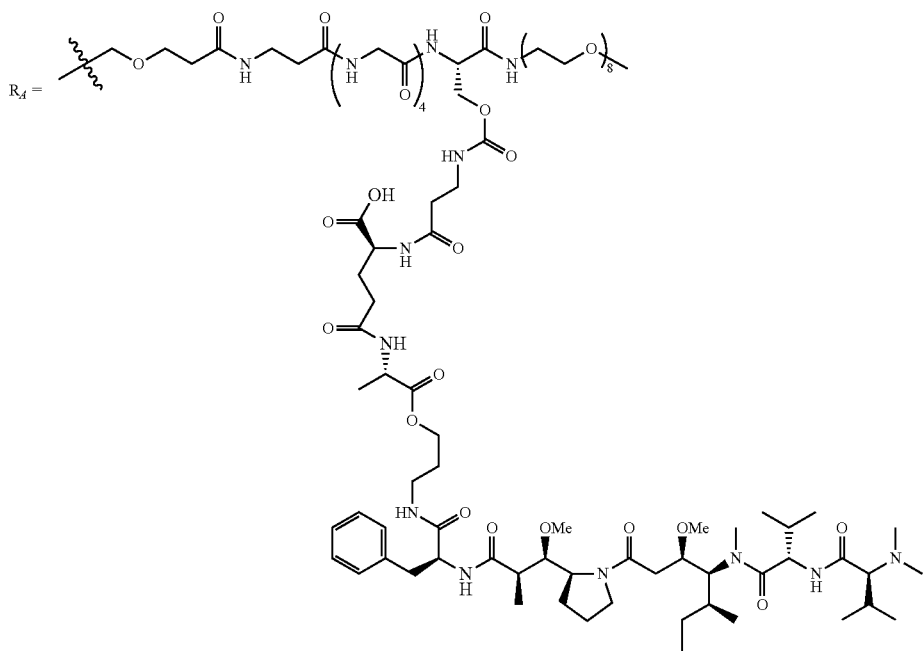

wherein $d_{13}$ is 2;

ANTIBODY is a B7-H4 antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55).

the Linker-Drug moiety is attached to the asparagine group at N297 of the B7-H4 antibody;

■ is GlcNAc; △ is Fuc; and □ is GalNAc.

In some embodiments, the modified B7-H4 antibody-drug conjugate is a conjugate of Formula (XXXVIII):

(XXXVIII)

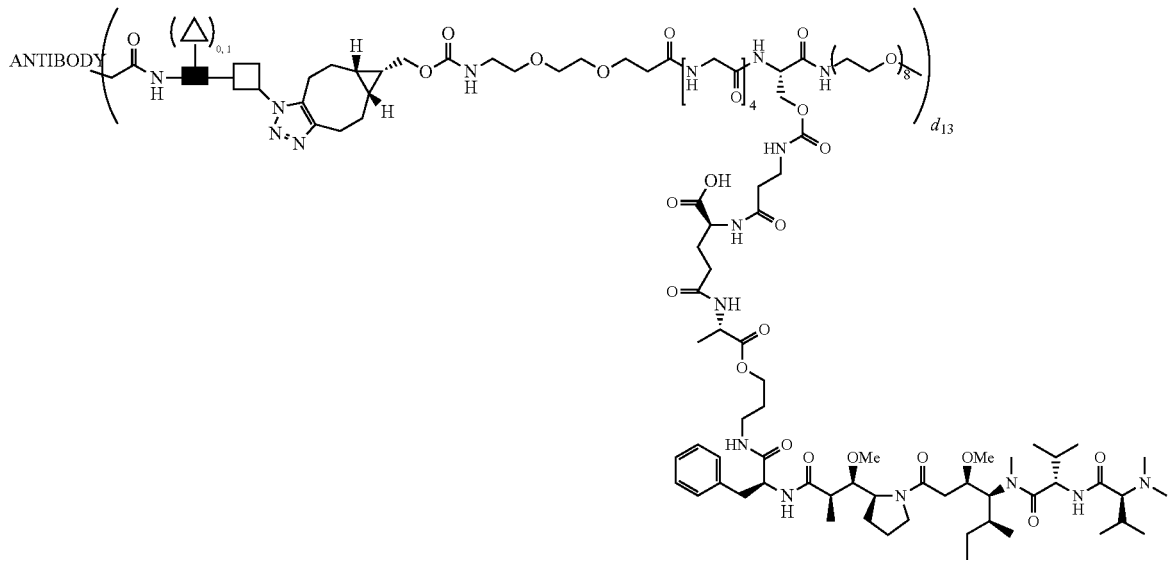

wherein
$d_{13}$ is an integer 2;
   ANTIBODY is a B7-H4 antibody comprising: a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), a variable light chain complementarity determining region 3 (CDRL3) comprising the amino acid sequence QQYGSSPLYT (SEQ ID NO: 55).
the Linker-Drug moiety is attached to the asparagine group at N297 of the antibody;
■ is GlcNAc; △ is Fuc; and □ is GalNAc.

Methods of Use

In some embodiments, the present disclosure provides a method of treating or preventing a disease or disorder in a subject in need thereof, comprising administering to the subject a therapeutically effective amount of a conjugate disclosed herein.

In some embodiments, the present disclosure provides a method of treating a disease or disorder in a subject in need thereof, comprising administering to the subject a therapeutically effective amount of a conjugate disclosed herein.

In some embodiments, the present disclosure provides a method of treating or preventing a disease or disorder in a subject in need thereof, comprising administering to the subject a conjugate disclosed herein.

In some embodiments, the present disclosure provides a method of treating a disease or disorder in a subject in need thereof, comprising administering to the subject a conjugate disclosed herein.

In some embodiments, the present disclosure relates to a method of treating a cancer in a subject in need thereof, comprising administering to the subject an effective amount of a conjugate disclosed herein. In some embodiments, the present disclosure relates to a method of treating a B7-H4-positive cancer in a subject in need thereof, comprising administering to the subject an effective amount of a conjugate disclosed herein.

In some embodiments, the present disclosure provides a conjugate disclosed herein for use in treating or preventing a disease or disorder in a subject in need thereof.

In some embodiments, the present disclosure provides a conjugate disclosed herein for use in treating a disease or disorder in a subject in need thereof.

In some embodiments, the present disclosure provides use of a conjugate disclosed herein for treating a cancer in a subject in need thereof. In some embodiments, the present disclosure provides use of a conjugate disclosed herein for treating a B7-H4-positive expressing cancer in a subject in need thereof.

In some embodiments, the present disclosure provides use of a conjugate disclosed herein in the manufacture of a medicament for treating a disease or disorder in a subject in need thereof.

In some embodiments, the present disclosure provides use of a conjugate disclosed herein in the manufacture of a medicament for treating or preventing a disease or disorder in a subject in need thereof.

In some embodiments, the present disclosure provides use of a conjugate disclosed herein in the manufacture of a medicament for treating a cancer in a subject in need thereof. In some embodiments, the present disclosure provides use of a conjugate disclosed herein in the manufacture of a medicament for treating a B7-H4-positive expressing cancer in a subject in need thereof.

In some embodiments, the present disclosure provides use of a conjugate for the treatment or prevention of a disease or disorder in a subject in need thereof.

In some embodiments, the present disclosure provides use of a conjugate for the treatment of a disease or disorder in a subject in need thereof.

In some embodiments, the present disclosure provides use of a conjugate for treatment of a cancer in a subject in need thereof, comprising administering to the subject an effective amount of a conjugate disclosed herein. In some embodiments, the present disclosure provides use of a conjugate for treatment of a B7-H4-positive expressing cancer in a subject in need thereof, comprising administering to the subject an effective amount of a conjugate disclosed herein.

In some embodiments, the present disclosure provides a method of treating or preventing a disease or disorder in a subject in need thereof, comprising administering to the subject an efficient amount of at least one conjugate of the disclosure; wherein said conjugate releases one or more therapeutic agents upon biodegradation.

In some embodiments, the present disclosure provides a method of treating a disease or disorder in a subject in need thereof, comprising administering to the subject an efficient amount of at least one conjugate of the disclosure; wherein said conjugate releases one or more therapeutic agents upon biodegradation.

In some embodiments, the disease is a cancer.

In some embodiments, the present disclosure provides the method comprises administering to the subject a therapeutically effective amount of a B7-H4 antibody-drug conjugate disclosed herein.

In some embodiments, the present disclosure provides the method comprises administering to the subject a B7-H4 antibody-drug conjugate disclosed herein.

In some embodiments, the present disclosure provides a method of inhibiting proliferation of an B7-H4-positive cell, the method comprising exposing the cell to the B7-H4 antibody-drug conjugate under conditions permissive for binding of the B7-H4 antibody-drug conjugate to B7-H4 on the surface of the cell followed by internalization, thereby inhibiting the proliferation of the cell. In certain embodiments, the method is an in vitro or an in vivo method. In further embodiments, the cell is a breast, ovarian, or endometrial cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In some embodiments, the present disclosure provides a B7-H4 antibody-drug conjugate for use as a medicament. In some embodiments, a B7-H4 antibody-drug conjugate for use in a method of treatment is provided. In some embodiments, a B7-H4 antibody-drug conjugate for use in treating B7-H4-positive cancer is provided. In some embodiments, the invention provides a B7-H4 antibody-drug conjugate for use in a method of treating an individual having a B7-H4-positive cancer, the method comprising administering to the individual an effective amount of the B7-H4 antibody-drug conjugate. In some embodiments, the method further comprises administering to the individual an effective amount of at least one additional therapeutic agent, e.g., as described below.

In some embodiments, the present disclosure provides for the use of a B7-H4 antibody-drug conjugate in the manufacture or preparation of a medicament. In some embodiments, the medicament is for treatment of B7-H4-positive cancer. In some embodiments, the medicament is for use in a method of treating B7-H4-positive cancer, the method comprising administering to an individual having B7-H4-positive cancer an effective amount of the medicament. In some embodiments, the method further comprises administering to the individual an effective amount of at least one additional therapeutic agent, e.g., as described below.

In some embodiments, the disclosure provides a method for treating B7-H4-positive cancer. In some embodiments, the method comprises administering to an individual having such B7-H4-positive cancer an effective amount of a B7-H4 antibody-drug conjugate. In some embodiments, the method further comprises administering to the individual an effective amount of at least one additional therapeutic agent, as described below.

In some embodiments, the B7-H4-positive cancer is, for example, breast cancer, endometrial cancer, ovarian cancer, non-small cell lung cancer (e.g., squamous cell carcinoma), pancreatic cancer, thyroid cancer, kidney cancer (e.g., renal cell carcinoma), bladder cancer (e.g., urothelial cell carcinoma), colon cancer, head and neck cancer, small cell lung cancer, gastric cancer, melanoma, bile duct carcinoma, uterine cancer, and cholangial carcinoma.

In some embodiments, the B7-H4-positive cancer is, for example, breast cancer endometrial cancer, ovarian cancer or cholangial carcinoma.

In some embodiments, the B7-H4-positive breast cancer is triple negative breast cancer, hormone receptor positive/ HER2 (−) (HR+/HER2 (−)) breast cancer or ductal carcinoma.

In some embodiments, the B7-H4-positive ovarian cancer is a serous adenocarcinoma ovarian cancer.

In some embodiments, the B7-H4-positive ovarian cancer is a high grade serous ovarian cancer. In some embodiments, the high grade serous ovarian cancer is fallopian tube or primary peritoneal cancer. In some embodiments, the fallopian tube or primary peritoneal cancer is metastatic. In some embodiments, the fallopian tube or primary peritoneal cancer is recurrent.

In some embodiments, the present disclosure relates to a method of treating triple negative breast cancer in a subject in need thereof, comprising administering to the subject an effective amount of a conjugate disclosed herein, or a pharmaceutical composition thereof.

In some embodiments, the present disclosure relates to a method of treating HR+/HER2 (−) breast cancer in a subject in need thereof, comprising administering to the subject an effective amount of a conjugate disclosed herein, or a pharmaceutical composition thereof.

In some embodiments, the present disclosure relates to a method of treating endometrial cancer in a subject in need thereof, comprising administering to the subject an effective amount of a conjugate disclosed herein, or a pharmaceutical composition thereof.

In some embodiments, the triple negative breast cancer subject has received prior treatment with a topoisomerase inhibitor or an ADC thereof, such as, for example sacituzumab govitecan; a chemotherapeutic agent, such as, for example, docetaxel, doxorubicin, cyclophosphamide, carboplatin, paclitaxel, nab-paclitaxel, gemcitabine, and cisplatin; an antineoplastic agent such as, for example, atezolizumab; an AKT inhibitor, such as, for example, ipatasertib; a PARP inhibitor, such as, for example, olaparib (Lynparza), rucaparib (Rubraca), talazoparib, and niraparib (Zejula) or a combination thereof.

In some embodiments, the HR+/HER2 (−) breast cancer subject has received prior treatment with a cyclin-dependent kinase 4 and 6 (CDK4/6) inhibitor, such as, for example, palbociclib, ribociclib and abemaciclib; a chemotherapeutic agent, such as, for example, docetaxel, doxorubicin, cyclophosphamide, carboplatin, paclitaxel, nab-paclitaxel, gemcitabine, and cisplatin; an angiogenesis inhibitors, such as, for example, bevacizumab (Avastin); an estrogen receptor antagonist, such as, for example, fulvestrant (Faslodex); a mTOR inhibitor, such, as, for example, everolimus; a PI3K inhibitor such as, for example, alpelisib; or a combination thereof.

In some embodiments, the ovarian cancer subject has received prior treatment with a chemotherapeutic agent, such as, for example, docetaxel, doxorubicin, cyclophosphamide, carboplatin, paclitaxel, nab-paclitaxel, gemcitabine, and cisplatin; an angiogenesis inhibitors, such as, for example, bevacizumab (Avastin); a PARP inhibitor, such as, for example, niraparib (Zejula), olaparib (Lynparza), and veliparib; olaparib (Lynparza) in combination with bevacizumab; or a combination thereof.

In some embodiments, the endometrial cancer subject has received prior treatment with a chemotherapeutic agent, such as, for example, docetaxel, doxorubicin, cyclophosphamide, carboplatin, paclitaxel, nab-paclitaxel, gemcitabine, and cisplatin; a progestin, such as, for example, medroxyprogesterone acetate (Provera®) and megestrol acetate (Megace); an anti-estrogen drug, such as, for example, tamoxifen; a luteinizing hormone-releasing hormone agonist (LHRH agonist), such as, for example, goserelin (Zoladex) and leuprolide (Lupron); an aromatase inhibitor, such as, for example, letrozole (Femara), anastrozole (Arimidex), and exemestane (Aromasin); a kinase inhibitor, such as, for example, Lenvatini; an angiogenesis inhibitors, such as, for example, bevacizumab (Avastin); a mTOR inhibitor, such as, for example, everolimus (Afinitor); a PD-1 antibody, such as, for example, nivolumab (OPDIVO), pembrolizumab (KEYTRUDA), MEDI-0680 (AMP-514; WO2012/145493), camrelizumab (SHR-1210), tislelizumab (BGB-A317), and spartalizumab (NPVPDR001, NVS240118, PDR001); or a combination thereof.

In some embodiments, the present disclosure relates to a method of treating a cancer subject that is a PD-1/PD-L1 inhibitor inadequate responder comprising administering to the subject an effective amount of a conjugate disclosed herein, or a pharmaceutical composition thereof.

A cancer subject that is a PD-1/PD-L1 inhibitor inadequate responder, may have previously responded to a PD-1/PD-L1 inhibitor, but may have become less responsive to the PD-1/PD-L1 inhibitor, or the cancer may have never responded to the PD-1/PD-L1 inhibitor. Inadequate response to a PD-1/PD-L1 inhibitor means that aspects of the cancer that would be expected to improve following a standard dose of the PD-1/PD-L1 inhibitor do not improve, and/or improvement only occurs if greater than a standard dose is administered. In some embodiments, a subject with a cancer that is a PD-1/PD-L1 inhibitor inadequate responder has experienced, or is experiencing, an inadequate response to the PD-1/PD-L1 inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc. In some embodiments, a subject with a cancer that is a PD-1/PD-L1 inhibitor inadequate responder has experienced, or is experiencing, an inadequate response to an anti-PD-1 antibody and/or an anti-PD-L1 antibody. In some embodiments, a subject with cancer that is a PD-1/PD-L1 inhibitor inadequate responder has experienced, or is experiencing, an inadequate response to AMP-224. In some embodiments, a subject with cancer that is a PD-1/PD-L1 inhibitor inadequate responder has experienced, or is experiencing, an inadequate response to a PD-1/PD-L1 inhibitor selected from nivolumab, pembrolizumab, and atezolizumab.

In some embodiments, the present disclosure relates to a method of treating a cancer that expresses a low level of PD-L1 comprising administering to the subject an effective amount of a conjugate disclosed herein, or a pharmaceutical composition thereof. In some embodiments, a cancer that expresses a "low level of PD-L1," or expresses "PD-L1 at a low level," denotes that the level of PD-L1 is under the level of expression for a cancer that is indicated for treatment with a PD-1 or PD-L1 antagonist in which subjects are selected for treatment based on PD-L1 expression levels. In some embodiments, a "low level of PD-L1" is one in which less than 1% of the cells in the tumor have membrane staining. In some embodiments, a "low level" in regard to PD-L1 is less than 1% staining, for example, 0.9, 0.8, 0.7, 0.6, 0.5, 0.4, 0.3, 0.2, 0.1% or 0% of the cells of the tumor are stained. In some embodiments, PD-L1 expression levels can be measured by chromogenic IHC or immunofluorescence IHC (Aqua scoring). In certain embodiments, PD-L1 staining of 5% or less (including tumor and/or immune cells) can indicate that a sample expresses a "low level of PD-L1." In certain embodiments, PD-L1 staining of 10% or less (including tumor and/or immune cells) can indicate that a sample expresses a "low level of PD-L1." Unless indicated otherwise herein, a 5% threshold is used herein (i.e., 5% or less indicates a "low level of PD-L1").

In some embodiments, a conjugate disclosed herein, or a pharmaceutical composition thereof, is administered to a subject diagnosed with cancer to increase the proliferation of T cells, CD4+ T cells, or CD8+ T cells in the patient. In another embodiment, a conjugate disclosed herein, or a pharmaceutical composition thereof, is administered to a subject diagnosed with cancer to increase interferon-gamma (IFNγ) production in the subject. In another embodiment, a conjugate disclosed herein, or a pharmaceutical composition thereof, is administered to a subject diagnosed with cancer to block the inhibitory activity of B7-H4 against T cells in the subject. In another embodiment, a conjugate disclosed herein, or a pharmaceutical composition thereof, is administered to a subject diagnosed with cancer to deplete B7-H4 expressing cancer cells in the subject.

In some embodiments, a conjugate disclosed herein, or a pharmaceutical composition thereof, is administered to a subject as provided above, and further in combination with an additional therapeutic agent, e.g., a PD-1 antagonist; a PD-L1 antagonist; a topoisomerase inhibitor or an ADC thereof, such as, for example sacituzumab govitecan; a chemotherapeutic agent, such as, for example, docetaxel, doxorubicin, cyclophosphamide, carboplatin, paclitaxel, nab-paclitaxel, gemcitabine, and cisplatin; an antineoplastic agent such as, for example, atezolizumab; an angiogenesis inhibitors, such as, for example, bevacizumab (Avastin); an AKT inhibitor, such as, for example, ipatasertib; a PARP inhibitor, such as, for example, olaparib (Lynparza), rucaparib (Rubraca), talazoparib, and niraparib (Zejula); a cyclin-dependent kinase 4 and 6 (CDK4/6) inhibitor, such as, for example, palbociclib, ribociclib and abemaciclib; a selective estrogen receptor antagonist, such as, for example, fulvestrant (Faslodex); a mTOR inhibitor, such, as, for example, everolimus (Afinitor); a PI3K inhibitor such as, for example, alpelisib; or a combination thereof.

In some embodiments, the additional therapeutic agent is a PD-1 antagonist, such as an antagonistic PD-1 antibody. Suitable PD-1 antibodies include, for example, nivolumab (OPDIVO), pembrolizumab (KEYTRUDA), MEDI-0680 (AMP-514; WO2012/145493). camrelizumab (SHR-1210), tislelizumab (BGB-A317), or spartalizumab (NPVPDR001, NVS240118, PDR001). The additional therapeutic agent may also include pidilizumab (CT-011). A recombinant protein composed of the extracellular domain of PD-L2 (B7-DC) fused to the Fc portion of IgG1, called AMP-224, can also be used to antagonize the PD-1 receptor.

In some embodiment, the PD-L1 antagonist, is an antagonistic PD-L1 antibody. Suitable PD-L1 antibodies include, for example, atezolizumab (TECENTRIQ), durvalumab (MEDI4736), BMS-936559 (WO2007/005874), avelumab (WO2013/79174) or rHigMi2B7.

In some embodiments, e.g., when the cancer is a Her2 cancer, an additional therapeutic agent is trastuzumab, Trastuzumab emtansine (Kadcyla®) pertuzumab (Perjeta®), tyrosine kinase inhibitors, such as, for example, lapatinib and tucatinib.

Such combination therapies noted above encompass combined administration (where two or more therapeutic agents are included in the same or separate formulations), and separate administration, in which case, administration of the antibody or antibody-drug conjugate of the invention can occur prior to, simultaneously, and/or following, administration of the additional therapeutic agent and/or adjuvant. B7-H4 antibody-drug conjugates of the invention can also be used in combination with radiation therapy.

It is within the level of one of skill in the art to determine the precise amounts of active agents, including B7-H4 antibody-drug conjugates to be administered to a subject. For example, such agents and uses for treating cancers and solid tumors, are well-known in the art. Thus, dosages of such agents can be chosen based on standard dosing regimens for that agent under a given route of administration.

It is understood that the precise dosage and duration of treatment is a function of the tissue or tumor being treated and may be determined empirically using known testing protocols or by extrapolation from in vivo or in vitro test data and/or can be determined from known dosing regimens of the particular agent. It is to be noted that concentrations and dosage values may also vary with the age of the individual treated, the weight of the individual, the route of administration and/or the extent or severity of the disease and other factors that are within the level of a skilled medical practitioner to consider. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects). It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Throughout the description, where compounds, scaffolds, and compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

EXAMPLES

The following working examples are illustrative of the linkers, drug molecules and antibodies or antibody fragments, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples Abbreviations ACN Acetonitrile
AF Auristatin F
AF-HPA Auristatin F hydroxypropyl amide
aq Aqueous
CE Capillary electrophoresis
CR Complete regression
DAD Diode array detector
DAR Drug-to-antibody ratio
DMEM Dulbecco's Modified Eagle Medium ELISA Enzyme-linked immunosorbent assay
Endo SH Endoglycosidase SH
FBS Fetal bovine serum
Fuc Fucose
GalNAcT Glycosyltransferase
HIC Hydrophobic interaction chromatography
HRP Horse radish peroxidase
IV Intravenous
LC Liquid chromatography
MS Mass spectrometry
MTV Median tumor volume
NMR Nuclear magnetic resonance
PBS Phosphate buffered saline
PBST Phosphate-buffered saline containing Tween
PR Partial regression
RP-HPLC Reverse-phase high performance liquid chromatography
SEC Size exclusion chromatography
TFS Tumor free survival
TGI Tumor growth inhibition
TCEP Tris[2-carboxyethyl] phosphine
TEAA Triethylammonium acetate
TMB Tetramethylbenzidine
UDP Uridine diphosphate
UF/DF Ultrafiltration/diafiltration
WCX Weak cation exchange chromatography General Information All reagents were purchased from relevant providers unless otherwise stated.

B7-H4_2F9 parental antibody (anti-B7-H4 antibody) and 2A7 are disclosed in US 2011/0085970 A1. 1D11 antibody is disclosed in US20160159910A1. Endo SH was prepared as described in PCT application WO 2017137459, the entire contents of which are incorporated herein by reference. UDP-azido sugar and GalNAcT were prepared as described in U.S. Pat. No. 9,988,662, the entire contents of which is incorporated herein by reference.

The diABZI STING agonist was prepared as described in Ramanjulu et al (Nature, 564(7736):439-443 (2018)).

Tumor growth inhibition (% TGI) was defined as the percent difference in median tumor volumes (MTVs) between treated and control groups. Tumor size was measured throughout each efficacy study to determine tumor growth inhibition (TGI).

When applicable, the drug content of the conjugates was determined spectrophotometrically, otherwise RP-HPLC or LC/MS as performed for quantitative determination of the drug content.

The protein content of the antibody-drug conjugates was determined spectrophotometrically or by ELISA.

Antibody-drug conjugates, drug carrying scaffolds, or antibody scaffolds were purified (i.e., removal of residual unreacted drug, unconjugated antibody, enzymes or starting materials) by extensive diafiltration, CHT chromatography or HIC, as required. If necessary, additional purification by SEC or HIC were conducted to remove aggregated antibody-drug conjugates. In general, the antibody-drug conjugates, as purified, contained <5% (w/w) (e.g., <2% (w/w)) aggregated antibody-drug conjugates as determined by SEC; <0.5% (w/w) (e.g., <0.1% (w/w)) free (unconjugated) drug as determined by RP-HPLC and/or LC-MS/MS; <1% (w/w) of free drug conjugate as determined by SEC and/or RP-HPLC; and <10% (w/w) (e.g., <1% (w/w)) unconjugated antibody or antibody fragments as determined by HIC-HPLC and/or RP-HPLC. Reduced or partially reduced antibodies were prepared using procedures described in the literature, see, for example, Francisco et al., Blood 102 (4): 1458-1465 (2003). The total drug (conjugated and unconjugated) concentration was determined by UV-Vis spectrophotometry or RP-HPLC.

To determine the concentration of the free AF-HPA drug in a biological sample, an acidified sample was treated with ACN. The free drug was extracted and the ACN supernatant was analyzed. To determine the concentration of conjugated AF-HPA in a non-clinical sample, the sample was subjected to immunocapture using anti-IgG1 antibody-coated magnetic beads followed by exhaustive basic hydrolysis. The ACN supernatant containing the released AF-HPA drug was analyzed by LC-MS/MS. The total antibody concentration in non-clinical samples was measured by LC-MS/MS after immunocapture using an anti-IgG1 antibody via detection of a peptide sequence unique for the antibody after tryptic digestion. For clinical samples, the same procedure could be followed except that an anti-idiotype antibody would be used for immunocapture to avoid the interference of endogenous antibodies.

Analysis of free AF and AF-HPA was conducted by RP-HPLC using a C4 column, an ACN gradient, and UV detection. Peak areas are integrated and compared to AF and AF-HPA standards. The method is quantitative for AF and AF-HPA in plasma and tissue homogenates and linear over the concentration ranges of 0.1 ng/mL to 150 ng/mL. The total drug (AF-HPA) released after hydrolysis with NaOH (aq) was measured under the same condition with the dynamic range from 1 ng/mL to 5,000 ng/mL. The total antibody standards range from 0.1 µg/mL to 100 µg/mL.

The hydrophobicity of the antibody-drug conjugate was determined by HIC-HPLC on a Shimadzu Prominence HPLC system equipped with a DAD. A TSK gel butyl-NPR column (2.5 µm particle size) was held at 35° C. for these analyses. Mobile phase A was 1.5 M ammonium sulfate, 25 mM sodium phosphate, and pH 7.0, and mobile phase B was 25 mM sodium phosphate, 10% isopropyl alcohol, and pH 7.0. Separations were performed with a 0-100% linear gradient of mobile phase B over 25 minutes. The flow rate was 1 mL/min. Sample injections ranged from ~10 µg to 100 µg.

The drug to antibody ratio (DAR) for conjugates comprising the cytotoxic agent drug moiety was determined by subjecting the antibody-drug conjugates to exhaustive base hydrolysis. The released AF-HPA was then quantified from a standard curve with RP-HPLC. The measured AF-HPA concentrations were correlated to the antibody content to determine DAR.

The drug to antibody ratio (DAR)) for conjugates comprising the STING agonist drug moiety was determined by measuring the absorption of the conjugates. The DAR value was calculated using the appropriate molar extinction coefficients of the antibody and the STING agonist payload.

Tumors were measured twice weekly using digital calipers and tumor volumes were calculated using the formula: tumor volume (mm$^3$)=(width$^2$×length)/2. Body weights were recorded daily for the first week and twice weekly thereafter. Animals remained on study until individual tumor volume reached ≥1000 mm$^3$.≥1500 mm$^3$ or as indicated. Percent change in body weight was calculated using the formula: body weight change (%)=((weight$^{study\ day\ X}$−weight$^{study\ day\ 1}$)/weight$^{study\ day\ 1}$)*100. Tumor volumes are reported as mean±standard error of the mean (SEM). Tumor growth inhibition (% TGI) was defined as the percent difference in mean tumor volumes (MTVs) between treated and control groups. Tumor size was measured throughout each efficacy study to determine tumor growth inhibition (TGI). Percent tumor regression was calculated using the formula: % regression=(1−(mean tumor volume$^{final}$)/(mean tumor volume$^{day\ 1}$))*100.

For xenograft studies the regression responses for individual animals are classified into categories. A partial response (PR) is defined as a tumor volume of 50% or less for day 1 volume for three consecutive measurements and equal to or greater than 13.5 mm³ for at least one of these three measurements. A complete response (CR) is defined as a tumor volume less than 13.5 mm³ for three consecutive measurements. A tumor-free survivor (TFS) is classified as having a CR at the end of study. Animals were scored only once during the study for a PR or CR event and only as CR if both PR and CR criteria were satisfied. An animal with a CR response at the termination of a study was additionally classified as a tumor-free survivor (TFS).

For PDX studies the regression responses for individual animals are classified into categories:

TS (Tumor Stabilization)=number of mice presenting a constant tumor size during several consecutive measurements.

PR (Partial Regression)=number of mice presenting a tumor size lower than initial tumor size during several consecutive measurements.

CR (Complete Regression)=number of mice presenting a 0 to 13 mm³ tumor size during several consecutive measurements.

TFS (Tumor Free Survivor)=number of compete regressions recorded up to Group day end.

Example 1: Synthesis of XMT-1604 (B7-H4_2F9V18) Cytotoxic Drug Conjugate 1

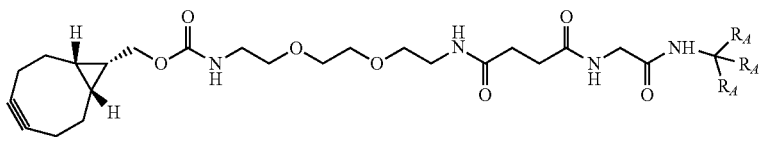

$R_A =$ 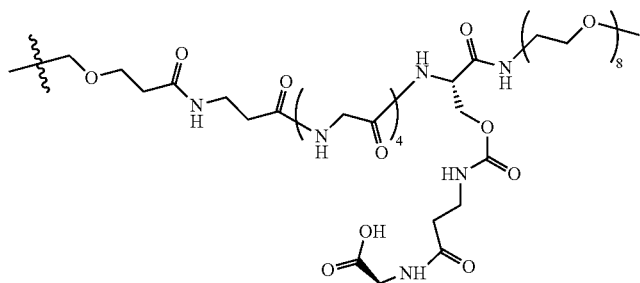

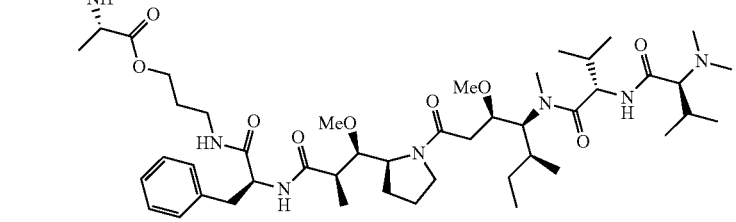

1A

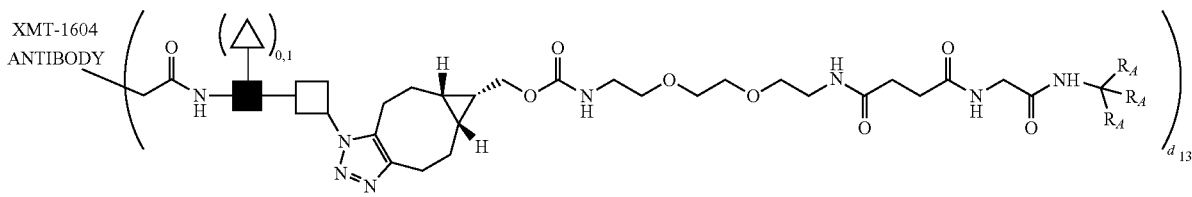

$R_A =$ 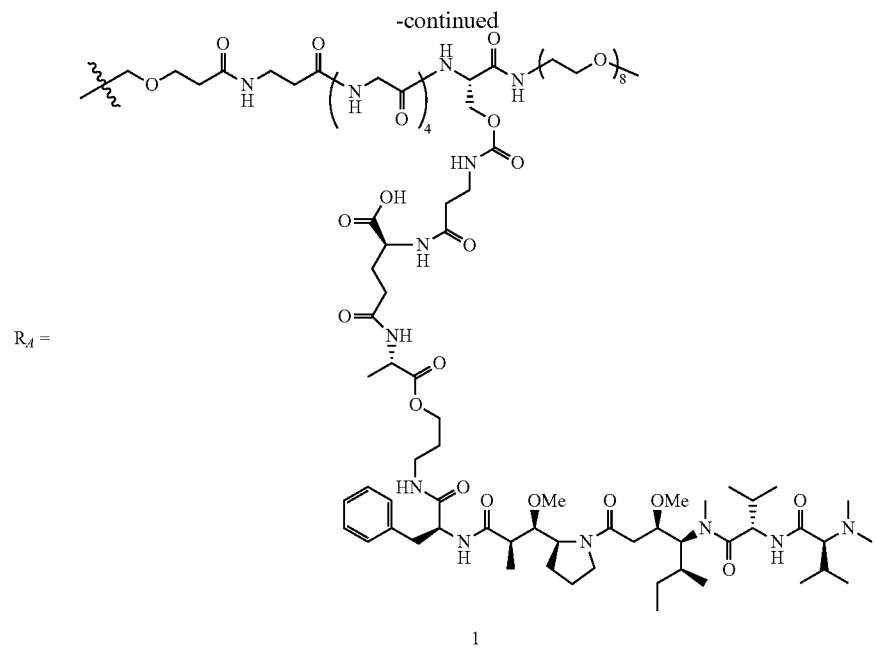

wherein: ■ is GlcNAc; △ is Fuc; and □ is GalNAc.

Step 1. Azido-Modified XMT-1604 (B7-H4_2F9V18) Antibody

To the XMT-1604 (B7-H4_2F9V18) antibody (12.71 mg, 0.088 μmole) in 50 mM Tris-HCl, pH 7.6, was added in the following order: Endo SH (0.127 mg, 1 w-%), GalNAcT (0.64 mg, 5 w-%), UDP-azido sugar (1.34 mg, 2.12 μmole), and MnCl$_2$ (1.18 mg, 9.4 μmole), to achieve a final antibody concentration of 13.5 g/L. The reaction was stirred at 30 rpm for 17 hours at 30° C. The crude azido-modified XMT-1604 (B7-H4_2F9V18) antibody was purified by Protein A chromatography and dialysis to give the azido-modified XMT-1604 (B7-H4_2F9V18) antibody (10.53 mg, 83% yield).

Step 2. XMT-1604 (B7-H4_2F9V18) Drug Conjugate 1

Azido-modified XMT-1604 (B7-H4_2F9V18) antibody (10.03 mg, 0.070 μmole) in PBS, pH 7.2 and Scaffold 1A (4.25 mg, 0.67 μmole, prepared as described in U.S. Ser. No. 17/144,378) in water, were gently mixed, then left for 20 hours at 30° C. without shaking or rocking. The crude product was purified by UF/DF and HIC to give Conjugate 1-1 (5.85 mg, 58% yield), that had a DAR of 5.9 as determined by reduced RP-HPLC.

The details of Conjugates 1-1, 1-2 and 1-3 are given below

| Conjugate | DAR |
| --- | --- |
| 1-1 | 5.9 |
| XMT-1604 (K+) | |
| 1-2 | 5.9 |
| 1-3 | 5.8 |

Example 2: Synthesis of XMT-1604 (B7-H4_2F9V18) Cytotoxic Drug Conjugate 2, DAR 2.0

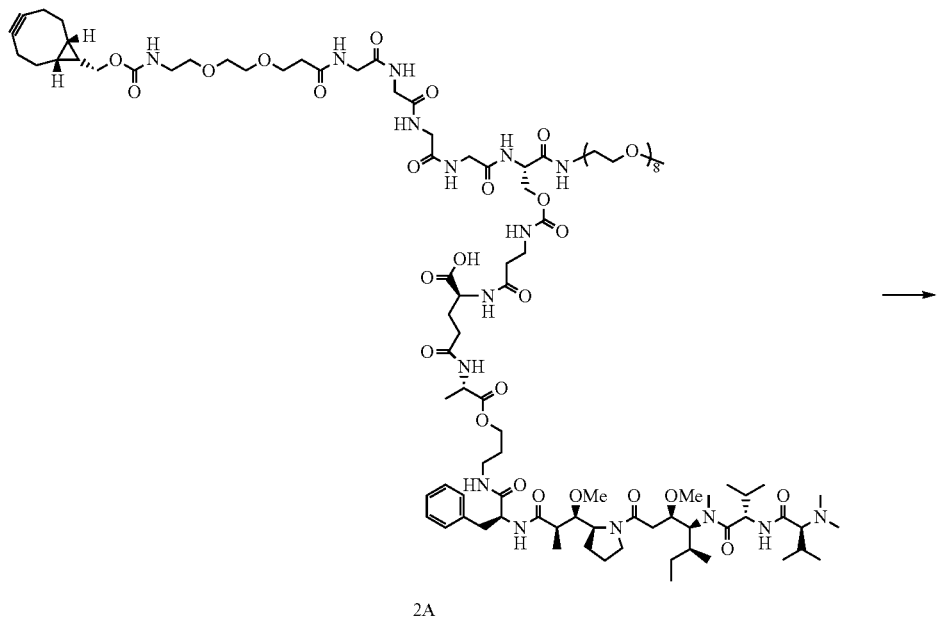

2A wherein: ■ is GlcNAc; △ is Fuc; and □ is GalNAc.

Conjugate 2 was synthesized as described in Example 1, except azido-modified XMT-1604 (B7-H4_2F9V18) antibody (50 mg, 0.346 μmole) and Scaffold 2A (7.12 mg, 3.34 μmole) instead of Scaffold 1A were used in Step 2. The purified Conjugate 2 (30.1 mg, 60% yield) had a DAR of 2.0 as determined by reduced RP-HPLC. The details of Conjugates 2-1 and 2-2 are given below

| Conjugate | DAR |
|-----------|-----|
| 2-1 | 2.0 |
| 2-2 | 2.0 |

Example 3: Synthesis of XMT-1603 (K+) (B7-H4_2F9V7) Cytotoxic Drug Conjugate 3, DAR 5.9

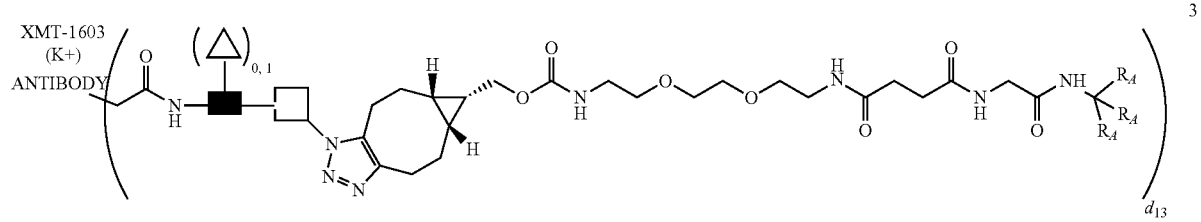

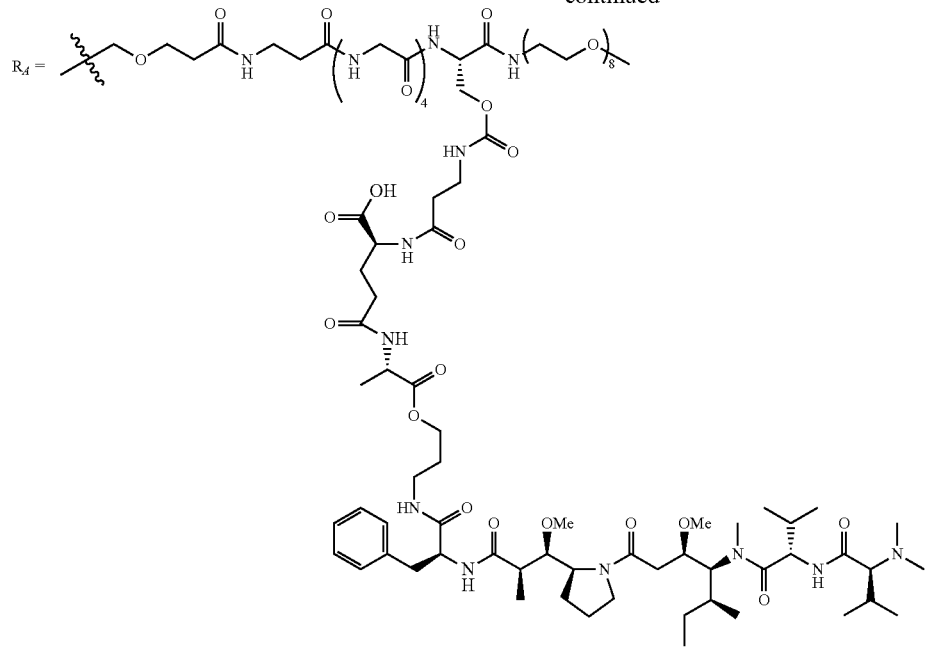

wherein: ■ is GlcNAc; △ is Fuc; and □ is GalNAc.

Conjugate 3 was synthesized as described in Example 1, except azido-modified XMT-1603 (K+) (B7-H4_2F9V7) antibody (13.7 mg, 0.095 μmole, prepared as described in Example 1, Step 1), was used in Step 2 instead of azido-modified XMT-1604 (B7-H4_2F9V18) antibody. The purified Conjugate 3 (8.8 mg, 64% yield) had a DAR of 5.9 as determined by reduced RP-HPLC.

Example 4: Synthesis of XMT-1603 (B7-H4_2F9V7) Cytotoxic Drug Conjugate 4, DAR 5.9

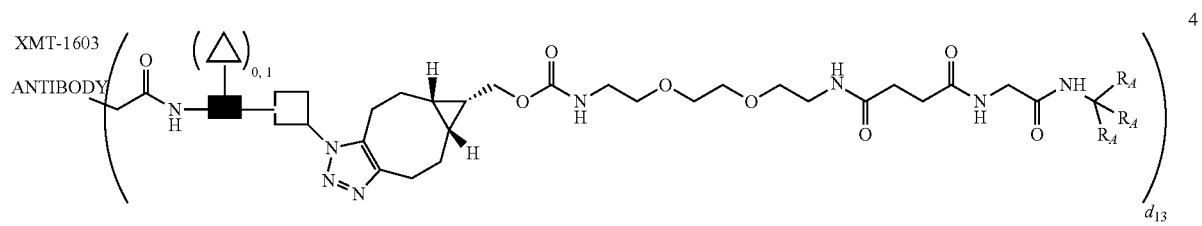

-continued

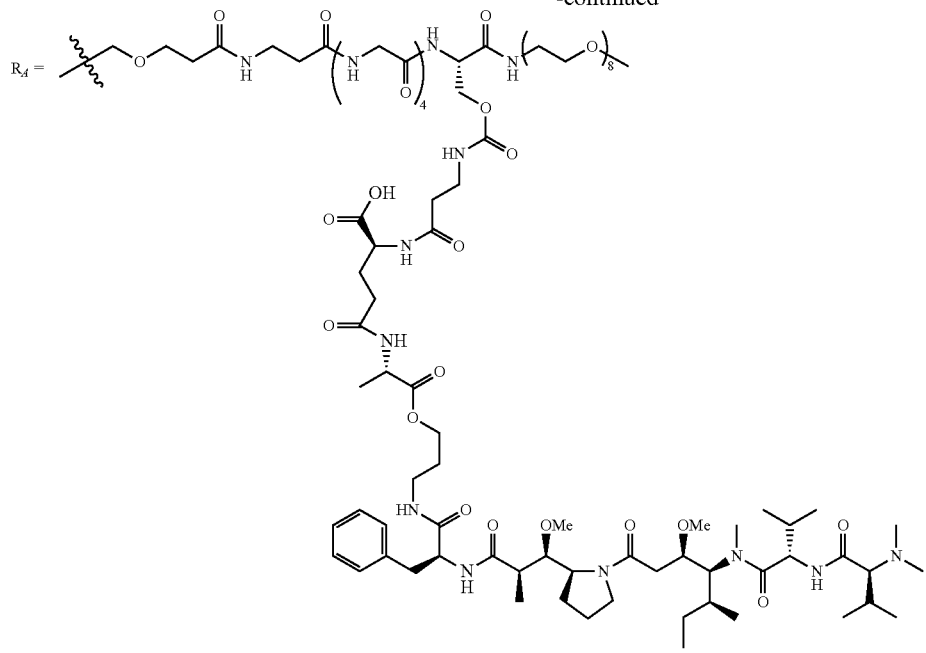

wherein: ■ is GlcNAc; △ is Fuc; and □ is GalNAc.

Conjugate 4 was synthesized as described in Example 1, except azido-modified XMT-1603 (B7-H4_2F9V7) antibody (22 mg, 0.153 μmole, prepared as described in Example 1, Step 1), was used in Step 2 instead of azido-modified XMT-1604 (B7-H4_2F9V18) antibody. The purified Conjugate 4 (13.8 mg, 63% yield) had a DAR of 5.9 as determined by reduced RP-HPLC.

Example 5: Synthesis of XMT-1603 (B7-H4_2F9V7) Cytotoxic Drug Conjugate 5, DAR 1.9

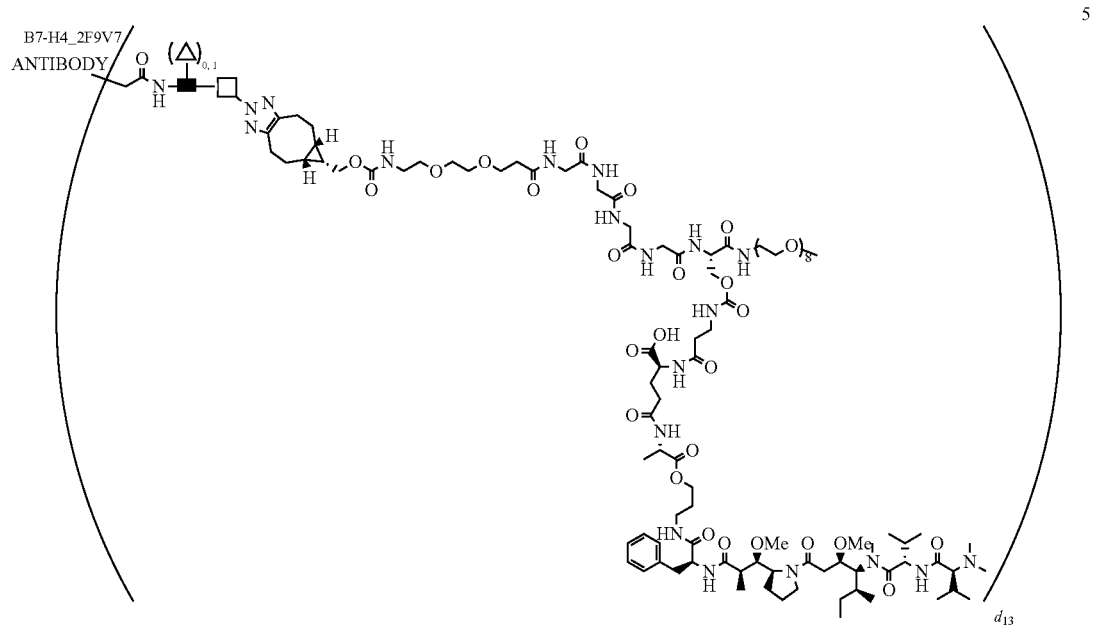

wherein: ■ is GlcNAc; △ is Fuc; and □ is GalNAc.

Conjugate 5 was synthesized as described in Example 2, except azido-modified XMT-1603 (B7-H4_2F9V7) antibody (50 mg, 0.347 μmole, prepared as described in Example 1, Step 1), was used in Step 2 instead of azido-modified XMT-1604 (B7-H4_2F9V18) antibody. The purified Conjugate 5 (30.5 mg, 61% yield) had a DAR of 1.9 as determined by reduced RP-HPLC.

Example 6: Synthesis of B7-H4_2F9V11 (K+) Cytotoxic Drug Conjugate 6, DAR 5.9

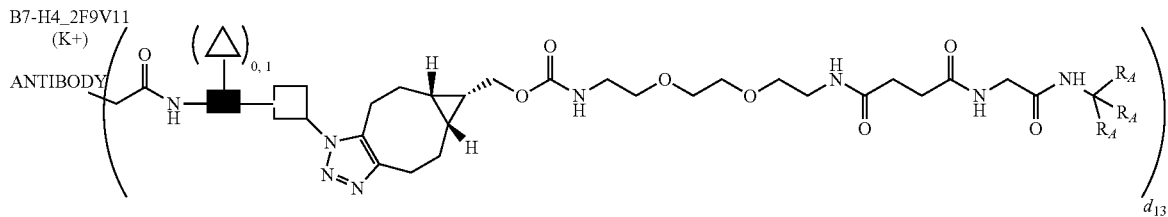

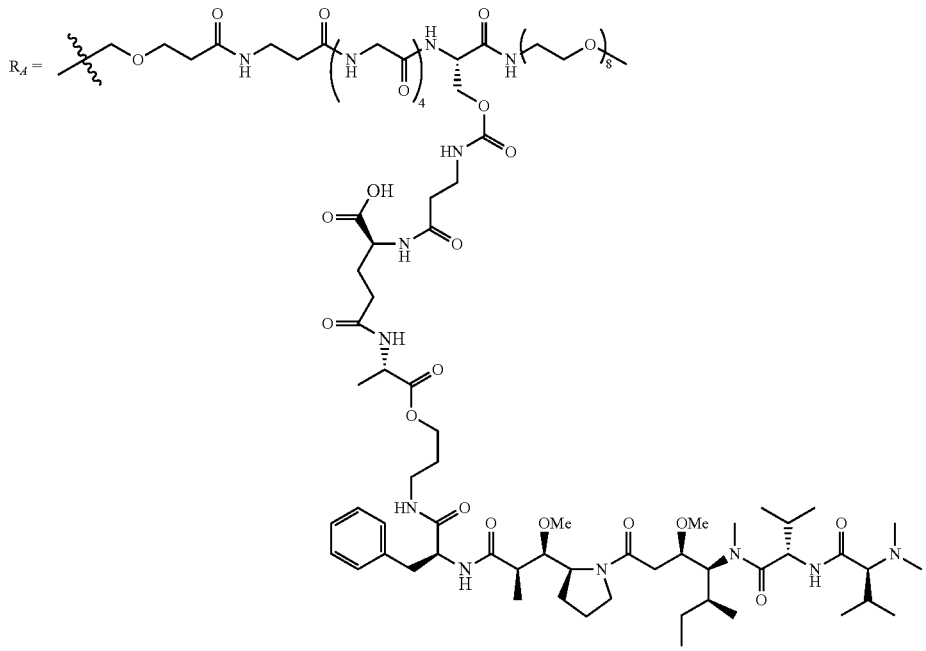

wherein: ■ is GlcNAc; △ is Fuc; and □ is GalNAc.

Conjugate 6 was synthesized as described in Example 1, except azido-modified B7-H4_2F9V11 (K+) antibody (16.66 mg, 0.116 μmole, prepared as described in Example 1, Step 1), was used in Step 2 instead of azido-modified XMT-1604 (B7-H4_2F9V18) antibody. The purified Conjugate 6 (10.75 mg, 65% yield) had a DAR of 5.9 as determined by reduced RP-HPLC.

Example 7: Synthesis of B7-H4_2F9V17 (K+) Cytotoxic Drug Conjugate 7, DAR 5.9

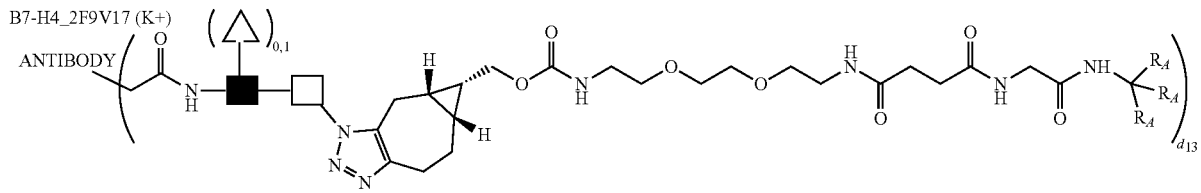

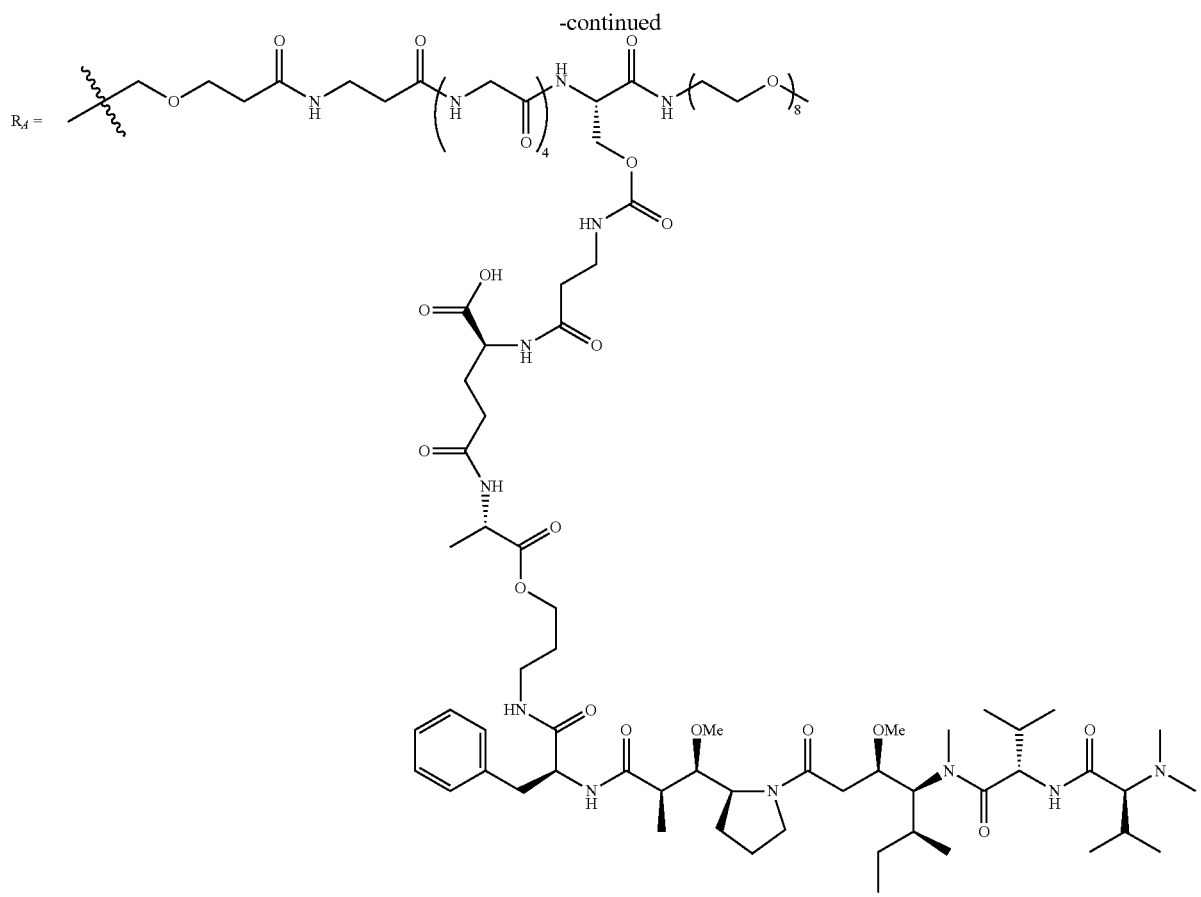

wherein: ■ is GlcNAc; △ is Fuc; and □ is GalNAc.

Conjugate 7 was synthesized as described in Example 1, except azido-modified B7-H4_2F9V17 (K+) antibody (13.62 mg, 0.094 μmole, prepared as described in Example 1, Step 1), was used in Step 2 instead of azido-modified XMT-1604 (B7-H4_2F9V18) antibody. The purified Conjugate 7 (8.1 mg, 59% yield) had a DAR of 5.9 as determined by reduced RP-HPLC.

Example 8: Synthesis of 1D11 Cytotoxic Drug Conjugate 8, DAR 5.8

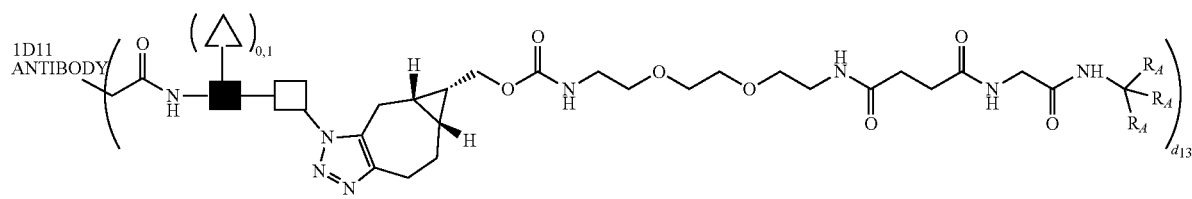

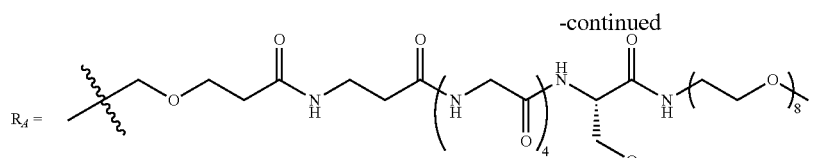

-continued

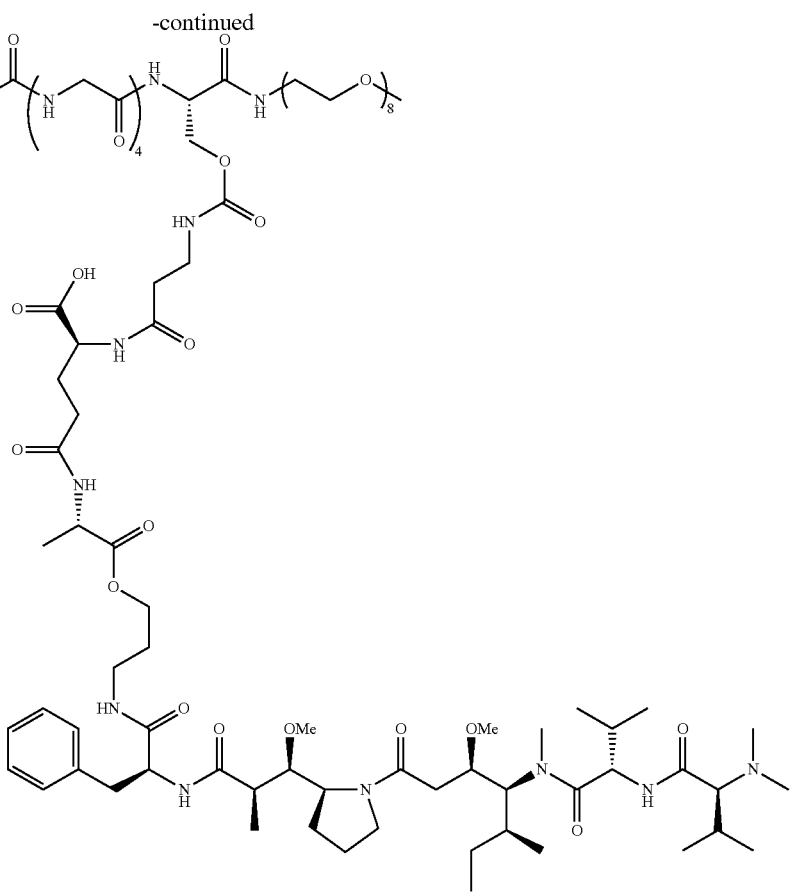

wherein: ■ is GlcNAc; △ is Fuc; and □ is GalNAc.

Conjugate 8 was synthesized as described in Example 1, except azido-modified 1D11 antibody (15 mg, 1.04 μmole, prepared as described in Example 1, Step 1), was used in Step 2 instead of azido-modified XMT-1604 ( )B7-H4_2F9V18 antibody. The details of the purified Conjugates 8-1 and 8-2 are given in the Table below.

| Conjugate | DAR |
|---|---|
| 8-1 | 5.9 |
| 8-2 | 6.0 |

Example 9: Synthesis of Rituximab Cytotoxic Drug Conjugate 9, DAR 5.7

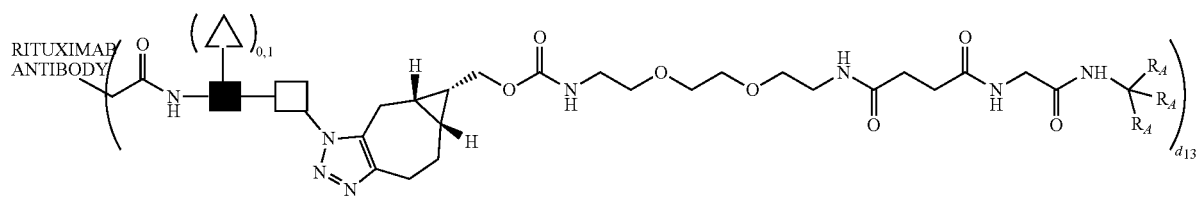

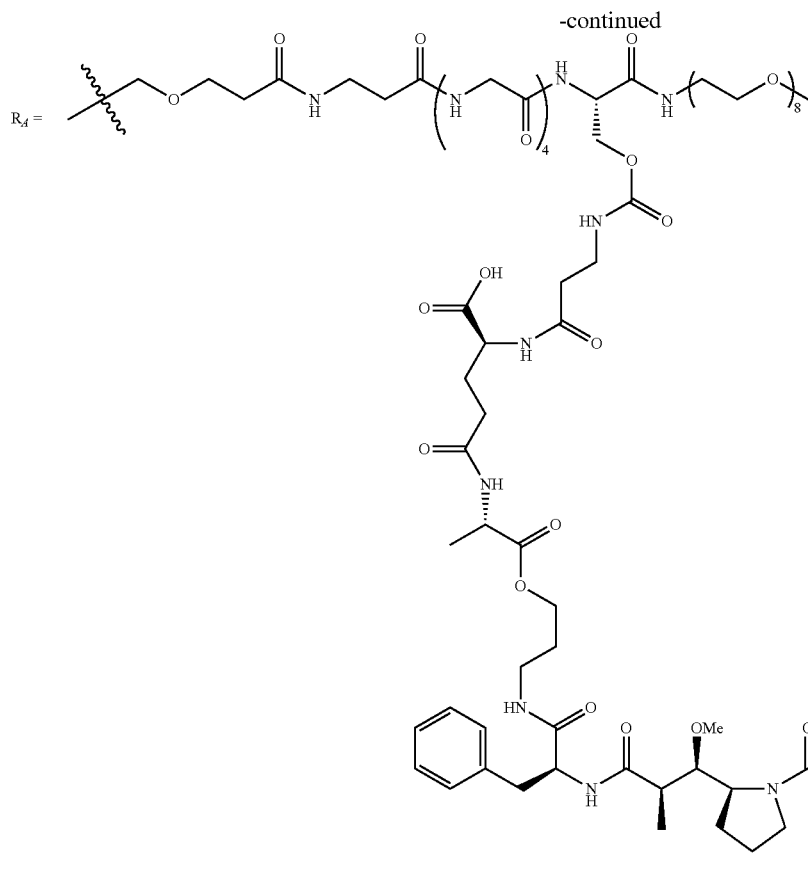

wherein: ■ is GlcNAc; △ is Fuc; and ☐ is GalNAc.

Conjugate 9 was synthesized as described in Example 1, except azido-modified Rituximab antibody (131.4 mg, 0.91 μmole, prepared as described in Example 1, Step 1), was used in Step 2 instead of azido-modified XMT-1604 (B7-H4_2F9V18) antibody. The details of the purified Conjugates 9-1 and 9-2 are given in the Table below.

| Conjugate | DAR |
|-----------|-----|
| 9-1 | 5.7 |
| 9-2 | 5.9 |

Example 10: Synthesis of Rituximab Cytotoxic Drug Conjugate 10, DAR 1.9

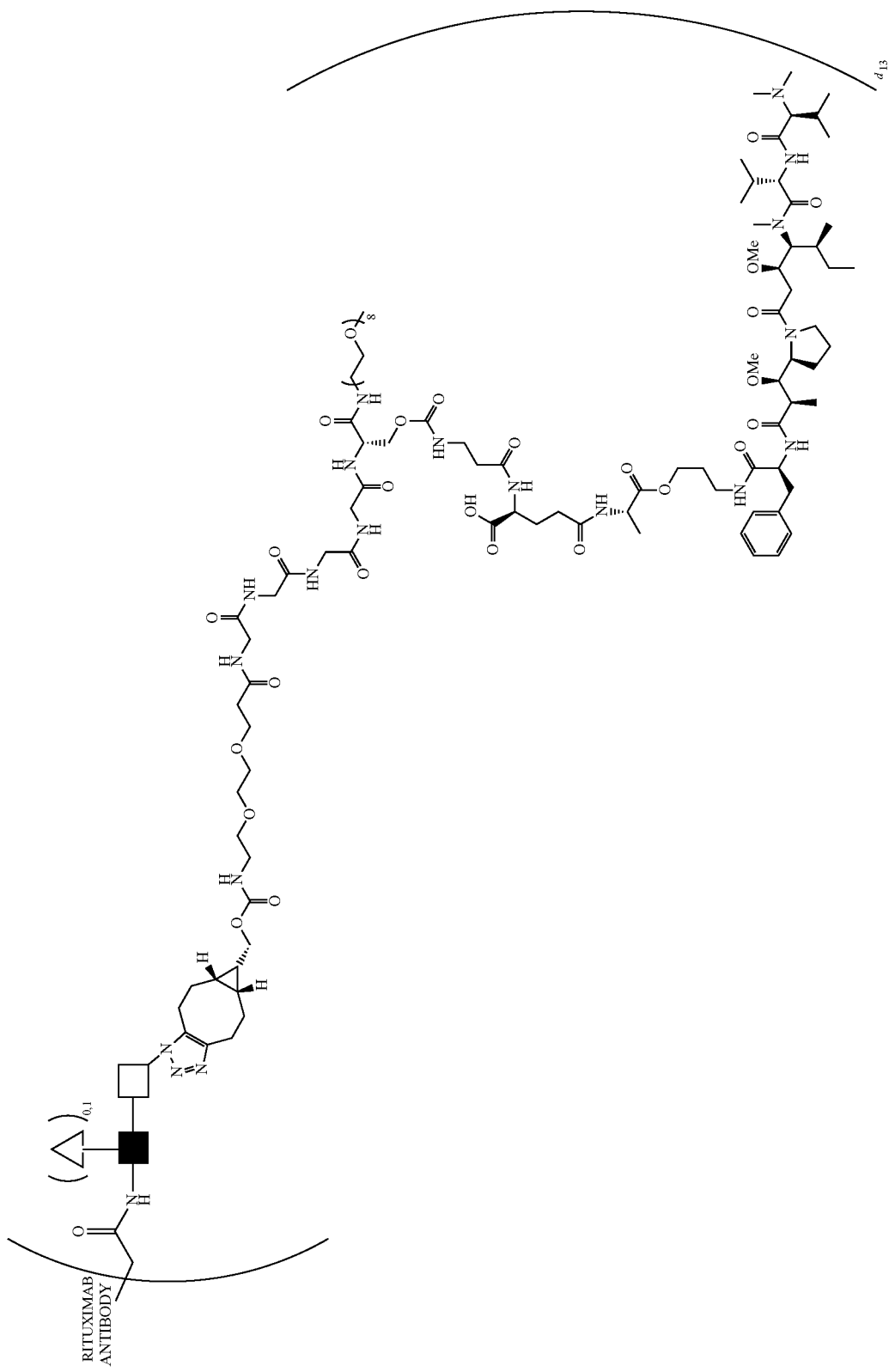

wherein: ■ is GlcNAc; △ is Fuc; and □ is GalNAc.

Conjugate 10 was synthesized as described in Example 2, except azido-modified Rituximab antibody (35 mg, 0.242 μmole, prepared as described in Example 1, Step 1), was used in Step 2 instead of azido-modified XMT-1604 (B7-H4_2F9V18) antibody. The purified Conjugate 10 (24 mg, 69% yield) had a DAR of 1.9 as determined by reduced RP-HPLC.

Example 11: Synthesis of B7-H4_2F9 Cytotoxic Drug Conjugate 11, DAR 5.9

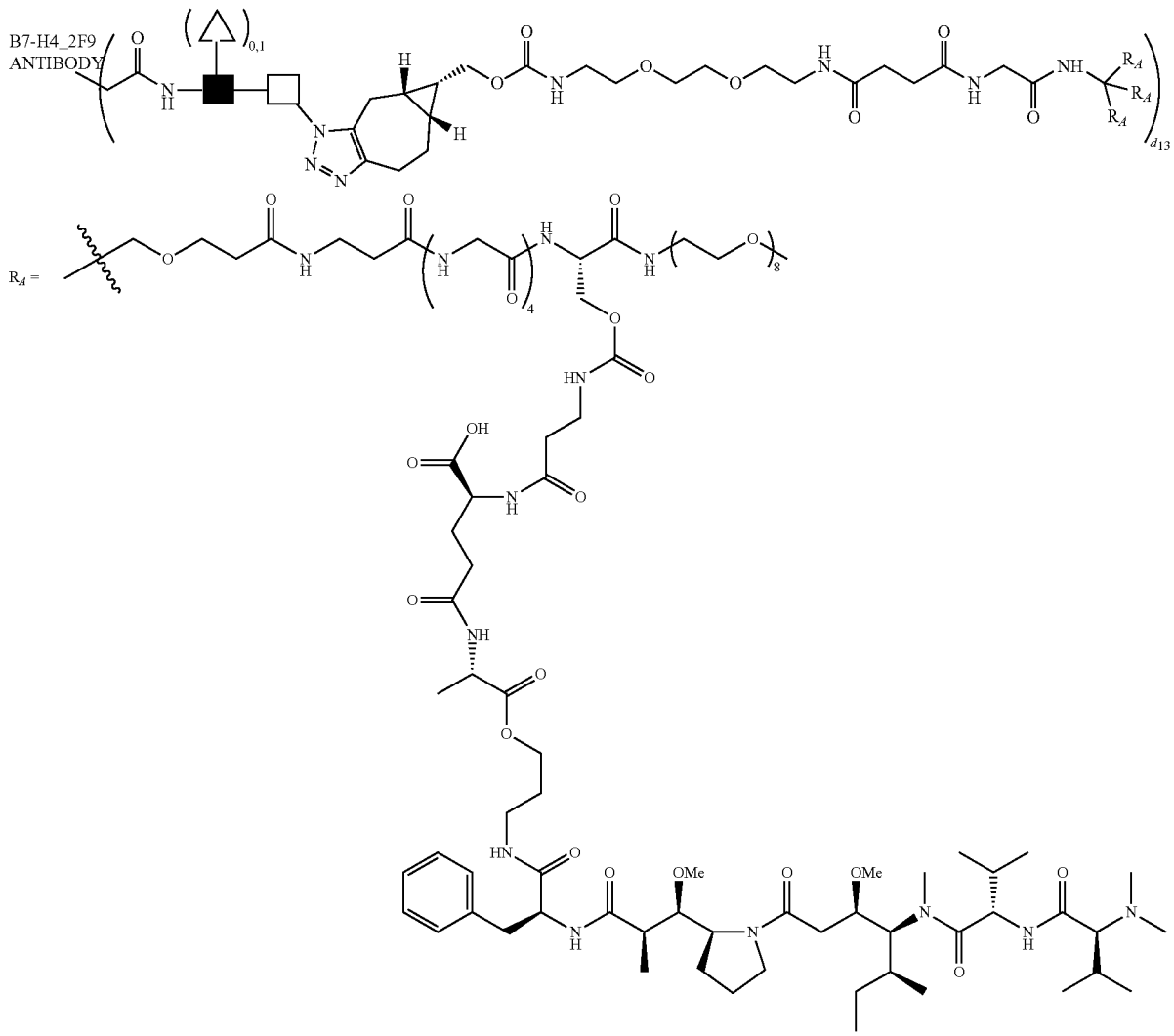

wherein: ■ is GlcNAc; △ is Fuc; and □ is GalNAc.

Conjugate 11 was synthesized as described in Example 1, except azido-modified B7-H4_2F9 antibody (21.2 mg, 0.147 μmole, prepared as described in Example 1, Step 1), was used in Step 2 instead of azido-modified XMT-1604 (B7-H4_2F9V18) antibody. The purified Conjugate 11 (11.2 mg, 53% yield) had a DAR of 5.9 as determined by reduced RP-HPLC.

Example 12: Synthesis of XMT-1604 (B7-H4_2F9V18) Cytotoxic Drug Conjugate 12, DAR 11.9

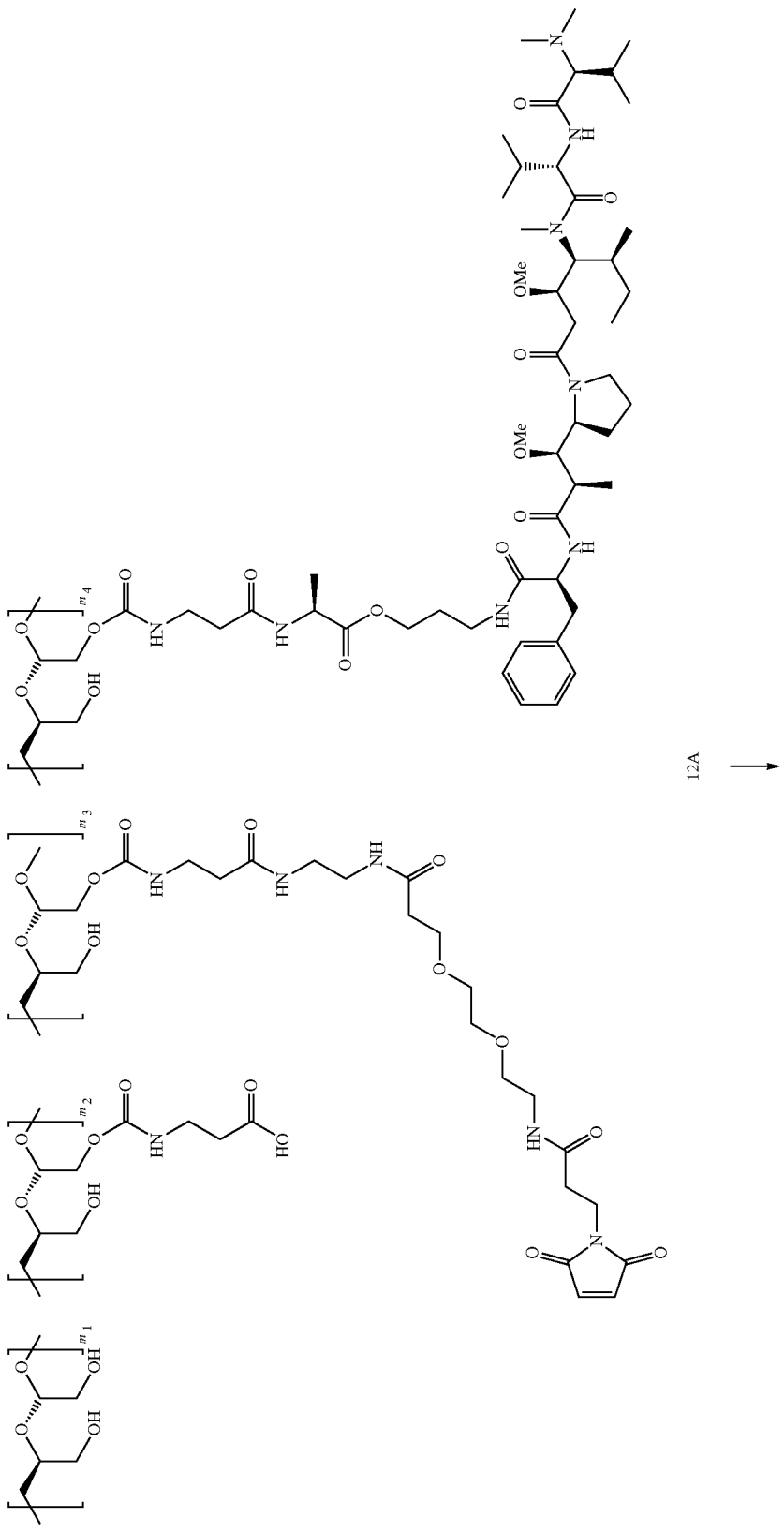

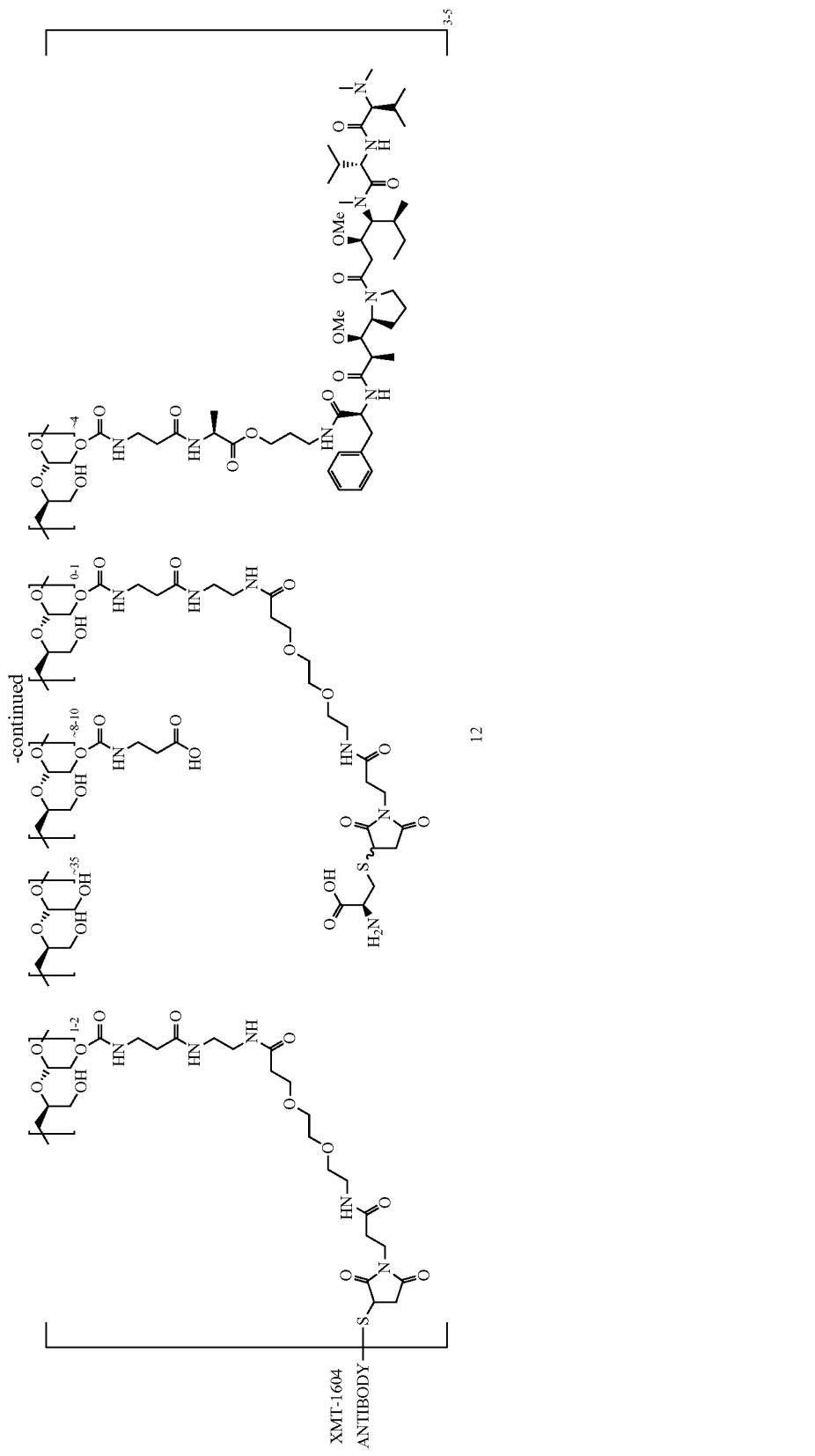

To a solution of XMT-1604 (B7-H4_2F9V18) antibody (20 mg, 0.139 μmole) in TEAA buffer, pH 7 (4 mL) was added a solution of TCEP (0.0993 mg, 0.347 μmole) while stirring. The mixture was incubated for 1.5 h at room temperature. The partially reduced XMT-1604 (B7-H4_2F9V18) antibody was then added to a vigorously stirred solution of Scaffold 12A (18 mg, 1.807 μmole, prepared as described in U.S. Pat. No. 9,849,191) in TEAA buffer, pH 6 (1.8 mL). The stirring was continued for 1 h at room temperature. The reaction was quenched with an aqueous solution of cysteine (0.421 mg, 3.47 μmole) in TEAA buffer, pH 7 (0.084 mL). After stirring for 30 minutes at ambient temperature at pH 7.0, the reaction mixture was acidified to pH 5.8. The crude product was purified by WCX to give Conjugate 12 (10 mg, 50% yield), that had a DAR of 11.9 as determined by hydrolysis followed by RP-HPLC.

Example 13: Synthesis of XMT-1603 (B7-H4_2F9V7) Cytotoxic Drug Conjugate 13, DAR 11.8

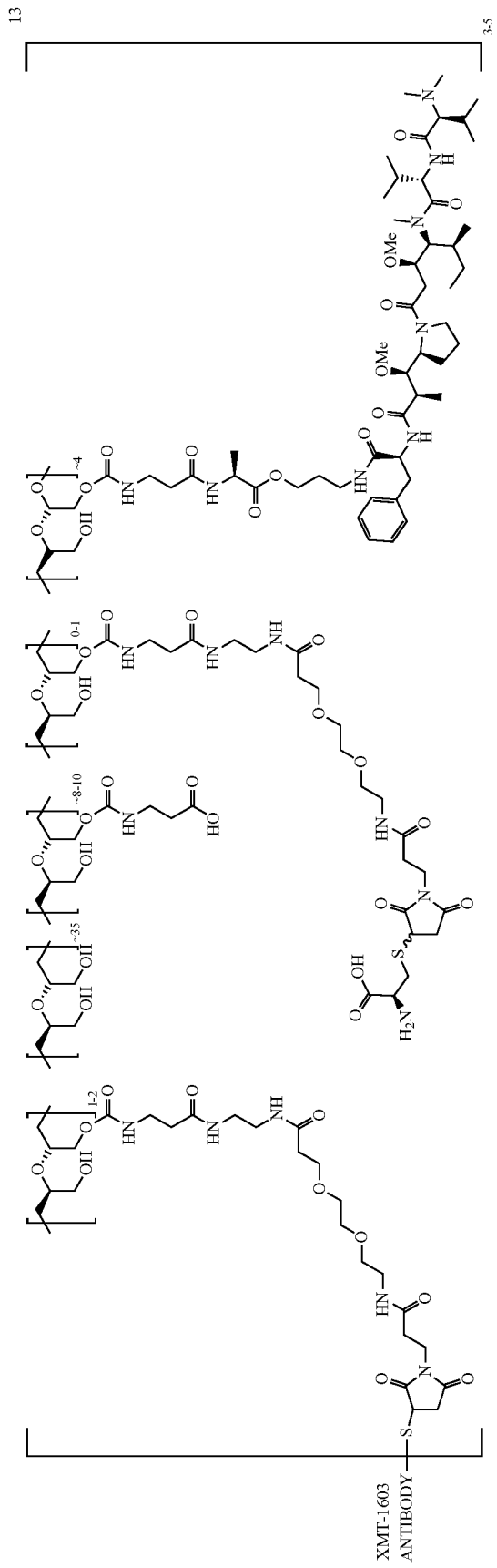

Conjugate 13 was synthesized as described in Example 12, except XMT-1603 (B7-H4_2F9V7) antibody (20 mg, 6.99 μmole) was used instead of XMT-1604 (B7-H4_2F9V18) antibody. The purified Conjugate 13 (11.5 mg, 58% yield) had a DAR of 11.8 as determined by hydrolysis followed by RP-HPLC.

Example 14: Synthesis of Rituximab Cytotoxic Drug Conjugate 14, DAR 10.8

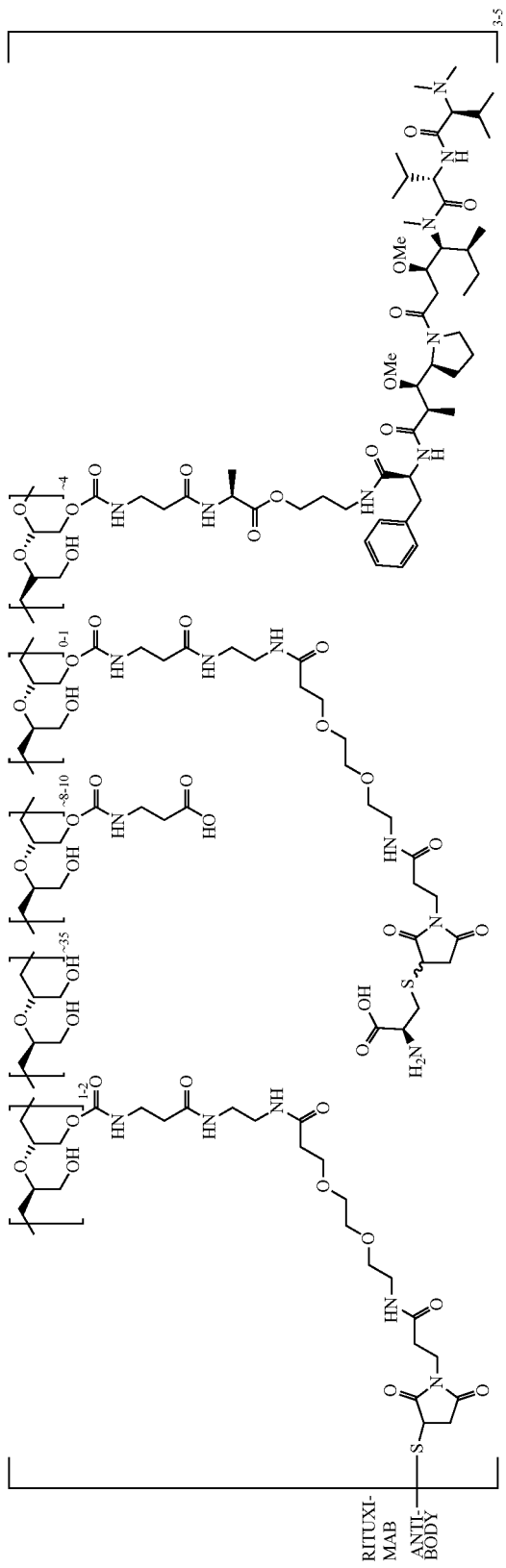

Conjugate 14 was synthesized as described in Example 12, except Rituximab antibody (100 mg, 6.99 μmole) was used instead of XMT-1604 (B7-H4_2F9V18) antibody. The purified Conjugate 14 (62.6 mg, 63% yield) had a DAR of 10.8 as determined by hydrolysis followed by RP-HPLC.

Example 15: Synthesis of XMT-1604 (B7-H4_2F9V18) STING Agonist Drug Conjugate 15, DAR 6.8

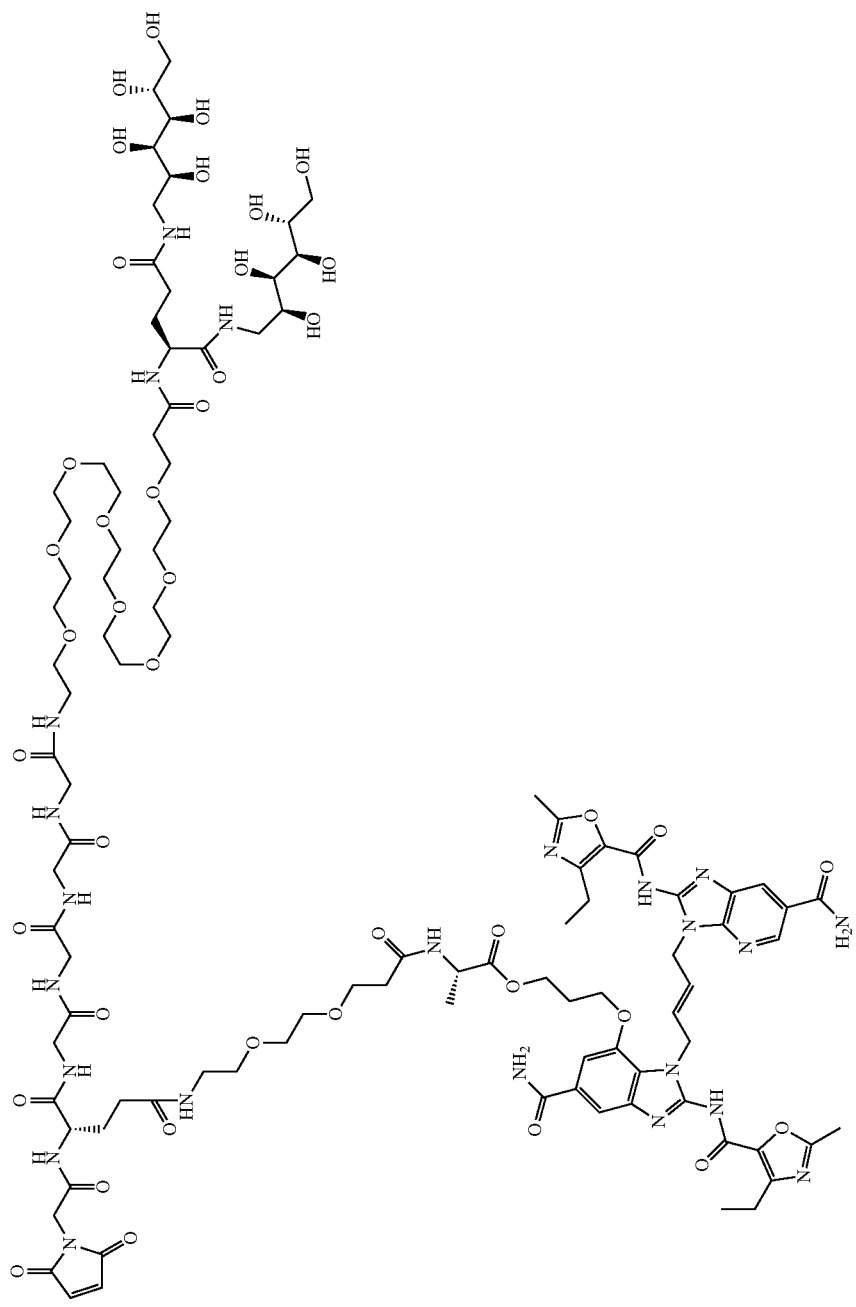
15A

-continued
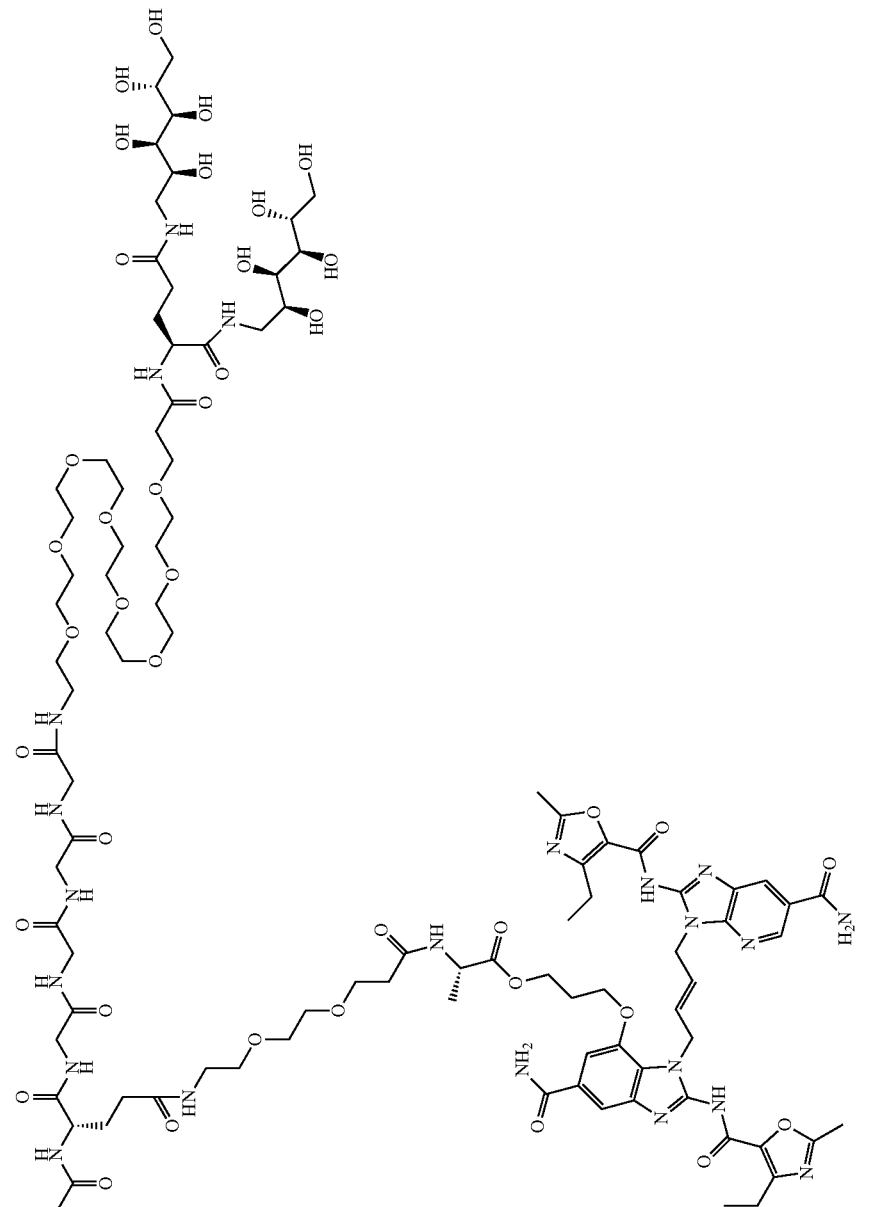

To a solution of XMT-1604 (B7-H4_2F9V18) (8 mg, 0.055 μmole) in 50 mM HEPES, 1 mM EDTA buffer, pH 7.0 (1.53 mL) was added a solution of TCEP (8 mg, 0.055 μmole) in 50 mM HEPES, 1 mM EDTA buffer, pH 7.0 (0.075 mL) while stirring. The mixture was incubated for 1.5 h at 37° C. The reduced XMT-1604 (B7-H4_2F9V18) was then added a solution of Scaffold 15A (prepared as described in U.S. Ser. No. 17/221,341, 1.18 mg, 0.5 μmole) in DMA (0.16 mL) while stirred. The stirring was continued for 1 h at 37° C. The reaction was quenched with an aqueous solution of cysteine (0.1 mg, 0.83 μmole) in 50 mM HEPES, 1 mM EDTA buffer, pH 7 (0.02 mL). After stirring for 45 minutes at ambient temperature at pH 7, the crude product was purified by CHT chromatography to give Conjugate 15 (7.6 mg, 95% yield), that had a DAR of 6.8 as determined by UV-Vis. Conjugates 15-1 and 15-2 were synthesized in a similar way and the details of the corresponding purified conjugates are provided in the table below.

| Conjugate | DAR | XMT-1604(B7-H4_2F9V18) | TCEP | Scaffold 15A |
|---|---|---|---|---|
| 15 | 6.8 | 8 mg, 0.055 μmole | 8 mg, 0.055 μmole | 1.18 mg, 0.5 μmole |
| 15-1 | 7.9 | 330 mg, 2.29 μmole | 3.11 mg, 10.86 μmole | 51.2 mg, 22 μmole |
| 15-2 | 7 | 250 mg, 1.73 μmole | 2.36 mg, 8.23 μmole | 38.8 mg, 16.67 μmole |

Example 16: Synthesis of 1D11 STING Agonist Conjugate 16, DAR 6.5

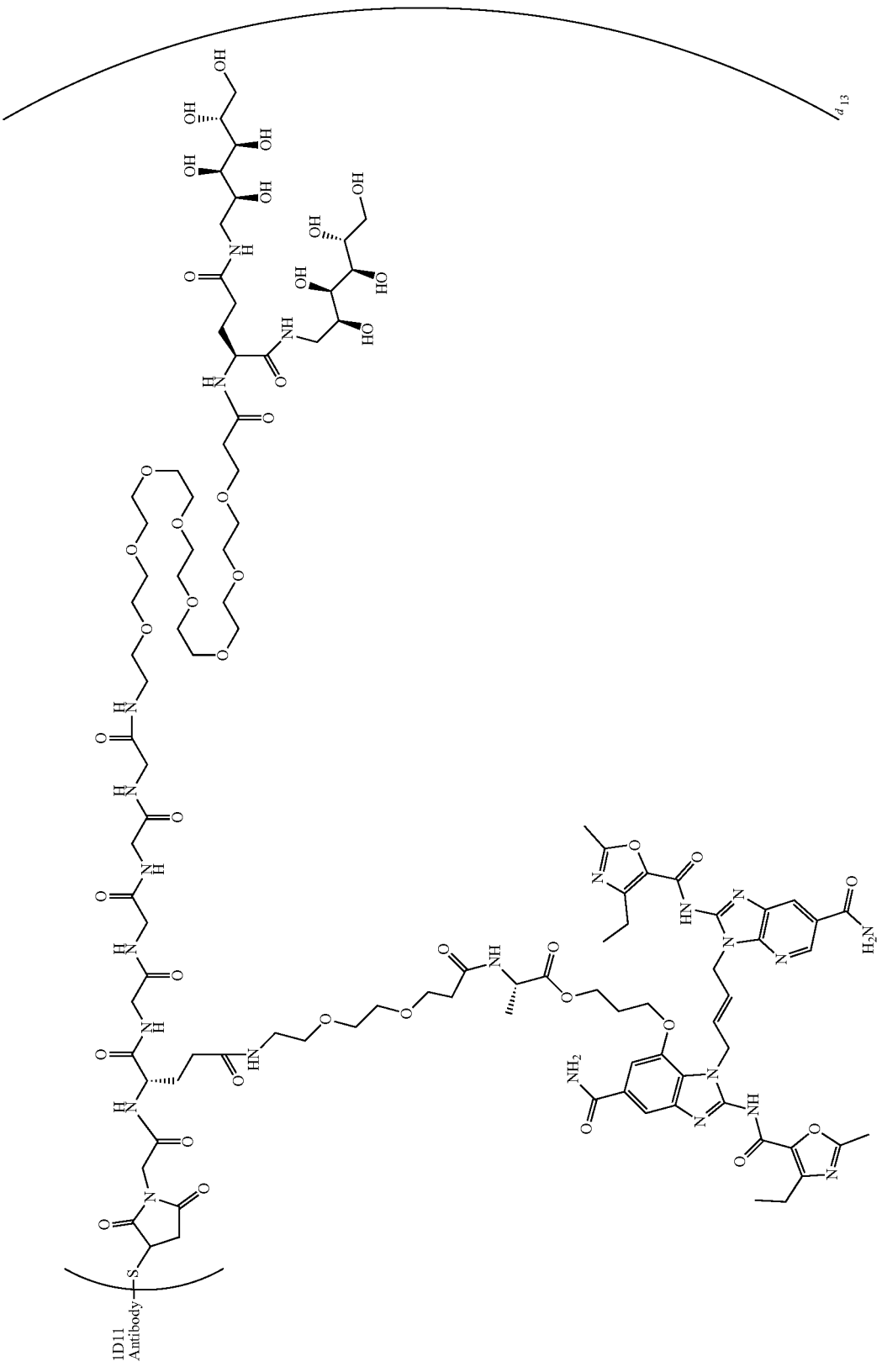

Conjugate 16 was synthesized as described in Example 15, except 1D11 antibody (8 mg, 0.055 μmole) was used instead of XMT-1604 (B7-H4_2F9V18) antibody. The purified Conjugate 16 (7 mg, 87.5% yield) had a DAR of 6.5 as determined by UV-Vis.

Example 17: Synthesis of Palivizumab STING Agonist Conjugate 17, DAR 6.8

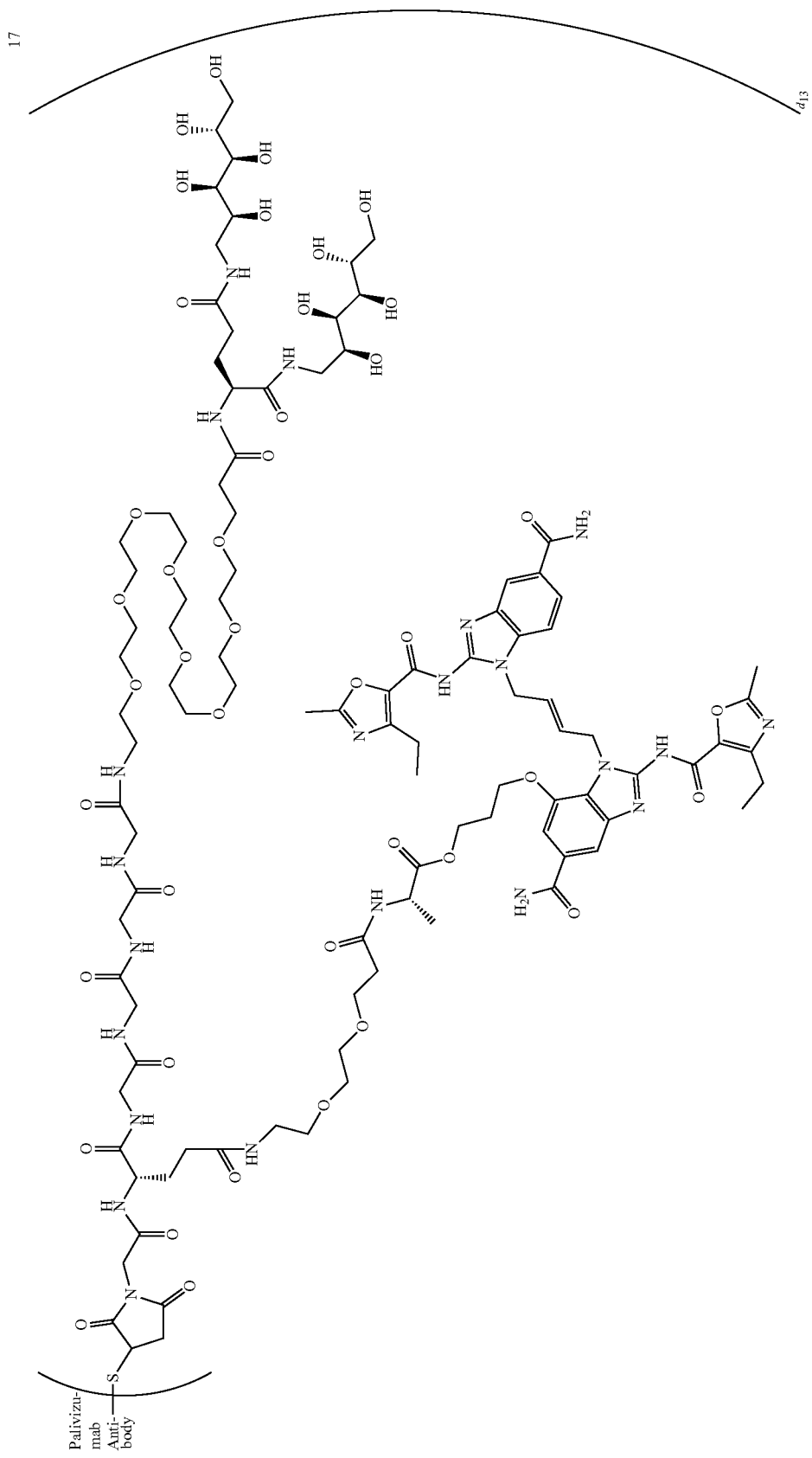

Conjugate 17 was synthesized as described in Example 15, except Palivizumab was used instead of XMT-1604 (B7-H4_2F9V18) antibody. The purified Conjugate 17 (7 mg, 87.5% yield) had a DAR of 6.8 as determined by UV-Vis.

Example 18: Synthesis of 1D11 STING Agonist Conjugate 18, DAR 6.9

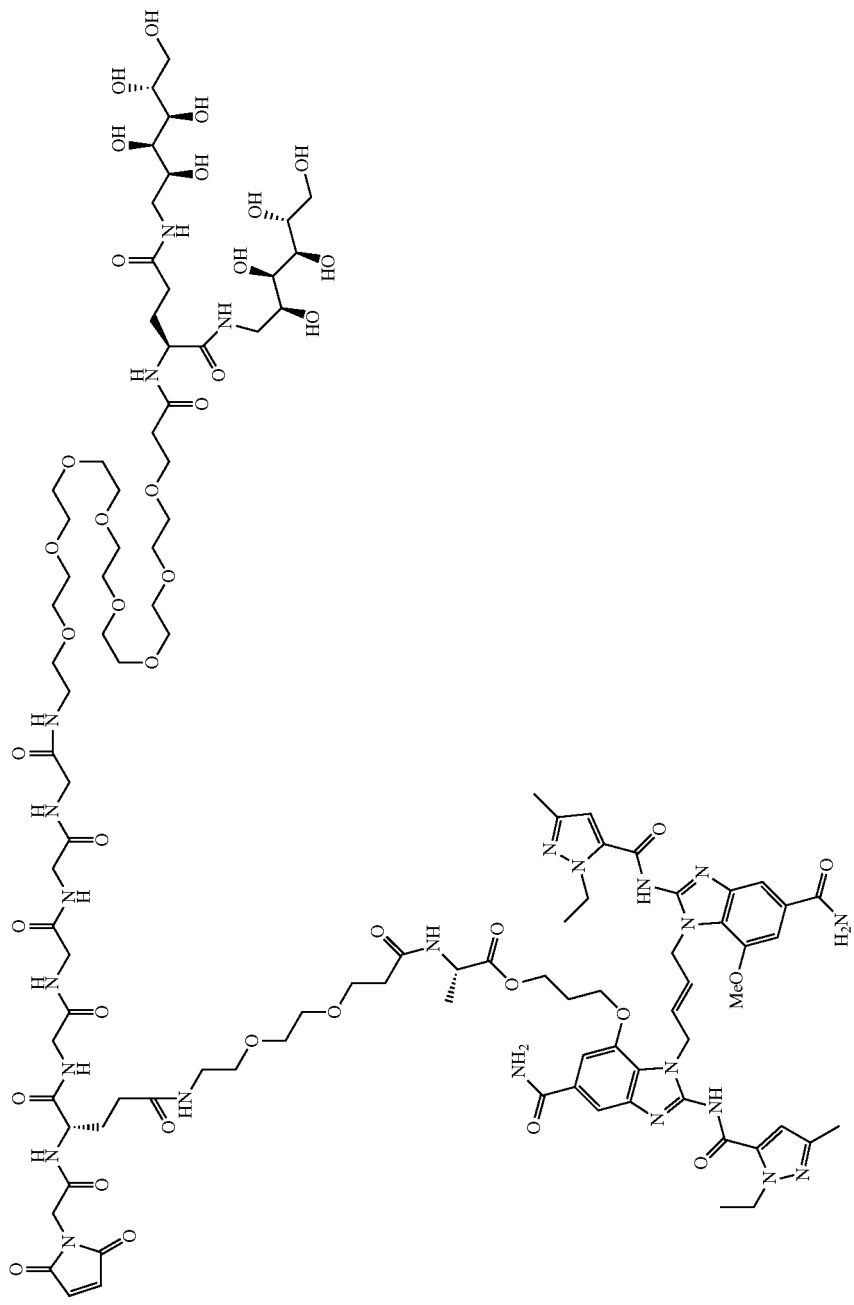

-continued
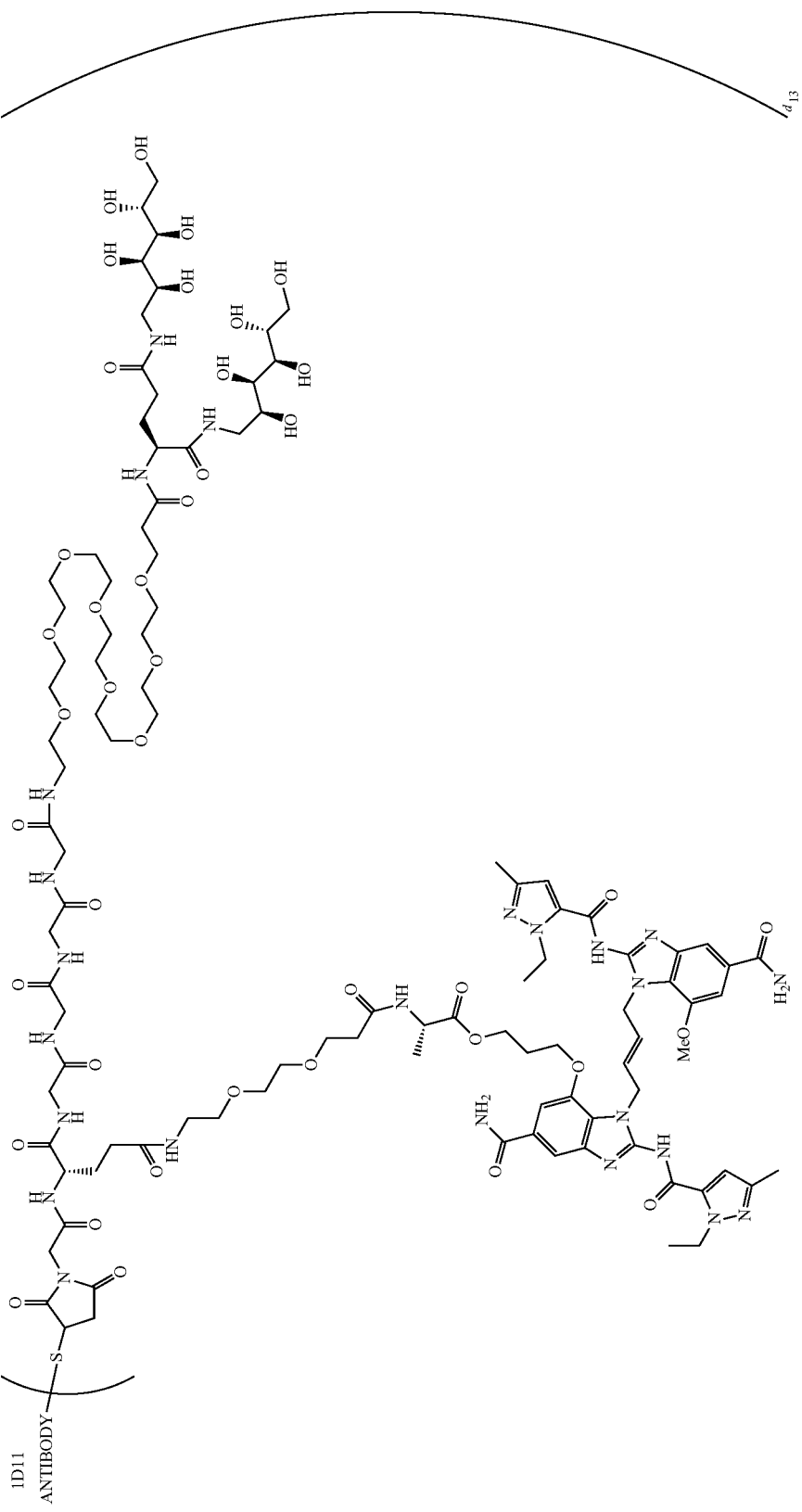

To a solution of 1D11 (15.9 mg, 0.109 μmole) in 50 mM HEPES, 1 mM EDTA buffer, pH 7.0 (3.105 mL) was added a solution of TCEP (0.125 mg, 0.436 μmole) in 50 mM HEPES, 1 mM EDTA buffer, pH 7.0 (0.075 mL) while stirring. The mixture was incubated for 1.5 h at 37° C. The reduced 1D11 was then added a solution of Scaffold 18A (prepared as described in U.S. Ser. No. 17/221,341, 2.084 mg, 0.872 μmole) in DMA (0.31 mL) while stirred. The stirring was continued for 1 h at 37° C. The reaction was quenched with an aqueous solution of cysteine (0.198 mg, 1.635 μmole) in 50 mM HEPES, 1 mM EDTA buffer, pH 7 (0.04 mL). After stirring for 45 minutes at ambient temperature at pH 7, the crude product was purified by CHT chromatography to give Conjugate 18 (10.8 mg, 68% yield), that had a DAR of 6.9 as determined by UV-Vis.

Example 19: Synthesis of 1D11 STING Agonist Conjugate 19, DAR 6.5

To a solution of 1D11 (10 mg, 0.069 μmole) in 50 mM HEPES, 1 mM EDTA buffer, pH 7.0 (1.921 mL) was added a solution of TCEP (0.079 mg, 0.276 μmole) in 50 mM HEPES, 1 mM EDTA buffer, pH 7.0 (0.079 mL) while stirring. The mixture was incubated for 1.5 h at 37° C. The reduced 1D11 was then added a solution of Scaffold 20A (prepared as described in U.S. Ser. No. 17/221,341, 0.606 mg, 0.552 μmole) in DMA (0.2 mL) while stirred. The stirring was continued for 1 h at 37° C. The reaction was quenched with an aqueous solution of cysteine (0.125 mg, 1.035 μmole) in 50 mM HEPES, 1 mM EDTA buffer, pH 7 (0.013 mL). After stirring for 45 minutes at ambient temperature at pH 7, the crude product was purified by CHT chromatography to give Conjugate 19 (8.2 mg, 82% yield), that had a DAR of 6.5 as determined by UV-Vis.

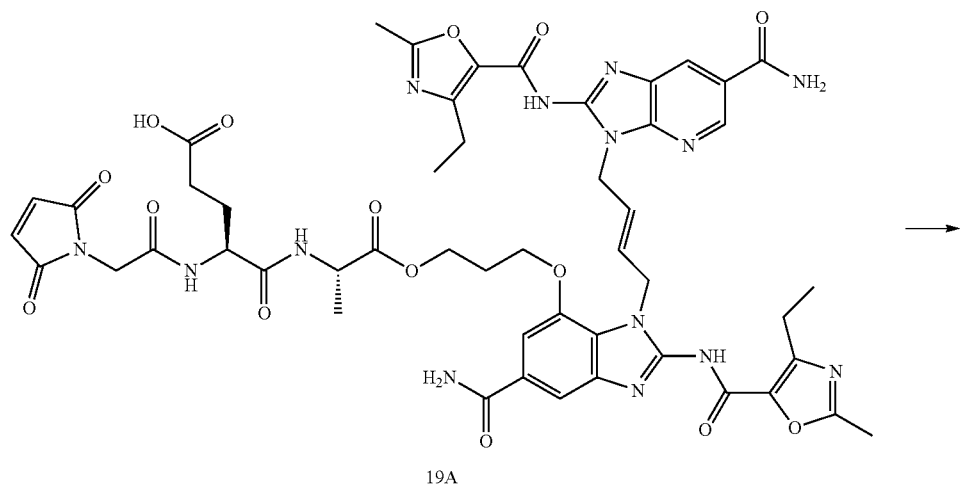

19A

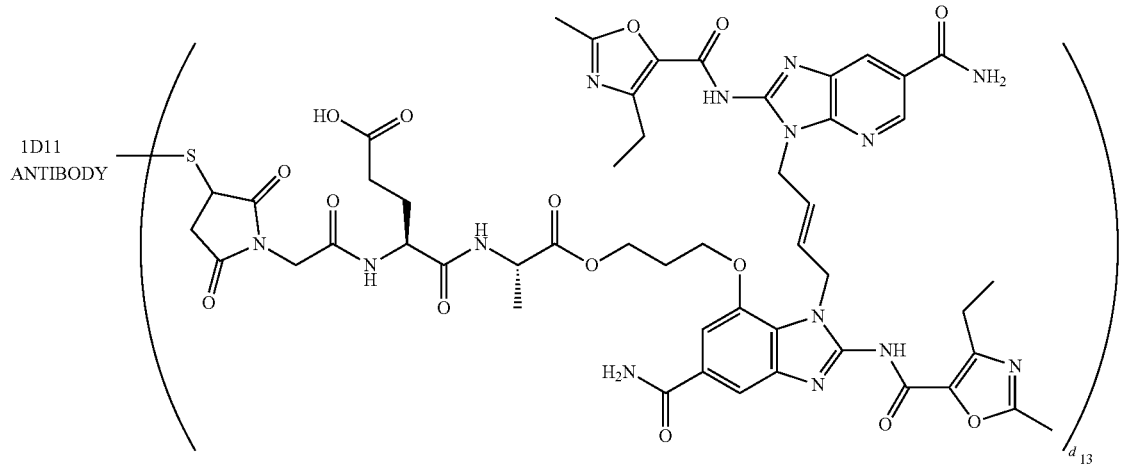

19

Example 20: Synthesis of B7-H4_2F9V18 STING Agonist Conjugate 21, DAR 6.9
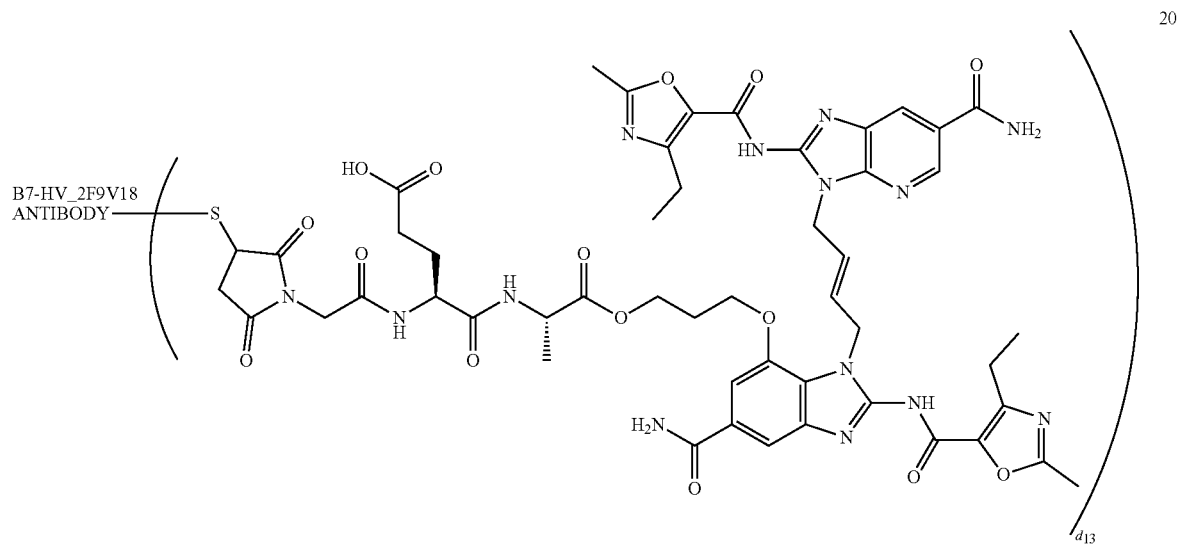
Conjugate 20 was synthesized as described in Example 19 except XMT-1604 (B7-H4_2F9V18) antibody (10 mg, 0.069 μmole) was used instead of 1D11 antibody. The purified Conjugate 20 (6.2 mg, 62% yield) had a DAR of 6.9 as determined by UV-Vis.
Example 21: Synthesis of Scaffold 24
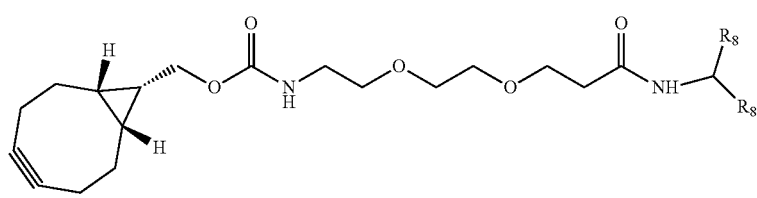

R_8 =
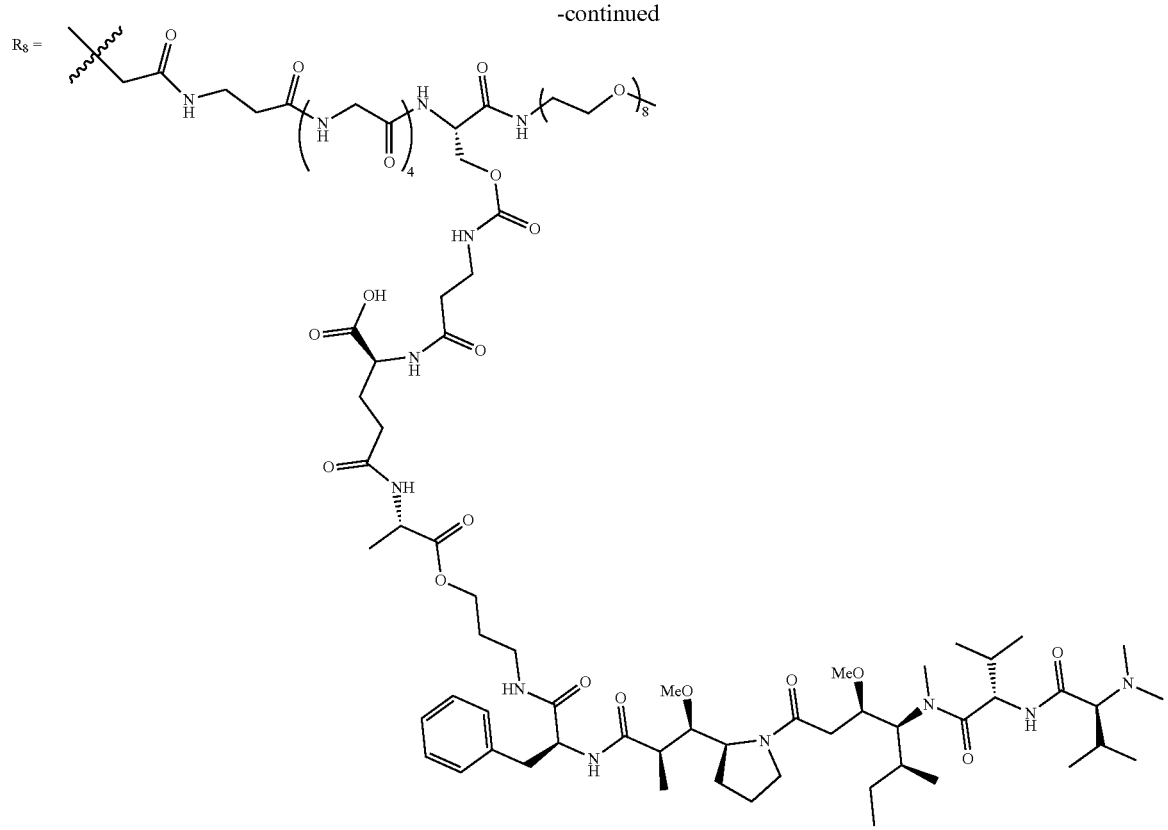
Step 1. Compound 22
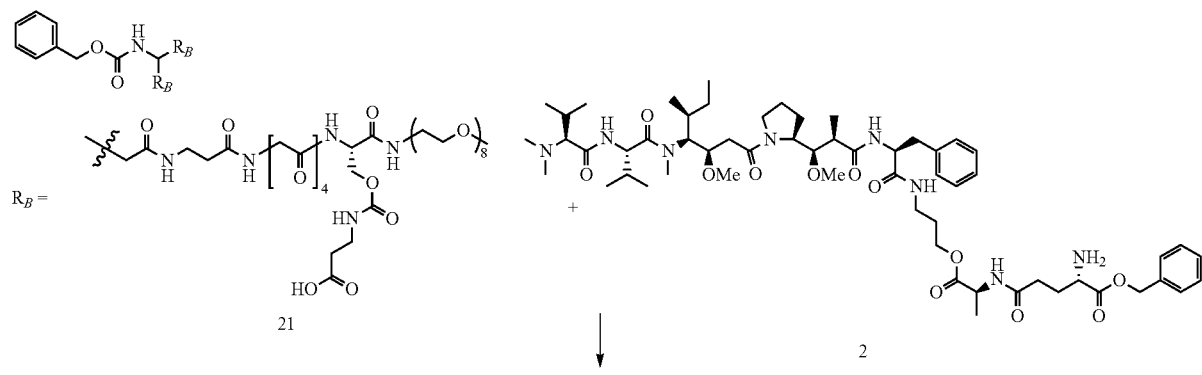

541

542

-continued

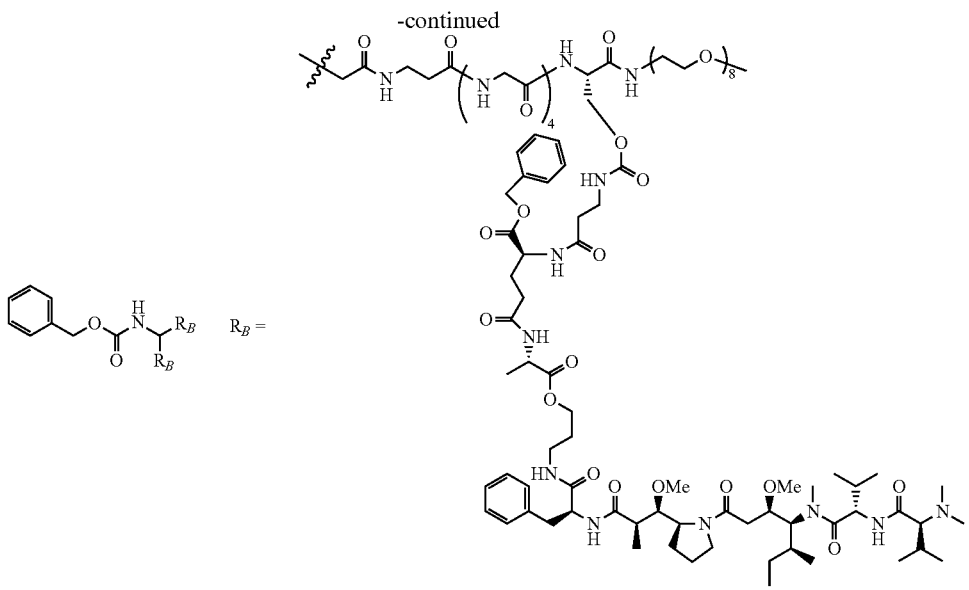

22

Compound 21 (250 mg, 0.124 mmol, prepared using procedures described in U.S. Ser. No. 15/819,650, the entire contents of which are incorporated herein by reference), water (5.9 mL), NMP (1.5 mL), EDC (166 mg, 0.868 mmol), and HOAt (0.041 mg, 0.298 mmol) were stirred in an ice-bath, and the pH was adjusted to ~6.5 with 1N $NaHCO_3$ (aq). Compound 2 (631 mg, 0.558 mmol) was added, followed by pH adjustment to ~6.5. The resulting mixture was stirred cold for 3 h. Additional EDC, HOAt, and compound 2 (198 mg, 0.164 mmol) were added and the stirring continued overnight. The reaction mixture was purified on a C18 cartridge (100 g) with a step gradient of $ACN/H_2O$ from 10% to 60% to 100% v/v $ACN/H_2O$. The desired fractions were lyophilized to give compound 22 as a white amorphous solid (275 mg, 53% yield). MS: 2083.64 (2$^+$), 1389.43 (3$^+$), 1042.35 (4$^+$).

Step 2. Compound 23

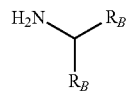

23

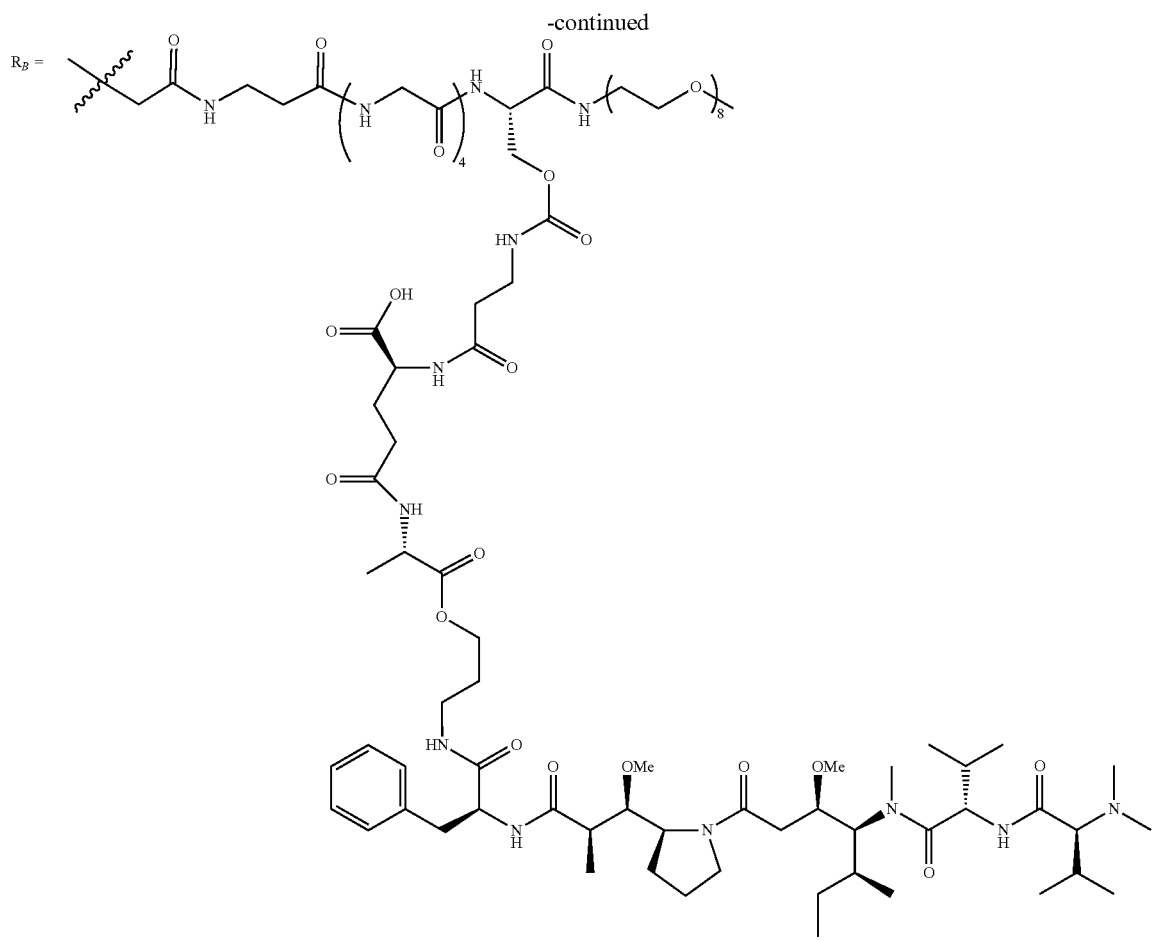

To a mixture of compound 22 (375 mg, 0.09 mmol), EtOH (1.5 mL), and water (1.5 mL) in a glass Parr bottle: Argon was bubbled through the mixture, followed by the addition of Pd/C (9.5 mg, 0.009 mmol). The bottle was attached to the hydrogenation equipment then successively vacuum pumped, filled with argon, then filled with hydrogen (0.762 mg, 0.378 mmol) to 30 psi, and the mixture was stirred vigorously overnight. The reaction mixture was filtered through a plug of silica gel and concentrated to an oil. The oil was dissolved in ACN/H$_2$O and lyophilized to obtain compound 23 as a white amorphous solid (220 mg, 63% yield). MS: 1926.60 (2$^+$), 1284.74 (3$^+$), 963.80 (4$^+$).

Step 3. Scaffold 24

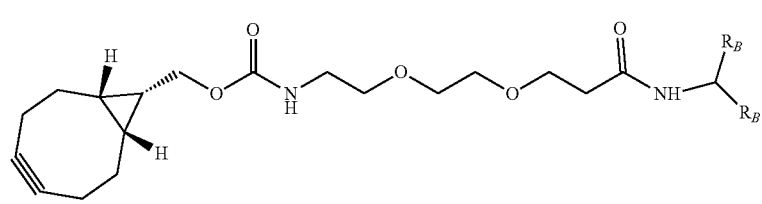

-continued

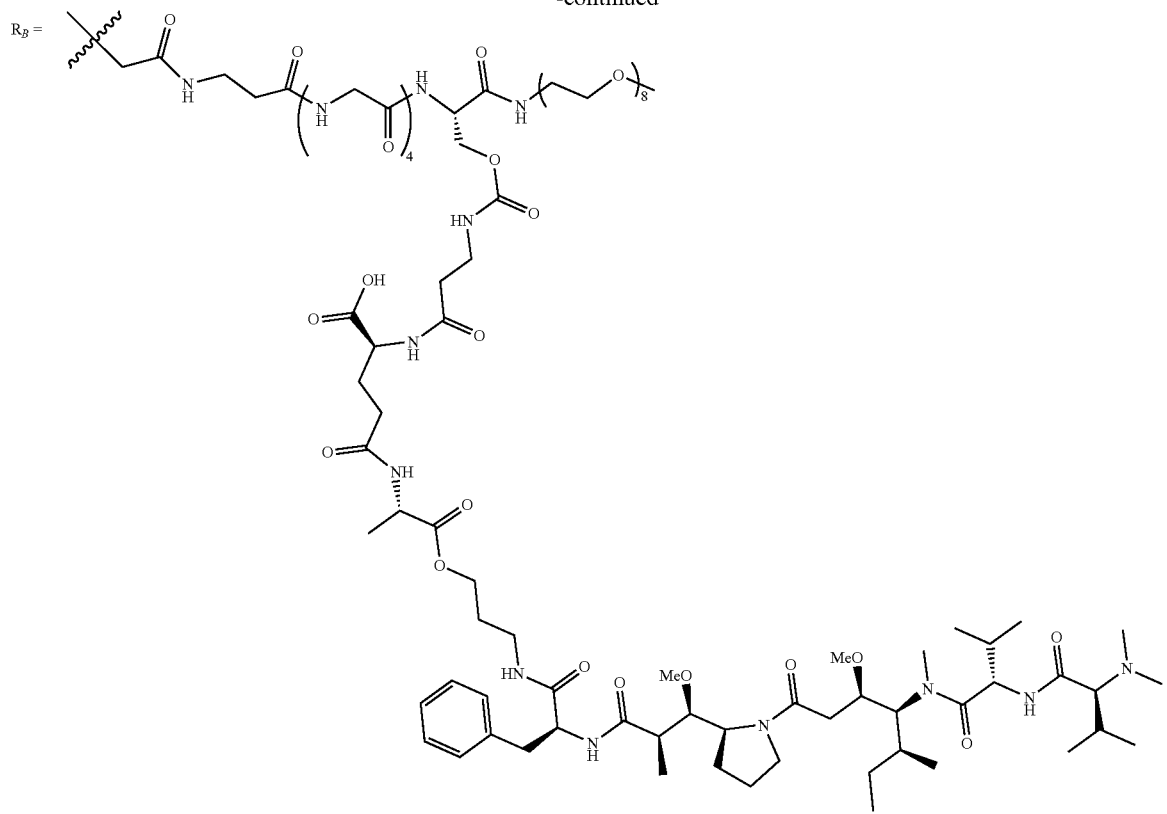

To an ice-cold solution of compound 23 (150 mg, 0.039 mmol) in ACN (1.04 mL) and DMF (0.500 mL) was added 2,5-dioxopyrrolidin-1-yl 1-((1R,8S,9s)-bicyclo[6.1.0]non-4-yn-9-yl)-3-oxo-2,7,10-trioxa-4-azatridecan-13-oate (35 mg, 0.078 mmol) and DIPEA (0.027 mL, 0.156 mmol), final pH ~8-9. The mixture was stirred at room temperature for 2 h, then concentrated and purified on a preparative HPLC using ACN/H$_2$O (0.1% TFA) as the mobile phase. The desired fractions were lyophilized to give Scaffold 24 as a white amorphous solid (93.1 mg, 57% yield). MS: 2094.23 (2+), 1396.43 (3+), 1047.62 (4+) 838.30 (5+).

Example 22: Identification of Post-Translational Modification Risks to B7-H4_2F9 and Generation of B7-H4 Variants Analysis of the VH and VL regions of B7-H4_2F9 and B7-H4_2A7 (disclosed in US20110085970A1) identified potential post-translational modification (PTM) liabilities, considered to be undesirable due to potential risks to antibody developability. As shown below, the result of this analysis identified potential risks in the VH chain of B4-H4_2F9. These included, in order of descending theoretical risk, a non-canonical cysteine residue, a potential Asp isomerization site, and a potential Met oxidation site for B7-H4_2F9 shown below.

```
B7H4-2A7-vH  EVQLVESGGGLIQPGGSLRLSCAASGFTVSSNYMNWCRQAPGKGLEWVSVIYGSGRTYYA
B7H4-2F9-vH  EVQLVESGGGLIQPGGSLRLSCAASGFIVSRNYMNWVRQAPGKGLEWVSVIYGSGRTDCA
             *************************** ** ***************************  *

B7H4-2A7-vH  DSVKGRVTISRDNSKNTLYLQMNSLRAEDTAVYYCARDT-YAMDVWGQGTTVTVSS
B7H4-2F9-vH  DSVKGRFTISRDNSKNTLYLQMNSLRAEDTAVYYCARDGDYGMDVWGQGTTVTVSS
             ****** *******************************  * ***************
```

SEQ ID NO: 60
SEQ ID NO: 1

Asp isomerization
DG motif

Met oxidation

Variants of the antibody B4-H4_2F9 were generated in order to eliminate potential PTM hazards, while retaining desired antibody properties, as summarized in Table 1. Each variant antibody generated contained one of four changes to eliminate the non-canonical cysteine risk (DC to YY, DY, DA, or DS). Variants contained these mutations alone (B7-H4_2F9V1, B7-H4_2F9V6, B7-H4_2F9V11, B7-H4_2F9V16), or in combination with other mutations, including four variants which also had mutations that removed the potential Asp isomerization site (DG to DA), in addition to addressing the non-canonical cysteine risk: B7-H4_2F9V2, B7-H4_2F9V7, B7-H4_2F9V12, B7-H4_2F9V17. Four variants had these mutations, plus an additional mutation to address the potential methionine oxidation hazard (MDV to LDV; B7-H4_2F9V3, B7-H4_2F9V8, B7-H4_2F9V13, B7-H4_2F9V18), hence addressing all three potential PTM liabilities. Four variants were designed to eliminate the Asp isomerization sequence by adding in the 2A7 HCDR3 region instead of the B4-H4_2F9 HCDR3 region (B7-H4_2F9V4, B7-H4_2F9V9, B7-H4_2F9V14, B7-H4_2F9V19), in addition to containing the mutations to address the non-canonical cysteine risk. The remaining four variants contained mutations to address the non-canonical cysteine risk, the Asp isomerization risk by including the 2A7 HCDR3 region, and the MDV to LDV mutation to address the methionine oxidation risk (B7-H4_2F9V5, B7-H4_2F9V10, B7-H4_2F9V15, B7-H4_2F9V20). Table 1 summarizes B4-H4_2F9 antibody sequence variations and PTM liabilities addressed.

Example 23: Binding of B7-H4_F9 Parental Antibody and 20 B7-H4_2F9 Antibody Variants Thereof to Human B7-H4 Protein by ELISA Recombinant human B7-H4 protein (R&D Systems #6576-B7-050) was coated onto the surface of each well of a 96-well plate by incubation with the peptide (1 µg/mL in PBS), overnight at 4° C. The wells were then blocked by incubation with BSA (5% in PBS, containing 0.1% Tween 20 (PBST)) for 1 hour at room temperature. A range of dilutions (0.0061 nM to 100 nM; 4-fold serial dilutions in 3% BSA in PBS) of the test articles (B7-H4_2F9 and 20 B7-H4_2F9 antibody variants) were then added to each well and the plate was incubated for 1 hour at room temperature with gentle rocking. The unbound test article was removed by washing with PBST (3×). A secondary anti-human IgG conjugated to HRP (0.16 µg/mL in PBST) was incubated in each well for 1 hour. The unbound secondary antibody was removed by washing with PBST (3×). The HRP substrate, TMB, was added to each well and incubated until a blue color was visible. The reaction was quenched by the addition of sulfuric acid (0.2 N, 100 µL). The absorbance at 450 nm was measured in a plate reader (Molecular Devices, Spectramax M5). The values were plotted using GraphPad Prism software. $EC_{50}$ values were determined by four-parameter curve fitting. Table 2 summarizes the binding values ($EC_{50}$).

TABLE 2

| Antibody | Binding to Human B7-H4 Protein $EC_{50}$, nM |
| --- | --- |
| B7-H4_2F9 | 1.46 |
| B7-H4_2F9V1 | 11.67 |
| B7-H4_2F9V2 | 4.23 |
| B7-H4_2F9V3 | 2.81 |
| B7-H4_2F9V4 | 11.41 |
| B7-H4_2F9V5 | 2.04 |
| B7-H4_2F9V6 | 5.43 |
| XMT-1603(+K) B7-H4_2F9V7 | 4.33 |
| B7-H4_2F9V8 | 2.74 |
| B7-H4_2F9V9 | 3.00 |

TABLE 1

| PTM Risks Addressed | Mutations | Mutations To Address Non-Canonical Cysteine | | | |
| --- | --- | --- | --- | --- | --- |
| | | DC to YY | DC to DY | DC to DA | DC to DS |
| No Additional Changes | | B7-H4_2F9V1 | B7-H4_2F9V6 | B7-H4_2F9V11 | B7-H4_2F9V16 |
| Asp Isomerization | DG to DA | B7-H4_2F9V2 | XMT-1603(+K) B7-H4_2F9V7 | B7-H4_2F9V12 | B7-H4_2F9V17 |
| Asp Isomerization + Met Oxidation | DG to DA MDV to LDV | B7-H4_2F9V3 | B7-H4_2F9V8 | B7-H4_2F9V13 | XMT-1604(+K) B7-H4_2F9V18 |
| Asp Isomerization | 2A7 HCDR3 | B7-H4_2F9V4 | B7-H4_2F9V9 | B7-H4_2F9V14 | B7-H4_2F9V19 |
| Asp Isomerization + Met Oxidation | 2A7 HCDR3 MDV to LDV | B7-H4_2F9V5 | B7-H4_2F9V10 | B7-H4_2F9V15 | B7-H4_2F9V20 |

TABLE 2-continued

| Antibody | Binding to Human B7-H4 Protein EC$_{50}$, nM |
|---|---|
| B7-H4_2F9V10 | 2.13 |
| B7-H4_2F9V11 | 6.74 |
| B7-H4_2F9V12 | >100 |
| B7-H4_2F9V13 | 3.71 |
| B7-H4_2F9V14 | 4.40 |
| B7-H4_2F9V15 | 1.24 |
| B7-H4_2F9V16 | 4.23 |
| B7-H4_2F9V17 | 3.35 |
| XMT-1604(+K) | 3.97 |
| B7-H4_2F9V18 |  |
| B7-H4_2F9V19 | 0.94 |
| B7-H4_2F9V20 | 0.95 |

As shown in Table 2, the B7-H4_2F9 parental antibody binds to human B7-H4 protein with an EC$_{50}$ value of 1.46 nM, and that the B4-H4_2F9 variants bind to human B7-H4 protein with EC$_{50}$ values between 0.94 nM and >100 nM. Most variants bind with similar EC$_{50}$ values (within three-fold) of B4-H4_2F9, except for B7-H4_2F9V1, B7-H4_2F9V4, B7-H4_2F9V6, B7-H4_2F9V11, and B7-H4_2F9V14, which bind to B7-H4 with EC$_{50}$ values between 4.40 and 11.67 nM, and B7-H4_2F9V12, which had no measurable binding in this assay.

Example 24: Cellular Binding of 20 B7-H4_2F9 Antibody Variants by FACS

The cell surface binding of B7-H4_2F9 variant antibodies and a tool B7-H4 antibody 1D11, to cultured MX-1 and HCC1569 cells was evaluated using a MACSQuant flow cytometer (Miltenyi Biotec, Bergisch Gladbach, Germany). MX-1 cells were grown in DMEM:F12K (Life Technologies) with 10% FBS (Life Technologies) and 1% penicillin/streptomycin (Life Technologies). HCC1569 cells were grown in RPMI (ATCC) with 10% FBS (Life Technologies) and 1% penicillin/streptomycin (Life Technologies). For staining, cells were detached by treatment with Accutase cell detachment solution (Innovative Cell Technologies). The detached cells were triturated in media, and plated in 96 well U-bottom plates, at a density of 50,000 cells in medium (75 µL). Cells were incubated on ice for 3 hours with a range of concentrations (100 nM to 0.0128 nM; 3-fold serial dilutions) of the test articles in a total volume of 100 µl medium with 6% goat serum. The cells were washed with ice cold PBS (3x), pelleted at 1,000xRCF between each wash step, and resuspended in RPMI-1640 with 2% goat serum (100 µL) and a secondary fluorescently labeled antibody, Alexa Fluor® 647-labelled goat anti-human IgG (5 µg/mL, Life Technologies) for 1 hour on ice. The cells were washed with ice cold PBS (3x) and resuspended in ice cold PBS with 1% paraformaldehyde (100 µL). The fluorescence per cell was determined by analyzing 5,000 cells for each treatment on the flow cytometer. The median fluorescence value for each treatment was plotted, and EC$_{50}$ values were calculated with Graphpad Prism software by four-parameter curve fitting.

Table 3 summarizes the EC$_{50}$ values of the 20 B7-H4_2F9 antibody variants antibodies for binding to the indicated cell lines.

TABLE 3

| Antibody | Binding to MX-1 Cells EC$_{50}$, nM | Binding to HCC1569 Cells EC$_{50}$, nM |
|---|---|---|
| 1D11 | 4.9 | 3.44 |
| B7-H4_2F9 | 1.58 | 1.26 |
| B7-H4_2F9V1 | 1.95 | 1.6 |
| B7-H4_2F9V2 | 4.43 | 2.28 |
| B7-H4_2F9V3 | 1.16 | 0.71 |
| B7-H4_2F9V5 | 0.92 | 0.69 |
| B7-H4_2F9V6 | 1.6 | 1.15 |
| XMT-1603(+K) | 1.94 | 1.59 |
| B7-H4_2F9V7 |  |  |
| B7-H4_2F9V8 | 1.86 | 1.45 |
| B7-H4_2F9V9 | 1.06 | 1.05 |
| B7-H4_2F9V10 | 0.89 | 0.84 |
| B7-H4_2F9V11 | 1.28 | 1.25 |
| B7-H4_2F9V13 | 1.75 | 1.1 |
| B7-H4_2F9V15 | 0.92 | 0.52 |
| B7-H4_2F9V16 | 1.7 | 1.21 |
| B7-H4_2F9V17 | 1.97 | 1.47 |
| XMT-1604(+K) | 1.28 | 1.12 |
| B7-H4_2F9V18 |  |  |
| B7-H4_2F9V19 | 1.3 | 0.66 |
| B7-H4_2F9V20 | 1.34 | 0.88 |

As shown in Table 3 the EC$_{50}$ values for binding to the surface of MX-1 cells were within the range of 0.9 to 4.43 nM, versus 1.58 nM for B4-H4_2F9. The EC$_{50}$ values for binding of most of the B7-H4_2F9 variants to MX-1 cells were very similar (within twofold) of B4-H4_2F9, except for B7-H4_2F9V2, which was 4.43 nM. The EC$_{50}$ value for binding of 1D11 antibody to MX-1 cells was 4.9 nM. The EC$_{50}$ values for binding of the B4-H4_2F9 variants to the surface of HCC1569 cells were within the range of 0.52 to 2.28 nM, versus 1.26 nM for B4-H4_2F9. The EC$_{50}$ values for binding of most variants to HCC1569 cells were very similar to B4-H4_2F9, except for B7-H4_2F9V15, which was 0.52 nM. The EC$_{50}$ value for binding of 1D11 antibody to the surface of HCC1569 cells was 3.44 nM.

Example 25: Assessment of Polyreactivity of 20 B7-H4_2F9 Antibody Variants by ELISA Polyreactivity of the 20 B7-H4_2F9 antibody variants and controls was assessed by Baculovirus particle (BVP) ELISA. Plates were coated with 1% BVP extract in carbonate buffer, pH 9.6, 4° C. overnight. Test antibodies at 150, 50, 16.7, and 5.6 µg/mL were tested in triplicate. Assay was performed following the standard ELISA protocol using positive control antibody (Human IgG1 Poly-Specificity Control Antibody; MEDNA Cat #H1308) and negative control antibody (Human IgG1 isotype control MEDNA Cat #1301; Mouse IgG isotype control (Invitrogen Cat #31903). BVP score was calculated based on the ELISA signal over background signal (secondary antibody only) of test antibody at the concentration of 150 µg/ml in triplicate. Table 4 summarizes the average BVP score of the antibodies.

TABLE 4

| Test Articles | BVP Score | Test Articles | BVP Score |
|---|---|---|---|
| Positive Control | 15.0 | Negative Control | 2.2 |
| B7-H4_2F9 | 10.7 | B7-H4_2F9V10 | 21.3 |
| 1D11 | 11.2 | B7-H4_2F9V11 | 4.6 |
| B7-H4_2F9V1 | 14.5 | B7-H4_2F9V13 | 12.4 |
| B7-H4_2F9V2 | 12.5 | B7-H4_2F9V15 | 23.1 |
| B7-H4_2F9V3 | 26.7 | B7-H4_2F9V16 | 6.3 |
| B7-H4_2F9V5 | 27.4 | B7-H4_2F9V17 | 3.6 |
| B7-H4_2F9V6 | 6.8 | XMT-1604(+K) | 3.8 |

TABLE 4-continued

| Test Articles | BVP Score | Test Articles | BVP Score |
|---|---|---|---|
| XMT-1603(+K) | 4.0 | B7-H4_2F9V18 | |
| B7-H4_2F9V7 | | B7-H4_2F9V19 | 22.8 |
| B7-H4_2F9V8 | 3.4 | B7-H4_2F9V20 | 18.8 |
| B7-H4_2F9V9 | 24.8 | Secondary antibody only | 1.0 |

As shown in Table 4, the BVP score of B7-H4_2F9 (10.7) is similar to that of 1D11 antibody. The results showed a wide range of BVP scores resulting from small sequence changes made in the variants relative to the B4-H4_2F9 antibody. Variants B7-H4_2F9V6, XMT-1603(+K) B7-H4_2F9V7, B7-H4_2F9V8, B7-H4_2F9V11, B7-H4_2F9V16, B7-H4_2F9V17, and XMT-1604(+K) B7-H4_2F9V18 all had BVP scores that were lower than that of B7-H4_2F9 and 1D11 antibodies, indicating a desired reduction in the polyreactivity. The remaining variants had BVP scores that were greater than that of B7-H4_2F9 antibody, 1D11 antibody, and the positive control, include B7-H4_2F9V3, B7-H4_2F9V5, B7-H4_2F9V9, B7-H4_2F9V10, B7-H4_2F9V15, B7-H4_2F9V19, and B7-H4_2F9V20 antibodies. The 5 variants (XMT-1603(+K) B7-H4_2F9V7, B7-H4_2F9V8, B7-H4_2F9V11, B7-H4_2F9V17, and XMT-1604(+K) B7-H4_2F9V18) with the lowest BVP scores show a desired reduction in polyreactivity. The sequence changes and the resulting BVP scores could not have been predicted.

Example 26: Binding Affinity of B7-H4_2F9 Antibody Variants to Human B7-H4 Protein by Octet The binding kinetics of B4-H4_2F9, the tool antibody 1D11 and 5 B7-H4 variant antibodies (XMT-1603(+K) (B7-H4_2F9V7), B7-H4_2F9V11, B7-H4_2F9V16, B7-H4_2F9V17, and XMT-1604(+K) (B7-H4_2F9V18) were determined by Biolayer Interferometry (BLI; Octet; ForteBio), and affinity values were determined using standard Octet procedures (ForteBio). Antibodies were immobilized to anti-human Fc biosensors in 1× Kinetics buffer. Increasing concentrations of recombinant human B7-H4 protein (R&D Systems #6576-B7-050) were then associated with immobilized peptide in 1× kinetics buffer. Table 5 summarizes the $K_d$ (equilibrium dissociation constant), $k_{on}$ (rate of association), and $k_{off}$ (rate of dissociation) at 25° C. for the tested antibodies.

TABLE 5

| Test Articles | $K_d$ (M) | $k_{on}$ (M$^{-1}$s$^{-1}$) | $k_{off}$ (s$^{-1}$) |
|---|---|---|---|
| B7-H4_2F9 | 1.39E-08 | 1.59E+05 | 2.21E-03 |
| 1D11 | 1.17E-10 | 1.25E+05 | 1.46E-05 |
| XMT-1603(+K) B7-H4_2F9V7 | 1.40E-08 | 1.15E+05 | 1.61E-03 |
| B7-H4_2F9V11 | 1.45E-08 | 1.84E+05 | 2.67E-03 |
| B7-H4_2F9V16 | 1.62E-08 | 1.38E+05 | 2.24E-03 |
| B7-H4_2F9V17 | 2.23E-08 | 7.39E+04 | 1.65E-03 |
| XMT-1604 (+K) B7-H4_2F9V18 | 1.10E-08 | 1.57E+05 | 1.72E-03 |

As shown in Table 5, B7-H4_2F9 antibody and the tested B7-H4_2F9 antibody variants: XMT-1603(+K) (B7-H4_2F9V7), B7-H4_2F9V11, B7-H4_2F9V16, B7-H4_2F9V17, and XMT-1604(+K) (B7-H4_2F9V18) have comparable affinity values for binding to human B7-H4. $K_d$ values for the B4-H4_2F9 variants are within the range of 1.10E-08 to 2.23E-08 M, in comparison to 1.39E-08M for B4-H4_2F9. The $k_{on}$ values for the B4-H4_2F9 variants are within the range of 7.39E+04 to 1.84E+05 (M$^{-1}$s$^{-1}$), in comparison to 1.59E+05 (M$^{-1}$s$^{-1}$) for B4-H4_2F9. The $k_{off}$ values for the B4-H4_2F9 variants are within the range of 1.61E-03 to 2.67E-03 s$^{-1}$, in comparison to 2.21E-03 s$^{-1}$ for B4-H4_2F9. The tool antibody 1D11 has a $K_d$ value that is more than 100-fold lower than that of B4-H4_2F9. The $k_{on}$ value of 1D11 antibody is very similar (within twofold) of the values of B4-H4_2F9 and variant antibodies, but more than 100-fold lower than that of B7-H4_2F9 and the variants.

Example 27: Assessment of XMT-1604 (B7-H4_2F9V18) Antibody for T-Cell Suppression Wildtype HEK-293 cells (HEK-293-WT) or HEK293 cells engineered to express B7-H4 (HEK-293-B7-H4) were plated and cultured in Eagle's Minimum Essential Medium supplemented with 10% FBS and 5% penicillin/streptomycin at a density of 50,000 cells in 96-well plate and allowed to adhere overnight at 37° C. in a humidified atmosphere of 5% $CO_2$. Next day, the media was removed and replaced with T cell media (Iscove's Modified Dulbecco's Medium with 10% FBS and 5% penicillin/streptomycin). Cells were incubated with 1D11 tool antibody, XMT-1604(+K) (B7-H4_2F9V18) antibody or a nonbinding control antibody, Palivizumab, at 50 nM final concentrations for 2 hours at 37° C., prior to the addition of CD3+ T cells prepared as follows. Frozen human PBMCs (2.5×10$^7$ cells) were thawed and enriched for CD3+ T cells using Easy Step™ human T cell isolation kit (StemCell Technologies). CD3+ T cells were labeled with CellTrace™ Violet cell proliferation kit (CTV; ThermoFisher Scientific) and adjusted to 2×10$^6$ cells/mL. CTV-labeled T cells (1×10$^5$) were added to test article-treated HEK-293-WT or HEK-293-B7-H4 cells, stimulated with Immunocult™ Human CD3/CD28 T Cell Activator (StemCell Technologies), and incubated at 37° C. in 5% $CO_2$. After 4 day of coculture of HEK-293-WT or HEK-293-B7-H4 with CTV-labeled T cells, T cell proliferation was assessed by the dilution of CTV-labeled T cells using flow cytometry. Cocultured cells (CTV-labeled T cells and HEK-293-WT/HEK-293-B7-H4 cells) from each group were transferred to a U-bottom 96-well plate, washed with PBS, stained with live/dead Fixable Aqua dead cell staining dye (ThermoFisher Scientific), and then additionally stained with fluorophore conjugated target specific or isotype control antibodies (FITC anti-human CD45, PE/Cy7 anti-human CD4, PE anti-human CD8). Cells were fixed and surface expression of the proteins of interest was determined by flow cytometry analysis on a MACSQuant flow cytometer. Data analysis was performed by FlowJo software using the following hierarchical flow: 1) single gate, 2) live cells, 3) CD45+ cells, and 4) diluted CTV (compared to unstimulated T cells). Percentage of proliferating CD4+ or CD8+ T cell were calculated using CD4+ combined with diluted CTV and CD8+ combined with diluted CTV, respectively. Data represent the mean (±standard deviation) of triplicate wells for each test article. Table 6 gives the population (%) of live cells, CD45+, proliferating CD4+ T cells, and proliferating CD8+ T cells for each condition.

TABLE 6

| % Population | HEK-293-WT | | | HEK-293-B7-H4 | | |
|---|---|---|---|---|---|---|
| | Palivizumab | 1D11 | 2F9 V18 | Palivizumab | 1D11 | 2F9 V18 |
| [a] Live cells | 78.2 ± 0.4 | | 81.1 ± 0.8 | 80.1 ± 2.0 | | 79.1 ± 1.4 |
| | 85.6 ± 11.2 | 82.7 ± 6.4 | 77.0 ± 10.6 | 95.5 ± 2.8 | 96.2 ± 3.3 | 96.3 ± 1.5 |
| [b] CD45+ | 69.0 ± 5.1 | | 70.5 ± 2.4 | 48.3 ± 4.1 | | 58 ± 3.4 |
| | 43.0 ± 11.0 | 43.2 ± 9.5 | 46.0 ± 5.2 | 50.1 ± 3.7 | 46.1 ± 5.5 | 43.6 ± 1.9 |
| [c] Proliferating CD4+ | 32.9 ± 2.6 | | 35.9 ± 3.1 | 14.0 ± 1.6 | | 20.1 ± 06.0 |
| | 22.4 ± 2.3 | 30.1 ± 2.9 | 34.9 ± 8.1 | 3.4 ± 2.1 | 2.1 ± 0.4 | 4.1 ± 1.8 |
| [c] Proliferating CD8+ | 9.5 ± 1.6 | | 11.0 ± 0.9 | 3.4 ± 0.5 | | 5.5 ± 1.6 |
| | 3.5 ± 0.8 | 5.8 ± 1.2 | 5.1 ± 1.8 | 1.1 ± 0.6 | 0.4 ± 0.2 | 1.1 ± 0.5 |

[a] Gated on single;
[b] Gated on live cells;
[c] Gated on single/live cells/CD45+

As shown in Table 6, the proportions of proliferating CD4+ cells and proliferating CD8+ T cells decreased significantly when the T cells were cultured with ITEK-293-B7-H4 cells as compared to ITEK-293-WT cells in the control group (palivizumab) (student's t-test; P≤0.001 and P≤0.05, respectively). Treatment with 1D11 B7-H4_or 1604 (+K) (B7-H4_2F9V18) antibody did not significantly restore proliferation to either CD4+ T cells or CD8+ T cells. Thus, the XMT-1604(+K) (B7-H4_2F9V18) did not inhibit the anti-proliferative effect of HEK-293-B7-H4 cells on cocultured CD4+ or CD8+ T cells.

Example 28: Binding of Variant B7-H14 Cytotoxic Drug Antibody-Drug Conjugates to B7-H4 Protein by ELISA Binding of ADC DAR 6 conjugates generated from B4-H4_2F9 Variants XMT-1603(+K); Conjugate 3), B7-H4_2F9V11 Conjugate 6, B7-H4_2F9V17 Conjugate 7, XMT-1604(+K); Conjugate 1-1, and Conjugate 8-1, the corresponding unconjugated antibodies, nonbinding control ADC Conjugate 9-1 and nonbinding control mAb (Palivizumab), to B7-H4 protein by ELISA was conducted as described in Example 23 except that the wells were blocked by incubation with blocking buffer (4% BSA in PBS) and a range of dilutions (0.0013 nM to 100 nM; 5-fold serial dilutions in 1% BSA in PBS) of the B7-H4 test articles and nonbinding controls were used. Table 7 summarizes the binding values ($EC_{50}$).

TABLE 7

| Test Articles | B7-H4 Binding Values $EC_{50}$ (nM) |
|---|---|
| XMT-1603(+K) B7-H4_2F9V7 | 0.27 |
| Conjugate 3 | 0.21 |
| B7-H4_2F9V11 | 0.11 |
| Conjugate 6 | 0.25 |
| B7-H4_2F9V17 | 0.061 |
| Conjugate 7 | 0.26 |
| XMT-1604(+K) B7-H4_2F9V18 | 0.12 |
| Conjugate 1-1 | 0.23 |
| 1D11 | 0.52 |
| Conjugate 8-1 | 0.41 |
| Conjugate 9-1 | >100 |
| Palivizumab | >100 |

As is shown in Table 7, $EC_{50}$ values of antibody-drug conjugates made with B4-H4_2F9 variant antibodies XMT-1603(+K) (B7-H4_2F9V7), B7-H4_2F9V11, and XMT-1604(+K) (B7-H4_2F9V18), and 1D11 had similar binding values (within 2.5-fold) of the corresponding unconjugated antibody. Binding of Conjugate 7 was shown to be greater than 4× less potent than its unconjugated antibody B7-H4_2F9V17. Lack of binding observed with control antibodies and their corresponding ADCs indicates the binding specificity of the B7-H4-targeting antibodies and ADCs.

Example 29: Binding of XMT-1603 (B7-H4_2F9V7) and XMT-1604 (B7-H4_2F9V18) Cytotoxic Drug Conjugates to Human B7-H4 Protein by ELISA Binding to human B7-H4 protein by XMT-1603(+K) (B7-H4_2F9V7), XMT-1604 (+K) (B7-H4_2F9V18), and their corresponding cytotoxic drug conjugates were tested by ELISA as described in Example 23 except a range of dilutions (0.0013 nM to 100 nM; 5-fold serial dilutions in 1% BSA in PBS) of the test articles were used. Test articles were Conjugate 5, Conjugate 4, Conjugate 13, Conjugate 2-1, Conjugate 1-2, and Conjugate 12. Controls used in this study included nonbinding antibody and nonbinding control ADCs Conjugate 10, Conjugate 9-2, and Conjugate 14 (Dolaflexin DAR10.9). Table 8 summarizes binding values ($EC_{50}$).

TABLE 8

| Test Articles | B7-H4 Binding Values $EC_{50}$ (nM) |
|---|---|
| XMT-1603 B7-H4_2F9V7 | 0.45 |
| Conjugate 13 | 0.76 |
| Conjugate 4 | 0.54 |
| Conjugate 5 | 0.51 |
| XMT-1604 B7-H4_2F9V18 | 0.35 |
| Conjugate 12 | 0.53 |
| Conjugate 1-2 | 0.36 |
| Conjugate 2-1 | 0.28 |
| Conjugate 9-2 | >100 |
| Conjugate 10 | >100 |
| Conjugate 14 | >100 |
| Palivizumab | >100 |

As is shown in Table 8, $EC_{50}$ values of conjugates made with B4-H4_2F9 variant antibodies XMT-1603 B7-H4_2F9V7 and XMT-1604 B7-H4_2F9V18 were similar (within twofold) of their unconjugated antibodies. Lack of binding observed with control antibodies indicates the binding specificity of the B7-H4-targeting antibodies and ADCs.

Example 30: Binding of XMT-1604 B7-H4_2F9V18 and Cytotoxic Drug Conjugates to B7-H4 Proteins from Human, Monkey, Rat, and Mouse by ELISA Binding to B7-H4 protein from human, monkey, rat, and mouse B7-H4 by XMT-1604 (B7H4_2F9V18), and the corresponding cytotoxic drug conjugates were tested by ELISA as described in Example 23. Proteins used in these studies were: human B7-H4 (R&D Systems; 6576-B7-050), monkey B7-H4 (Creative Biomart; VTCN1-1519R), rat (R&D Systems 10085-B7), and mouse (Creative Biomart; VTCN1-1519R). Test articles were Conjugate 2-1, Conjugate 1-2, and Conjugate 12. Controls used in this study included nonbinding hu-IgG1 antibody and nonbinding control ADCs Conjugate 10, Conjugate 9-2, and Conjugate 14. Table 9 summarizes the binding values ($EC_{50}$). For human, monkey, rat, and mouse B7-H4. The results are a mean of two studies.

TABLE 9

| Test Articles | Mean B7-H4 Binding Values $EC_{50}$ (nM) | | | |
|---|---|---|---|---|
| | Human | Monkey | Rat | Mouse |
| XMT-1604 B7-H4_2F9V18 | 0.24 | 0.17 | 0.19 | 0.30 |
| Conjugate 12 | 0.30 | 0.24 | 0.15 | 0.50 |
| Conjugate 1-2 | 0.21 | 0.21 | 0.15 | 0.38 |
| Conjugate 2-1 | 0.20 | 0.17 | 0.13 | 0.52 |
| Conjugate 9-2 | >100 | >100 | >100 | >100 |
| Conjugate 10 | >100 | >100 | >100 | >100 |
| Conjugate 14 | >100 | >100 | >100 | >100 |
| Palivizumab | >100 | >100 | >100 | >100 |

As shown in Table 9, binding values for XMT-1604 (B7H4_2F9V18), and the corresponding cytotoxic drug conjugates Conjugate 12, Conjugate 1-2, and Conjugate 2-1 were similar to each other across the four species tested. The range of $EC_{50}$ values is between 0.20 and 0.30 nM for binding to human B7-H4 protein, 0.17 and 0.24 nM for monkey protein, 0.13 to 0.18 nM for rat protein, and 0.30 to 0.52 nM for mouse protein. Control cytotoxic drug conjugates and antibody showed no binding to B7-H4 protein.

Example 31: Binding Affinity of XMT-1604 B7-H4_2F9V18 and Cytotoxic Drug Conjugates to Human B7-H4 Protein by Octet Binding kinetics of two batches of XMT-1604 B7-H4_2F9V18—batch 1, and its XMT-cytotoxic drug conjugates Conjugate 2-1, Conjugate 1-2, and Conjugate 12, and XMT-1604 B7-H4_2F9V18-batch 2 and its cytotoxic drug conjugates and Conjugate 2-2, Conjugate 1-3, to human B7-H4 were evaluated by Biolayer Interferometry (Octet) as described in Example 23. Table 10 summarizes results. For human, monkey, rat, and mouse B7-H4. The results for XMT-1604 B7H4_2F9V18—batch 1, Conjugate 12, Conjugate 1-2, and Conjugate 2-1 are the mean of three studies, and XMT-1604 B7_H4_2F9V18—batch 2, Conjugate 2-2 and Conjugate 1-3 were analyzed once.

TABLE 10

| Test Articles | $K_d$ (M) | $k_{on}$ ($M^{-1}s^{-1}$) | $k_{off}$ ($s^{-1}$) |
|---|---|---|---|
| XMT-1604 B7H4_2F9V18 Batch 1 | 2.51E−08 ± 1.08E−08 | 8.13E+04 ± 1.64E+04 | 1.94E−03 ± 5.73E−04 |
| Conjugate 12 | 2.29E−08 ± 1.22E−08 | 8.31E+04 ± 1.20E+04 | 1.81E−03 ± 8.56E−04 |
| Conjugate 1-2 | 1.87E−08 ± 9.11E−09 | 1.09E+05 ± 1.68E+04 | 1.93E−03 ± 7.14E−04 |
| Conjugate 2-1 | 2.56E−08 ± 2.10E−08 | 1.02E+05 ± 5.75E+04 | 1.80E−03 ± 5.50E−04 |
| XMT-1604 B7H4_2F9V18 Batch 2 | 2.15E−08 | 9.34E+04 | 2.01E−03 |
| Conjugate 1-3 | 2.51E−08 | 8.51E+04 | 2.14E−03 |
| Conjugate 2-2 | 2.31E−08 | 1.06E+05 | 2.44E−03 |

As is shown in Table 10, $K_d$, $k_{on}$, and $k_{off}$ values of XMT-1604 (B7H4_2F9V18 cytotoxic drug conjugates and XMT-1604 B7H4_2F9V18 antibody were similar to the unconjugated antibodies. For XMT-1604 B7H4_2F9V18—batch land its conjugates Conjugate 12, Conjugate 1-2, and Conjugate 2-1, $K_d$ values range between 1.87E-08 to 2.56E-08 M, $k_{on}$ values between 8.13E+04 to 1.09E+05 $M^{-1}s^{-1}$, and $k_{off}$ values between 1.80E-03 to 1.94E-03 $s^{-1}$. For XMT-1604 B7H4_2F9V18—batch 2 and its cytotoxic drug conjugates Conjugate 1-3 and Conjugate 2-2, $K_d$ values are between 2.15E-08 to 2.51E-08 M, $k_{on}$ values between 8.51E+04 to 1.06E+05, and $k_{off}$ values between 2.01E-03 to 2.44E-03.

Example 32: Cellular Binding Assay for XMT-1604 (B7-H4_2F9V18) B7-H4 Cytotoxic Drug-Drug Conjugates by FACS Cell surface binding to human B7-H4 by XMT-1604 (B7-H4_2F9V18) and its conjugates Conjugate 2-1, Conjugate 1-2, and Conjugate 12 were evaluated by flow cytometry Controls used in this study included nonbinding hu-IgG1 antibody, Palivizumab, and ADCs Conjugate 10, Conjugate 9-2, and Conjugate 14.

Binding of test articles to the cell lines MX-1 and HEK-293 cells stably transfected with human B7-H4 and untransfected HEK-293 cells was evaluated using a MACSQuant flow cytometer (Miltenyi Biotec, Bergisch Gladbach, Germany) as described in Example 24 except test articles were evaluated at a concentration of 0.0013 nM to 100 nM; 5-fold serial dilutions in 1% BSA in PBS. MX-1 cells were grown as described in Example 24. HEK-293-B7-H4 cells were grown in EMEM (ATCC), 10% FBS, 1% penicillin/streptomycin, and 3 µg/ml puromycin (Life Technologies) and untransfected HEK-293 cells were grown in EMEM, 10% FBS, 1% penicillin/streptomycin. Table 11 summarizes the $EC_{50}$ values of test articles on the surface of MX-1, HEK- 293-B7-H4, and HEK-293 cells. Results are mean values for two replicate experiments for each test article.

TABLE 11

| Test Article | MX-1 Binding $EC_{50}$, nM | HEK-293-B7-H4 Binding $EC_{50}$, nM | Untransfected HEK-293 Binding $EC_{50}$, nM |
| --- | --- | --- | --- |
| XMT-1604 B7-H4_2F9V18 | 1.32 | 2.45 | >100 |
| Conjugate 12 | 2.16 | 2.37 | >100 |
| Conjugate 1-2 | 1.12 | 1.84 | >100 |
| Conjugate 2-1 | 1.18 | 1.57 | >100 |
| Conjugate 9-2 | >100 | >100 | >100 |
| Conjugate 10 | >100 | >100 | >100 |
| Conjugate 14 | >100 | >100 | >100 |
| Palivizumab | >100 | >100 | >100 |

As shown in Table 11, the binding of XMT-1604 (B7-H4_2F9V18) to MX-1 and HEK-293-B7-H4 cells were very similar to that of its cytotoxic drug conjugates Conjugate 12, Conjugate 1-2, and Conjugate 2-1 (all within twofold). Nonbinding control antibody and its cytotoxic drug conjugates did not bind to MX-1 or HEK-293-B7-H4 cells, and none of the test articles bound to untransfected HEK-293 cells. These results indicate specific, potent binding of XMT-1604 (B7-H4_2F9V18) and its cytotoxic drug conjugates to cell surface B7-H4.

Example 33: Cytotoxicity Assay for XMT-1604 (B7-H4_2F9V18)—Cytotoxic Drug Conjugates Antiproliferative activity of XMT-1604 (B7-H4_2F9V18) cytotoxic drug conjugates were tested in a cytotoxicity assays. Test cytotoxic drug conjugates were Conjugate 2-1, Conjugate 1-2, Conjugate 1-3, and Conjugate 12. Controls used in this study included nonbinding control conjugates Conjugate 10, Conjugate 9-2, and Conjugate 14.

Cytotoxicity assays were performed using HEK-293-B7-H4 and untransfected HEK-293 cells in vitro using CellTiter-Glo® (Promega Corp). Cells were plated at a density of 2,000 cells per well in white-walled (volume) 96-well plate and allowed to adhere overnight at 37° C. in a humidified atmosphere of 5% $CO_2$. Cells were incubated with increasing concentrations of the test articles. Three days later, or five days later for CAMA-1 cells, CellTiter-Glo® reagent was added to the wells at room temperature. The luminescent signal was measured after 10 minutes using a SpectraMax M5 plate reader (Molecular Devices). Dose-response curves were generated using Graphpad Prism software. $EC_{50}$ values were determined from four-parameter curve fitting. Table 12 summarizes the $EC_{50}$ values. Values shown are mean values for two replicate experiments for each test article.

TABLE 12

| Test Article | CAMA-1 Cytotoxicity $EC_{50}$, nM | HEK-293-B7-H4 Cytotoxicity $EC_{50}$, nM | Untransfected HEK-293 Cytotoxicity $EC_{50}$, nM |
| --- | --- | --- | --- |
| Conjugate 12 | | 0.82 | 139 |
| Conjugate 1-2 | | 0.85 | 122 |
| Conjugate 1-3 | 0.052 | | |
| Conjugate 2-1 | | 0.45 | 145 |
| Conjugate 9-2 | 11.8 | 144 | 190 |
| Conjugate 10 | | 299 | 190 |
| Conjugate 14 | | 219 | 105 |

As shown in Table 12, for CAMA-1 cells, Conjugate 1-3 was more than 200 fold more potent than Conjugate 9-2. For HEK-293-B7-H4 cells, Conjugate 12, Conjugate 1-2, and Conjugate 2-1 showed similar cytotoxic potency (within twofold), whereas nonbinding control conjugates, Conjugate 9-2, Conjugate 10, and Conjugate 14 were more than 100× less potent. In untransfected HEK-293 cells, which do not express B7-H4, all conjugates showed similar $EC_{50}$ values (within twofold) that were greater than 100 nM. Results of these studies indicate specific, potent induction of cellular cytotoxicity by B7-H4 conjugates.

Example 34: Binding of XMT-1604 (B7-H4_2F9V18) and 1D11 STING Agonist Conjugates to Recombinant Human B7-H4 Protein by ELISA The binding of XMT-1604 (B7-H4_2F9V18) and its STING agonist conjugate, Conjugate 15 and Conjugate 19, to recombinant human B7-H4 protein was conducted by ELISA as described in Example 23 except that the wells were blocked by incubation with blocking buffer (3% BSA in PBST) and a range of dilutions for the test articles from 0 to 100 nM (4-fold serial dilutions in 1% BSA in PBST) was used. Other test articles in this study are 1D11 antibody and its STING agonist conjugate (Conjugate 16, Conjugate 18 and Conjugate 20), non-binding antibody (palivizumab) and its STING agonist conjugate, Conjugate 17. Table 13 summarizes the binding values ($EC_{50}$).

TABLE 13

| Test Article | Binding to Human B7-H4 Protein $EC_{50}$, nM |
| --- | --- |
| 1D11 | 0.86 |
| Conjugate 16 | 1.08 |
| B7-H4_2F9V18 | 0.50 |
| Conjugate 15 | 0.99 |
| Conjugate 20 | 1.54 |
| Conjugate 18 | 0.76 |
| Conjugate 19 | 0.47 |
| Palivizumab | >100 |
| Conjugate 17 | >100 |

As shown in Table 13, the $EC_{50}$ values of the Conjugate 15, Conjugate 16, Conjugate 18, Conjugate 19, and Conjugate 20 of 0.991.08 nM, 0.76, 0.47, and 1.54 respectively were comparable whereas the control antibody and its conjugate did not show any binding. These results indicate specific binding of XMT-1604 (B7-H4_2F9V18) and its conjugates to human B7-H4 protein.

Example 35: Cellular Binding Assay of XMT-1604 (B7-H4_2F9V18) and 1D11 STING Agonist Conjugates by FACS The cell surface binding of XMT-1604 (B7-H4_2F9V18) and its conjugate (Conjugate 15, Conjugate 15-1 and Conjugate 20) to MX-1 cells were assessed using a MACSQuant flow cytometer (Miltenyi Biotec, Bergisch Gladbach, Germany). Controls used in this study included 1D11 antibody and its conjugates (Conjugate 16 and Conjugate 19) and non-binding antibody (palivizumab) and its conjugate, Conjugate 17. The experiment was performed as described in Example 24 except cells were incubated on ice for 2 hours with a range of concentrations from 0.0122 nM to 200 nM (4-fold serial dilutions) of the test articles in a total volume of 100 µl medium amended with 6% goat serum. The cells were washed with ice cold PBS (2×), pelleted at 1,000×RCF between each wash step, and resuspended in RPMI-1640 with 2% goat serum (100 L) and a secondary fluorescently labeled antibody, Alexa Fluor® 647-labelled goat anti-human IgG (6 µg/mL, Life Technologies) for 1 hour on ice. The cells were washed with ice cold PBS (2×) and resuspended in ice cold PBS with 1% paraformaldehyde (100 µL). The fluorescence per cell was determined by analyzing 10,000 cells for each treatment on the flow cytometer. Table 14 summarizes the $EC_{50}$ values of the antibodies and their corresponding STING agonist conjugates for binding to the MX-1 cells.

TABLE 14

| Test Article | Binding to MX-1 cells $EC_{50}$, nM |
| --- | --- |
| 1D11 | 8.83 |
| Conjugate 16 | 7.51 |
| B7-H4_2F9V18 | 1.13 |
| Conjugate 15 | 1.70 |
| Conjugate 20 | 1.69 |
| Conjugate 15-1 | 0.99 |
| Conjugate 19 | 3.49 |
| Palivizumab | >200 |
| Conjugate 17 | >200 |

As shown in Table 14, the binding of XMT-1604 (B7-H4_2F9V18) and its conjugate (Conjugate 15, Conjugate 15-1 and Conjugate 20) to MX-1 cells was comparable and their $EC_{50}$ values were greater than those observed for 1D11 antibody and its conjugates (Conjugate 16 and Conjugate 19) (within 2-4-fold). Non-binding control antibody (palivizumab) and its conjugate, Conjugate 17, did not bind to MX-1 cells. These results indicate specific low nM binding of B7-H4_2F9V18 and its conjugates, Conjugate 15, Conjugate 15-1 and Conjugate 20 to cell surface B7-H4.

Example 36: STING Activation In Vitro Functional Assay of XMT-1604 (B7-H4_2F9V18) and 1D11 STING Agonist Conjugates Using Cancer Cell/THP1 Luciferase Reporter Cell Co-Cultures The induction of the STING pathway in immune cells by B7-H4-targeted STING agonist conjugates was evaluated by a cancer cell/THP1-IRF3-Luciferase reporter cell co-culture assay. MX-1 cells were seeded in 96-well CellBind surface tissue culture plates (17,000 cells/well) and allowed to attach for 4 hours in RPMI-1640 medium with 10% FBS and 1% penicillin/streptomycin. A range of dilutions (0.01 nM to 100 nM based on payload; 4-fold serial dilutions in growth medium) of conjugates: Conjugate 15, Conjugate 16, Conjugate 19, Conjugate 20, Conjugate 15-1, Conjugate 15-2, and Conjugate 17 or free STING agonist (prepared as described in U.S. Pat. No. 11,155,567) were added to each well and the plate was incubated for 20 min at 37° C. THP1-Dual™ Cells (InvivoGen) (50,000 cells) were then added to each well and the incubation continued for 24 hours at 37° C. in a humidified atmosphere of 5% $CO_2$. Cell culture supernatants (20 µL) from each incubated sample was added to resuspended QUANTI-Luc (InvivoGen) (50 µL) and the luminescent signal was measured immediately using a SpectraMax M5 plate reader (Molecular Devices). The $EC_{50}$ values were determined from the dose response curve. Table 15 provides the $EC_{50}$ values in THP1-Dual cells co-cultured with MX-1 cancer cells.

TABLE 15

| Test Article | THP1-Dual cells/MX-1 co-cultures $EC_{50}$, nM |
| --- | --- |
| Conjugate 16 | 0.53 |
| Conjugate 15 | 0.34 |
| Conjugate 19 | 0.29 |
| Conjugate 20 | 0.85 |
| Conjugate 15-1 | 0.18 |
| Conjugate 15-2 | 0.46 |
| Conjugate 17 | >100 |
| STING agonist | >100 |

As shown in Table 15, both STING agonist conjugates, Conjugate 15, Conjugate 16, Conjugate 19, Conjugate 20, Conjugate 15-1, Conjugate 15-2, exhibited similar Luciferase reporter activity with $EC_{50}$ values below 1 nM, and at least 200-fold lower than the non-binding antibody (palivizumab) conjugate, Conjugate 17, and free STING agonist, respectively. Thus, B7-H4_2F9V18 STING agonist conjugate demonstrates target specificity and a role of Fc receptor mediated delivery to immune cells (THP1) for activity.

Example 37: Tumor Growth Response to Administration of B7-H4_2F9 Cytotoxic Drug Conjugates in MX-1 TNBC Xenograft Mouse Model Female athymic nude mice were implanted subcutaneously with MX-1 human breast cancer xenograft tumor fragments (~1 mm³ per mouse). Animals were randomized into treatment groups when tumor volumes were between 63-196 mm³ (mean=119-123 mm³/group) (n=10/group). Vehicle, Conjugate 9-1 (2.46/0.075 or 4.92/0.150 mg/kg), Conjugate 11 (2.28/0.075 or 4.56/0.150 mg/kg), Conjugate 3 (2.30/0.075 or 4.60/0.150 mg/kg), Conjugate 6 (2.30/0.075 or 4.61/0.150 mg/kg), 3740 (2.30/0.075 or 4.60/0.150 mg/kg) or Conjugate 1-1 (2.30/0.075 or 4.60/0.150 mg/kg) were dosed intravenously on day 1 (all doses are given by antibody/payload). No significant body weight loss or clinical observations were noted.

Figure 7:
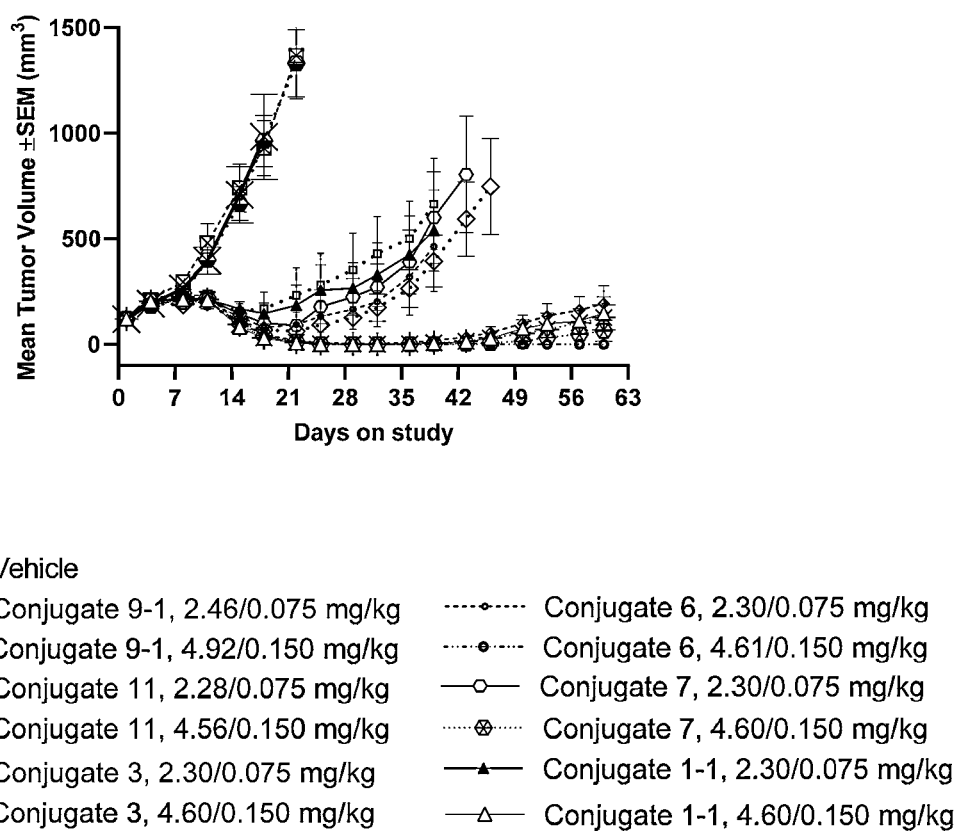
FIG. 7 is a graph showing the anti-tumor efficacy of the B7-H4_2F9 Cytotoxic Drug Conjugates: Conjugate 9-1 (2.46/0.075 or 4.92/0.150 mg/kg), Conjugate 11 (2.28/0.075 or 4.56/0.150 mg/kg), Conjugate 3 (2.30/0.075 or 4.60/0.150 mg/kg), Conjugate 6 (2.30/0.075 or 4.61/0.150 mg/kg), Conjugate 7 (2.30/0.075 or 4.60/0.150 mg/kg) and Conjugate 1-1 (2.30/0.075 or 4.60/0.150 mg/kg) (all doses are given by antibody/payload) in a MX-1 TNBC xenograft mouse model.

FIG. 7 provides the results for the tumor volumes of MX-1 tumor-bearing mice treated with B7-H4_2F9 cytotoxic drug conjugates: Conjugate 9-1, Conjugate 11, Conjugate 3, Conjugate 6, Conjugate 7 and Conjugate 1-1. Treatment with Conjugate 11 2.28/0.075 mg/kg resulted in 4 CRs. Treatment with Conjugate 3 2.30/0.075 mg/kg resulted in 1 PR and 1 CR. Treatment with Conjugate 6 2.30/0.075 mg/kg resulted in 1 PR, 2 CRs, 1 TFS. Treatment with Conjugate 7 2.30/0.075 mg/kg resulted in 1 PR, 3 CRs, 1 TFS. Treatment with Conjugate 1-1 2.30/0.075 mg/kg resulted in 2 PRs, 1 CR, 1 TFS. Treatment with Conjugate 11 4.56/0.150 mg/kg resulted in 1 PR, 9 CRs, 4 TFS. Treatment with Conjugate 34.60/0.150 mg/kg resulted in 10 CRs, 6 TFS. Treatment with Conjugate 6 4.61/0.150 mg/kg resulted in 10 CRs, 10 TFS. Treatment with Conjugate 7 4.60/0.150 mg/kg resulted in 10 CRs, 8 TFS. Treatment with Conjugate 1-1 4.60/0.150 mg/kg resulted in 10 CRs, 7 TFS. No other treatments induced a regression response.

Example 38: Tumor Growth Response to Administration of B7-H4_2F9V18 Cytotoxic Drug Conjugates in MX-1 TNBC Xenograft Mouse Model Female athymic nude mice were implanted subcutaneously with MX-1 human breast cancer xenograft tumor fragments (~1 mm$^3$ per mouse). Animals were randomized into treatment groups when tumor volumes were between 75-221 mm$^3$ (mean=123.5-126.8 mm$^3$/group) (n=10/group). Vehicle, Conjugate 14 (2.57/0.150 mg/kg), Conjugate 9-2 (4.56/0.150 mg/kg), Conjugate 10 (14.37/0.150 mg/kg), Conjugate 12 (2.26/0.150 or 0.75/0.050 mg/kg), Conjugate 1-2 (5.37/0.177, 2.33/0.077 or 1.79/0.059 mg/kg), Conjugate 2-1 (13.45/0.150, 4.60/0.050, or 2.30/0.025 mg/kg) or XMT-1604 B7-H4_2F9V18 (13.80/0 mg/kg) were dosed intravenously on day 1 (all doses are given by antibody/by payload). No significant body weight loss or clinical observations were noted.

Figure 8:
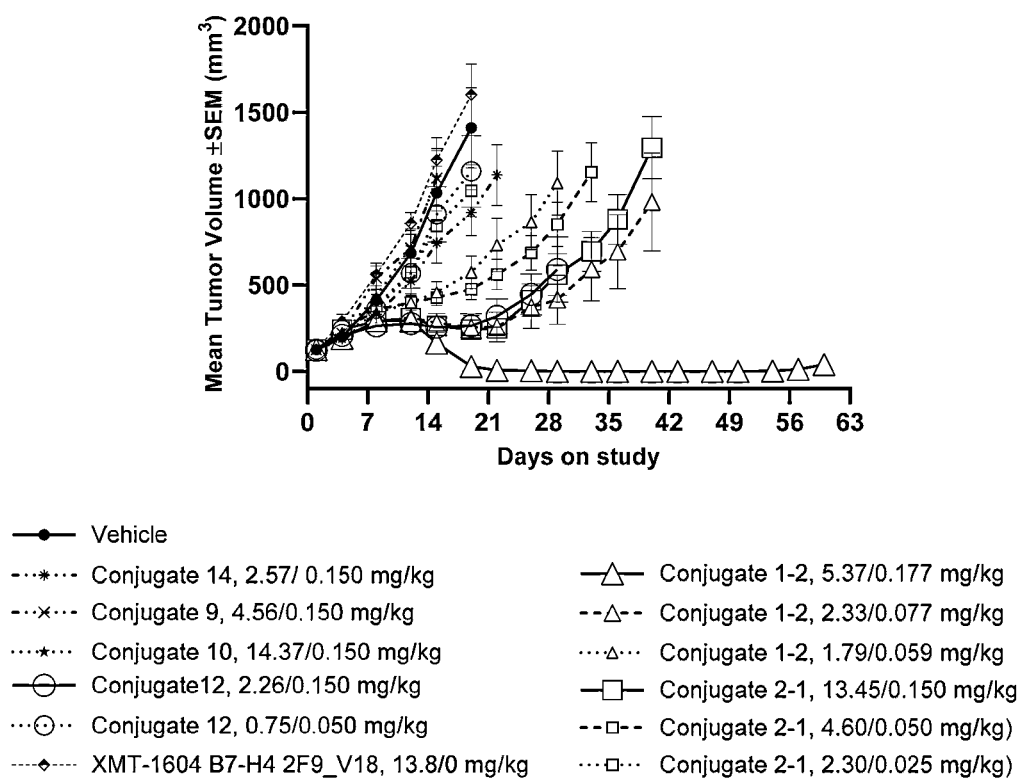
FIG. 8 is a graph showing the anti-tumor efficacy of the B7-H4_2F9 Cytotoxic Drug Conjugates: Conjugate 14 (2.57/0.150 mg/kg), Conjugate 9-2 (4.56/0.150 mg/kg), Conjugate 10 (14.37/0.150 mg/kg), Conjugate 12 (2.26/0.150 or 0.75/0.050 mg/kg), Conjugate 1-2 (5.37/0.177, 2.33/0.077 or 1.79/0.059 mg/kg), Conjugate 2-1 (13.45/0.150, 4.60/0.050, or 2.30/0.025 mg/kg) and XMT-1604 B7-H4_2F9V18 (13.80/0 mg/kg) (all doses are given by antibody/payload) in a MX-1 TNBC xenograft mouse model.

FIG. 8 provides the results for the tumor volumes of MX-1 tumor-bearing mice treated with B7-H4_2F9 cytotoxic drug conjugates: Conjugate 14, Conjugate 9-2, Conjugate 10, Conjugate 12, Conjugate 1-2, Conjugate 2-1, and XMT-1604 (B7-H4_2F9V18). Treatment with Conjugate 14 2.57/0.150 mg/kg resulted in 1 CR, 1 TFS. Treatment with Conjugate 12 2.26/0.150 mg/kg resulted in 1 PR. Treatment with Conjugate 1-2 5.37/0.177 mg/kg resulted in 10 CRs, 8 TFS. Treatment with Conjugate 1-2 2.33/0.077 mg/kg resulted in 1 PR, 2 CRs, 2 TFS. Treatment with Conjugate 1-2 1.79/0.050 mg/kg resulted in 1 CR. No other treatments induced a regression response.

Example 39: Tumor Growth Response to Administration of B7-H4_2F9V18 Cytotoxic Drug Conjugates in HBCx-19 Patient Derived Xenograft Model Female athymic nude mice were implanted subcutaneously with HBCx-19 human breast cancer xenograft tumor fragments (4×3 mm per mouse). Animals were randomized into treatment groups when tumor volumes were between 75-221 mm$^3$ (mean=123.5-126.8 mm$^3$/group) (n=10/group). Vehicle, Conjugate 1-2 (1.79/0.059 or 5.37/0.177 mg/kg), Conjugate 9-2 (4.56/0.150 mg/kg), Conjugate 2-1 (4.60/0.050 or 13.45/0.150 mg/kg) or Conjugate 10 (14.37/0.150 mg/kg) were dosed intravenously on day 1 (all doses are given by antibody/by payload). No significant body weight loss or clinical observations were noted.

Figure 9:
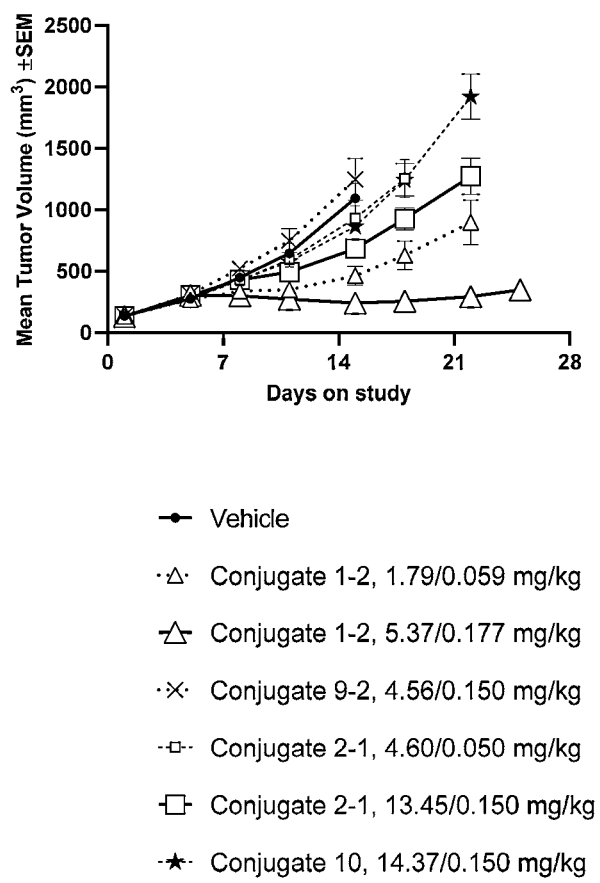
FIG. 9 is a graph showing the anti-tumor efficacy of the B7-H4_2F9 Cytotoxic Drug Conjugates: Conjugate 1-2 (1.79/0.059 or 5.37/0.177 mg/kg), Conjugate 9-2 (4.56/0.150 mg/kg), Conjugate 2-1 (4.60/0.050 or 13.45/0.150 mg/kg) and Conjugate 10 (14.37/0.150 mg/kg) (all doses are given by antibody/payload) in a HBCx-19 patient derived xenograft model.

FIG. 9 provides the results for the tumor volumes of HBCx-19 tumor-bearing mice treated with B7-H4_2F9 cytotoxic drug conjugates: Conjugate 9-2, Conjugate 10, Conjugate 1-21 and Conjugate 2-1. Treatment with Conjugate 1-2 (5.37/0.177 mg/kg) resulted in 7 TFS showing that this conjugate was the most efficacious. No other treatments induced an anti-tumor response.

Example 40: Tumor Growth Response to Administration of B7-H4_2F9V18 Cytotoxic Drug Conjugates in HBCx-24 Patient Derived Xenograft Model Female athymic nude mice were implanted subcutaneously with HBCx-24 human breast cancer xenograft tumor fragments (4×3 mm per mouse). Animals were randomized into treatment groups when tumor volumes were between 62.5-256 mm$^3$ (mean=141.40-149.25 mm$^3$/group) (n=10/group). Vehicle, Conjugate 14 (2.57/0.150 mg/kg), Conjugate 9-2 (4.56/0.150 mg/kg), Conjugate 10 (14.37/0.150 mg/kg), Conjugate 12 (2.26/0.150 or 0.75/0.050 mg/kg), Conjugate 1-2 (4.56/0.150, 2.30/0.076 or 1.52/0.05 mg/kg), Conjugate 2-1 (13.45/0.150, 4.60/0.050, or 2.30/0.025 mg/kg) or XMT-1604 (B7-H4_2F9V18) (13.80/0 mg/kg) were dosed intravenously on day 1 (all doses are given by antibody/by payload). No significant body weight loss or clinical observations were noted.

Figure 10:
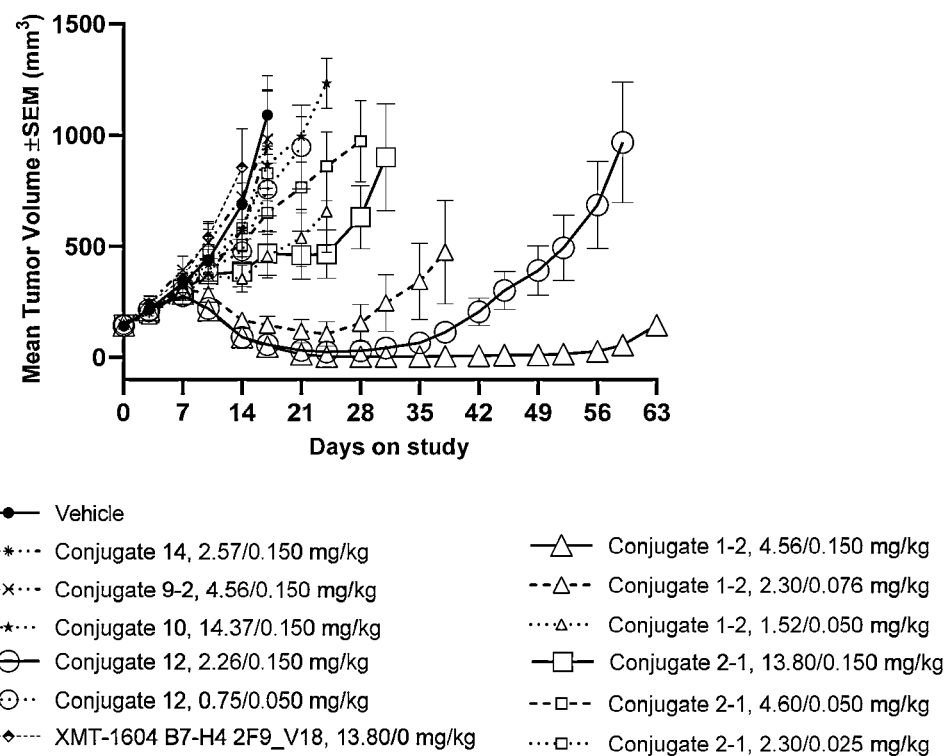
FIG. 10 is a graph showing the anti-tumor efficacy of the B7-H4_2F9 Cytotoxic Drug Conjugates: Conjugate 14 (2.57/0.150 mg/kg), Conjugate 9-2 (4.56/0.150 mg/kg), Conjugate 10 (14.37/0.150 mg/kg), Conjugate 12 (2.26/0.150 or 0.75/0.050 mg/kg), Conjugate 1-2 (4.56/0.150, 2.30/0.076 or 1.52/0.05 mg/kg), Conjugate 2-1 (13.45/0.150, 4.60/0.050, or 2.30/0.025 mg/kg) and XMT-1604 (13.80/0 mg/kg) (all doses are given by antibody/payload) in a HBCx-24 patient derived xenograft model.

FIG. 10 provides the results for the tumor volumes of HBCx-24 tumor-bearing mice treated with B7-H4_2F9 cytotoxic drug conjugates: Conjugate 14, Conjugate 9-2, Conjugate 10, Conjugate 12, Conjugate 1-2, Conjugate 2-1, and XMT-1604 (B7-H4_2F9V18). Treatment with Conjugate 12 (2.26/0.150 mg/kg) resulted in 3 PRs, 6 CRs, 1 TFS. Treatment with Conjugate 1-2 (1.52/0.050 mg/kg (resulted in 5 TFSs. Treatment with Conjugate 1-2 (2.30/0.076 mg/kg) resulted in 3 PRs and 4 CRs. Treatment with Conjugate 1-2 (4.56/0.150 mg/kg) resulted in 10 CRs, and 3 TFS. Treatment with Conjugate 2-1 (4.60/0.050 mg/kg) resulted in 5 TSs. Treatment with Conjugate 2-1 (13.80/0.150 mg/kg) resulted in 7 TSs. No other treatments induced an anti-tumor response.

Example 41: Plasma Exposure of Total Drug in MX-1 Tumor Mice after Administration of B7-H4_2F9V18 Cytotoxic Drug Conjugates Female athymic nude mice were implanted subcutaneously with MX-1 tumor fragments (n=4 for each group). Conjugate 12 (2.26/0.150 or 0.75/0.050 mg/kg), Conjugate 1-2 (5.37/0.177, 2.33/0.077 or 1.79/0.059 mg/kg) or Conjugate 2-1 (13.80/0.150, 4.60/0.050, or 2.30/0.025 mg/kg) were dosed intravenously on day 1 (all doses are given by antibody/payload). Tail snip blood samples (0.04 mL) were collected at the following time points: 15 minutes, 24 hours (Day 2), 72 hours (Day 4), 168 hours (Day 8), 240 hours (Day 11), and 336 hours (Day 15) after dosing. Blood was processed to plasma with K$_2$EDTA anti-coagulant for collection. Samples were snap frozen and stored at −80° C. until shipment.

Total antibody was measured using an MSD-ECL sandwich immunoassay. Conjugated drug was measured by LC-MS after the samples were immunocaptured using generic anti-human Fc magnetic beads and treated with sodium hydroxide in order to release the conjugated drug. Tables 16 and 17 gives the PK parameters for total antibody and conjugated drug respectively

TABLE 16

| Test Articles | Dose mAb/ Payload (mg/kg) | Cmax (ng/ mL) | Half life (day) | AUC∞ (ng/ ml*day) | Cl_obs (mL/ day/ kg) | Vss_obs (mL/ kg) |
| --- | --- | --- | --- | --- | --- | --- |
| Conjugate 12 | 2.26/ 0.150 | 39700 | 3.48 | 122000 | 18.6 | 86.7 |
| Conjugate 12 | 0.75/ 0.050 | 12900 | 2.16 | 27900 | 27.5 | 79.2 |
| Conjugate 1-2 | 5.38/ 0.177 | 97600 | 7.79 | 579000 | 9.99 | 98.0 |
| Conjugate 1-2 | 2.33/ 0.077 | 38800 | 4.96 | 173000 | 14.4 | 92.0 |
| Conjugate 1-2 | 1.79/ 0.059 | 26900 | 2.73 | 81000 | 24.5 | 94.4 |

TABLE 16-continued

| Test Articles | Dose mAb/ Payload (mg/kg) | Cmax (ng/ mL) | Half life (day) | AUC∞ (ng/ ml*day) | Cl_obs (mL/ day/ kg) | Vss_obs (mL/ kg) |
|---|---|---|---|---|---|---|
| Conjugate 2-1 | 13.45/ 0.150 | 236000 | 8.93 | 1240000 | 11.2 | 128 |
| Conjugate 2-1 | 4.48/ 0.050 | 77300 | 4.28 | 287000 | 17.9 | 98.9 |
| Conjugate 2-1 | 2.24/ 0.025 | 33500 | 3.08 | 104000 | 23.0 | 104 |

TABLE 17

| Test Articles | Dose mAb/ Payload (mg/kg) | Cmax (ng/ mL) | Half life (day) | AUC∞ (ng/ ml*day) | Cl_obs (mL/ day/ kg) | Vss_obs (mL/ kg) |
|---|---|---|---|---|---|---|
| Conjugate 12 | 2.26/ 0.150 | 3010 | 2.78 | 6960 | 21.6 | 78.6 |
| Conjugate 12 | 0.75/ 0.050 | 1030 | 2.68 | 1980 | 25.6 | 78.9 |
| Conjugate 1-2 | 5.38/ 0.177 | 3030 | 6.23 | 14200 | 12.9 | 103 |
| Conjugate 1-2 | 2.33/ 0.077 | 1330 | 3.89 | 4830 | 16.6 | 86.1 |
| Conjugate 1-2 | 1.79/ 0.059 | 887 | 3.12 | 2530 | 25.0 | 102 |
| Conjugate 2-1 | 13.45/ 0.150 | 2630 | 6.44 | 11500 | 13.1 | 110 |
| Conjugate 2-1 | 4.48/ 0.050 | 923 | 3.52 | 2900 | 18.8 | 86.2 |
| Conjugate 2-1 | 2.24/ 0.025 | 438 | 3.24 | 1210 | 21.7 | 91.2 |

For total antibody, Conjugate 12, Conjugate 1-2 and Conjugate 2-1 appear to have dose proportional $C_{max}$. All test articles appear to demonstrate a decrease in clearance as the doses are increased. Conjugate 1-2 has comparable clearance to Conjugate 2-1 at different dose levels, yet with low exposure (AUC) of antibody due to DAR difference and equal payload dosing.

For antibody conjugated drug, Conjugate 12, Conjugate 1-2 and Conjugate 2-1 appear to have dose proportional $C_{max}$. Conjugate 12 with payload doses of 0.15 mg/kg and 0.05 mg/kg, was observed to have lower exposure and faster clearance, compared to Conjugate 1-2 and Conjugate 2-1. Conjugate 1-2 has comparable exposure and clearance to Conjugate 2-1 at different dose levels.

Example 42: Plasma Exposure of Total Drug in MX-1 Tumor Mice after Administration of B7-H4_2F9 Cytotoxic Drug Conjugates Female athymic nude mice were implanted subcutaneously with MX-1 tumor fragments (n=4 for each group). Vehicle, Conjugate 11 (4.56/0.150 mg/kg), Conjugate 3 (4.60/0.150 mg/kg), Conjugate 6 (4.61/0.150 mg/kg), 3740 (4.60/0.150 mg/kg) or Conjugate 1-1 (4.60/0.150 mg/kg) were dosed intravenously on day 1 (all doses are given by antibody/payload). Tail snip blood samples (0.04 mL) were collected at the following time points: 15 minutes, 24 hours (Day 2), 72 hours (Day 4), 168 hours (Day 8), 240 hours (Day 11), and 336 hours (Day 15) after dosing. Blood was processed to plasma with K₂EDTA anti-coagulant for collection. Samples were snap frozen and stored at −80° C. until shipment.

Total antibody was measured using an MSD-ECL sandwich immunoassay. Total drug was measured by LC-MS after the samples were directly treated with sodium hydroxide in order to release the conjugated drug. Tables 18 and 19 gives the PK parameters for total antibody and total drug respectively

TABLE 18

| Test Articles | Dose mAb/ Payload (mg/kg) | Cmax (ng/ mL) | Half life (day) | AUC∞ (ng/ ml*day) | Cl_obs (mL/day /kg) | Vss_obs (mL/ kg) |
|---|---|---|---|---|---|---|
| Conjugate 11 | 4.55/ 0.150 | 70700 | 7.19 | 413000 | 11.0 | 110 |
| Conjugate 3 | 4.60/ 0.150 | 80800 | 8.12 | 512000 | 8.98 | 103 |
| Conjugate 6 | 4.61/ 0.150 | 87500 | 12.6 | 766000 | 6.02 | 105 |
| Conjugate 7 | 4.60/ 0.150 | 84500 | 9.93 | 558000 | 8.24 | 111 |
| Conjugate 1-1 | 4.60/ 0.150 | 78500 | 7.35 | 436000 | 10.5 | 107 |

TABLE 19

| Test Articles | Dose mAb/ Payload (mg/kg) | Cmax (ng/ mL) | Half life (day) | AUC∞ (ng/ ml*day) | Cl_obs (mL/ day/kg) | Vss_obs (mL/ kg) |
|---|---|---|---|---|---|---|
| Conjugate 11 | 4.55/0.150 | 2530 | 5.29 | 11400 | 13.1 | 95.7 |
| Conjugate 3 | 4.60/0.150 | 2450 | 5.40 | 11300 | 13.3 | 99.7 |
| Conjugate 6 | 4.61/0.150 | 2560 | 7.74 | 15200 | 9.86 | 103 |
| Conjugate 7 | 4.60/0.150 | 2530 | 5.51 | 14500 | 10.4 | 82.6 |
| Conjugate 1-1 | 4.60/0.150 | 2480 | 5.40 | 12100 | 12.4 | 94.0 |

For total antibody, all test articles have approximate comparable $C_{max}$, clearance and exposure, expressed as AUC∞. For conjugated drug, all test articles have comparable PK parameters in terms of $C_{max}$, clearance and exposure, expressed as AUC∞.

Example 43: Tumor Growth Response to Administration of B7-H4_2F9V18 and 1D11 STING Agonist Drug Conjugates in MX-1 Xenograft Mouse Model Female CB.17 SCID mice were inoculated subcutaneously with MX-1 human breast cancer xenograft tumor fragments (~1 mm³ per mouse). Animals were randomized into treatment groups when tumor volumes were between 63-108 mm³ (mean=76.8-82 mm³/group) (n=10/group). Vehicle, Conjugate 17 (0.085/0.030 or 2.84/0.100 mg/kg), Conjugate 16 (0.89/0.030 or 2.97/0.100 mg/kg), Conjugate 15 (0.85/0.030 or 2.83/0.100 mg/kg), or diABZI IV STING agonist (5 mg/kg) were dosed intravenously on day 1 (all doses are written as antibody/payload).

Figure 11:
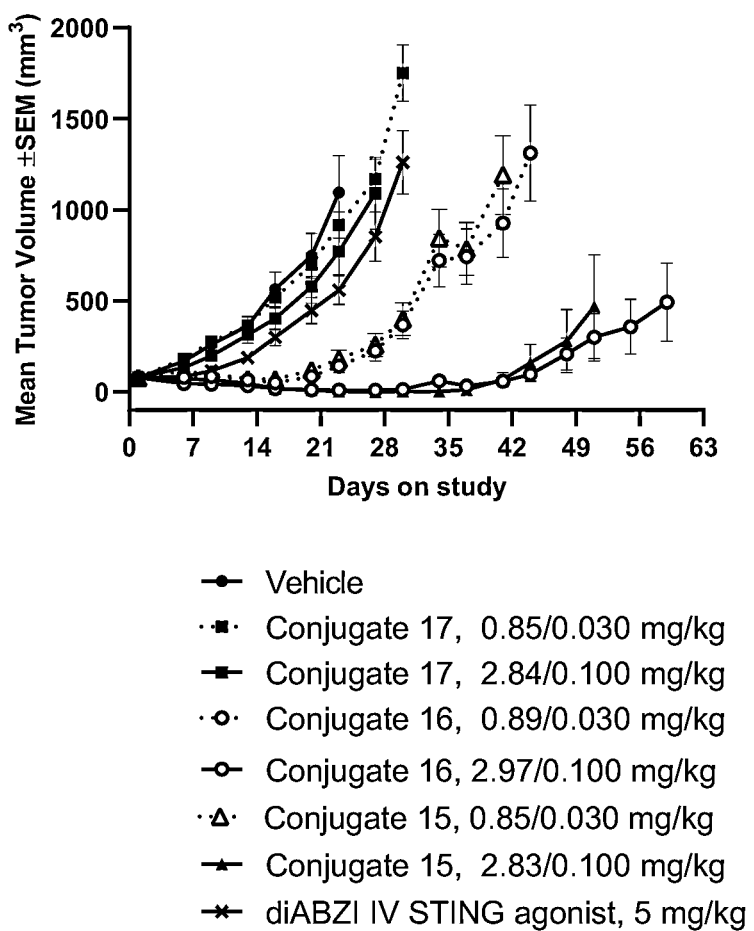
FIG. 11 is a graph showing the anti-tumor efficacy of the B7-H4_2F9 STING Agonist Drug Conjugates: Conjugate 17 (0.085/0.030 or 2.84/0.100 mg/kg), Conjugate 16 (0.89/0.030 or 2.97/0.100 mg/kg), Conjugate 15 (0.85/0.030 or 2.83/0.100 mg/kg), and diABZI IV STING agonist (5 mg/kg) (all doses are given by antibody/payload) in a MX-1 xenograft mouse model.

FIG. 11 provides the results for the tumor volumes of MX-1 tumor-bearing mice treated with STING agonist drug conjugates: Conjugate 17, Conjugate 16, Conjugate 15 and diABZI IV STING agonist. Treatment with Conjugate 17 (2.84/0.100 mg/kg) resulted in 1 CR; this animal was classified as a tumor-free survivor at the time of study termination (day 60). Treatment with Conjugate 16 (0.89/0.030 mg/kg) resulted in 1 PR and 2 CRs; 1 TFS. Treatment with Conjugate 16 (2.97/0.100 mg/kg) resulted in 8 CRs, 6 TFS. Treatment with Conjugate 15 (0.85/0.030 mg/kg) resulted in 1 CR and 1 TFS. Treatment with Conjugate 15 (2.83/0.100 mg/kg) resulted in 10 CRs, 5 TFS. Treatment with diABZI IV STING agonist (5 mg/kg) resulted in 1 CR. The results show that Conjugate 15 (2.83/0.100 mg/kg) was the most efficacious.

Example 44: Tumor Growth Response to Administration of B7-H4_2F9V18 Cytotoxic Drug Conjugates in MX-1 TNBC Xenograft Model Female athymic nude mice were implanted subcutaneously with MX-1 human breast cancer xenograft tumor fragments (1 mm³ per mouse). Animals were randomized into treatment groups when tumor volumes were between 75 to 196 mm³ (mean=125-128 mm³/group) (n=10/group). Vehicle, Conjugate 14 (2.57/0.150 mg/kg), Conjugate 9-2 (4.56/0.150 mg/kg), Conjugate 12 (2.26/0.150 or 1.13/0.075 mg/kg), Conjugate 1-3 (4.68/0.150 or 2.34/0.075 mg/kg), or Conjugate 2-2 (13.81/0.150 or 6.90/0.075 mg/kg) were dosed intravenously on day 1 (all doses are written as antibody/payload). No significant body weight loss or clinical observations were noted.

Figure 12:
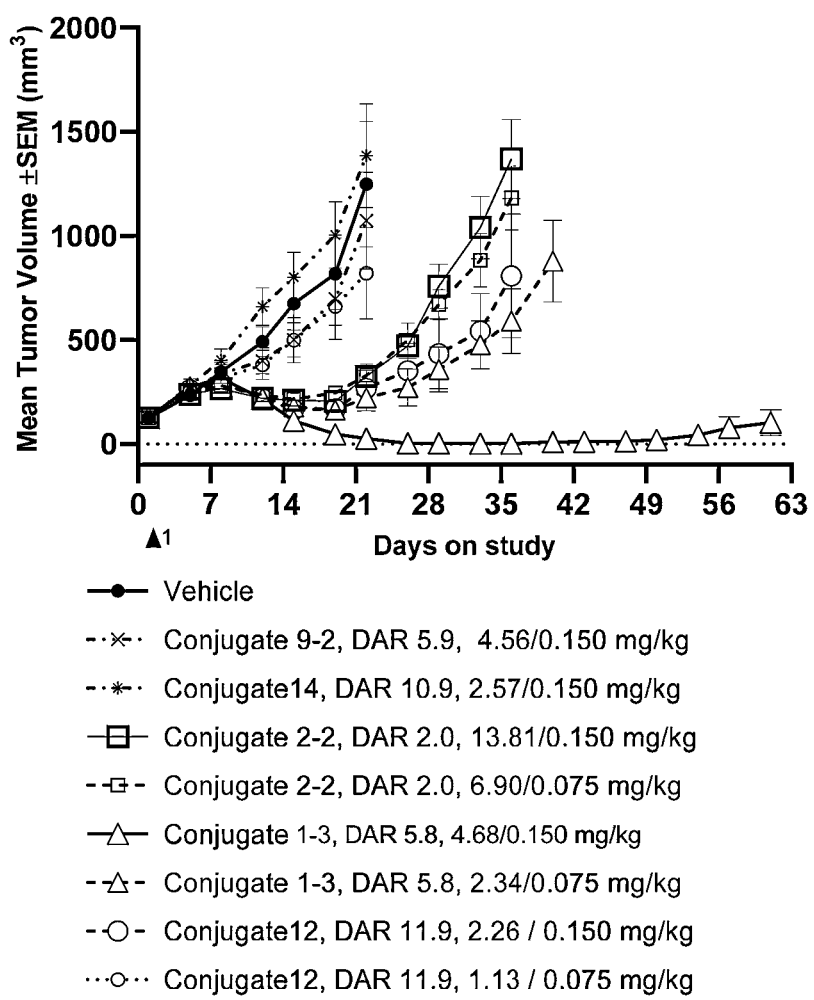
FIG. 12 is a graph showing the anti-tumor efficacy of the B7-H4_2F9 STING Agonist Drug Conjugates: Conjugate 14 (2.57/0.150 mg/kg), Conjugate 9-2 (4.56/0.150 mg/kg), Conjugate 12 (2.26/0.150 or 1.13/0.075 mg/kg), Conjugate 1-3 (4.68/0.150 or 2.34/0.075 mg/kg), and Conjugate 2-2 (13.81/0.150 or 6.90/0.075 mg/kg) (all doses are written as antibody/payload) in a MX-1 TNBC Xenograft model.

FIG. 12 provides the results for the tumor volumes of MX-1 tumor-bearing mice treated with Conjugate 14, Conjugate 9-2, Conjugate 12, Conjugate 1-3, or Conjugate 2-2. Treatment with Conjugate 12 (2.26/0.150 mg/kg) resulted in 1 CR. Treatment with Conjugate 1-3 (4.68/0.150 mg/kg) resulted in 10 CRs, 7 TFSs. Treatment with Conjugate 1-3 (2.34/0.075 mg/kg) resulted in 2 PRs. No other treatments induced a regression response.

Example 45: Plasma Exposure in Mice after Administration of B7-H4_2F9V18 Cytotoxic Drug Conjugates Female athymic nude mice were implanted subcutaneously with MX-1 human breast cancer xenograft tumor fragments (~1 mm³ per mouse). Vehicle, Conjugate 1-3 (2.32/0.075; 4.65/0.15), Conjugate 2-2 (6.74/0.075; 13.5/0.15), or Conjugate 12 (1.13/0.075; 2.26/0.15) were dosed intravenously as a single dose on day 1 (all doses are written as antibody/payload). Tail snip blood samples (0.04 mL) were collected at the following time points: 15 minutes, 24 hours (Day 2), 72 hours (Day 4), 168 hours (Day 8), 240 hours (Day 11), and 336 hours (Day 15) after dosing. Blood was processed to plasma with K₂EDTA anti-coagulant for collection. Samples were snap frozen and stored at −80° C. until shipment.

Total antibody was measured using an MSD-ECL sandwich immunoassay. Conjugated drug was measured by LC-MS after the samples were subjected to immunocapture by an anti-human IgG1 Fc antibody immobilized on magnetic beads, followed by AF-HPA release by hydrolysis. Tables 20 and 21 gives the PK parameters for total antibody and conjugated drug, respectively.

TABLE 20

|  | Dose mAb/ Payload (mg/kg) | $C_{max}$ (ng/mL) | $t_{1/2}$ (hr) | $AUC_{inf}$ (hr · ng/mL) | $Cl_{obs}$ (mL/hr/kg) | $Vol_{ss}$ (mL/kg) |
| --- | --- | --- | --- | --- | --- | --- |
| Conjugate 1-3 | 2.32/0.075 | 37500 | 89.8 | 3650000 | 0.637 | 81.6 |
| Conjugate 1-3 | 4.65/0.15 | 69600 | 154 | 10900000 | 0.425 | 93.1 |
| Conjugate 2-2 | 6.74/0.075 | 106000 | 175 | 14900000 | 0.452 | 109 |
| Conjugate 2-2 | 13.5/0.15 | 154000 | 141 | 21600000 | 0.623 | 128 |
| Conjugate 12 | 1.13/0.075 | 11400 | 60.1 | 704000 | 1.61 | 134 |
| Conjugate 12 | 2.26/0.15 | 25800 | 65.8 | 2250000 | 1.00 | 100 |

TABLE 21

|  | Dose mAb/ Payload (mg/kg) | $C_{max}$ (ng/mL) | $t_{1/2}$ (hr) | $AUC_{inf}$ (hr · ng/mL) | $Cl_{obs}$ (mL/hr/kg) | $Vol_{ss}$ (mL/kg) |
| --- | --- | --- | --- | --- | --- | --- |
| Conjugate 1-3 | 2.32/0.075 | 1430 | 93.6 | 142000 | 0.529 | 75.9 |
| Conjugate 1-3 | 4.65/0.15 | 2630 | 73.6 | 309000 | 0.486 | 68.2 |
| Conjugate 2-2 | 6.74/0.075 | 1360 | 150 | 143000 | 0.524 | 102 |
| Conjugate 2-2 | 13.5/0.15 | 1920 | 109 | 199000 | 0.755 | 109 |
| Conjugate 12 | 1.13/0.075 | 801 | 56.7 | 37900 | 1.98 | 163 |
| Conjugate 12 | 2.26/0.15 | 1830 | 51.3 | 109000 | 1.38 | 108 |

For total antibody, Conjugate 1-3, Conjugate 2-2, and Conjugate 12 appear to have dose proportional $C_{max}$. Conjugate 12 was observed to have lower exposure and faster clearance, compared to Conjugates 1-2 and 2-2. Conjugate 1-3 has comparable clearance to Conjugate 2-2 at different dose levels, but with low exposure (AUC) of antibody.

For antibody conjugated drug, Conjugate 1-3, Conjugate 2-2 and Conjugate 12 appear to have dose proportional $C_{max}$. Conjugate 12 was observed to have lower exposure and faster clearance, compared to Conjugates 1-2 and 2-2. Conjugate 1-3 has comparable exposure and clearance to Conjugate 2-1 at different dose levels.

Example 46: Plasma Exposure in Cynomolgus Monkey after Administration of B7-H4-Cytotoxic Drug Conjugates Study Cynomolgus monkeys were injected intravenously with Vehicle, Conjugate 1-3 (2.81/0.09), or Conjugate 2-2 (8.28/0.09) by IV infusion over 45 minutes (One male and one female for each group). Blood samples were collected predose and at 1 hour, 6 hours, 24 hours (Day 1), 96 hours (Day 5), 168 hours (Day 8), 240 hours (Day 11), and 336 hours (Day 15), and 504 hours (Day 22) after the end of infusion. Blood was processed to plasma with K2-EDTA anti-coagulant for collection. Samples were frozen on dry ice and stored at −80° C. until shipment.

Total antibody was measured using an MSD-ECL sandwich immunoassay. Free drug was measured by LC-MS. Conjugated drug was measured by LC-MS after the samples were subjected to immunocapture by an anti-human IgG1 Fc antibody immobilized on magnetic beads, followed by AF-HPA release by hydrolysis. Tables 22, 23, and 24 give the PK parameters for total antibody, conjugated drug, and free drug respectively.

TABLE 22

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 1-3 | 2.81/0.09 | 2570 | 112 | 312000 | 0.295 | 47.4 |
| Conjugate 2-2 | 8.28/0.09 | 2600 | 126 | 305000 | 0.296 | 51.7 |

TABLE 23

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 1-3 | 2.81/0.09 | 69400 | 161 | 12300000 | 0.243 | 56.7 |
| Conjugate 2-2 | 8.28/0.09 | 189000 | 176 | 34900000 | 0.238 | 65.3 |

TABLE 24

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 1-3 | 2.81/0.09 | 0.508 | 329 | 187 | N/A | N/A |
| Conjugate 2-2 | 8.28/0.09 | 1.05 | N/A | N/A | N/A | N/A |

For total antibody, Conjugate 1-3 has comparable clearance to Conjugate 2-2 at different dose levels. For conjugated drug, Conjugate 1-3 has comparable exposure and clearance to Conjugate 2-2. Conjugate 1-3 and Conjugate 2-2 both have low levels of free AF-HPA.

Example 47: Plasma Exposure in Cynomolgus Monkey after Administration of B7-H4 STING Agonist Drug Conjugates Study Cynomolgus monkeys were injected intravenously with Conjugate 15-2 (9.0/0.33) by IV infusion over 45 minutes (one male and one female). Blood samples were collected predose and at 1 hour, 6 hours, 24 hours (Day 1), 48 hours (Day 2), 96 hours (Day 5), 168 hours (Day 8), 240 hours (Day 11), 336 hours (Day 15), and 504 hours (Day 22) after the end of infusion. Blood was processed to plasma with K2-EDTA anti-coagulant for collection. Samples were frozen on dry ice and stored at −80° C. until shipment.

Total antibody was measured using an MSD-ECL sandwich immunoassay. Free drug was measured by LC-MS. Conjugated drug was measured by LC-MS after the samples were subjected to immunocapture by an anti-human IgG1 Fc antibody immobilized on magnetic beads, followed by drug release by hydrolysis. Tables 25, 26, and 27 give the PK parameters for total antibody, conjugated drug, and free drug respectively.

TABLE 25

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 15-2 | 9.0/0.33 | 191000 | 105 | 18200000 | 0.494 | 73.8 |

TABLE 26

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 15-2 | 9.0/0.33 | 5540 | 98.4 | 416000 | 0.794 | 107 |

TABLE 27

| Test Articles | Dose mAb/ Payload (mg/kg) | $C_{max}$ (ng/ mL) | $t_{1/2}$ (hr) | $AUC_{inf}$ (hr · ng/ mL) | $Cl_{obs}$ (mL/ hr/kg) | $Vol_{ss}$ (mL/ kg) |
|---|---|---|---|---|---|---|
| Conjugate 15-2 | 9.0/0.33 | 40.1 | 107 | 462 | N/A | N/A |

Example 48. Efficacy of B7-H4_2F9V18 Cytotoxic Drug Conjugate in an Unselected Series of Human Breast Primary Cancer Xenografts A panel of twenty-eight breast cancer patient-derived xenograft models, (Champions Oncology) annotated by the supplier by prior treatment history, and divided between TNBC and ER-positive subtypes, was implanted into athymic Nude-Foxn1n mice. When the tumors reached an average volume of 150-300 mm³, animals (n=3) were treated with a single intravenous administration of either Conjugate 1-3 (4.71 mg/kg/0.15 mg/kg, antibody/payload) or saline vehicle on day 1. Tumor volumes were measured until the planned endpoint of mean tumor volume of the control group of 1500 mm³ or day 28. At the endpoint, xenografts, or tumor beds (in the case of no palpable mass) were collected as formalin fixed paraffin embedded material. Two additional ER positive models, originally proposed for this study, were excluded from summary analysis due to unexpectedly rapid growth/ambiguous tumor origin (CTG-3277) or very slow growth in vehicle animals (CTG-2611).

Figure 13:
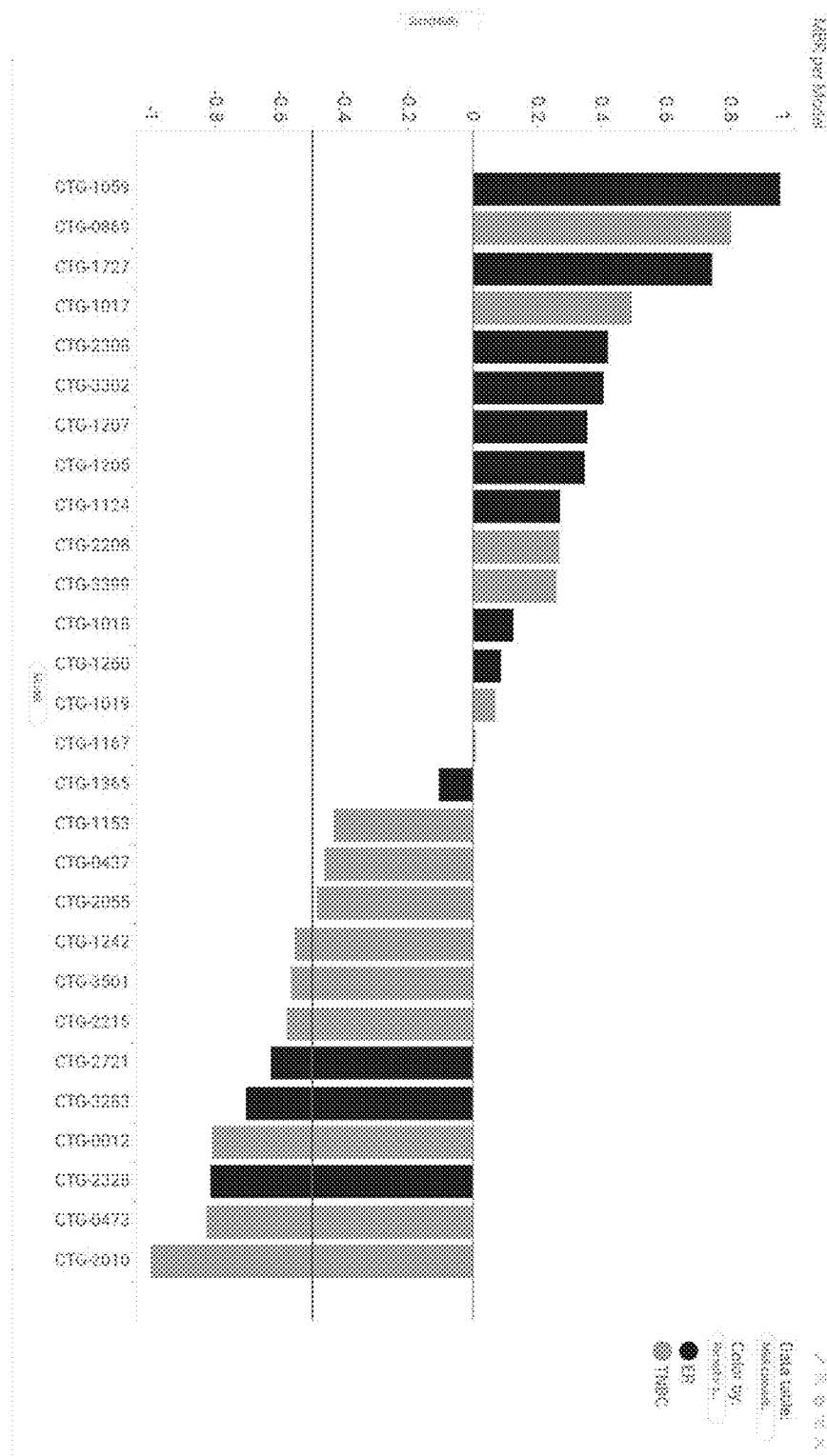
FIG. 13 shows the efficacy of Conjugate 1-3 ordered by median best response (MBR), broken out by receptor status for an unselected series of TNBC and ER-positive breast cancer patient-derived xenograft models. The Y axis shows the MBR achieved by each model and the X axis identifies the model ID.

FIG. 13 shows the efficacy of Conjugate 1-3 ordered by median best response (MBR), broken out by receptor status (TNBC vs ER-positive), as annotated by the vendor. The Y axis shows the MBR achieved by each model and the X axis identifies the model ID. In this study, 9/28 (32%) of breast carcinoma models achieved a median best response of 50% (shown as −0.5 on the Y Axis) or better following a single dose of Conjugate 1-3, and the anti-tumor effect of MBR of 50% or more was more frequent in TNBC models 6/15 (40%) compared to ER-positive models 3/13 (23%).

Example 49. Protein and RNA Expression of B7-H4 in Mouse Primary Xenograft Tissues Based on availability of xenograft tissues from Example 44, RNA and Protein Analysis were performed. RNA was extracted from FFPE samples using the Qiagen Rneasy FFPE kit according to the manufacturers instructions. Samples were equalized based on nanodrop reading and cDNA produced using the Thermofisher SuperScript IV VILO Master Mix with exDNase Enzyme. Gene expression assays were set up with the TaqMan Fast Advanced Master Mix. ABI assay Hs01552471_g1 was used for VTCN1. Hs99999903_ml ACTB and Hs03929097_g1 GAPDH were used as endogenous controls. Expression data was analyzed as AA Ct of the average of animals in each vehicle treated group (generally n=3) relative to a Universal RNA control.

IHC to detect B7-H4 expression was performed on a single vehicle treated animal from each model. Briefly, tissues were sectioned at 4μ onto positively charged slides and dried overnight. Using the Leica BOND III platform, sections were baked, dewaxed and subjected to antigen retrieval (LEICA BOND III ER1+Proteinase K). The primary B7-H4 antibody (Abcam ab209242) was used at a concentration of 0.2 μg/ml (prepared in DAKO/Agilent diluent 53022). Signal was detected using the Leica BOND Polymer Refine system/DAB chromogen. Slides were evaluated by light microscopy and scored using H-Score and TPS methods.

Figure 14:
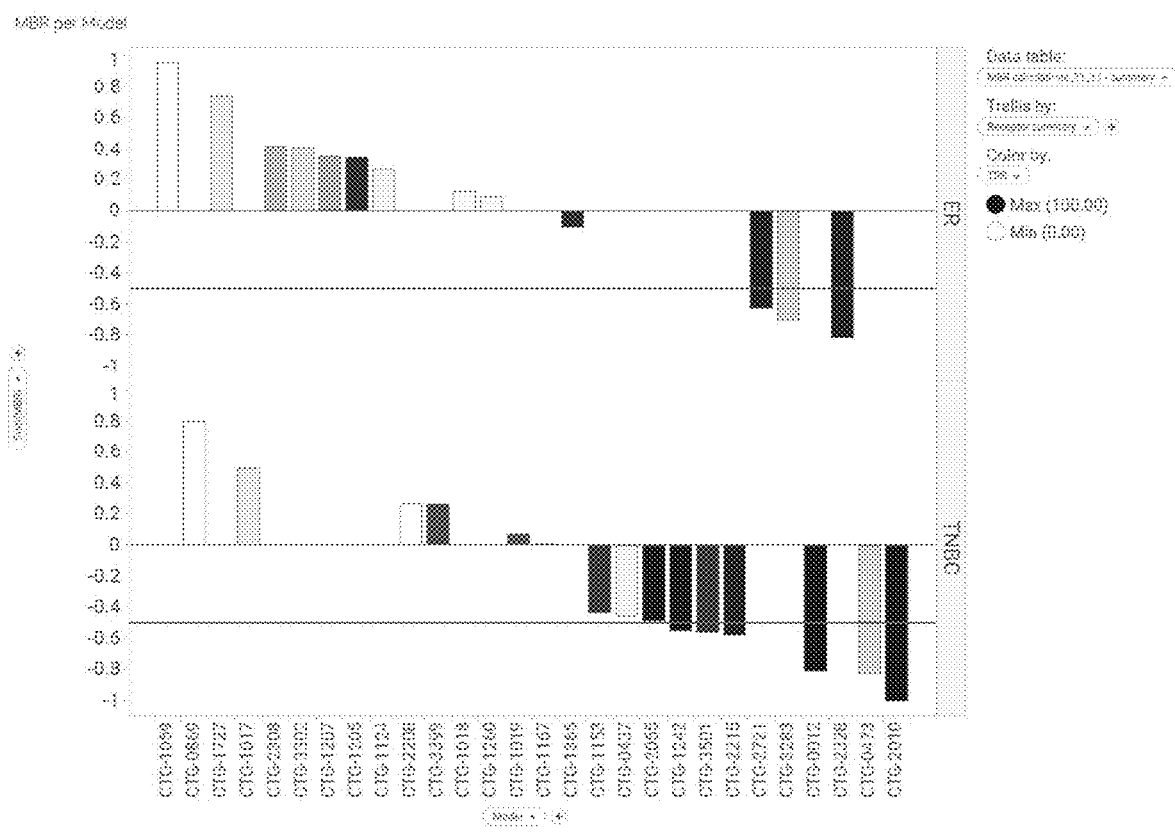
FIG. 14 shows the protein expression on a subset of TNBC and ER-positive breast cancer patient-derived xenograft models from Example 44 as evaluated by TPS score.

FIG. 14 shows the protein expression as evaluated by TPS score. There appeared to be an efficacy/expression relationship. When TPS score was trellised by receptor status, higher expression was more likely in models annotated as TNBC. A similar pattern was seen comparing H score or relative RNA expression values to compound efficacy.

EQUIVALENTS

The details of one or more embodiments of the invention are set forth in the accompanying description above. Although any methods and materials similar or equivalent to those described herein can be used in the practice or testing of the present disclosure, the methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

What is claimed is:

1. An isolated antibody that specifically binds B7-H4 comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1)

comprising the amino acid sequence QSVSSSY (SEQ ID NO: 53), a variable light chain complementarity determining region 2 (CDRL2) comprising the amino acid sequence GAS (SEQ ID NO: 54), and a variable light chain complementarity determining region 3 (CDRL3) comprising the amino acid sequence QQYGSSPLYT (SEQ ID NO: 55).

2. The isolated antibody of claim 1, wherein the isolated antibody comprises a heavy chain variable sequence comprising the amino acid sequence of SEQ ID NO: 44 and a light chain variable sequence comprising the amino acid sequence of SEQ ID NO: 50.

3. The isolated antibody of claim 1, wherein the isolated antibody comprises (i) a heavy chain comprising the amino acid sequence of SEQ ID NO: 45 and a light chain comprising the amino acid sequence of SEQ ID NO: 52; (ii) a heavy chain variable sequence comprising the amino acid sequence of SEQ ID NO: 22 and a light chain variable sequence comprising the amino acid sequence of SEQ ID NO: 50; or (iii) a heavy chain comprising the amino acid sequence of SEQ ID NO: 23 and a light chain comprising the amino acid sequence of SEQ ID NO: 52.

4. The isolated antibody of claim 1, wherein the isolated antibody is a monoclonal antibody.

5. The isolated antibody of claim 4, wherein the isolated antibody is a chimeric, humanized or fully human monoclonal antibody.

6. The isolated antibody of claim 1, wherein the isolated antibody is an IgG isotype or an IgG1 isotype antibody.

7. The isolated antibody of claim 1, wherein the isolated antibody competes for specific binding to human B7-H4 with an isolated antibody comprising a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16) or the amino acid sequence ARDADYGMDV (SEQ ID NO: 10), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), and a variable light chain complementarity determining region 3 (CDRL3) comprising the amino acid sequence QQYGSSPLYT (SEQ ID NO: 55).

8. The isolated antibody of claim 1, wherein the isolated antibody competes for specific binding to human B7-H4 with an isolated antibody comprising a heavy chain variable sequence comprising the amino acid sequence of SEQ ID NO: 44 and a light chain variable sequence comprising the amino acid sequence of SEQ ID NO: 50 or with an isolated antibody comprising a heavy chain comprising the amino acid sequence of SEQ ID NO: 45 and a light chain comprising the amino acid sequence of SEQ ID NO: 52.

9. A B7-H4 antibody-drug conjugate comprising the isolated antibody of claim 1.

10. The B7-H4 antibody-drug conjugate of claim 9, comprising one or more Linker-Drug moieties covalently linked to the antibody, wherein:
  each Linker-Drug moiety comprises a Multifunctional Linker that connects the antibody to one or more Drug Units through intermediacy of a Releasable Assembly Unit for each Drug Unit, and connects a hydrophilic group to the Drug Unit of each Linker-Drug moiety;
  the Releasable Assembly unit is capable of releasing free drug in proximity to a target site targeted by the antibody; and
  the Multifunctional Linker comprises a peptide moiety between the antibody and the hydrophilic group, wherein the peptide moiety comprises at least two amino acids.

11. The B7-H4 antibody-drug conjugate of claim 9, wherein the B7-H4 antibody-drug conjugate is

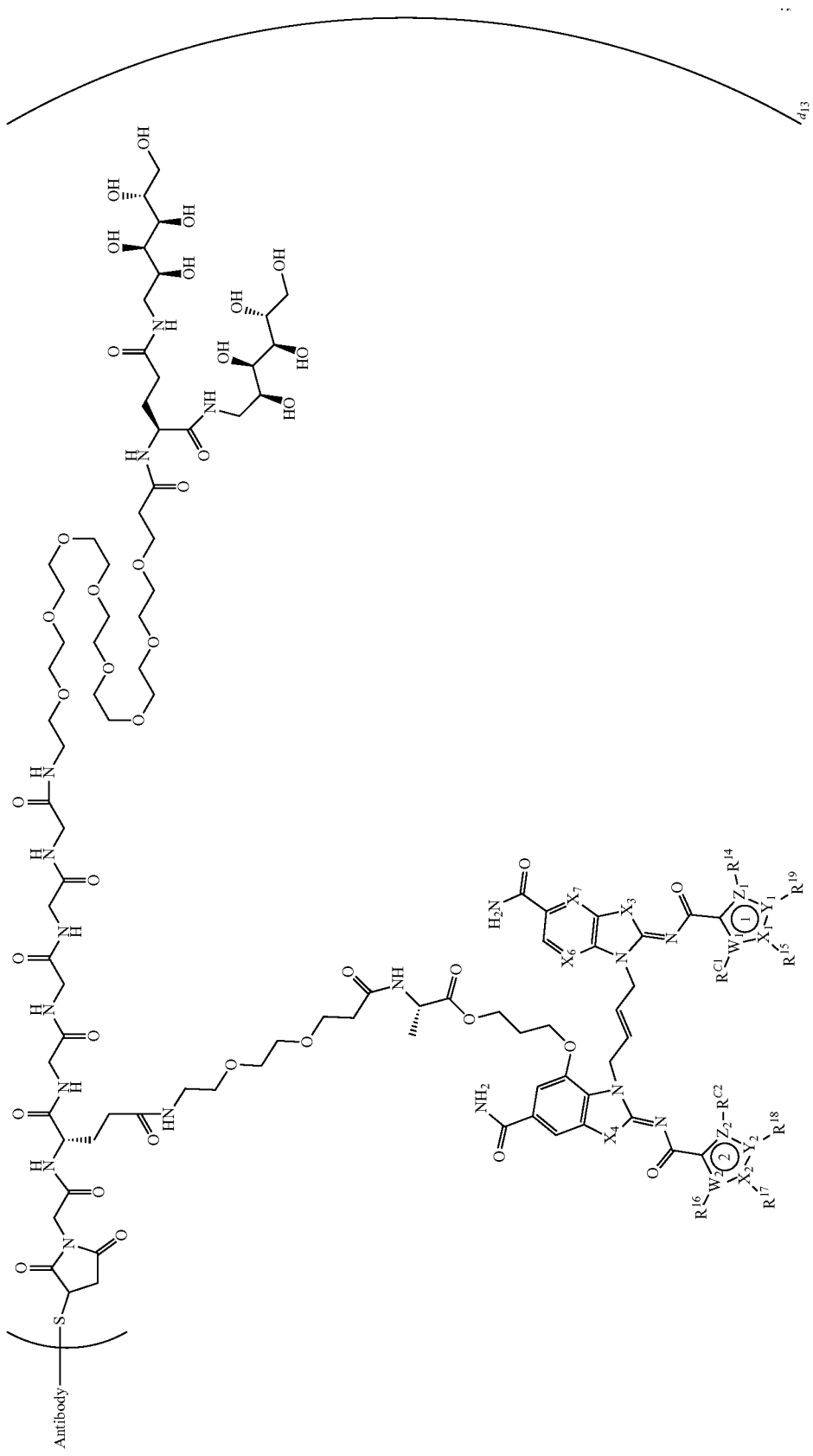

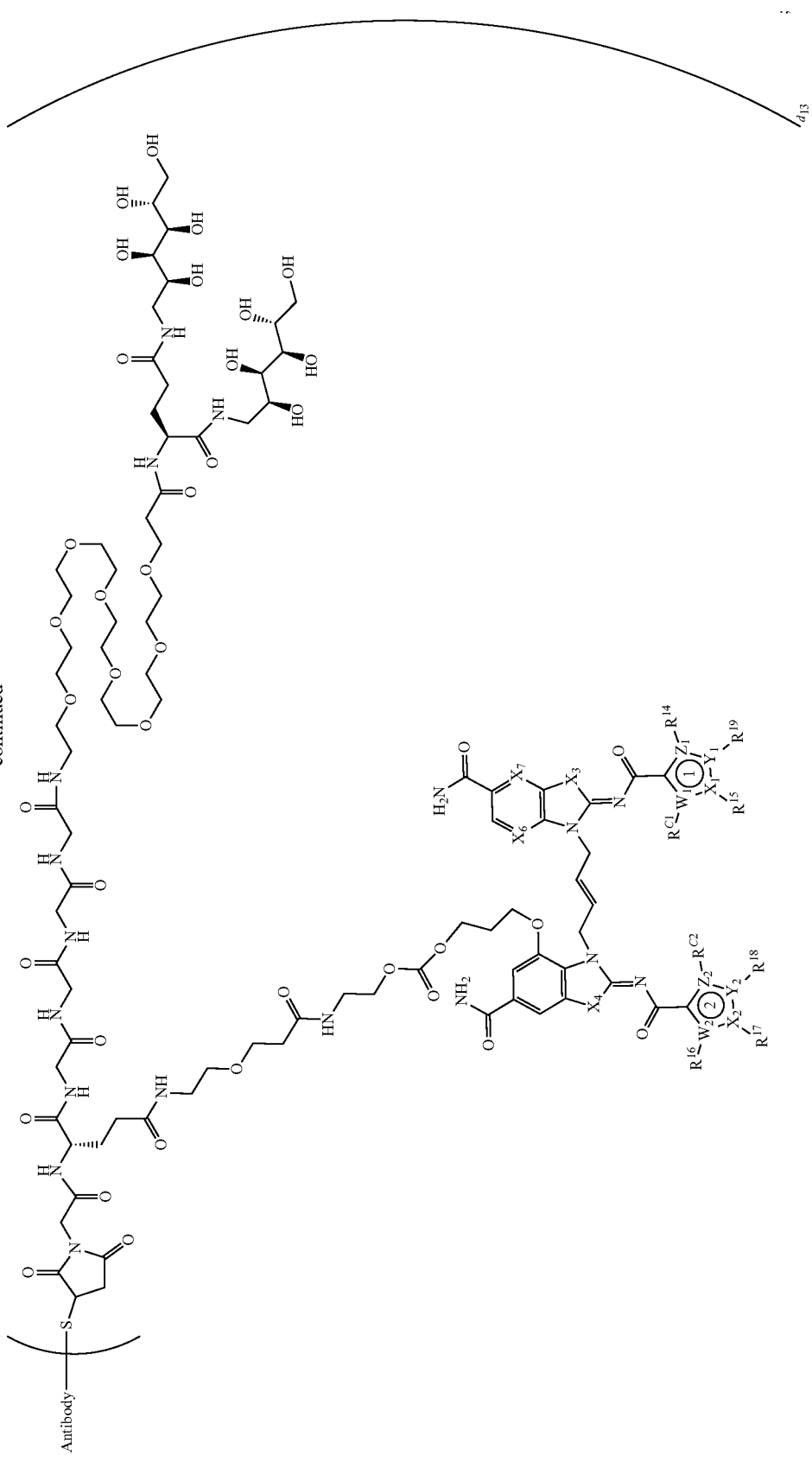

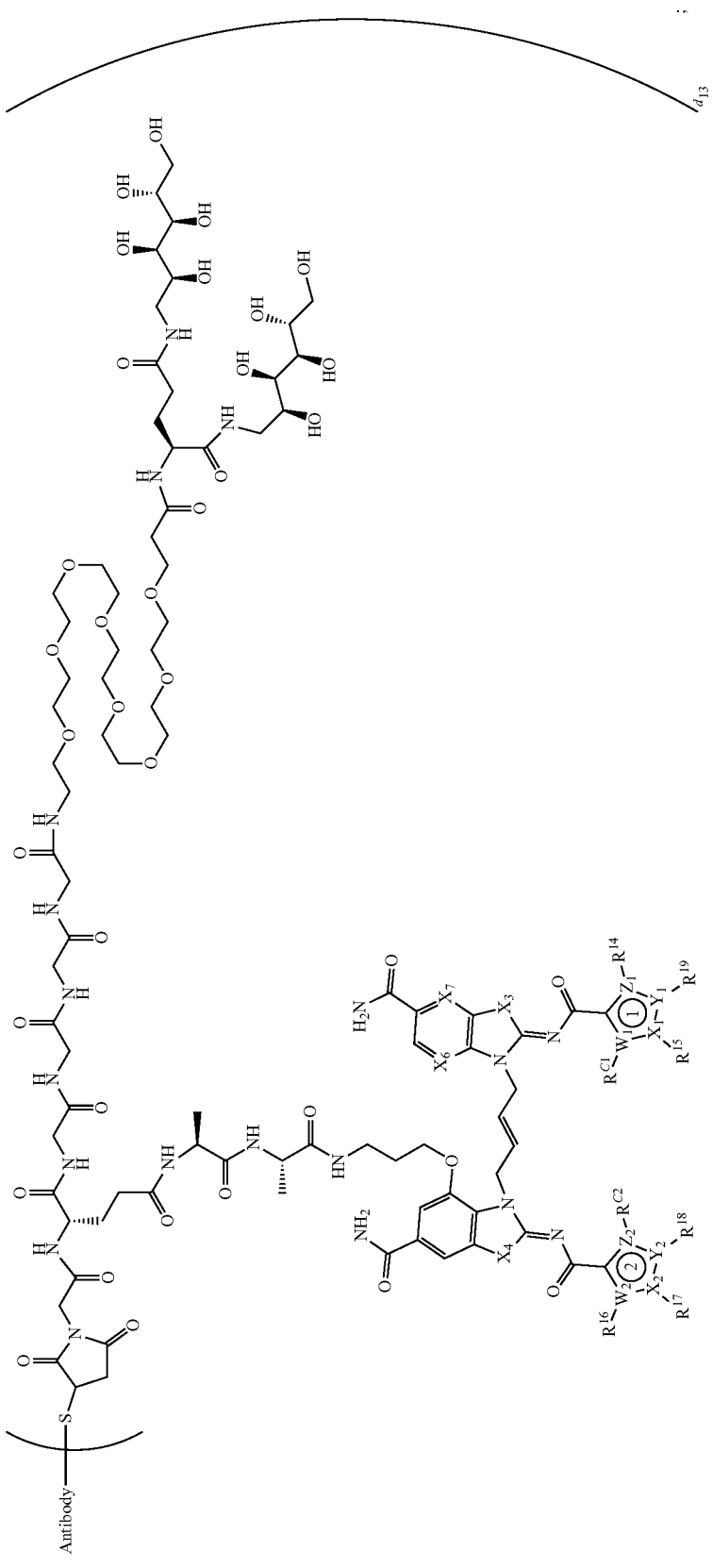

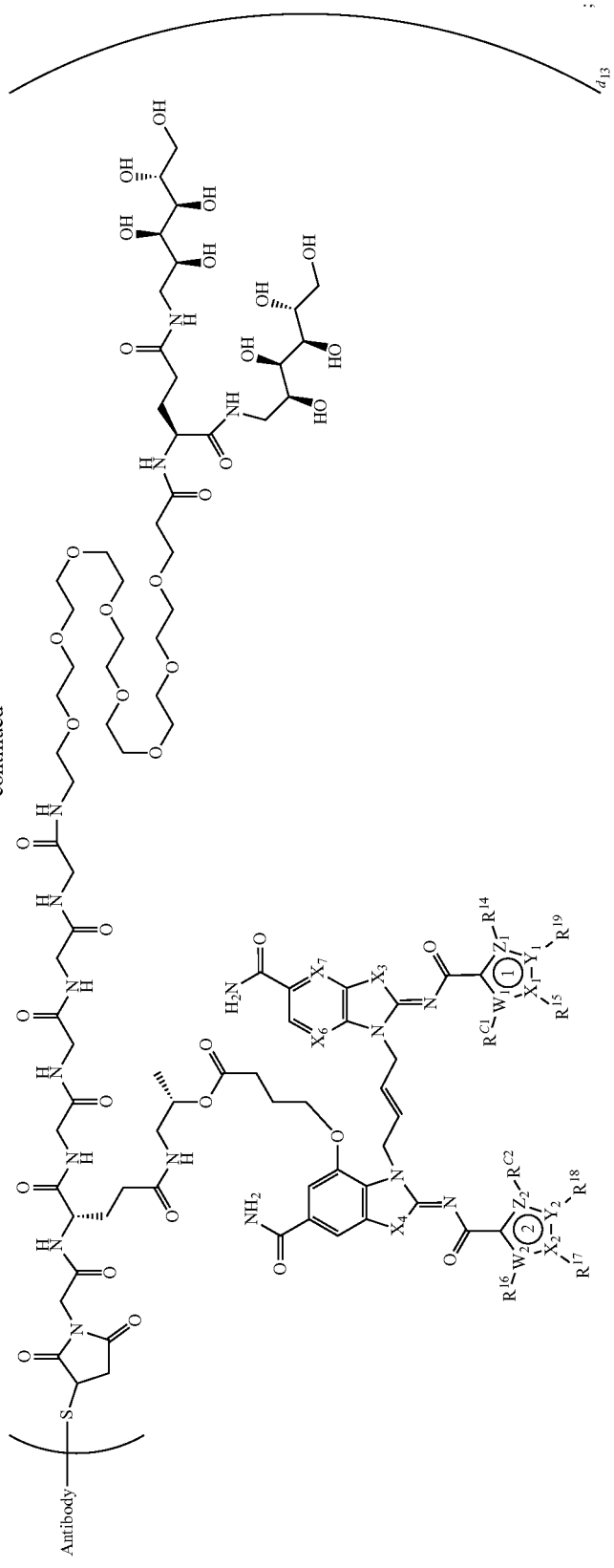

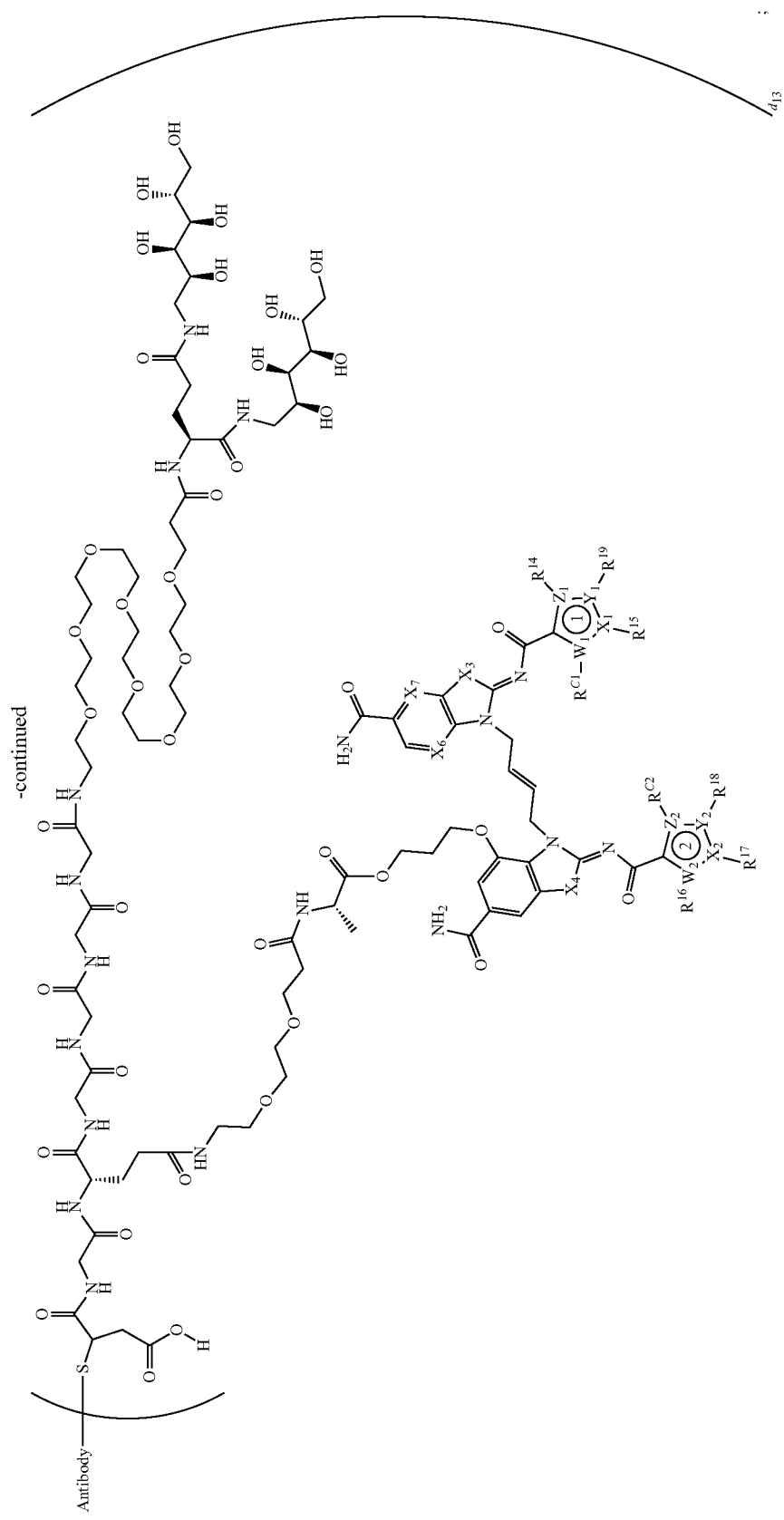

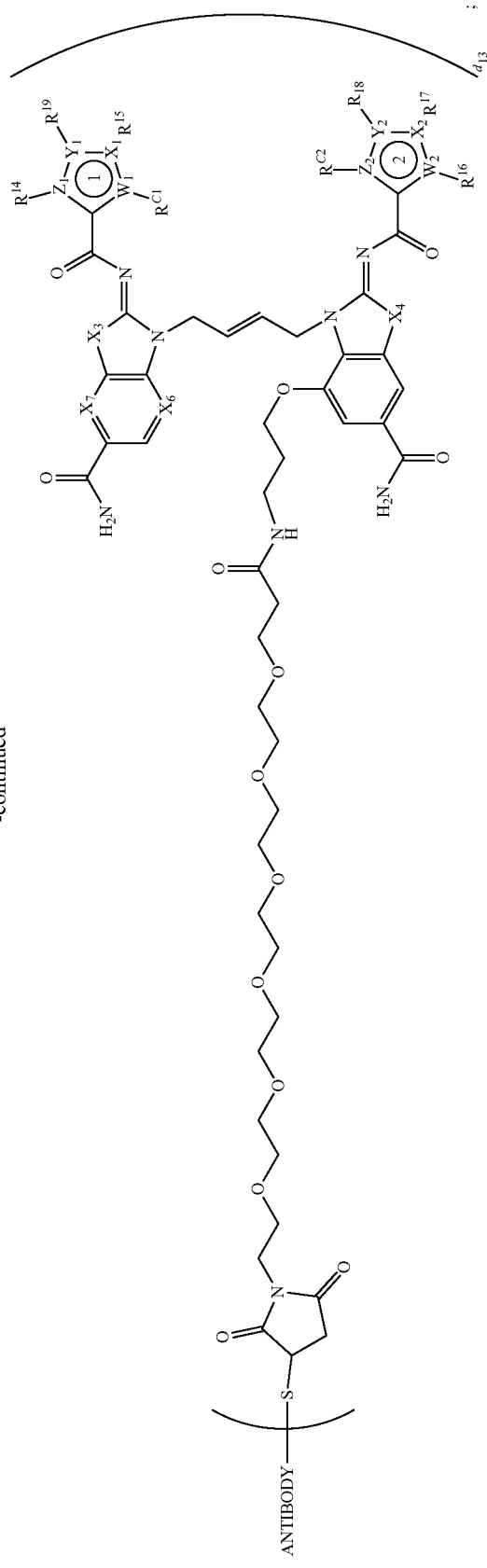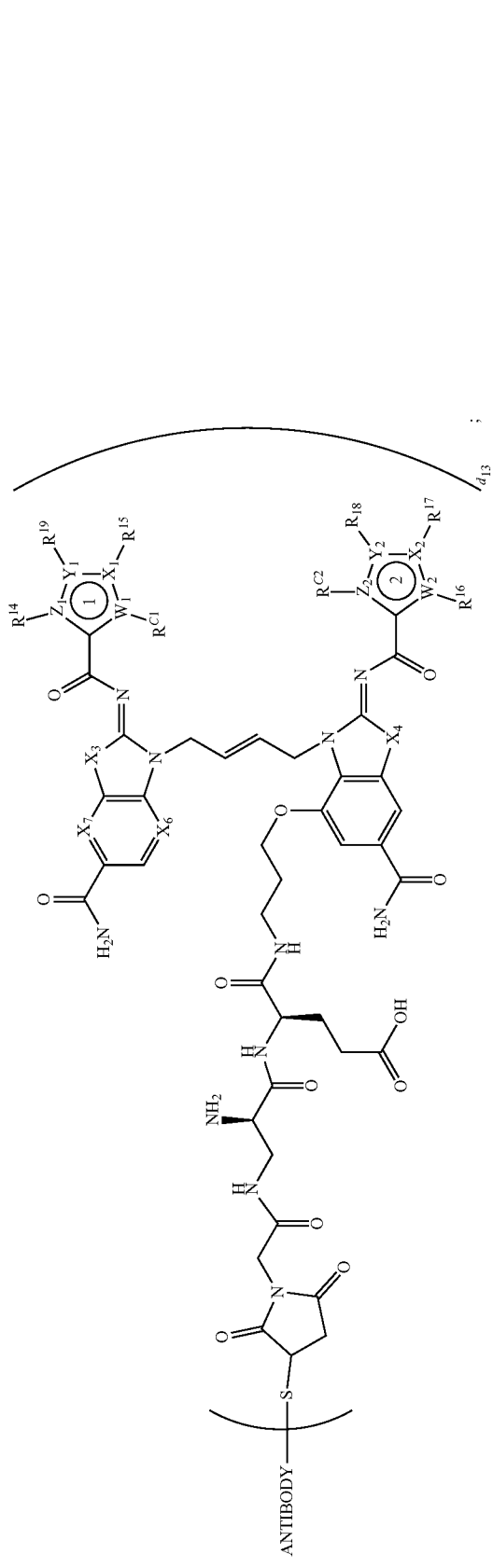

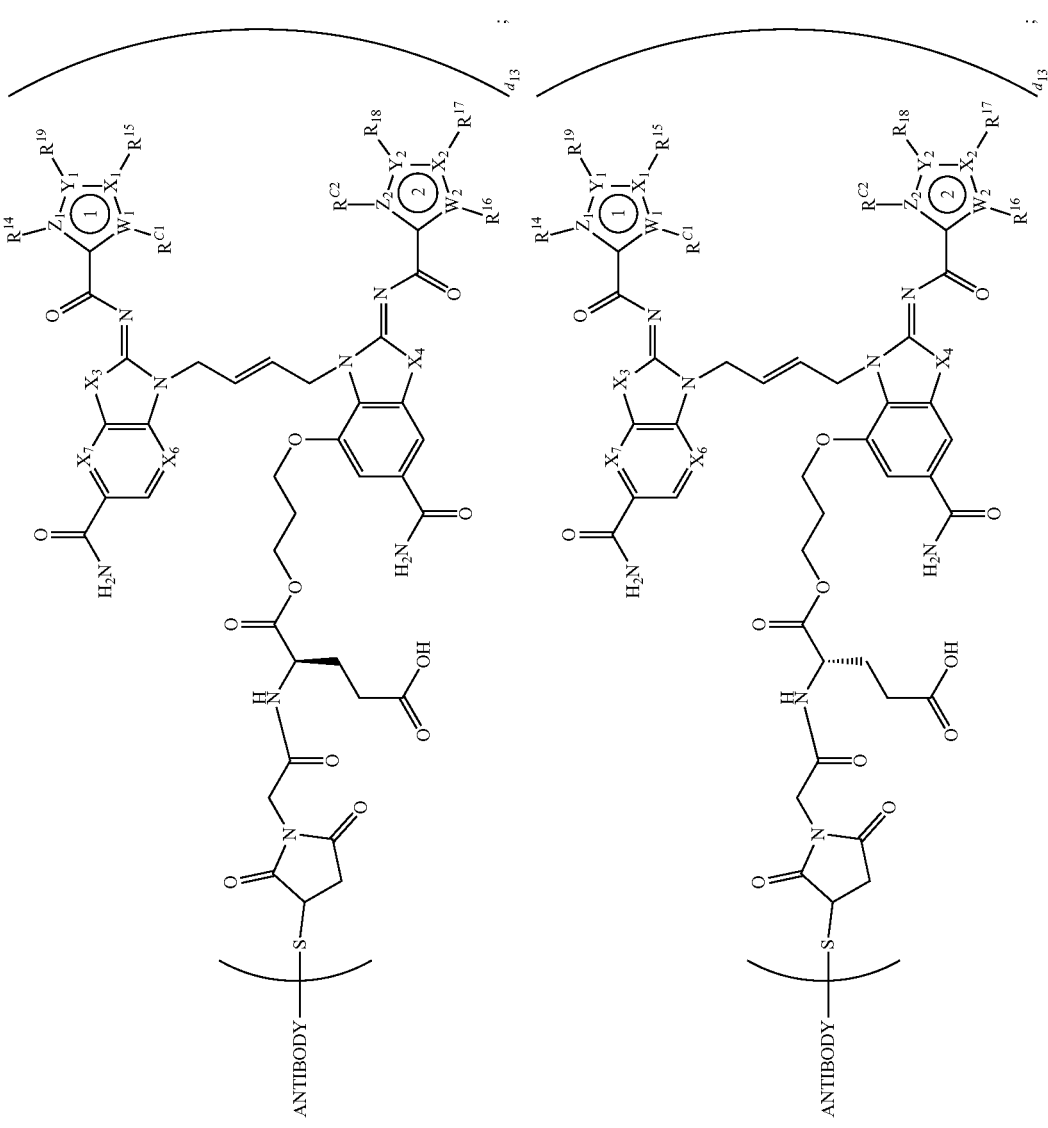

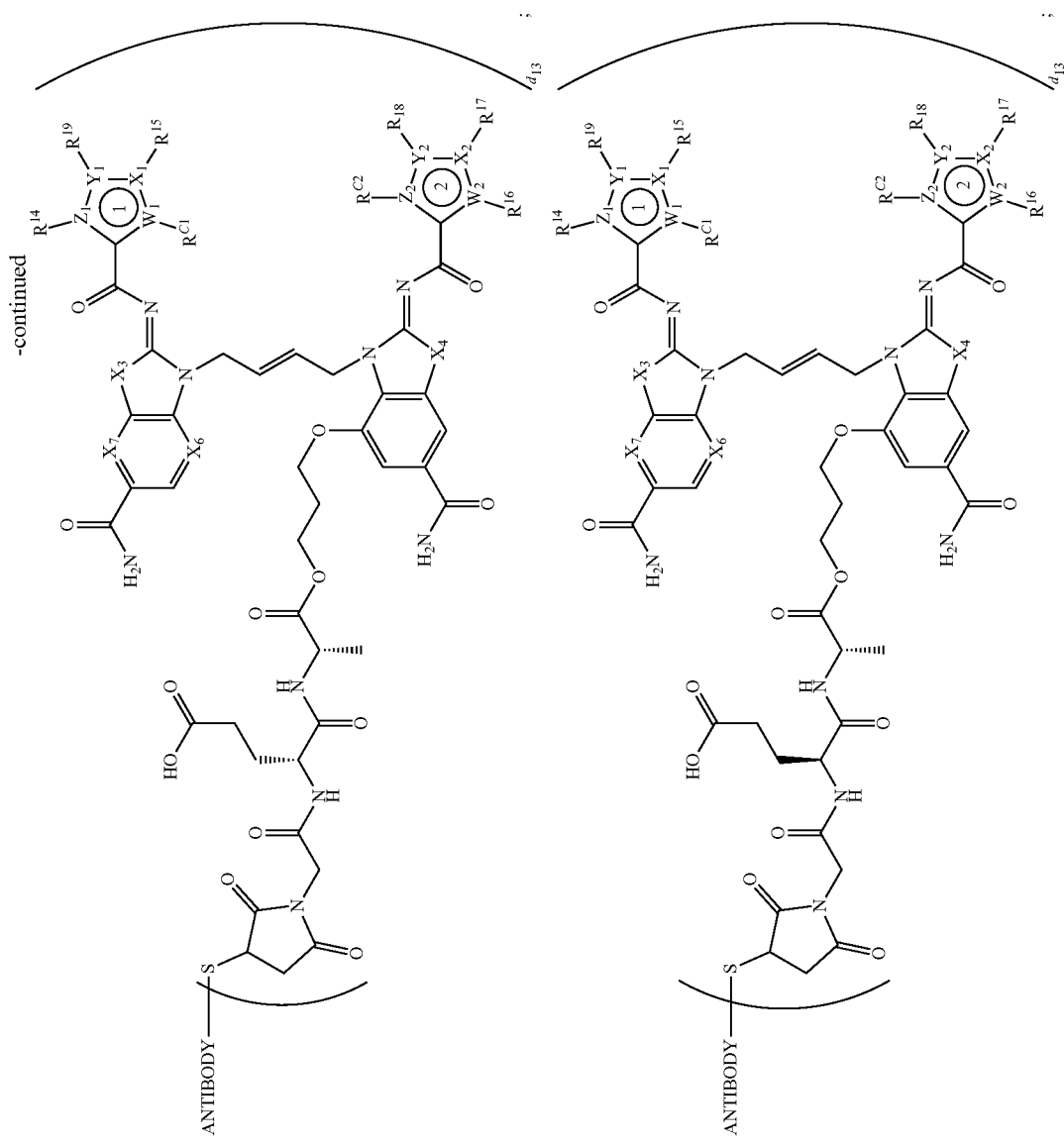

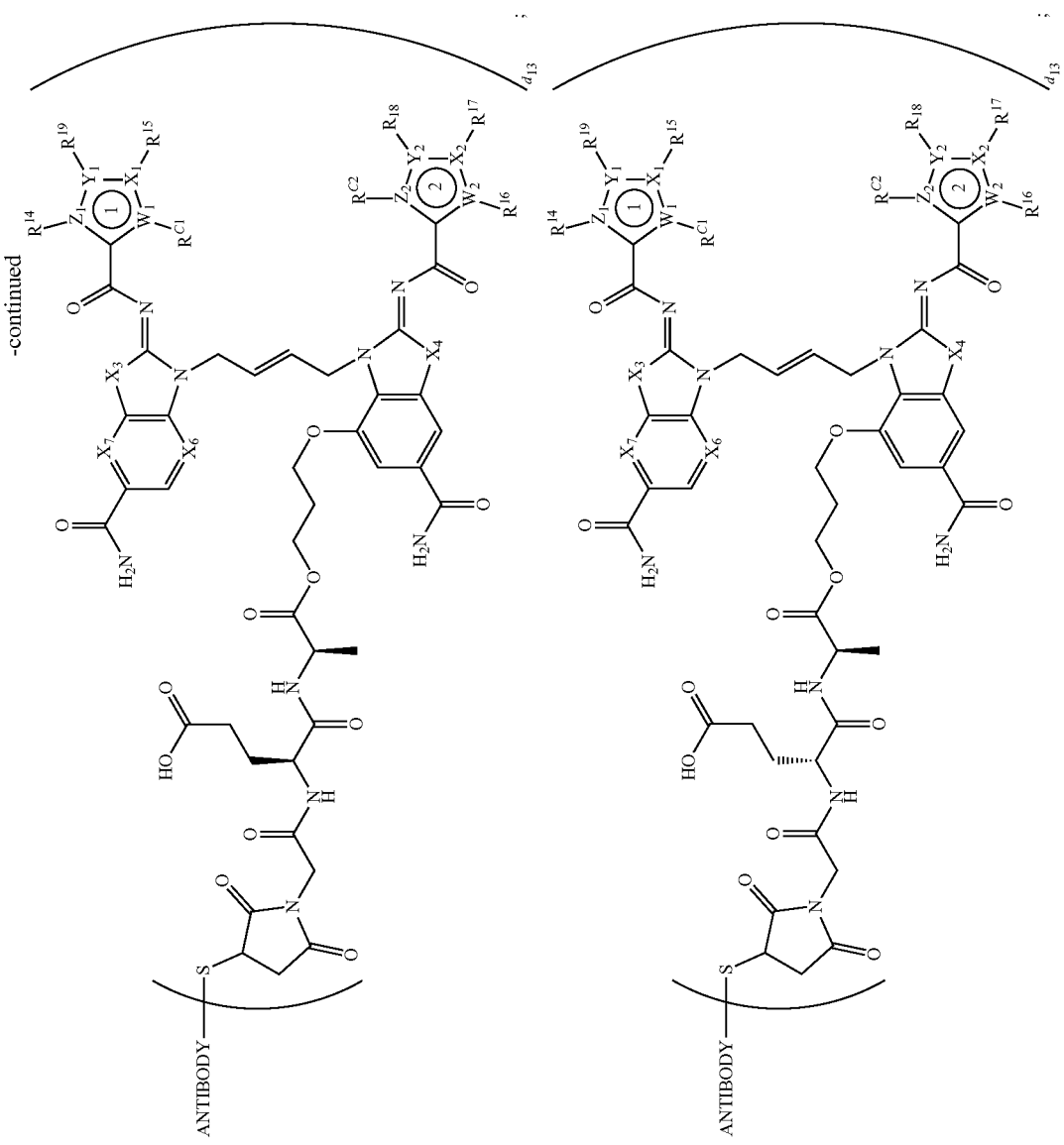

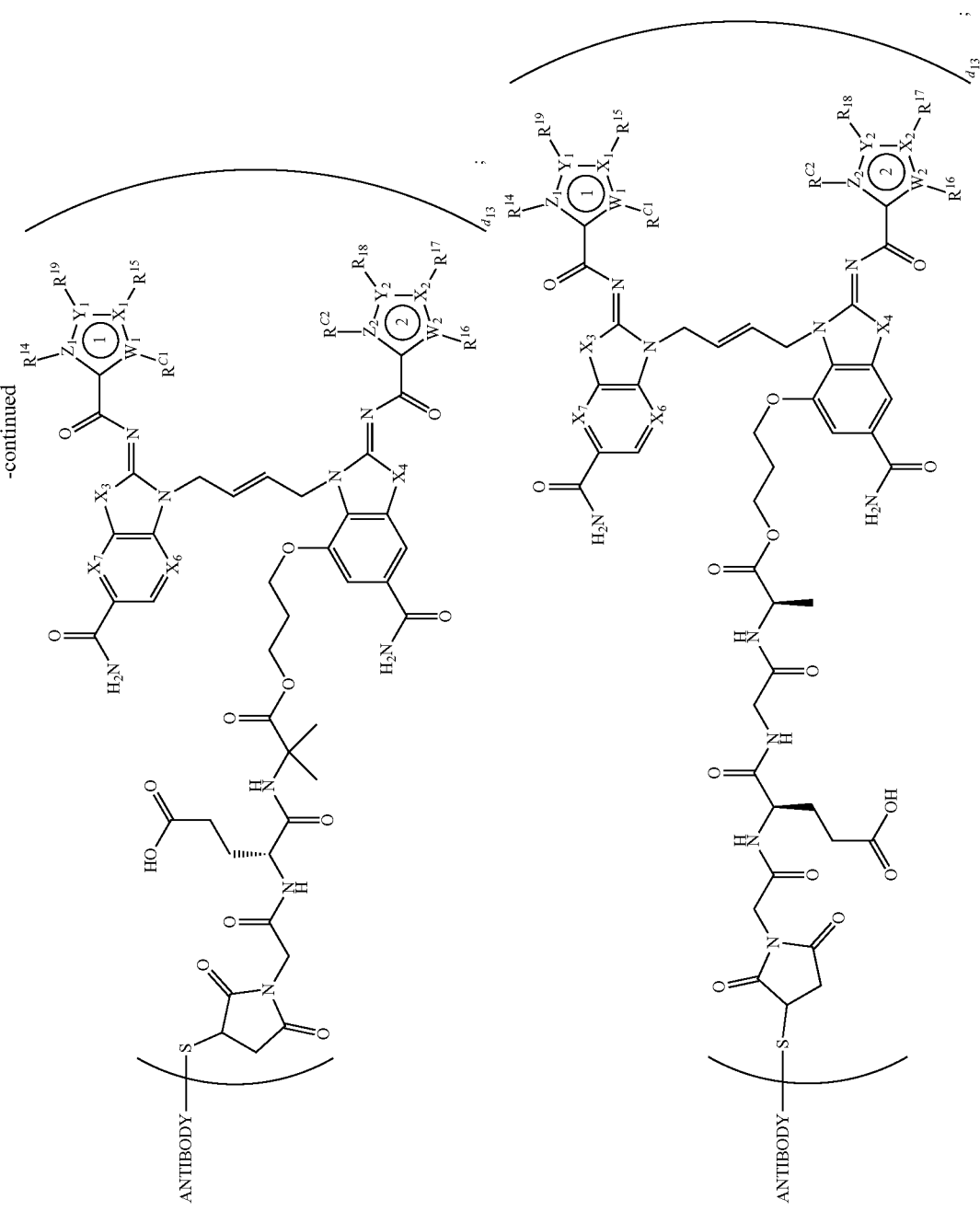

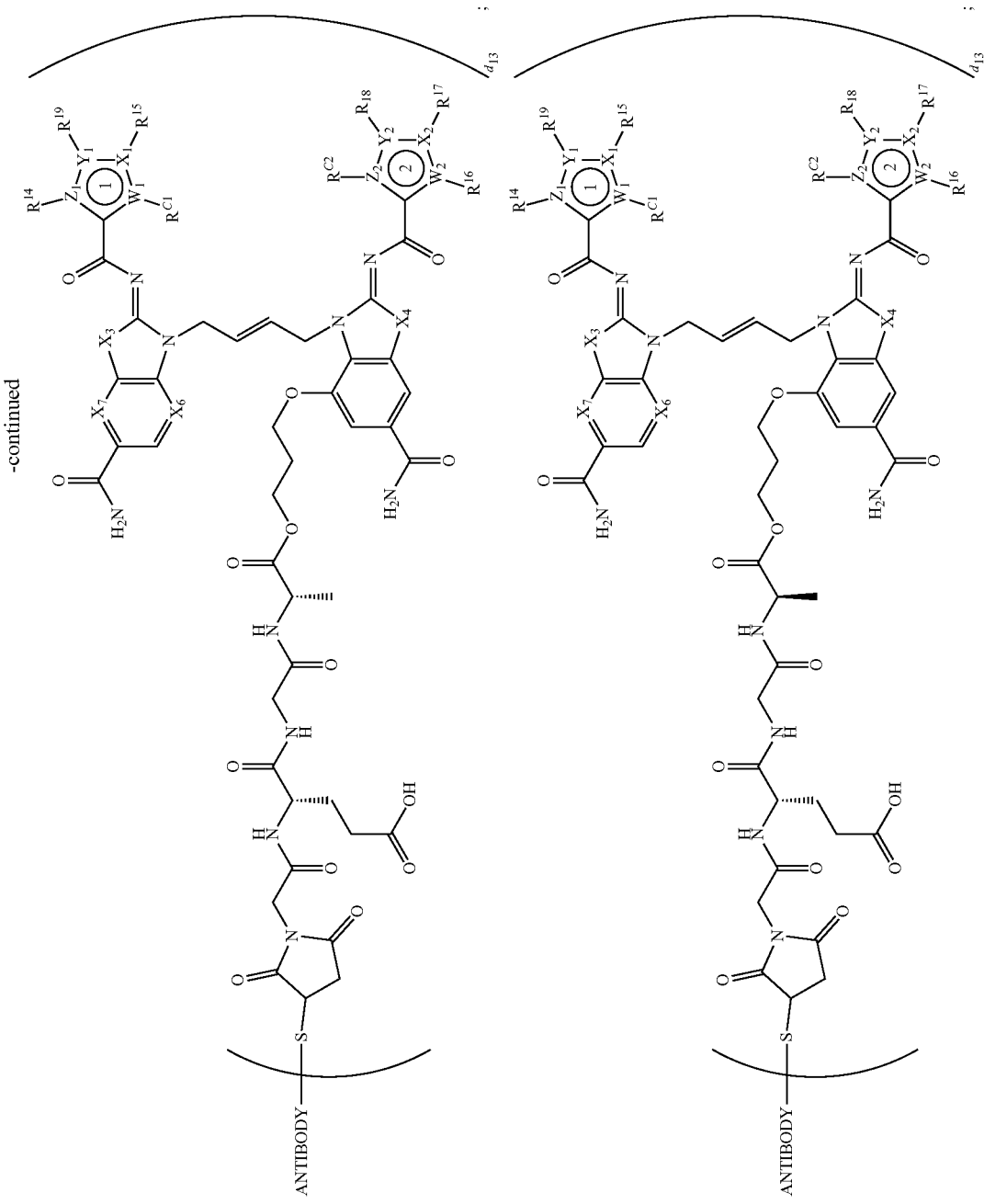

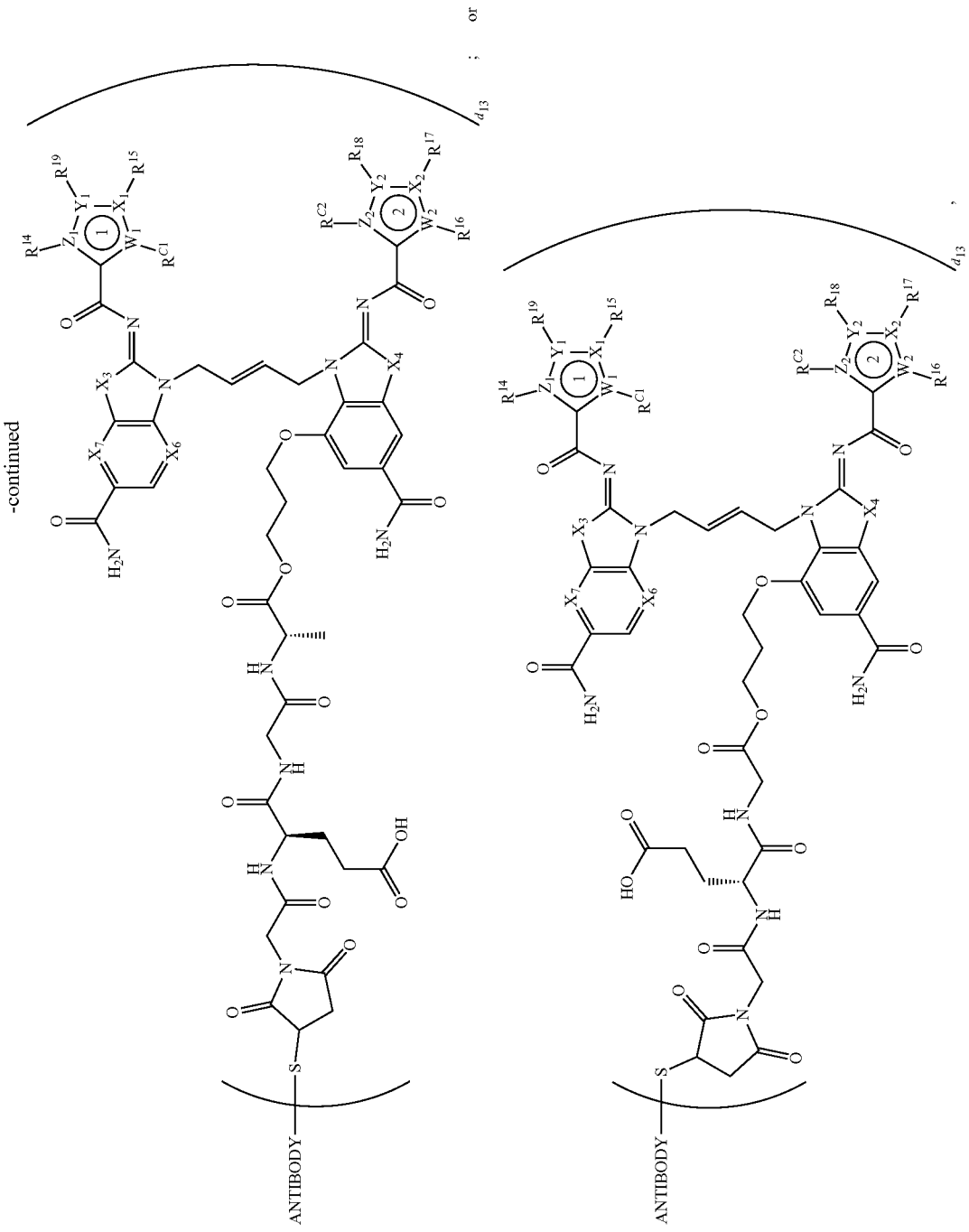

wherein:

$d_{13}$ is from about 2 to about 12;

$Y_1$, $Y_2$, $Z_1$ and $Z_2$ are each independently O, S, C or N;

$X_1$, $X_2$, $W_1$ and $W_2$ are each independently C or N;

$X_3$ and $X_4$ are each independently S or $NR^f$;

$X_6$ is N or $CR^{41}$;

$X_7$ is N or $CR^4$;

$R^e$ is $C_{1-4}$ alkyl;

$R^{41}$, and $R^4$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —N($R^e$)($R^f$), —CO$_2$($R^f$), —CON($R^e$)($R^f$), and —COOH;

each $R^d$ is independently H, hydroxy, or $C_{1-4}$ alkyl;

$R^e$ is selected from H, ($C_{1-4}$ alkyl), -CO($C_{1-4}$ alkyl), —OCO($C_{1-4}$ alkyl), and -CO$_2$($C_{1-4}$ alkyl);

each $R^f$ is independently H, hydroxy, or ($C_{1-4}$ alkyl);

$R^{14}$ and $R^{C2}$ are each independently absent or $C_{1-4}$ alkyl, wherein $C_{1-4}$ alkyl is optionally substituted by a substituent selected from halogen, —$OR^c$, —$NR^c R^d$, -$CO_2R^c$, —$CONR^c R^d$, —$SO_2NR^c R^d$, and —$OCONR^c R^d$;

$R^{16}$ and $R^{C1}$ are each independently absent, H or $C_{1-4}$ alkyl; and $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^c R^d$, -$CO_2R^c$, —$CONR^c R^d$, —$SO_2NR^c R^d$, and —$OCONR^c R^d$.

12. The B7-H4 antibody-drug conjugate of claim 9, the B7-H4 antibody-drug conjugate being of Formula (XXXVII):

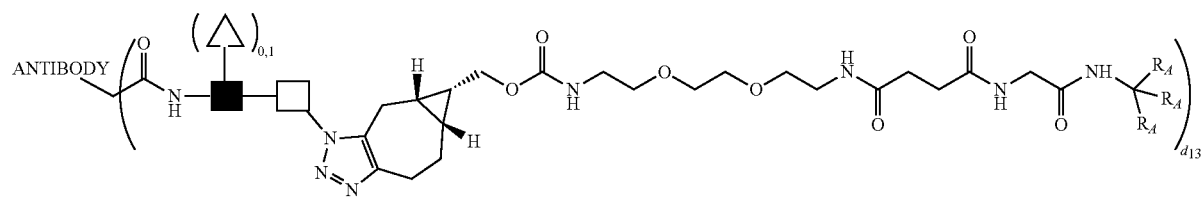

(XXXVII)

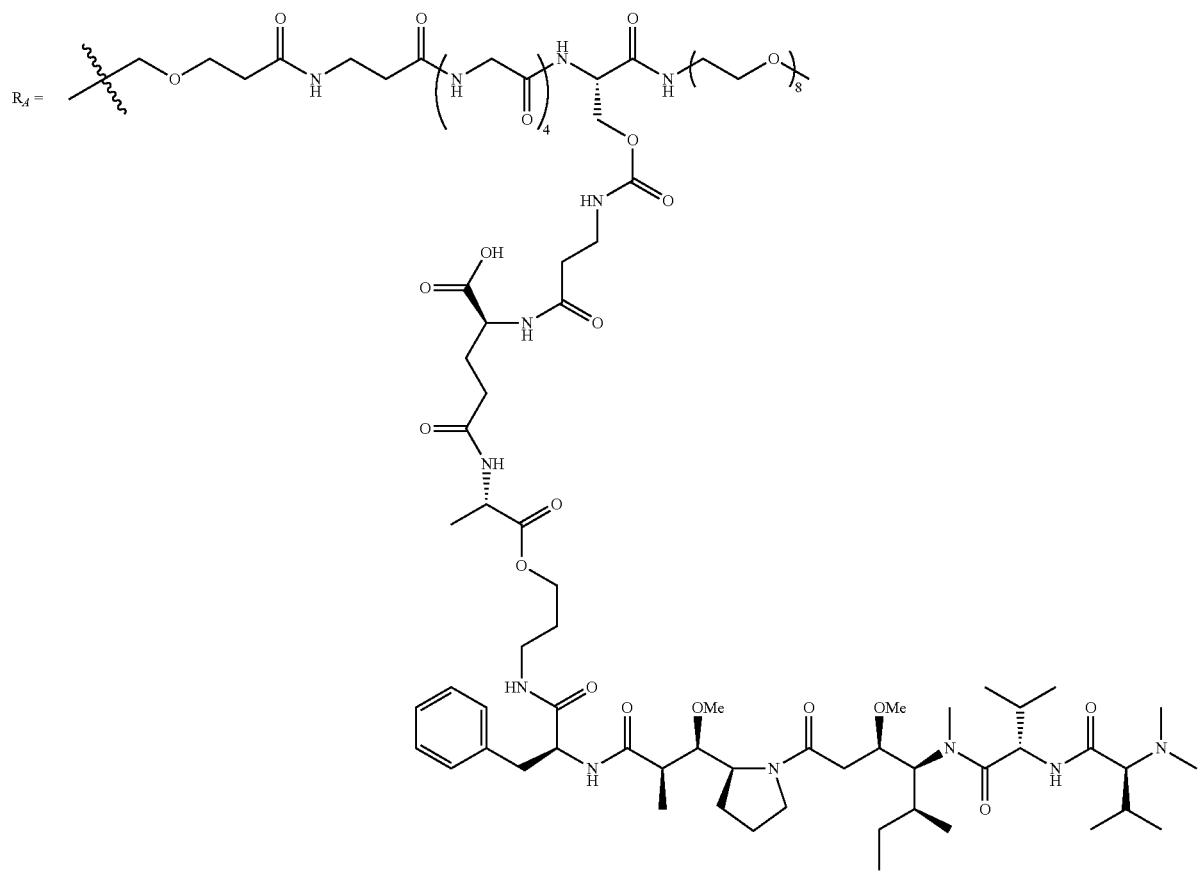

wherein
$d_{13}$ is about 2;
the drug is attached to a heavy chain of the antibody via a linker moiety at an asparagine residue at position 297 when numbered in accordance with EU numbering; and ■ is GlcNAc; △ is Fuc; and □ is GalNAc.

13. The B7-H4 antibody-drug conjugate of claim 9, the B7-H4 antibody-drug conjugate being of Formula (XXXVIII):

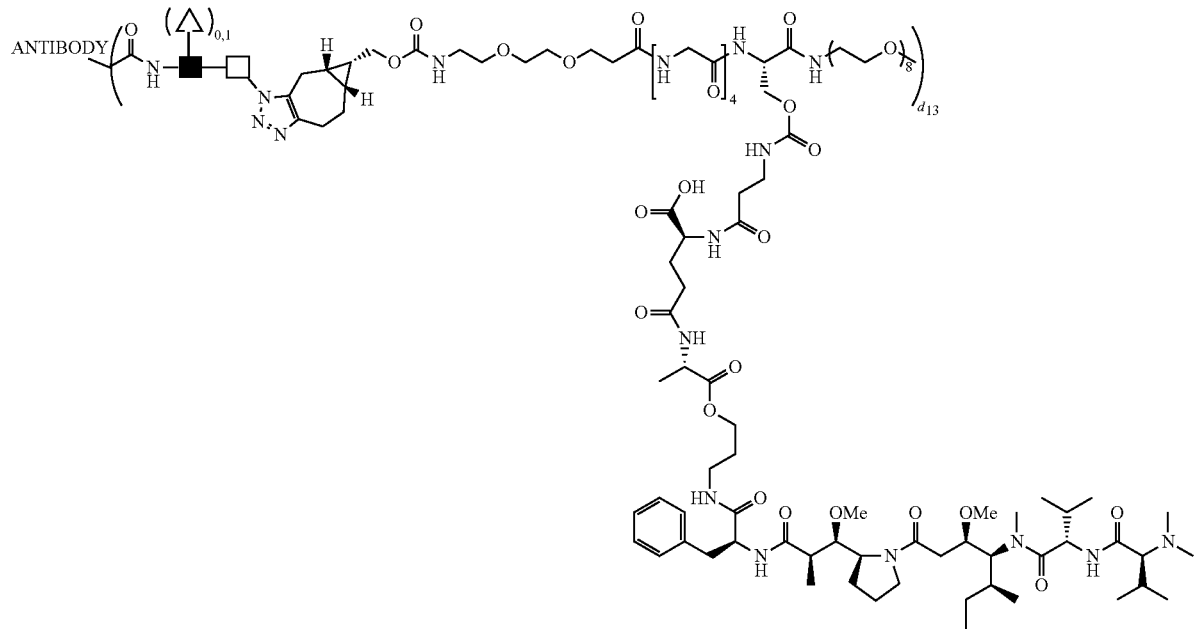

(XXXVIII)

wherein
$d_{13}$ is an integer about 2;
the drug is attached to a heavy chain of the antibody via a linker moiety at an asparagine residue at position 297 when numbered in accordance with EU numbering; and
■ is GlcNAc; △ is Fuc; and □ is GalNAc.

14. The B7-H4 antibody-drug conjugate of claim 9, wherein the B7-H4 antibody-drug conjugate is:

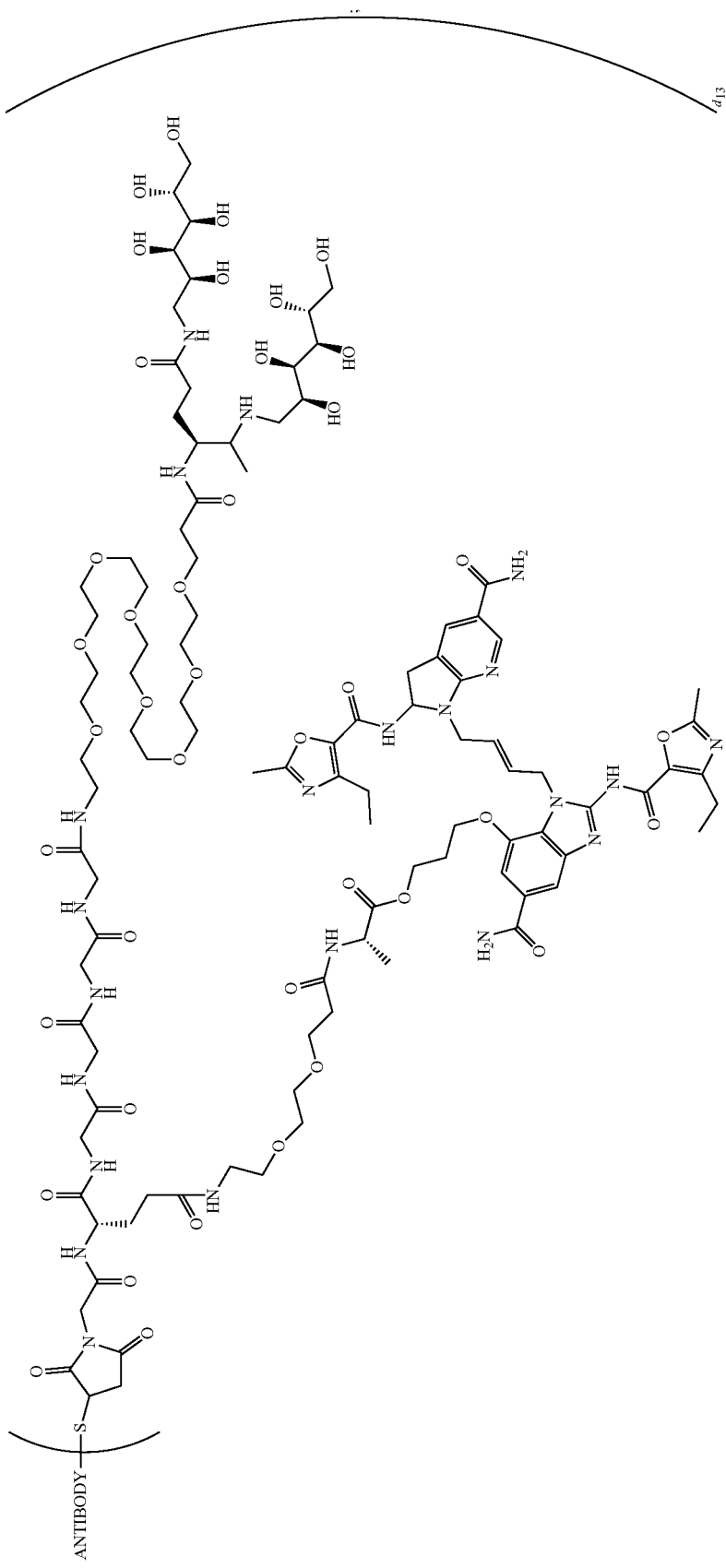

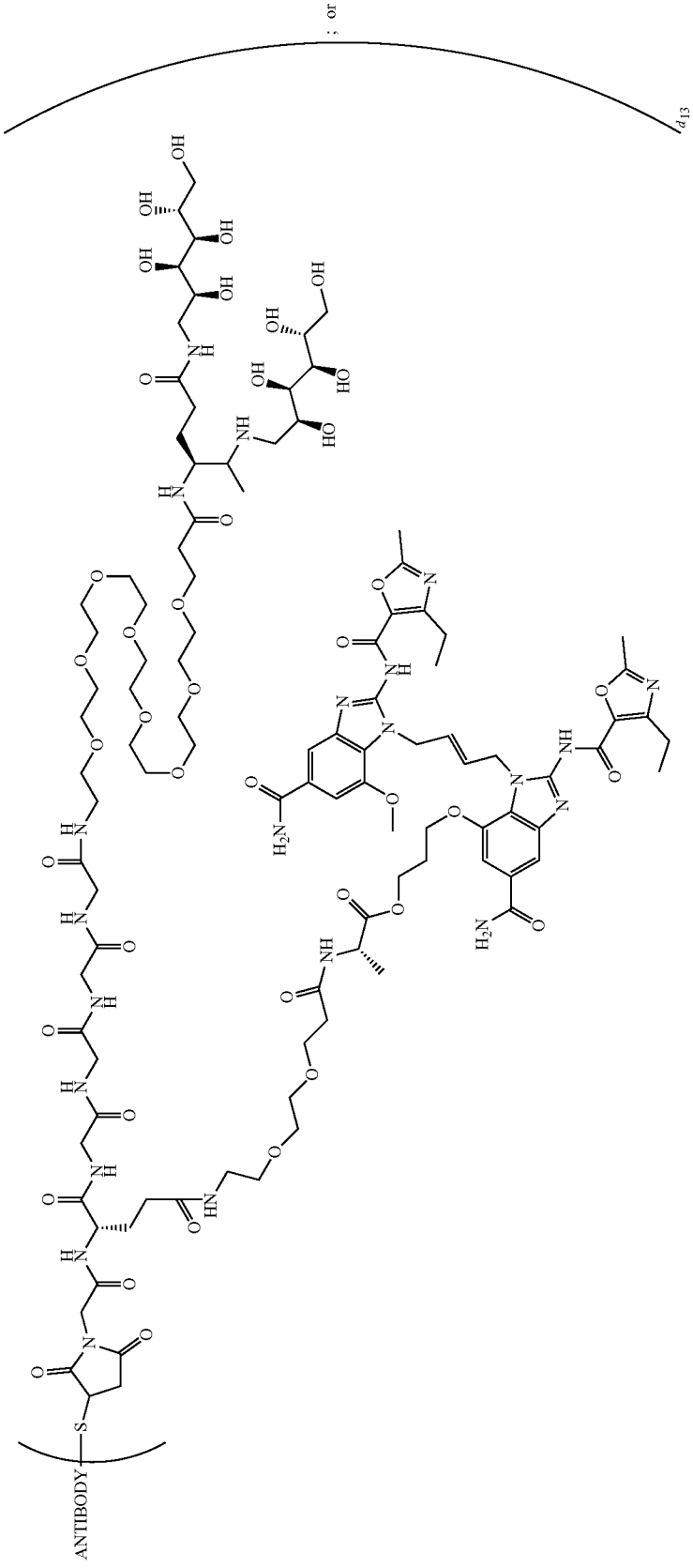

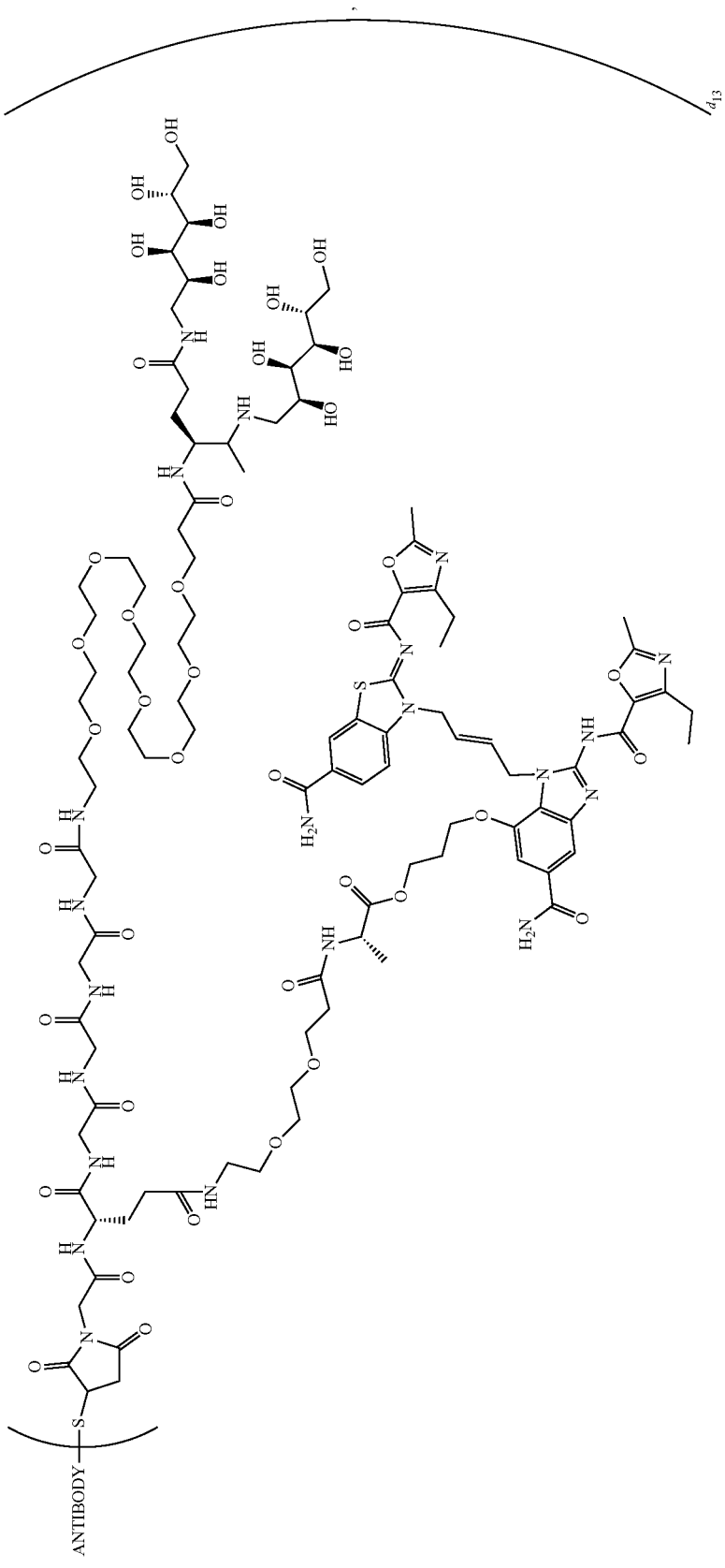

or a pharmaceutically acceptable salt or siomer thereof, wherein $d_{13}$ is about 8.

15. A method of treating a B7-H4 positive disease or disorder in a subject in need thereof, comprising administering to the subject a B7-H4 antibody-drug conjugate of claim 9.

16. The method of claim 15, wherein the B7-H4 positive disease or disorder is a B7-H4 positive cancer.

17. The method of claim 16, wherein the B7-H4 positive cancer is bile duct carcinoma, breast cancer, endometrial cancer, ovarian cancer, non-small cell lung cancer, small cell lung cancer, uterine cancer, thyroid cancer, kidney cancer, head and neck cancer, gastric cancer, melanoma, bile duct carcinoma, cholangial carcinoma, pancreatic cancer, colon cancer or bladder cancer.

18. The method of claim 17, wherein the B7-H4 positive cancer is breast cancer, endometrial cancer, ovarian cancer, or cholangial carcinoma.

19. The method of claim 15, further comprising administration of a therapeutic agent to the subject.

20. A pharmaceutical composition comprising the B7-H4 antibody-drug conjugate of claim 9 and a pharmaceutically acceptable carrier.

21. The B7-H4 antibody-drug conjugate of claim 11, wherein the B7-H4 antibody-drug conjugate is:

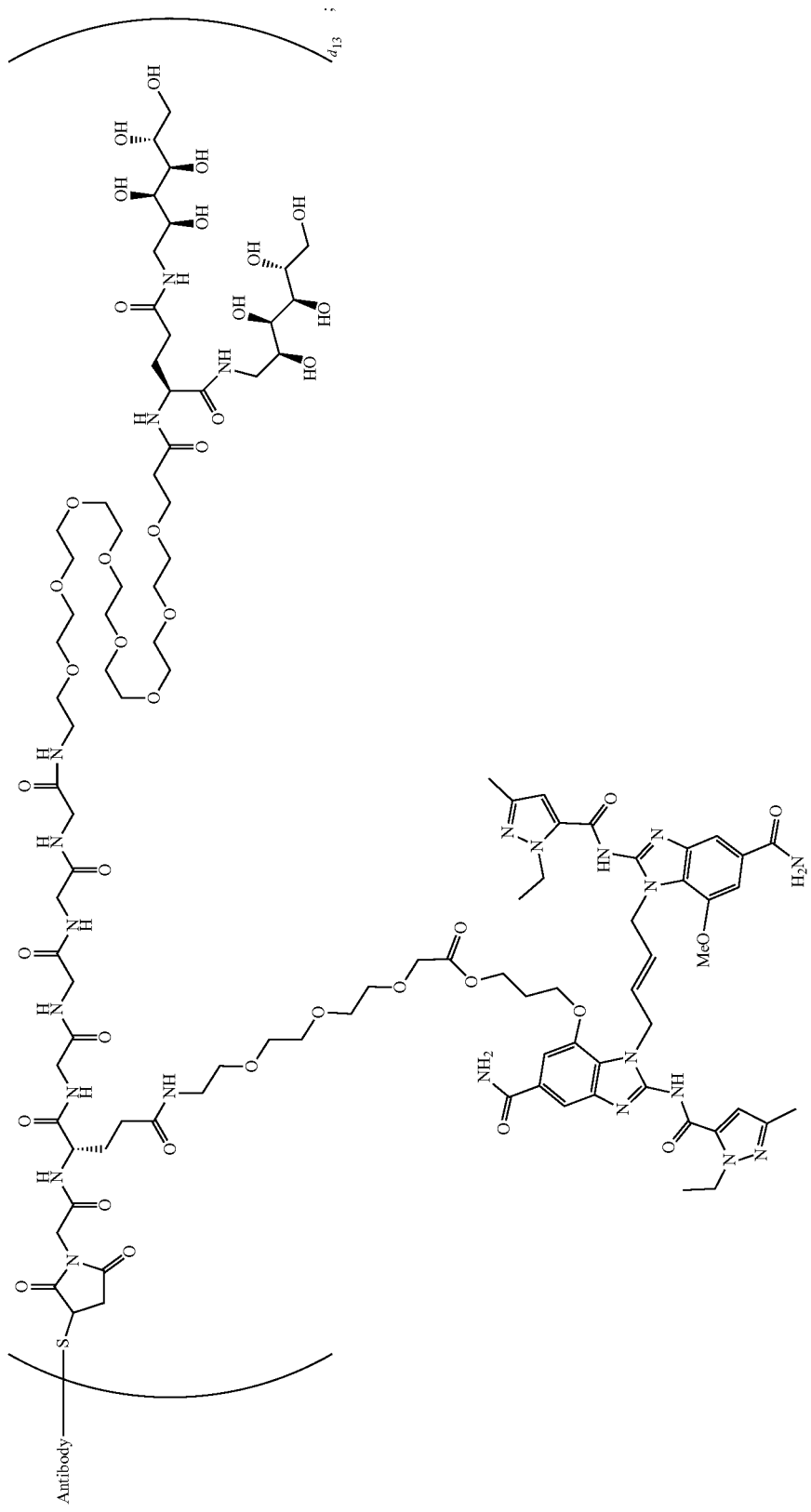

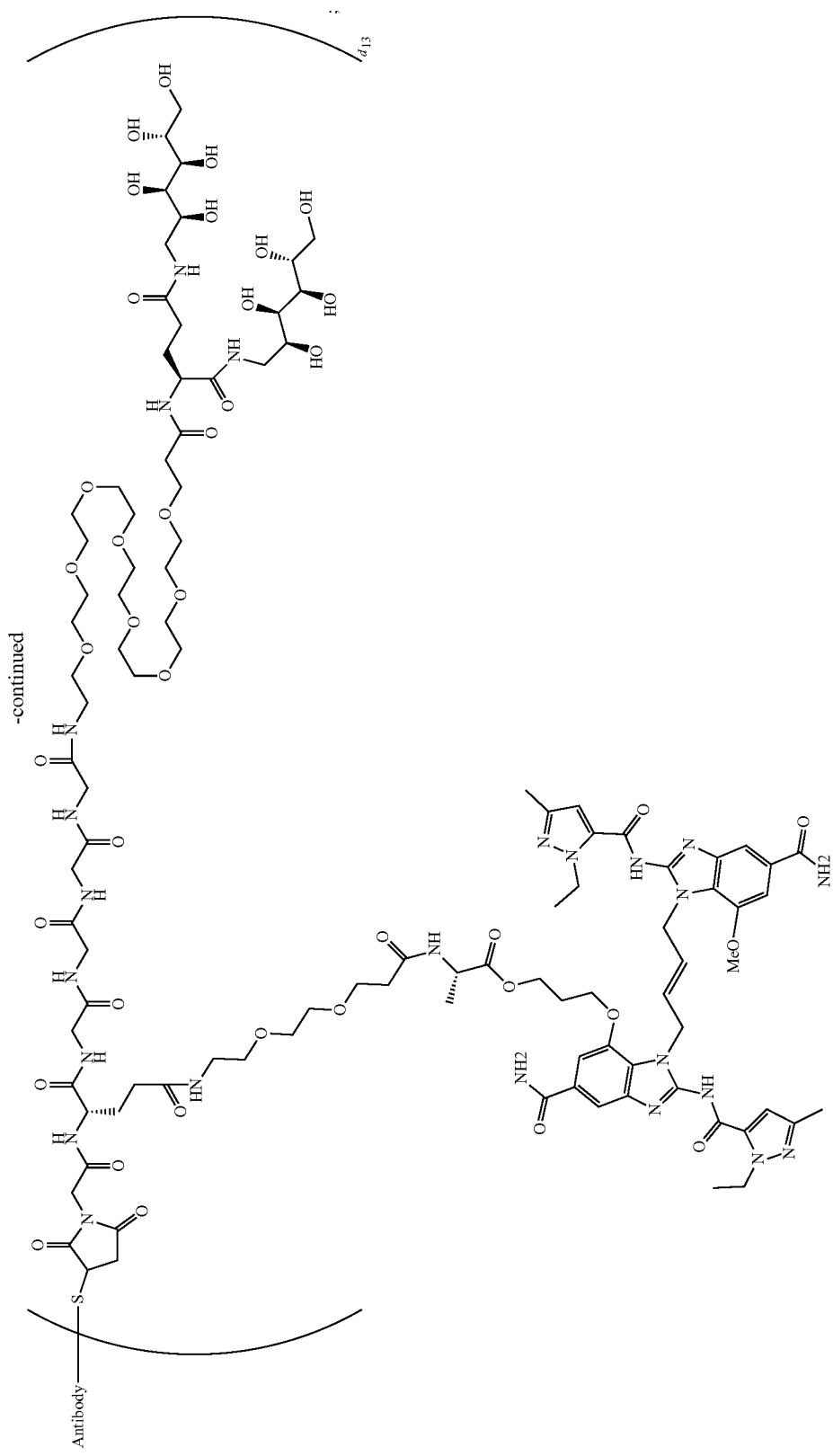

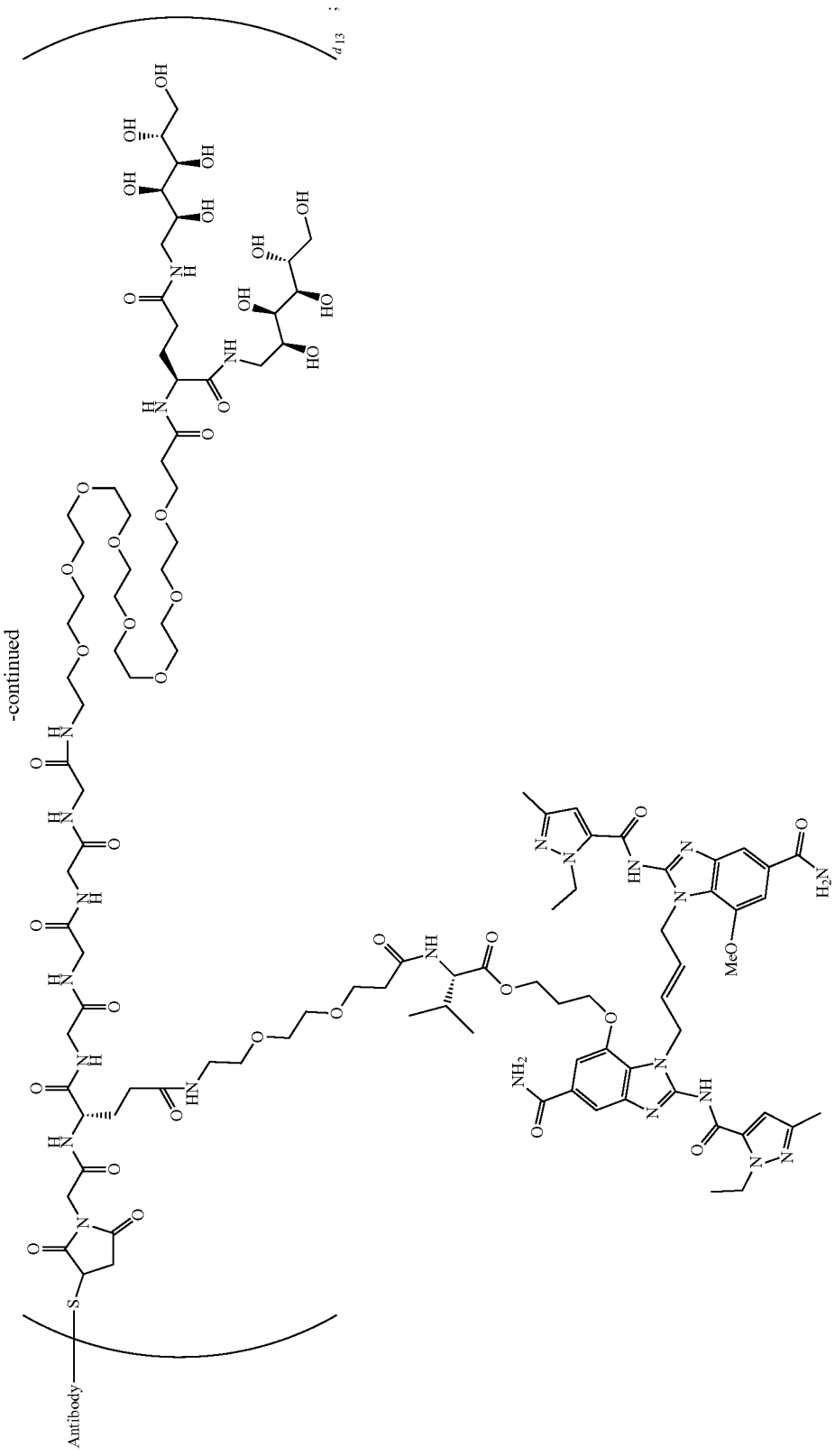

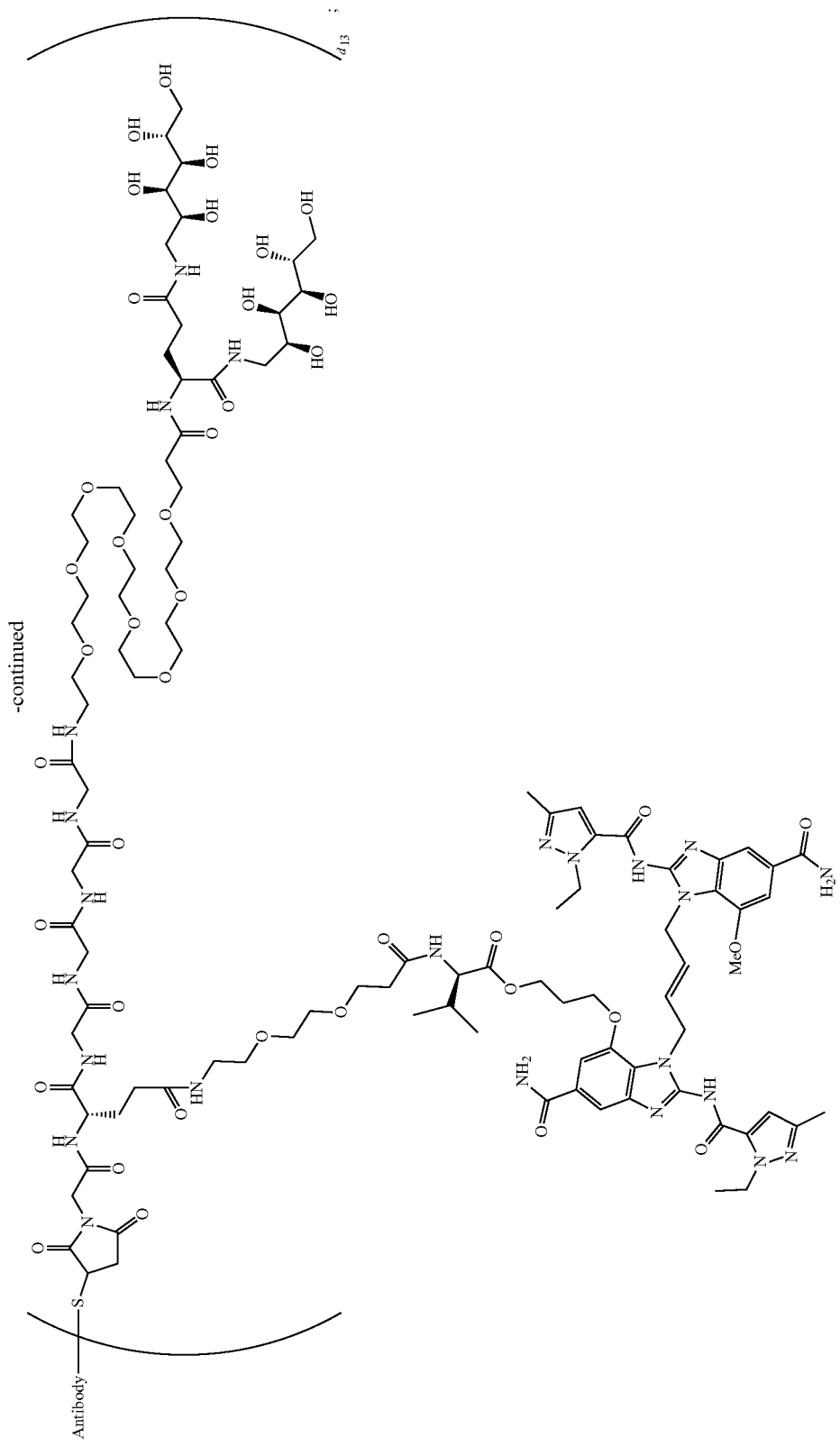

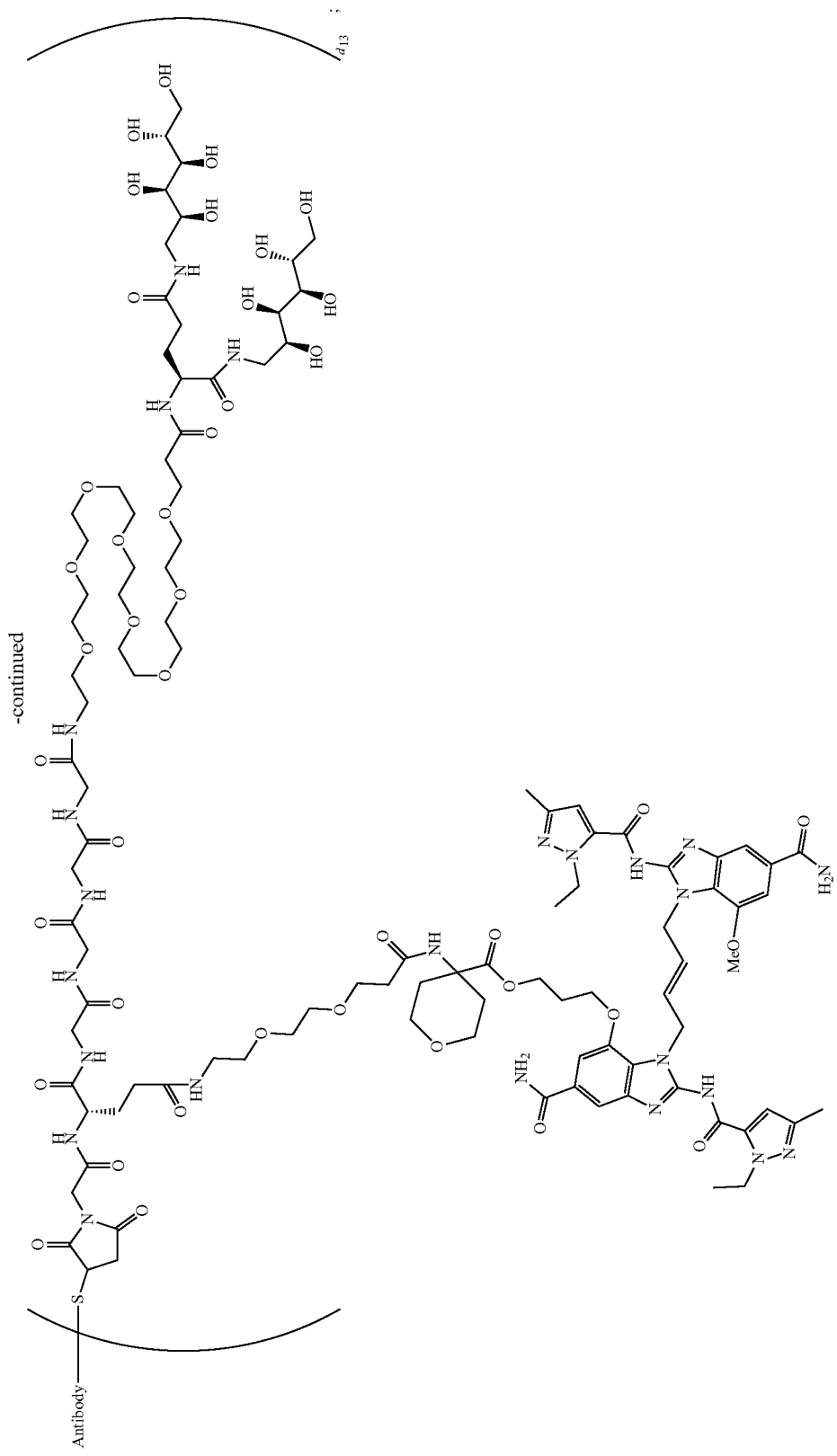

-continued
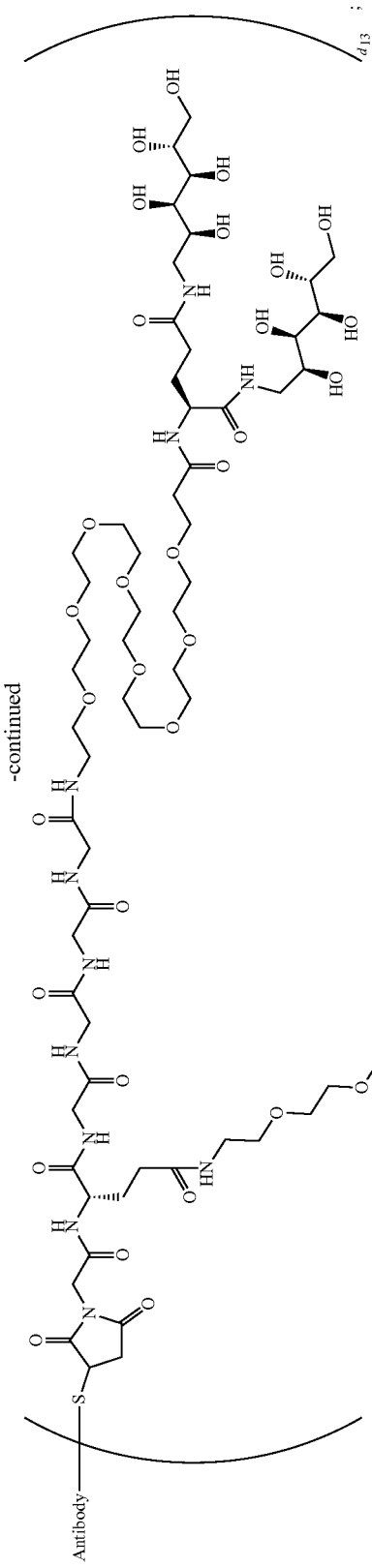
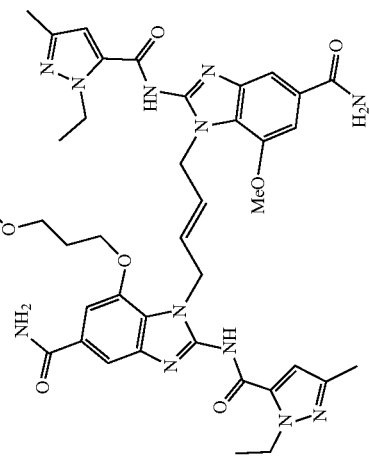

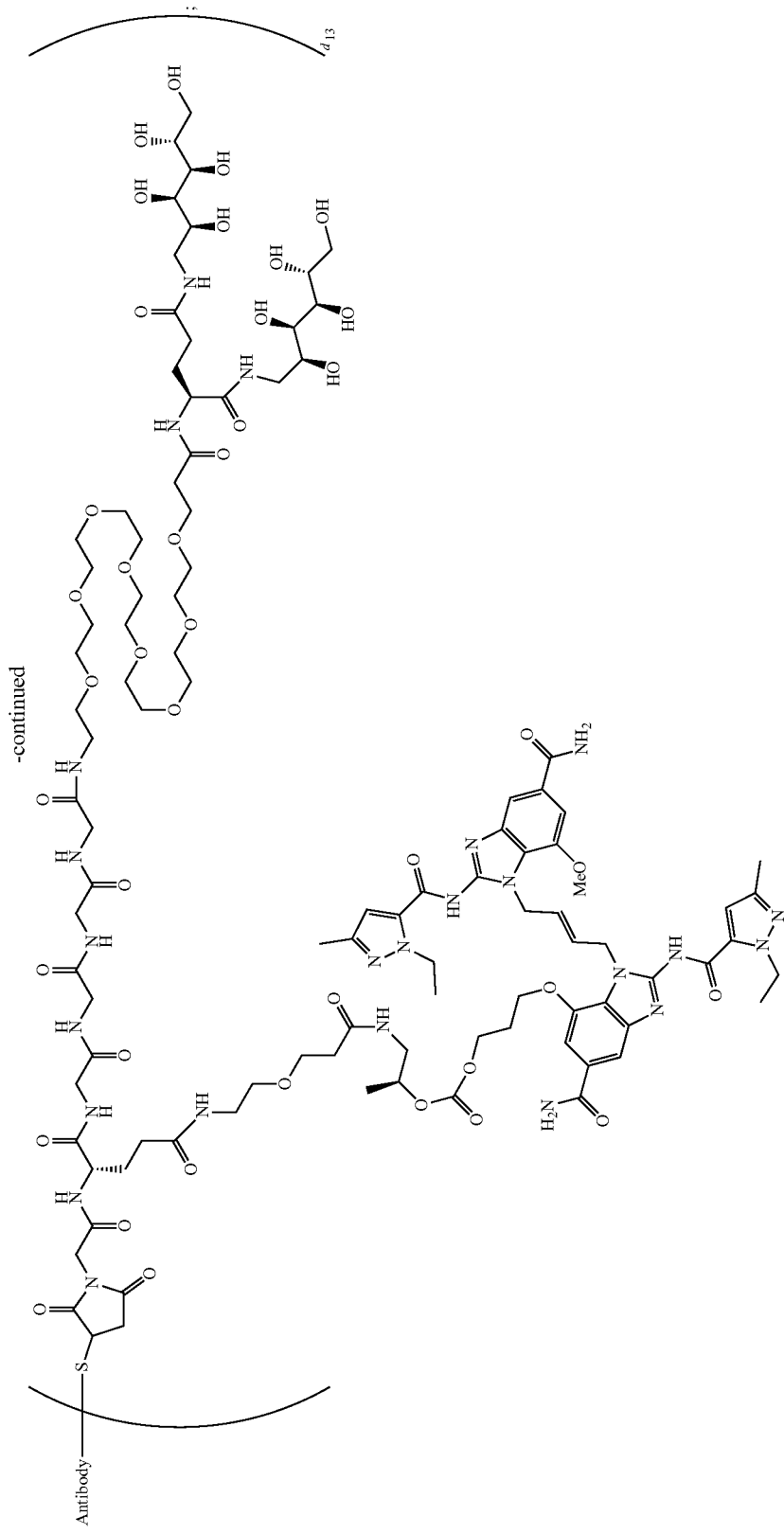

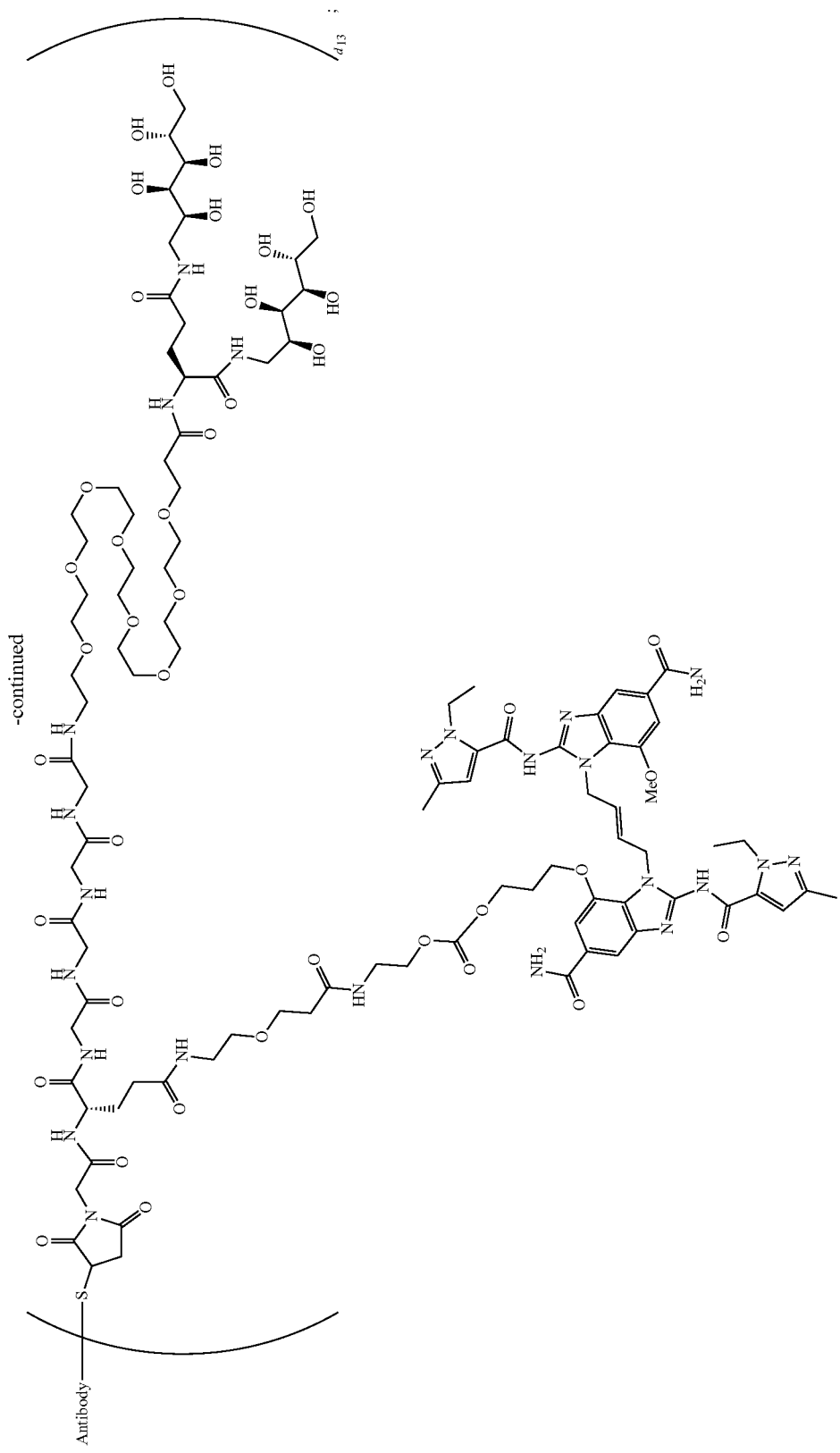

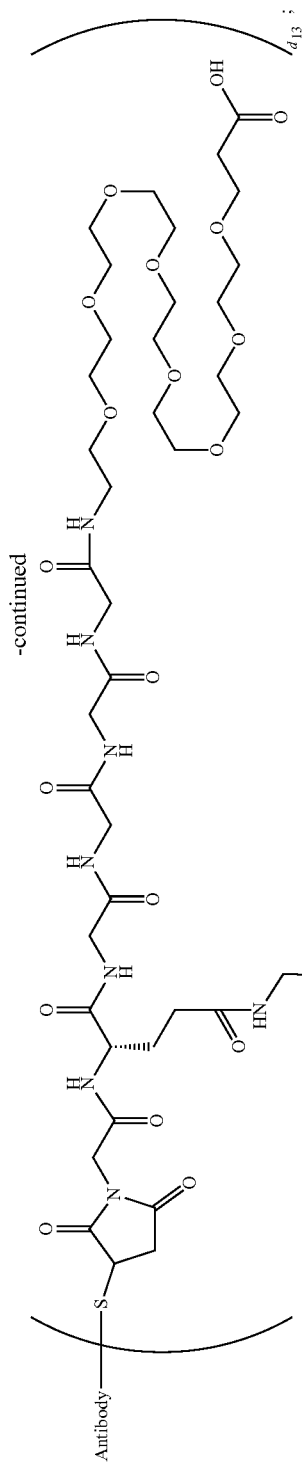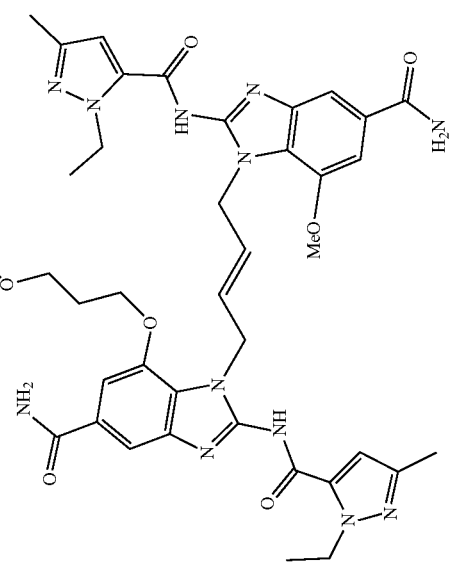

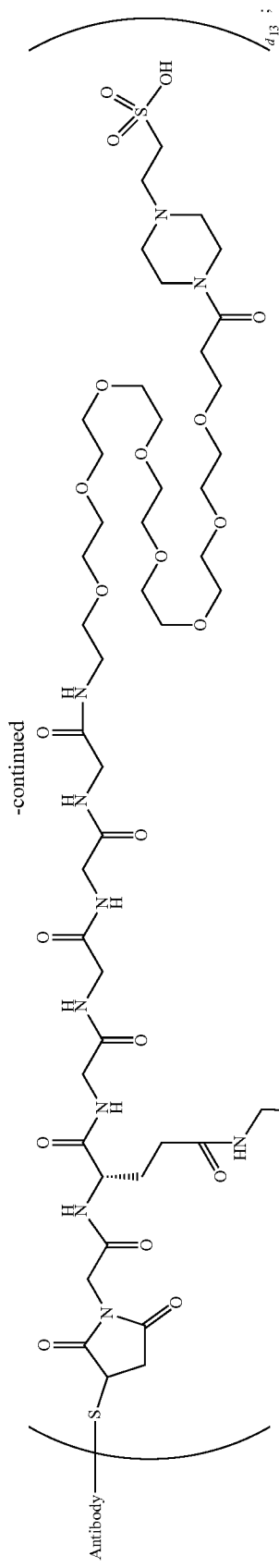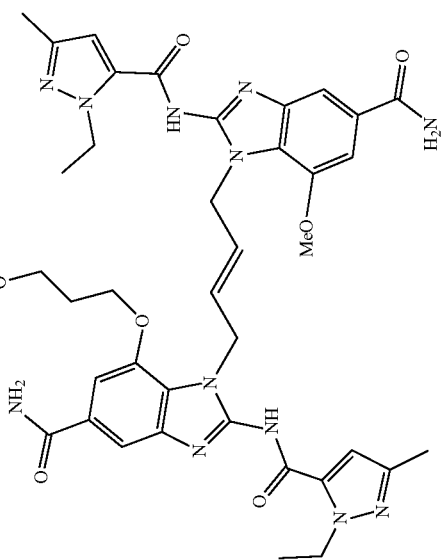

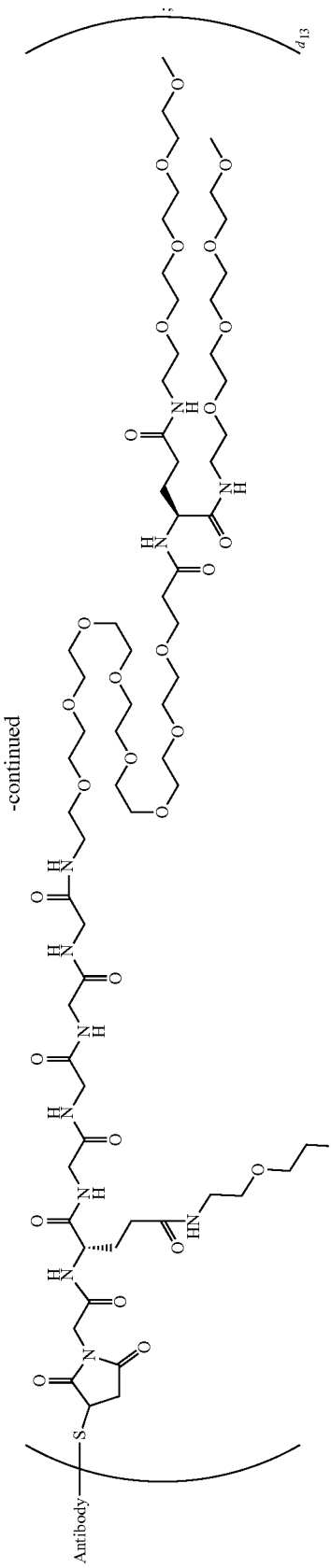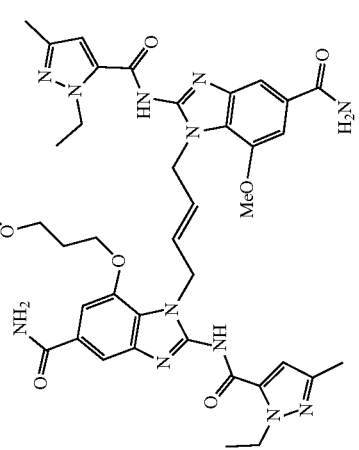

-continued
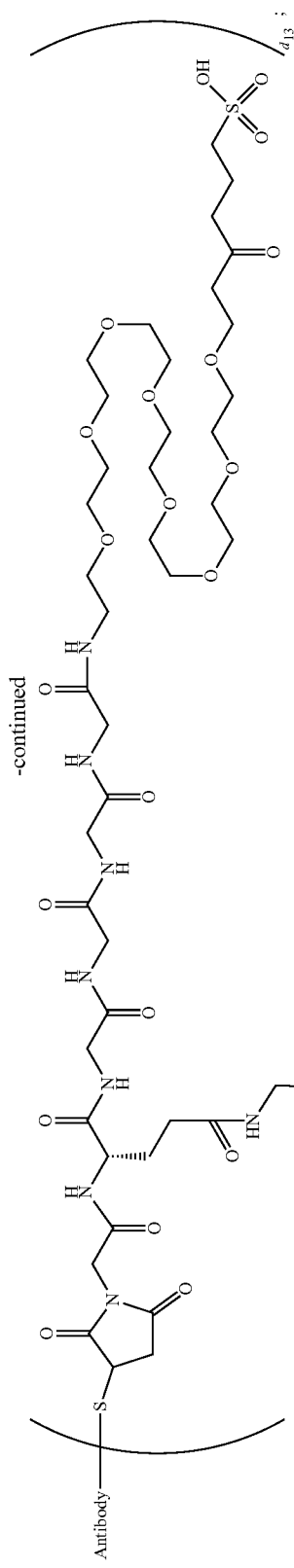
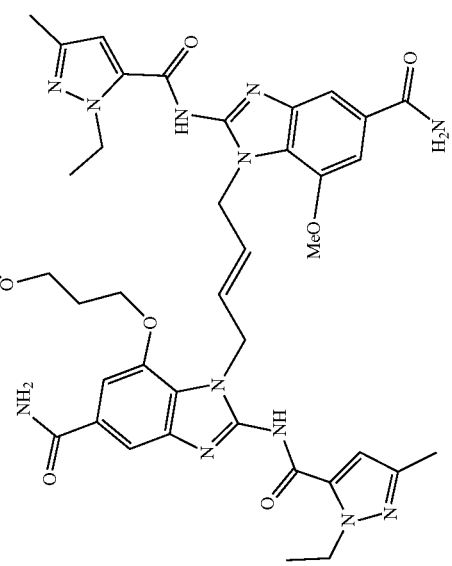

-continued
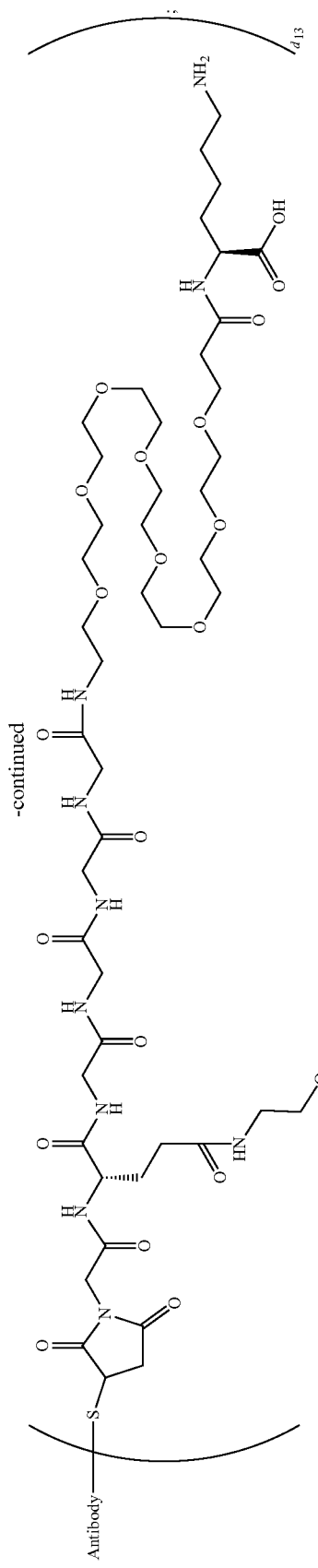
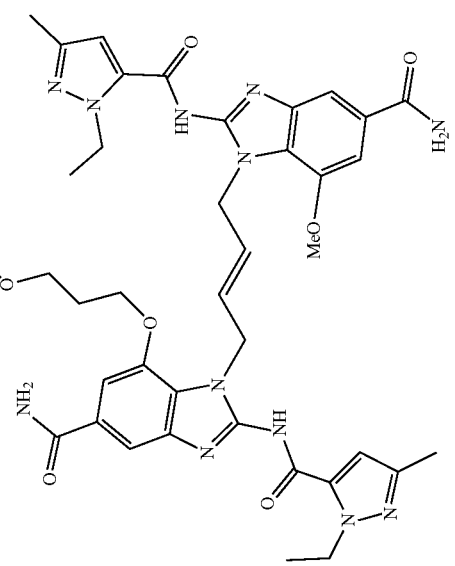

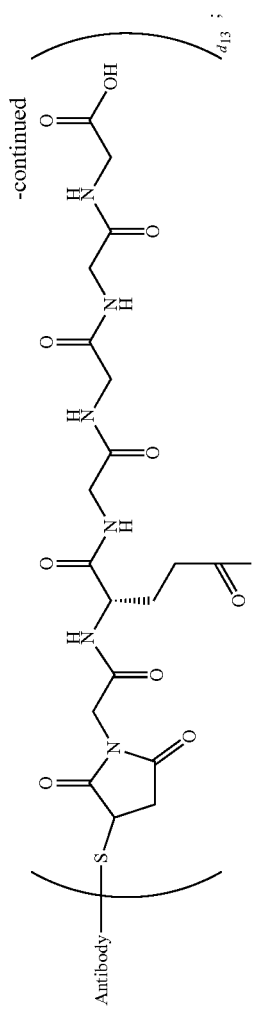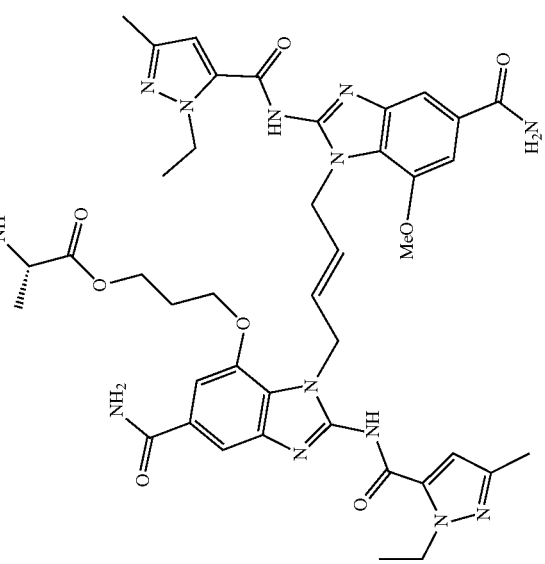

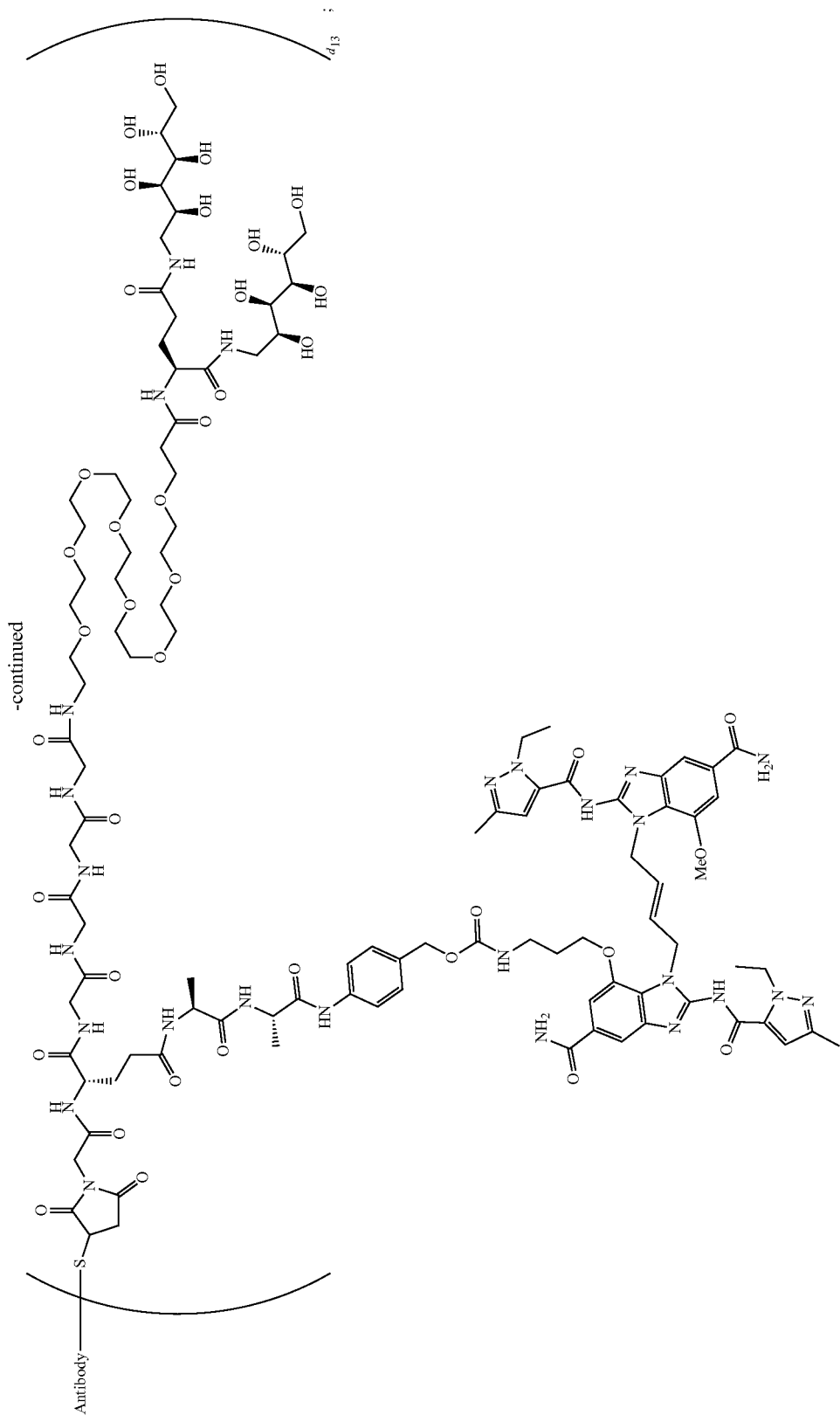

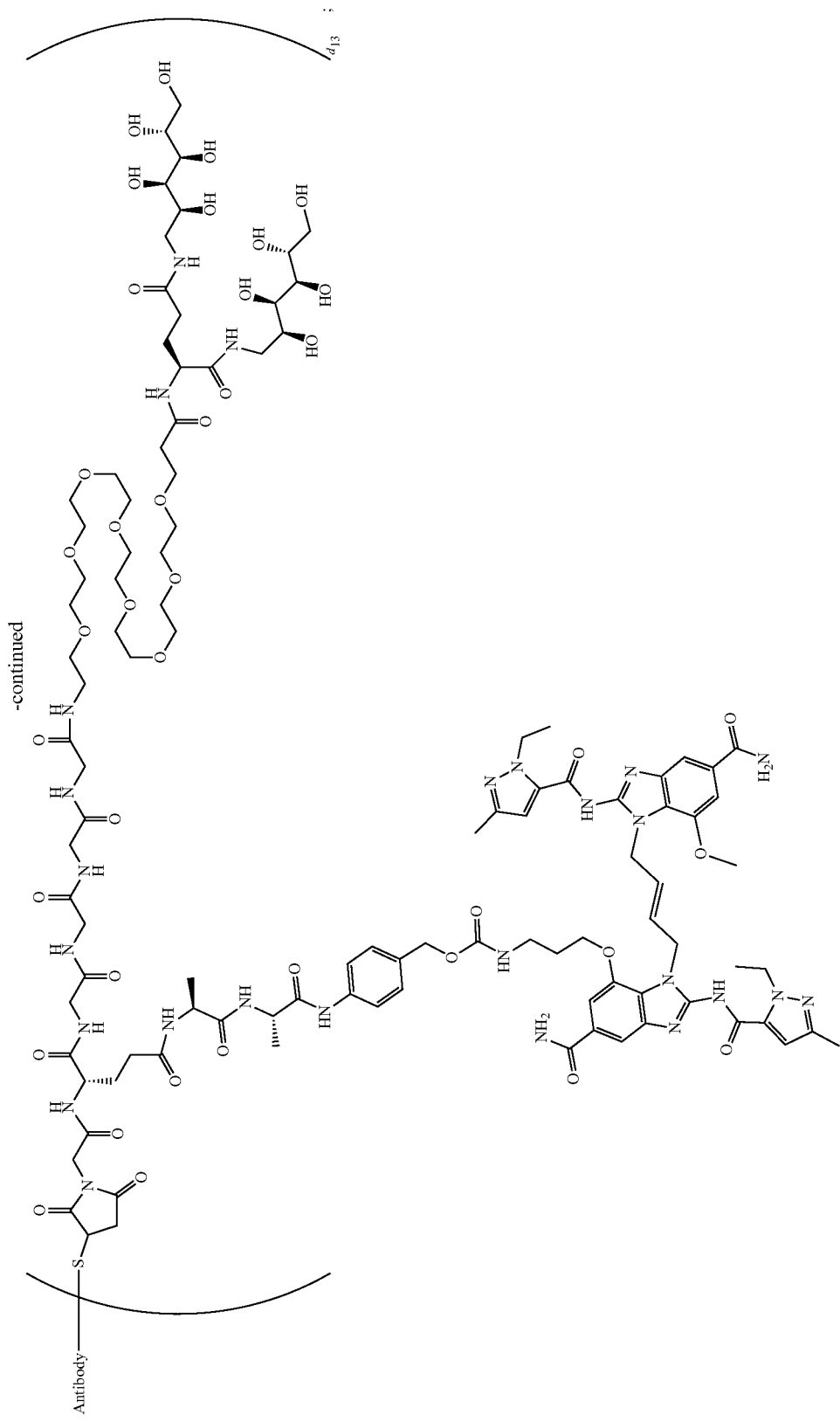

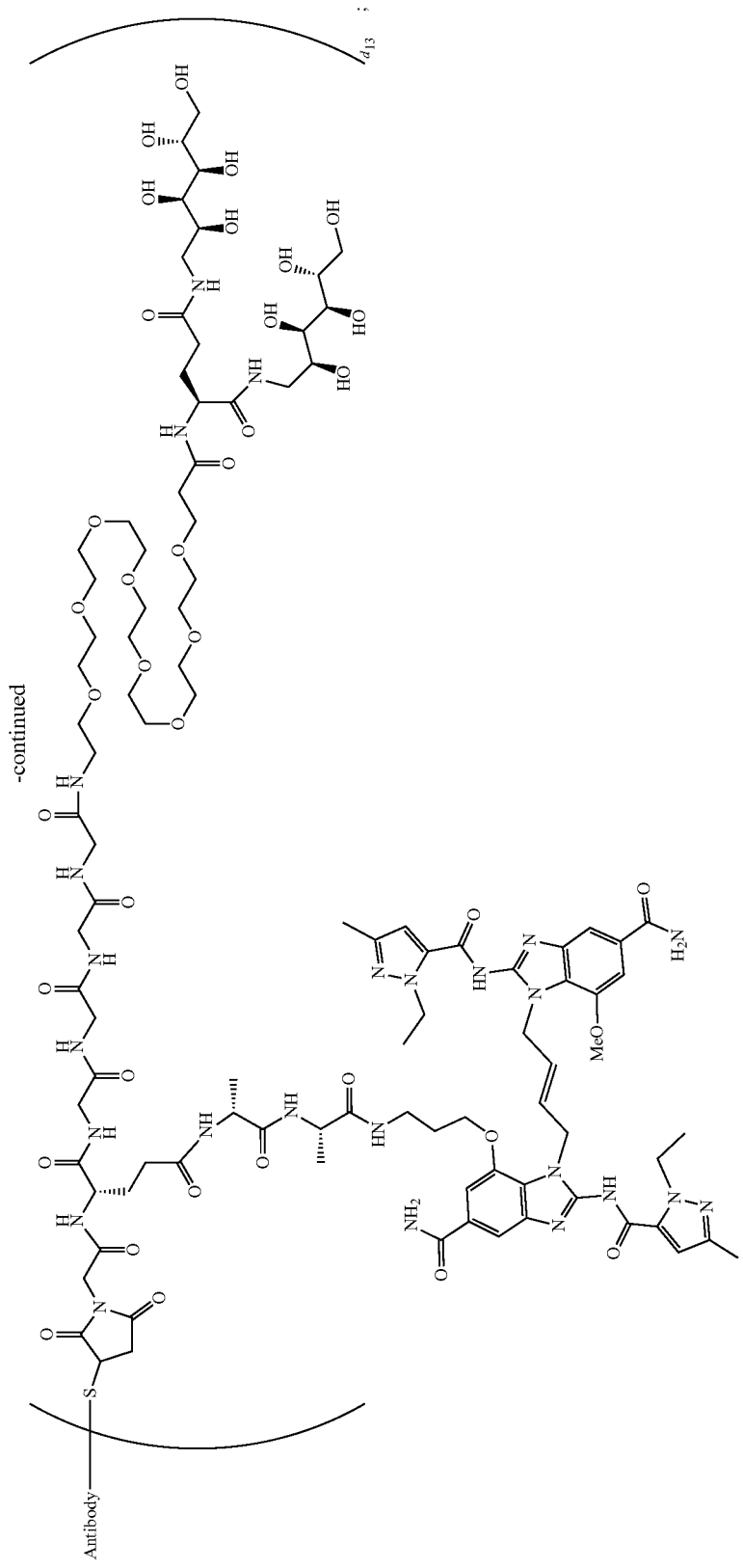

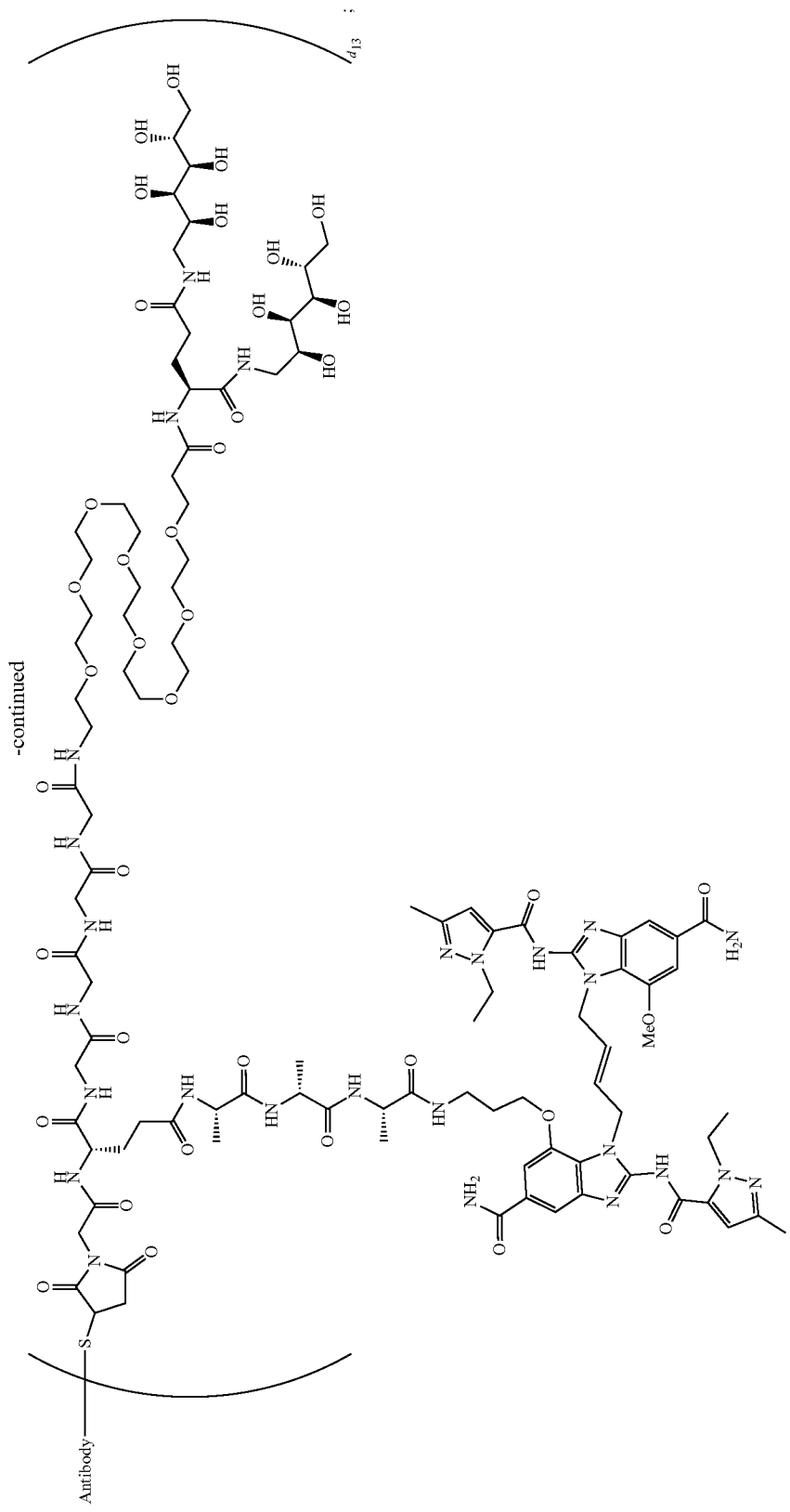

-continued

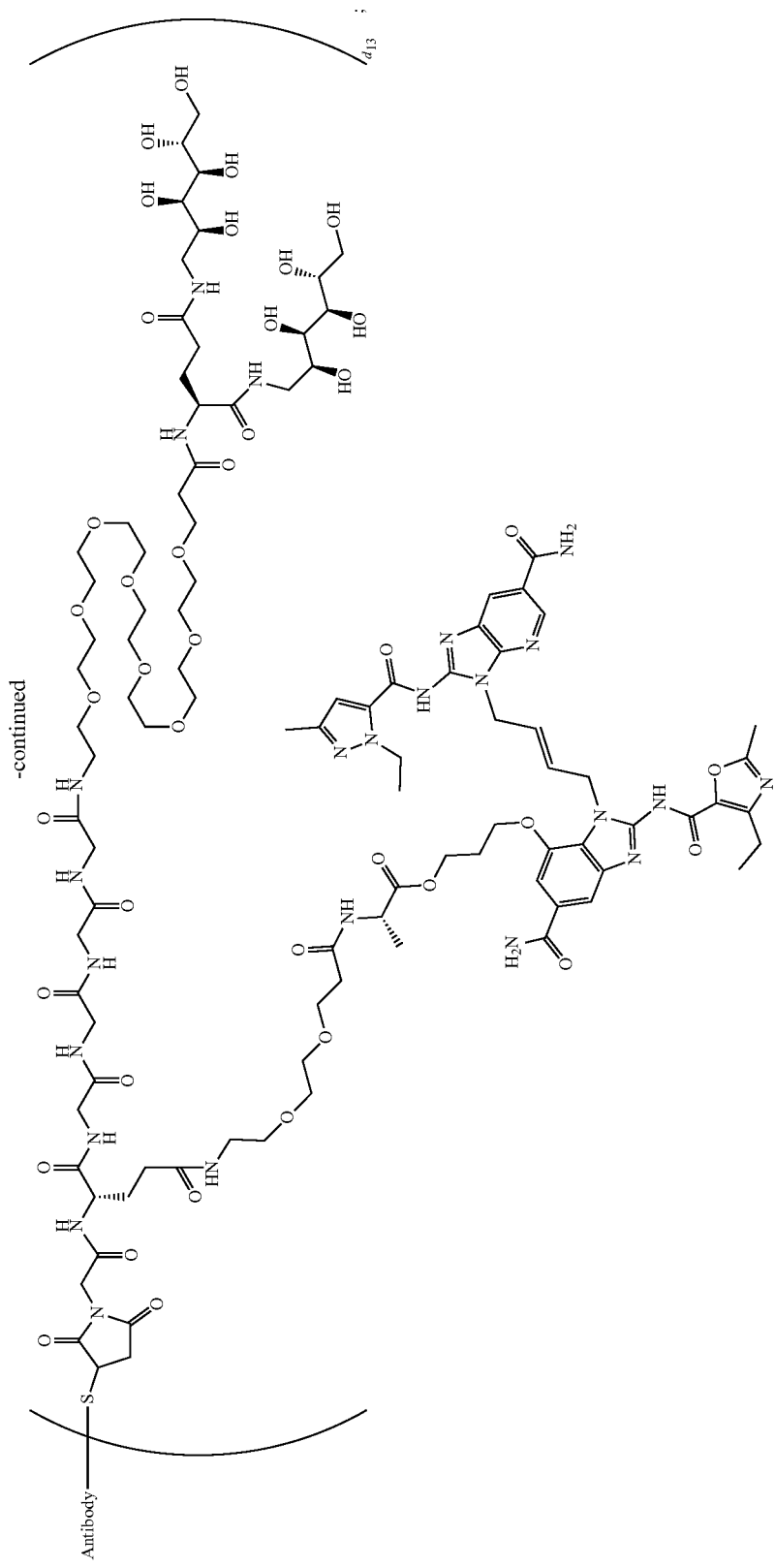

-continued
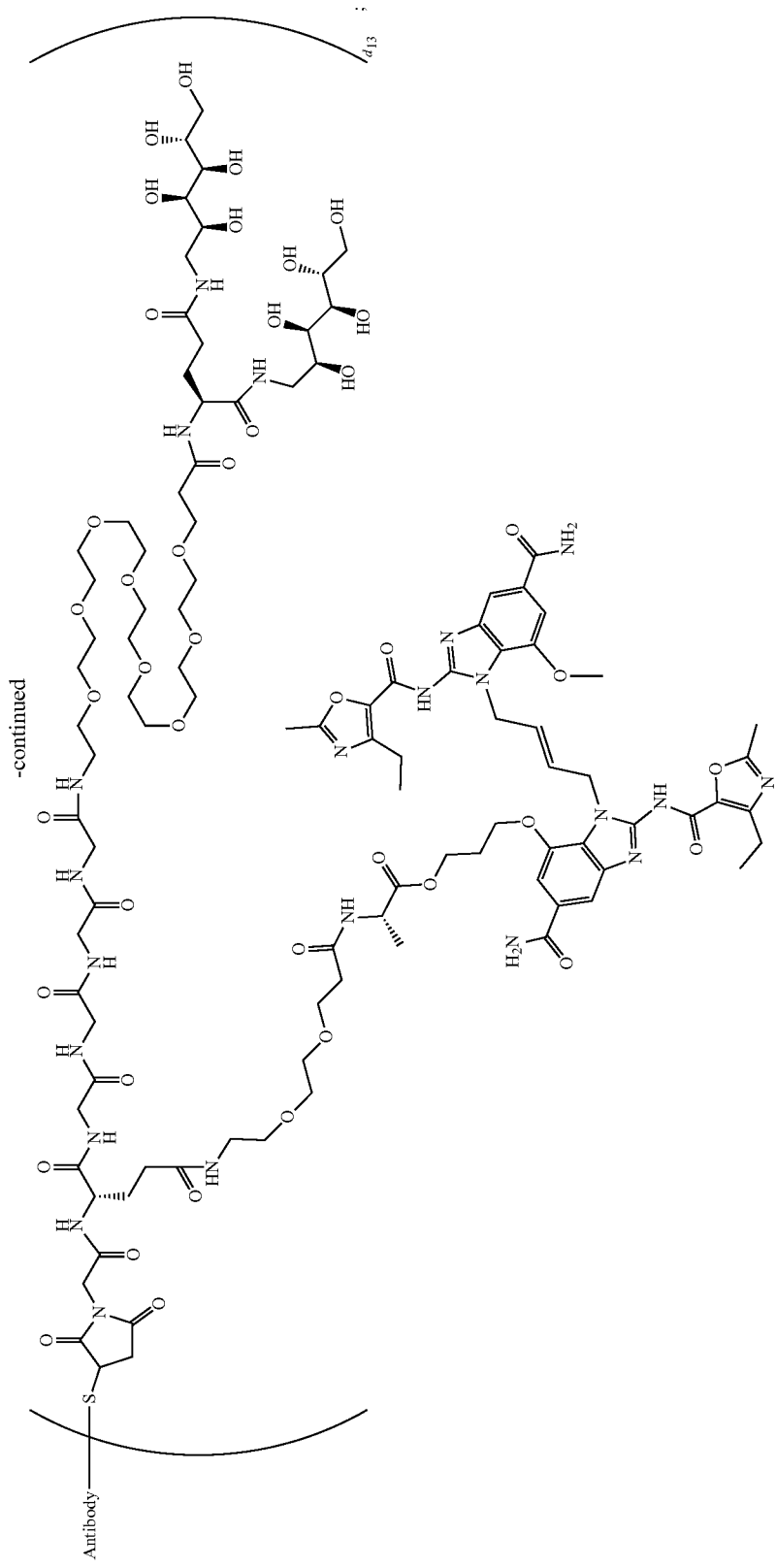

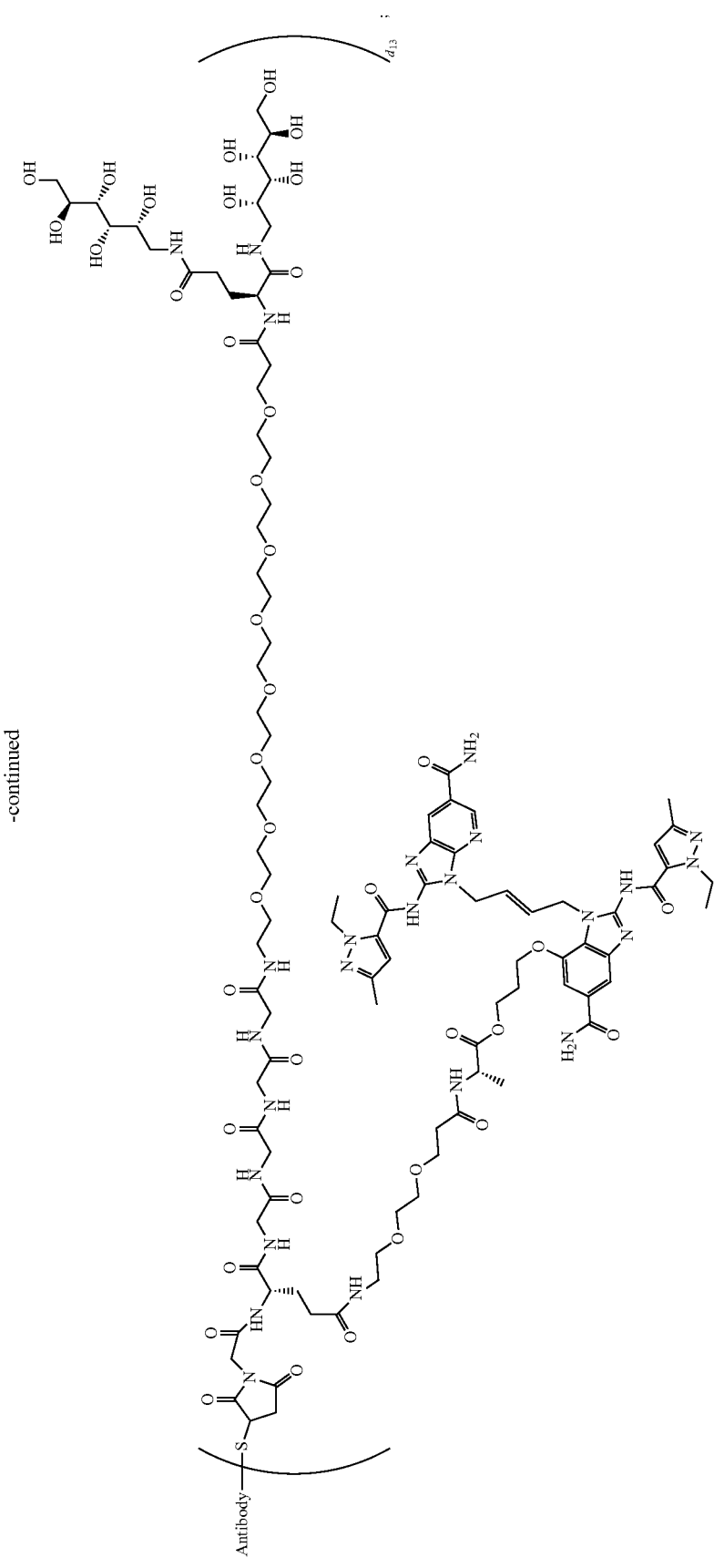

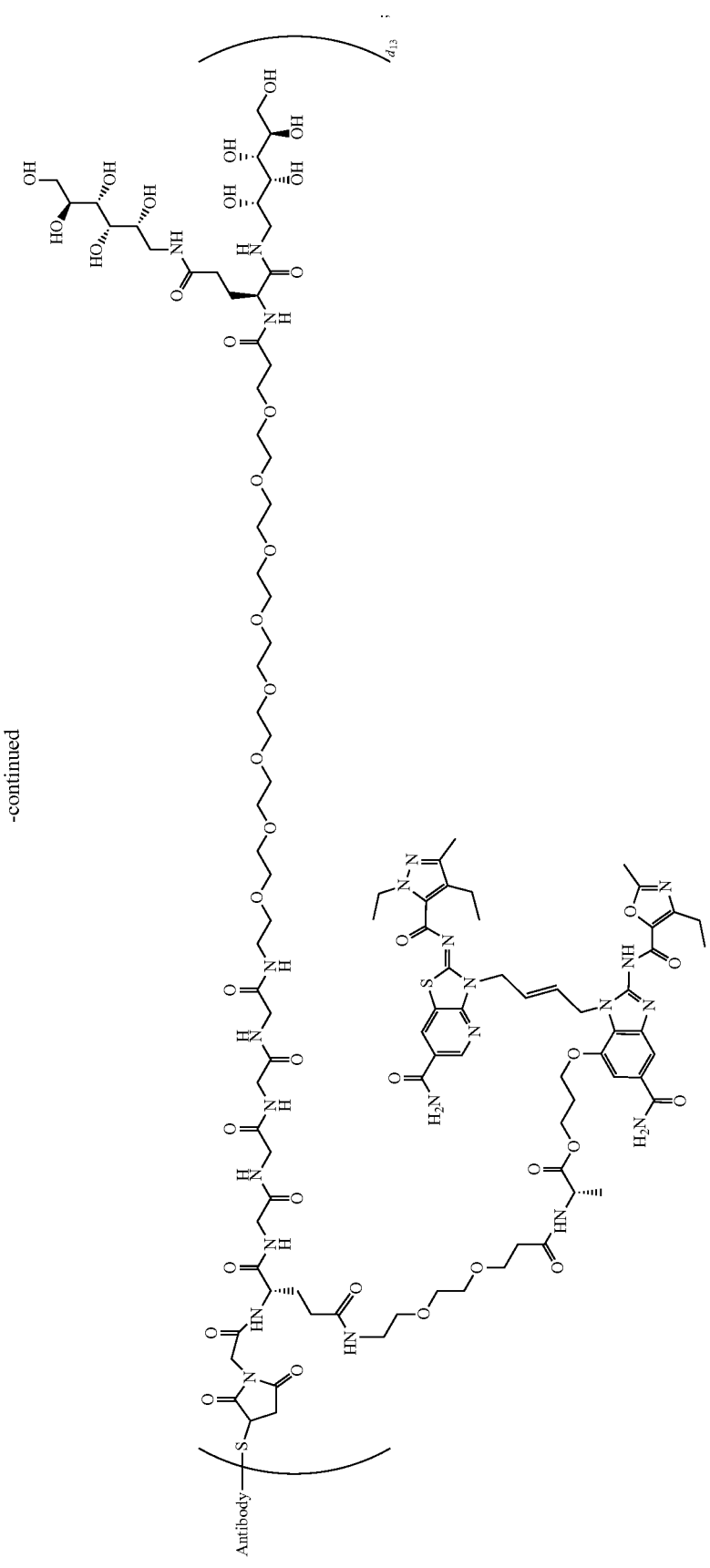

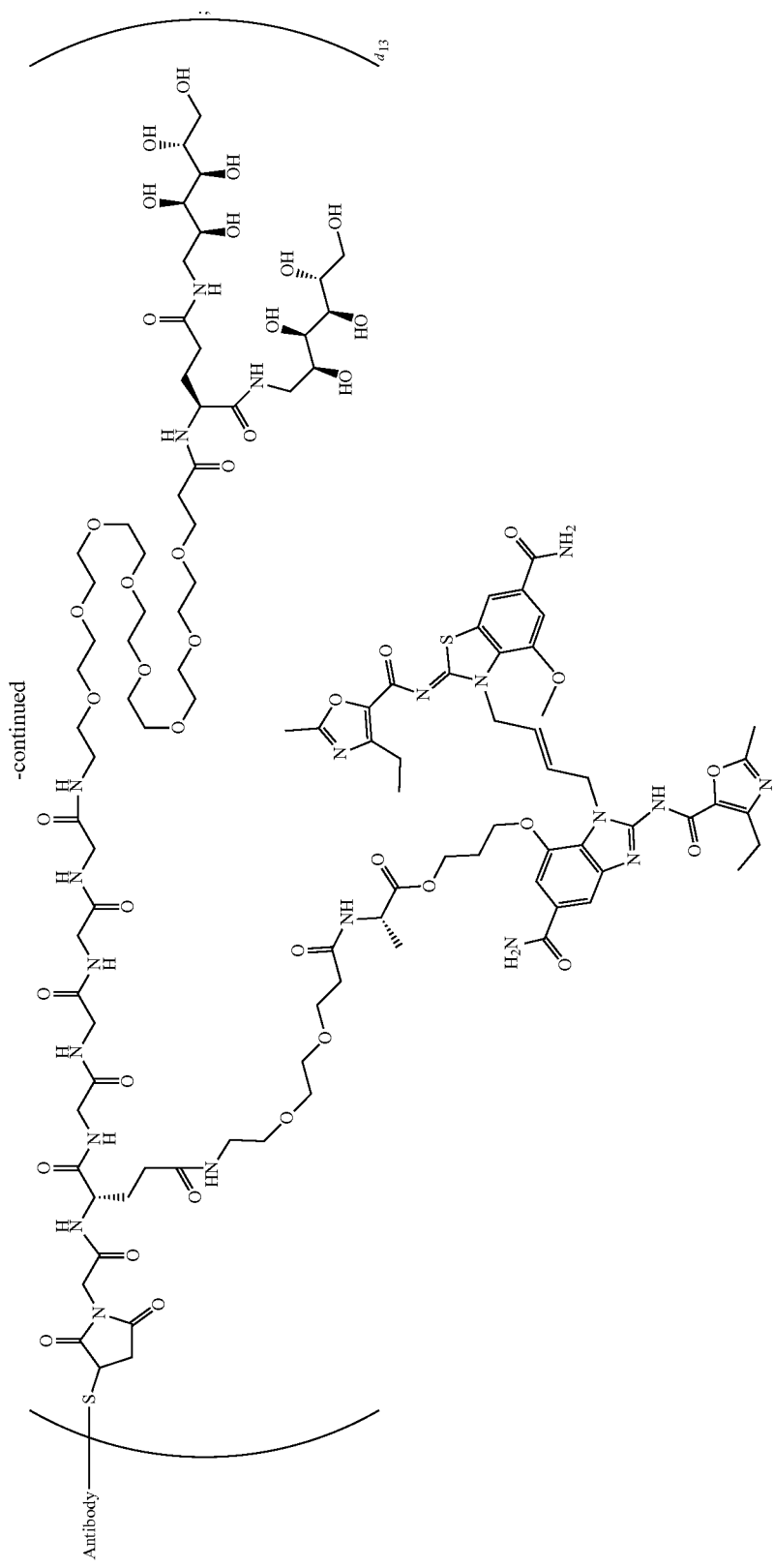

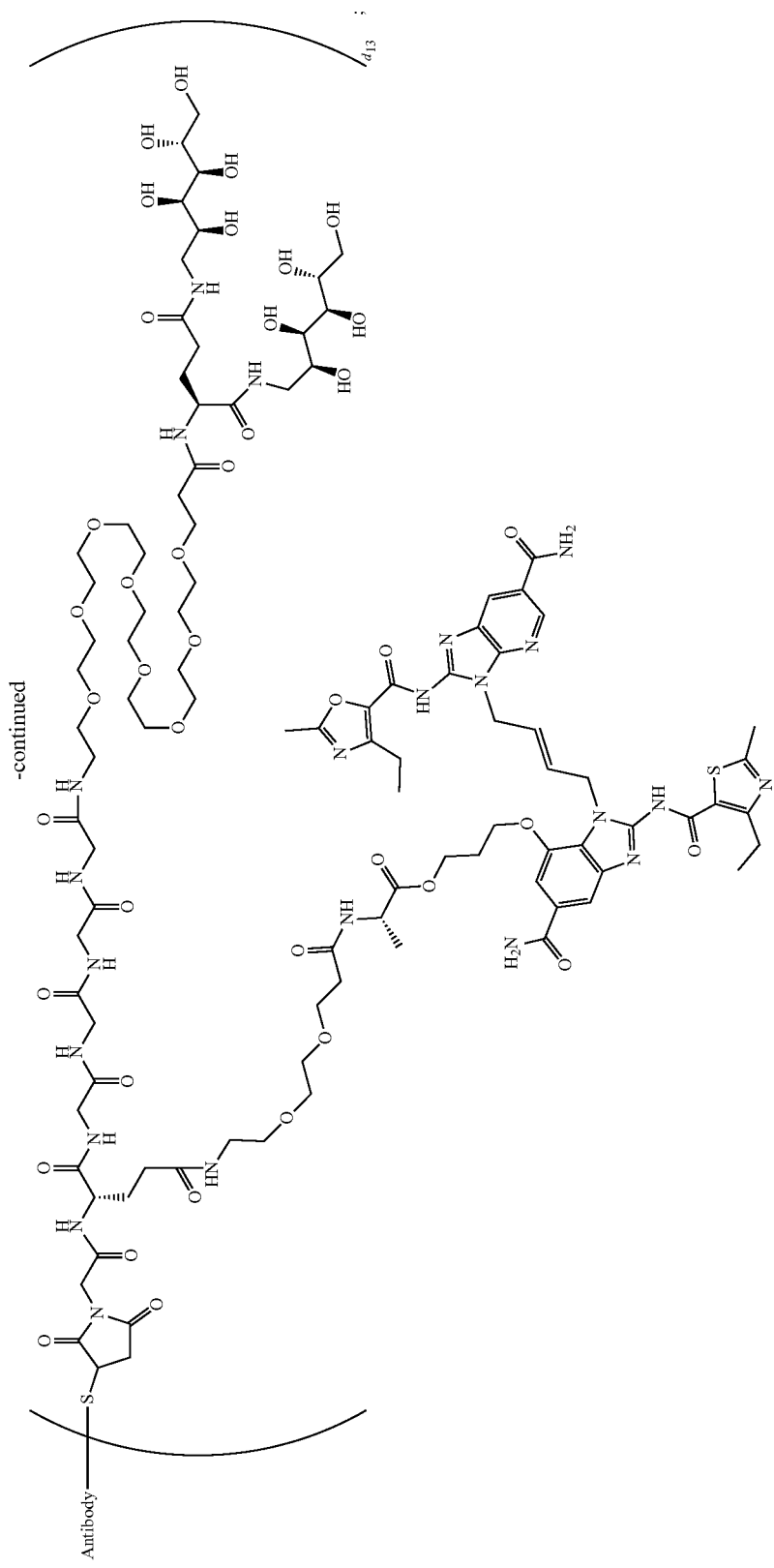

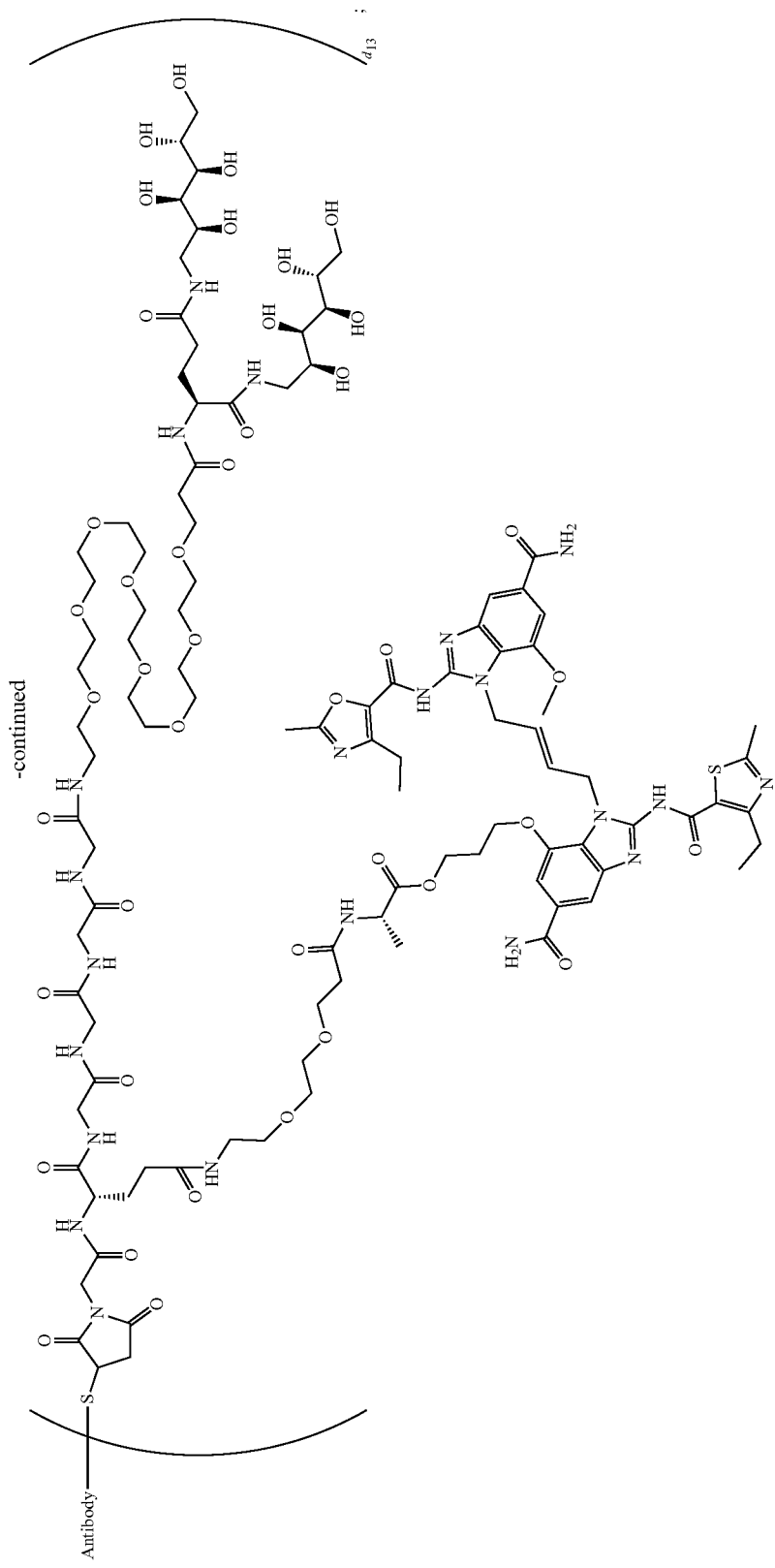

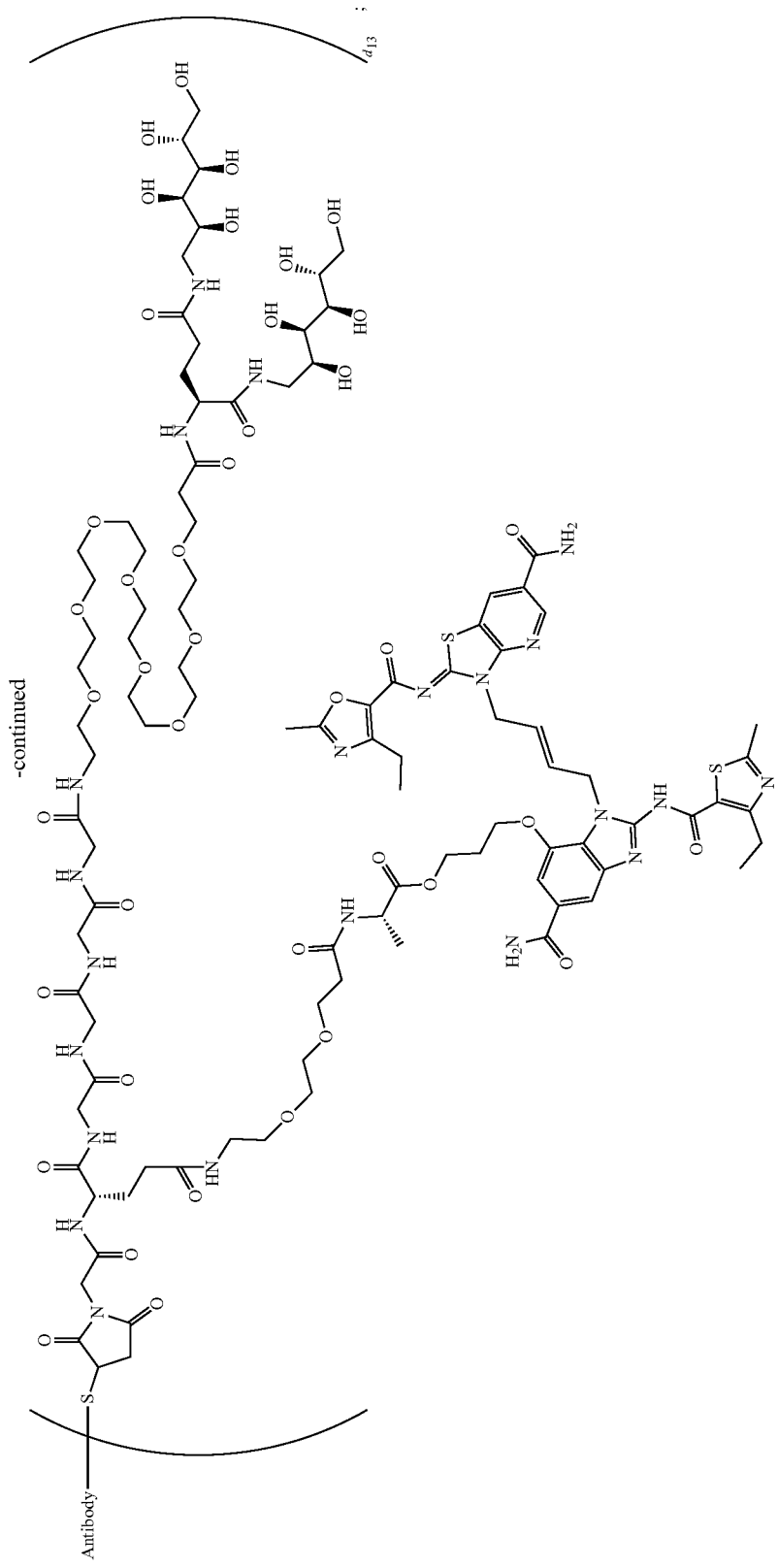

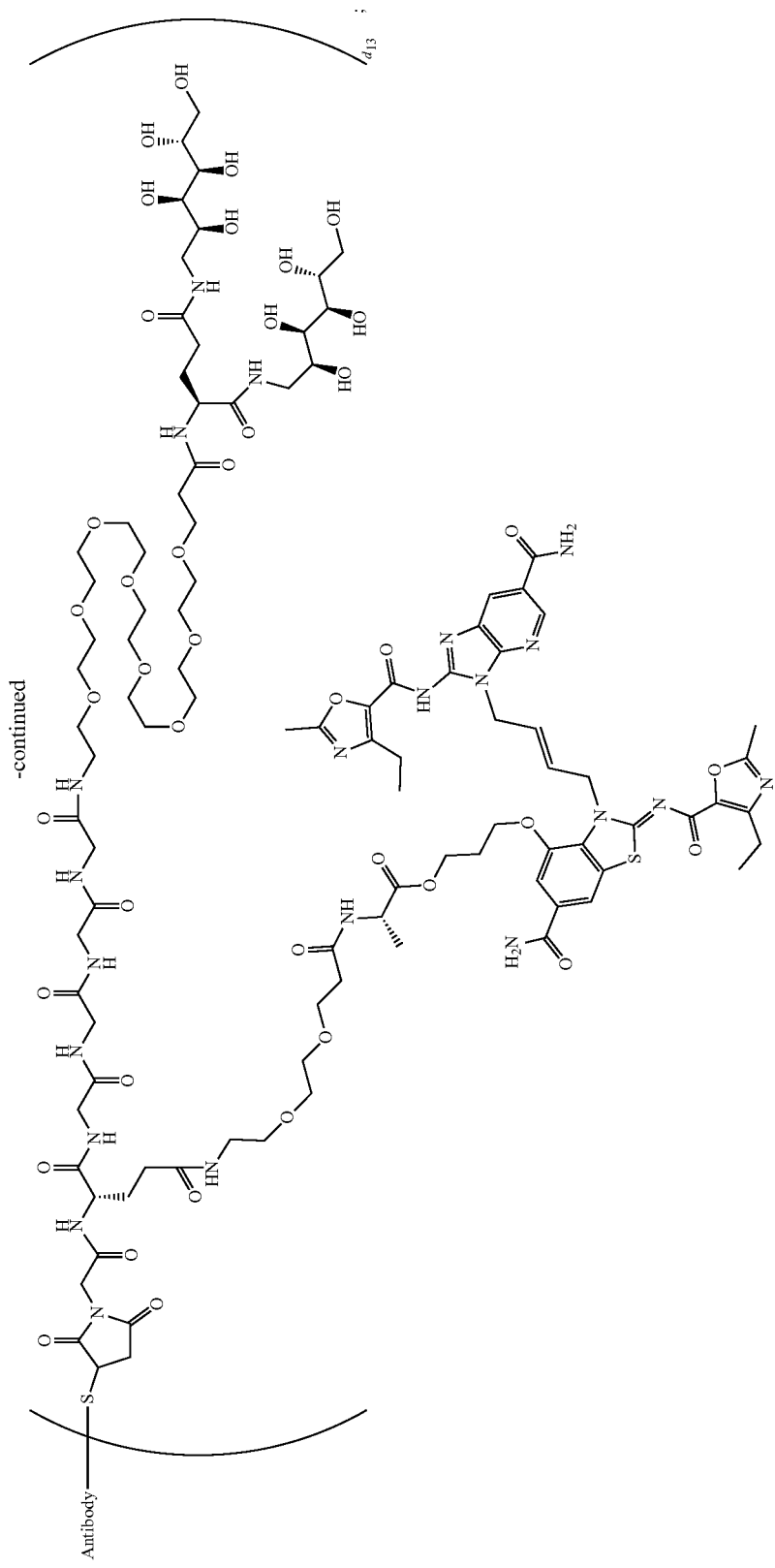

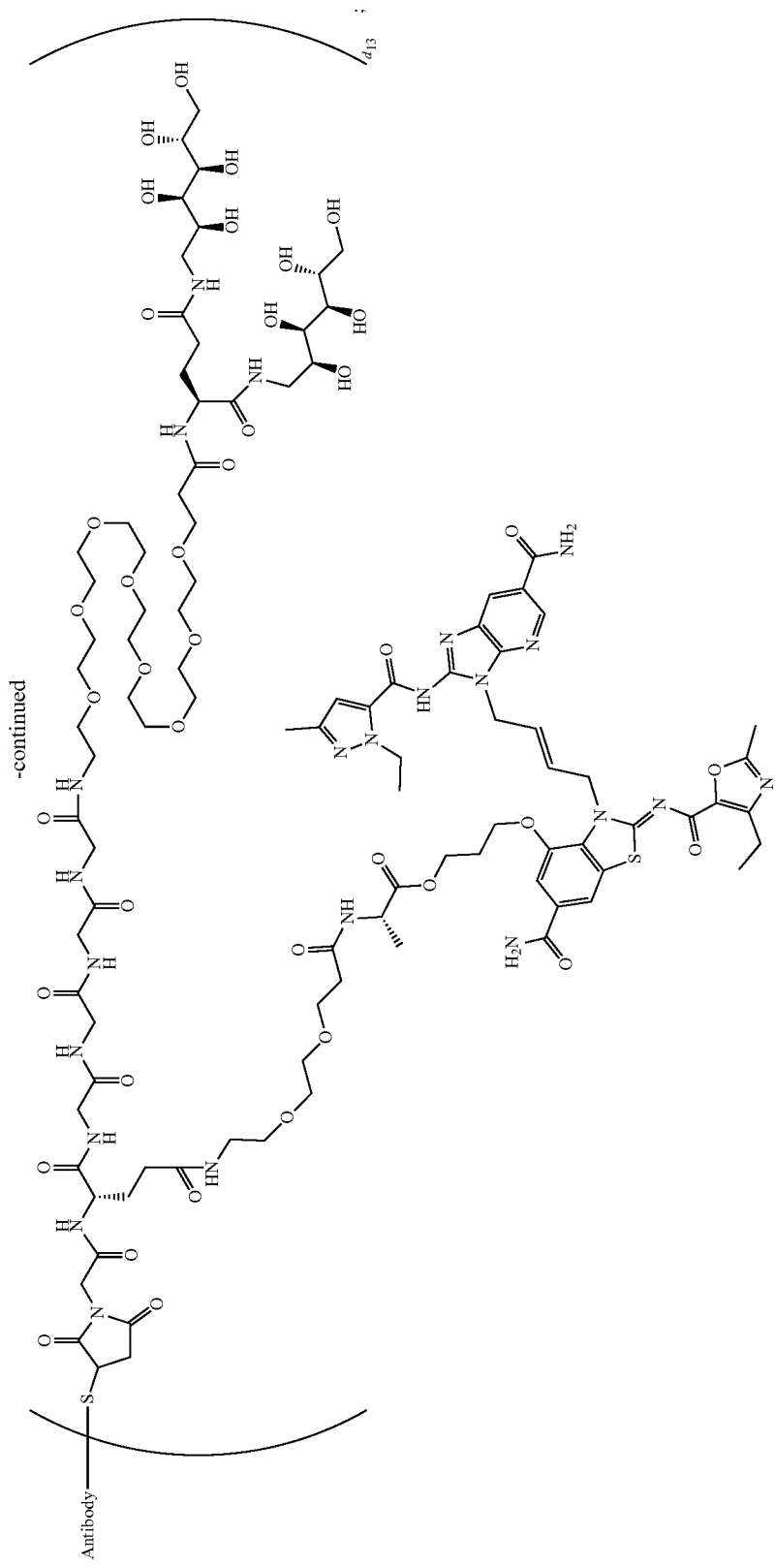

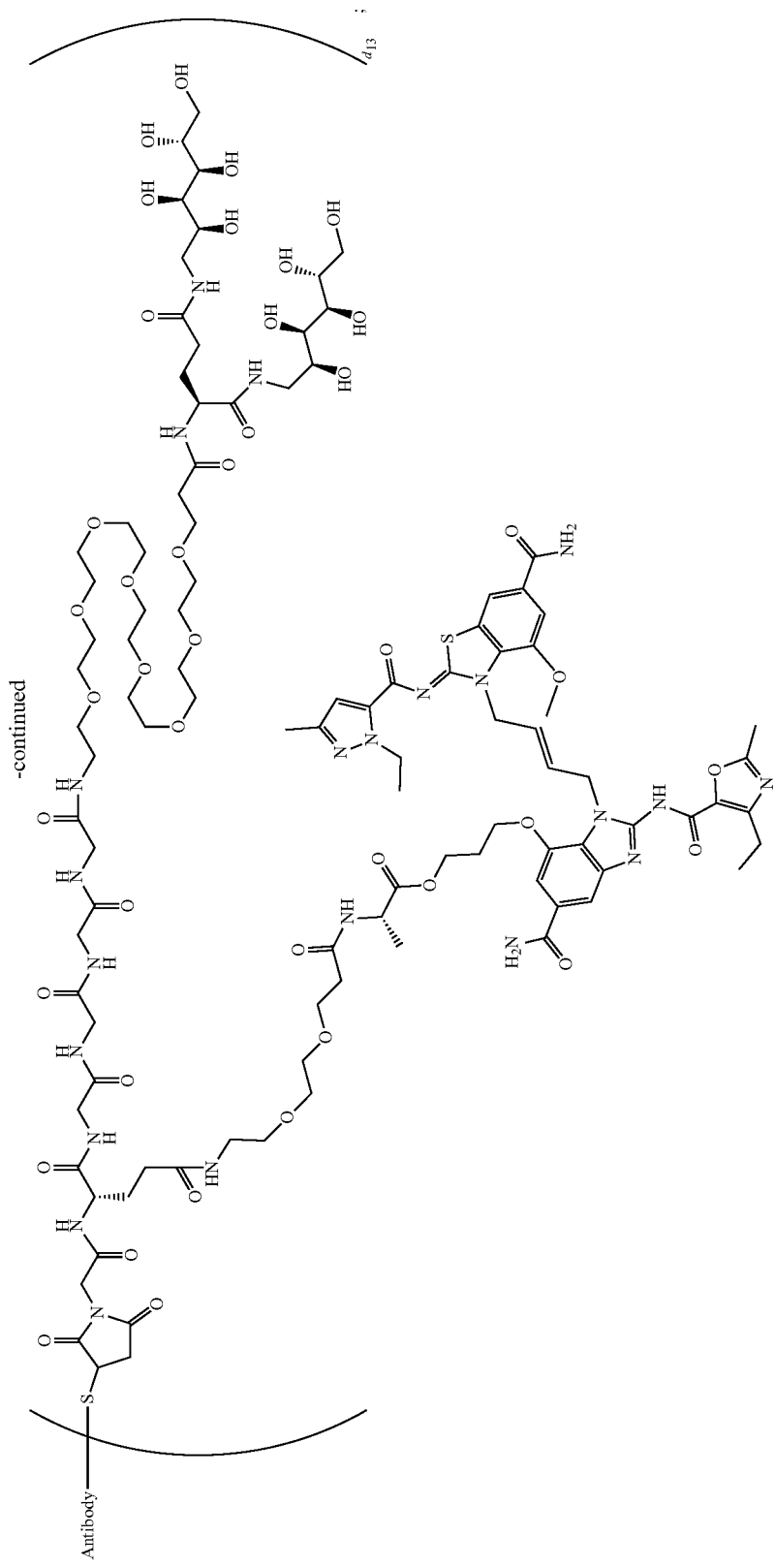

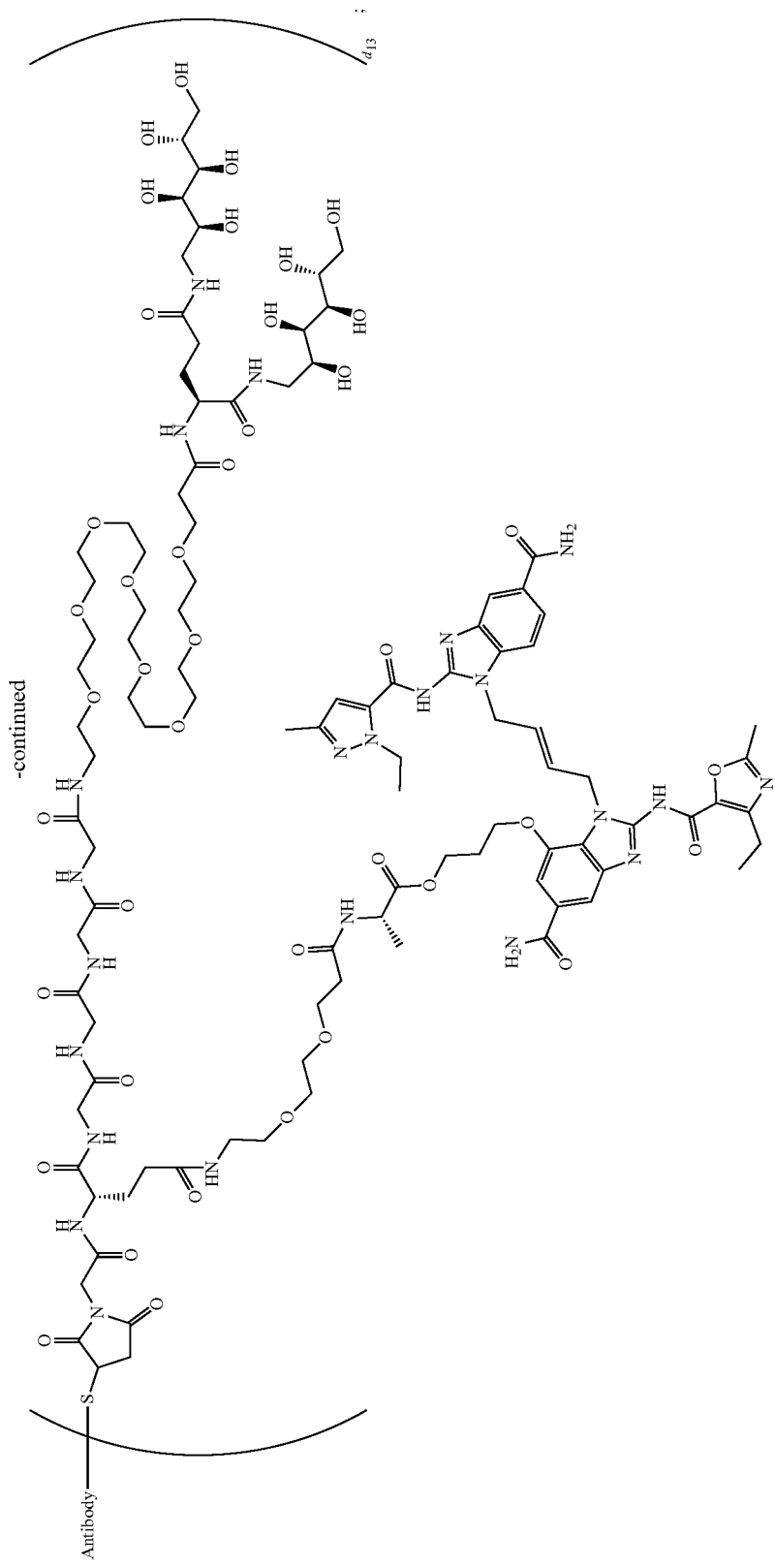

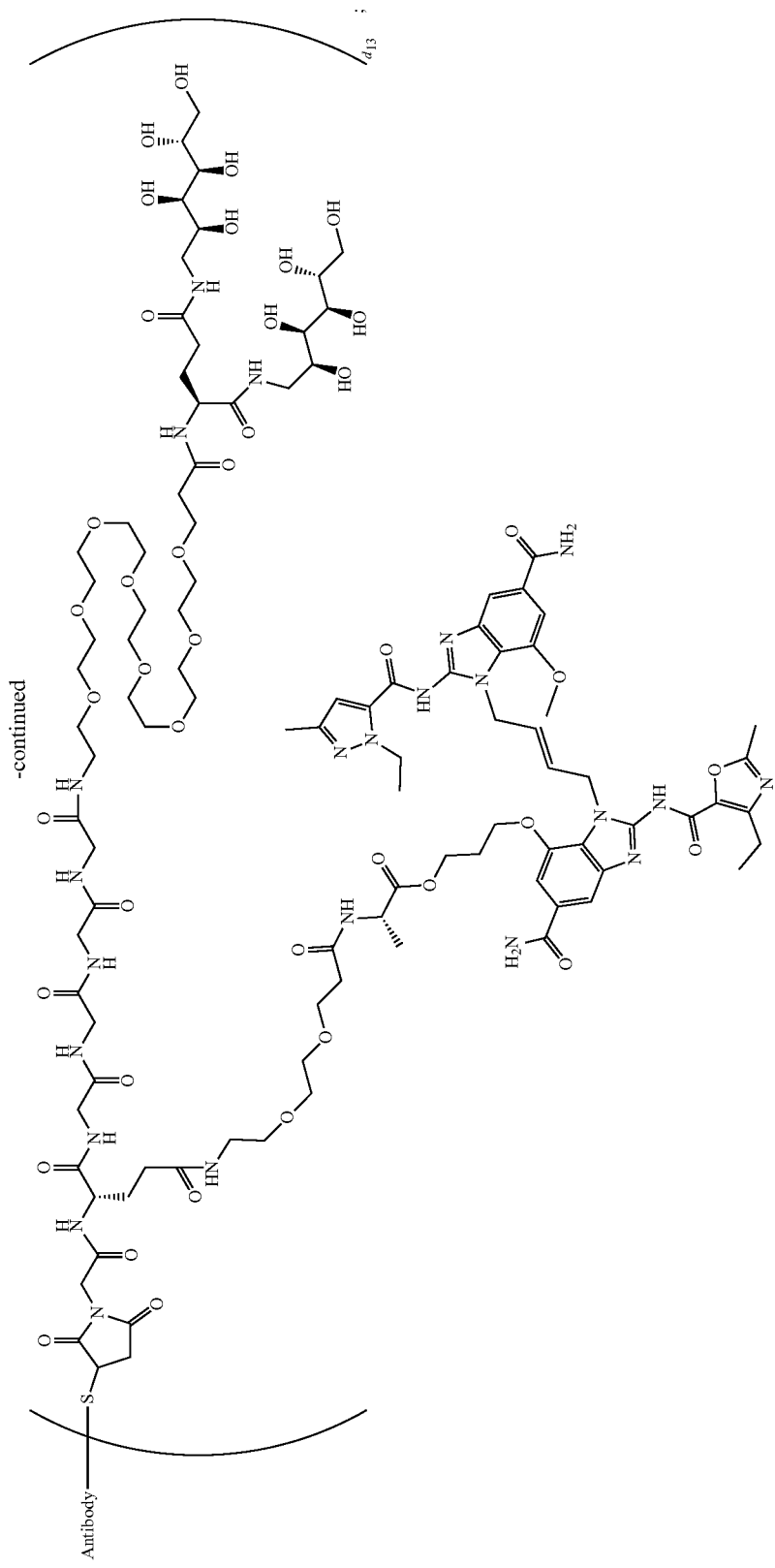

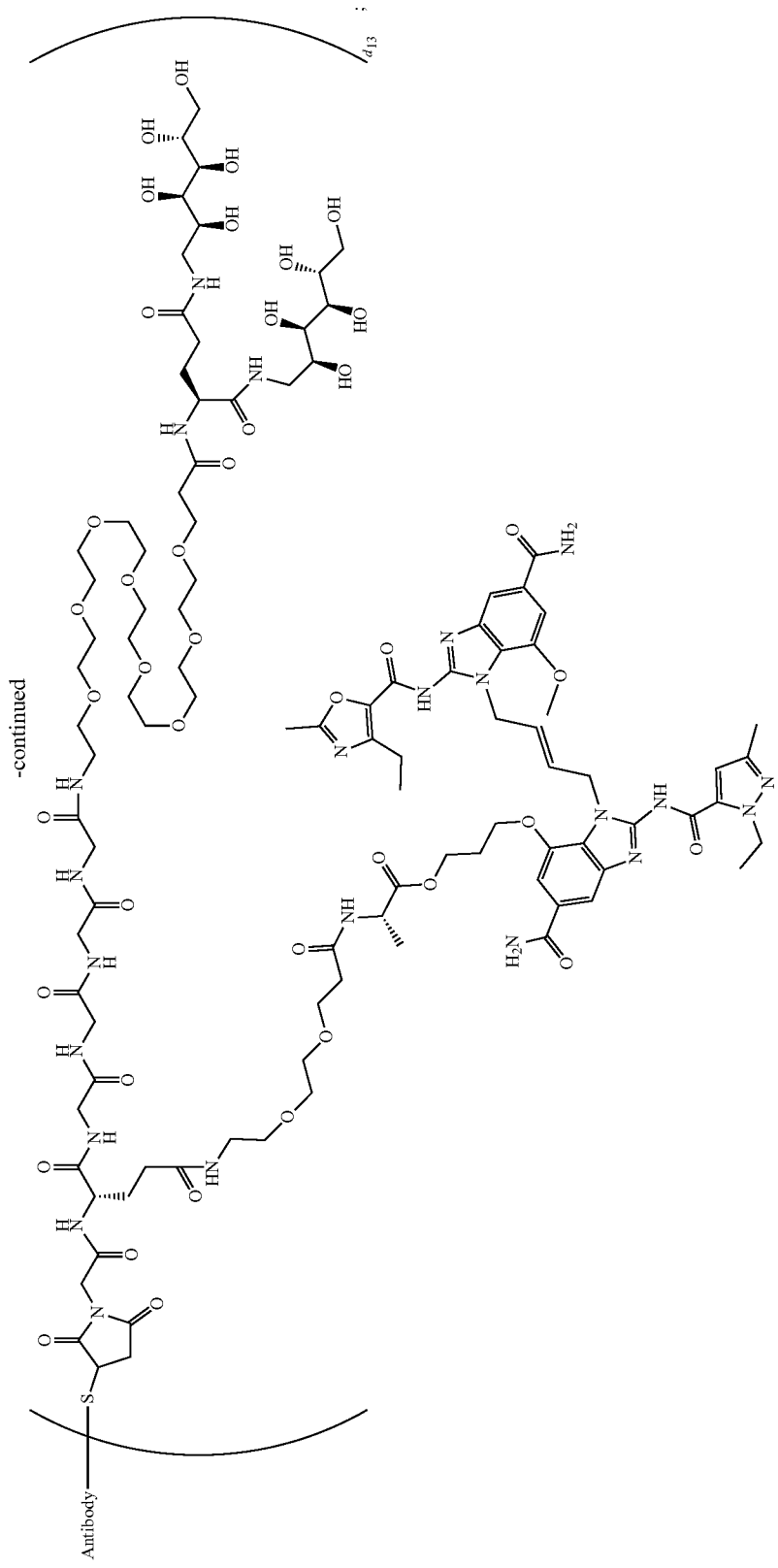

-continued

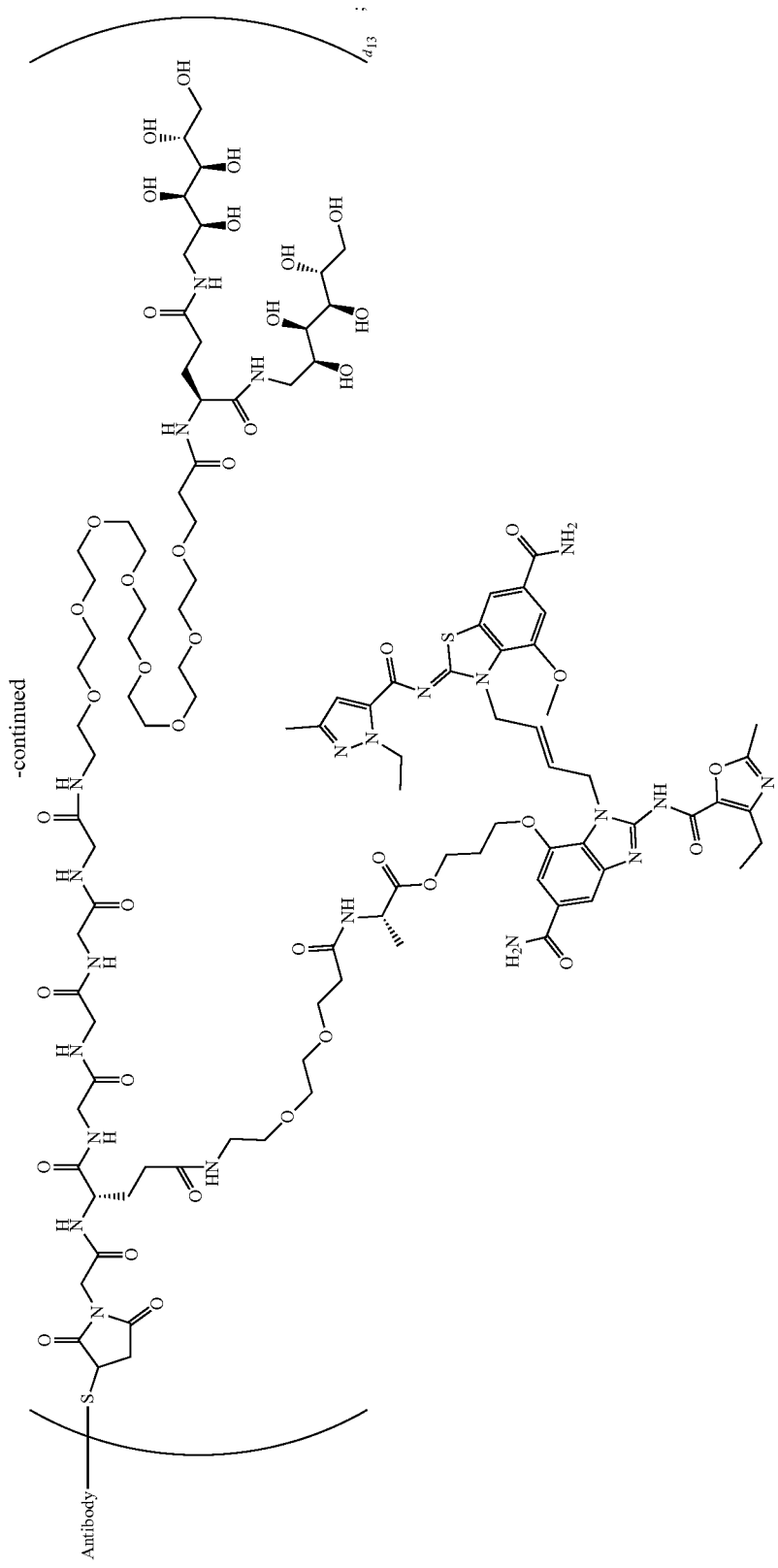

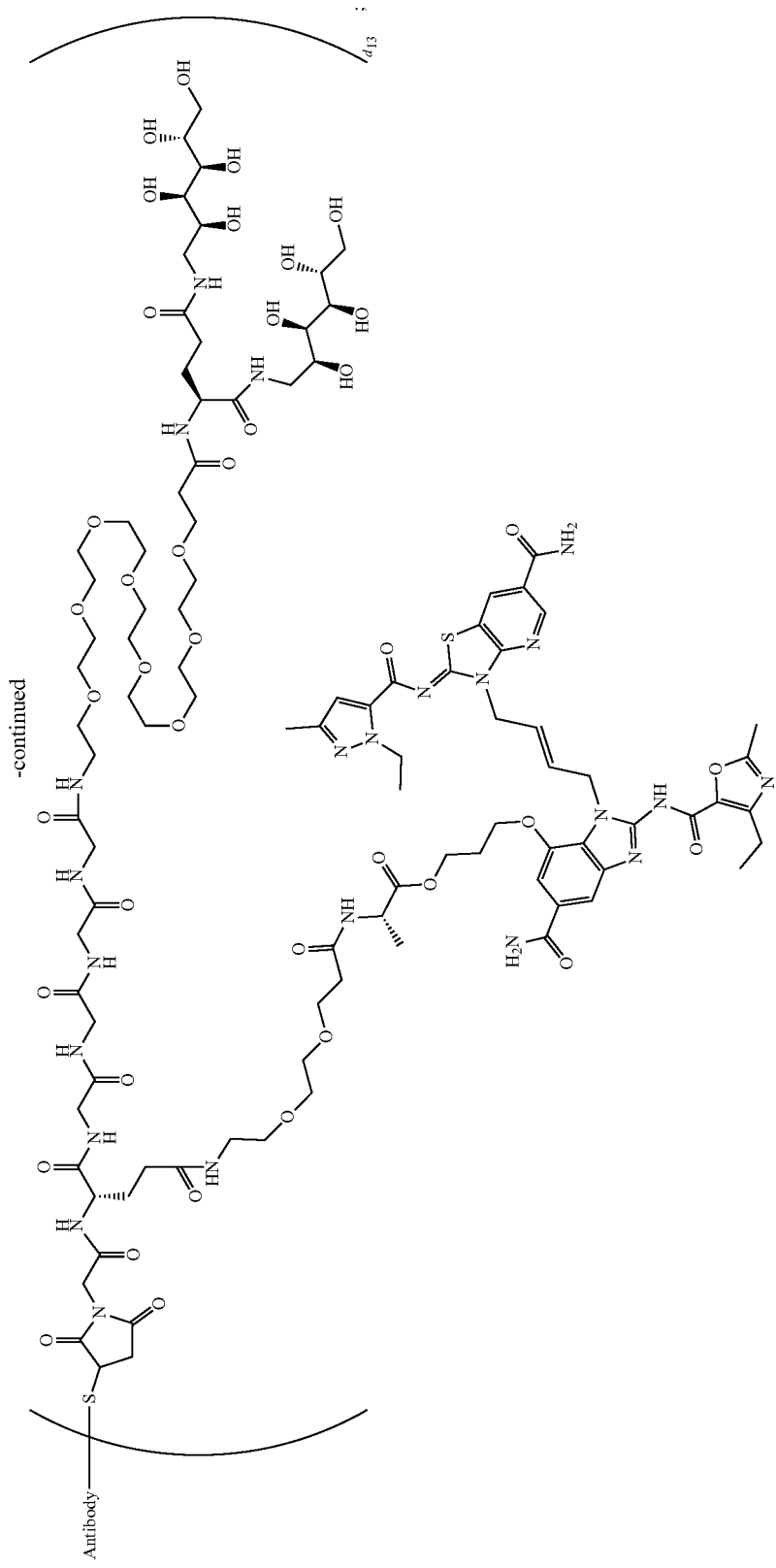

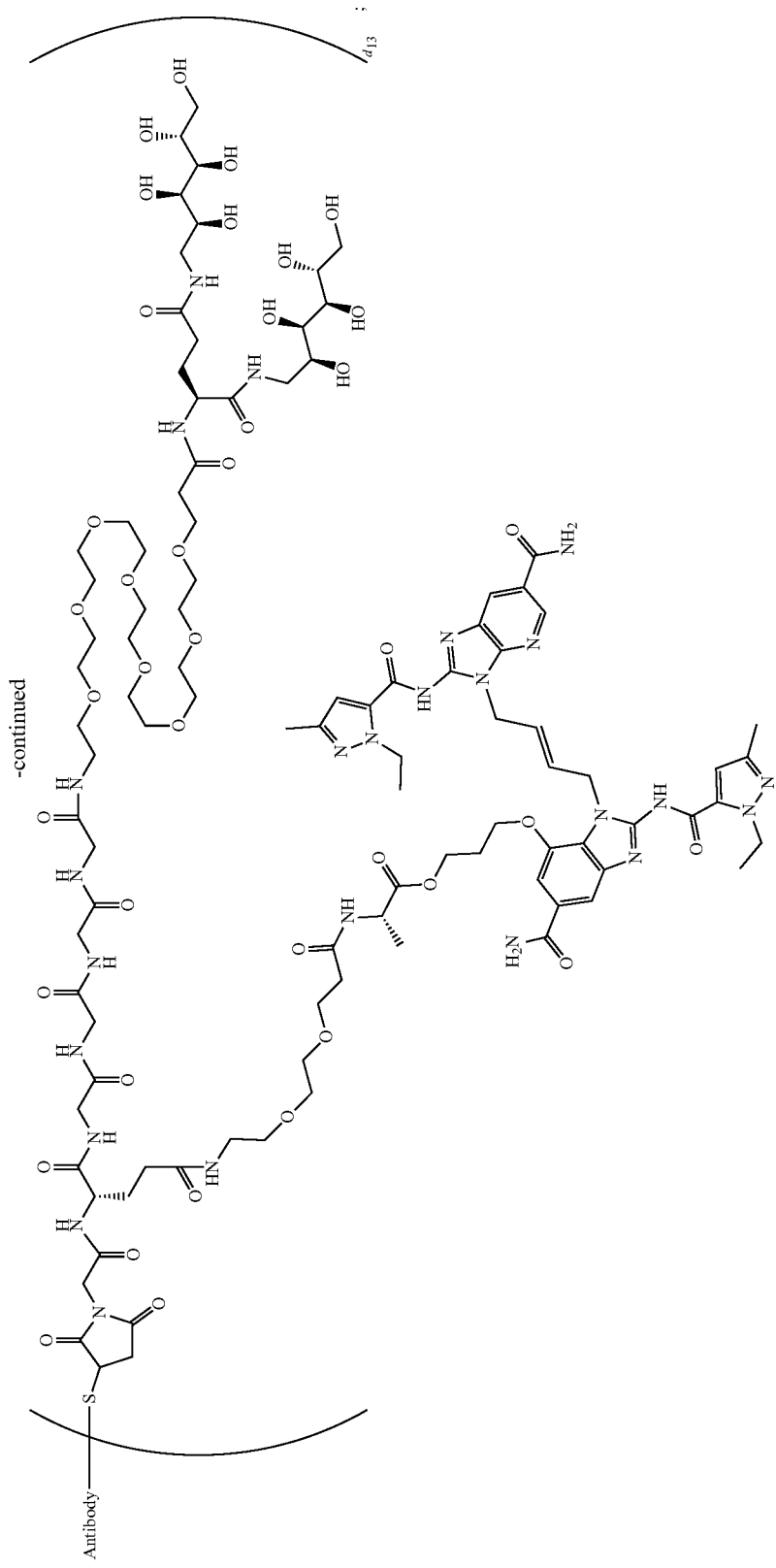

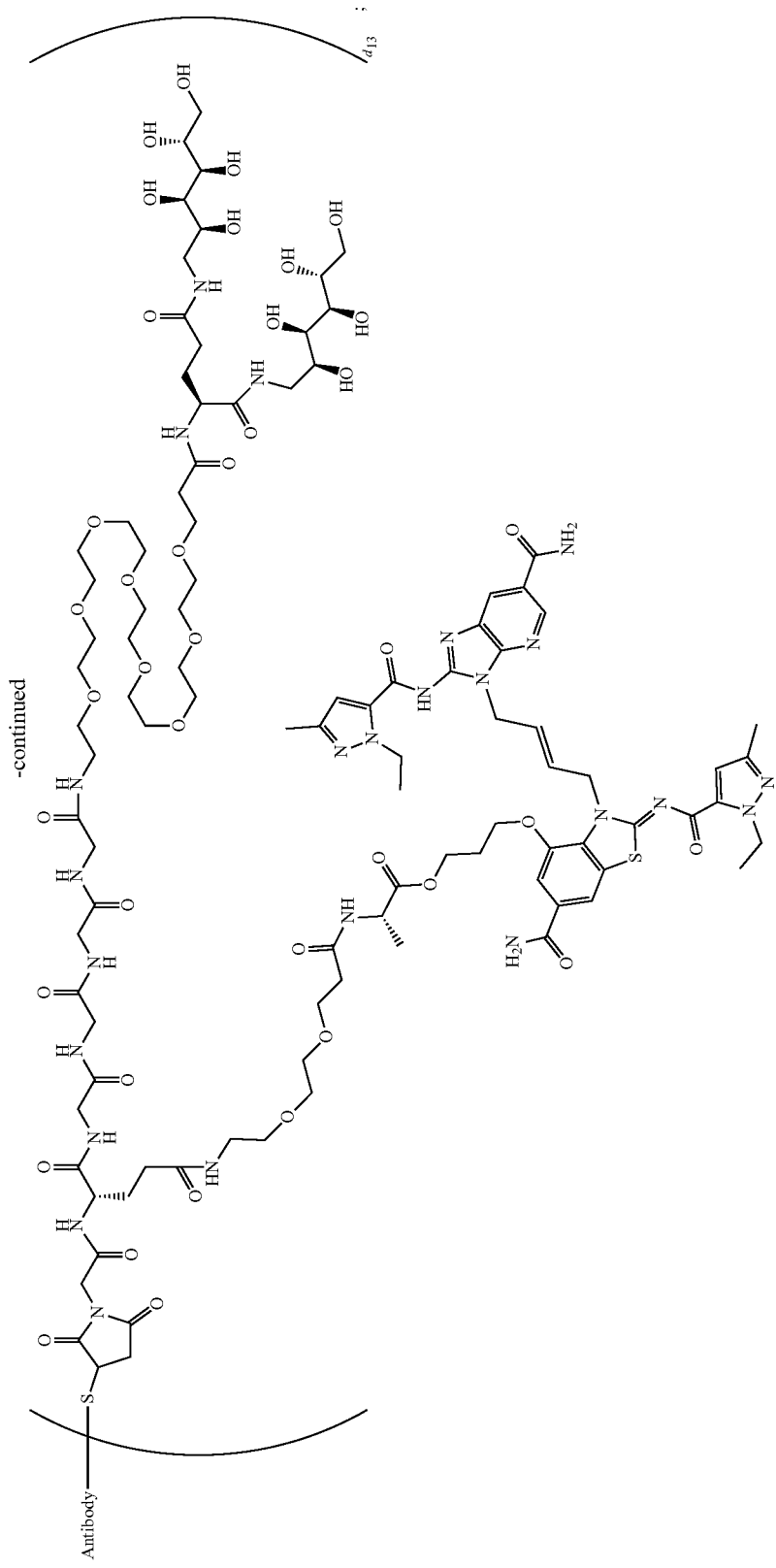

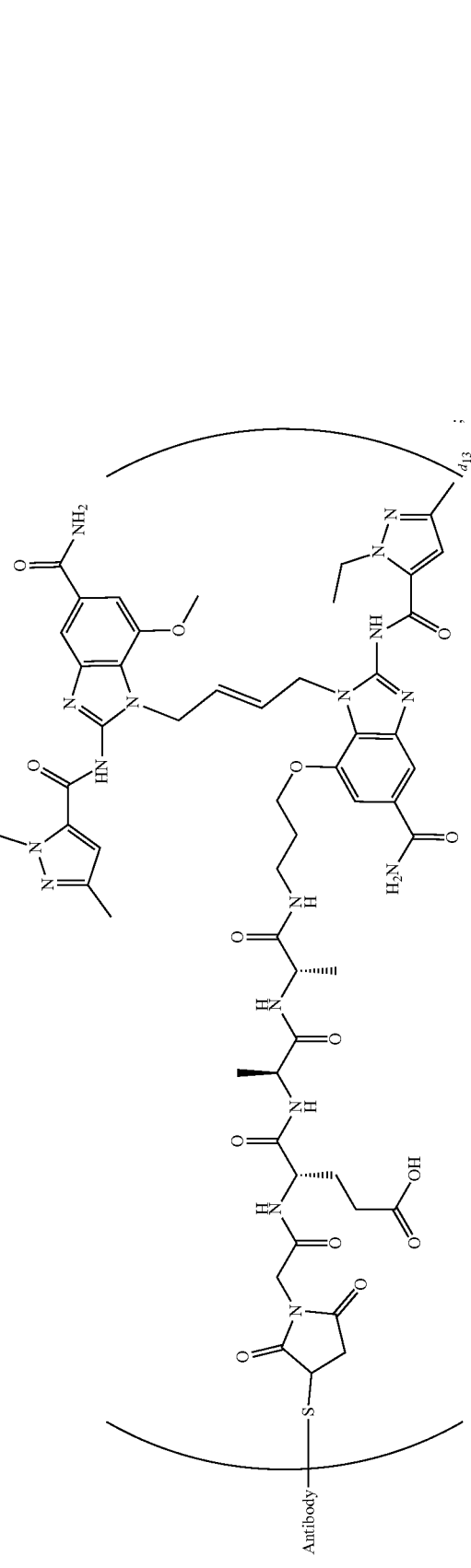
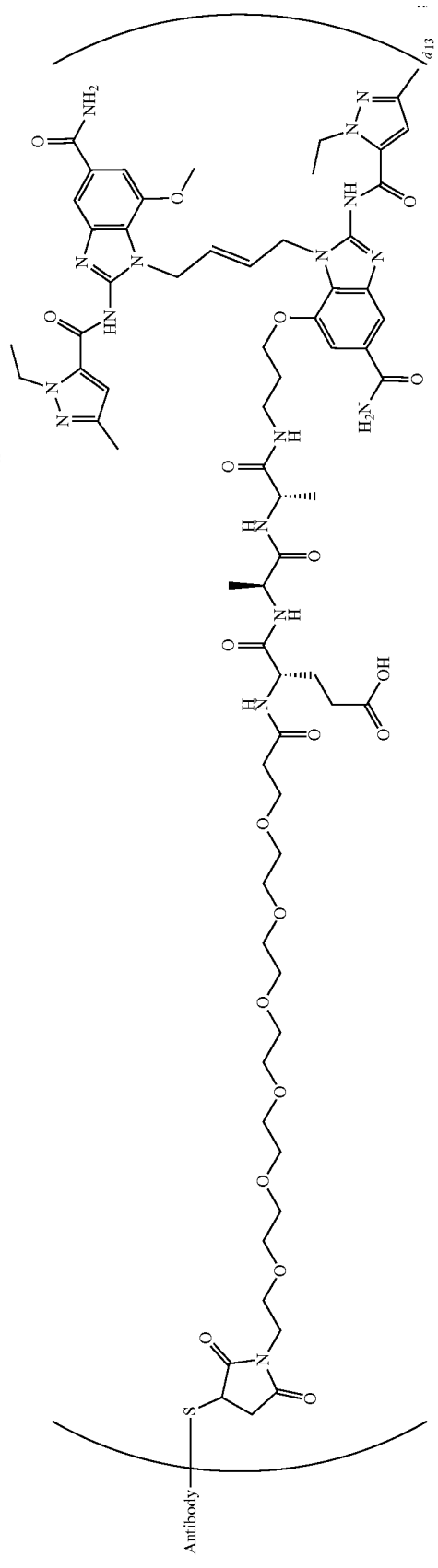

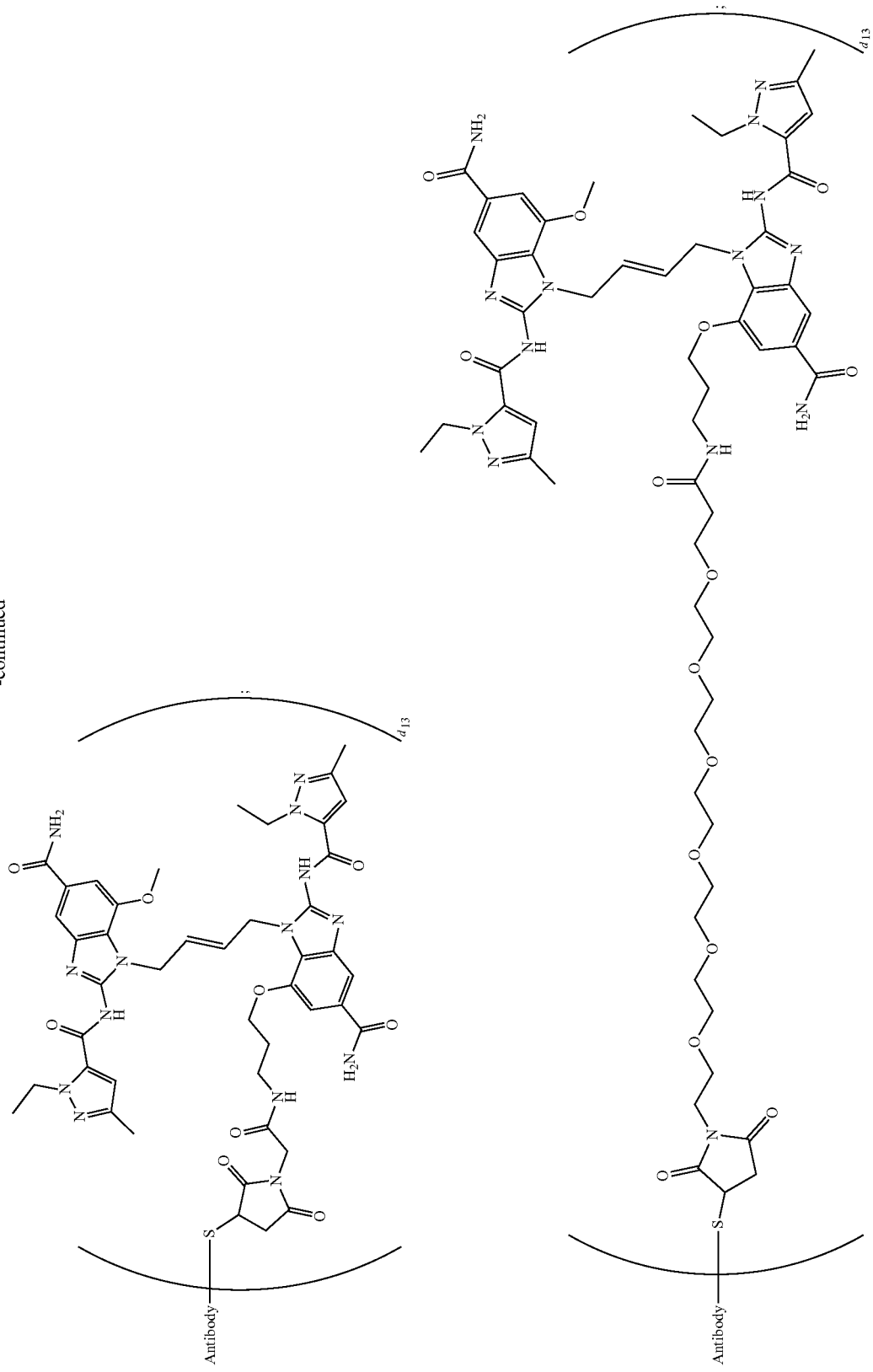

769
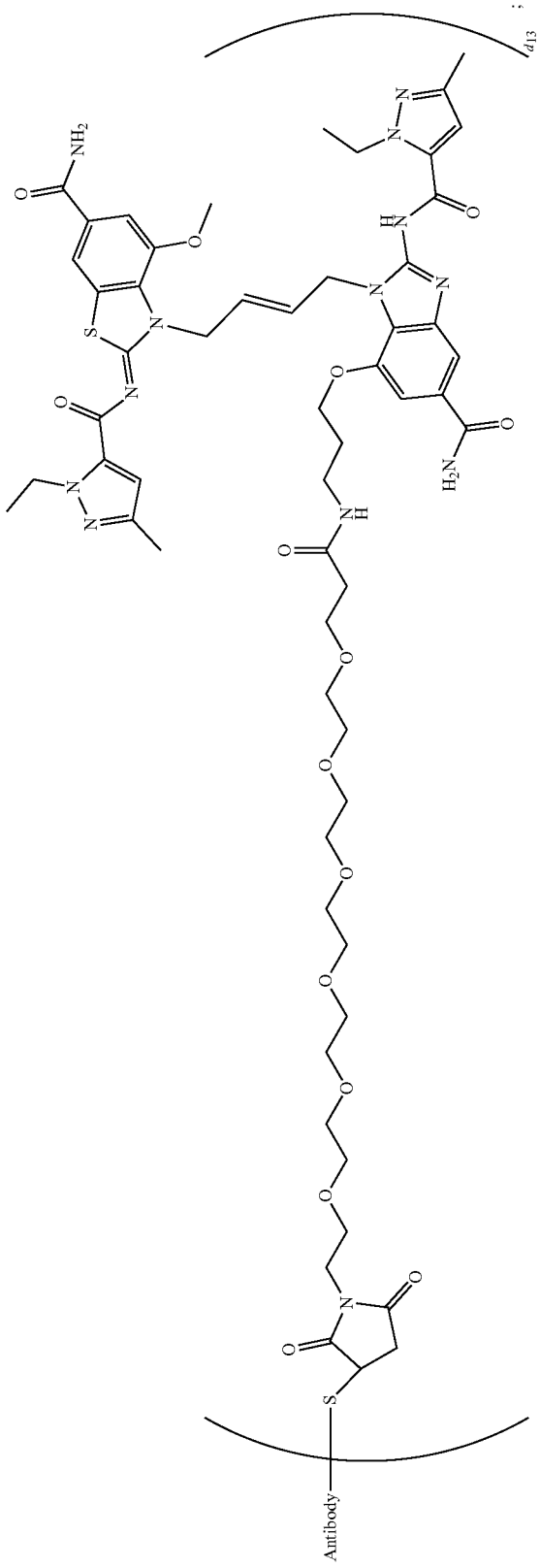
770
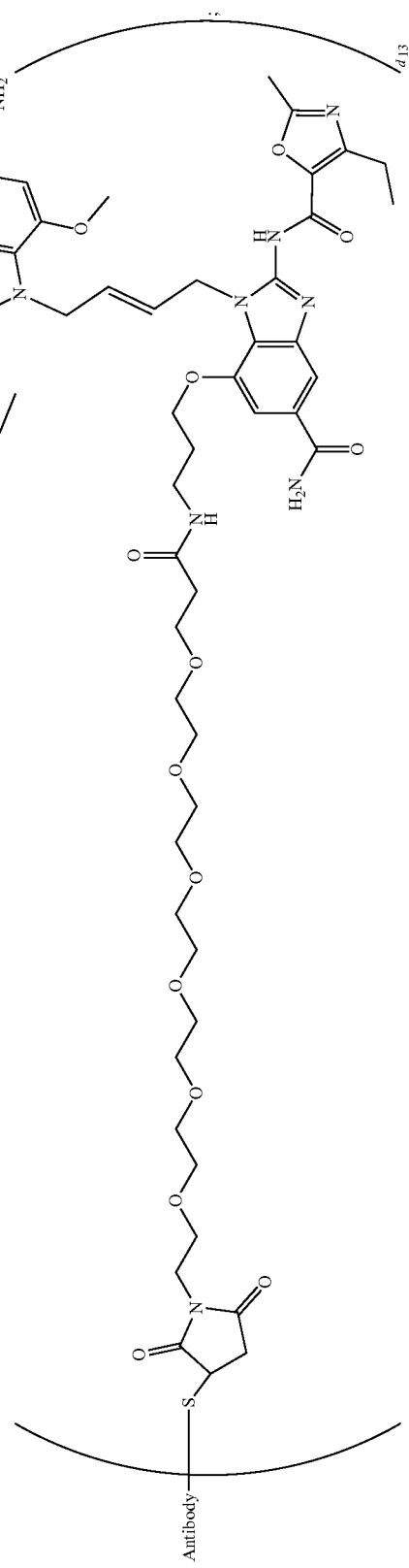

771
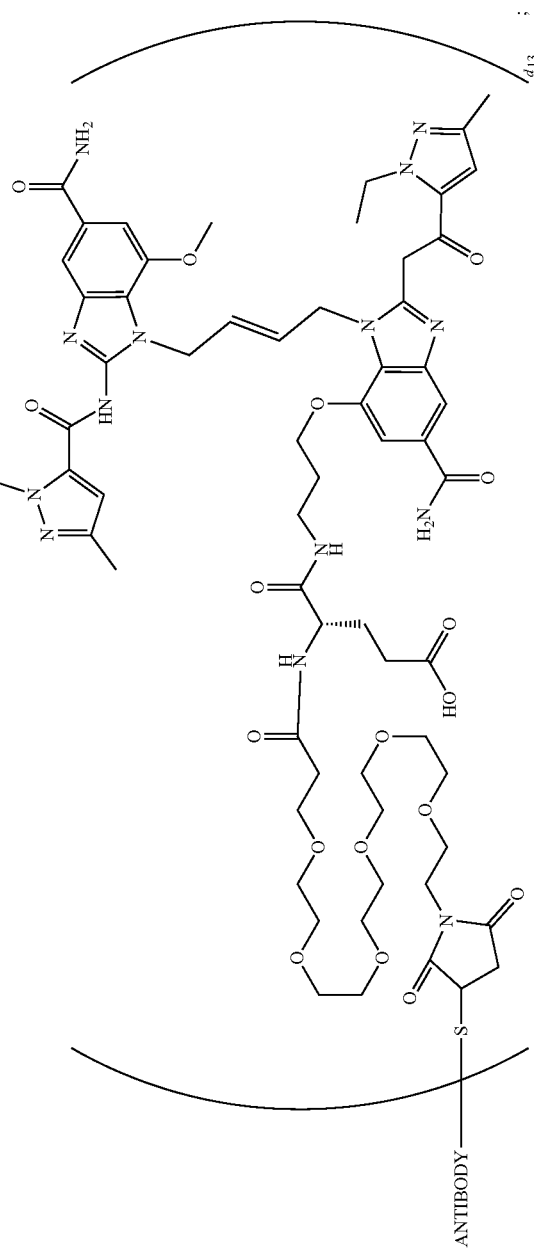
772
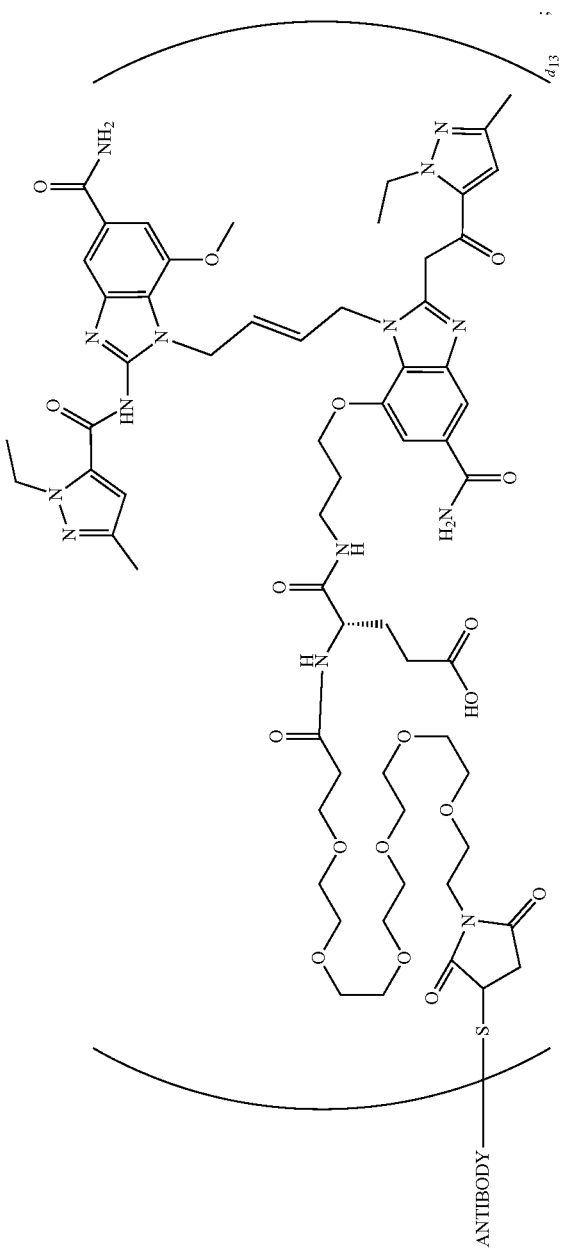

-continued
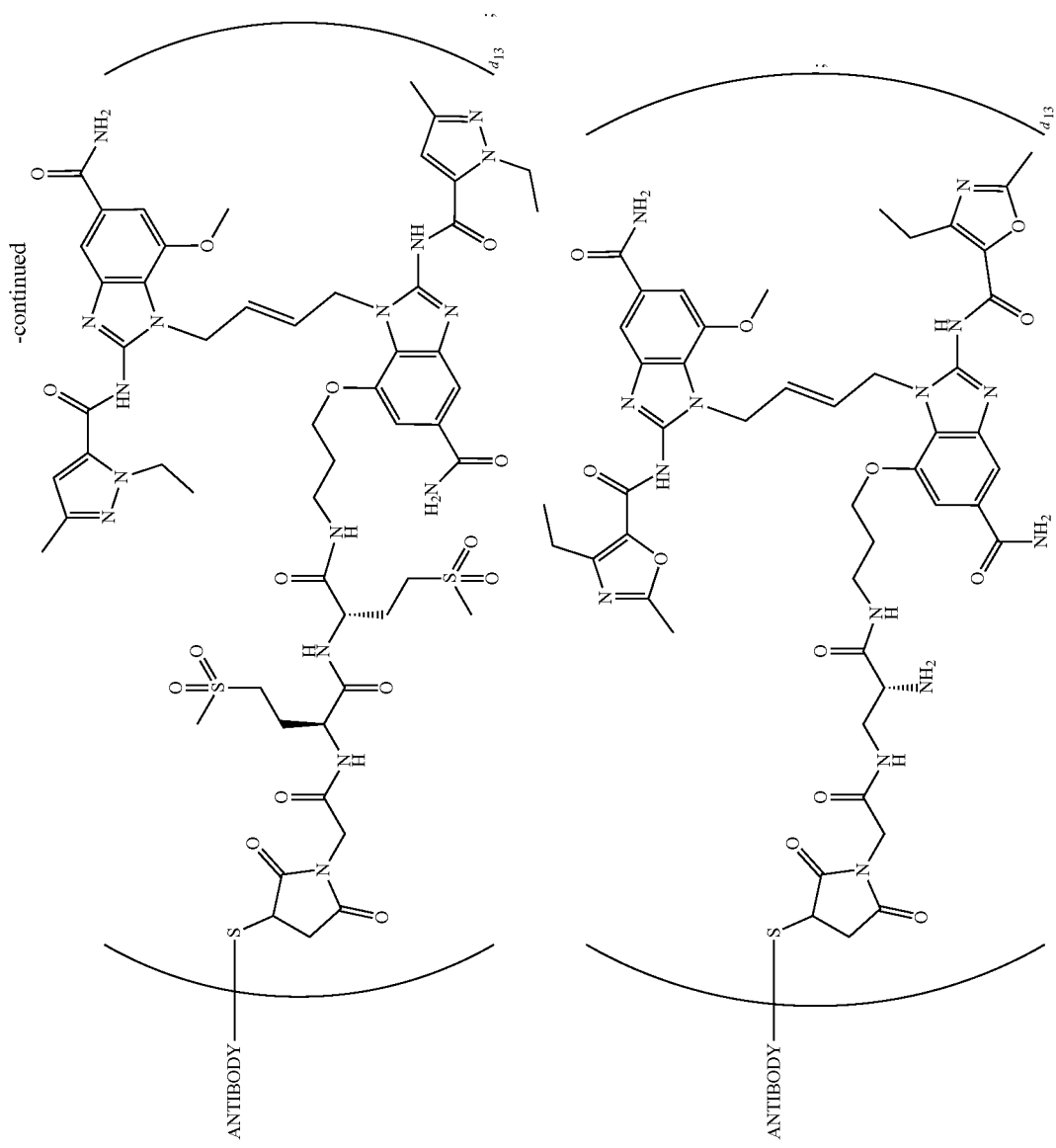

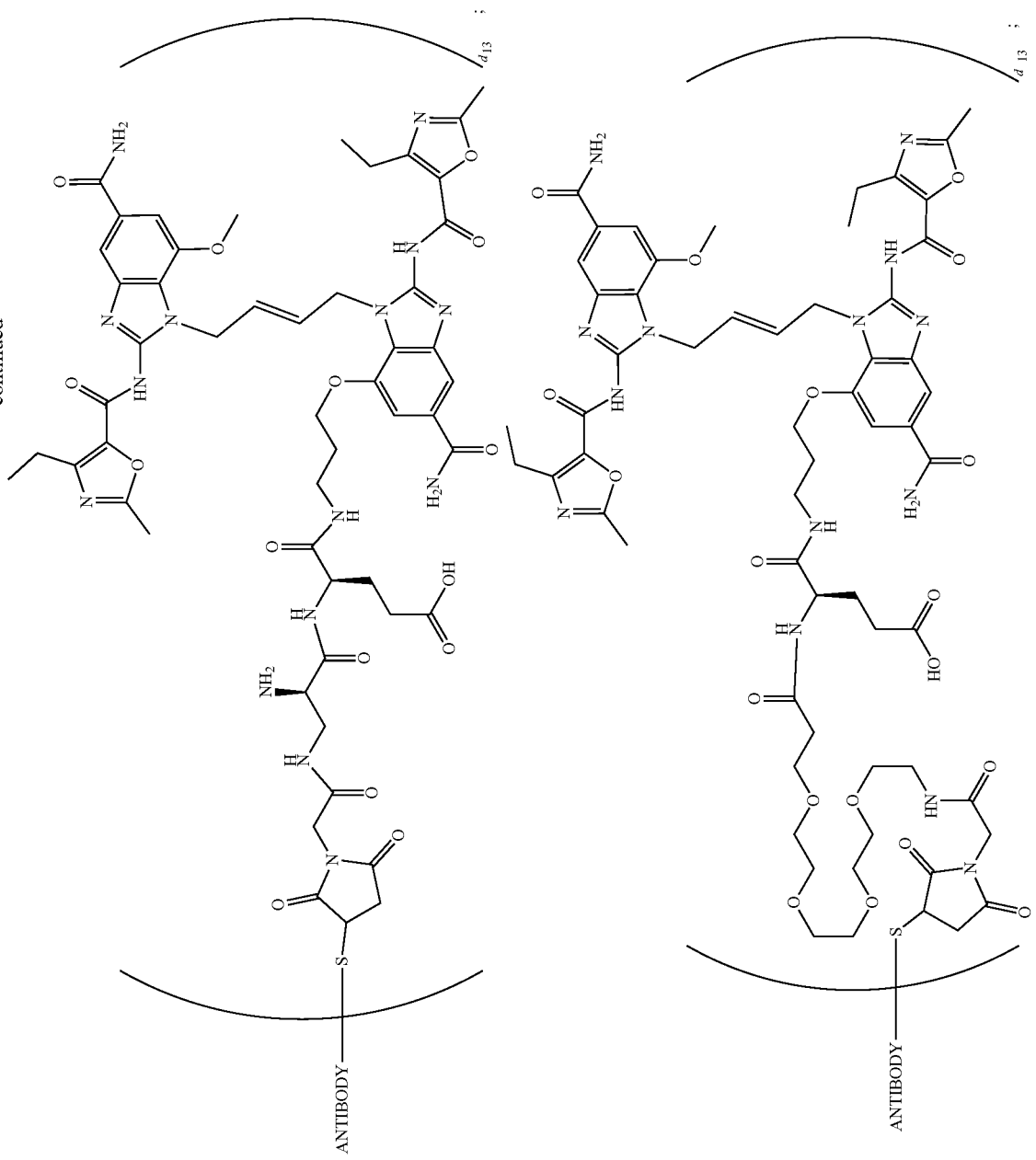

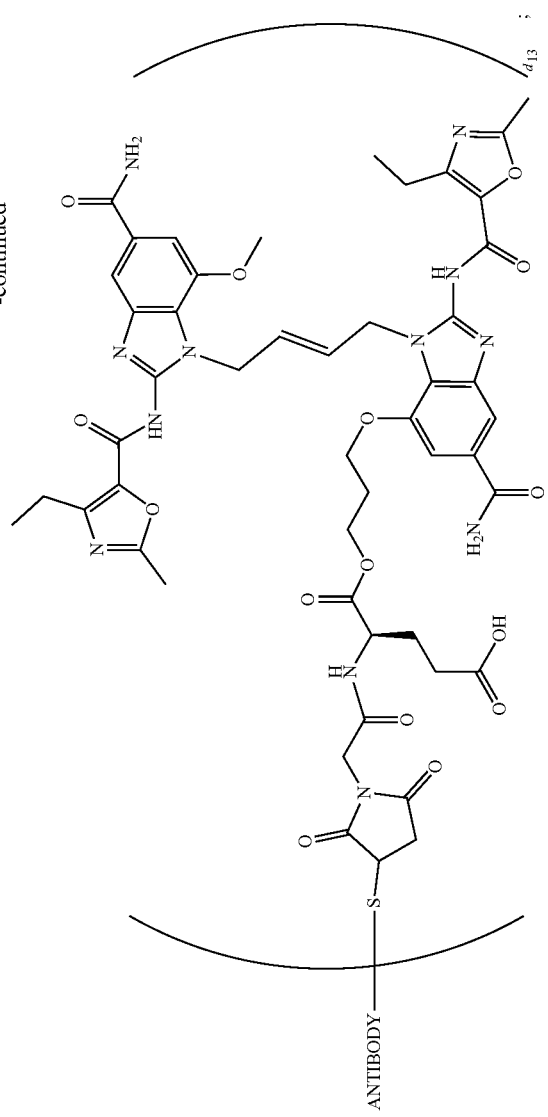
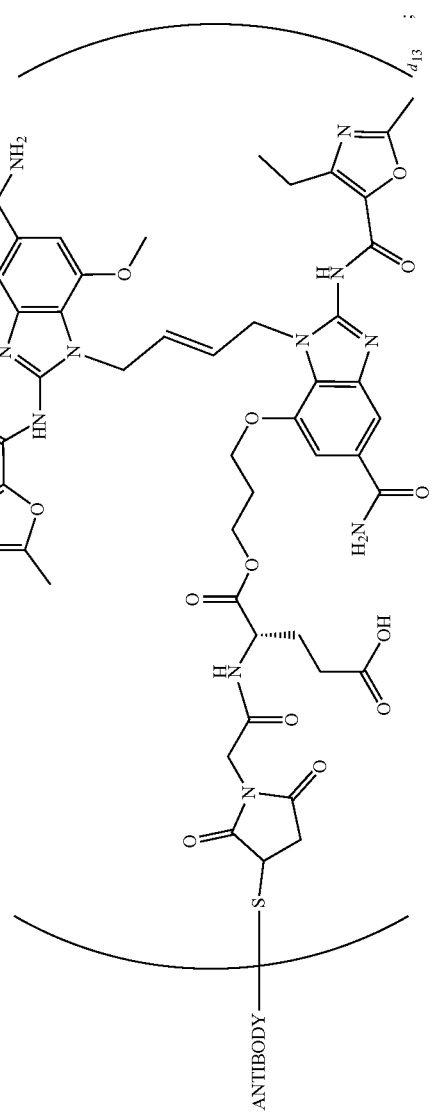

779 780
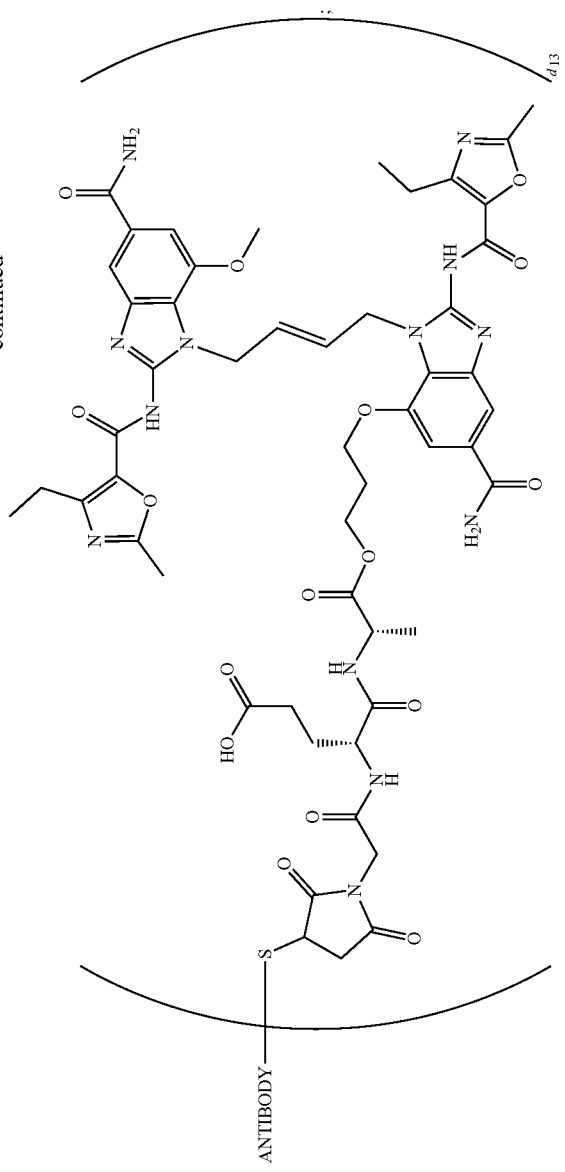
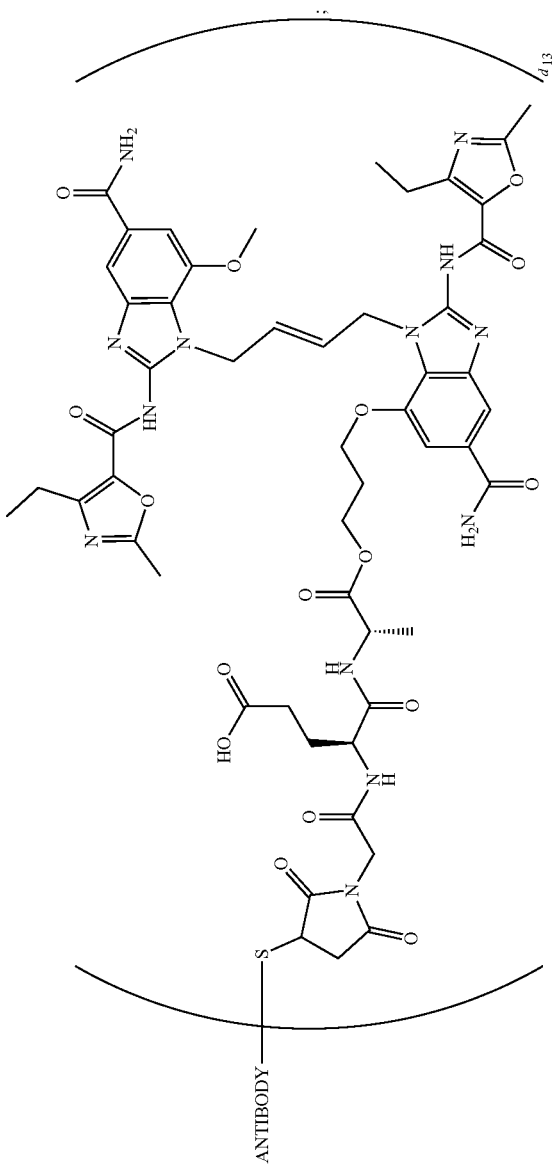

781 782
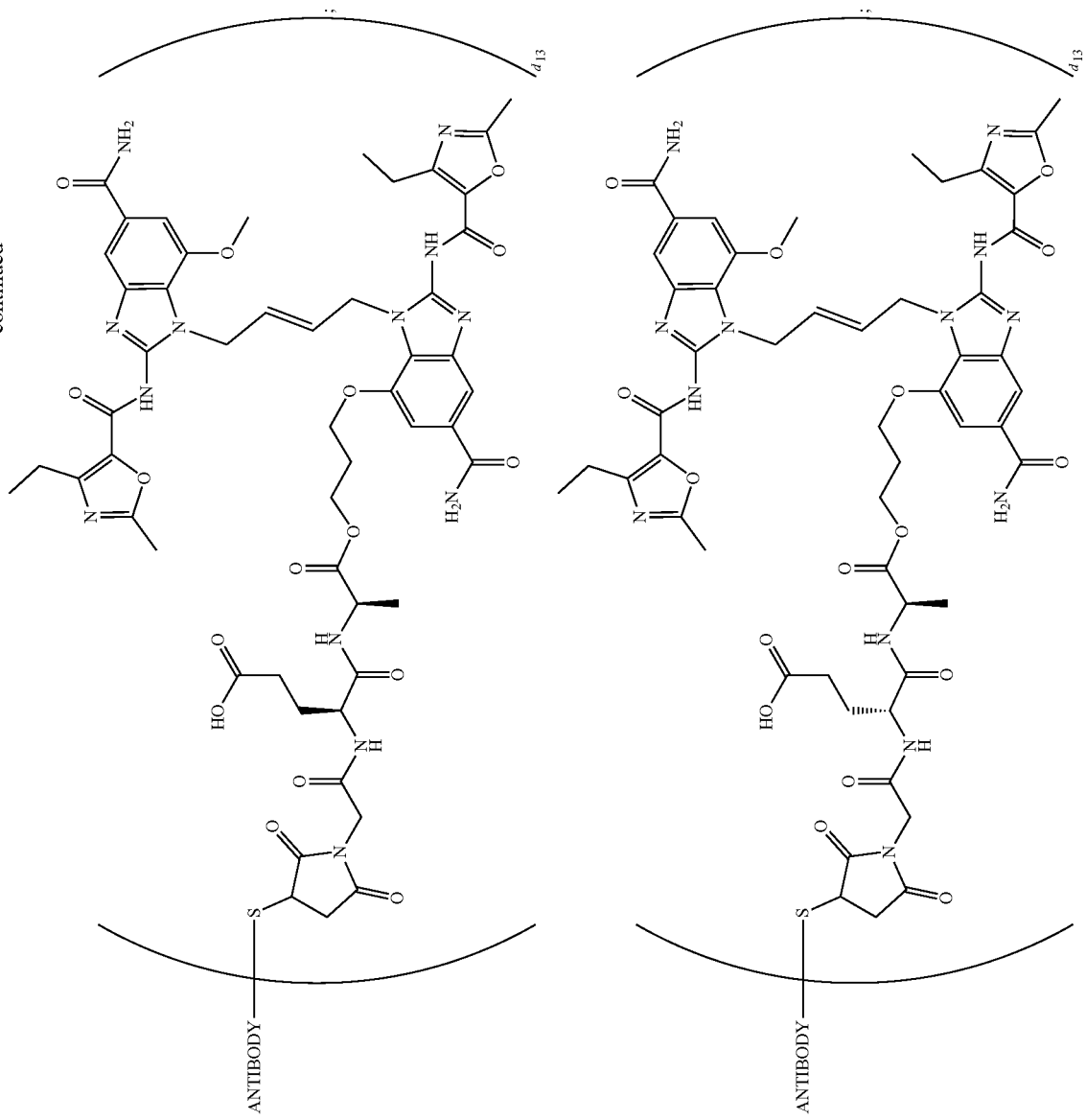

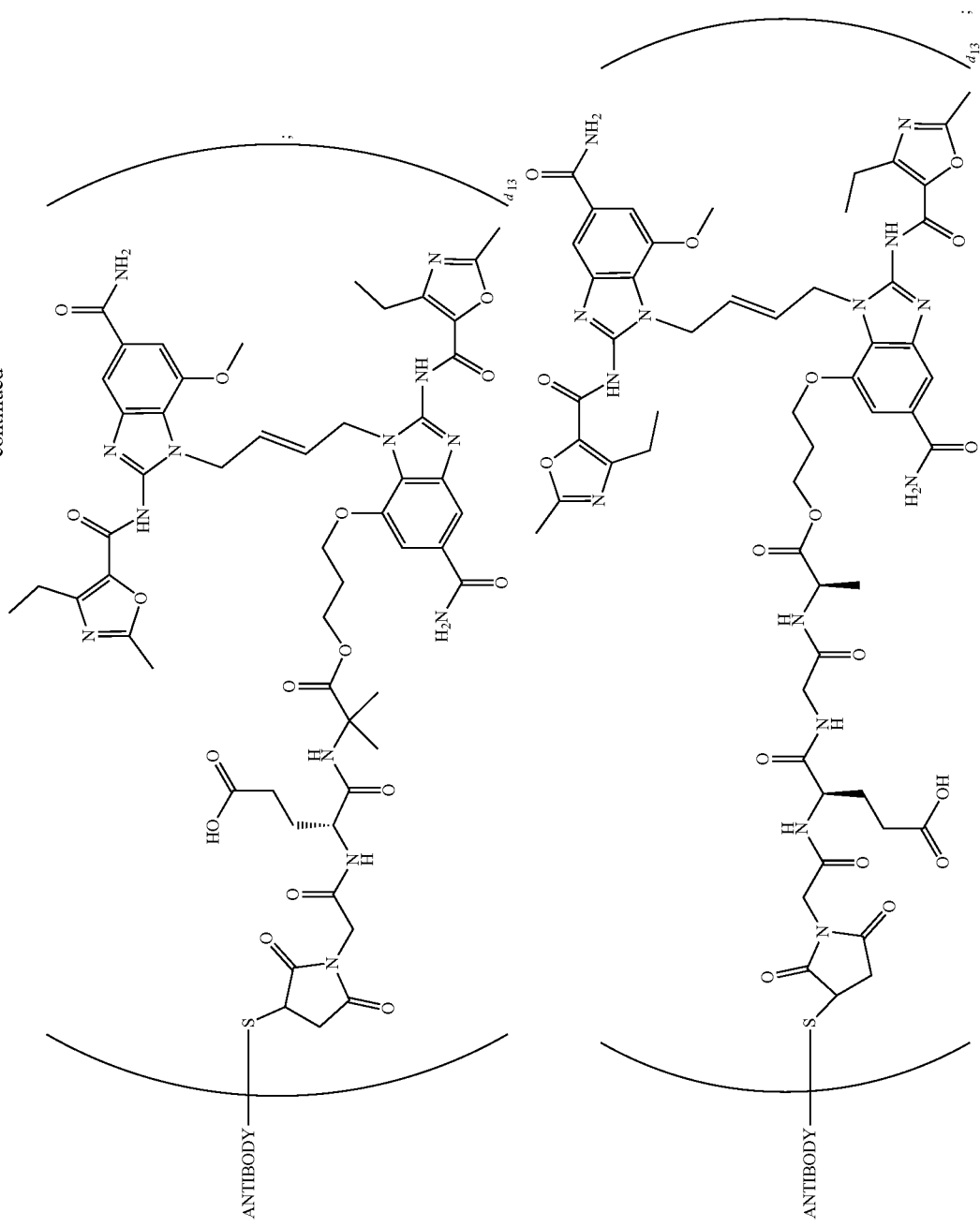

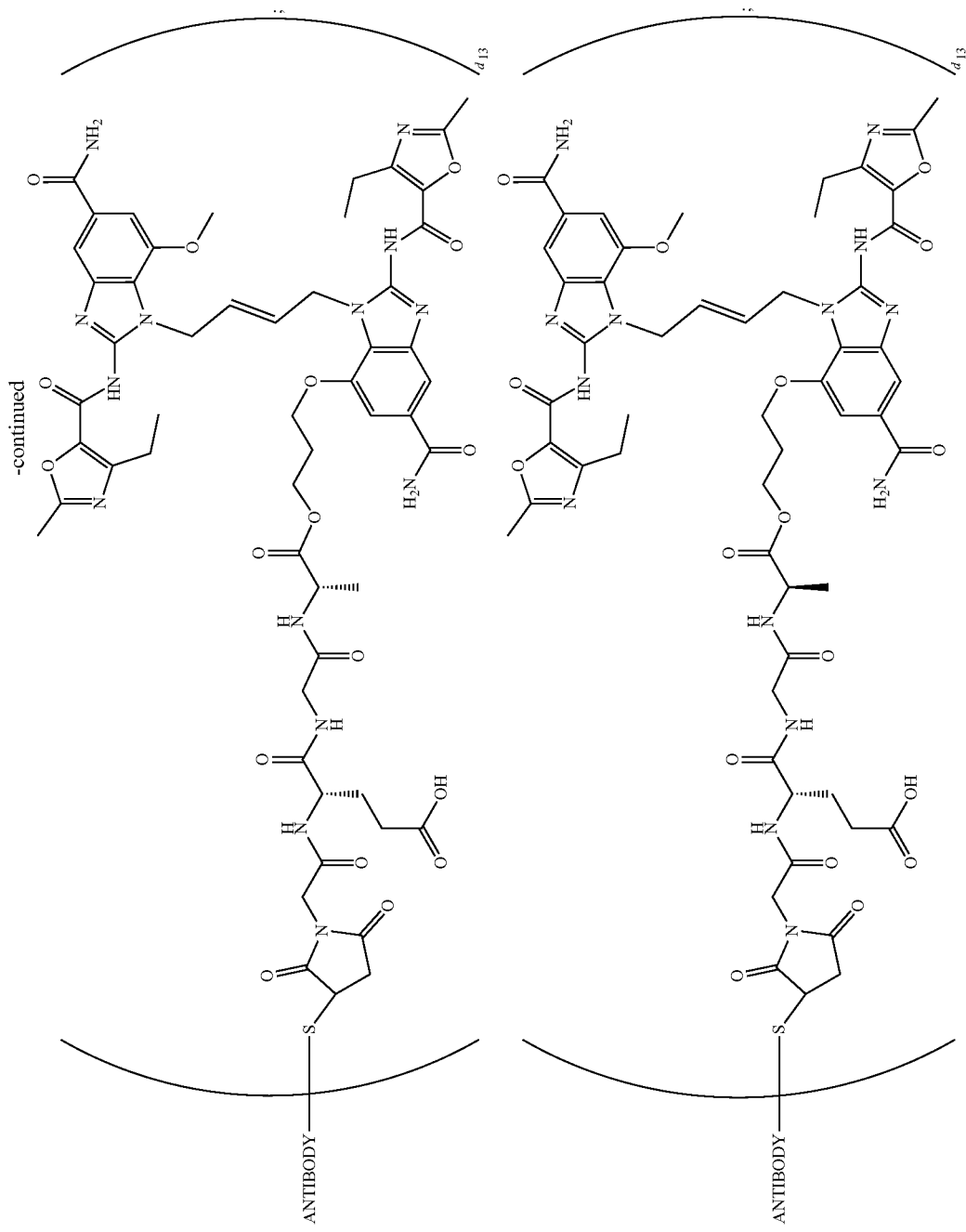

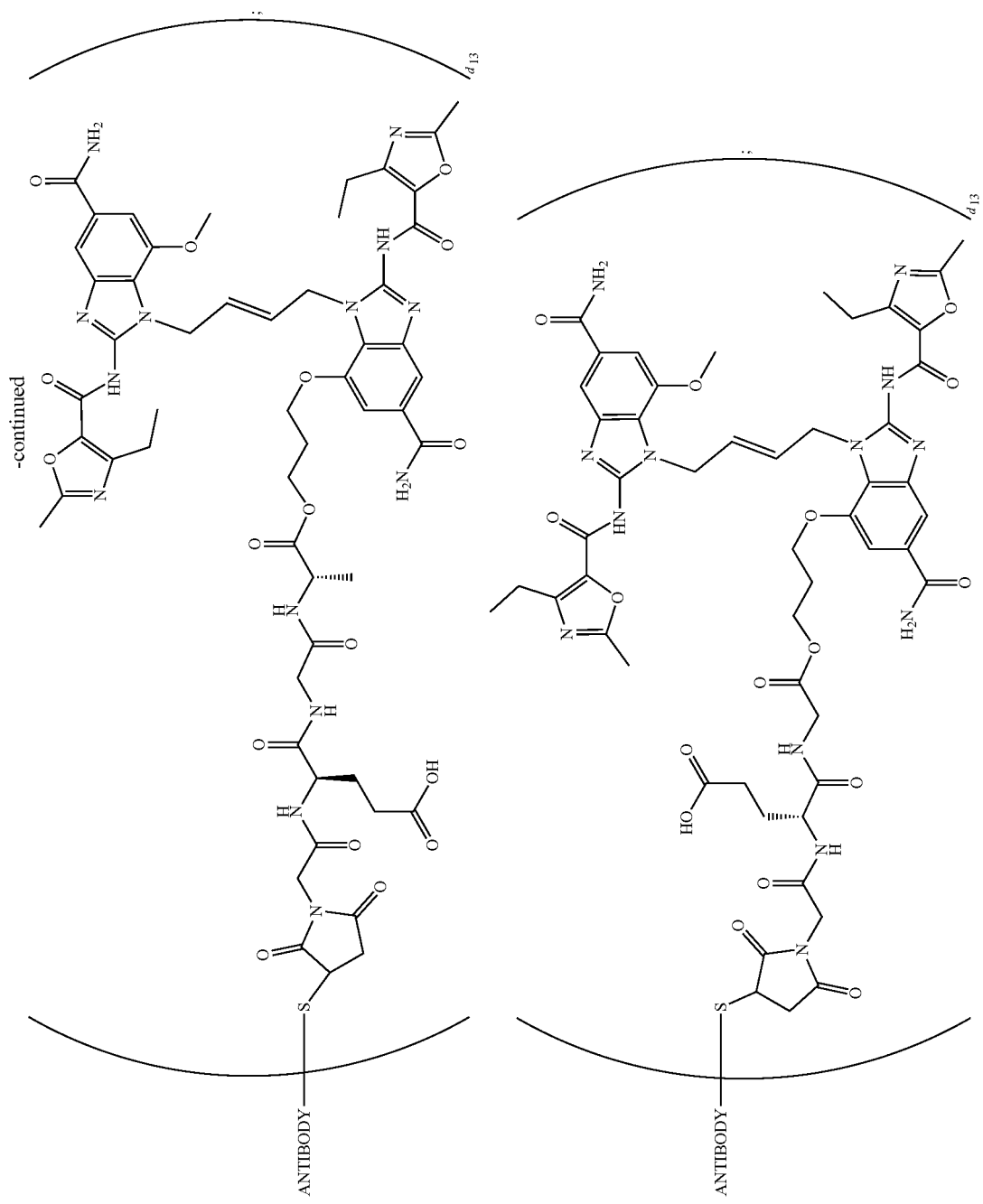

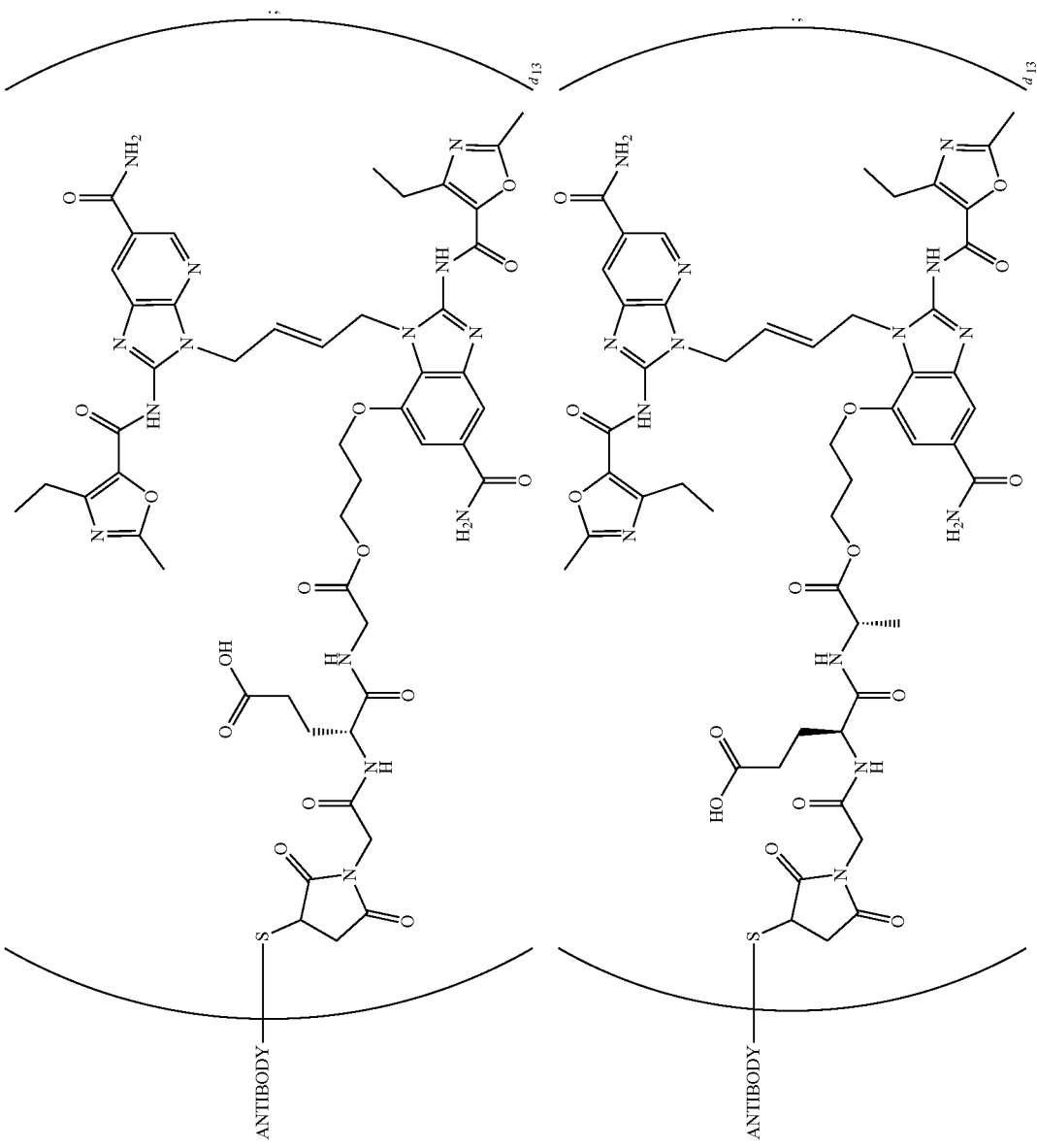

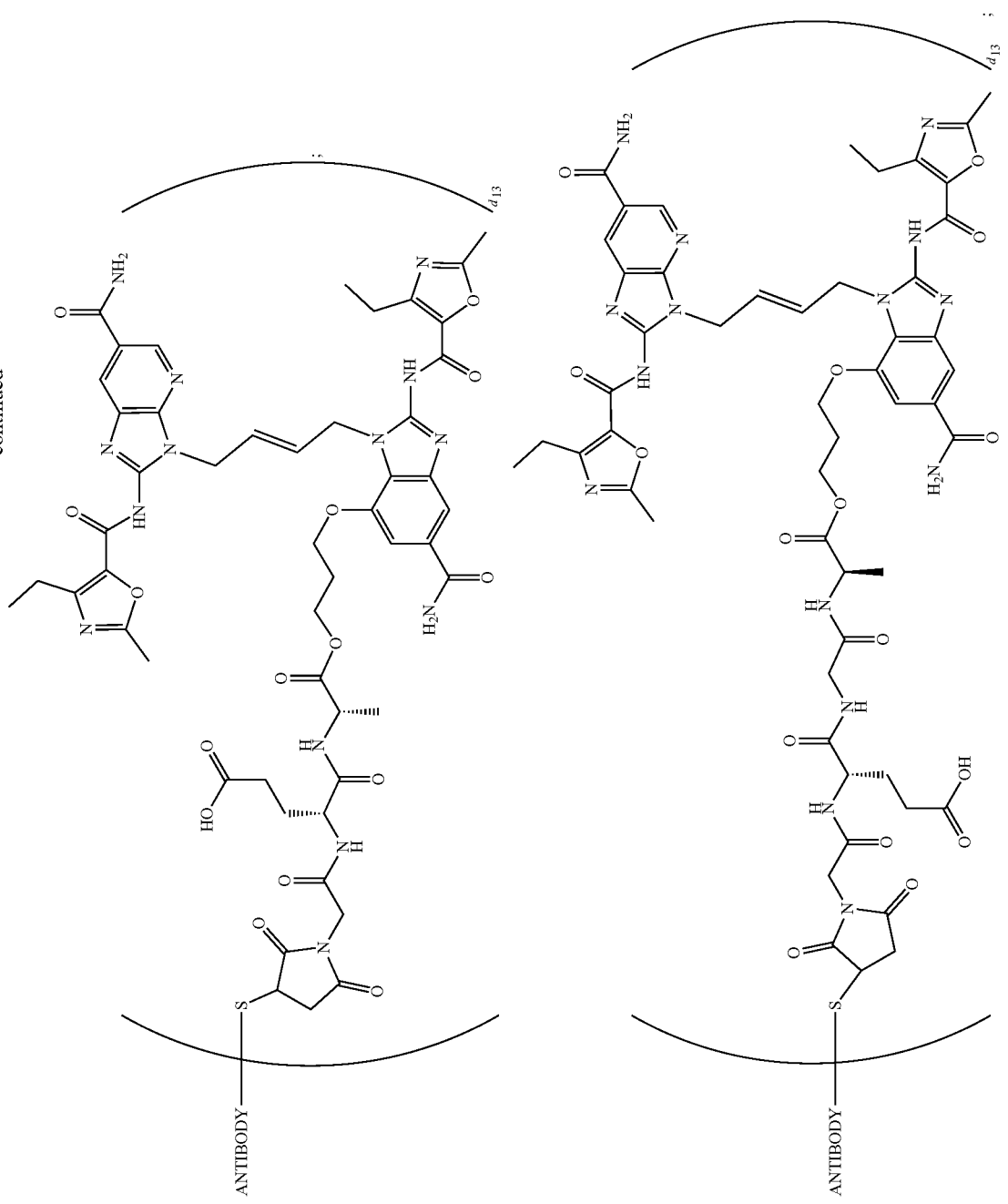

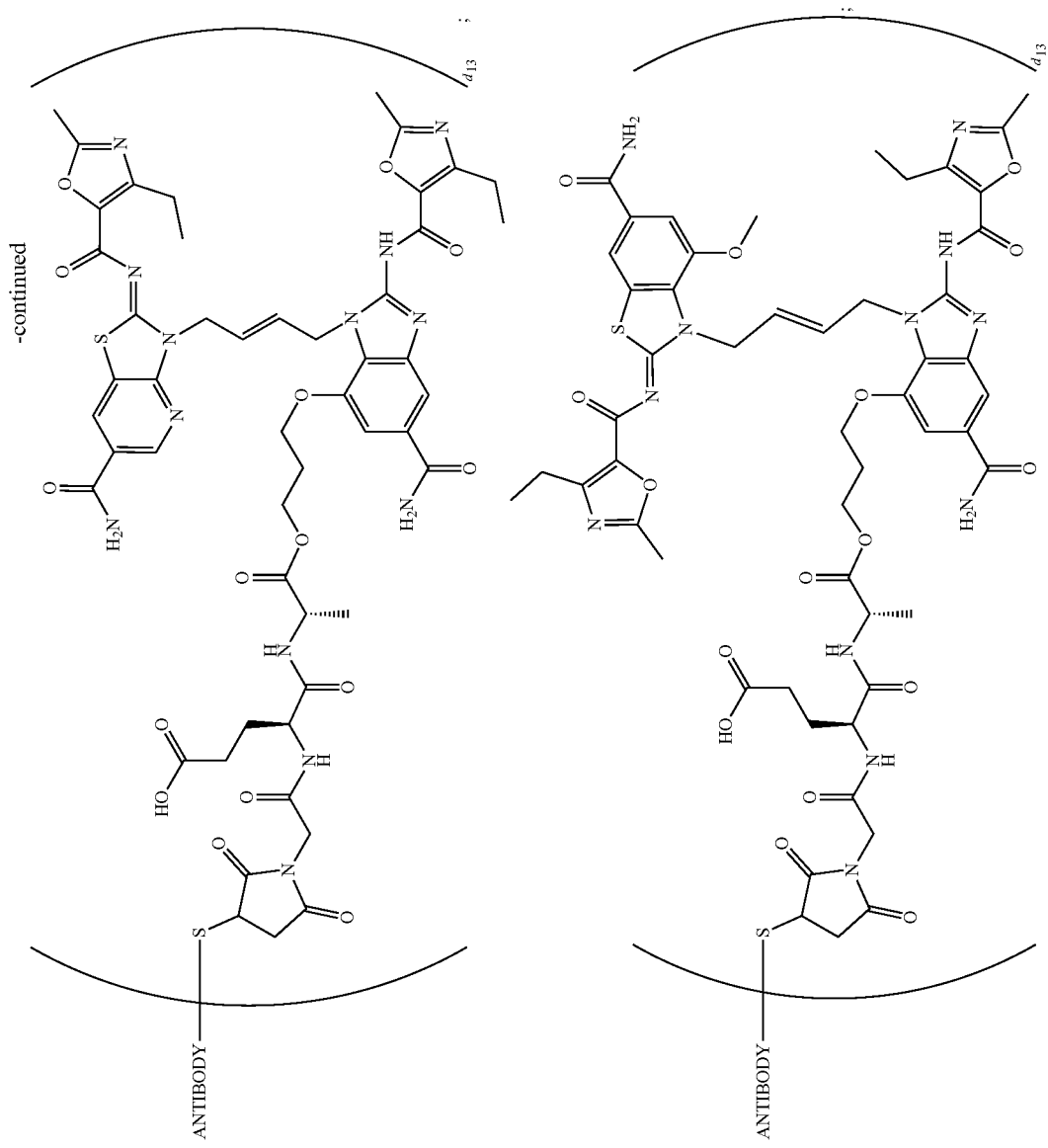

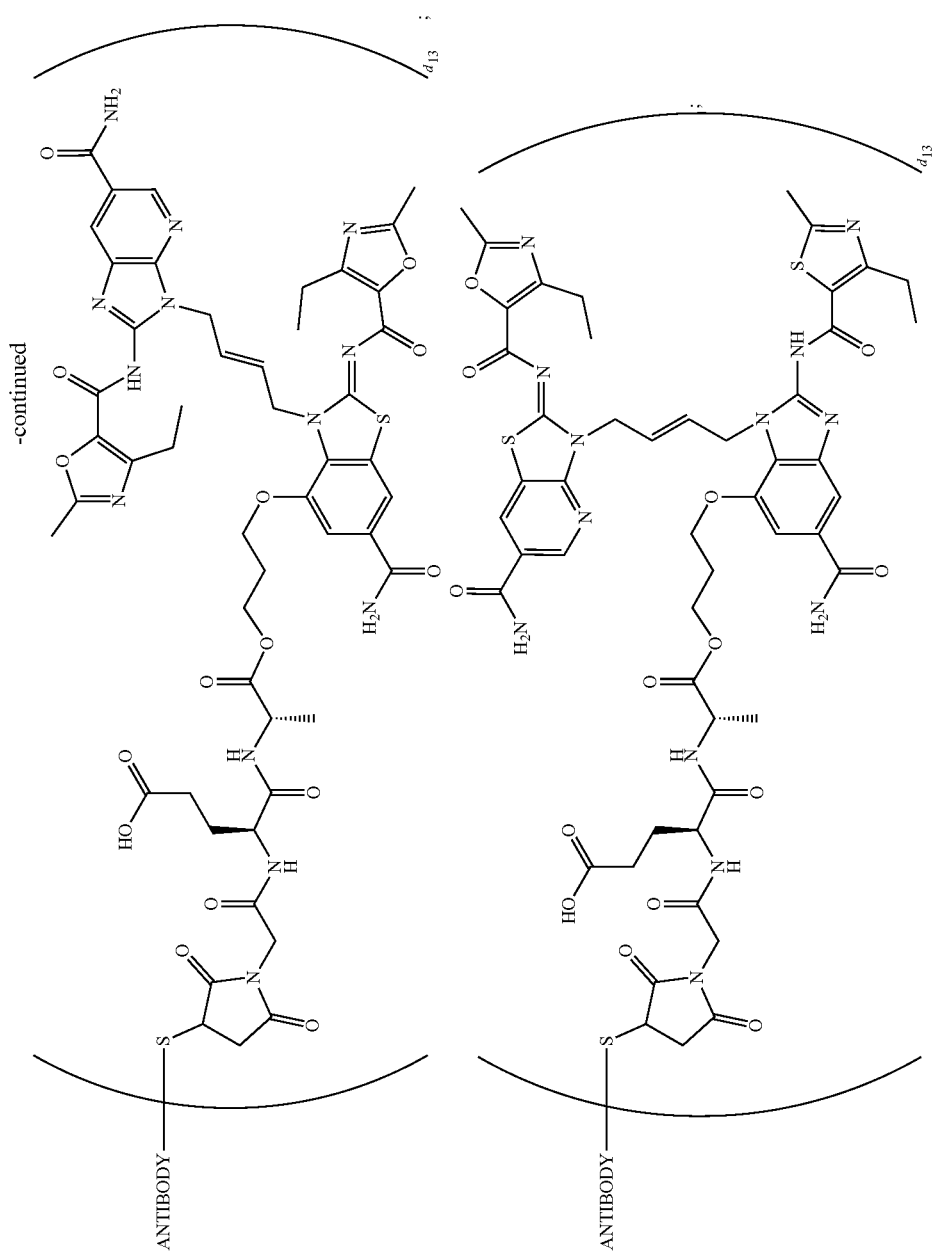

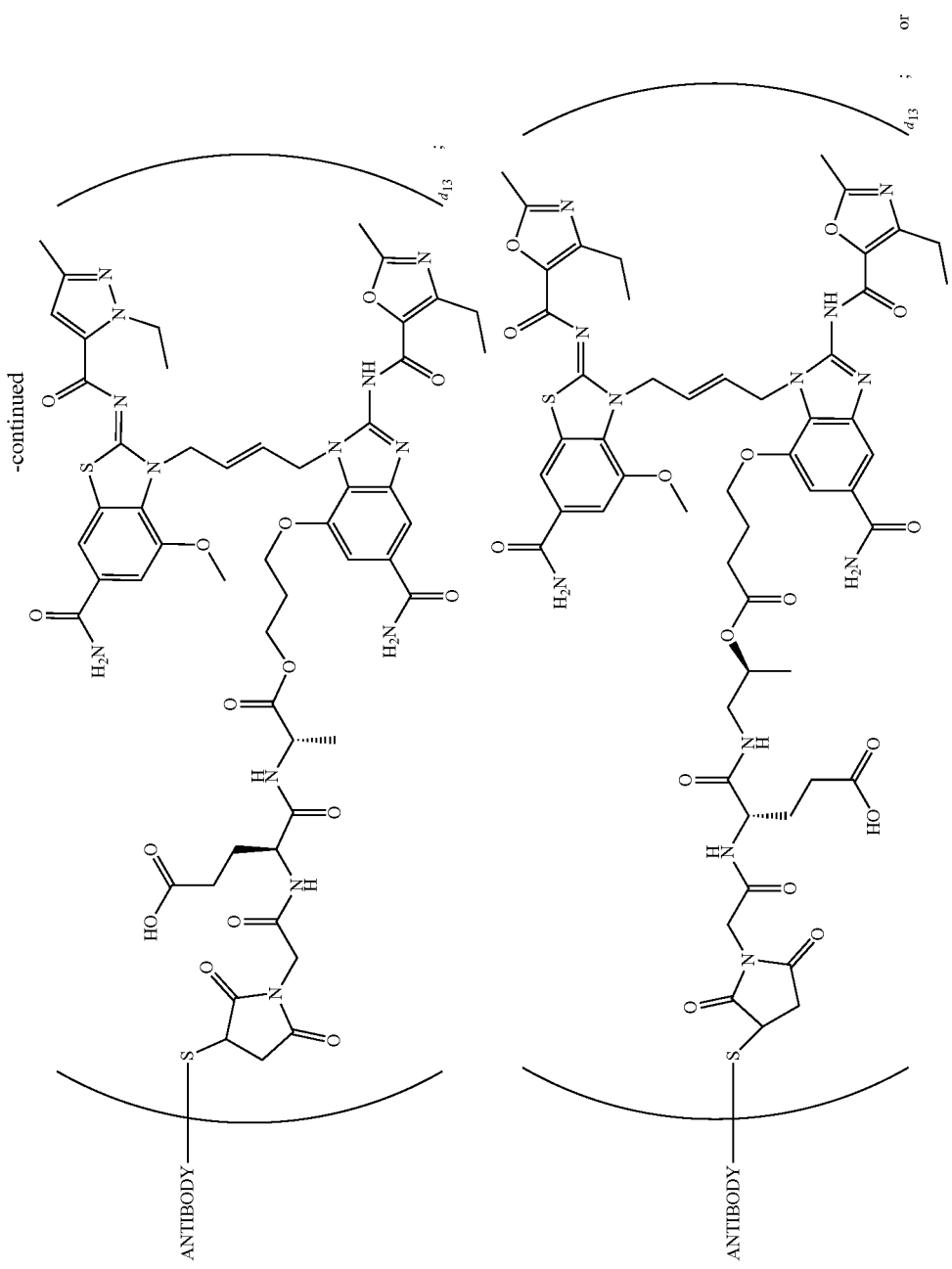

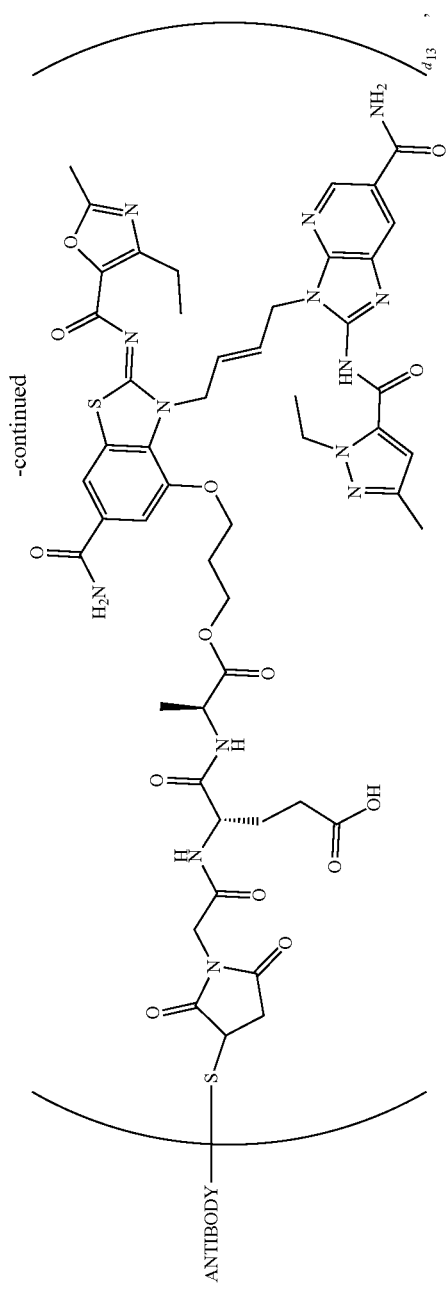

wherein $d_{13}$ is from about 2 to about 12.
22. The B7-H4 antibody-drug conjugate of claim 9, wherein the B7-H4 antibody-drug conjugate is:
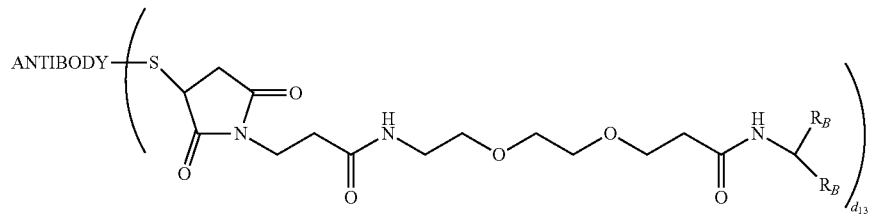
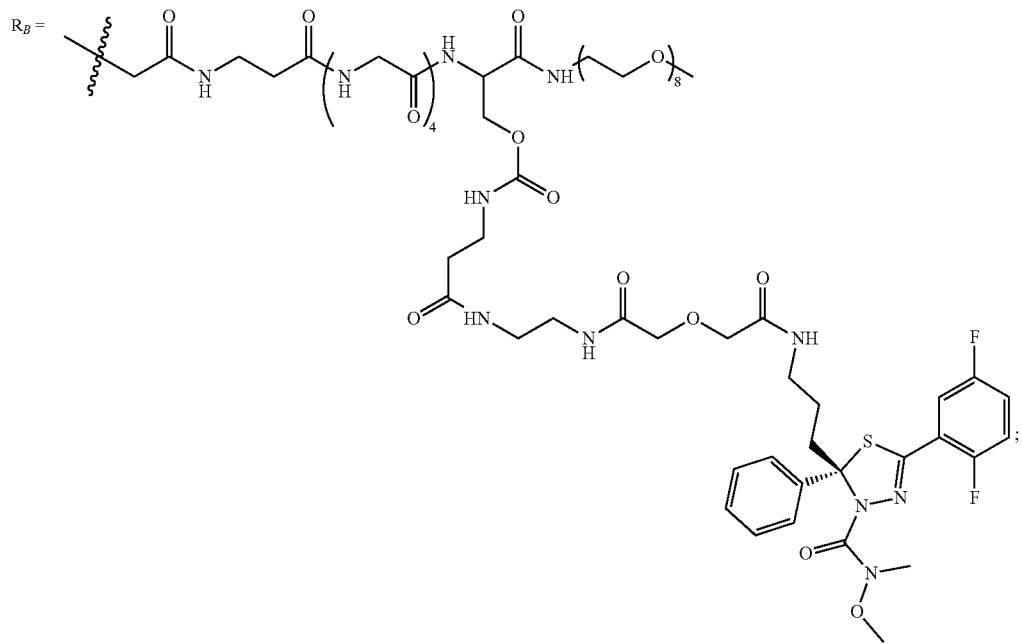
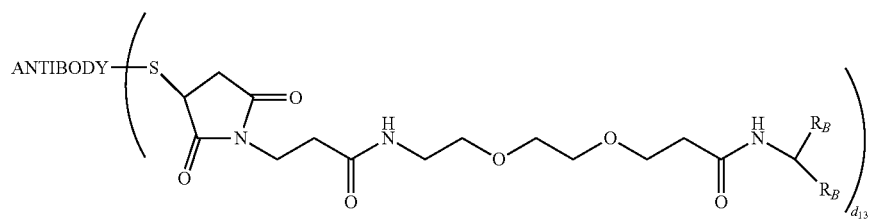

803                                                                                            804
-continued
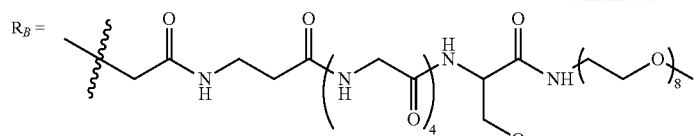
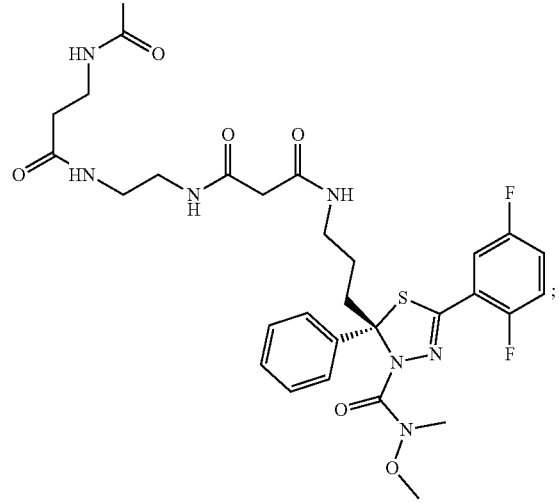
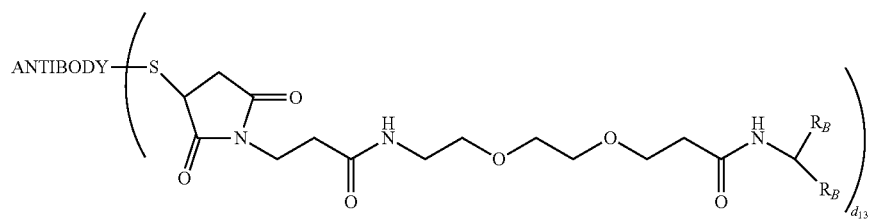
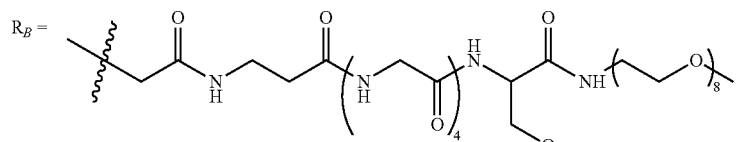
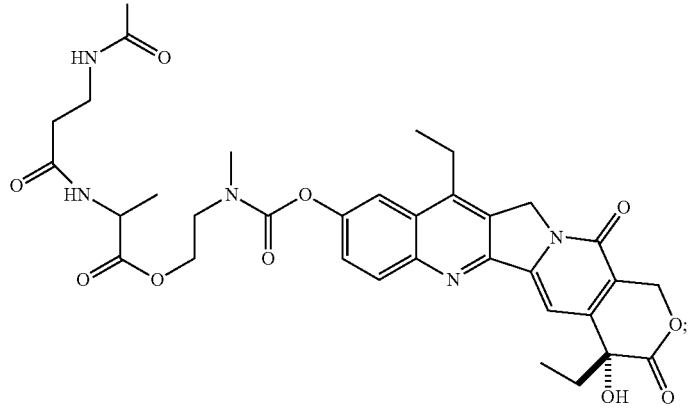
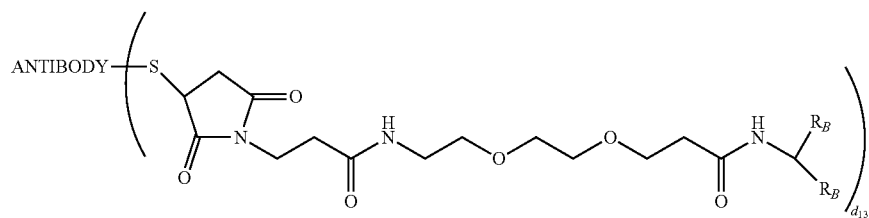

-continued
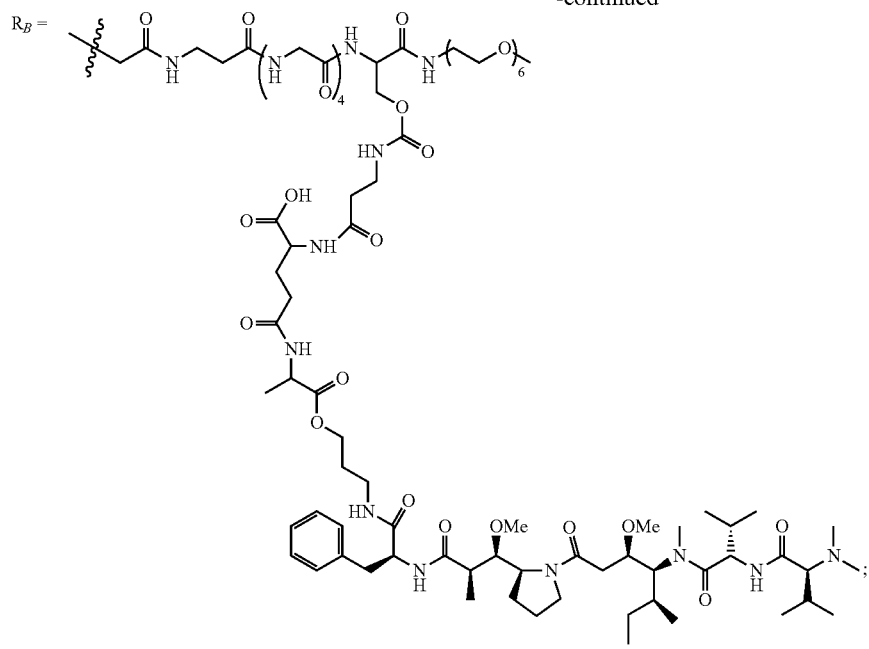
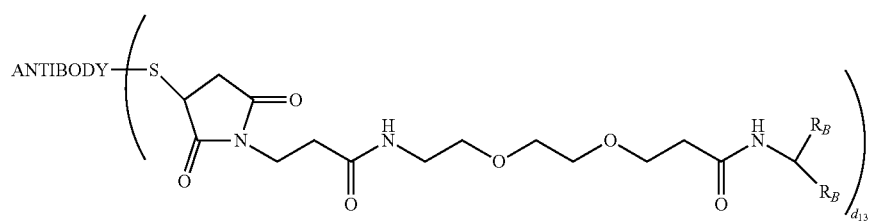
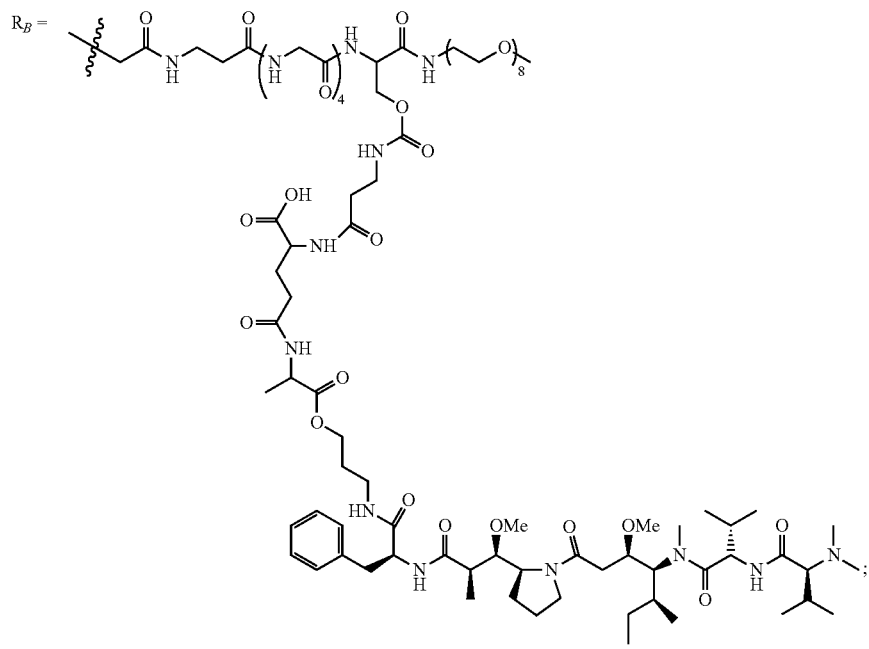
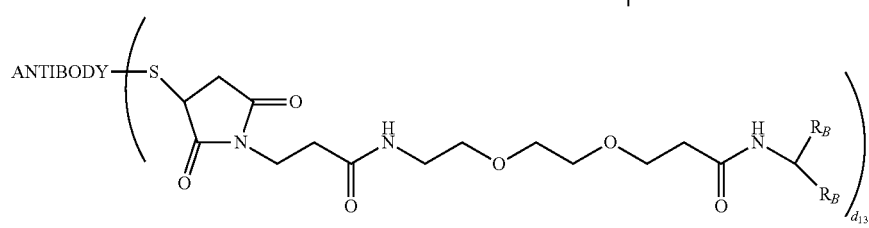

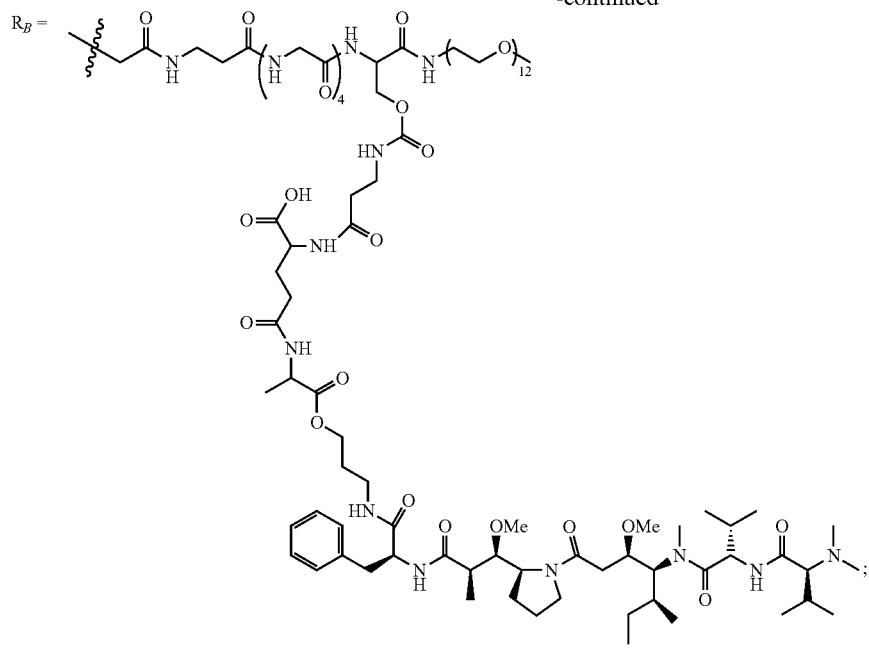
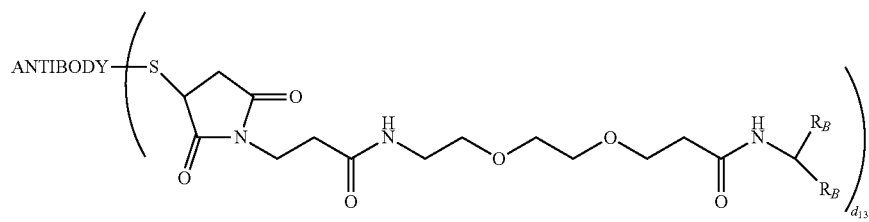
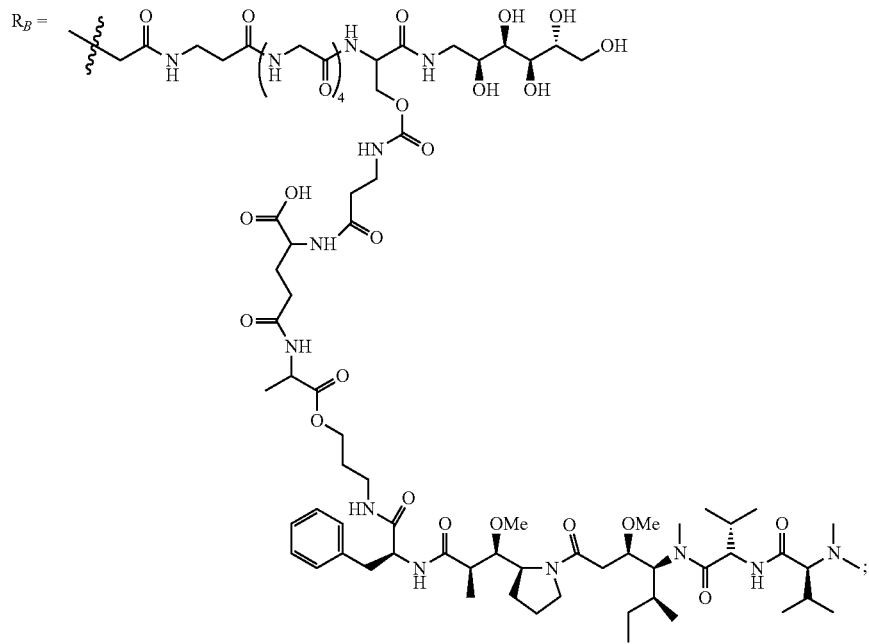

-continued
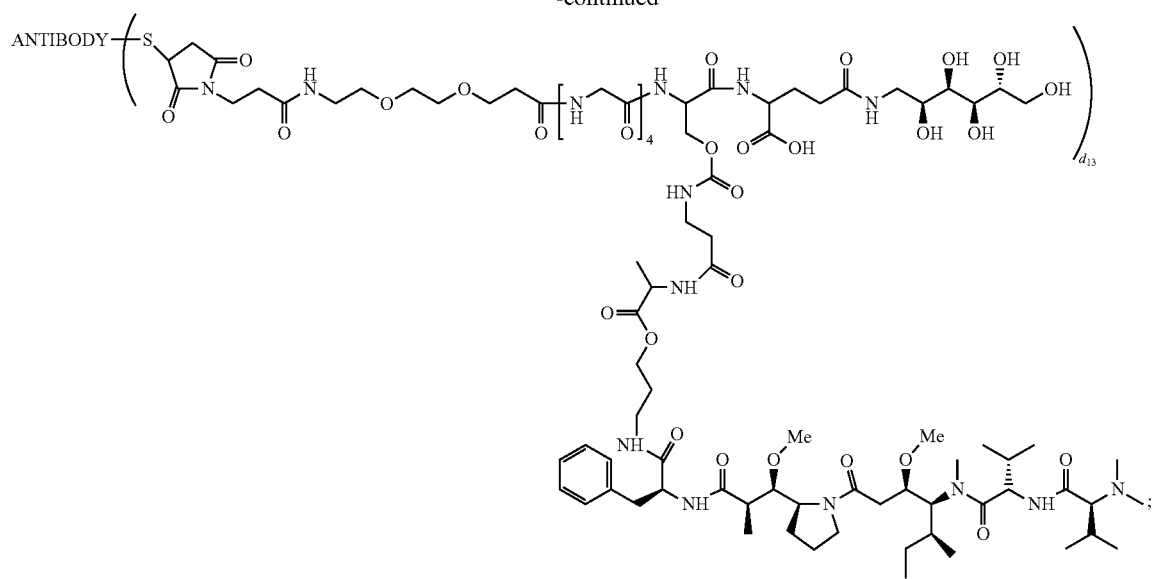
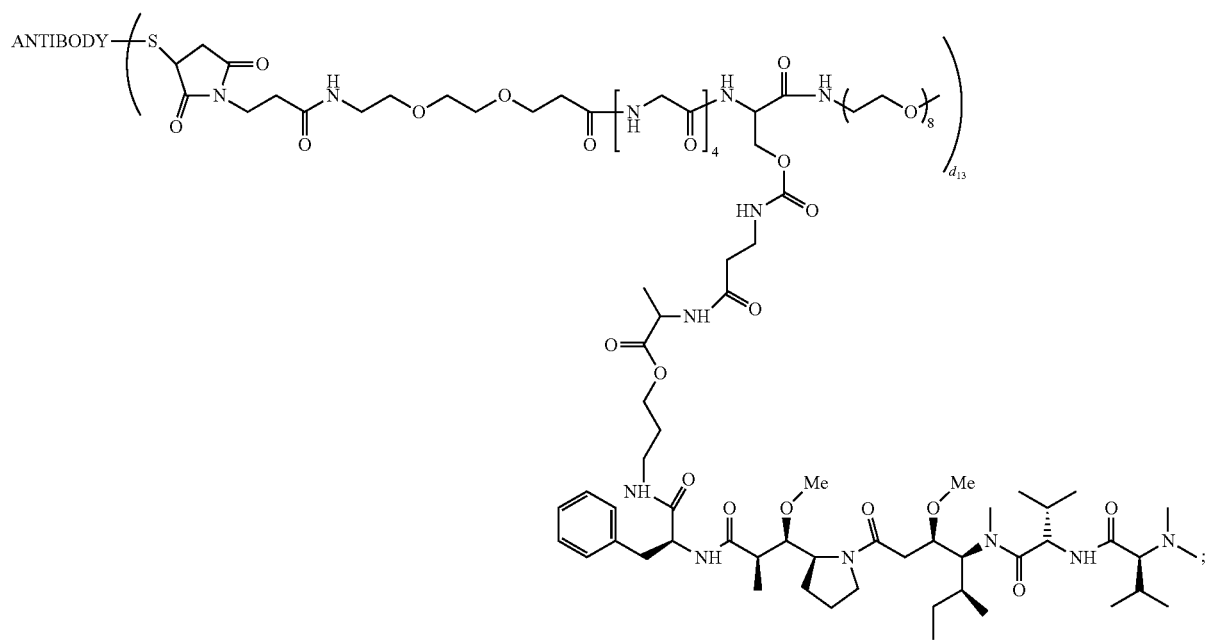

-continued
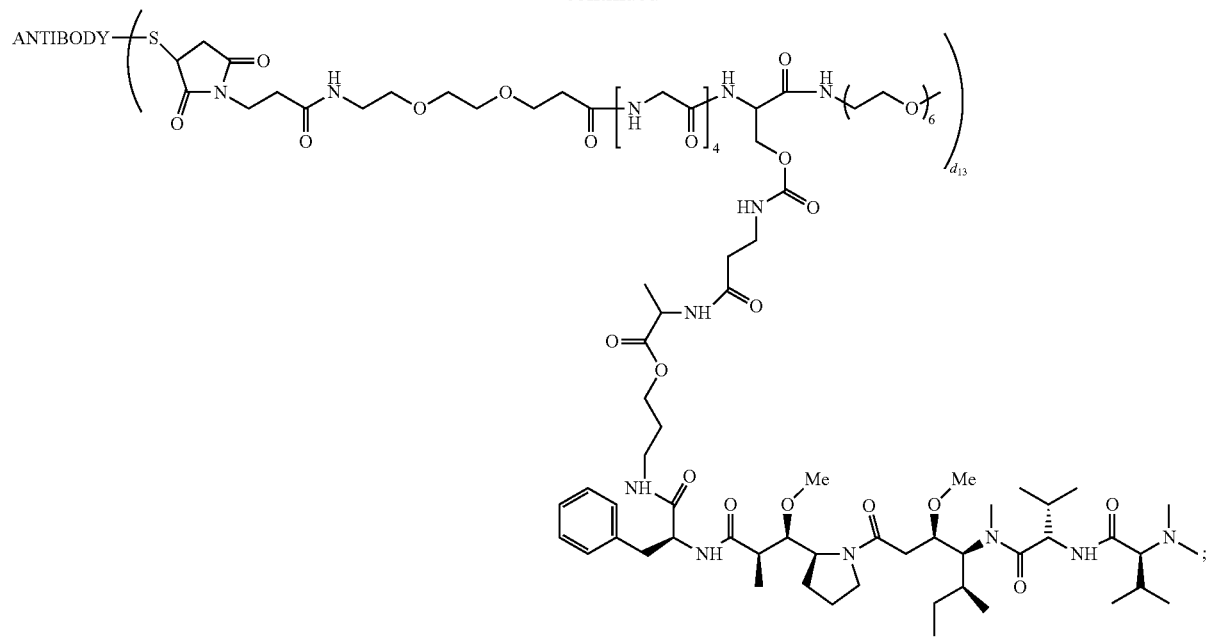
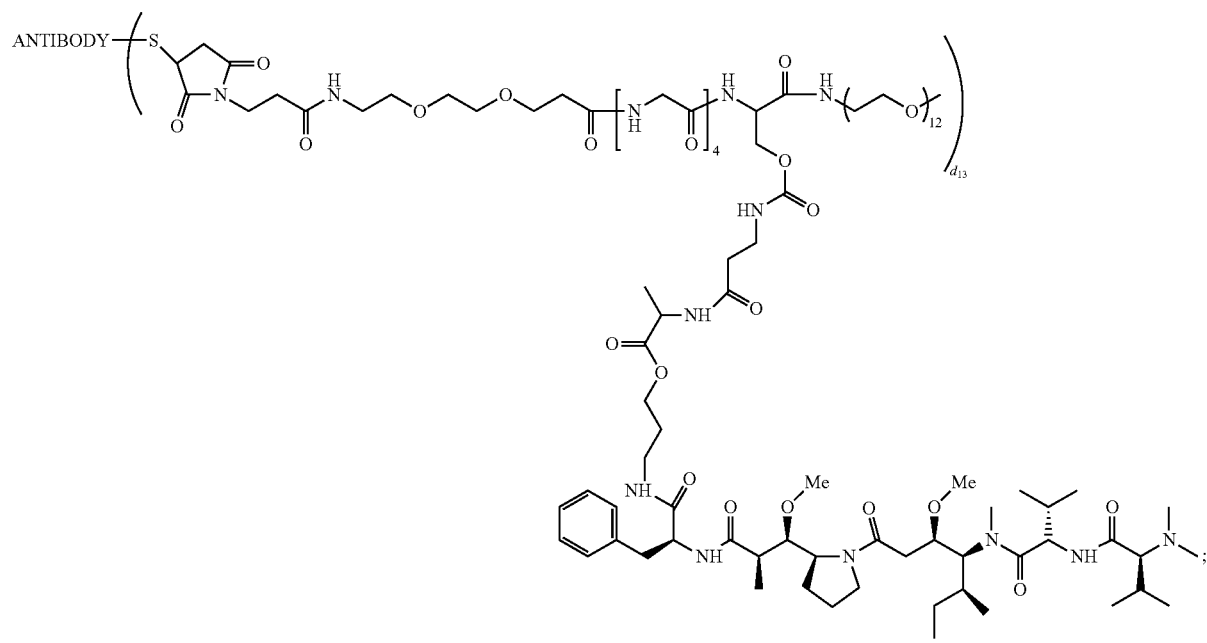

-continued
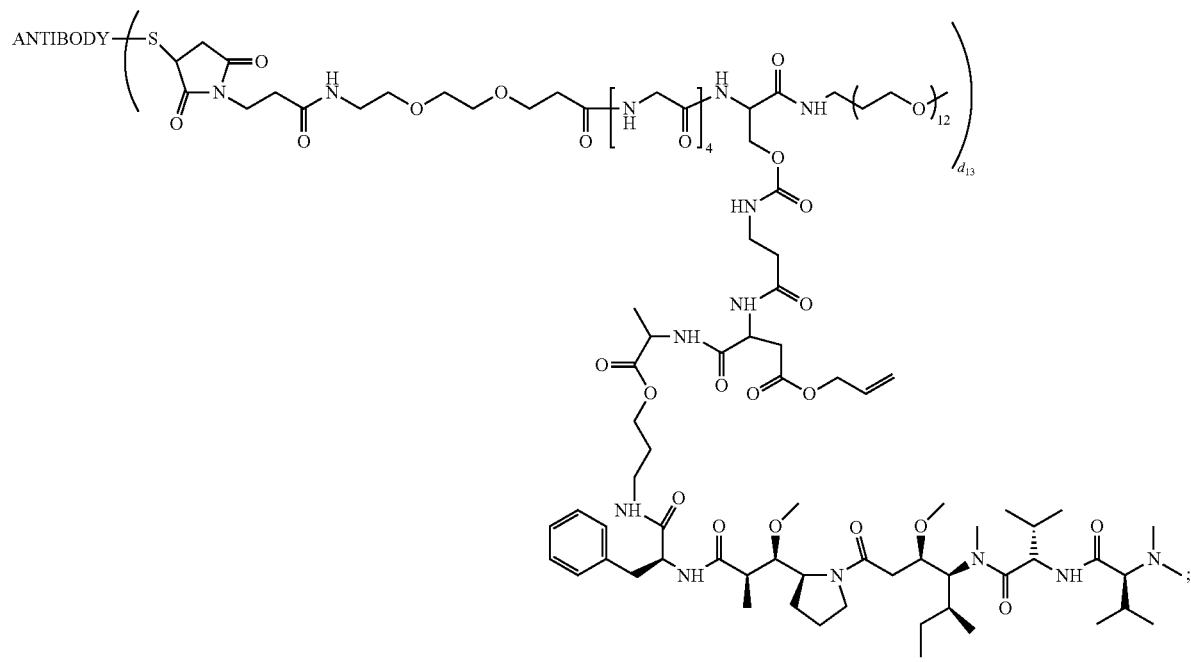
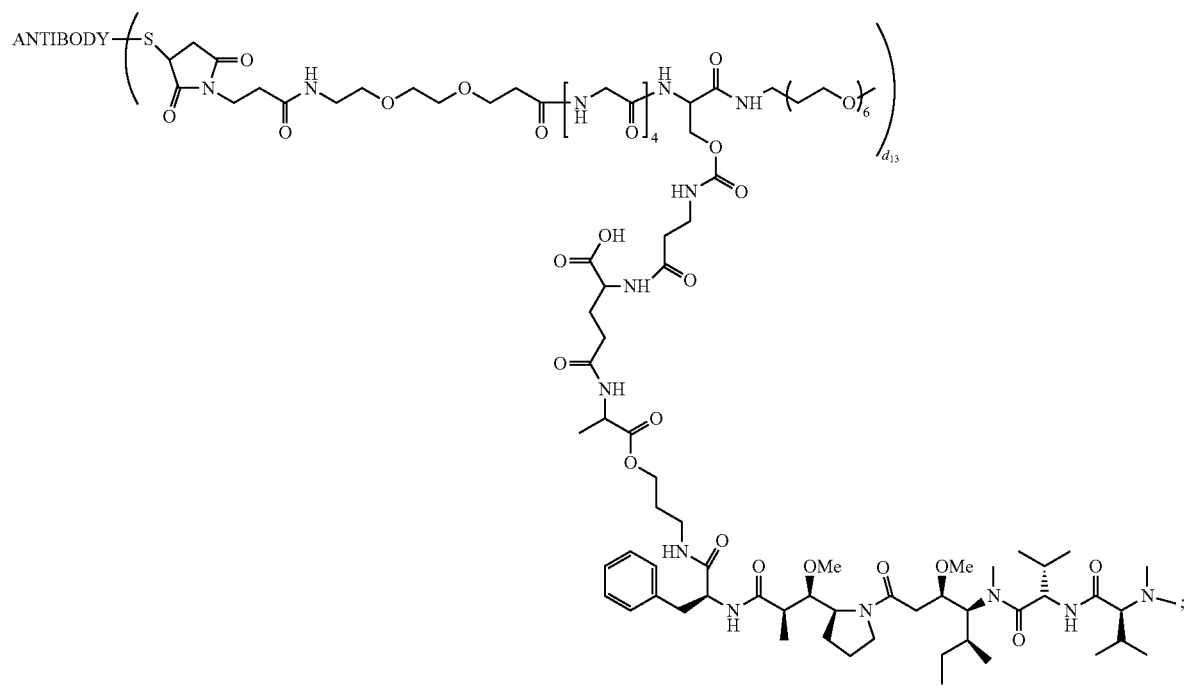

815
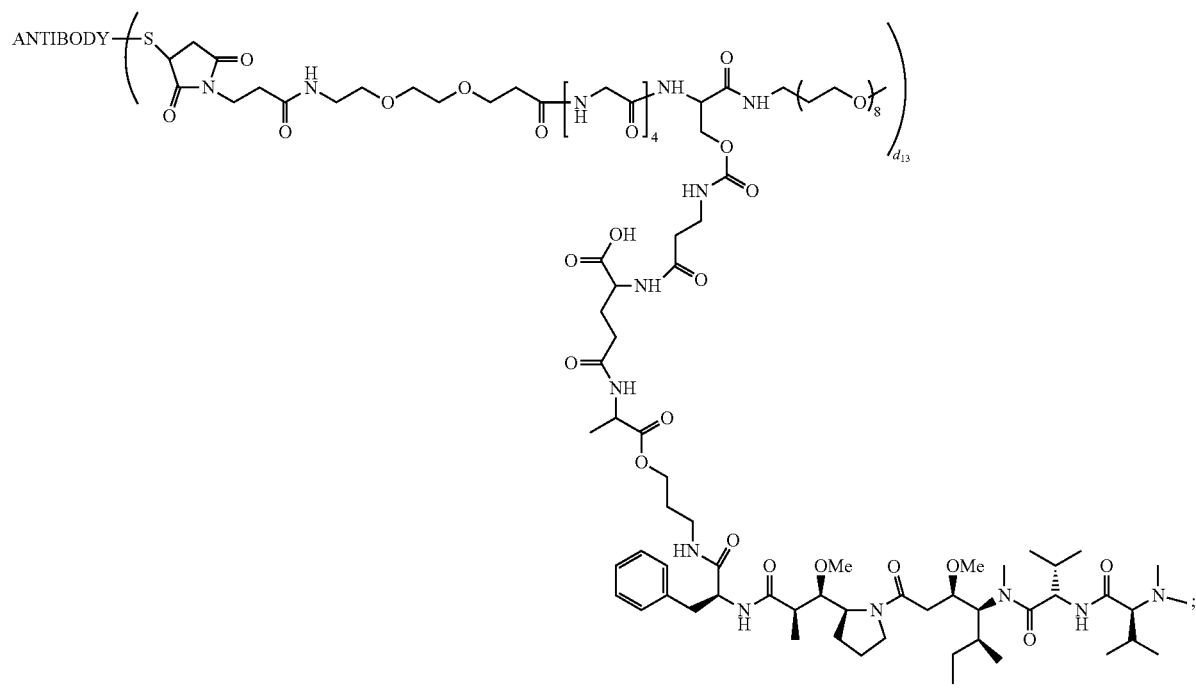
-continued
816
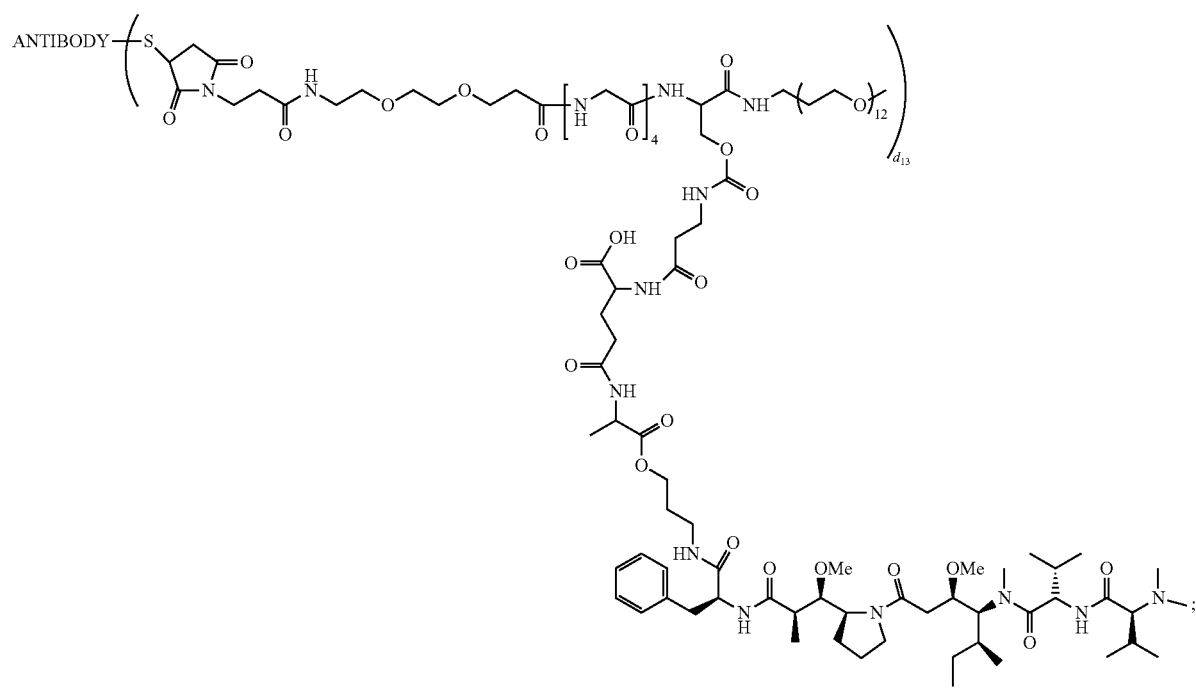

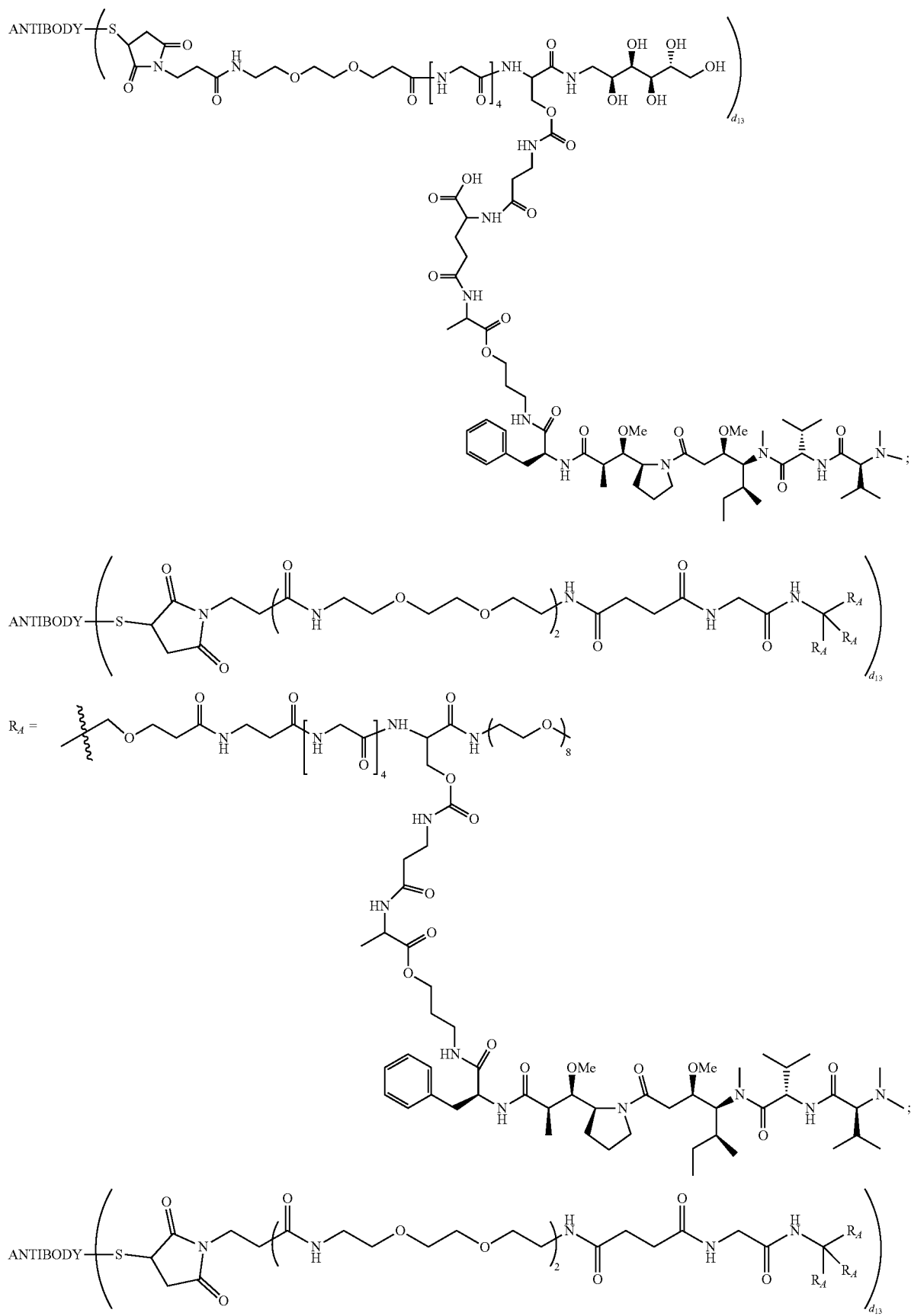

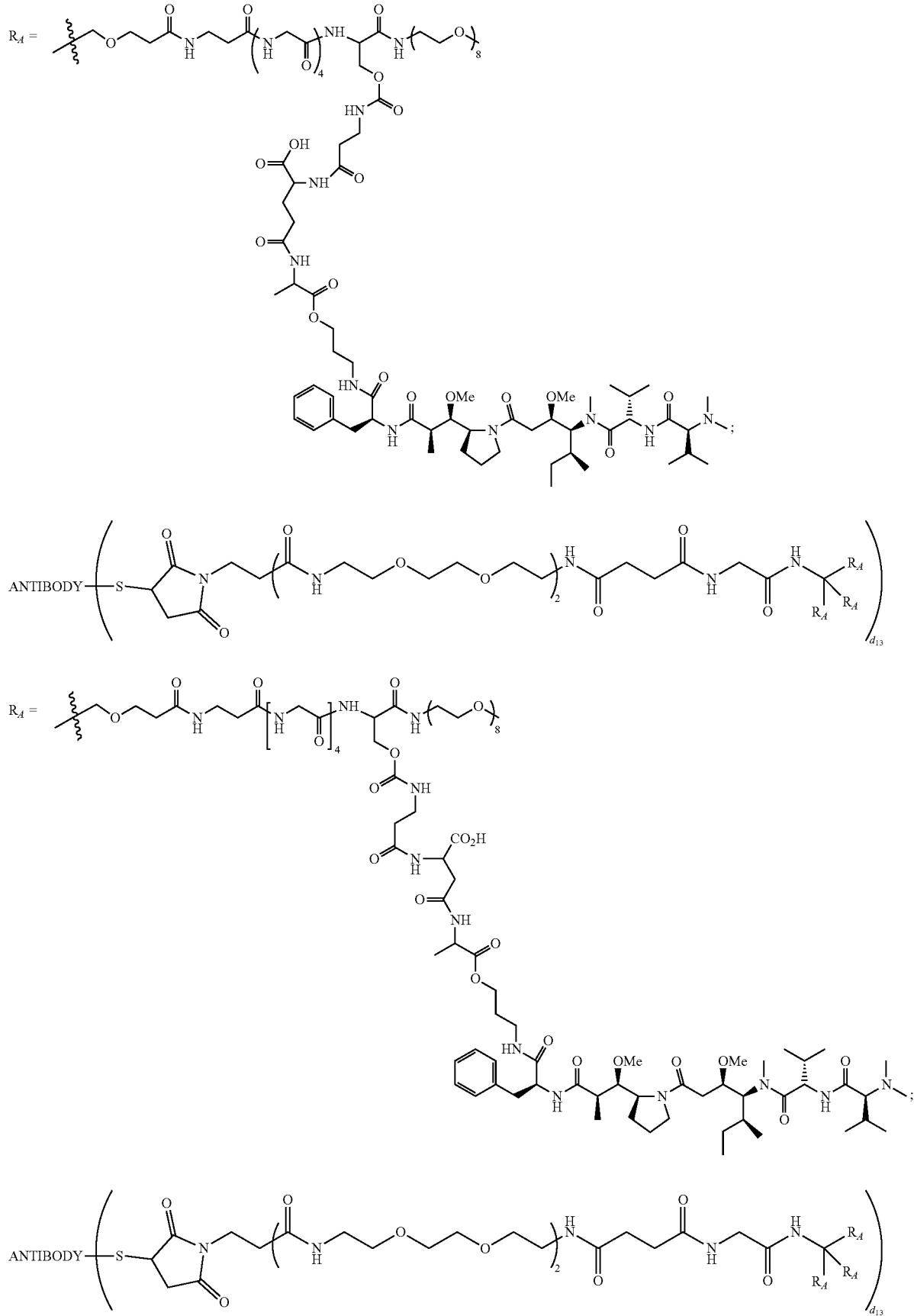

-continued
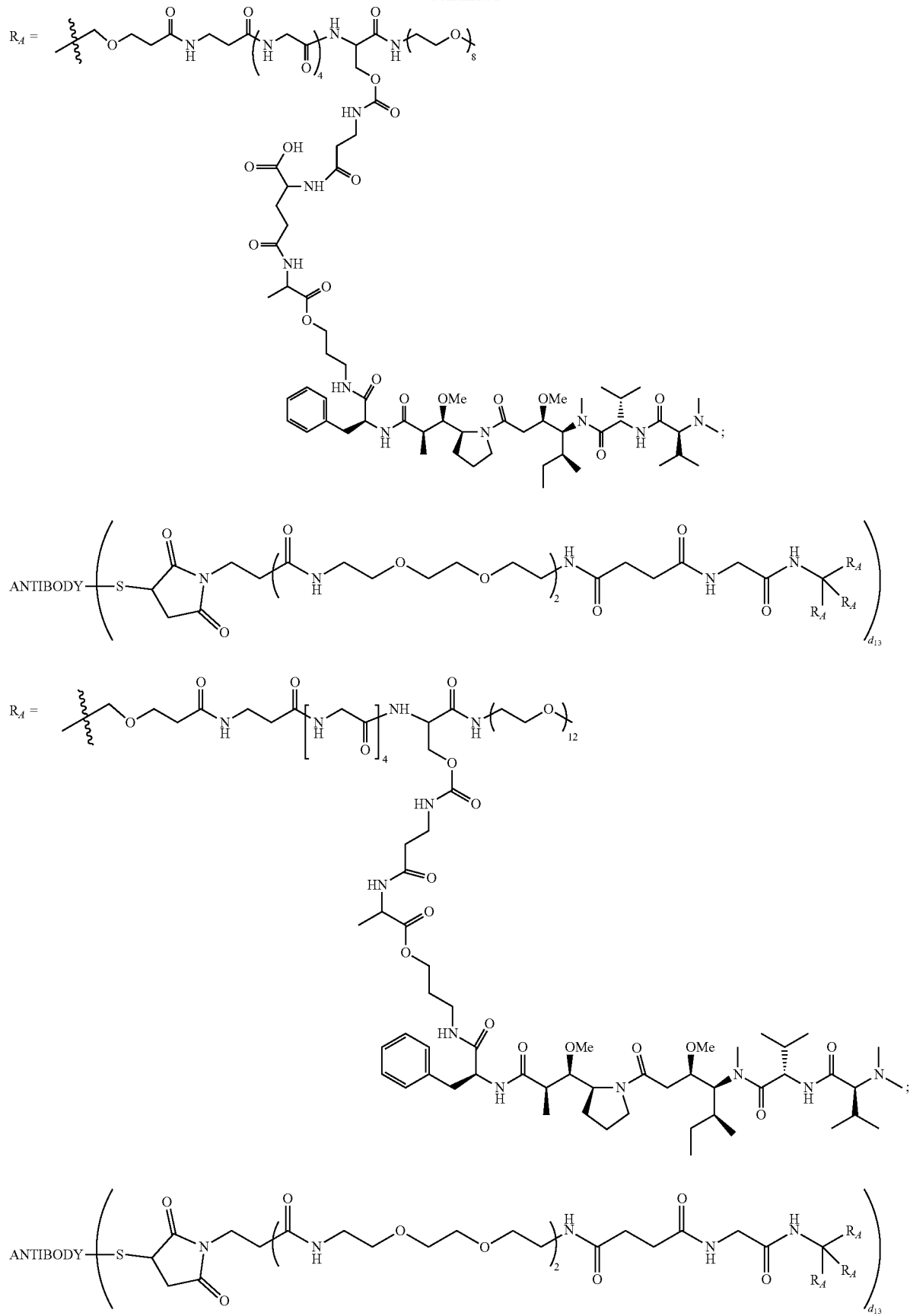

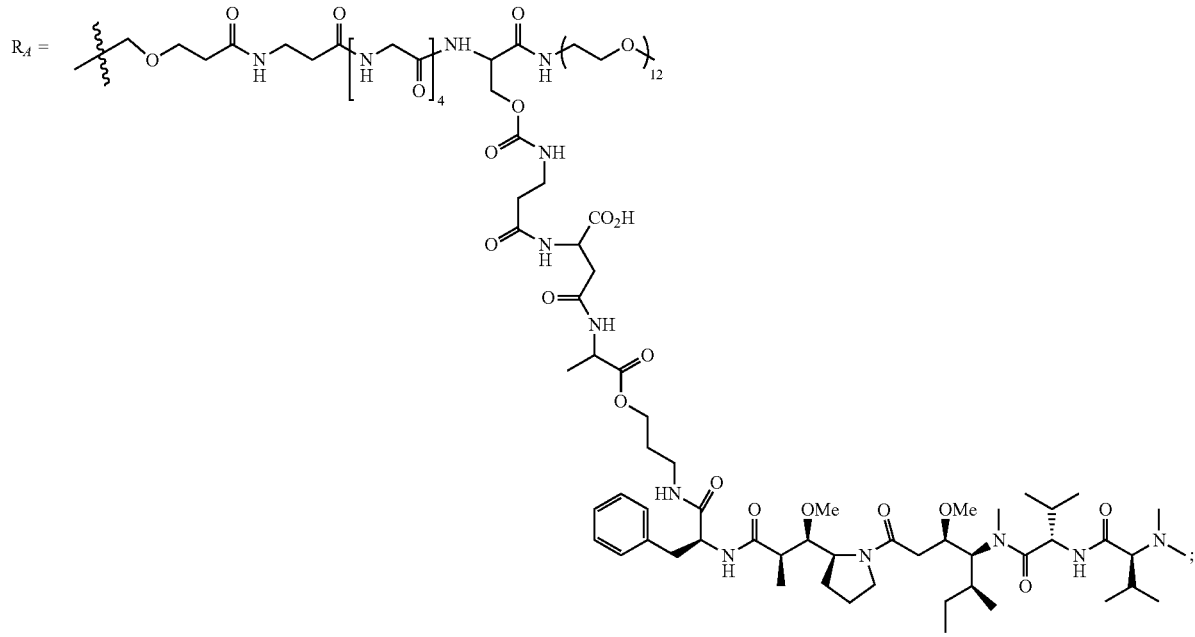
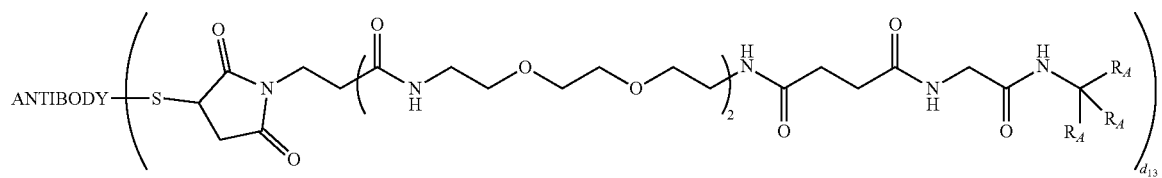
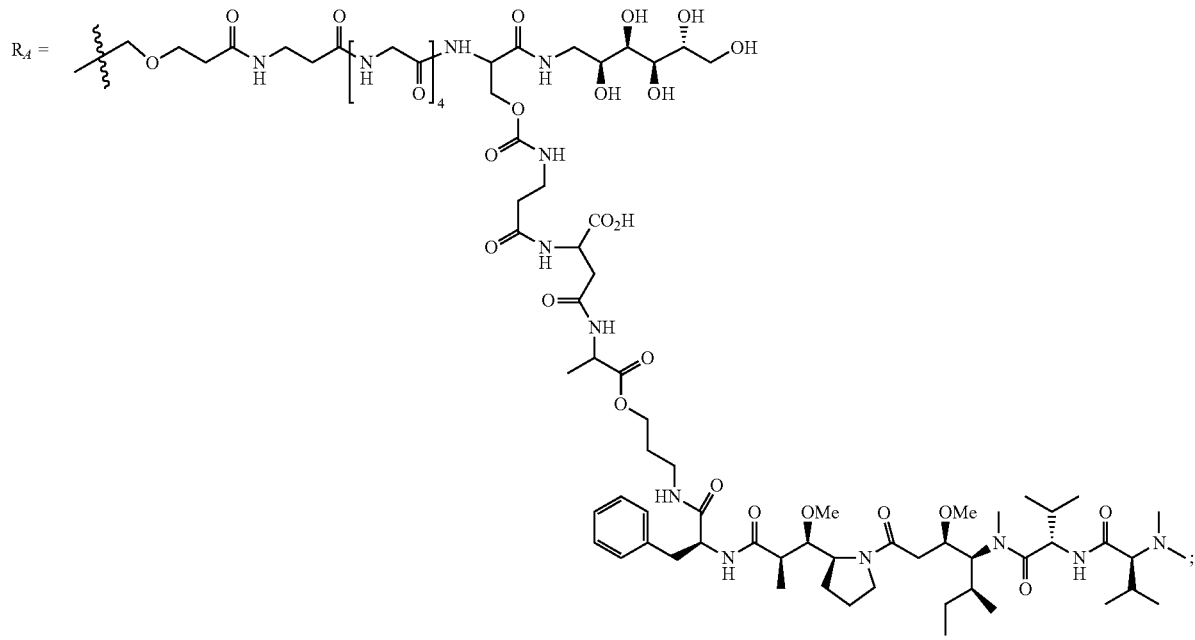
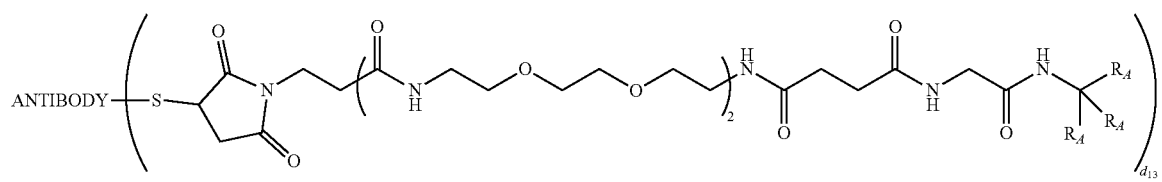

825
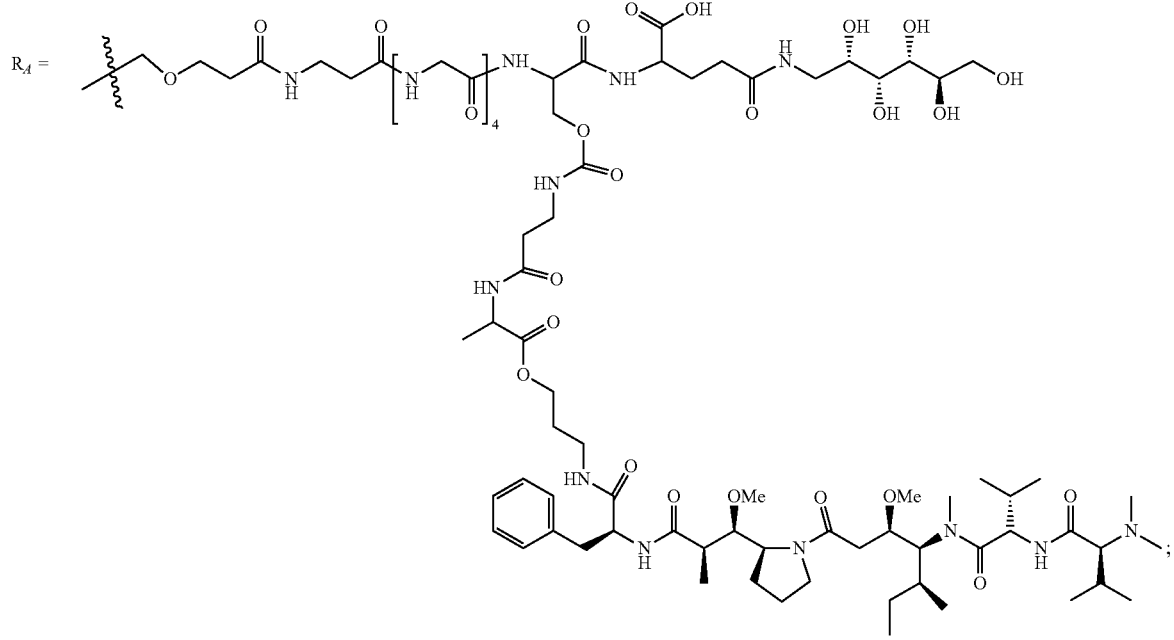
-continued
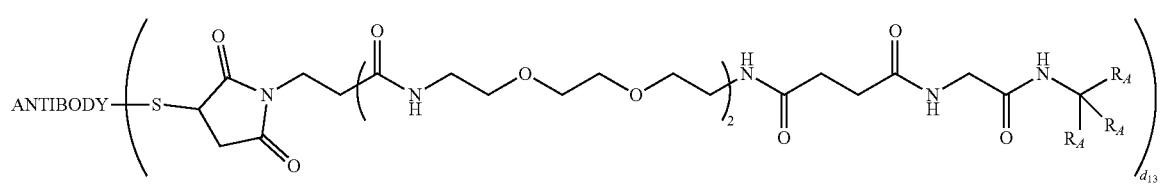
826
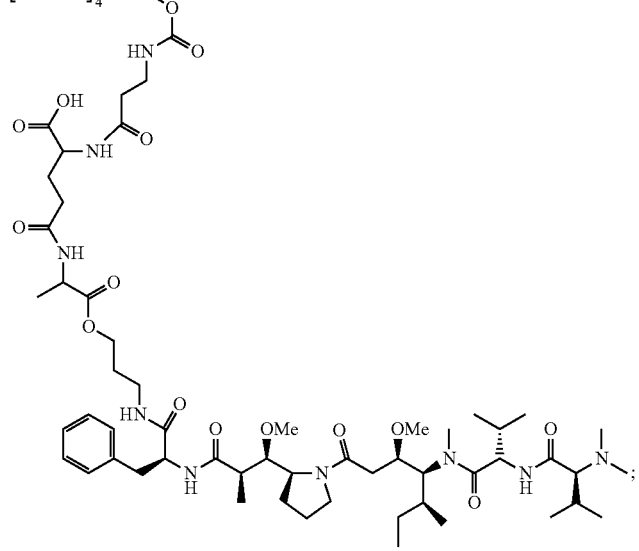
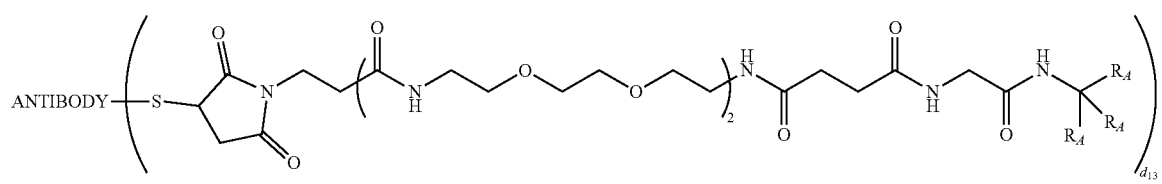

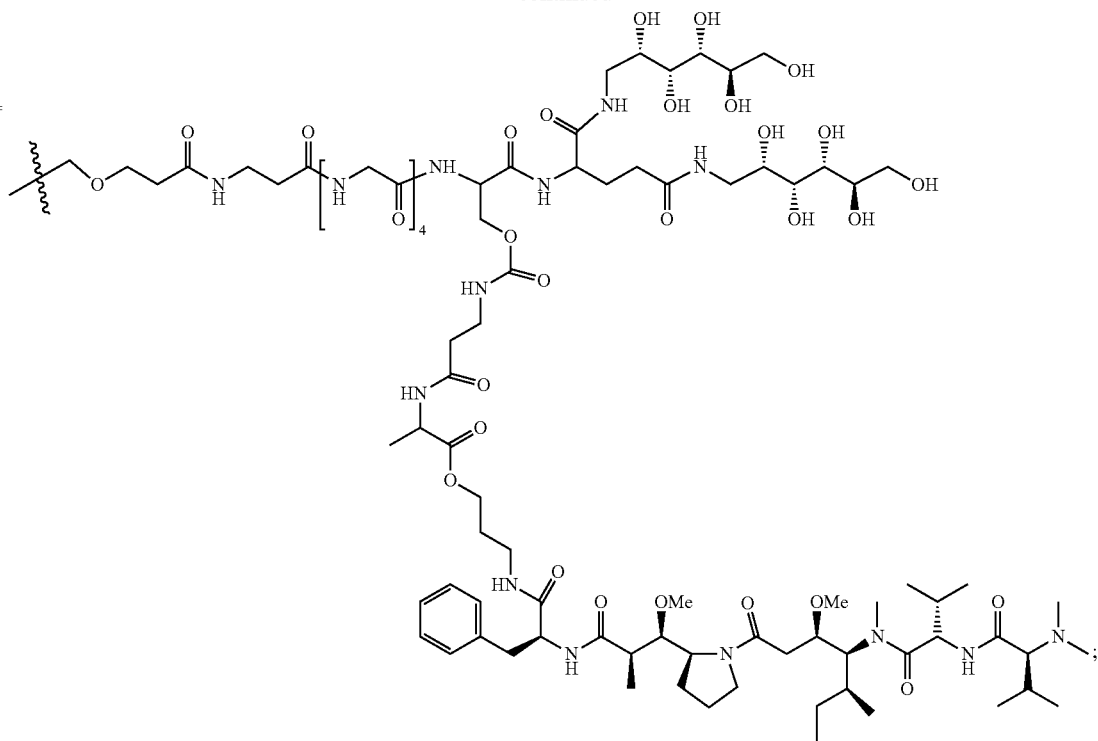
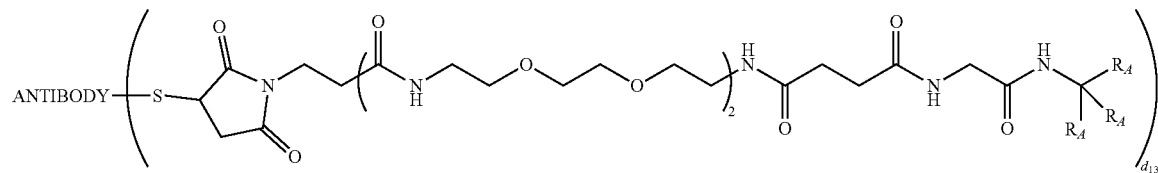
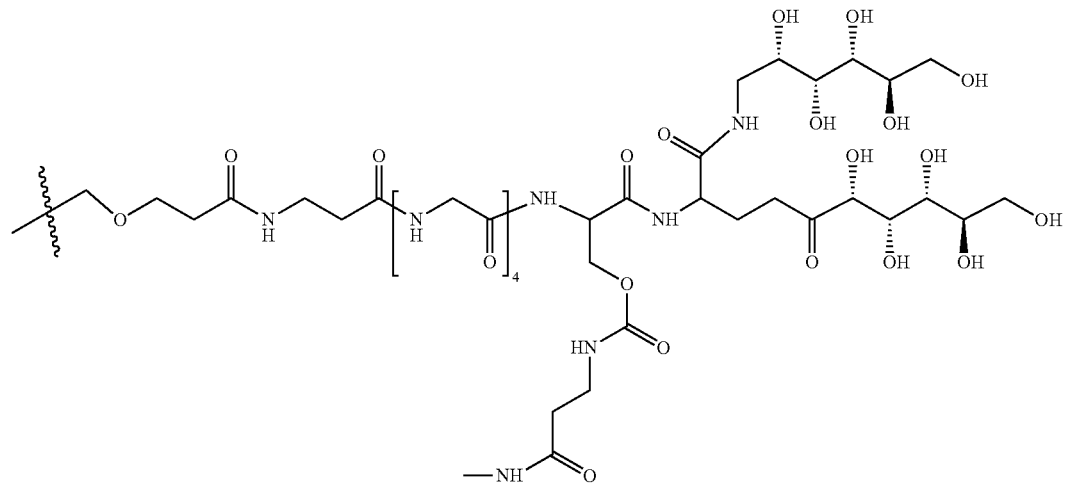

-continued
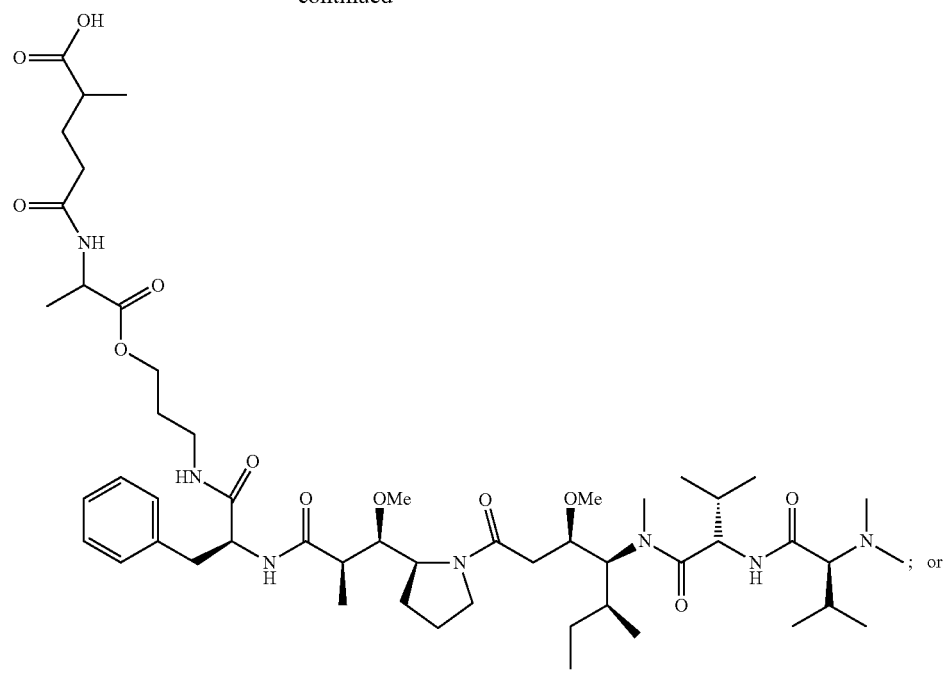
; or
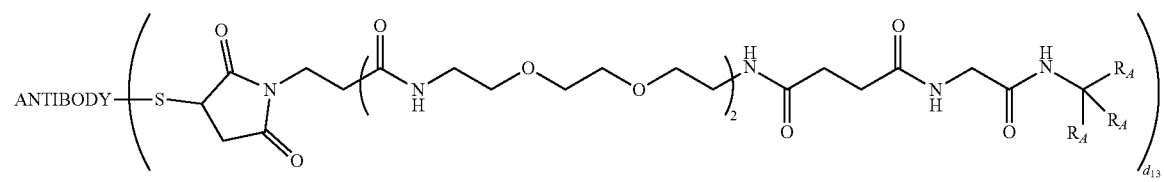
$R_A =$ 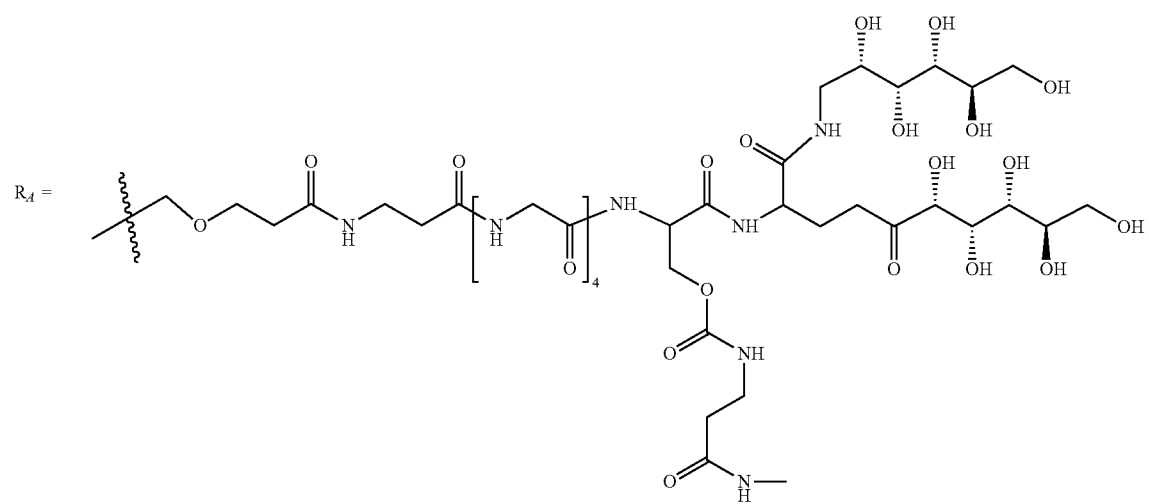

-continued
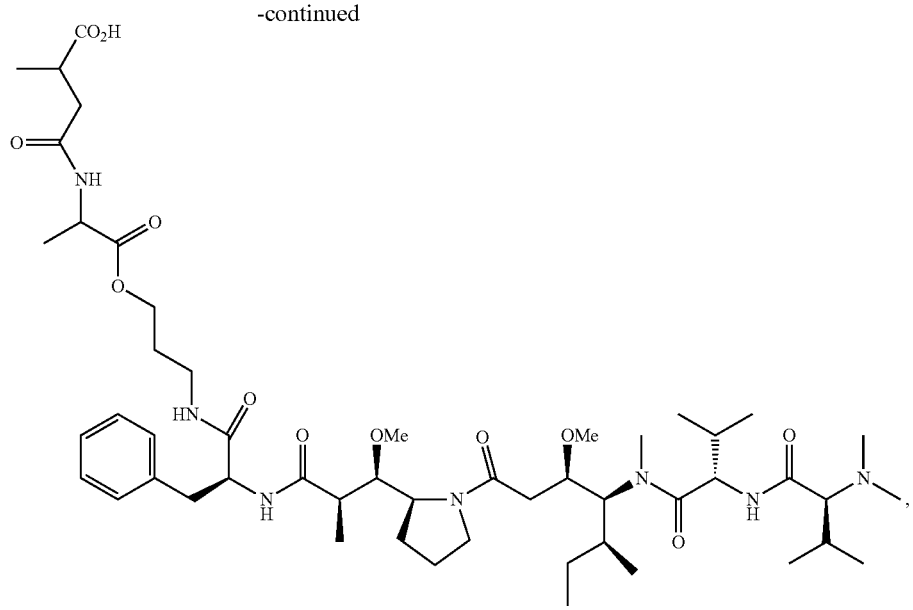
wherein $d_{13}$ is from about 2 to about 12.
23. The B7-H4 antibody-drug conjugate of claim 9, wherein the B7-H4 antibody-drug conjugate is:
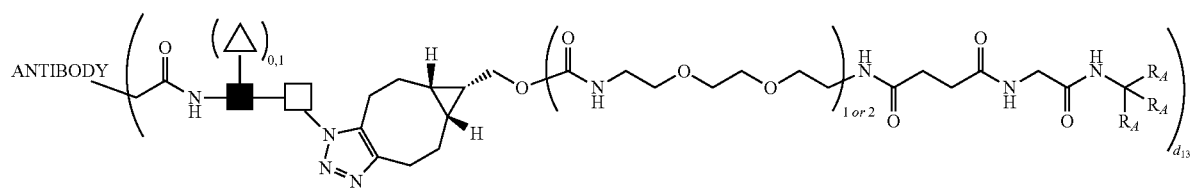
$R_A =$
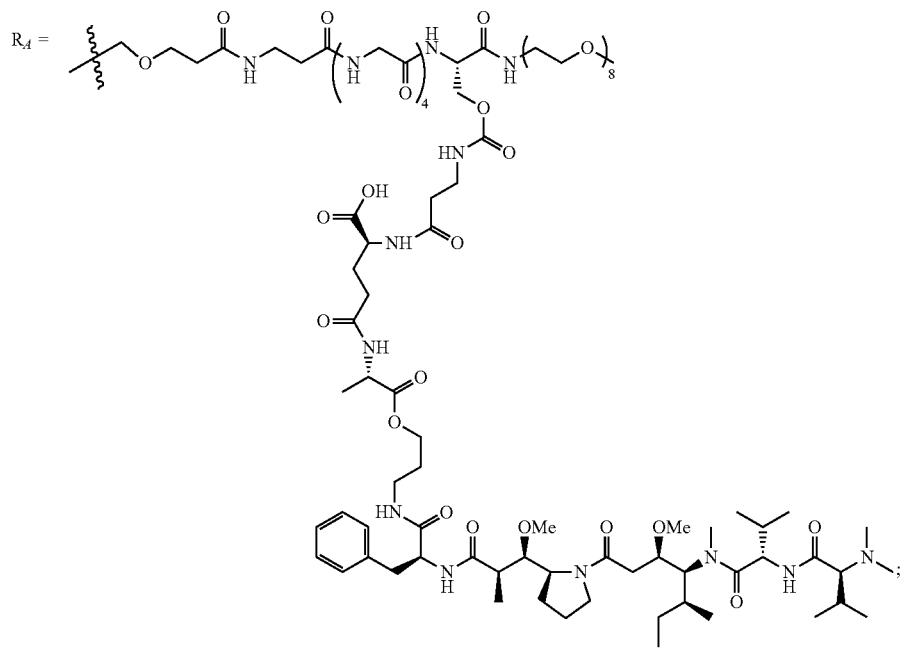

833 834
-continued
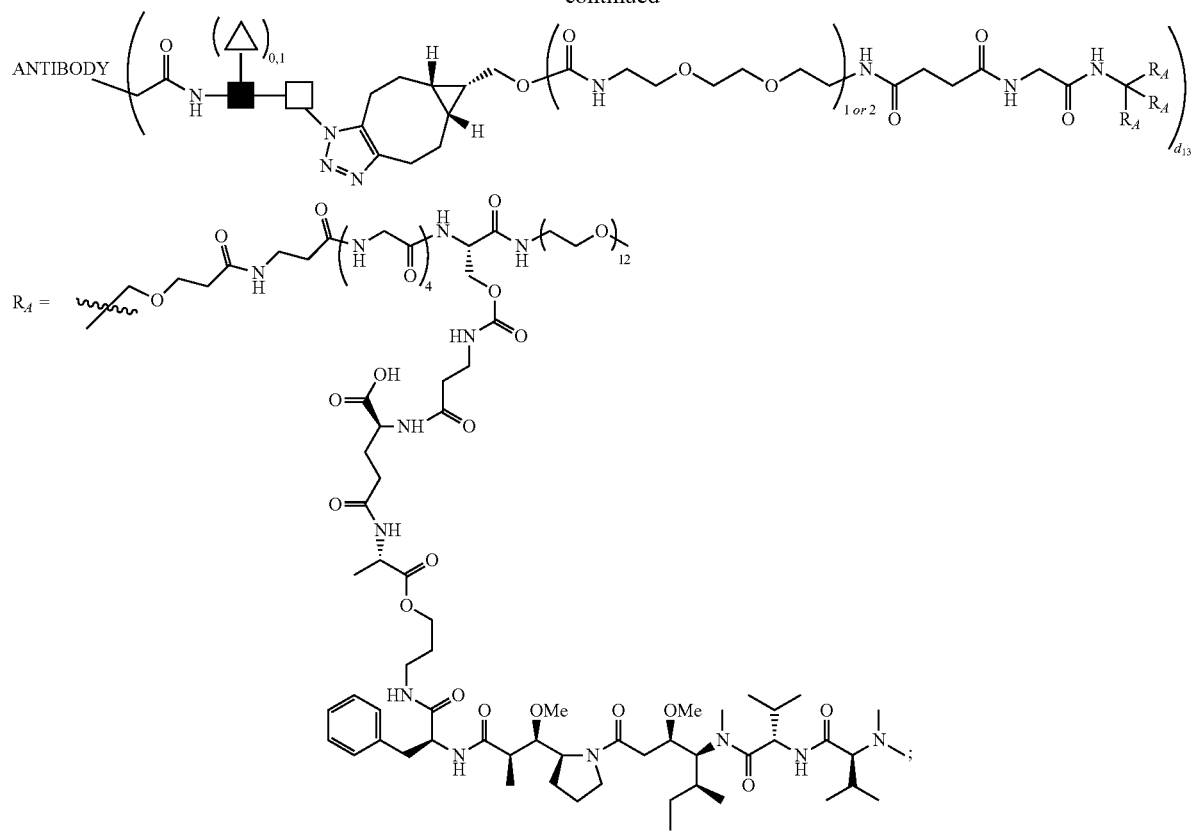
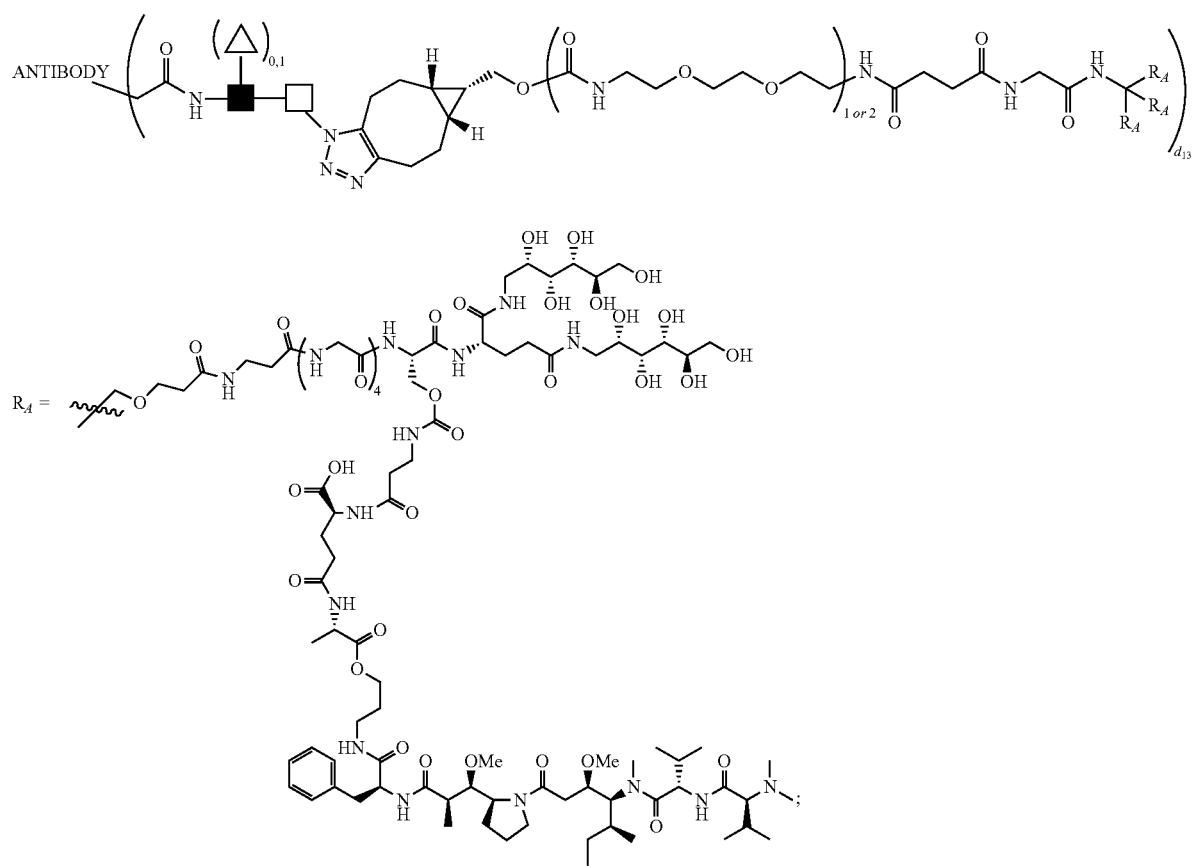

835
836
-continued
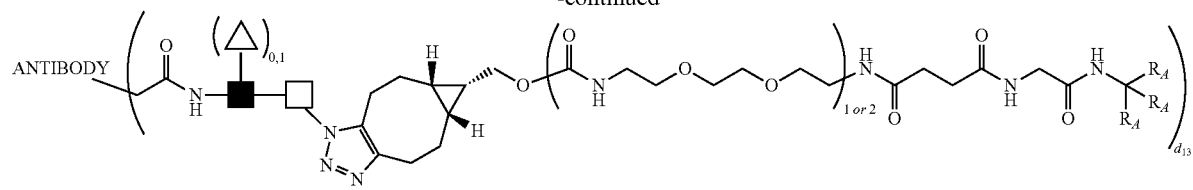
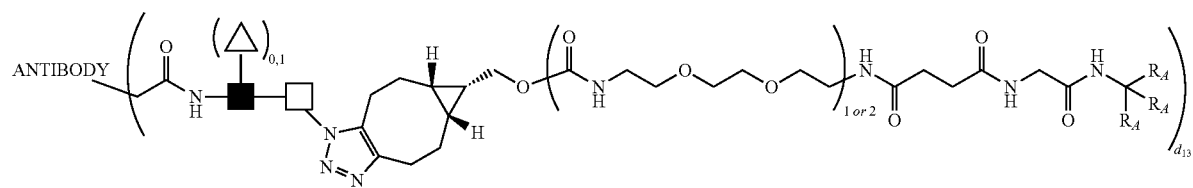

837                                                838
-continued
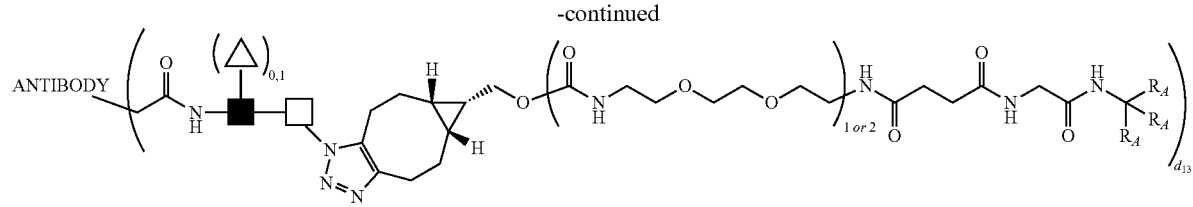
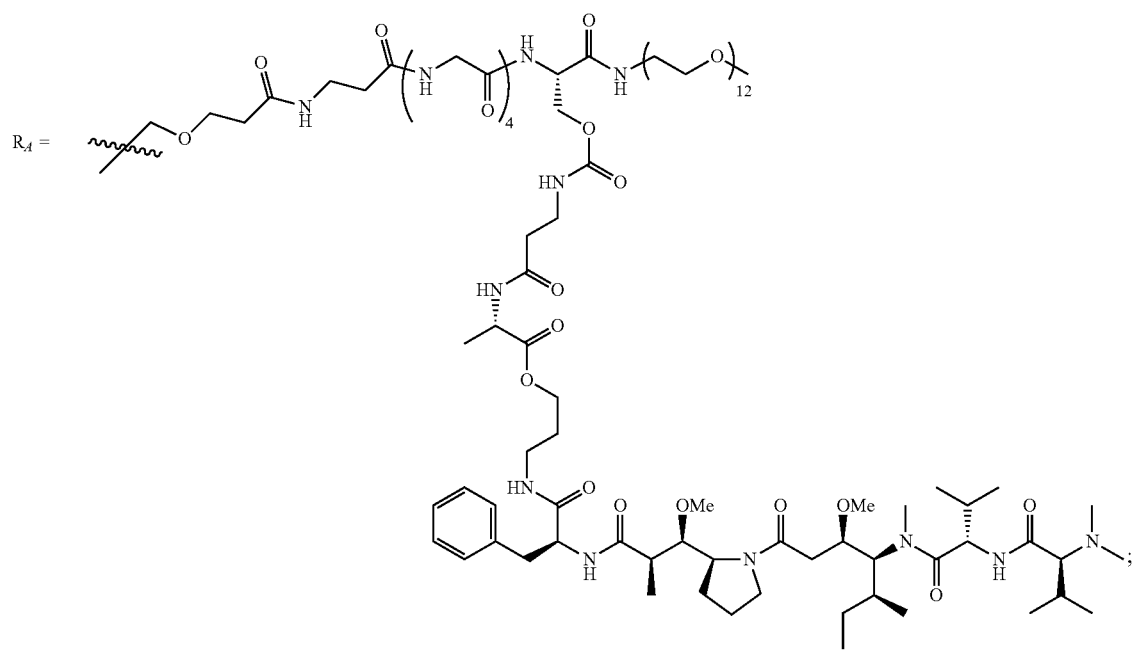
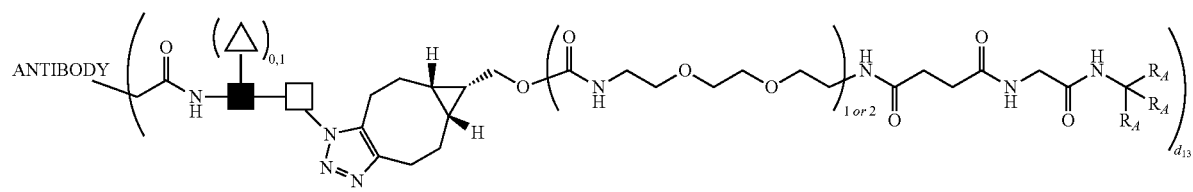
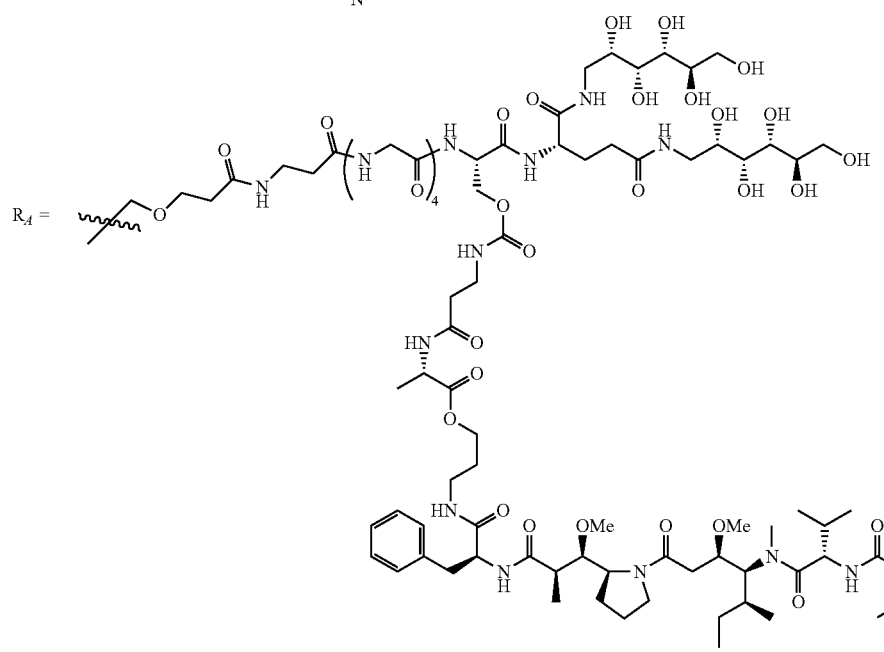

839
840
-continued
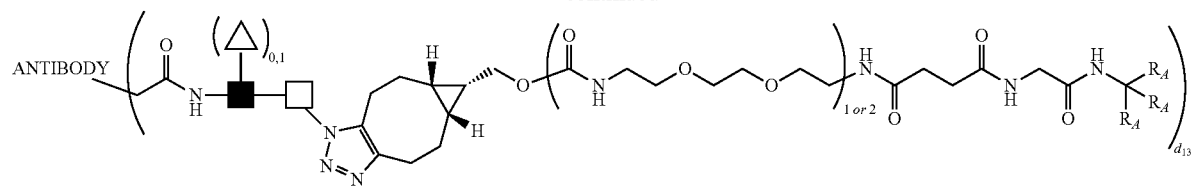
$R_A =$
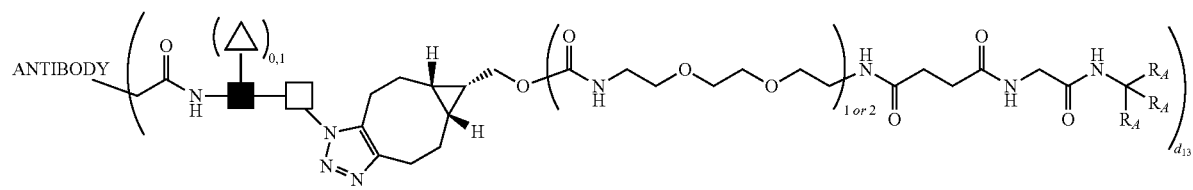
$R_A =$

-continued
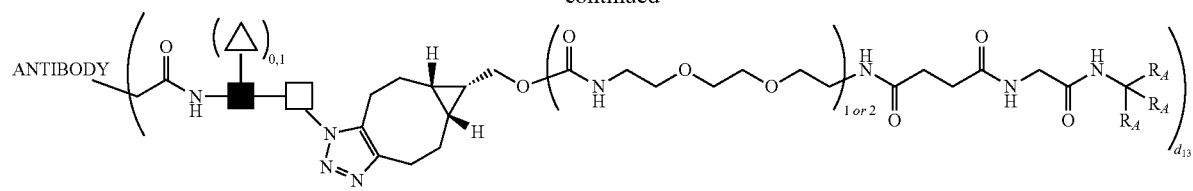
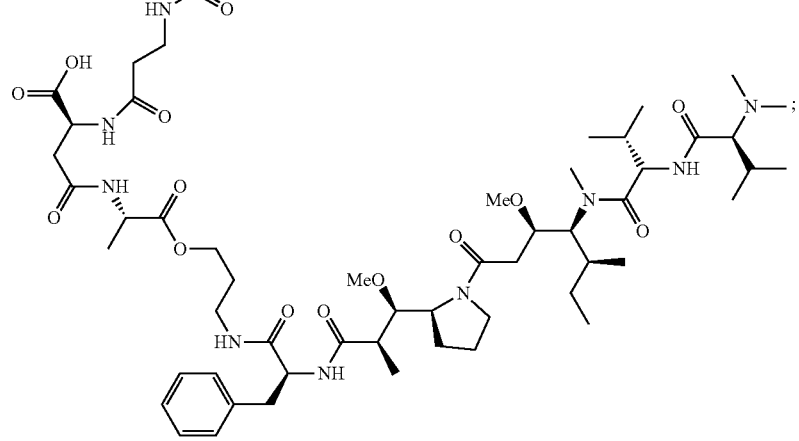
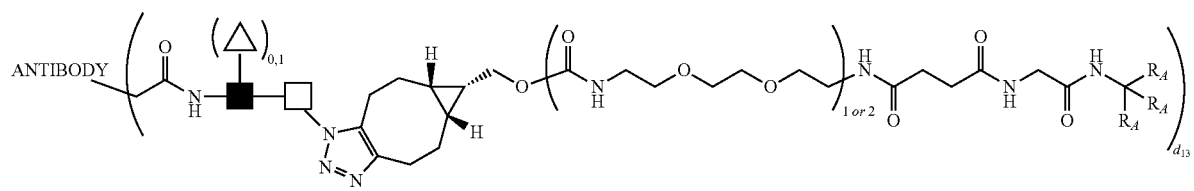
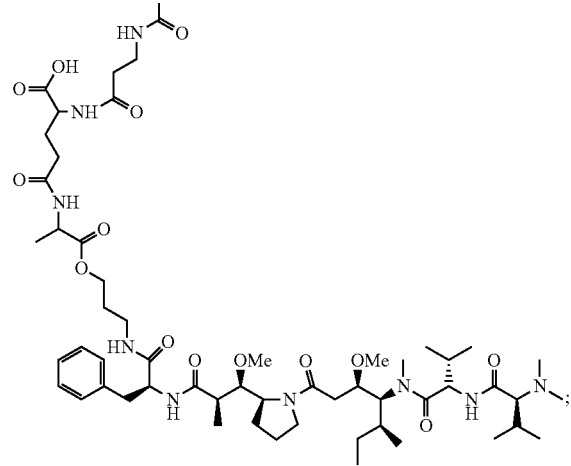

-continued
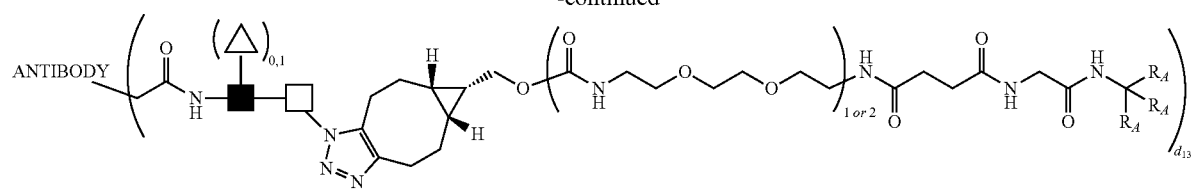
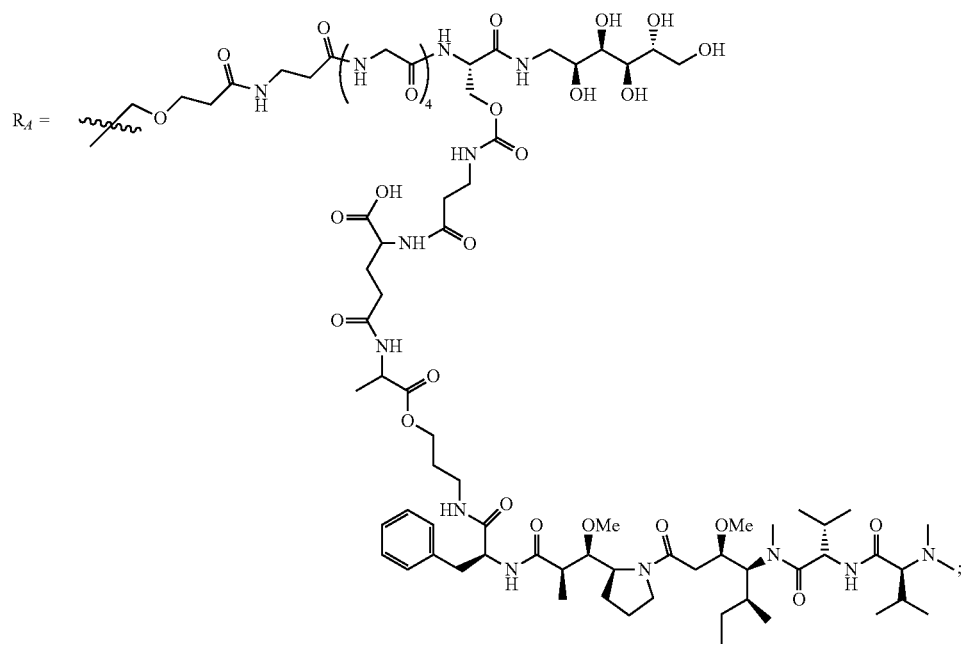
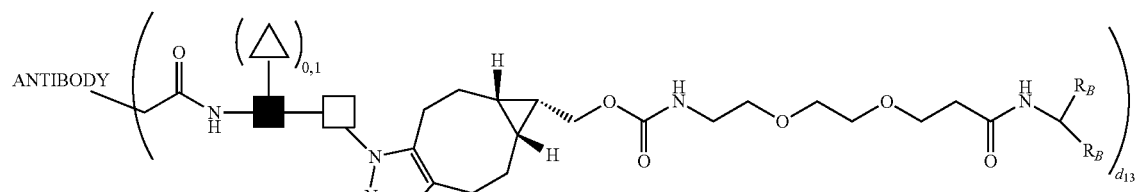
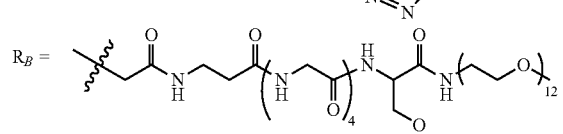
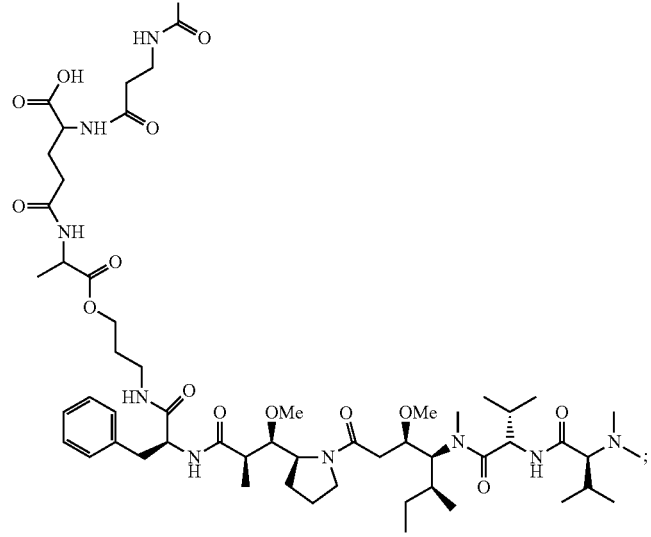

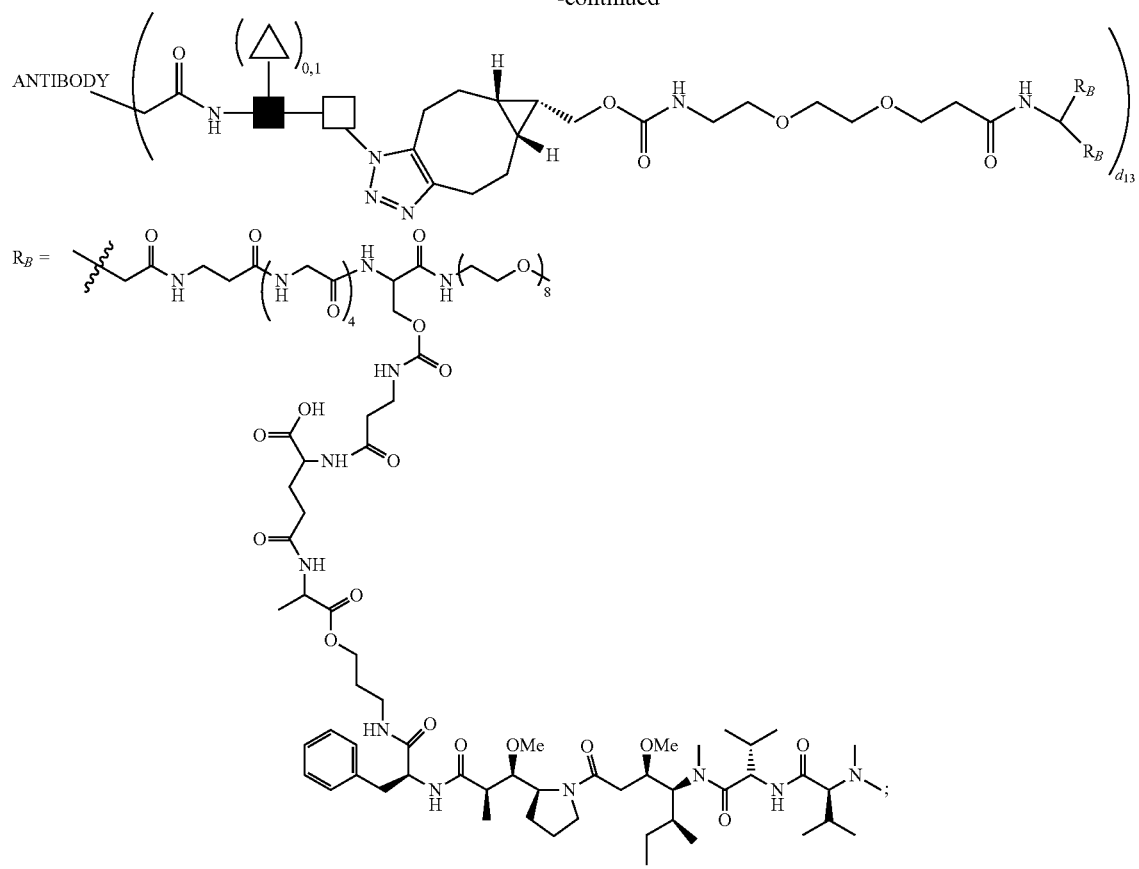
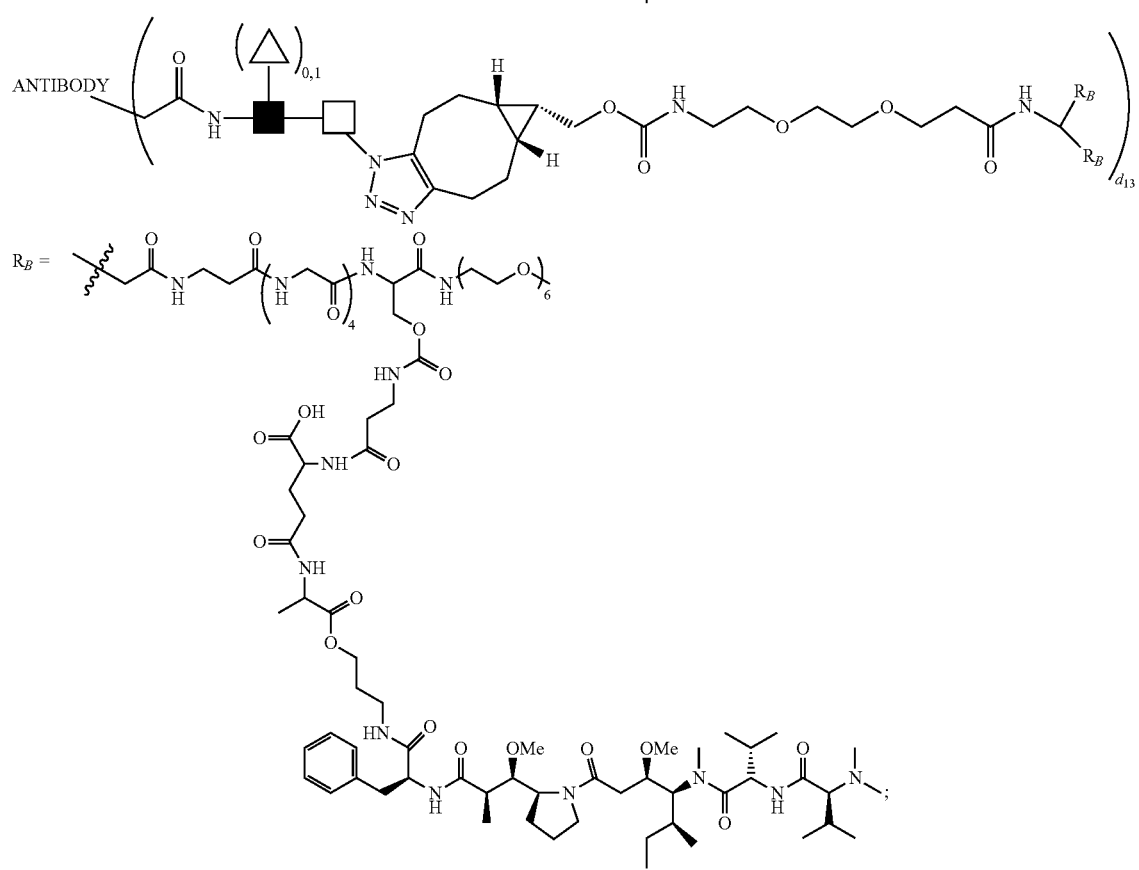

-continued
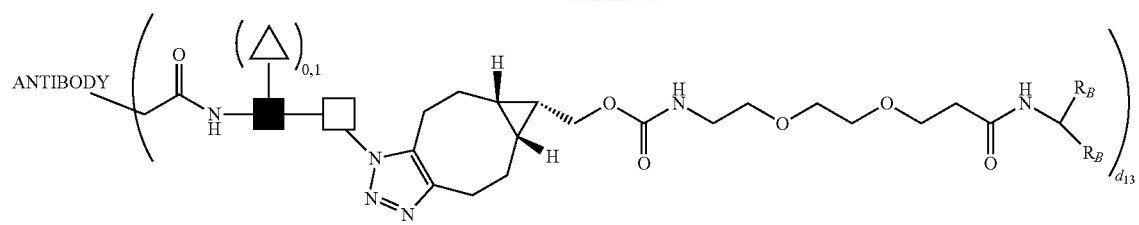
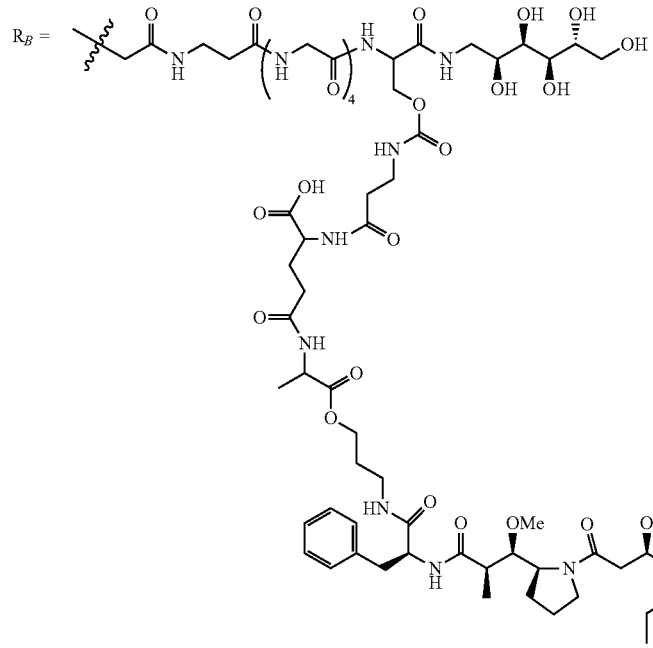
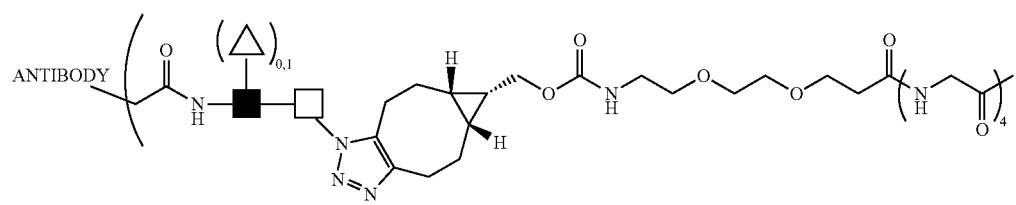
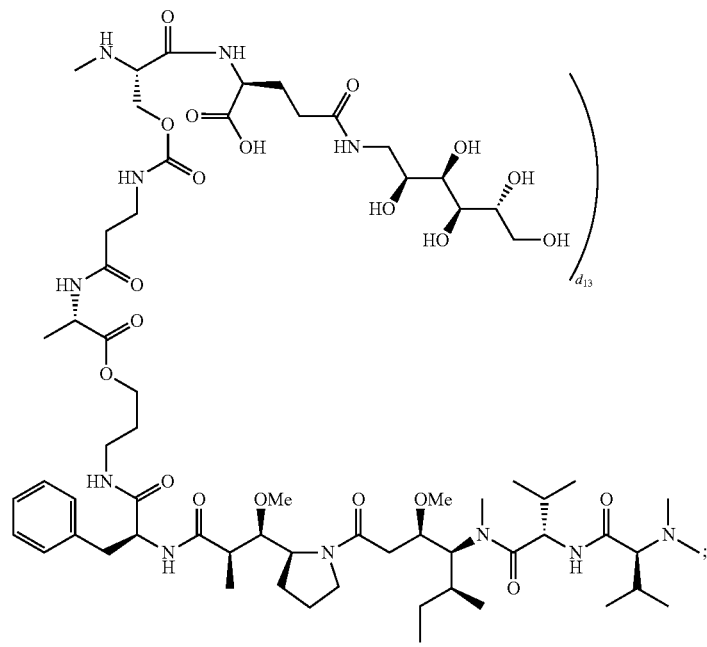

849
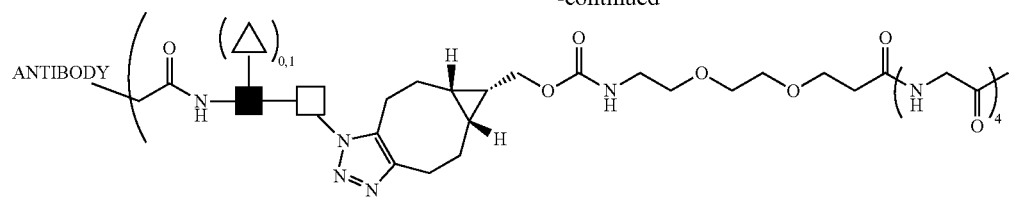
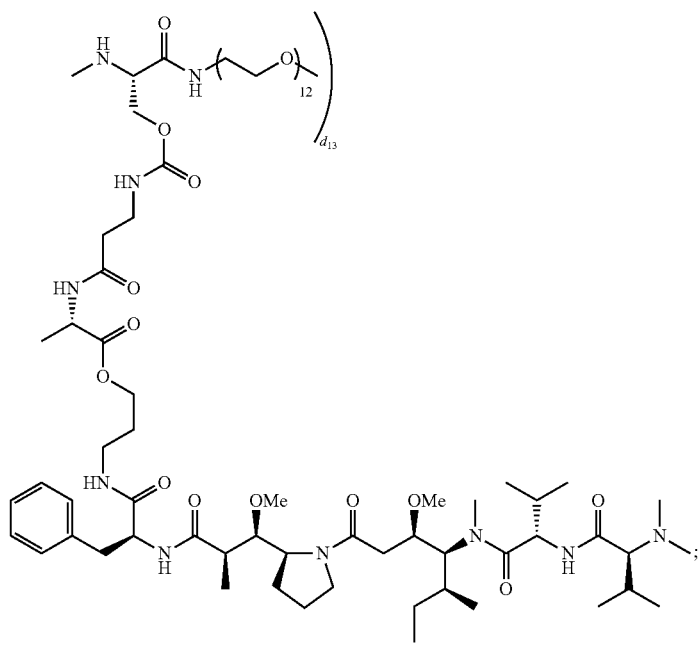
850
-continued
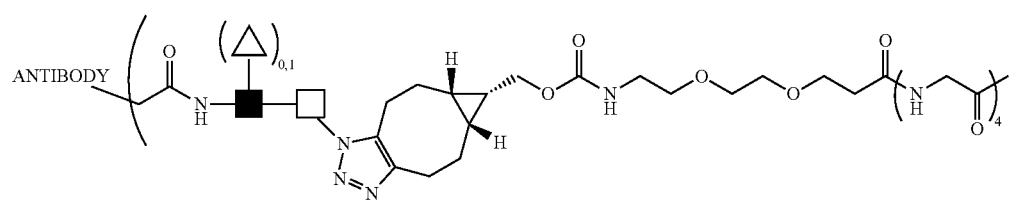
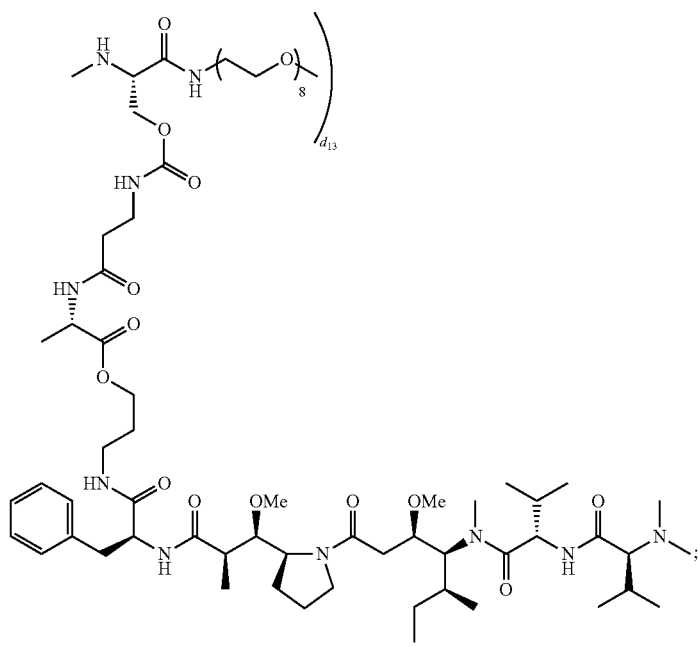

851 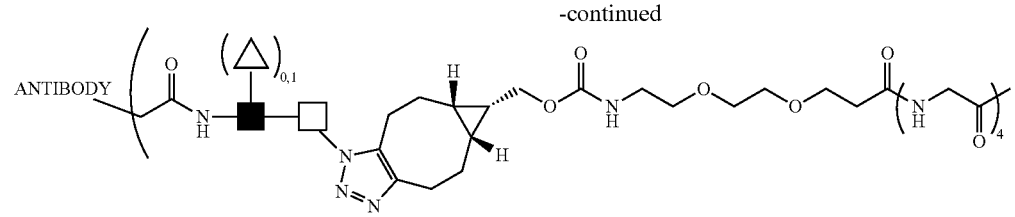 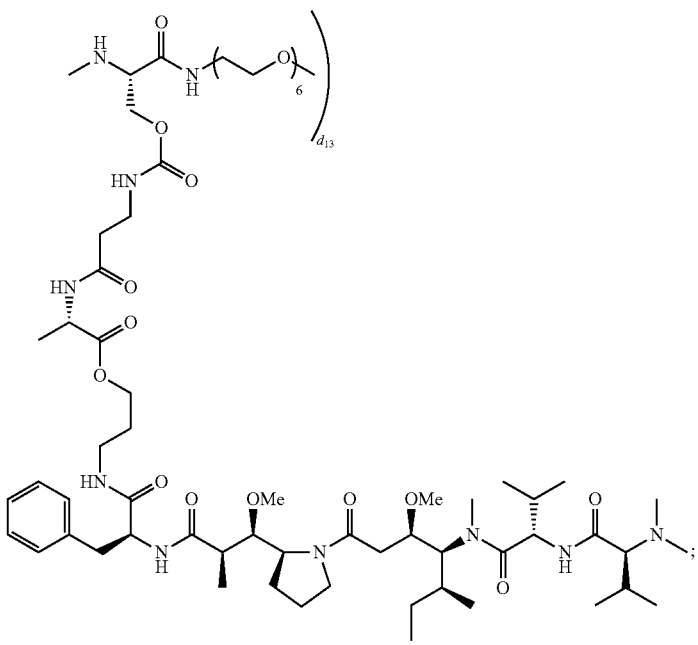
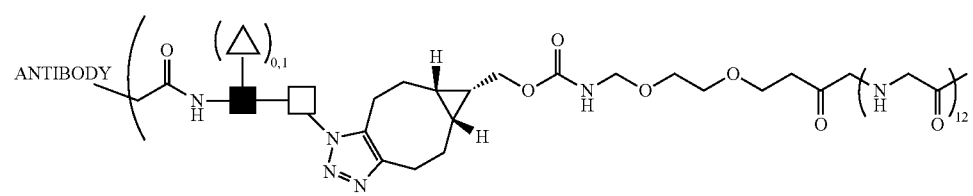 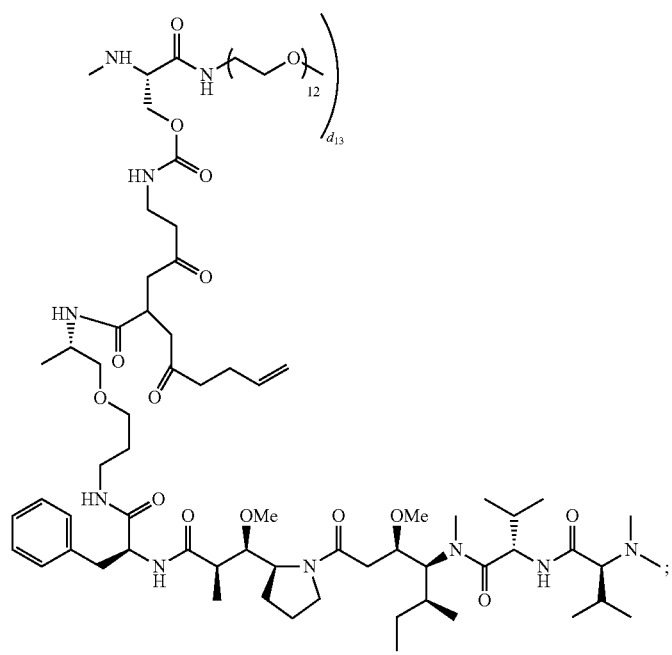

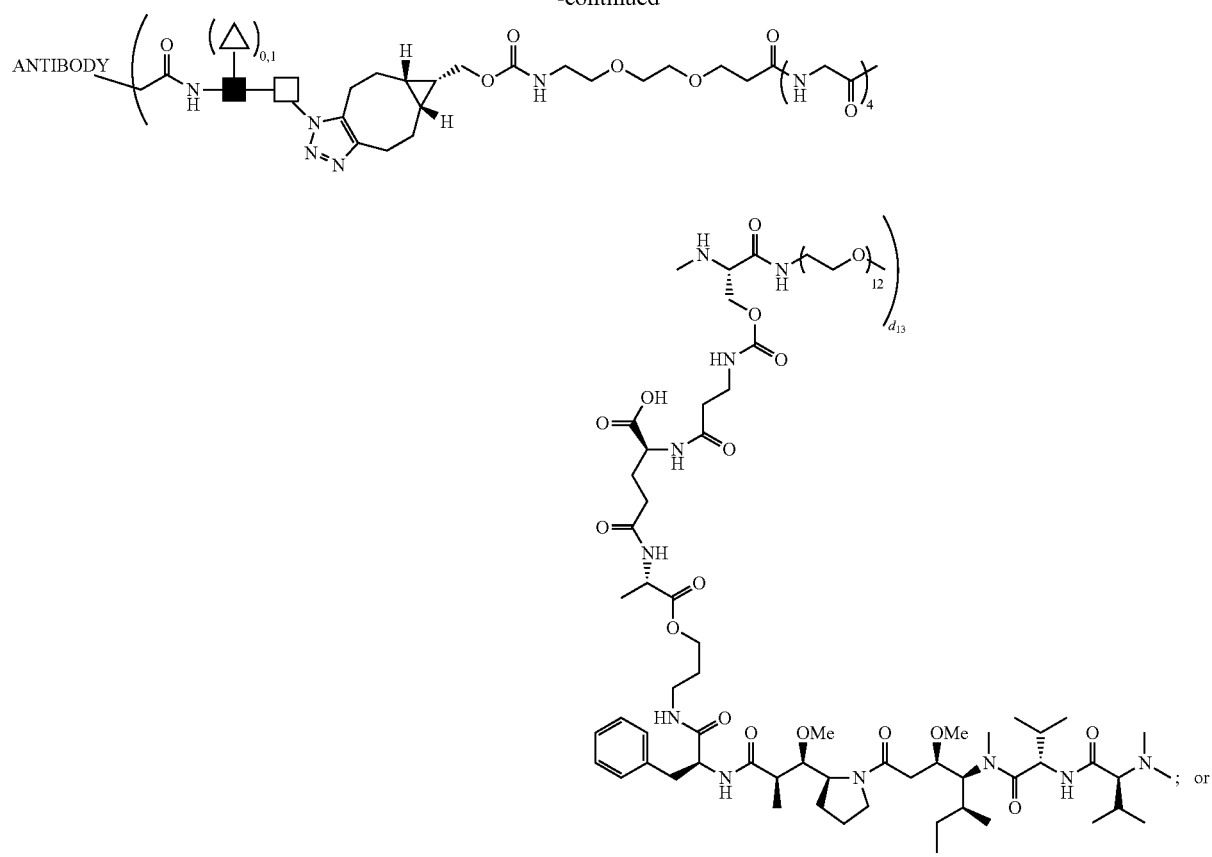
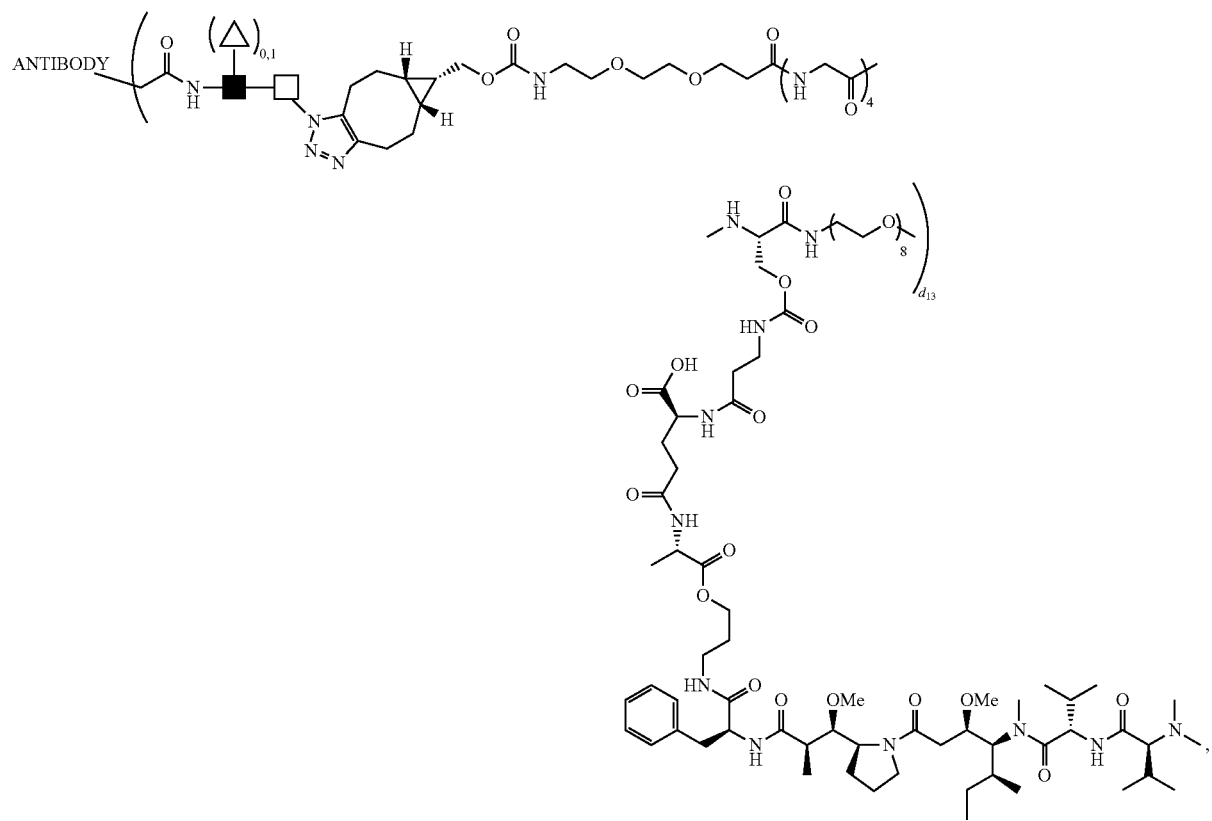

wherein:
the drug is attached to a heavy chain of the antibody via a linker moiety at an asparagine residue at position 297 when numbered in accordance with EU numbering;

■ is GlcNAc; △ is Fuc; □ is GalNAc; and $d_{13}$ is about 2.

24. The isolated antibody of claim 1, wherein the antibody is a cysteine engineered antibody.

25. The isolated antibody of claim 1, wherein the isolated antibody comprises a heavy chain comprising a heavy chain variable sequence comprising the amino acid sequence of SEQ ID NO: 44 and a heavy chain constant region comprising the amino acid sequence of SEQ ID NO: 6; and
a light chain comprising a light chain variable sequence comprising the amino acid sequence of SEQ ID NO: 50 and a light chain constant region comprising the amino acid sequence of SEQ ID NO: 51.

26. The isolated antibody of claim 1, wherein the isolated antibody comprises a heavy chain comprising a heavy chain variable sequence comprising the amino acid sequence of SEQ ID NO: 22 and a heavy chain constant region comprising the amino acid sequence of SEQ ID NO: 6; and
a light chain comprising a light chain variable sequence comprising the amino acid sequence of SEQ ID NO: 50 and a light chain constant region comprising the amino acid sequence of SEQ ID NO: 51.

27. A B7-H4 antibody-drug conjugate being of Formula (XXXVII):

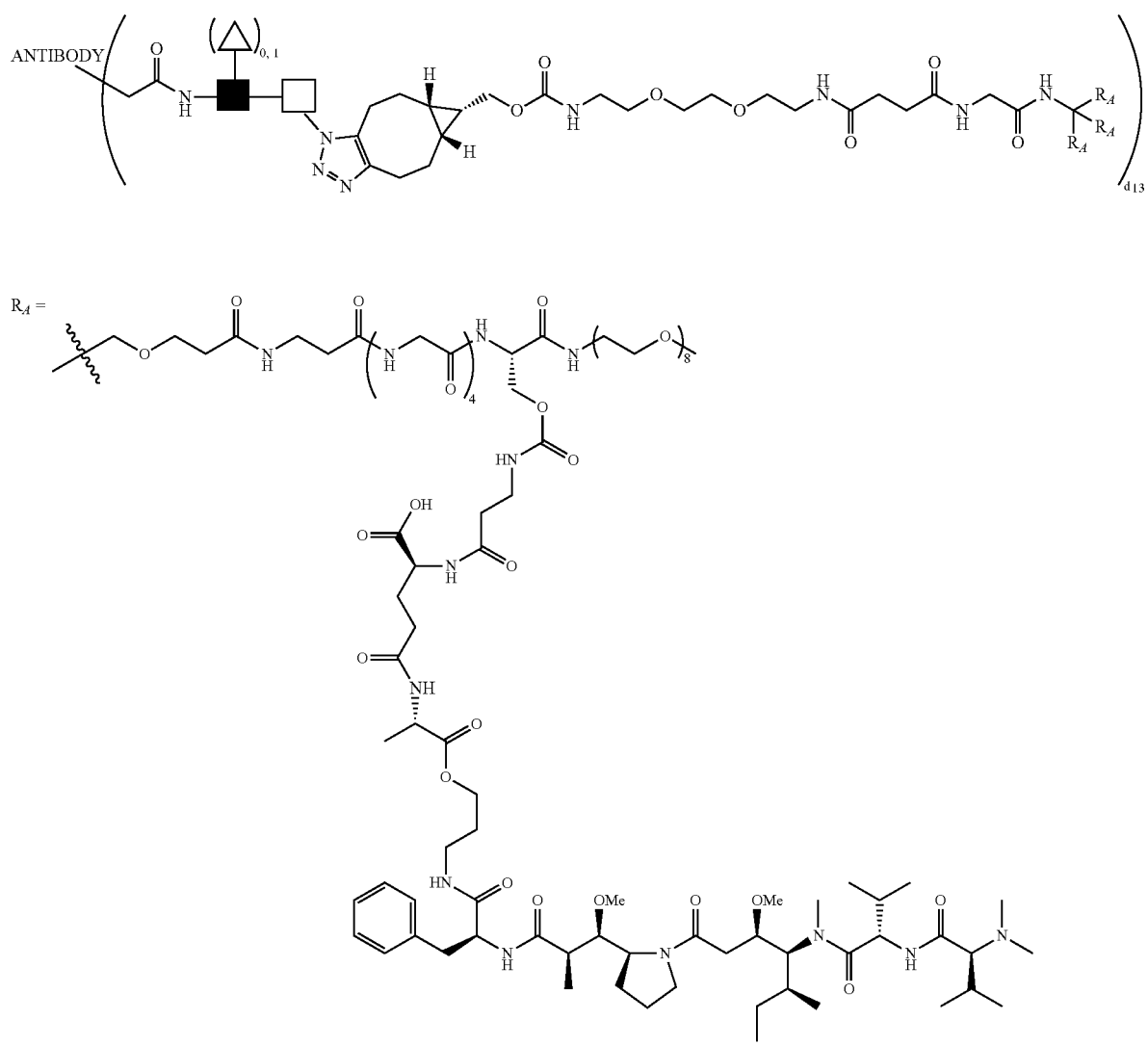

wherein
ANTIBODY binds B7-H4 and comprises a variable heavy chain complementarity determining region 1 (CDRH1) comprising the amino acid sequence GFIVSRNY (SEQ ID NO: 2), a variable heavy chain complementarity determining region 2 (CDRH2) comprising the amino acid sequence IYGSGRT (SEQ ID NO: 3), a variable heavy chain complementarity determining region 3 (CDRH3) comprising the amino acid sequence ARDADYGLDV (SEQ ID NO: 16), a variable light chain complementarity determining region 1 (CDRL1) comprising the amino acid sequence QSVSSSY (SEQ ID NO: 53), a variable light chain complementarity determining region 2 (CDRL2) comprising the amino acid sequence GAS (SEQ ID NO: 54), and a variable light chain complementarity determining region 3 (CDRL3) comprising the amino acid sequence QQYGSSPLYT (SEQ ID NO: 55);

$d_{13}$ is about 2;

the drug is attached to a heavy chain of the antibody via a linker moiety at an asparagine residue at position 296 when numbered in accordance with SEQ ID NO: 45;

■ is GlcNAc; △ is Fuc; and □ is GalNAc.

28. A B7-H4 antibody-drug conjugate being of Formula (XXXVII):

wherein

ANTIBODY binds B7-H4 and comprises a heavy chain comprising the amino acid sequence set forth in SEQ ID NO: 45 and a light chain comprising the amino acid sequence set forth in SEQ ID NO: 52;

$d_{13}$ is about 2;

the drug is attached to said heavy chain of the antibody via a linker moiety at an asparagine residue at position 296 according to SEQ ID NO: 45;

■ is GlcNAc; △ is Fuc; and □ is GalNAc.

29. A B7-H4 antibody-drug conjugate being of Formula (XXXVII):

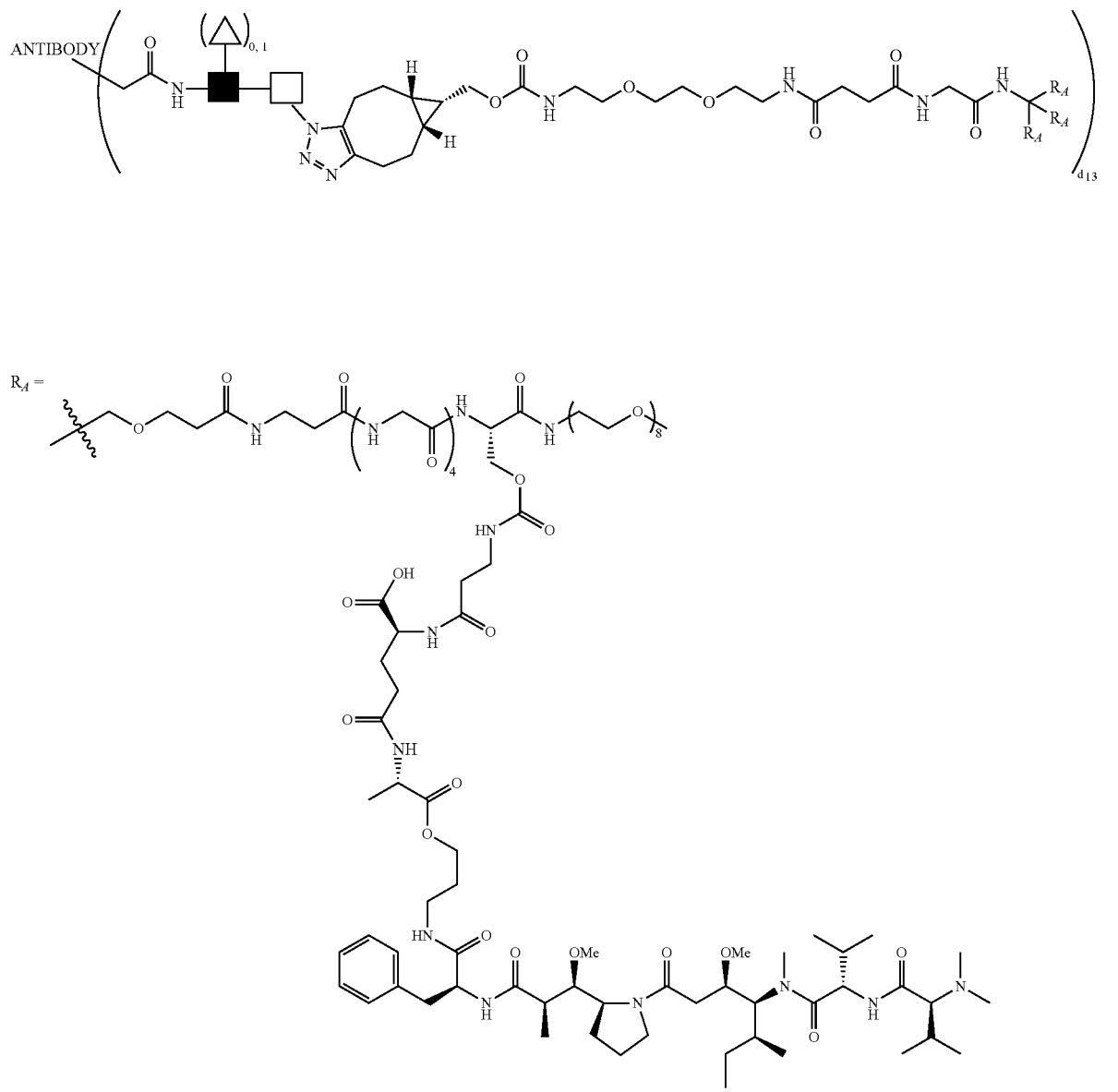

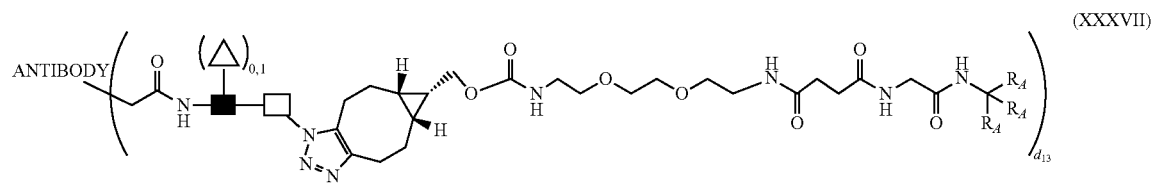

(XXXVII)

$$R_A = \text{[structure]}$$

wherein
ANTIBODY binds B7-H4 and comprises a heavy chain variable sequence comprising the amino acid sequence of SEQ ID NO: 44 and a light chain variable sequence comprising the amino acid sequence of SEQ ID NO: 50;
$d_{13}$ is about 2;

the drug is attached to a heavy chain of the antibody via a linker moiety at an asparagine residue at position 296 according to SEQ ID NO: 45;

■ is GlcNAc; △ is Fuc; and □ is GalNAc.

30. A B7-H4 antibody-drug conjugate being of Formula (XXXVII):

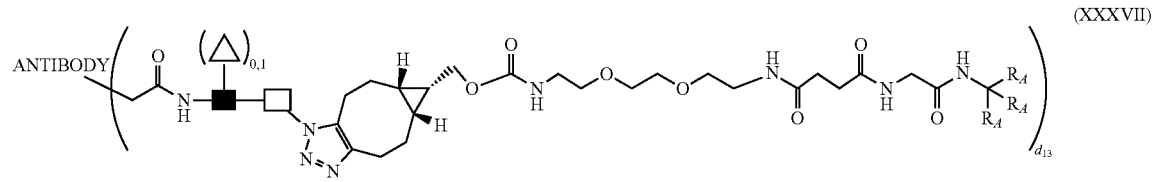

(XXXVII)

-continued

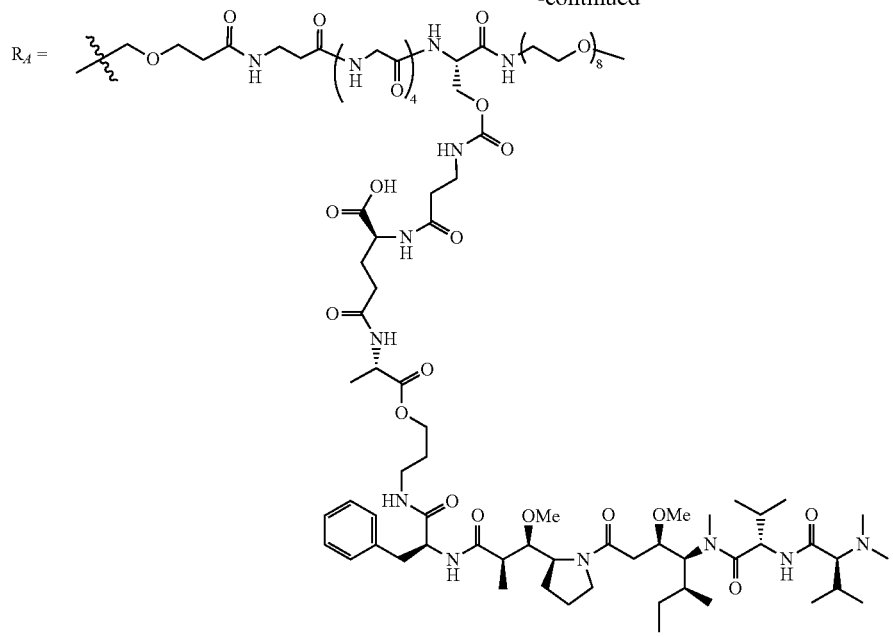

wherein

ANTIBODY binds B7-H4 and comprises a heavy chain comprising a heavy chain variable sequence comprising the amino acid sequence of SEQ ID NO: 44 and a heavy chain constant region comprising the amino acid sequence of SEQ ID NO: 6 and a light chain comprising a light chain variable sequence comprising the amino acid sequence of SEQ ID NO: 50 and a light chain constant region comprising the amino acid sequence of SEQ ID NO: 51;

$d_{13}$ is about 2;

the drug is attached to said heavy chain of the antibody via a linker moiety at an asparagine residue at position 296 according to SEQ ID NO: 45;

■ is GlcNAc; △ is Fuc; and □ is GalNAc.

* * * * *